US012528777B2

(12) United States Patent
Talukdar et al.

(10) Patent No.: US 12,528,777 B2
(45) Date of Patent: Jan. 20, 2026

(54) QUINAZOLINONES DERIVATIVES FOR TREATMENT OF NON-ALCOHOLIC FATTY LIVER DISEASE, PREPARATION AND USE THEREOF

(71) Applicant: Council of Scientific and Industrial Research, New Delhi (IN)

(72) Inventors: Arindam Talukdar, Kolkata (IN); Partha Chakrabarti, Kolkata (IN); Dipayan Sarkar, Kolkata (IN); Saheli Chowdhury, Kolkata (IN); Sunny Goon, Kolkata (IN); Subrata Das, Kolkata (IN); Nirmal Das, Kolkata (IN); Dipika Sarkar, Kolkata (IN)

(73) Assignee: Council of Scientific & Industrial Research, New Delhi (IN)

(*) Notice: Subject to any disclaimer, the term of this patent is extended or adjusted under 35 U.S.C. 154(b) by 492 days.

(21) Appl. No.: 18/013,681

(22) PCT Filed: Jun. 25, 2021

(86) PCT No.: PCT/IN2021/050621

§ 371 (c)(1),
(2) Date: Dec. 29, 2022

(87) PCT Pub. No.: WO2022/003712

PCT Pub. Date: Jan. 6, 2022

(65) Prior Publication Data

US 2023/0357165 A1 Nov. 9, 2023

(30) Foreign Application Priority Data

Jun. 29, 2020 (IN) ............................ 202011027502

(51) Int. Cl.
*C07D 239/91* (2006.01)
*C07D 401/04* (2006.01)
*C07D 403/04* (2006.01)
*C07D 413/12* (2006.01)

(52) U.S. Cl.
CPC ......... *C07D 239/91* (2013.01); *C07D 401/04* (2013.01); *C07D 403/04* (2013.01); *C07D 413/12* (2013.01)

(58) Field of Classification Search
CPC .. C07D 239/91; C07D 401/04; C07D 403/04; C07D 413/12
USPC ...................................................... 514/234.5
See application file for complete search history.

(56) References Cited

U.S. PATENT DOCUMENTS

2011/0071148 A1 3/2011 Ding et al.
2019/0144453 A1 5/2019 Kim et al.

FOREIGN PATENT DOCUMENTS

WO 2010056230 A1 5/2010

OTHER PUBLICATIONS

International Search Report pertaining to PCT/IN2021/050621 filed Jun. 25, 2021, mailed Sep. 30, 2021.
Written Opinion pertaining to PCT/IN2021/050621 filed Jun. 25, 2021, mailed Sep. 30, 2021.
Niyogi, S. et al,. Biochemical and Biophysical Research Communications. 2019. "PEDF promotes nuclear degradation of ATGL through COP1."
Ghosh, M. et al., Diabetes. vol. 65. 2016. "Ubiquitin Ligase COP1 Controls Hepatic Fat Metabolism by Targeting ATGL for Degradation."
Ong, K. et al., Hepatology, vol. 53, No. 1, 2011. "Adipose Triglyceride Lipase Is a Major Hepatic Lipase That Regulates Triacylglycerol Turnover and Fatty Acid Signaling and Partitioning."
Jha, P. et al., Hepatology, vol. 59, No. 3, 2014. "Role of Adipose Triglyceride Lipase (PNPLA2) in Protection From Hepatic Inflammation in Mouse Models of Steatohepatitis and Endotoxemia."

*Primary Examiner* — Kristin A Vajda
(74) *Attorney, Agent, or Firm* — DINSMORE & SHOHL LLP

(57) ABSTRACT

Compounds having Structure I are provided for treating diseases and disorders for which inhibition or modulation of the Ubiquitin Ligase COP1 enzyme produces a physiologically beneficial response, in particular for the treatment of Non-Alcoholic Fatty Liver Disease (NAFLD). These compounds having Structure I are capable of increasing the level of adipose triglyceride lipase (ATGL). Also provided is the process of preparing compounds having Structure I.

Structure I

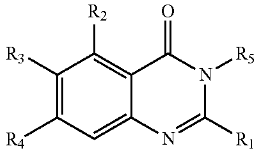

9 Claims, 13 Drawing Sheets

QUINAZOLINONES DERIVATIVES FOR TREATMENT OF NON-ALCOHOLIC FATTY LIVER DISEASE, PREPARATION AND USE THEREOF

CROSS-REFERENCES TO RELATED APPLICATIONS

This application is a national-stage application under 35 U.S.C. § 371 of International Application PCT/IN2021/050621, filed Jun. 25, 2021, which claims benefit of priority to Indian Patent Application No. 202011027502, filed Jun. 29, 2020.

TECHNICAL FIELD

The present disclosure relates to the preparation of new compounds having Structure I in free form or in an acceptable salt form for modulation of Ubiquitin Ligase COP1 through its stabilization as a potential therapeutic target for Non-Alcoholic Fatty Liver Disease (NAFLD).

Structure I

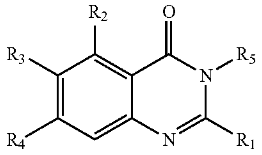

The present disclosure relates to a compound having Structure I, where $R_1$, $R_2$, $R_3$, $R_4$ and $R_5$ are as defined in the description. Some of the synthesized molecules are capable of increasing the level of adipose triglyceride lipase (ATGL) through modulation of Ubiquitin Ligase COP1 through its stabilization as a potential therapeutic target for treatment of Non-Alcoholic Fatty Liver Disease (NAFLD).

BACKGROUND

Non Alcoholic Fatty Liver Disease (NAFLD) has garnered considerable attention due to the increasing worldwide prevalence of this disease spectrum. NAFLD is an umbrella term encompassing simple steatosis progressing to steatohepatitis, fibrosis, cirrhosis, and hepatocellular carcinoma (HCC). Steatosis is mostly a reversible condition whereby fat droplets, mostly in the form of triglycerides, accumulate in the liver without pronounced hepatocyte injury. Steatohepatitis (nonalcoholic steatohepatitis, NASH) denotes the stage wherein hepatocytes are significantly injured and is histologically characterized by the presence of ballooned hepatocytes, Mallory-Denk bodies, glycogenated nuclei and other distinguishing features. NASH may, in some cases, progress to fibrosis and cirrhosis which are more critical stages whereby extracellular matrix proteins, notably collagen fibres, accumulate in the liver encircling hepatocytes and forming scar tissue resulting in irreversible damage to the normal physiology of the liver. The prevalence of NAFLD is reported to be 20%-30% in Western countries and 5%-18% in Asia. While the incidence of NAFLD is rising at an alarming rate, with it being considered now as the second most common reason for liver transplantation, no robust therapies are available to reverse the advanced stages of this condition.

NAFLD is a complex multifactorial disorder involving the interplay of several molecules and their associated signaling pathways. A multitude of risk factors have been attributed to the development of NAFLD with type 2 diabetes and metabolic syndrome considered as the most important ones. As is evident, the most prominent feature of NAFLD is the deposition of excessive triacylglycerols (TAG) in hepatocytes and, therefore, deregulation of enzymes responsible for controlling intracellular lipid turnover and homeostasis may play an important role in NAFLD (Ong et al. Hepatology. 2011, 53, 116-126). A pivotal enzyme associated with the intracellular degradation of TAG is Adipose triglyceride lipase (ATGL) also known as patatin-like phospholipase domain-containing protein 2 (PNPLA2). It catalyses the initial and rate limiting step in the TAG lipolysis cascade. Indeed, studies have shown that ATGL levels are decreased in NAFLD patients and liver injury is aggravated in mice with liver specific ATGL depletion (Jha et al. Hepatology, 2014, 59, 858-869).

Ubiquitin-proteasome system is a pivotal pathway for regulation of protein turnover in cells. Ubiquitination of a protein requires the stepwise involvement of 3 enzymes: E1-ubiquitin-activating enzymes, E2-ubiquitin-conjugating enzymes, and E3 ubiquitin ligases. COP1 is one such evolutionary conserved ubiquitin ligase which plays a central role in a myriad of important cellular pathways like insulin secretion from pancreatic β cells, regulating the stability of p53, etc.

Our previous study has identified a novel interaction between COP1 and the VP motif of ATGL. This interaction targets ATGL for proteasomal degradation by K-48 linked polyubiquitination, predominantly at the lysine 100 residue. In NAFLD, increased degradation of ATGL by COP1 would cause more TAG to accumulate in the liver manifesting a more severe form of the disease (Ghosh et al. Diabetes, 2016, 65, 3561-3572). Therefore, curtailing the ubiquitin mediated degradation of ATGL by inhibiting COP1 can be a potential area for therapeutics. In the same study, it was validated that steatosis in mice liver could be ameliorated with adenovirus mediated depletion of COP1 in mice. In this context, if small molecules with the potential to target the interacting site of COP1 and ATGL can be developed to target COP1 and hinder its capability to ubiquitinate ATGL, ATGL would be able to hydrolyze the accumulated TAG in the liver and abort the progression of NAFLD. Therefore, if this increased lipolysis in liver in the context of NAFLD can be achieved, then a robust therapy is available at hand to combat the progression of steatosis to steatohepatitis ultimately restricting NAFLD at its very onset (Niyogi et al., Biochemical and Biophysical Research Communications, 2019, 512, 806-811).

At present, treatment strategies are mainly directed towards various targets that mediate hepatocyte dysregulation, inflammation, apoptosis and oxidative stress. Extrahepatic targets whose role are implicated in NASH like microbiome, gut liver axis, organs like muscle and adipose tissue are also being considered for designing therapeutic targets. Certain drugs are in clinical trials at various phases. Notably, elafibranor (PPAR-α/δ ligand), selonsertib (ASK-1 inhibitor), obeticholic acid (FXR agonist), cenicriviroc (CCR 2/5 inhibitor) are in Phase 3 trial. All these drugs aim at a much advanced stage of fibrosis in NASH. Few drugs like Aramchol (SCD-1 inhibitor), IMM-124E (Anti-LPS), MGL-3196 (THR-β agonist), NGM282 (FGF19 analog), and PF-05221304 (ACC inhibitor), which are in Phase 2 clinical trials aim at an improvement in liver fat and therefore, target mainly the steatotic stage. Targeting the fibrotic stage in NASH may not always prove to be beneficial since mostly the stage is irreversible and much damage has already been inflicted in liver with deposition of collagen fibres and beginning of scar tissue formation. Hence, if the progression of NASH can be curbed at the reversible stage of steatosis by curtailing the deposition of fat, a much effective therapy can be established.

The main objective of the present disclosure is to provide a compound having Structure I.

Another objective of the present disclosure is to provide a process for the preparation of compound having Structure I.

Still another objective of the present disclosure is to evaluate the efficacy of active compounds using screening methods including fluorescence microscopy and measurement of levels of ATGL protein.

Yet another objective of the present disclosure is to provide a method for testing the specificity of the compounds for targeting the interaction of ATGL-COP1.

Still another objective of the present disclosure is to increase the level of ATGL in hepatocytes that can decrease the level of cellular lipids.

Yet another objective of the present disclosure is to decrease the ubiquitination and proteasomal degradation of ATGL.

Still another objective of the present disclosure is to identify the specific E1 and E2 enzyme in ubiquitination process.

Yet another objective of the present disclosure is to decrease the level of triglycerides in hepatocytes.

Still another objective of the present disclosure is to test the efficacy of the compounds in vivo in preclinical models.

Yet another objective of the present disclosure is to provide a composition comprising compounds of Structure I for use in a number of clinical applications, including pharmaceutical agents and methods for treating conditions like Non-Alcoholic Fatty Liver Disease (NAFLD).

Still another objective of the present disclosure is to provide a composition and methods of using the compounds having general Structure I without considerable cytotoxicity in hepatocytes.

SUMMARY

An embodiment of present disclosure provides compound having Structure I or a pharmaceutically acceptable salt thereof:

Structure I

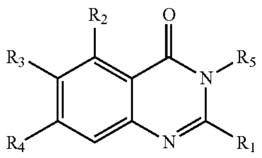

wherein $R_1$ is independently selected from the group consisting of:

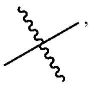, 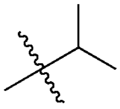, 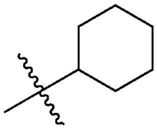,

-continued

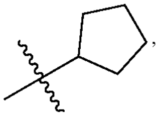, 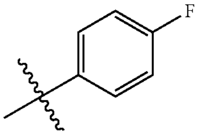,

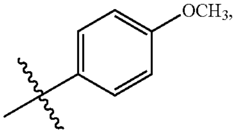, 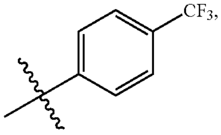,

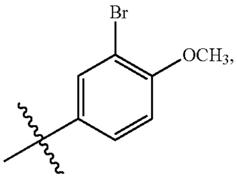, 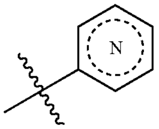,

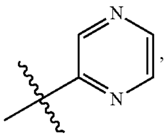, 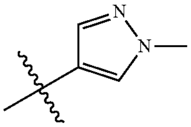,

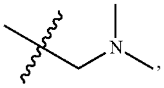, 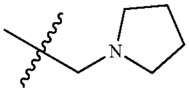,

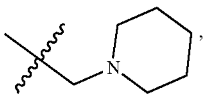, 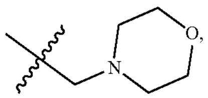,

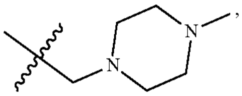, 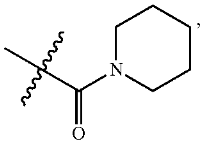,

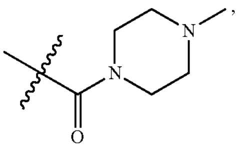, 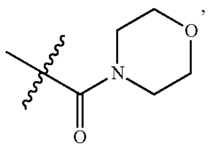,

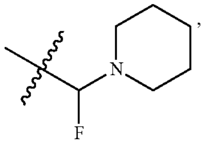, 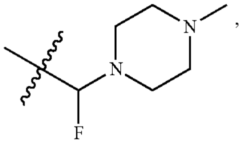,

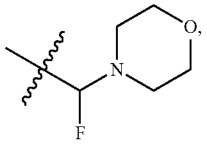, 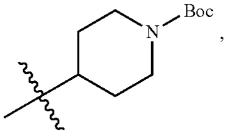,

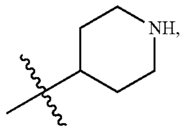, 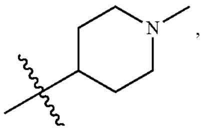,

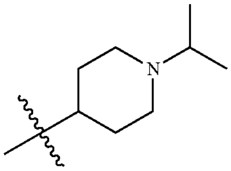 [SMILES: *C1CCN(C(C)C)CC1]

R$_2$ is independently selected from the group consisting of:
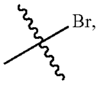, 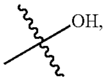, 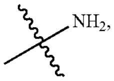, 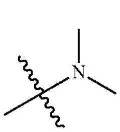,
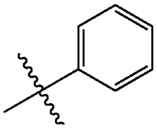, 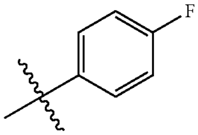,
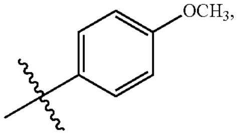, 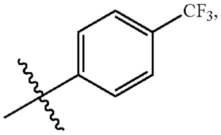,
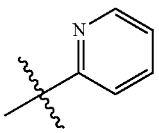, 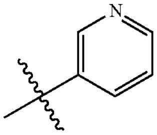, 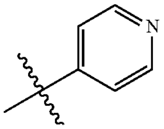,
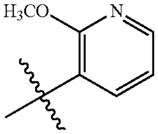, 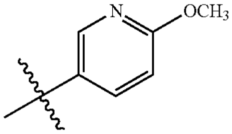,
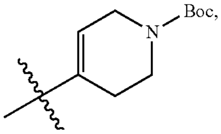, 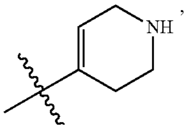,
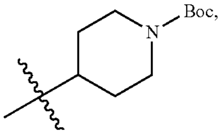, 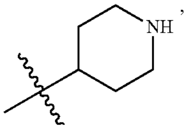,
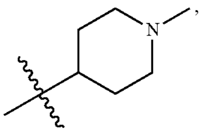, 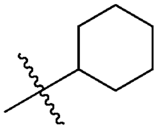,
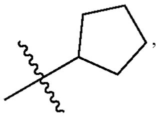, 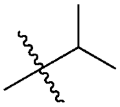
R$_3$ is independently selected from the group consisting of:
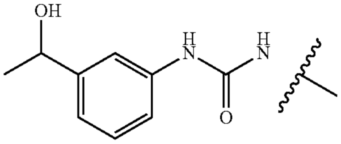,
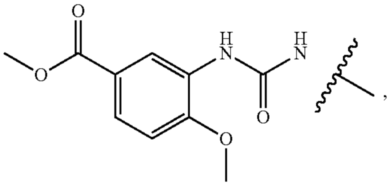,
-continued
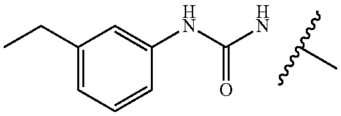,
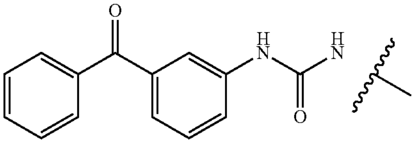,
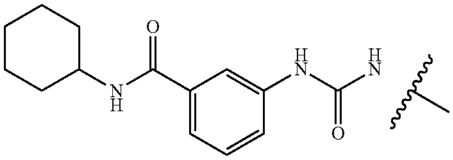,
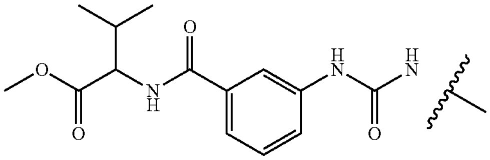,
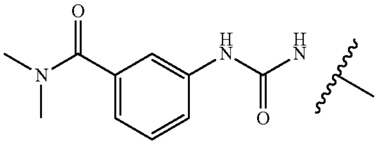,
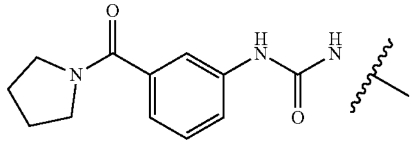,
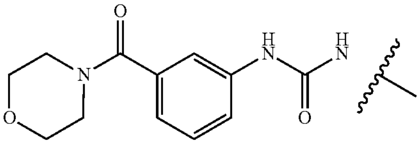,
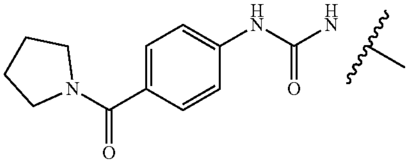,
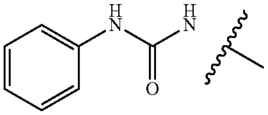,
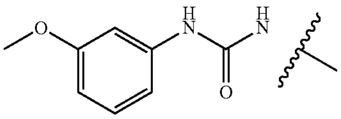,
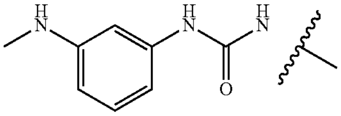,
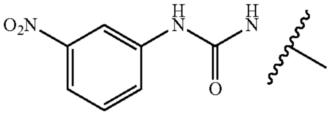, -continued
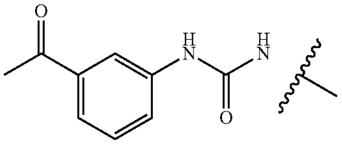
,
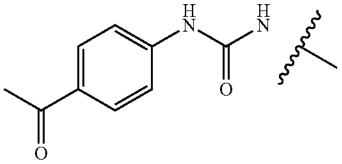
,
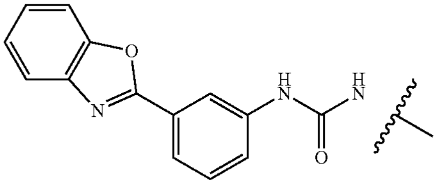
,
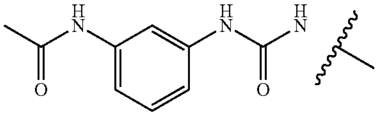
,
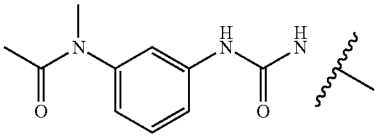
,
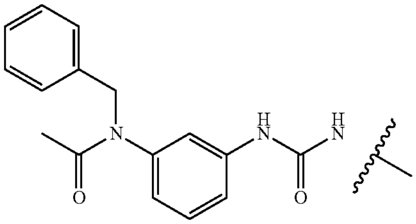
,
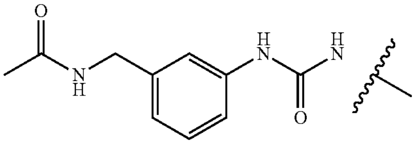
,
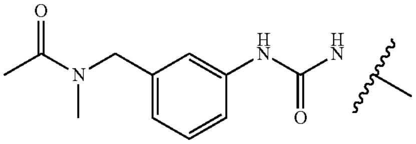
,
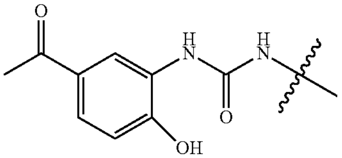
,
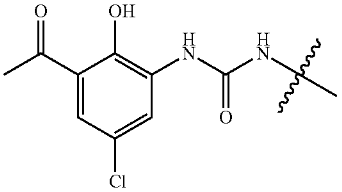
,
-continued
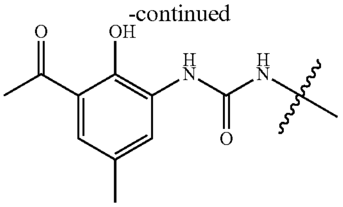
,
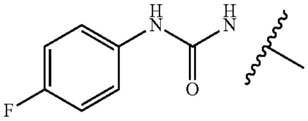
,
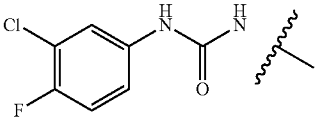
,
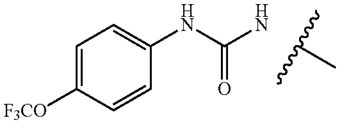
,
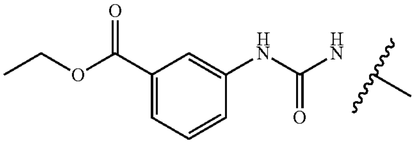
,
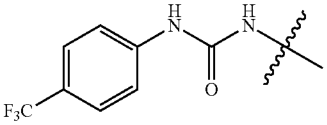
,
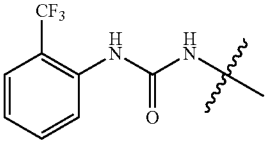
,
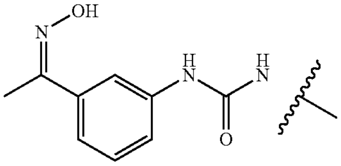
,
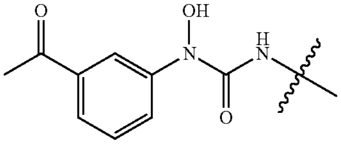
,
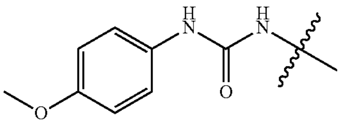
,
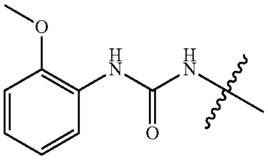
,
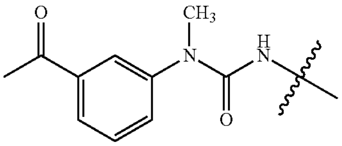

$R_4$ is independently selected from the group consisting of:
H, 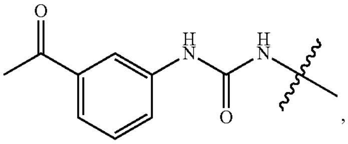 ,
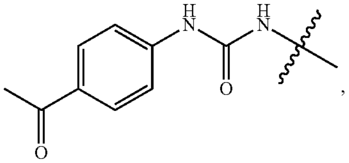 ,
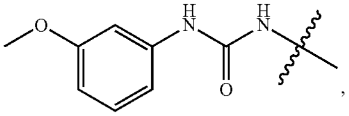 ,
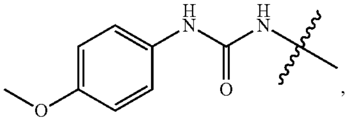 ,
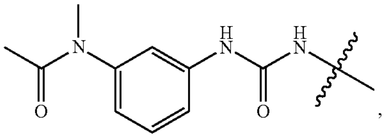 ,
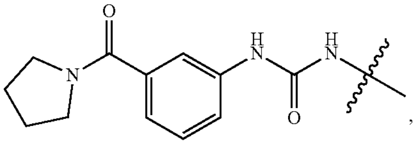 ,
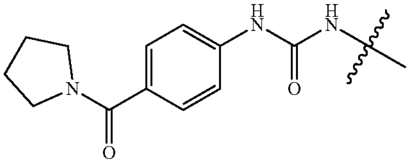
$R_5$ is independently selected from the group consisting of:
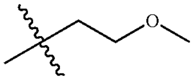 , 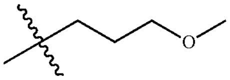 ,
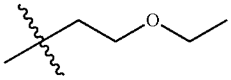 , 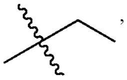 ,
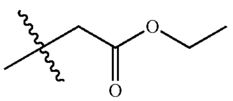 , 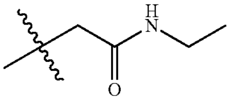 ,
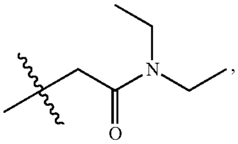 , 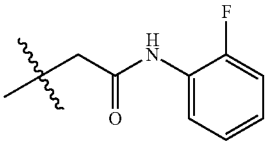 ,
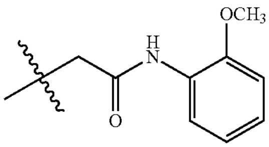 , 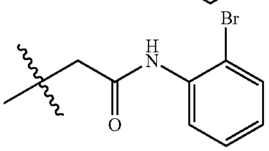 ,
-continued
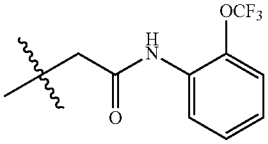 , 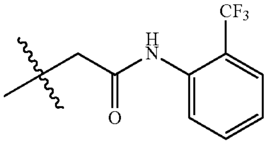 ,
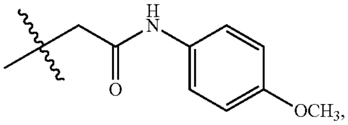
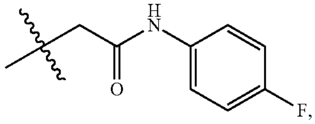
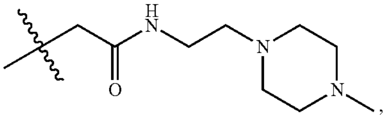 ,
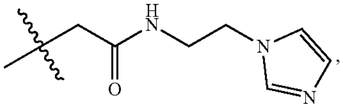 ,
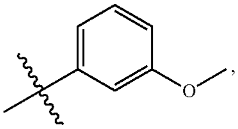 , 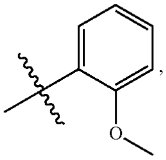 ,
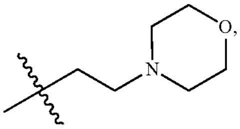 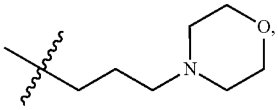
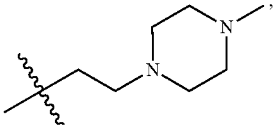 , 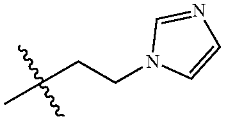 ,
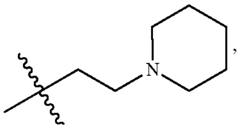 , 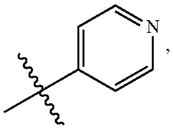 ,
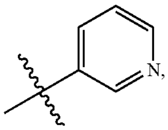 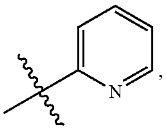 ,
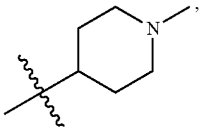 , 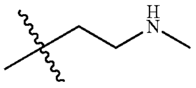 ,
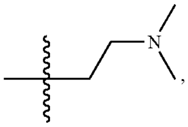 , 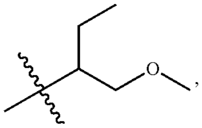 ,
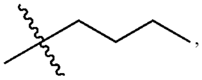 , 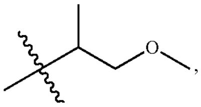 , -continued

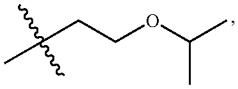,
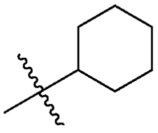

Another embodiment of the present disclosure provides the compound having Structure I selected from the group consisting of:

1-(3-(2-methoxyethyl)-4-oxo-3,4-dihydroquinazolin-6-yl)-3-phenylurea (5),
1-(3-(2-methoxyethyl)-4-oxo-3,4-dihydroquinazolin-6-yl)-3-(3-methoxyphenyl)urea (6),
1-(3-(2-methoxyethyl)-4-oxo-3,4-dihydroquinazolin-6-yl)-3-(3-(methylamino)phenyl)urea (7),
1-(3-(2-methoxyethyl)-4-oxo-3,4-dihydroquinazolin-6-yl)-3-(3-nitrophenyl)urea (8),
1-(3-acetylphenyl)-3-(3-(2-methoxyethyl)-4-oxo-3,4-dihydroquinazolin-6-yl)urea (9),
1-(4-acetylphenyl)-3-(3-(2-methoxyethyl)-4-oxo-3,4-dihydroquinazolin-6-yl)urea (10),
1-(3-(1-hydroxyethyl)phenyl)-3-(3-(2-methoxyethyl)-4-oxo-3,4-dihydroquinazolin-6-yl)urea (11),
methyl 4-methoxy-3-(3-(3-(2-methoxyethyl)-4-oxo-3,4-dihydroquinazolin-6-yl)ureido)benzoate (12),
1-(3-ethylphenyl)-3-(3-(2-methoxyethyl)-4-oxo-3,4-dihydroquinazolin-6-yl)urea (13),
1-(3-benzoylphenyl)-3-(3-(2-methoxyethyl)-4-oxo-3,4-dihydroquinazolin-6-yl)urea (14),
N-cyclohexyl-3-(3-(3-(2-methoxyethyl)-4-oxo-3,4-dihydroquinazolin-6-yl)ureido)benzamide (15),
methyl 2-(3-(3-(3-(2-methoxyethyl)-4-oxo-3,4-dihydroquinazolin-6-yl)ureido)benzamido)-3-methylbutanoate (16),
3-(3-(3-(2-methoxyethyl)-4-oxo-3,4-dihydroquinazolin-6-yl)ureido)-N,N-dimethylbenzamide (17),
1-(3-(2-methoxyethyl)-4-oxo-3,4-dihydroquinazolin-6-yl)-3-(3-(pyrrolidine-1-carbonyl)phenyl)urea (18),
1-(3-(2-methoxyethyl)-4-oxo-3,4-dihydroquinazolin-6-yl)-3-(3-(morpholine-4-carbonyl)phenyl)urea (19),
1-(3-(2-methoxyethyl)-4-oxo-3,4-dihydroquinazolin-6-yl)-3-(4-(pyrrolidine-1-carbonyl)phenyl)urea (20),
1-(3-(benzo[d]oxazol-2-yl)phenyl)-3-(3-(2-methoxyethyl)-4-oxo-3,4-dihydroquinazolin-6-yl)urea (21),
N-(3-(3-(3-(2-methoxyethyl)-4-oxo-3,4-dihydroquinazolin-6-yl)ureido)phenyl)acetamide (22),
N-(3-(3-(3-(2-methoxyethyl)-4-oxo-3,4-dihydroquinazolin-6-yl)ureido)phenyl)-N-methylacetamide (23),
N-benzyl-N-(3-(3-(3-(2-methoxyethyl)-4-oxo-3,4-dihydroquinazolin-6-yl)ureido)phenyl)acetamide (24),
N-(3-(3-(3-(2-methoxyethyl)-4-oxo-3,4-dihydroquinazolin-6-yl)ureido)benzyl)acetamide (25),
N-(3-(3-(3-(2-methoxyethyl)-4-oxo-3,4-dihydroquinazolin-6-yl)ureido)benzyl)-N-methylacetamide (26),
1-(5-acetyl-2-hydroxyphenyl)-3-(3-(2-methoxyethyl)-4-oxo-3,4-dihydroquinazolin-6-yl)urea (32),
1-(3-acetyl-5-chloro-2-hydroxyphenyl)-3-(3-(2-methoxyethyl)-4-oxo-3,4-dihydroquinazolin-6-yl)urea (33),
1-(3-acetyl-2-hydroxy-5-methylphenyl)-3-(3-(2-methoxyethyl)-4-oxo-3,4-dihydroquinazolin-6-yl)urea (34),
1-(4-fluorophenyl)-3-(3-(2-methoxyethyl)-4-oxo-3,4-dihydroquinazolin-6-yl)urea (35),
1-(3-chloro-4-fluorophenyl)-3-(3-(2-methoxyethyl)-4-oxo-3,4-dihydroquinazolin-6-yl)urea (36),
1-(3-(2-methoxyethyl)-4-oxo-3,4-dihydroquinazolin-6-yl)-3-(4-(trifluoromethoxy)phenyl)urea (37),
1-(3-(2-methoxyethyl)-4-oxo-3,4-dihydroquinazolin-6-yl)-3-(4-(trifluoromethyl)phenyl)urea (38),
1-(3-(2-methoxyethyl)-4-oxo-3,4-dihydroquinazolin-6-yl)-3-(2-(trifluoromethyl)phenyl)urea (39),
1-(3-(2-methoxyethyl)-4-oxo-3,4-dihydroquinazolin-6-yl)-3-(4-methoxyphenyl)urea (40),
1-(3-(2-methoxyethyl)-4-oxo-3,4-dihydroquinazolin-6-yl)-3-(2-methoxyphenyl)urea (41),
ethyl 3-(3-(3-(2-methoxyethyl)-4-oxo-3,4-dihydroquinazolin-6-yl)ureido)benzoate (42),
3-(3-(3-(2-methoxyethyl)-4-oxo-3,4-dihydroquinazolin-6-yl)ureido)benzoic acid (42a),
1-(3-acetylphenyl)-3-(3-(2-methoxyethyl)-4-oxo-5-phenyl-3,4-dihydroquinazolin-6-yl)urea (45),
1-(3-acetylphenyl)-3-(5-(4-fluorophenyl)-3-(2-methoxyethyl)-4-oxo-3,4-dihydroquinazolin-6-yl)urea (47),
1-(3-acetylphenyl)-3-(3-(2-methoxyethyl)-4-oxo-5-(pyridin-2-yl)-3,4-dihydroquinazolin-6-yl)urea (49),
1-(3-acetylphenyl)-3-(3-(2-methoxyethyl)-4-oxo-5-(pyridin-3-yl)-3,4-dihydroquinazolin-6-yl)urea (51),
1-(3-acetylphenyl)-3-(3-(2-methoxyethyl)-4-oxo-5-(pyridin-4-yl)-3,4-dihydroquinazolin-6-yl)urea (53),
1-(3-acetylphenyl)-3-(3-(2-methoxyethyl)-5-(6-methoxypyridin-3-yl)-4-oxo-3,4-dihydroquinazolin-6-yl)urea (55),
1-(3-acetylphenyl)-3-(3-(2-methoxyethyl)-5-(2-methoxypyridin-3-yl)-4-oxo-3,4-dihydroquinazolin-6-yl)urea (57),
tert-butyl 4-(6-(3-(3-acetylphenyl)ureido)-3-(2-methoxyethyl)-4-oxo-3,4-dihydroquinazolin-5-yl)-5,6-dihydropyridine-1 (2H)-carboxylate (59),
1-(3-acetylphenyl)-3-(3-(2-methoxyethyl)-4-oxo-5-(1,2,3,6-tetrahydropyridin-4-yl)-3,4-dihydroquinazolin-6-yl) urea (60),
tert-butyl 4-(6-(3-(3-acetylphenyl)ureido)-3-(2-methoxyethyl)-4-oxo-3,4-dihydroquinazolin-5-yl)piperidine-1-carboxylate (61),
1-(3-acetylphenyl)-3-(3-(2-methoxyethyl)-4-oxo-5-(piperidin-4-yl)-3,4-dihydroquinazolin-6-yl)urea (62),
1-(3-acetylphenyl)-3-(3-(2-methoxyethyl)-5-(4-methoxyphenyl)-4-oxo-3,4-dihydroquinazolin-6-yl)urea (64),
1-(3-acetylphenyl)-3-(3-(2-methoxyethyl)-4-oxo-5-(4-(trifluoromethyl)phenyl)-3,4-dihydroquinazolin-6-yl)urea (66),
1-(3-acetylphenyl)-3-(5-cyclohexyl-3-(2-methoxyethyl)-4-oxo-3,4-dihydroquinazolin-6-yl)urea (68),
1-(3-acetylphenyl)-3-(5-cyclopentyl-3-(2-methoxyethyl)-4-oxo-3,4-dihydroquinazolin-6-yl)urea (70),
1-(3-acetylphenyl)-3-(5-isopropyl-3-(2-methoxyethyl)-4-oxo-3,4-dihydroquinazolin-6-yl)urea (72),
1-(3-acetylphenyl)-3-(5-bromo-3-(2-methoxyethyl)-4-oxo-3,4-dihydroquinazolin-6-yl)urea (73),
ethyl 2-(6-(3-(3-chloro-4-fluorophenyl)ureido)-4-oxoquinazolin-3 (4H)-yl)acetate (83),
ethyl 2-(4-oxo-6-(3-(4-(trifluoromethoxy)phenyl)ureido) quinazolin-3 (4H)-yl)acetate (84),
ethyl 2-(6-(3-(3-acetylphenyl)ureido)-4-oxoquinazolin-3 (4H)-yl)acetate (85),
2-(6-(3-(3-acetylphenyl)ureido)-4-oxoquinazolin-3 (4H)-yl) acetic acid (85a),
1-(3-acetylphenyl)-3-(3-(3-methoxypropyl)-4-oxo-3,4-dihydroquinazolin-6-yl)urea (89),
1-(3-acetylphenyl)-3-(3-(2-ethoxyethyl)-4-oxo-3,4-dihydroquinazolin-6-yl)urea (93),
1-(4-acetylphenyl)-3-(3-(2-ethoxyethyl)-4-oxo-3,4-dihydroquinazolin-6-yl)urea (94), 1-(3-acetylphenyl)-3-(3-ethyl-4-oxo-3,4-dihydroquinazolin-6-yl)urea (98),
1-(4-acetylphenyl)-3-(3-ethyl-4-oxo-3,4-dihydroquinazolin-6-yl)urea (99),
1-(3-acetylphenyl)-3-(3-(3-methoxyphenyl)-4-oxo-3,4-dihydroquinazolin-6-yl)urea (103),
1-(3-acetylphenyl)-3-(3-(2-methoxyethyl)-2-methyl-4-oxo-3,4-dihydroquinazolin-6-yl)urea (107),
1-(3-acetylphenyl)-3-(2-isopropyl-3-(2-methoxyethyl)-4-oxo-3,4-dihydroquinazolin-6-yl)urea (111),
1-(3-acetylphenyl)-3-(2-(4-fluorophenyl)-3-(2-methoxyethyl)-4-oxo-3,4-dihydroquinazolin-6-yl)urea (115),
1-(3-acetylphenyl)-3-(3-(2-methoxyethyl)-2-(4-methoxyphenyl)-4-oxo-3,4-dihydroquinazolin-6-yl)urea (119),
1-(3-acetylphenyl)-3-(2-cyclohexyl-3-(2-methoxyethyl)-4-oxo-3,4-dihydroquinazolin-6-yl)urea (123),
1-(3-acetylphenyl)-3-(2-cyclopentyl-3-(2-methoxyethyl)-4-oxo-3,4-dihydroquinazolin-6-yl)urea (127),
1-(3-acetylphenyl)-3-(3-(2-methoxyphenyl)-4-oxo-3,4-dihydroquinazolin-6-yl)urea (131),
1-(3-acetylphenyl)-3-(3-(2-morpholinoethyl)-4-oxo-3,4-dihydroquinazolin-6-yl)urea (135),
1-(3-acetylphenyl)-3-(3-(3-morpholinopropyl)-4-oxo-3,4-dihydroquinazolin-6-yl)urea (139),
1-(3-acetylphenyl)-3-(3-(2-(dimethylamino)ethyl)-4-oxo-3,4-dihydroquinazolin-6-yl)urea (143),
1-(3-acetylphenyl)-3-(4-oxo-3-(2-(piperidin-1-yl)ethyl)-3,4-dihydroquinazolin-6-yl)urea (147),
1-(3-acetylphenyl)-3-(4-oxo-3-(pyridin-4-yl)-3,4-dihydroquinazolin-6-yl)urea (151),
1-(3-acetylphenyl)-3-(4-oxo-3-(pyridin-3-yl)-3,4-dihydroquinazolin-6-yl)urea (155),
1-(3-acetylphenyl)-3-(4-oxo-3-(pyridin-2-yl)-3,4-dihydroquinazolin-6-yl)urea (159),
1-(3-acetylphenyl)-3-(3-(1-methylpiperidin-4-yl)-4-oxo-3,4-dihydroquinazolin-6-yl)urea (163),
1-(3-acetylphenyl)-3-(3-(2-(methylamino)ethyl)-4-oxo-3,4-dihydroquinazolin-6-yl)urea (167),
1-(3-acetylphenyl)-3-(3-(1-methoxybutan-2-yl)-4-oxo-3,4-dihydroquinazolin-6-yl)urea (171),
1-(3-acetylphenyl)-3-(3-butyl-4-oxo-3,4-dihydroquinazolin-6-yl)urea (175),
1-(3-acetylphenyl)-3-(3-(1-methoxypropan-2-yl)-4-oxo-3,4-dihydroquinazolin-6-yl)urea (179),
1-(3-acetylphenyl)-3-(3-(2-isopropoxyethyl)-4-oxo-3,4-dihydroquinazolin-6-yl)urea (183),
1-(3-acetylphenyl)-3-(3-cyclohexyl-4-oxo-3,4-dihydroquinazolin-6-yl)urea (187),
1-(3-acetylphenyl)-3-(3-(2-methoxyethyl)-4-oxo-3,4-dihydroquinazolin-7-yl)urea (192),
1-(4-acetylphenyl)-3-(3-(2-methoxyethyl)-4-oxo-3,4-dihydroquinazolin-7-yl)urea (193),
1-(3-(2-methoxyethyl)-4-oxo-3,4-dihydroquinazolin-7-yl)-3-(3-methoxyphenyl)urea (194),
1-(3-(2-methoxyethyl)-4-oxo-3,4-dihydroquinazolin-7-yl)-3-(4-methoxyphenyl)urea (195),
1-(3-(2-methoxyethyl)-4-oxo-3,4-dihydroquinazolin-7-yl)-3-(3-(pyrrolidine-1-carbonyl)phenyl)urea (196),
1-(3-(2-methoxyethyl)-4-oxo-3,4-dihydroquinazolin-7-yl)-3-(4-(pyrrolidine-1-carbonyl)phenyl)urea (197),
1-(3-(1-hydroxyethyl)phenyl)-3-(3-(2-methoxyethyl)-4-oxo-3,4-dihydroquinazolin-7-yl)urea (198),
N-(3-(3-(3-(2-methoxyethyl)-4-oxo-3,4-dihydroquinazolin-7-yl)ureido)phenyl)-N-methylacetamide (199),
1-(3-acetylphenyl)-3-(3-(2-methoxyethyl)-4-oxo-2-(4-(trifluoromethyl)phenyl)-3,4-dihydroquinazolin-6-yl)urea (203),
1-(3-acetylphenyl)-3-(2-(3-bromo-4-methoxyphenyl)-3-(2-methoxyethyl)-4-oxo-3,4-dihydroquinazolin-6-yl)urea (207),
1-(3-acetylphenyl)-3-(3-(2-methoxyethyl)-4-oxo-2-(pyridin-2-yl)-3,4-dihydroquinazolin-6-yl)urea (211),
1-(3-acetylphenyl)-3-(3-(2-methoxyethyl)-4-oxo-2-(pyridin-3-yl)-3,4-dihydroquinazolin-6-yl)urea (215),
1-(3-acetylphenyl)-3-(3-(2-methoxyethyl)-4-oxo-2-(pyridin-4-yl)-3,4-dihydroquinazolin-6-yl)urea (219),
1-(3-acetylphenyl)-3-(3-(2-methoxyethyl)-4-oxo-2-(pyrazin-2-yl)-3,4-dihydroquinazolin-6-yl)urea (223),
1-(3-acetylphenyl)-3-(3-(2-methoxyethyl)-2-(1-methyl-1H-pyrazol-4-yl)-4-oxo-3,4-dihydroquinazolin-6-yl)urea (227),
1-(3-acetylphenyl)-3-(3-(2-methoxyethyl)-4-oxo-2-(pyrrolidin-1-ylmethyl)-3,4-dihydroquinazolin-6-yl)urea (232),
1-(3-acetylphenyl)-3-(2-((dimethylamino)methyl)-3-(2-methoxyethyl)-4-oxo-3,4-dihydroquinazolin-6-yl)urea (235),
1-(3-acetylphenyl)-3-(3-(2-methoxyethyl)-4-oxo-2-(piperidin-1-ylmethyl)-3,4-dihydroquinazolin-6-yl)urea (238),
1-(3-acetylphenyl)-3-(3-(2-methoxyethyl)-2-(morpholinomethyl)-4-oxo-3,4-dihydroquinazolin-6-yl)urea (241),
1-(3-acetylphenyl)-3-(3-(2-methoxyethyl)-2-((4-methylpiperazin-1-yl)methyl)-4-oxo-3,4-dihydroquinazolin-6-yl) urea (244),
2-(6-(3-(3-acetylphenyl)ureido)-4-oxoquinazolin-3 (4H)-yl)-N-ethylacetamide (247),
2-(6-(3-(3-acetylphenyl)ureido)-4-oxoquinazolin-3 (4H)-yl)-N,N-diethylacetamide (250),
2-(6-(3-(3-acetylphenyl)ureido)-4-oxoquinazolin-3 (4H)-yl)-N-(2-fluorophenyl)acetamide (253),
2-(6-(3-(3-acetylphenyl)ureido)-4-oxoquinazolin-3 (4H)-yl)-N-(2-methoxyphenyl)acetamide (256),
2-(6-(3-(3-acetylphenyl)ureido)-4-oxoquinazolin-3 (4H)-yl)-N-(2-bromophenyl)acetamide (259),
2-(6-(3-(3-acetylphenyl)ureido)-4-oxoquinazolin-3 (4H)-yl)-N-(2-(trifluoromethoxy)phenyl)acetamide (262),
2-(6-(3-(3-acetylphenyl)ureido)-4-oxoquinazolin-3 (4H)-yl)-N-(2-(trifluoromethyl)phenyl)acetamide (265),
2-(6-(3-(3-acetylphenyl)ureido)-4-oxoquinazolin-3 (4H)-yl)-N-(4-methoxyphenyl)acetamide (268),
2-(6-(3-(3-acetylphenyl)ureido)-4-oxoquinazolin-3 (4H)-yl)-N-(4-fluorophenyl)acetamide (271),
2-(6-(3-(3-acetylphenyl)ureido)-4-oxoquinazolin-3 (4H)-yl)-N-(2-(4-methylpiperazin-1-yl)ethyl)acetamide (274),
N-(2-(1H-imidazol-1-yl)ethyl)-2-(6-(3-(3-acetylphenyl)ureido)-4-oxoquinazolin-3 (4H)-yl)acetamide (277),
1-(3-acetylphenyl)-3-(3-(1-methoxybutan-2-yl)-2-methyl-4-oxo-3,4-dihydroquinazolin-6-yl)urea (281),
1-(3-acetylphenyl)-3-(3-(1-methoxypropan-2-yl)-2-methyl-4-oxo-3,4-dihydroquinazolin-6-yl)urea (285),
1-(3-acetylphenyl)-3-(2-cyclohexyl-3-(1-methoxypropan-2-yl)-4-oxo-3,4-dihydroquinazolin-6-yl)urea (289),
1-(3-acetylphenyl)-3-(2-cyclohexyl-5-(4-fluorophenyl)-3-(2-methoxyethyl)-4-oxo-3,4-dihydroquinazolin-6-yl)urea (292),
1-(3-acetylphenyl)-3-(5-(4-fluorophenyl)-3-(1-methoxypropan-2-yl)-4-oxo-3,4-dihydroquinazolin-6-yl)urea (295),
tert-butyl 4-(6-(3-(3-acetylphenyl)ureido)-3-(2-methoxyethyl)-4-oxo-3,4-dihydroquinazolin-2-yl)piperidine-1-carboxylate (299),
1-(3-acetylphenyl)-3-(3-(2-methoxyethyl)-4-oxo-2-(piperidin-4-yl)-3,4-dihydroquinazolin-6-yl)urea (300),
1-(3-acetylphenyl)-3-(3-(2-methoxyethyl)-2-(1-methylpiperidin-4-yl)-4-oxo-3,4-dihydroquinazolin-6-yl)urea (304), 1-(3-acetylphenyl)-3-(2-(1-isopropylpiperidin-4-yl)-3-(2-methoxyethyl)-4-oxo-3,4-dihydroquinazolin-6-yl)urea (307), 1-(3-acetylphenyl)-1-hydroxy-3-(3-(2-methoxyethyl)-4-oxo-3,4-dihydroquinazolin-6-yl)urea (308), 1-(3-acetylphenyl)-3-(3-(2-methoxyethyl)-4-oxo-3,4-dihydroquinazolin-6-yl)-1-methylurea (309), 1-(3-acetylphenyl)-3-(5-(4-fluorophenyl)-3-(2-methoxyethyl)-4-oxo-3,4-dihydroquinazolin-6-yl)-1-hydroxyurea (310), 1-(3-acetylphenyl)-3-(5-(4-fluorophenyl)-3-(2-methoxyethyl)-4-oxo-3,4-dihydroquinazolin-6-yl)-1-methylurea (311), 1-(3-acetylphenyl)-1-hydroxy-3-(3-(2-methoxyethyl)-4-oxo-2-(piperidin-1-ylmethyl)-3,4-dihydroquinazolin-6-yl)urea (312), 1-(3-acetylphenyl)-3-(3-(2-methoxyethyl)-4-oxo-2-(piperidin-1-ylmethyl)-3,4-dihydroquinazolin-6-yl)-1-methylurea (313), 2-(6-(3-(3-acetylphenyl)-3-hydroxyureido)-4-oxoquinazolin-3 (4H)-yl)-N-(2-fluorophenyl)acetamide (314), 2-(6-(3-(3-acetylphenyl)-3-methylureido)-4-oxoquinazolin-3 (4H)-yl)-N-(2-fluorophenyl)acetamide (315), 1-(3-(2-methoxyethyl)-4-oxo-3,4-dihydroquinazolin-6-yl)-3-(3-(2,2,2-trifluoroacetyl)phenyl)urea (316), 1-(3-(2-methoxyethyl)-2-methyl-4-oxo-3,4-dihydroquinazolin-6-yl)-3-(3-(2,2,2-trifluoroacetyl)phenyl)urea (317), 1-(3-(2-methoxyethyl)-4-oxo-2-(piperidin-1-ylmethyl)-3,4-dihydroquinazolin-6-yl)-3-(3-(2,2,2-trifluoroacetyl)phenyl)urea (318), 1-(3-(2-methoxyethyl)-2-((4-methylpiperazin-1-yl)methyl)-4-oxo-3,4-dihydroquinazolin-6-yl)-3-(3-(2,2,2-trifluoroacetyl)phenyl)urea (319), N-(2-fluorophenyl)-2-(4-oxo-6-(3-(3-(2,2,2-trifluoroacetyl)phenyl)ureido)quinazolin-3 (4H)-yl)acetamide (320), 1-(3-acetyl-4-fluorophenyl)-3-(3-(2-methoxyethyl)-4-oxo-3,4-dihydroquinazolin-6-yl)urea (321), 1-(3-acetyl-4-fluorophenyl)-3-(3-(2-methoxyethyl)-2-methyl-4-oxo-3,4-dihydroquinazolin-6-yl)urea (322), 1-(3-acetyl-4-fluorophenyl)-3-(3-(2-methoxyethyl)-4-oxo-2-(piperidin-1-ylmethyl)-3,4-dihydroquinazolin-6-yl)urea (323), 1-(3-acetyl-4-fluorophenyl)-3-(3-(2-methoxyethyl)-2-((4-methylpiperazin-1-yl)methyl)-4-oxo-3,4-dihydroquinazolin-6-yl)urea (324), 2-(6-(3-(3-acetyl-4-fluorophenyl)ureido)-4-oxoquinazolin-3 (4H)-yl)-N-(2-fluorophenyl)acetamide (325), 1-(3-acetylphenyl)-3-(2-(fluoro(piperidin-1-yl)methyl)-3-(2-methoxyethyl)-4-oxo-3,4-dihydroquinazolin-6-yl)urea (330), 1-(3-acetylphenyl)-3-(3-(2-methoxyethyl)-4-oxo-2-(piperidine-1-carbonyl)-3,4-dihydroquinazolin-6-yl)urea (330a), 1-(3-acetylphenyl)-3-(2-(fluoro(4-methylpiperazin-1-yl)methyl)-3-(2-methoxyethyl)-4-oxo-3,4-dihydroquinazolin-6-yl)urea (333), 1-(3-acetylphenyl)-3-(3-(2-methoxyethyl)-2-(4-methylpiperazine-1-carbonyl)-4-oxo-3,4-dihydroquinazolin-6-yl)urea (333 a), 1-(3-acetylphenyl)-3-(2-(fluoro(morpholino)methyl)-3-(2-methoxyethyl)-4-oxo-3,4-dihydroquinazolin-6-yl)urea (336), 1-(3-acetylphenyl)-3-(3-(2-methoxyethyl)-2-(morpholine-4-carbonyl)-4-oxo-3,4-dihydroquinazolin-6-yl)urea (336 a), 1-(3-acetylphenyl)-3-(3-morpholino-4-oxo-3,4-dihydroquinazolin-6-yl)urea (340), (Z)-1-(3-(1-(hydroxyimino)ethyl)phenyl)-3-(3-(2-methoxyethyl)-4-oxo-3,4-dihydroquinazolin-6-yl)urea (341), (Z)-1-(3-(1-(hydroxyimino)ethyl)phenyl)-3-(3-(2-methoxyethyl)-2-methyl-4-oxo-3,4-dihydroquinazolin-6-yl)urea (342), (Z)-1-(3-(1-(hydroxyimino)ethyl)phenyl)-3-(3-(2-methoxyethyl)-4-oxo-2-(piperidin-1-ylmethyl)-3,4-dihydroquinazolin-6-yl)urea (343), and 1-(3-acetylphenyl)-3-(5-bromo-3-(2-methoxyethyl)-2-methyl-4-oxo-3,4-dihydroquinazolin-6-yl)urea (345), Yet another embodiment of the present disclosure provides a process for the preparation of compounds having Structure I, wherein the steps comprising:

(i) reacting 2-amino-5-nitrobenzoic acid (compound 1) with an aliphatic or an aromatic amine selected from the group consisting of 2-methoxyethylamine, glycineethylester hydrochloride, 3-methoxypropylamine, 2-ethoxyethylamine, ethylamine 2M in THF, 4-(2-aminoethyl)morpholine, 3-(4-morpholinyl)propylamine, N,N-dimethylethylenediamine, 1-(2-aminoethyl)piperidine, 4-amino-1-methylpiperidine, N-methylethylenediamine, 2-amino-1-methoxybutane, 1-butylamine, 1-methoxy-2-propylamine, 2-aminoethyl isopropyl ether, cyclohexylamine, 4-aminomorpholine, m-anisidine, o-anisidine, 4-aminopyridine, 3-aminopyridine, and 2-aminopyridine in presence of HATU/DMF followed by TEA as a base at room temperature for 1-3 hours to obtain an amide compound selected from the group consisting of 2, 80, 86, 90, 95, 132, 136, 140, 144, 160, 164, 168, 172, 176, 180, 184, 337, 100, 128, 148, 152, and 156;

2

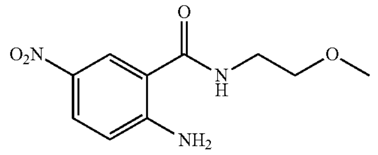

80

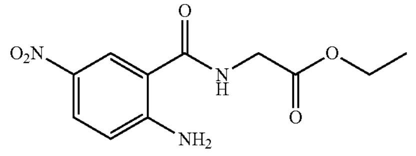

86

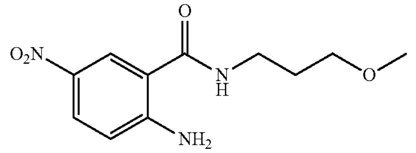

90

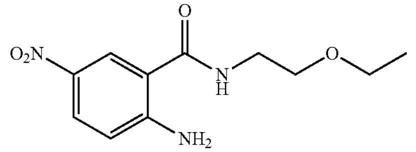

-continued
95
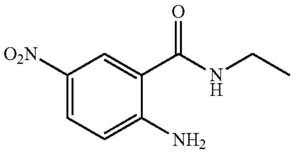
132
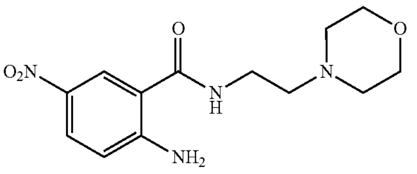
136
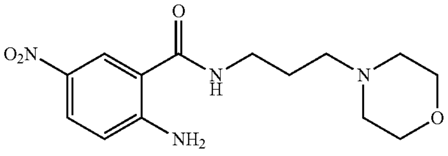
140
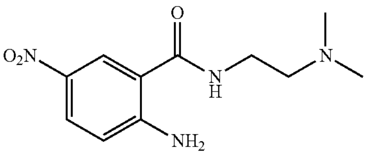
144
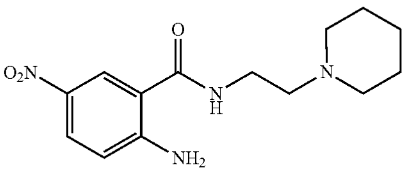
160
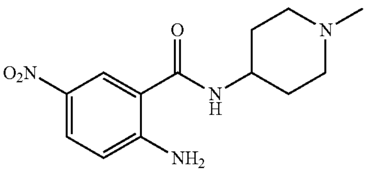
164
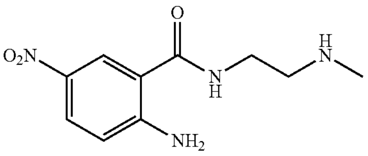
168
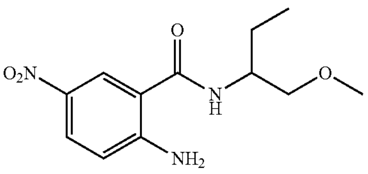
172
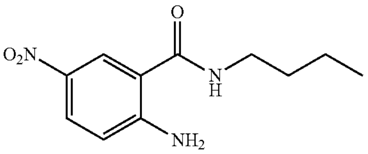
-continued
176
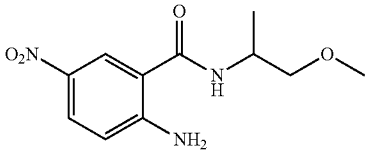
180
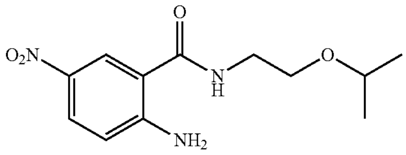
184
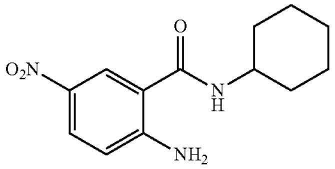
337
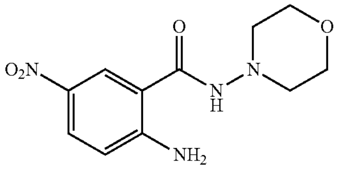
100
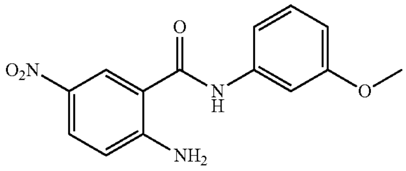
128
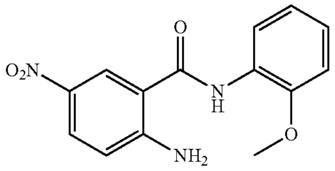
148
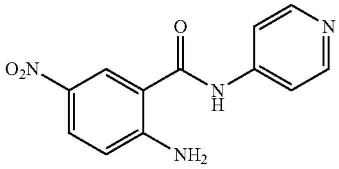
152
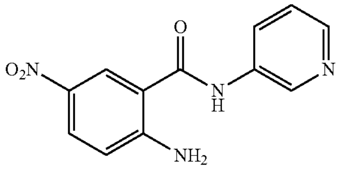
156
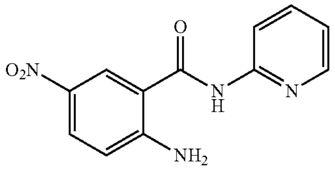

(ii) separately, reacting 2-amino-4-nitrobenzoic acid (compound 188) with 2-methoxyethylamine in presence of HATU/DMF followed by TEA as a base at room temperature for 1 hour to obtain a compound 189;

188

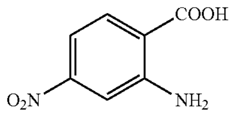

189

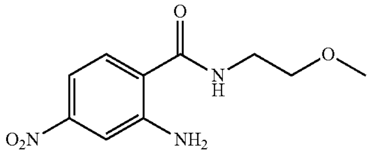

(iii) adding an acid chloride selected from the group consisting of acetyl chloride, isopropyl chloride, 4-fluorobenzoyl chloride, 4-methoxybenzoyl chloride, cyclohexanecarbonyl chloride, cyclopentanecarbonyl chloride, 4-(trifluoromethyl)benzoyl chloride, 3-Bromo-4-methoxybenzoyl chloride, Picolinoyl chloride, Nicotinoyl chloride, Isonicotinoyl chloride, Pyrazinecarbonyl chloride, 1-methyl-1H-pyrazole-4-carbonyl chloride, and 2-chloroacetyl chloride to compound 2 obtained in step (i) in DCM at a temperature range from 0° C. to room temperature for 1-8 hours to obtain a compound selected from the group consisting of 104, 108, 112, 116, 120,124, 200, 204, 208, 212, 216, 220, 224, and 228;

104

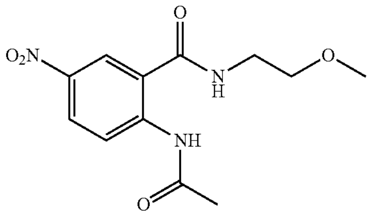

108

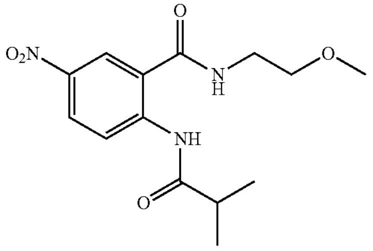

112

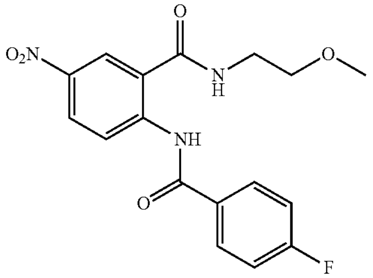

-continued

116

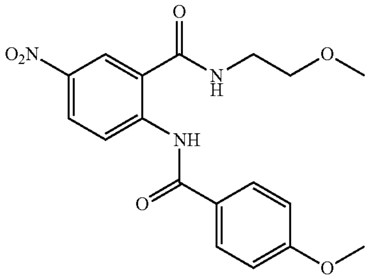

120

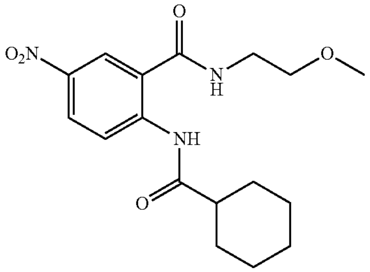

124

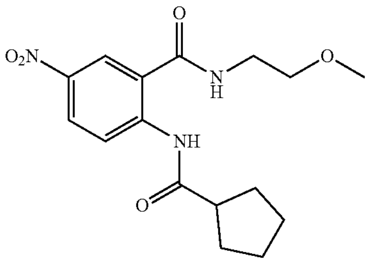

200

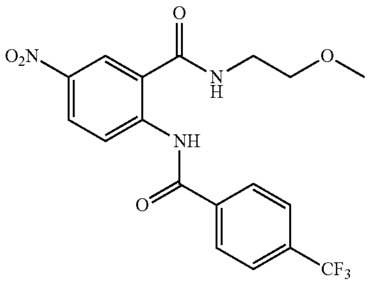

204

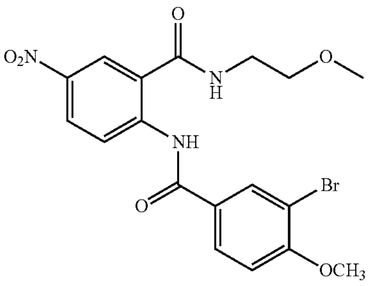

-continued

208

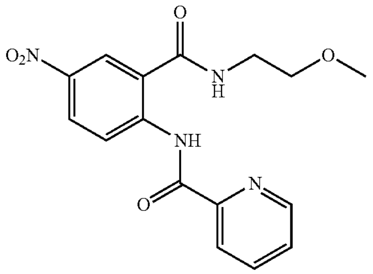

212

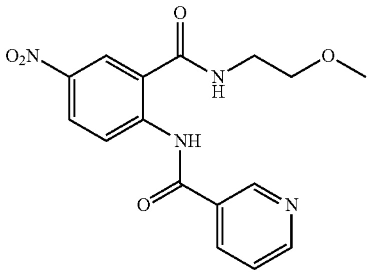

216

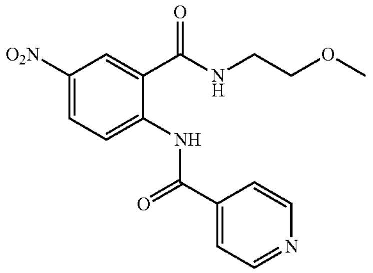

220

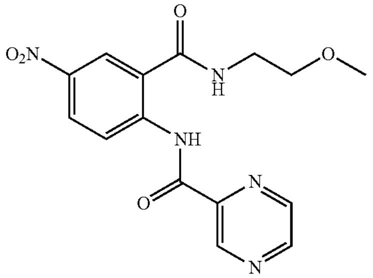

224

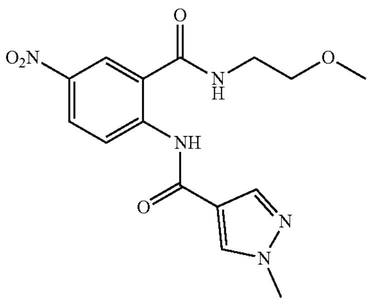

-continued

228

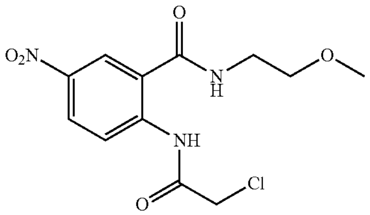

(iv) acetylating a compound selected from the group consisting of 168, and 176 obtained in step (i) using acetyl chloride and triethylamine (TEA) as a base in DCM at a temperature range of 0° C. to room temperature for 8 hours to obtain a compound selected from the group consisting of 278 and 282;

168

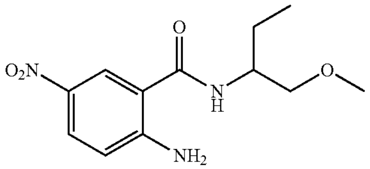

176

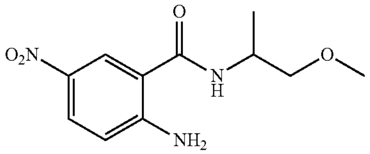

278

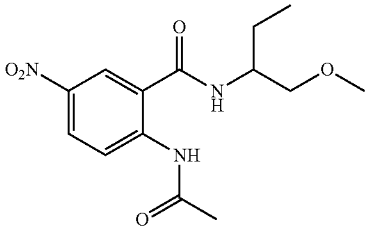

282

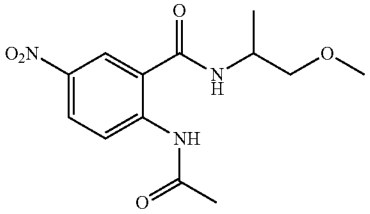

(v) alternately, adding cyclohexanecarbonyl chloride to compound 176 obtained in step (i) to obtain a compound 286;

286

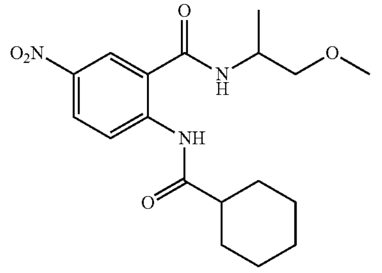

(vi) alternately, adding tert-butyl 4-(chlorocarbonyl)piperidine-1-carboxylate to compound 2 obtained in step (i) to obtain a compound 296;

296

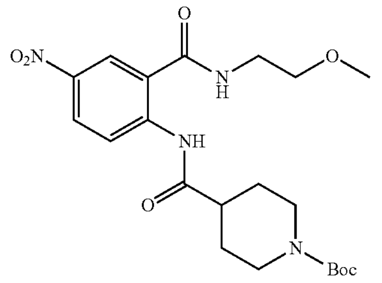

(vii) alternately, treating compound 2 obtained in step (i) with 2-chloro-2-fluoroacetic acid or 2-chloro-2-difluoroacetic acid along with $POCl_3$ in pyridine solvent to obtain a compound selected from the group consisting of 326 and 326a;

326

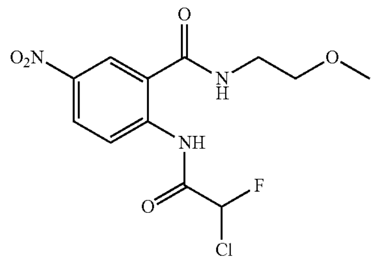

326a

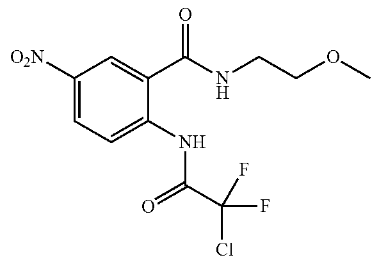

(viii) cyclizing the compound selected from the group consisting of 2, 80, 86, 90, 95, 100, 128, 132, 136, 140, 144, 148, 152, 156, 160, 164, 168, 172, 176, 180, 184, 189, and 337 obtained in step (i) and (ii) using a cyclizing agent selected from trimethylorthoformate or triethylorthoformate at 100° C. for 12-16 hours to obtain a compound selected from the group consisting of 3, 81, 87, 91, 96, 101, 129, 133, 137, 141, 145, 149, 153, 157, 161, 165, 169, 173, 177, 181, 185, 190 and 338;

3

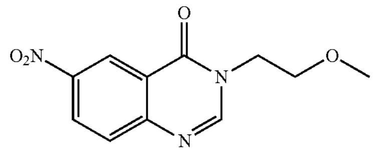

81

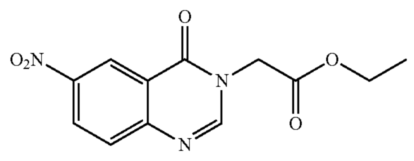

87

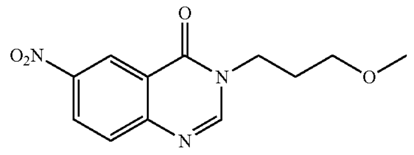

91

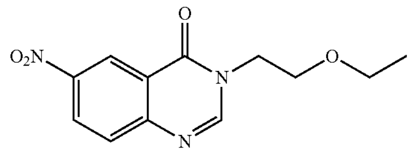

96

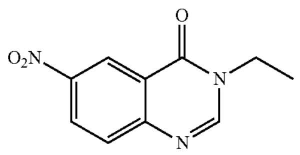

101

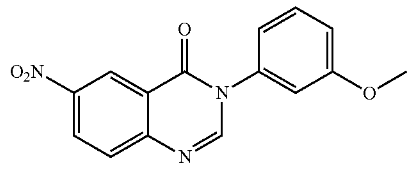

129

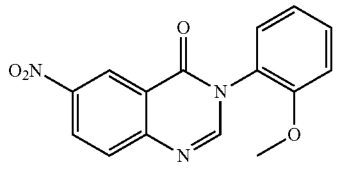

133

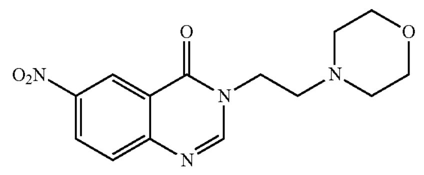

-continued
137
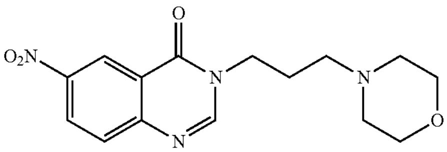
141
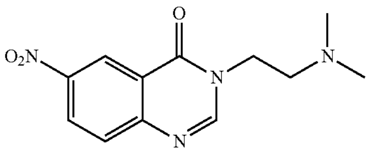
145
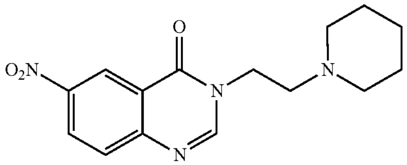
149
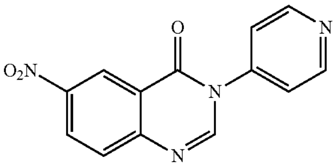
153
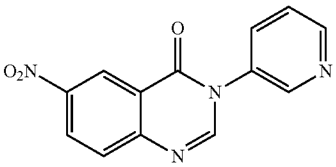
157
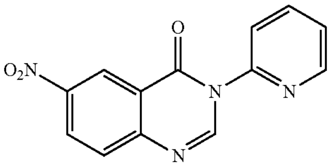
161
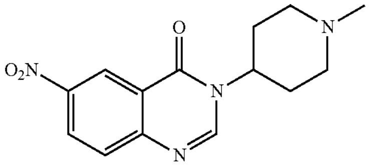
165
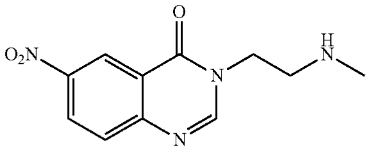
169
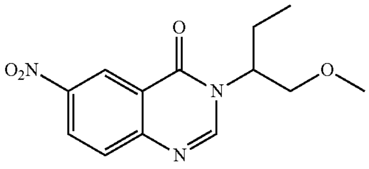
-continued
173
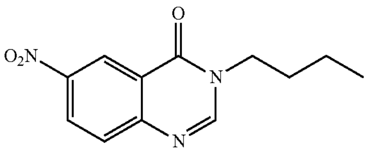
177
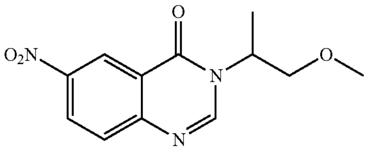
181
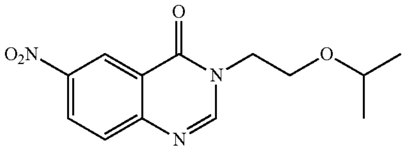
185
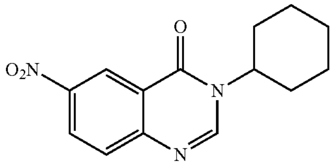
190
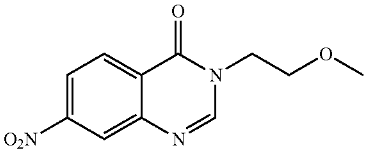
338
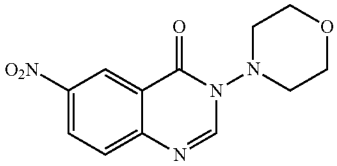
(ix) cyclizing the compound selected from the group consisting of 104, 108, 112, 116, 120, 124, 200, 204, 208, 212, 216, 220, 224, 228, 278, 282, 286, 296, 326, and 326a obtained in step (iii), (iv), (v), (vi) and (vii) using a cyclizing agent $ZnCl_2$ and hexamethyldisilazane (HMDS) in DMF at 100° C. for 12-16 hours to obtain a compound selected from the group consisting of 105, 109, 113, 117, 121, 125, 201, 205, 209, 213, 217, 221, 225, 229, 279, 283, 287, 297, 327 and 327a;
105
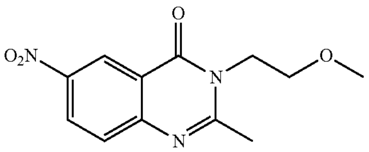

-continued
109
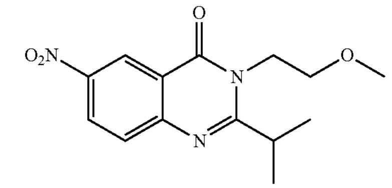
113
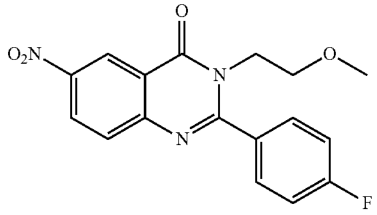
117
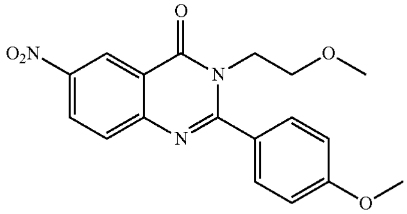
121
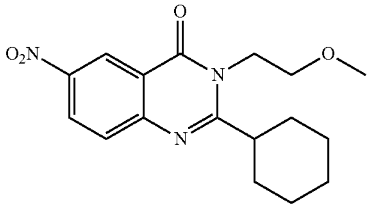
125
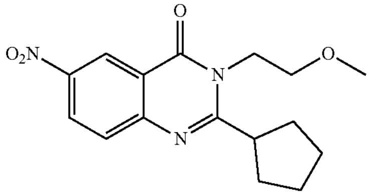
201
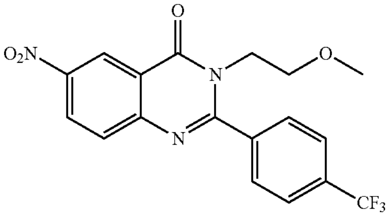
205
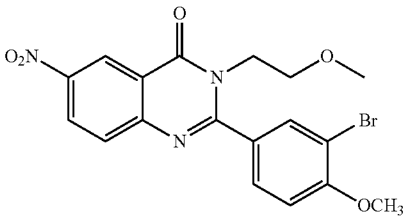
-continued
209
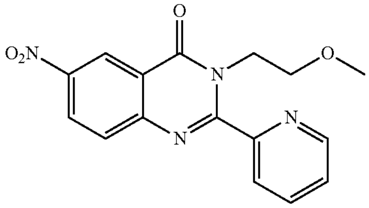
213
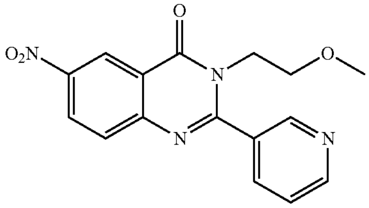
217
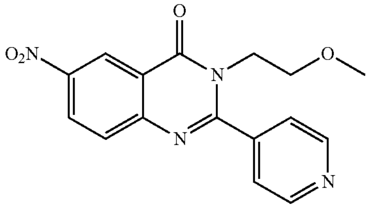
221
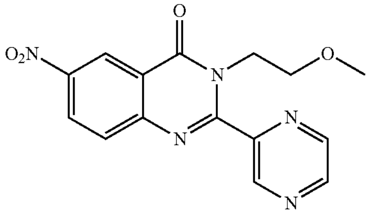
225
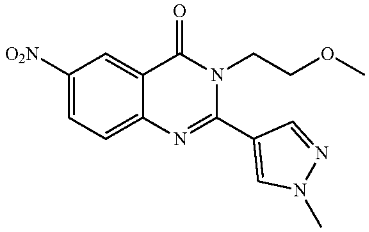
229
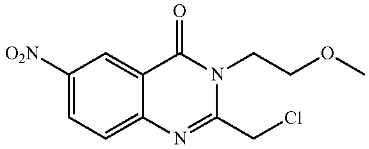
279
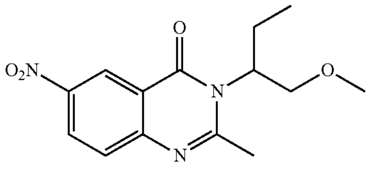
283
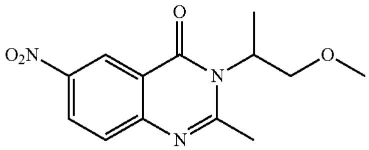

-continued

287

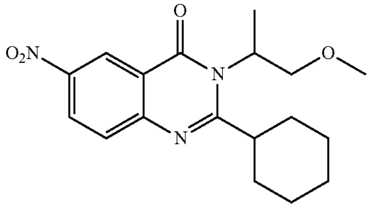

297

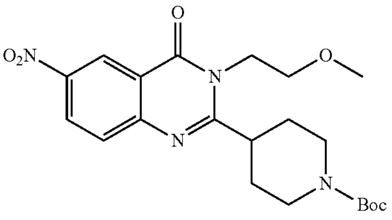

327

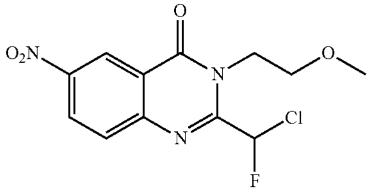

327a

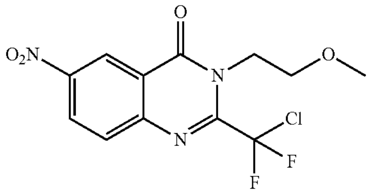

(x) reacting the compound 81 obtained in step (viii) with an amine selected from the group consisting of ethyl amine, diethylamine, 2-fluroaniline, o-anisidine, 2-bromoaniline, 2-(trifluoromethoxy)aniline, 2-(trifluoromethyl)aniline, p-anisidine, 4-fluoroaniline, 1-(2-aminoethyl)-4-methylpiperizine, and 1H-Imidazole-1-ethanamine in presence of anhydrous $AlCl_3$ in toluene at a temperature range from room temperature to 110° C. to obtain a compound selected from the group consisting of 245, 248, 251, 254, 257, 260, 263, 266, 269, 272 and 275;

245

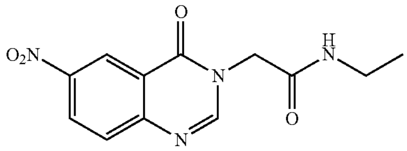

248

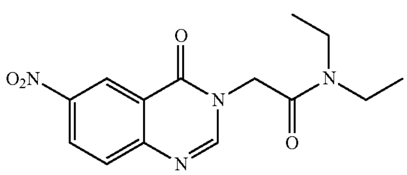

-continued

251

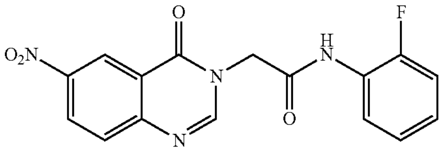

254

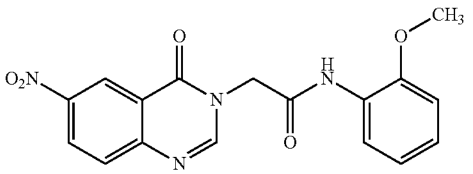

257

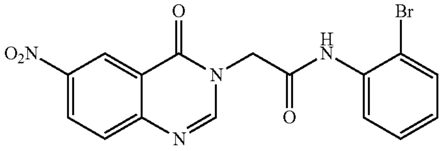

260

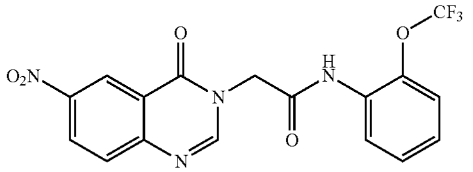

263

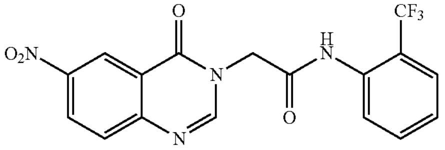

266

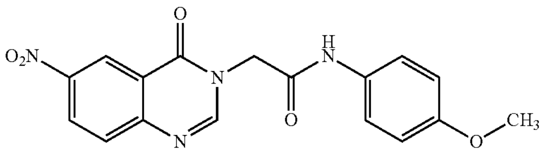

269

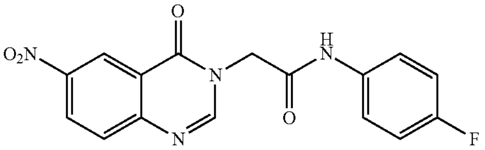

272

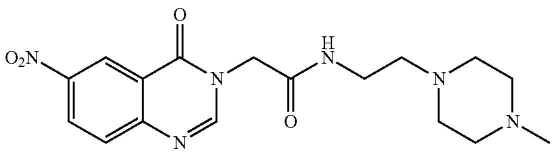

275

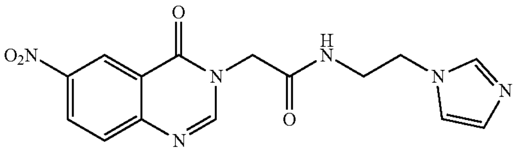

(xi) reacting the compound 229 obtained in step (ix) with an amine selected from the group consisting of pyrrolidine, dimethylamine, piperidine, morpholine, and 1-methylpiperazine in toluene at 100° C. for 2 hours to obtain a compound selected from the group consisting of 230, 233, 236, 239, and 242;

230

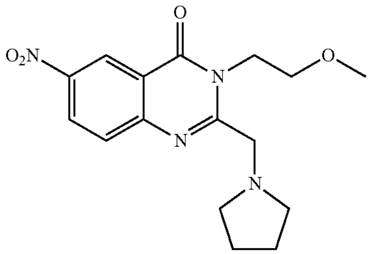

233

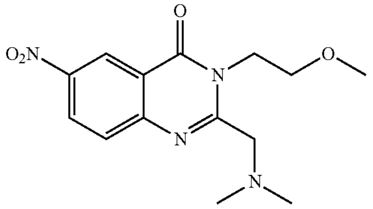

236

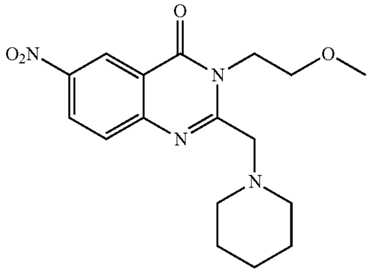

239

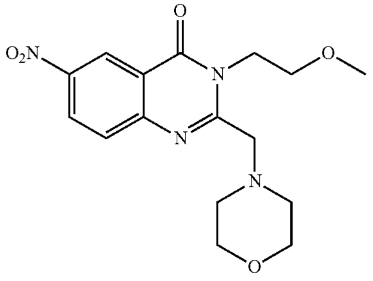

242

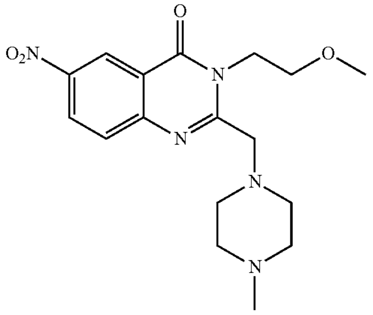

(xii) reacting the compound 327 obtained in step (ix) with an amine selected from the group consisting of piperidine, 1-methylpiperazine, and morpholine in presence of toluene to obtain a compound selected from the group consisting of 328, 331, and 334;

328

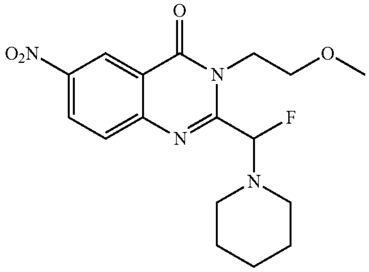

331

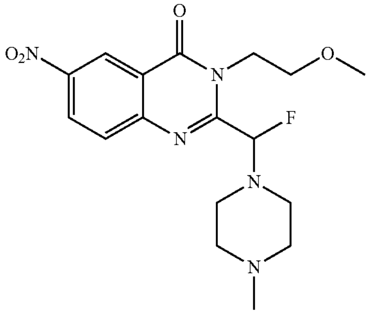

334

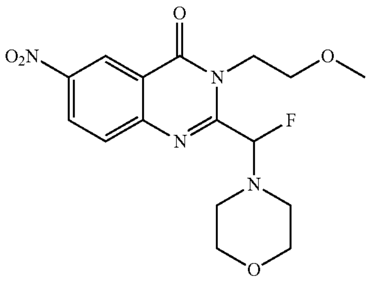

(xiii) reacting the compound 327a obtained in step (ix) with an amine selected from the group consisting of piperidine, 1-methylpiperazine, and morpholine in presence of a solvent selected from the group consisting of toluene, DMF, and THF in absence or presence of a base seleted from $K_2CO_3$, or N,N-diethylaniline to obtain a compound seleted from the group consisting of 328a, 331a, and 334a;

328a

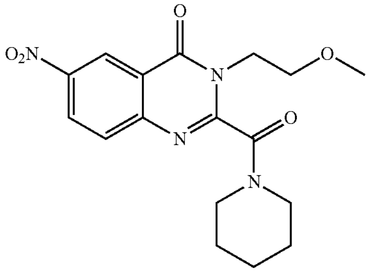

-continued

331a

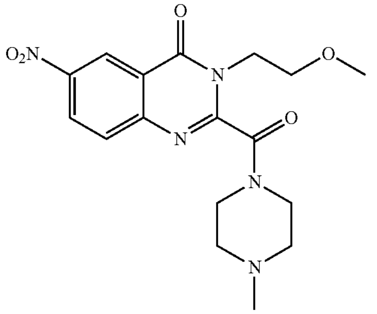

334a

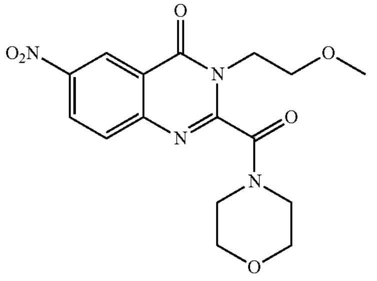

(xiv) separately reacting the compound 297 obtained in step (ix) with trifluoroacetic acid (TFA) in DCM at a temperature range of 0° C. to room temperature for 2 hours to obtain a compound 301;

301

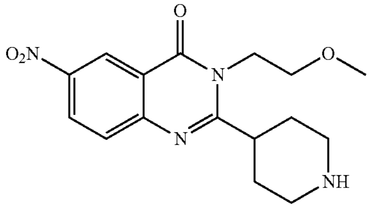

(xv) reacting the compound 301 obtained in step (xiv) with sodium hydride (NaH) in DMF at a temperature range of 0° C. to room temperature for 3 hours with methyl iodide and 2-chloropropane, respectively to obtain a compound selected from the group consisting of 302 and 305;

302

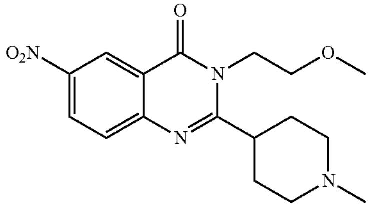

-continued

305

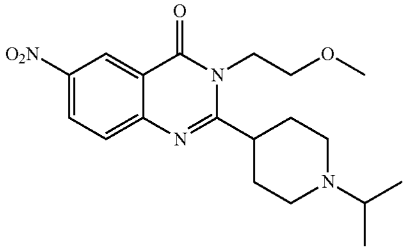

(xvi) reducing the compound selected from the group consisting of 3, 81, 87, 91, 96, 101, 105, 109, 113, 117, 121, 125, 129, 133, 137, 141, 145, 149, 153, 157, 161, 165, 169, 173, 177, 181, 185, 190, 201, 209, 213, 217, 221, 225, 230, 233, 236, 239, 242, 245, 248, 251, 254, 260, 263, 266, 269, 272, 275, 279, 283, 287, 297, 302, 305, 328, 328a, 331, 331a, 334, 334a and 338 obtained in steps (viii), (ix), (x), (xi), (xii), (xiii) and (xv) using Palladium-Charcoal (5% or 10% wet) at room temperature for 3-5 hours in presence of $H_2$ to obtain an amine compound selected from the group consisting of 4, 82, 88, 92, 97, 102, 106, 110, 114, 118, 122, 126, 130, 134, 138, 142, 146, 150, 154, 158, 162, 166, 170, 174, 178, 182, 186, 191, 202, 210, 214, 218, 222, 226, 231, 234, 237, 240, 243, 246, 249, 252, 255, 261, 264, 267, 270, 273, 276, 280, 284, 288, 298, 303, 306, 329, 329a, 332, 332a, 335, 335a, and 339;

4

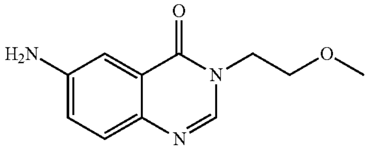

82

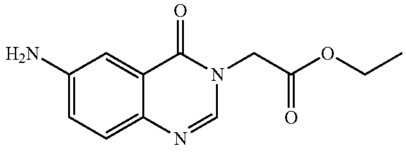

88

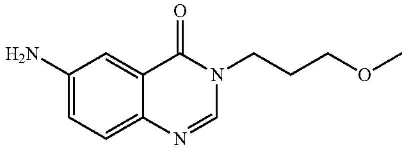

92

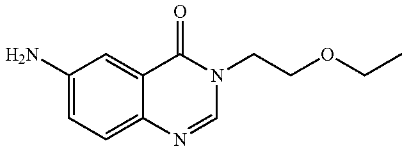

97

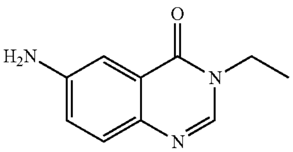

-continued
102
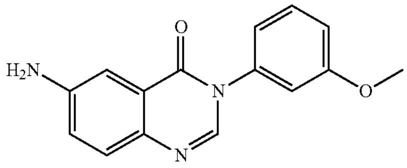
106
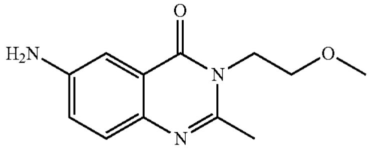
110
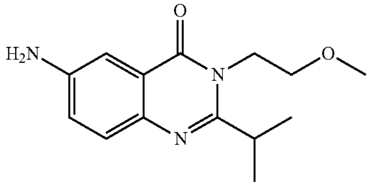
114
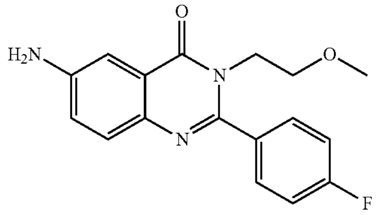
118
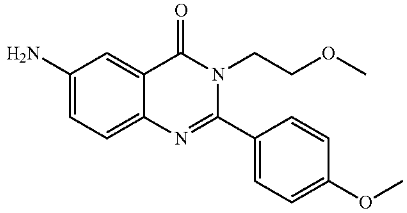
122
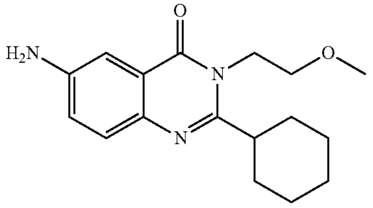
126
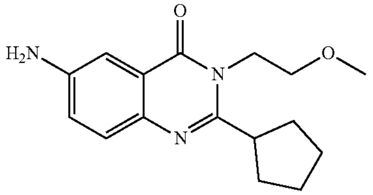
130
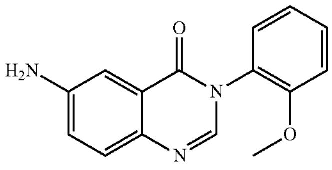
-continued
134
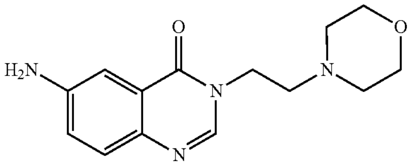
138
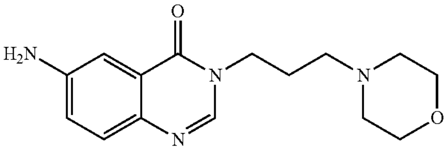
142
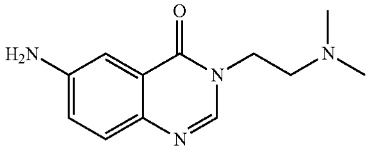
146
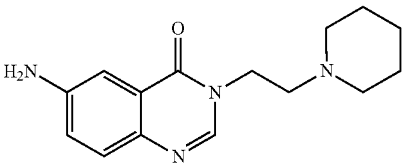
150
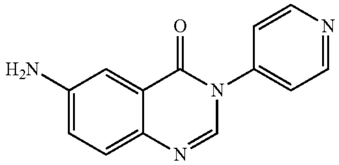
154
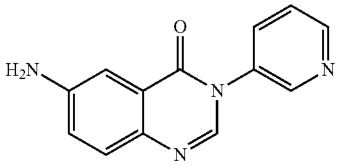
158
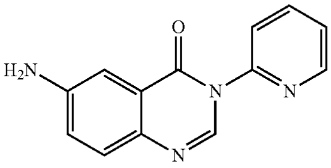
162
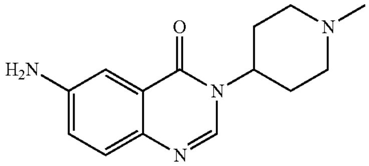
166
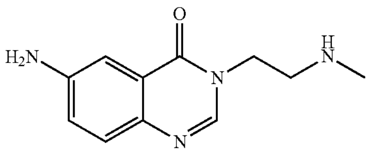

-continued
170
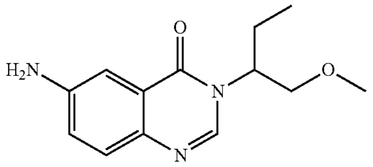
174
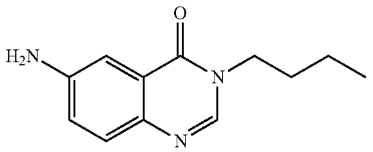
178
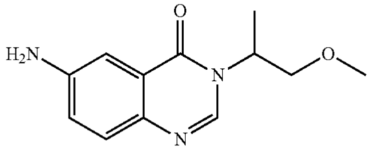
182
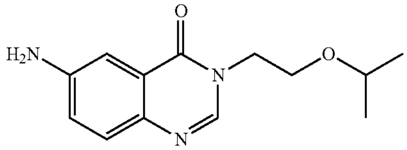
186
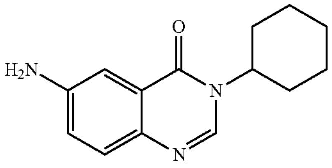
191
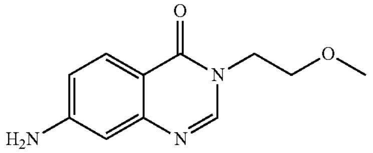
202
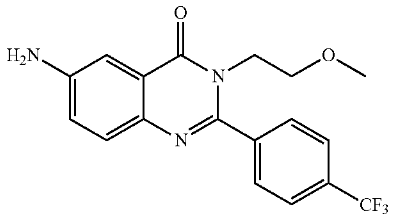
210
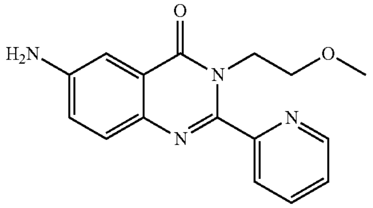
-continued
214
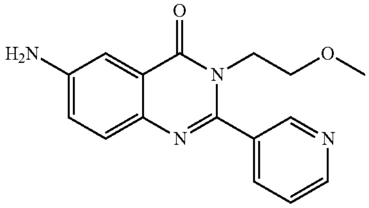
218
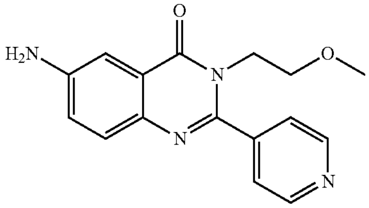
222
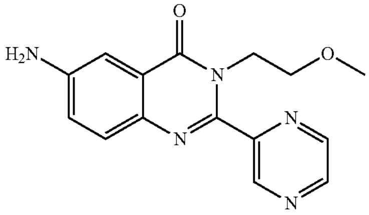
226
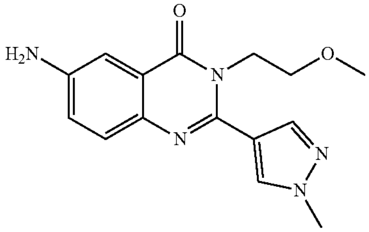
231
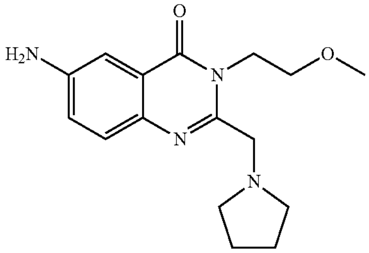
234
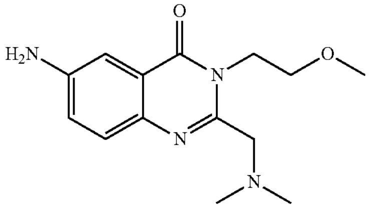

-continued
237
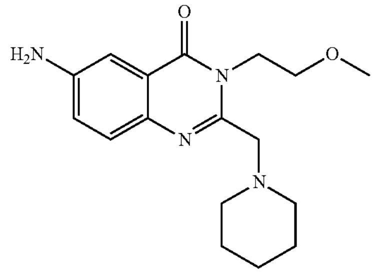
240
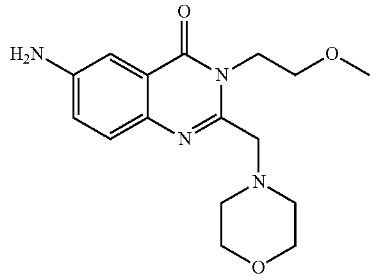
243
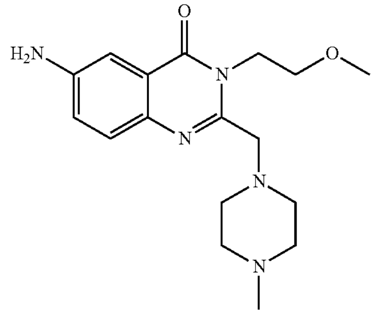
246
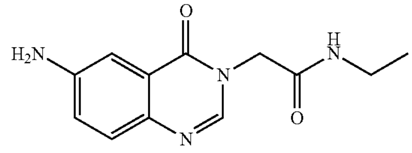
249
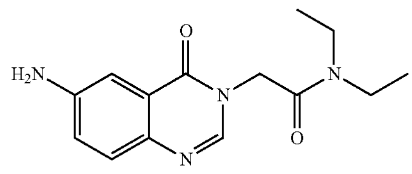
252
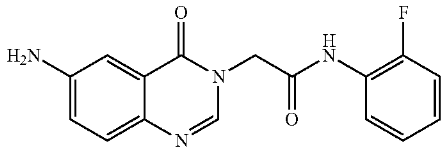
255
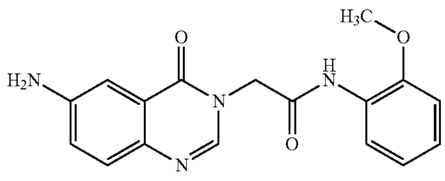
-continued
261
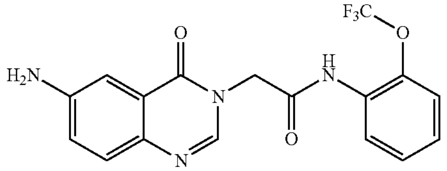
264
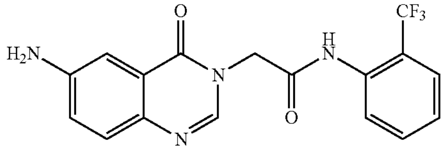
267
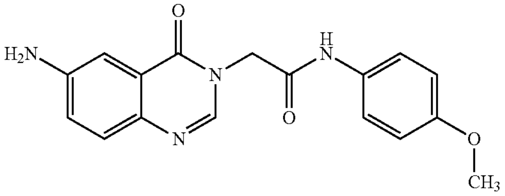
270
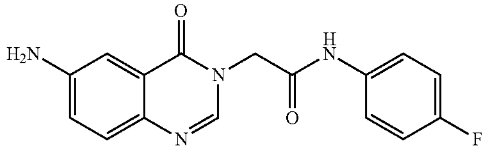
273
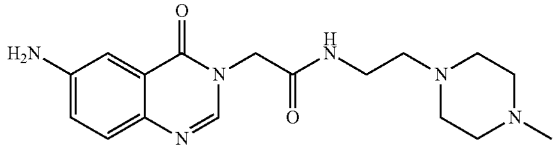
276
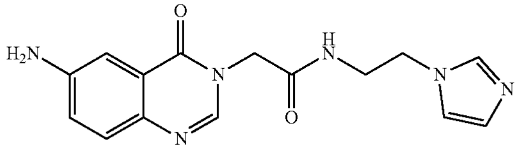
280
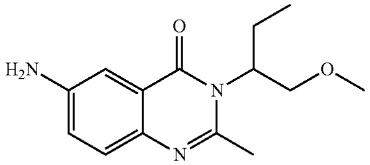
284
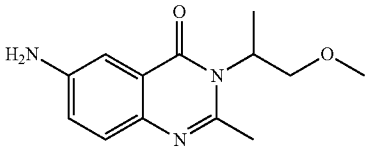
288
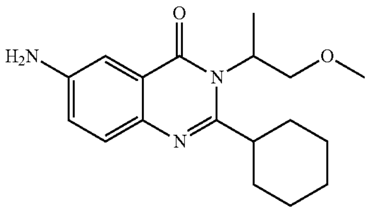

-continued
298
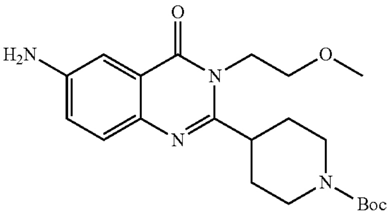
303
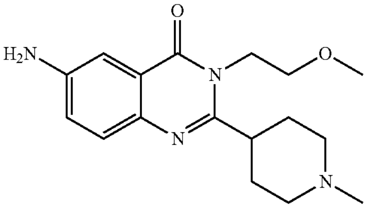
306
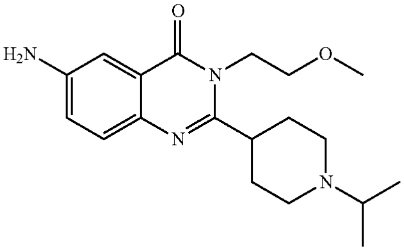
329
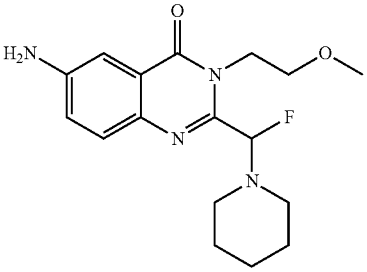
329a
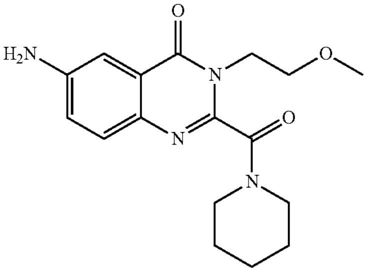
332
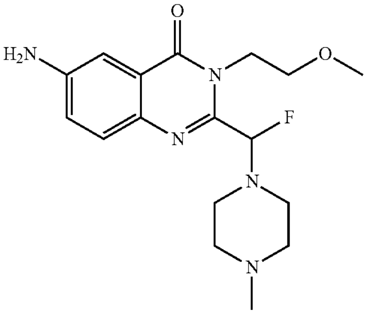
-continued
332a
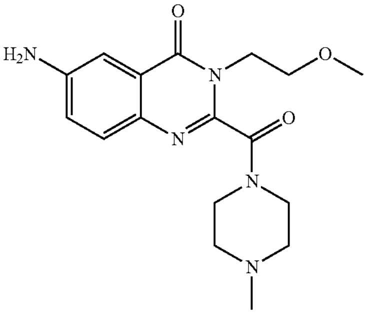
335
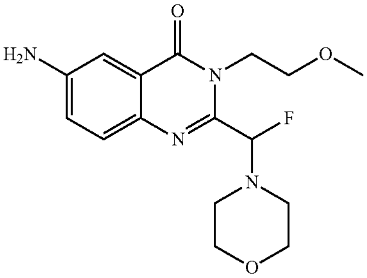
335a
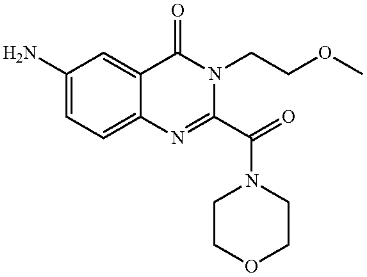
339
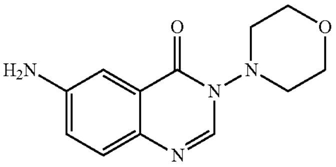
(xvii) reducing the compound selected from 205 or, 257 obtained in step (ix) and (x) using $SnCl_2 \cdot 2H_2O$ to obtain the compound selected from 206 or 258;
206
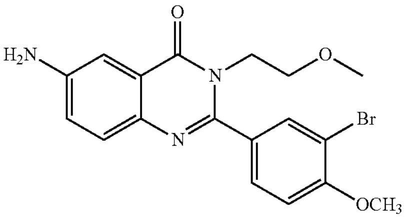
258
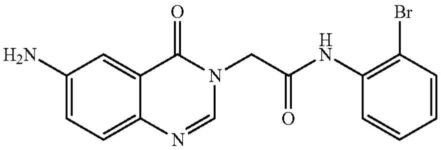

(xviii) brominating the compound selected from the group consisting of 4, 106, 122, and 178 obtained in step (xvi) diluted in dichloromethane or chloroform solution by carrying out reaction in acetic acid medium followed by dropwise addition of liquid bromine on the compound at room temperature for 3-4 hours to obtain a compound selected from the group consisting of 43, 344, 290, and 293;

43

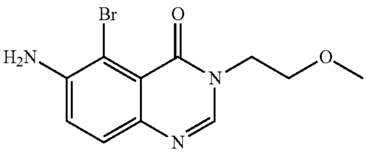

344

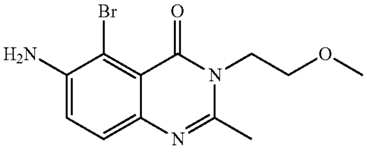

290

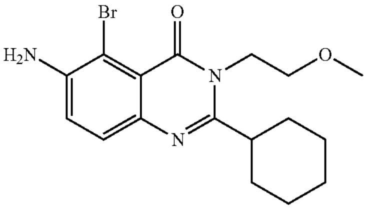

293

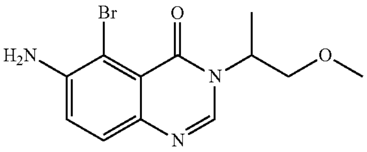

(xix) carrying out Suzuki reaction on a compound selected from the group consisting of 43, 290, and 293 obtained in step (xviii) by $Pd_2(dba)_3$ or $Pd(PPh_3)_4$ in presence of $Cs_2CO_3$ or 2M $Na_2CO_3$ solution in dioxane and X-Phos as a ligand at 100° C. over a period of 10-12 hours along with a boronic acid selected from the group consisting of benzeneboronic acid, 4-fluorobenzeneboronic acid, pyridine-2-boronic acid, pyridine-3-boronic acid, pyridine-4-boronic acid, 6-methoxypyridine-3-boronic acid, 2-methoxypyridine-3-boronic acid, (1-(tert-butoxycarbonyl)-1,2,3,6-tetrahydropyridin-4-yl)boronic acid, 4-methoxybenzeneboronic acid, 4-trifluoromethylbenzeneboronic acid, cyclohexylboronic acid, cyclopentyl boronic acid, and isopropylboronic acid to obtain a compound selected from the group consisting of 44, 46, 48, 50, 52, 54, 56, 58, 63, 65, 67, 69, 71, 291, and 294 which is treated with 4-nitrophenylchloroformate in presence of TEA as a base followed by reaction with 3-aminoacetophenone in dry THF at room temperature for 5-8 hours to obtain the compound having Structure I selected from the group consisting of 45, 47, 49, 51, 53, 55, 57, 59, 64, 66, 68, 70, 72, 292, and 295;

44

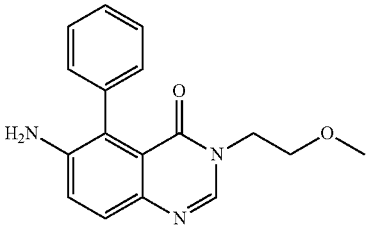

45

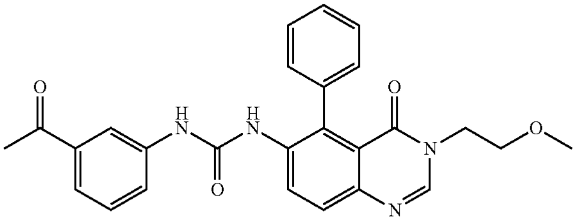

46

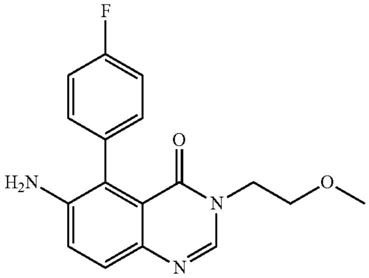

47

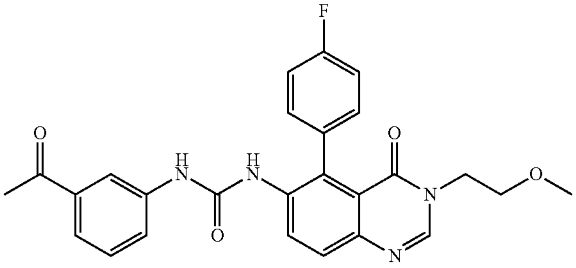

48

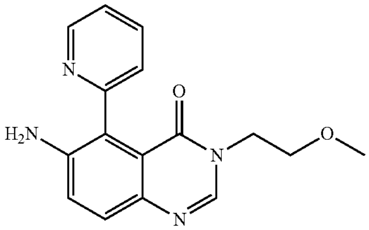

49

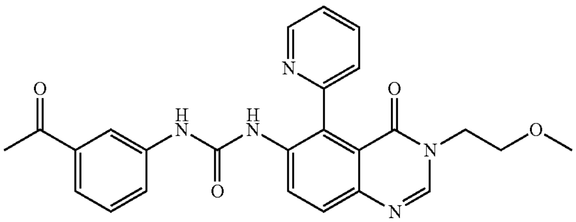

-continued
50
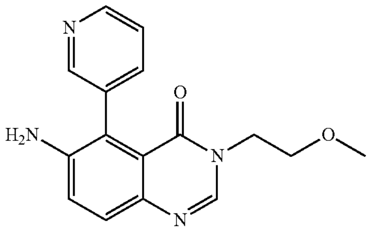
51
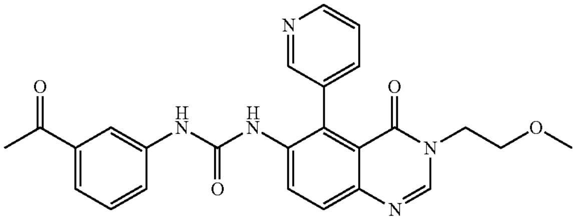
52
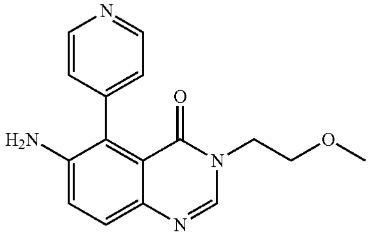
53
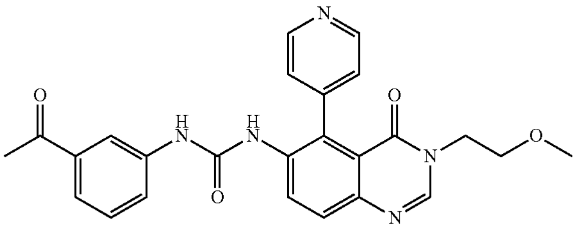
54
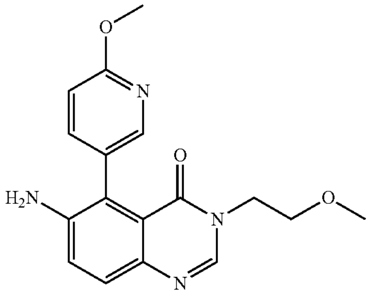
55
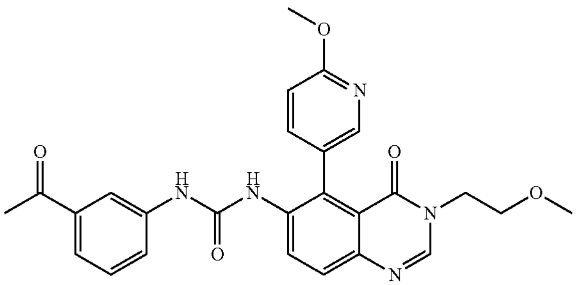
-continued
56
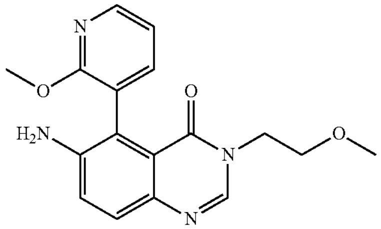
57
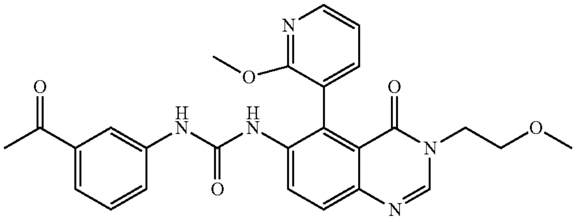
58
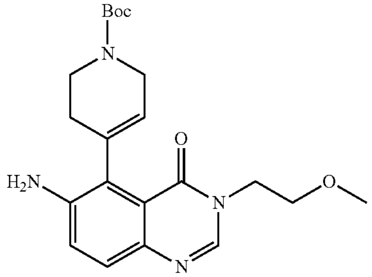
59
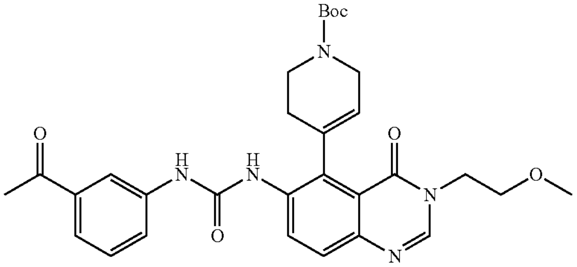
63
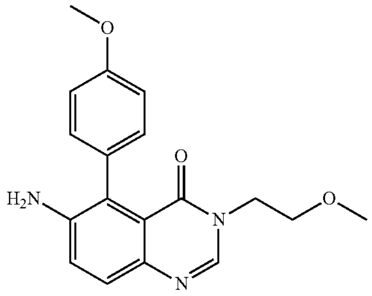

-continued
64
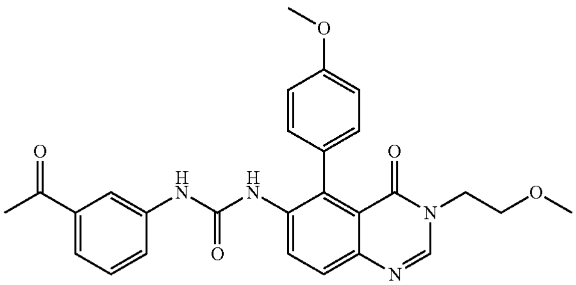
65
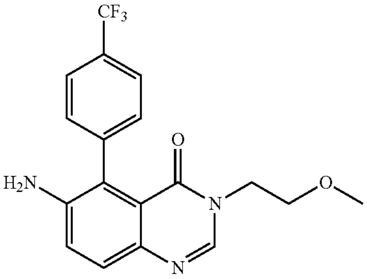
66
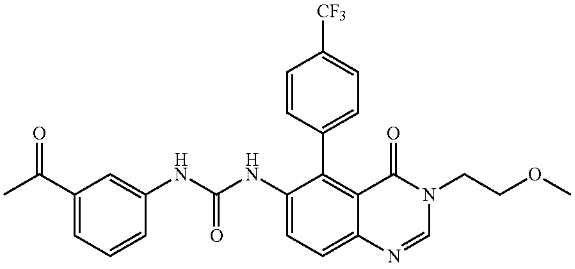
67
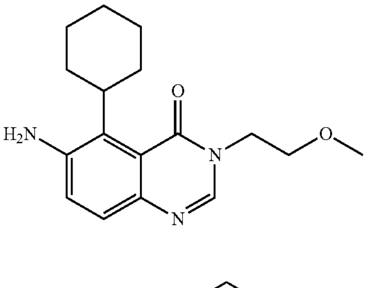
68
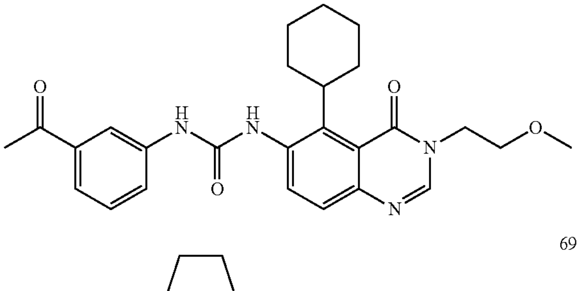
69
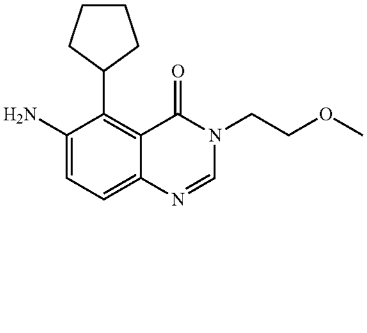
-continued
70
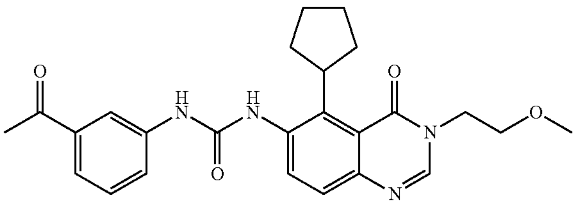
71
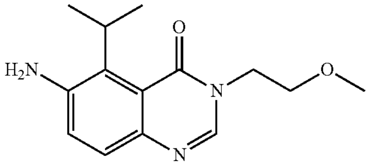
72
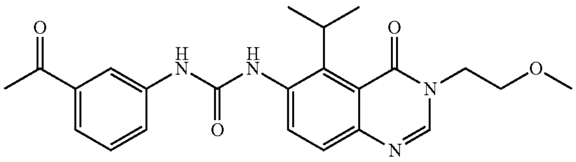
291
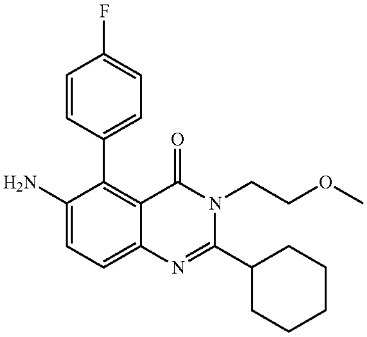
292
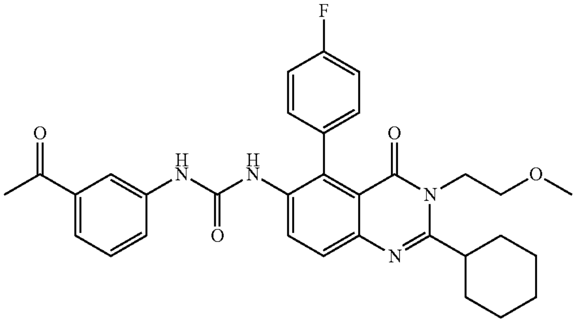
294
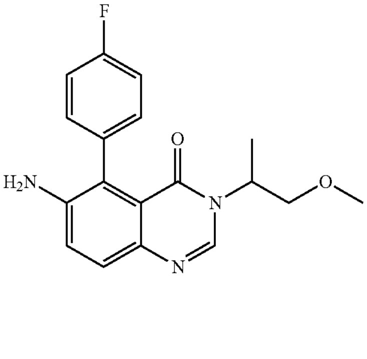

-continued

295

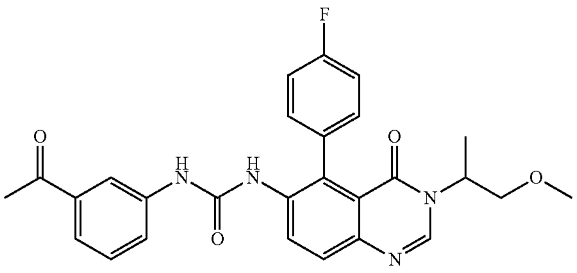

(xx) alternately, treating compound 4 obtained in step (xvi) with 4-nitrophenylchloroformate in presence of TEA as a base followed by reaction with an amine selected from the group consisting of aniline, m-anisidine, N1-methylbenzene-1,3-diamine, m-nitroaniline, 3-aminoacetophenone, 4-aminoacetophenone, 1-(3-aminophenyl)ethanol, methyl 3-amino-4-methoxybenzoate, 3-ethylaniline, 3'-aminobenzophenone, 3-amino-N-cyclohexylbenzamide, methyl 2-(3-aminobenzamido)-3-methylbutanoate, 3-amino-N,N-dimethylbenzamide, (3-aminophenyl)(pyrrolidin-1-yl) methanone, (3-aminophenyl)(pyrrolidin-1-yl) methanone, (4-aminophenyl)(pyrrolidin-1-yl) methanone, 3-(benzo[d]oxazol-2-yl)aniline, N-(3-aminophenyl)acetamide, N-(3-aminophenyl)-N-methylacetamide, N-(3-aminophenyl)-N-benzylacetamide, N-(3-aminobenzyl)acetamide, N-(3-aminobenzyl)-N-methylacetamide, dimethylamine, piperdine, 4-amino-1-methylpiperdine, 4-benzylpiperidine, 1-benzylpiperidin-4-amine, 1-(3-amino-4-hydroxyphenyl)ethanone, 1-(3-amino-5-chloro-2-hydroxyphenyl)ethanone, 1-(3-amino-2-hydroxy-5-methylphenyl)ethanone, 1-(3-aminophenyl)-2,2,2-trifluoroethanol in dry THF at room temperature for 3-8 hours to obtain the compound having Structure I selected from the group consisting of 5, 6, 7, 8, 9, 10, 11, 12, 13, 14, 15, 16, 17, 18, 19, 20, 21, 22, 23, 24, 25, 26, 27, 28, 29, 30, 31, 32, 33, and 34;

5

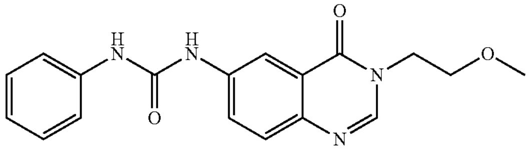

6

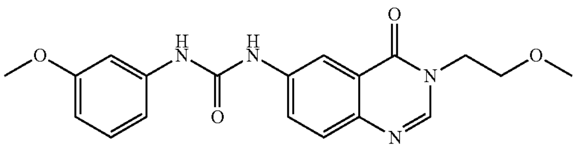

7

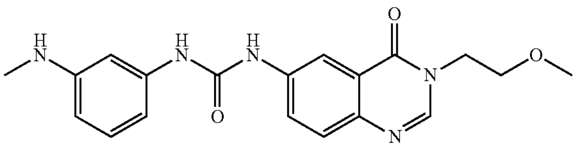

-continued

8

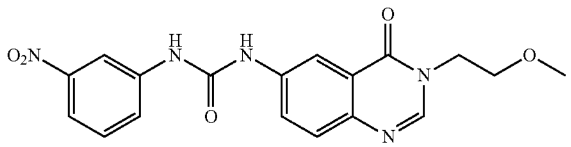

9

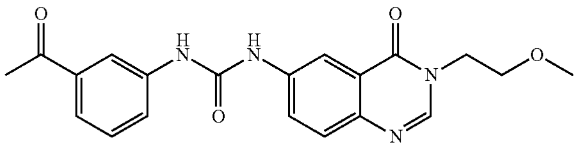

10

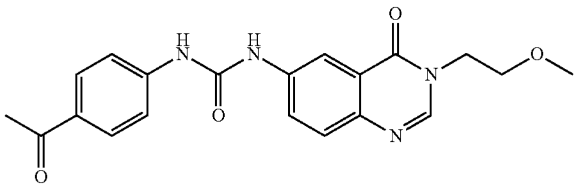

11

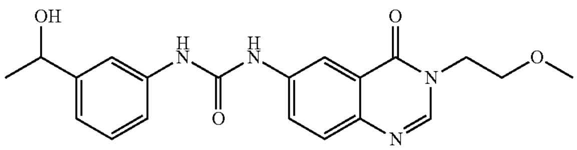

12

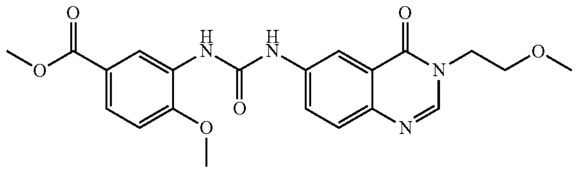

13

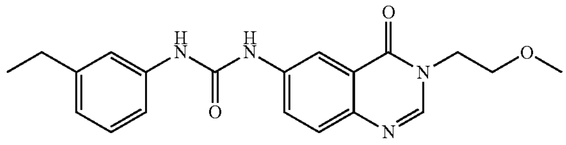

14

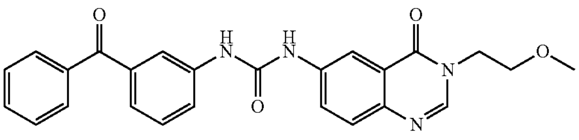

15

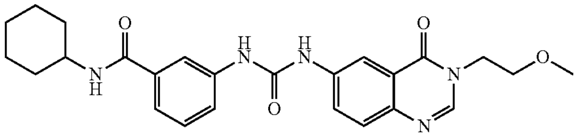

16

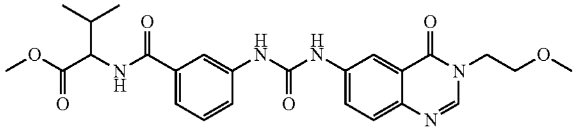

-continued
17
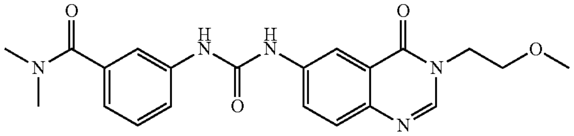
18
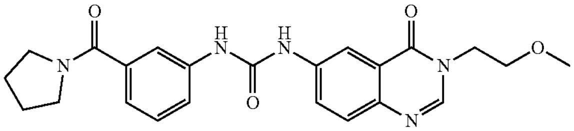
19
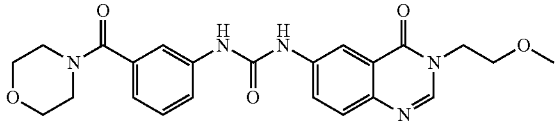
20
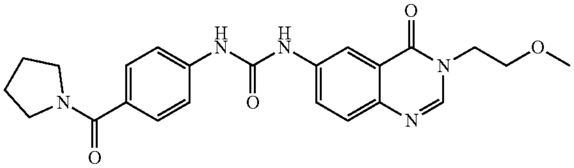
21
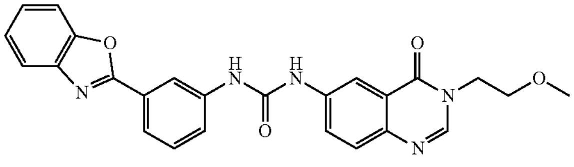
22
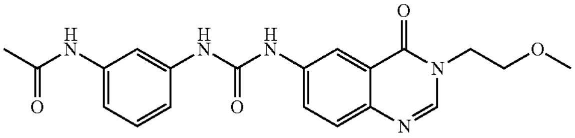
23
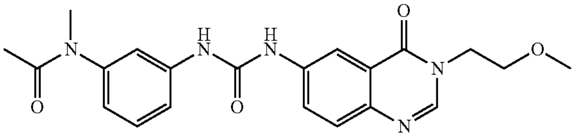
24
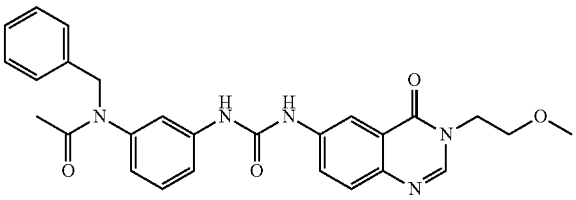
25
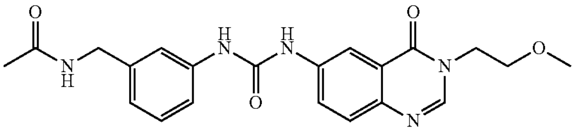
-continued
26
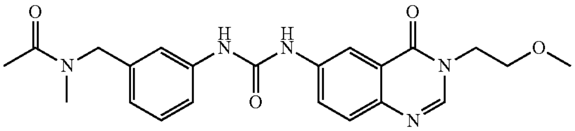
27
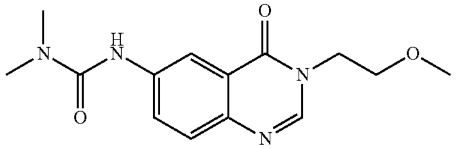
28
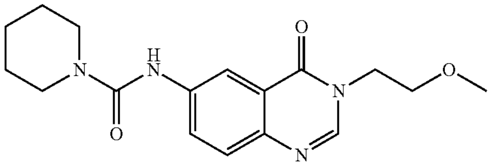
29
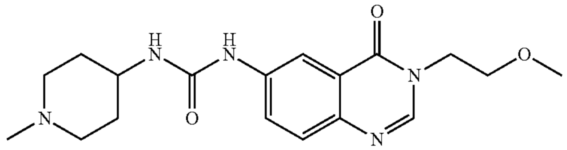
30
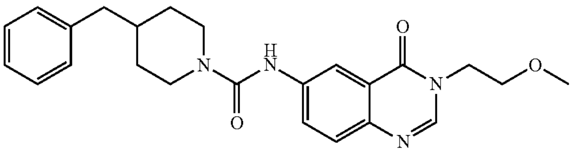
31
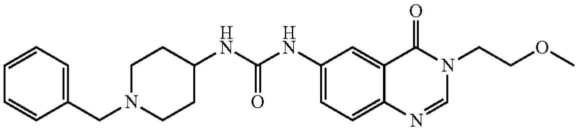
32
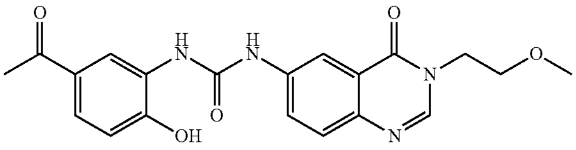
33
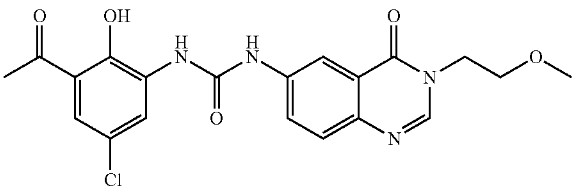

-continued

34

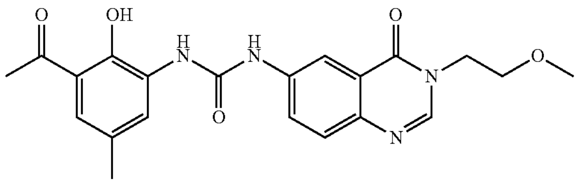

(xxi) alternately, treating the compound selected from the group consisting of 43, 88, 106, 110, 114, 118, 122, 126, 130, 138, 150, 154, 158, 162, 166, 170, 174, 178, 182, 186, 191, 202, 206, 210, 214, 218, 222, 226, 231, 234, 237, 240, 243, 246, 249, 252, 255, 258, 261, 264, 267, 270, 273, 276, 280, 284, 288, 298, 303, 306, 329, 329a, 332, 332a, 335, 335a, 339, and 344 obtained in step (xvi), (xvii) and (xviii) with 4-nitrophenylchloroformate in presence of TEA as a base followed by reaction with 3-aminoacetophenone in dry THF at room temperature for 3-8 hours to obtain the compound having Structure I selected from the group consisting of 73, 89, 107, 111, 115, 119, 123, 127, 131, 139, 151, 155, 159, 163, 167, 171, 175, 179, 183, 187, 192, 193, 194, 195, 196, 197, 198, 199, 203, 207, 211, 215, 219, 223, 227, 232, 235, 238, 241, 244, 247, 253, 256, 259, 262, 268, 274, 277, 281, 285, 289, 304, 307, 330, 330a, 333, 333a, 336, 336a, 340, and 345;

73

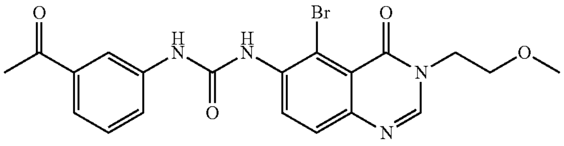

89

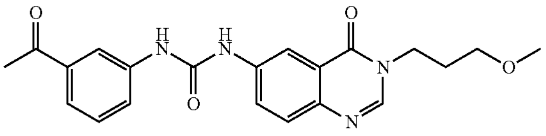

107

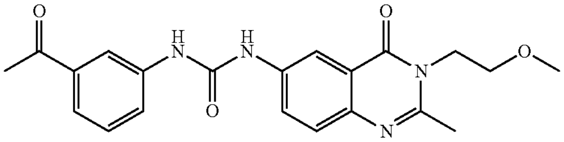

111

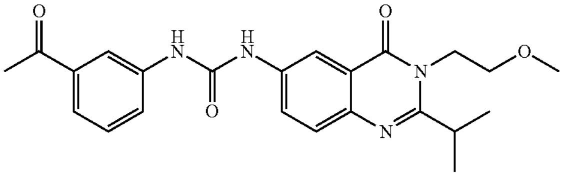

115

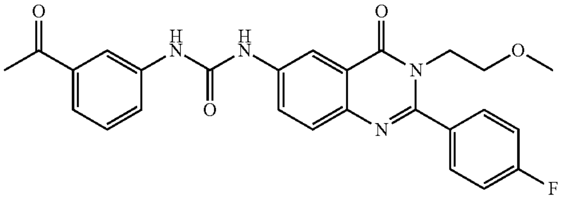

119

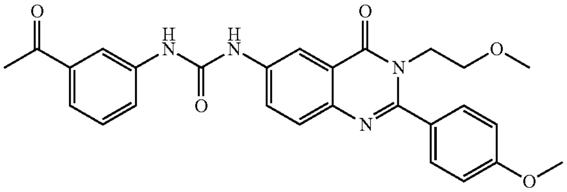

123

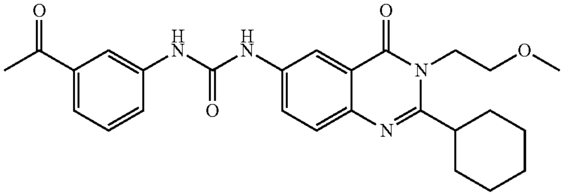

127

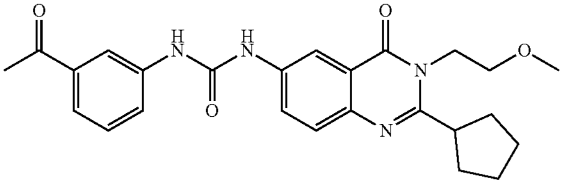

131

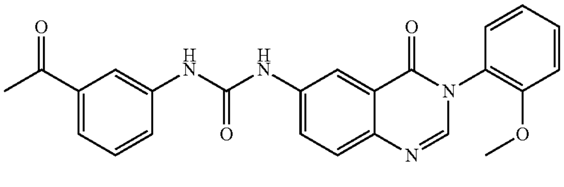

139

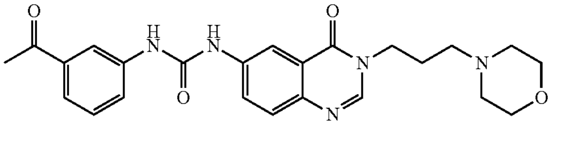

151

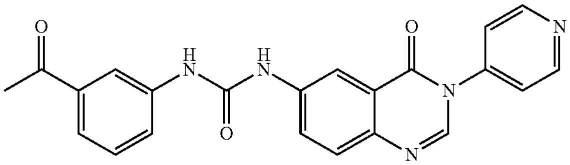

155

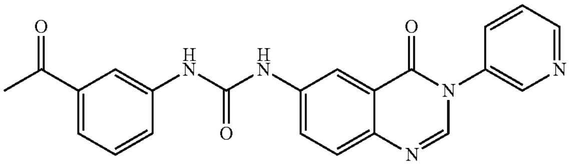

-continued
159
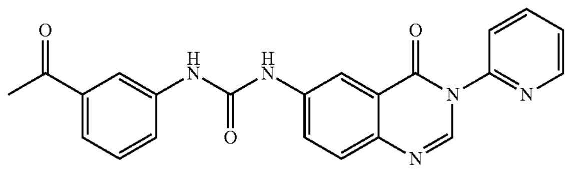
167
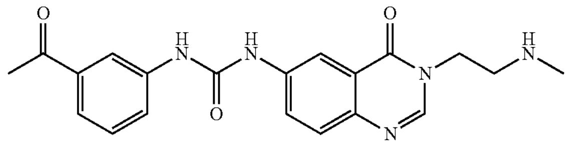
175
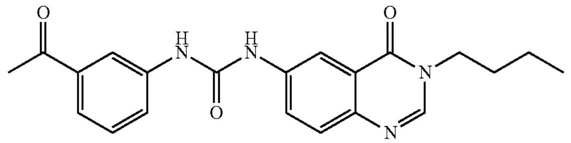
183
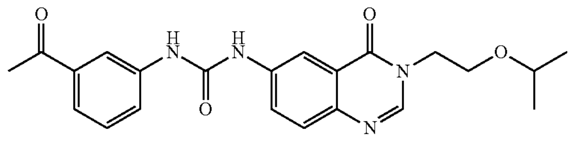
192
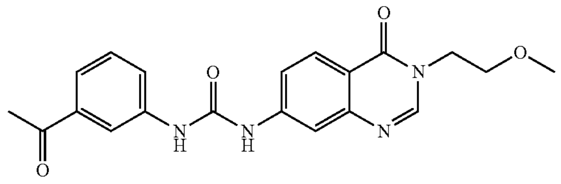
194
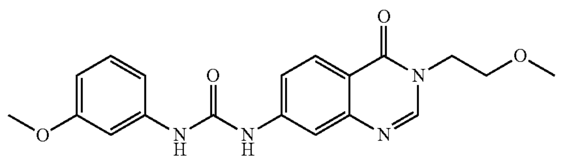
196
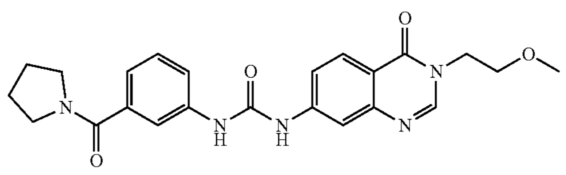
198
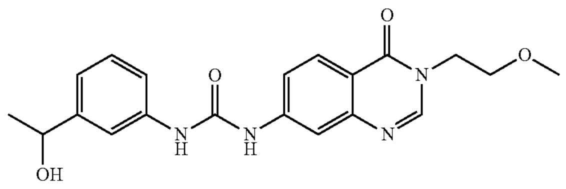
163
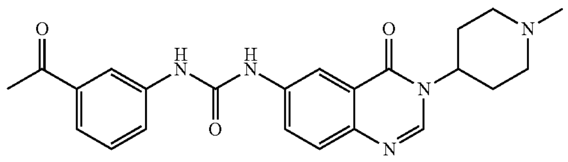
171
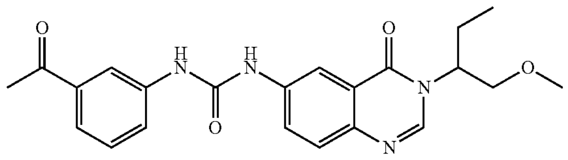
179
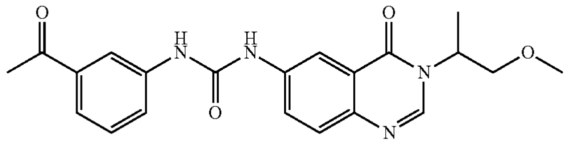
187
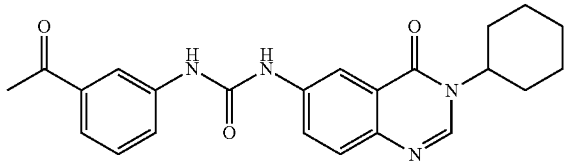
193
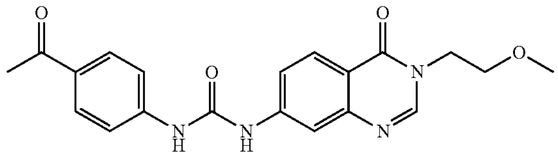
195
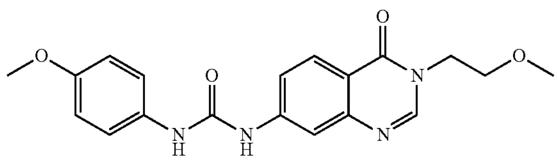
197
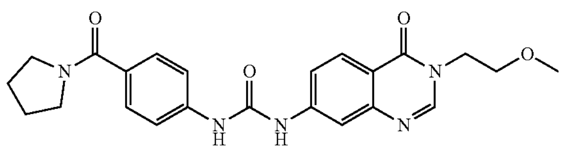
199
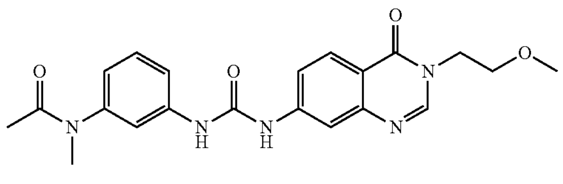

-continued
203
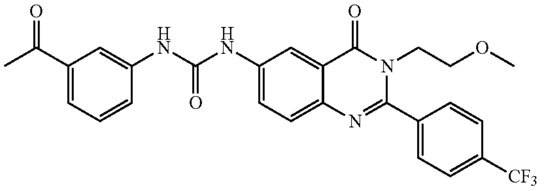
211
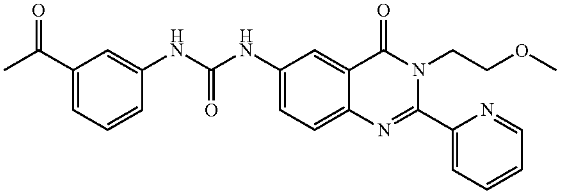
219
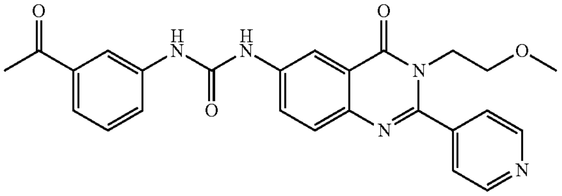
227
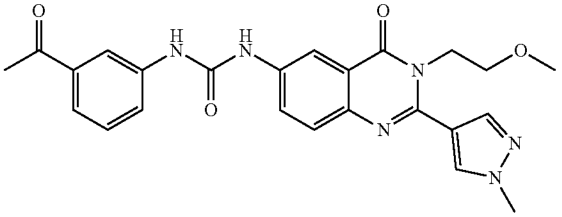
235
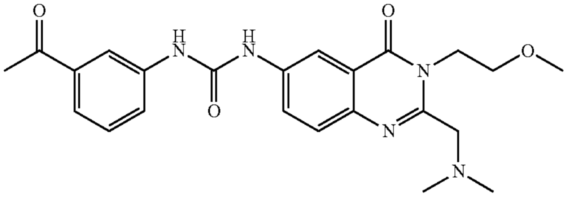
241
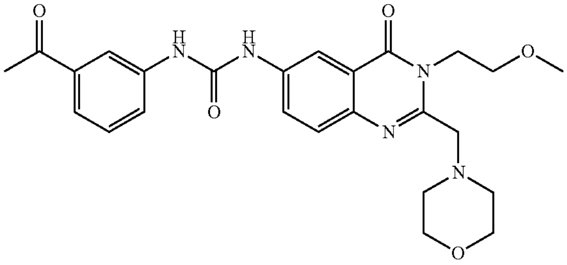
207
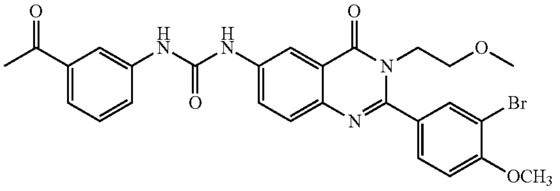
215
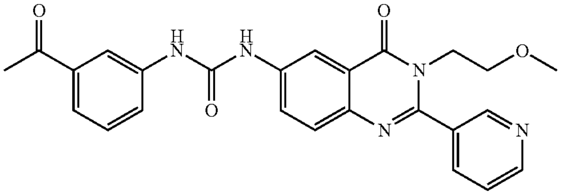
223
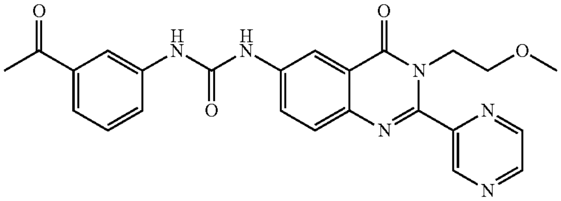
232
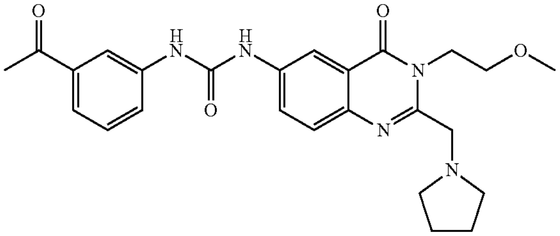
238
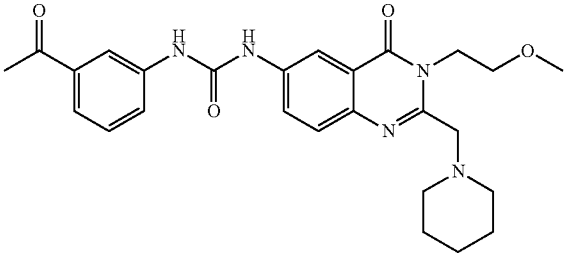
244
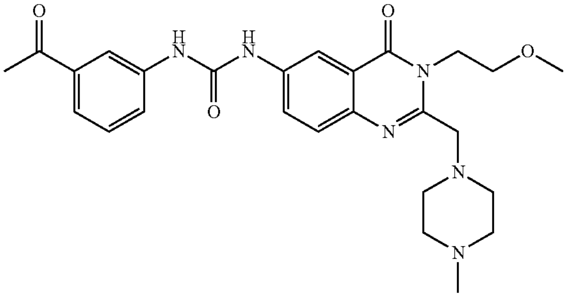

-continued
247
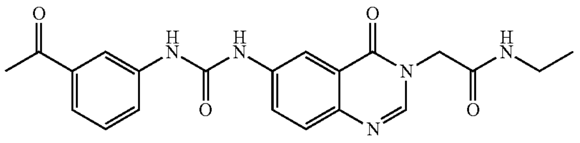
253
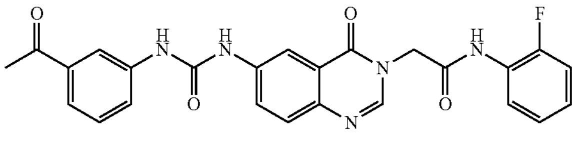
256
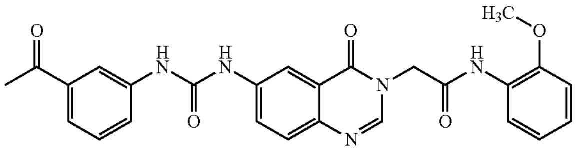
259
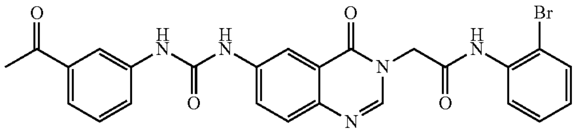
262
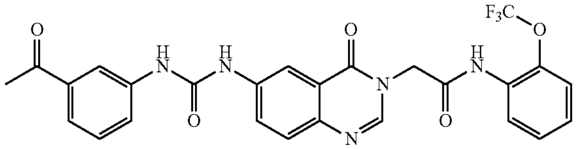
268
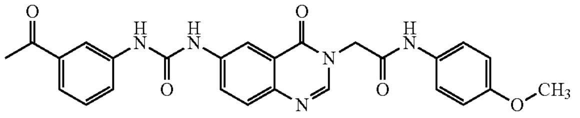
274
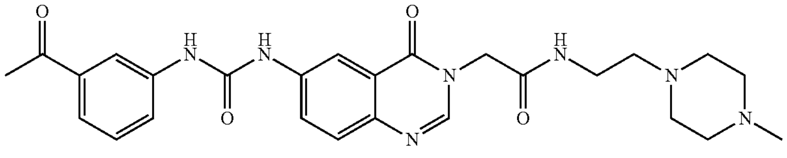
277
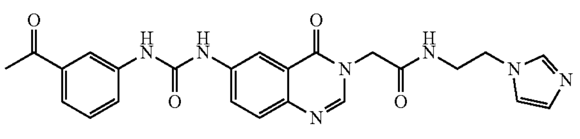
281
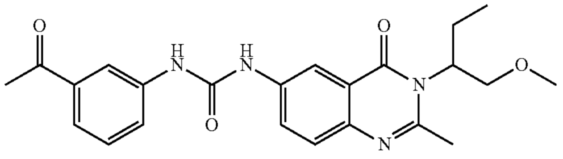
285
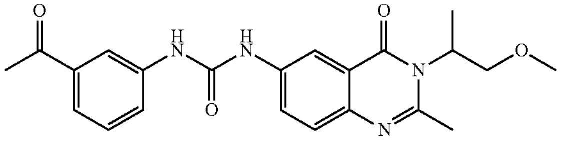
289
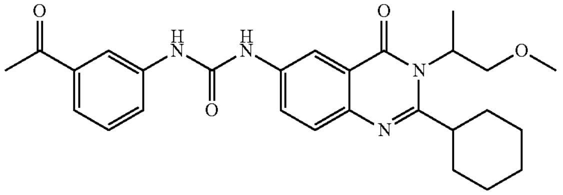
304
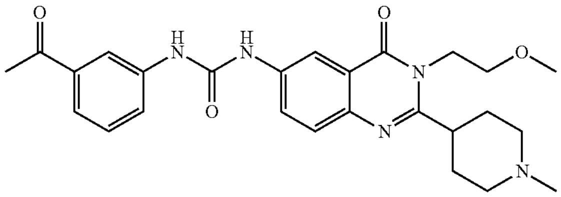
307
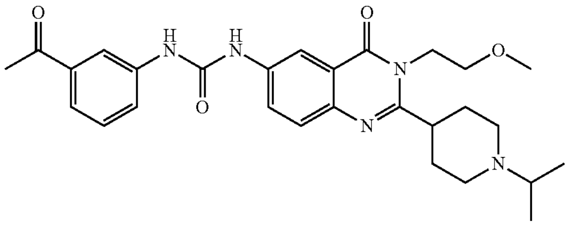
330
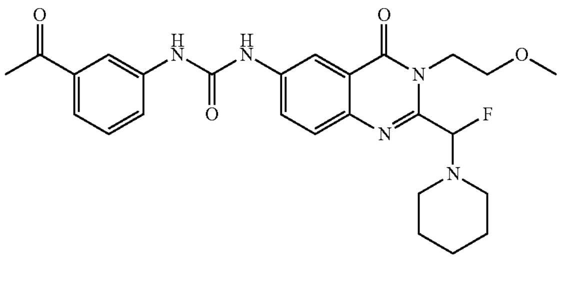
330a
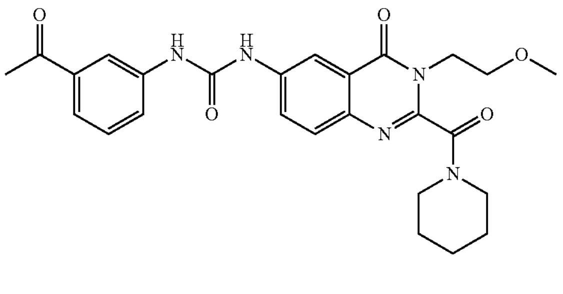

-continued

333

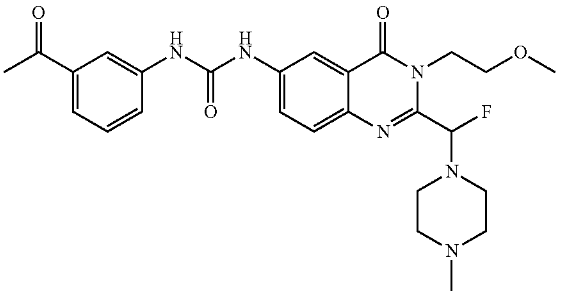

333a

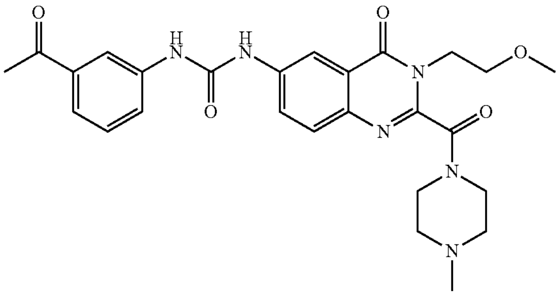

336

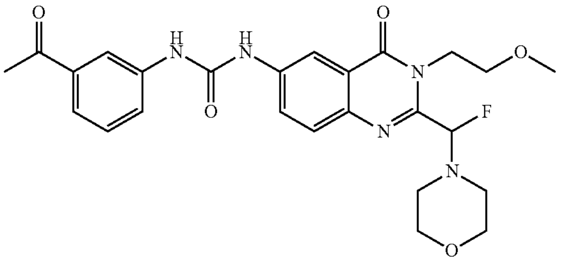

336a

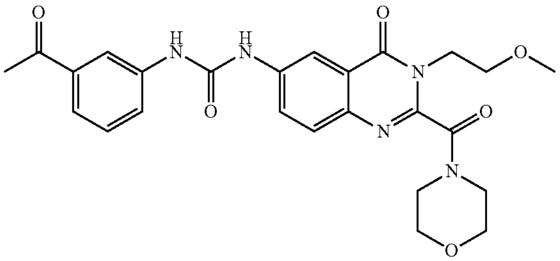

340

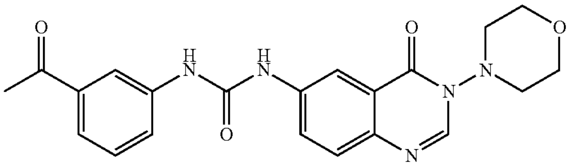

345

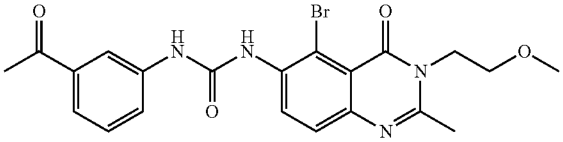

(xxii) alternately, treating the compound selected from the group consisting of 4, 82, 92, 97, 102, 134, 142, and 146 obtained in step (xvi) with a substituted aromatic isocyanate selected from the group consisting of 4-fluorophenylisocyanate, 3-chloro-4-fluorophenylisocyanate, (4-trifluoromethoxy)phenylisocyanate, (4-trifluoromethyl)phenylisocyanate, (2-trifluoromethyl) phenylisocyanate, 4-methoxyphenylisocyanate, 2-methoxyphenylisocyanate, ethyl 3-isocyanatobenzoate, 3-acetylphenylisocyanate, and 4-acetylphenylisocyanate in presence of TEA as a base in dry THF at room temperature for 3-8 hours to obtain the compound having Structure I selected from the group consisting of 35, 36, 37, 38, 39, 40, 41, 42, 83, 84, 85, 93, 94, 98, 99, 103, 135, 143, and 147;

35

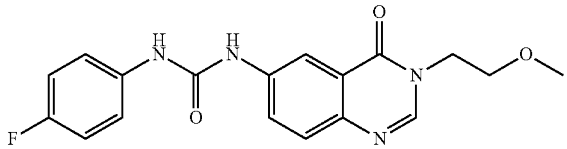

36

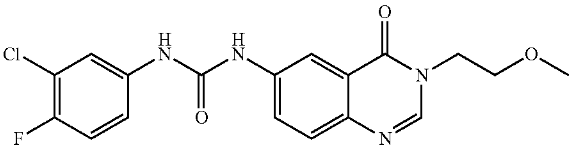

-continued

37

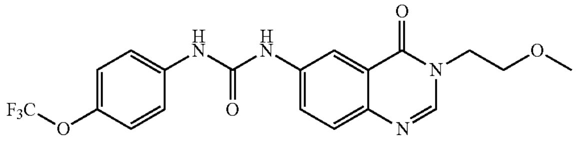

38

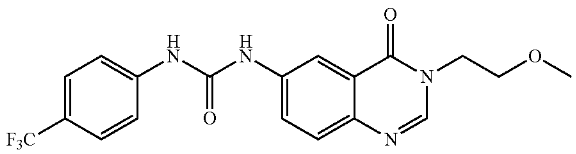

39

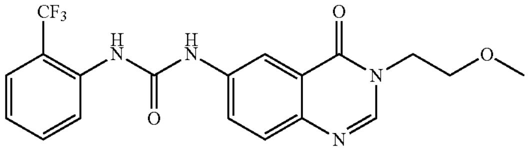

40

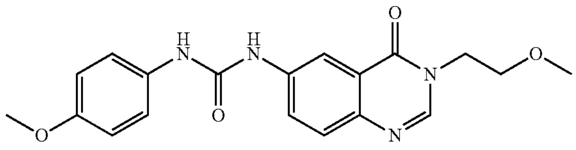

-continued

41

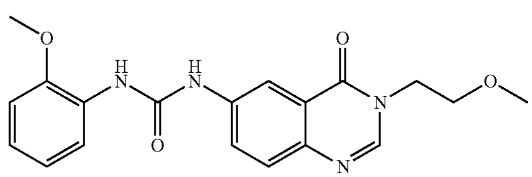

42

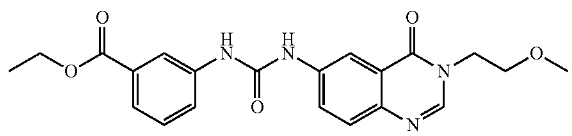

83

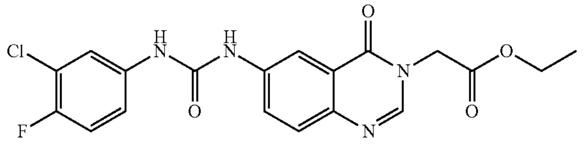

84

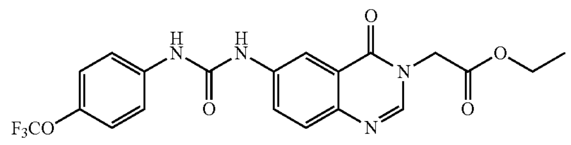

85

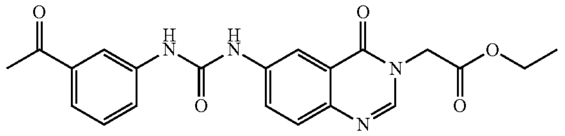

93

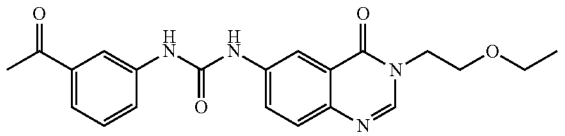

94

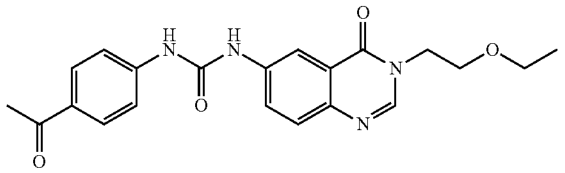

98

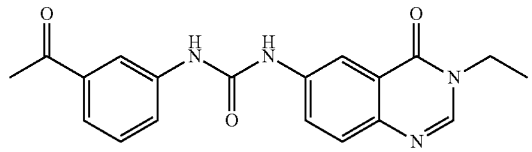

99

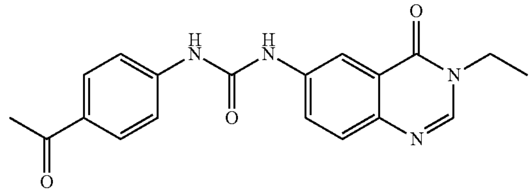

-continued

103

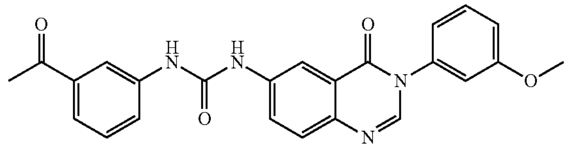

135

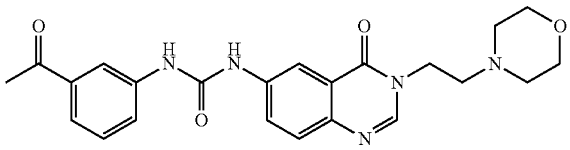

143

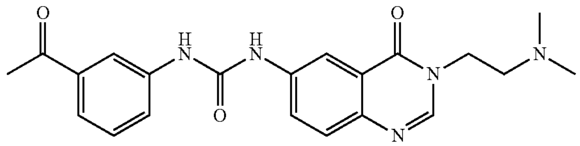

147

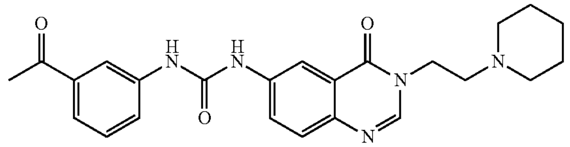

(xxiii) alternately, reacting compound 4 obtained in step (xvi) with HATU/TEA in DMF at room temperature with 5 hours of stirring to obtain a compound 74;

74

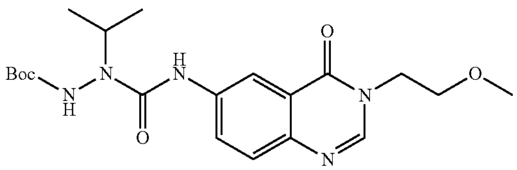

(xxiv) separately adding 3-nitrobenzoyl chloride (3-nitrobenzoic acid and Oxalyl Chloride) at 0° C. in DCM and TEA and stirring for 5 hours at room temperature to obtain a compound 77;

77

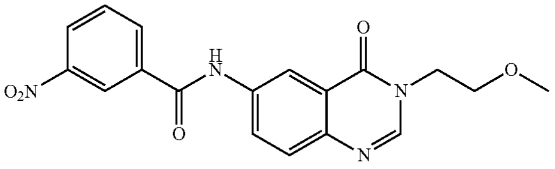

(xxv) separately Boc deprotecting the compound 59 obtained in step (xix) and the compound 74 obtained in step (xxiii) by TFA at room temperature for 2 hours to obtain a compound selected from 60 or 75;

60

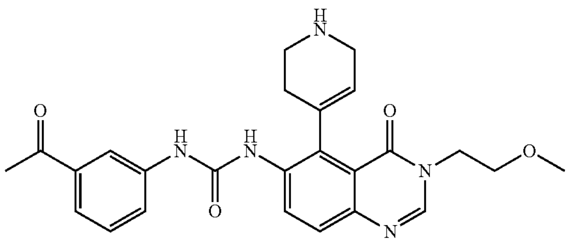

75

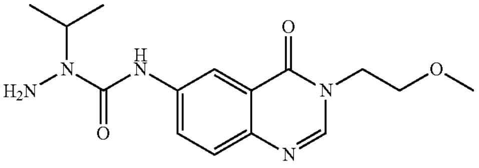

(xxvi) treating the compound 59 obtained in step (xix) and compound 60 obtained in step (xxv) with $H_2$/Pd—C (5% wet) to obtain the compound having Structure I selected from the group consisting of 61 and 62;

61

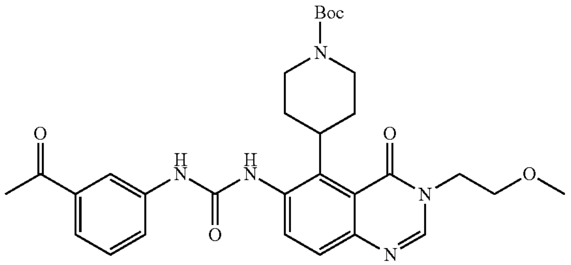

62

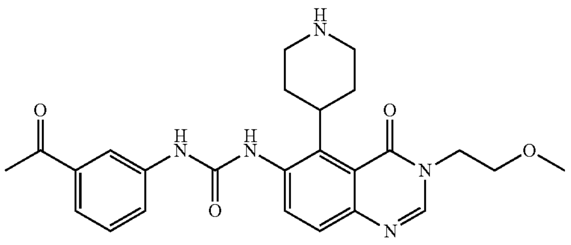

(xxvii) alternately, treating the compound selected from the group consisting of 191, 4, 46, 237, 249, 106, 243, and 252 obtained in step (xvi) and (xix) with 4-nitrophenylchloroformate in presence of TEA as a base followed by reaction with an amine selected from the group consisting of 3-aminoacetophenone, 4-aminoacetophenone, m-anisidine, p-anisidine, (3-aminophenyl)(pyrrolidin-1-yl)methanone, (4-aminophenyl)(pyrrolidin-1-yl)methanone, 1-(3-aminophenyl)-2,2,2-trifluoroethanol, -(3-aminophenyl)-N-methylacetamide, 1-(3-(hydroxyamino)phenyl) ethanone, 1-(3-(methylamino)phenyl)ethanone, and 1-(3-aminophenyl)-2,2,2-trifluoroethanone in dry THF at room temperature for 3-8 hours to obtain the compound having Structure I selected from the group consisting of 194, 195, 196, 197, 198, 199, 308, 309, 310, 311, 312, 313, 314, 315, 316, 317, 318, 319, 320, 321, 322, 323, 324, and 325;

194

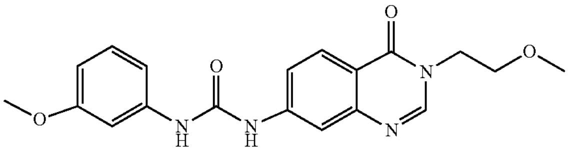

195

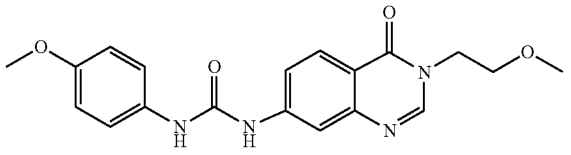

196

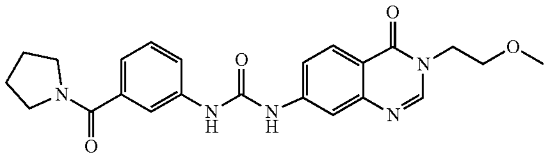

197

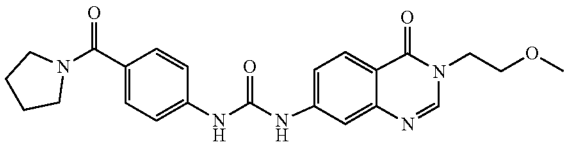

198

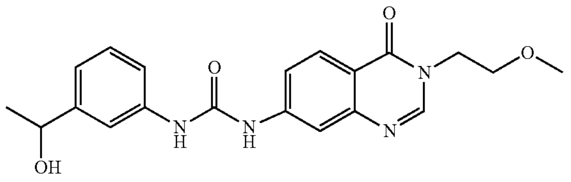

199

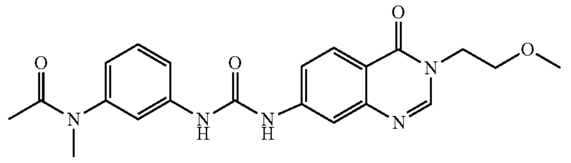

308

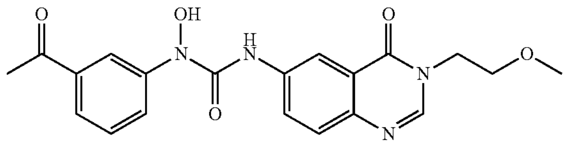

309

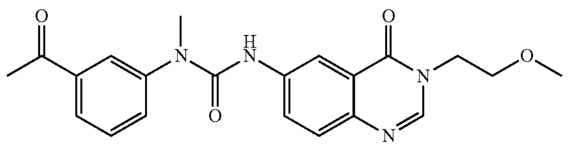

-continued
310
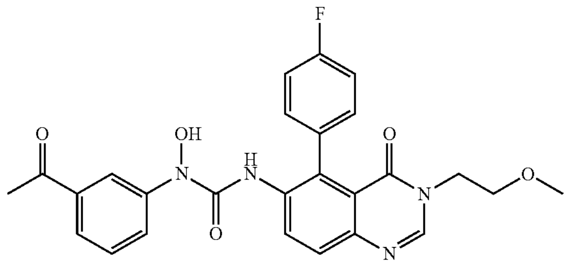
311
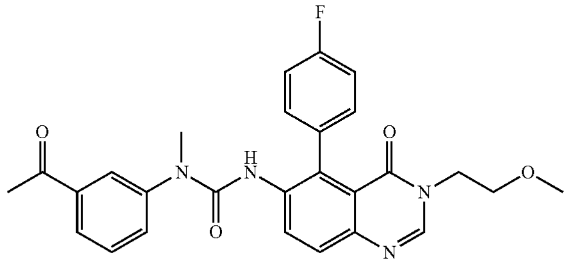
312
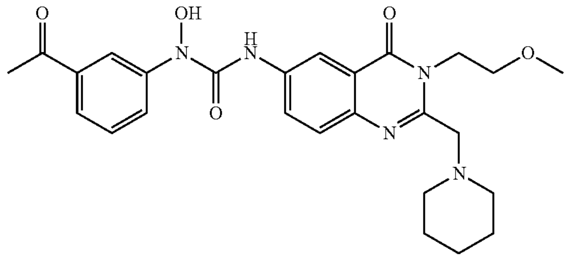
313
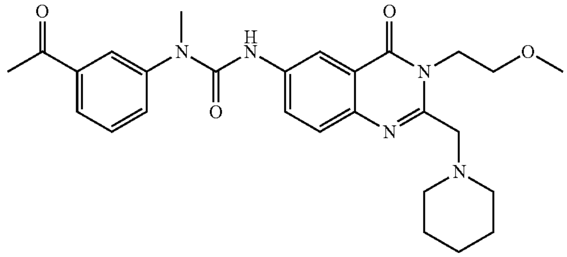
314
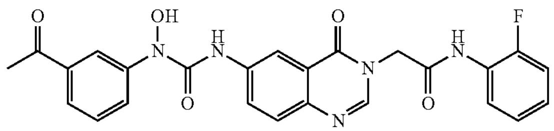
315
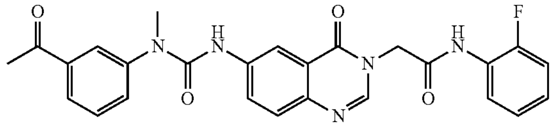
316
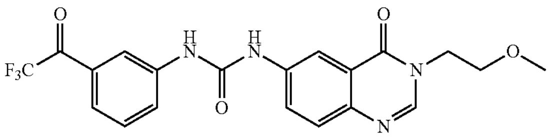
-continued
317
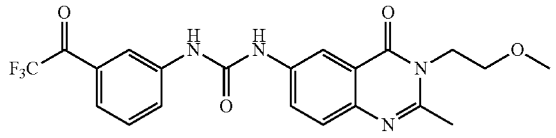
318
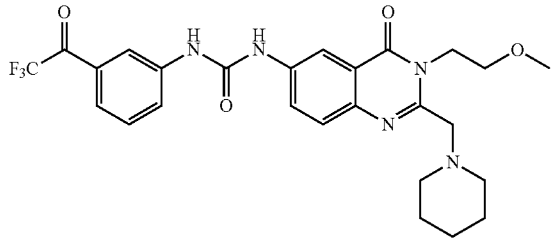
319
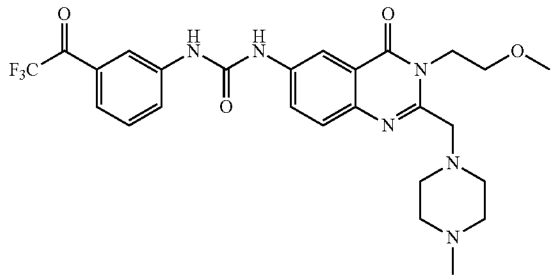
320
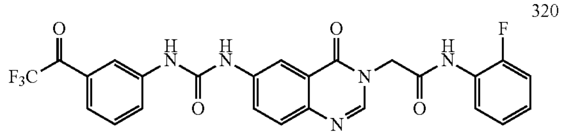
321
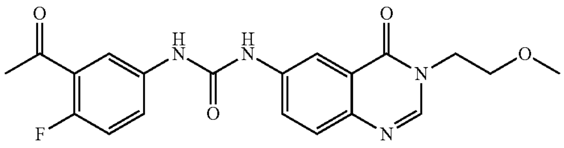
322
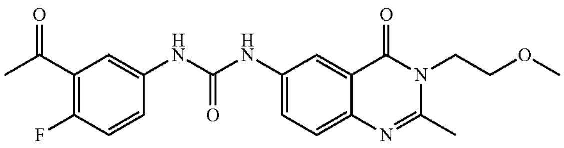
323
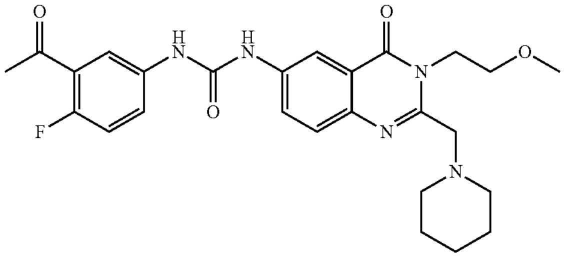

-continued

324

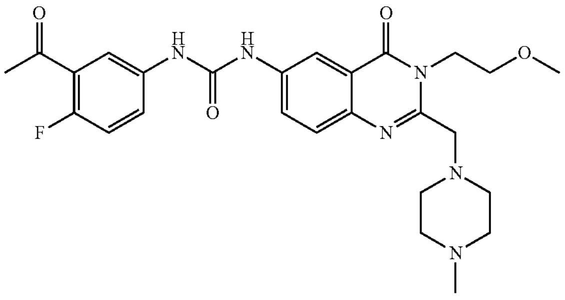

325

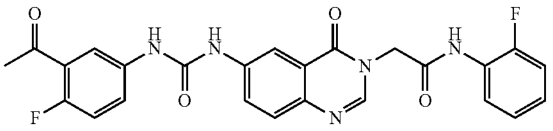

(xxviii) subjecting the compound selected from 42 and 85 obtained in step (xxii) to ester hydrolysis by LiOH monohydrate in presence of THF:EtOH:Water (3:2:1) proportion at room temperature for 1-2 hours to obtain the compound having Structure I selected from the group consisting of 42a and 85a;

42a

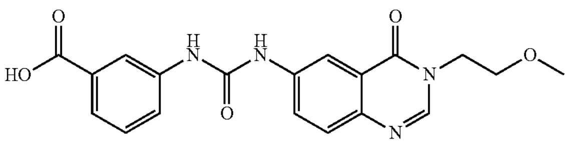

85a

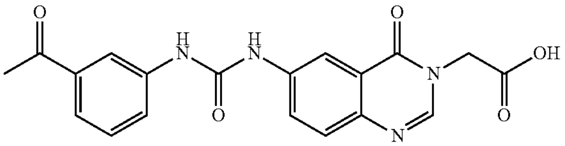

(xxix) reacting the compound 238 obtained in step (xxi) with 1M HCl in dioxane to obtain the compound having Structure I 238a; and 238a

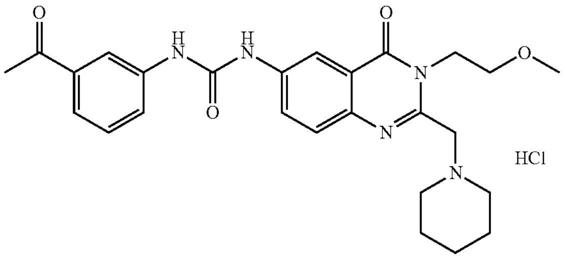

(xxx) reacting the compound selected from the group consisting of 9, 107, and 238 obtained in step (xx) and (xxi) with hydroxylamine hydrochloride ($NH_2OH \cdot HCl$) in ethanol (EtOH) at 80° C. for 12-16 hours to obtain the compound having Structure I selected from the group consisting of 341, 342 and 343

341

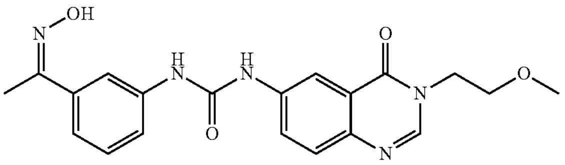

342

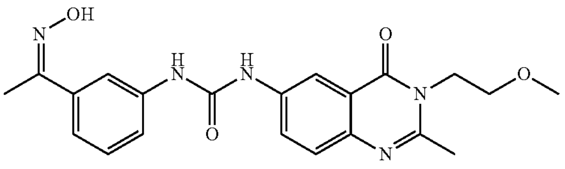

343

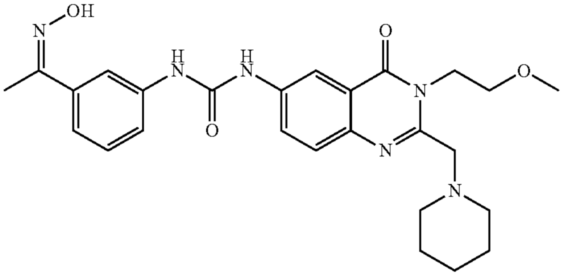

Still another embodiment of the present application provides a compound having Structure I or salts thereof for use in treating diseases and disorders related to modulation of COP1 enzyme through its stabilization or modulation of ATGL.

Another embodiment of the present disclosure provides a compound having Structure I or salts thereof for use in decreasing the level of triglycerides in hepatocytes.

Yet another embodiment of the present disclosure provides a compound having Structure I or salts thereof for use in treatment of disease selected from Non-Alcoholic Fatty Liver Disease (NAFLD) or Non-Alcoholic Steatohepatitis (NASH).

Another embodiment of the present disclosure provides a compound having Structure I or salts thereof along with pharmaceutically acceptable excipients.

Still another embodiment of the present disclosure provides a method of modulation COP1 enzyme through its stabilization by compound having Structure I.

Yet another aspect of the present disclosure provides a method of increasing the level of ATGL by compound having Structure I.

BRIEF DESCRIPTION OF DRAWINGS

The objects and features of the present disclosure will become apparent from the following detailed description, when taken in conjunction with the accompanying drawings.

DETAILED DESCRIPTION

Figure 1A:
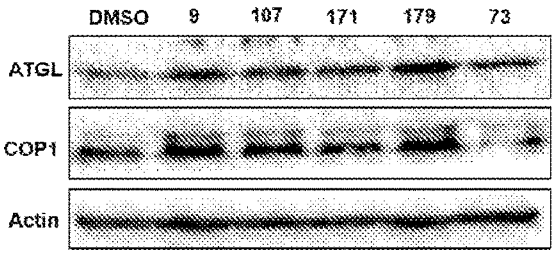
FIGS. 1A-1Y illustrate results of Western Blot Analysis in HepG2 cells after treatment with compounds 9, 10, 107, 171, 179, 73, 232, 238, 211, 340, 11, 17, 18, 23, 24, 123, 127, 139, 223, 241, 244, 299, 333a, 215, 219 and 308. Increase in intensity of ATGL and COP1 bands with respect to control denotes elevation in the respective protein levels upon compound treatment. Actin is used as a loading control.
Figure 1B:
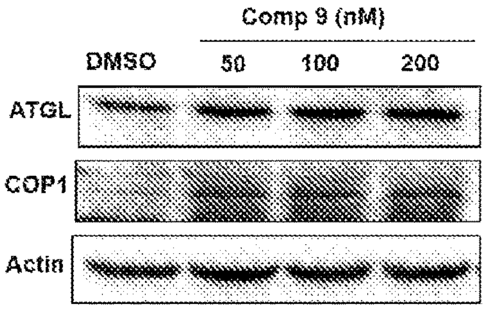
Figure 1C:
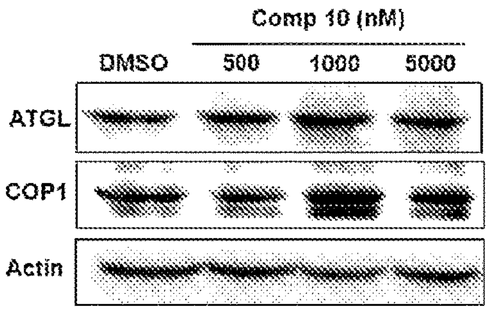
Figure 1D:
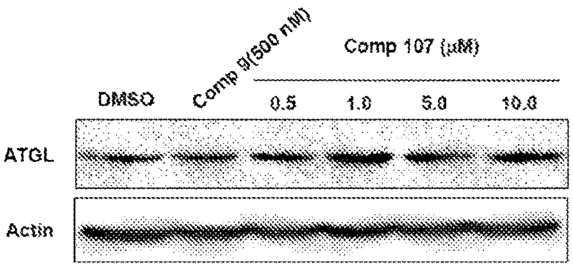
Figure 1E:
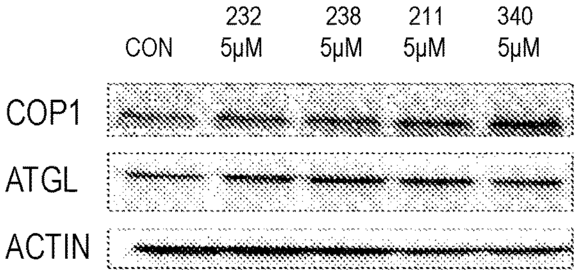
Figure 1F:
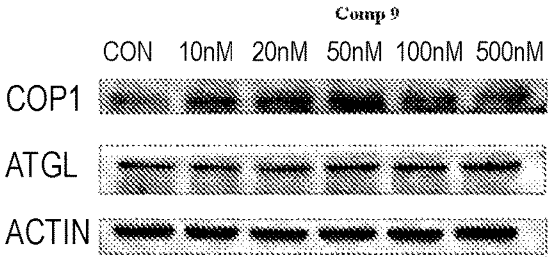
Figure 1G:
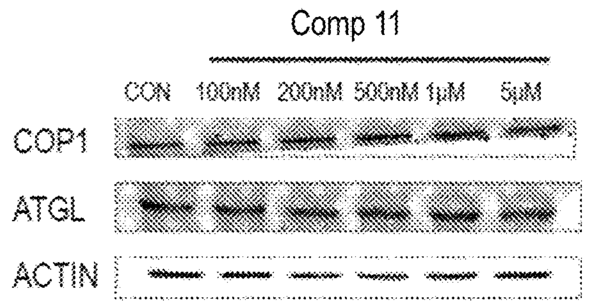
Figure 1H:
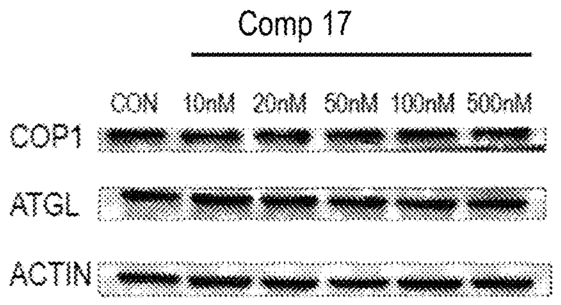
Figure 1I:
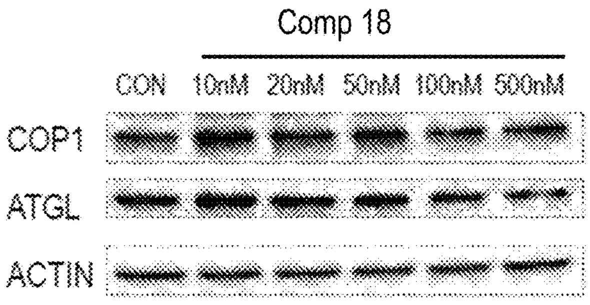
Figure 1J:
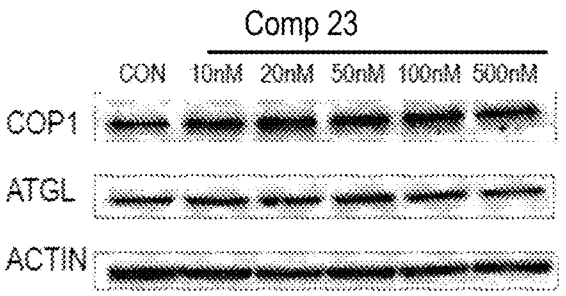
Figure 1K:
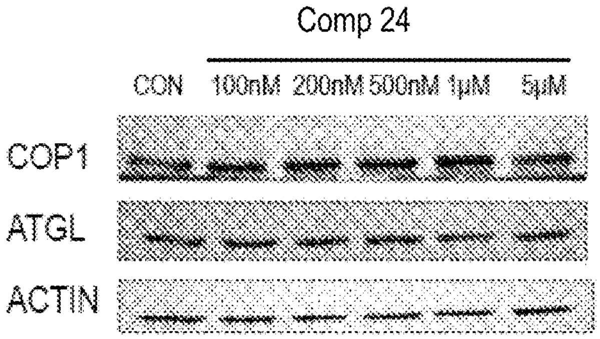
Figure 1L:
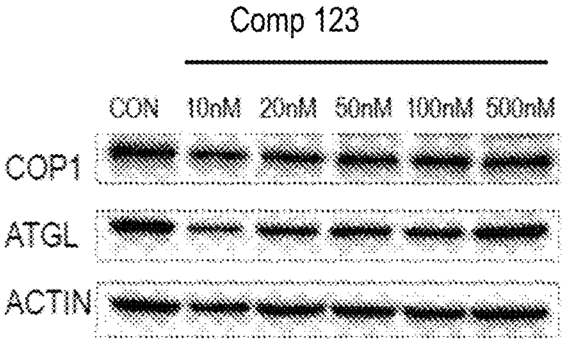
Figure 1M:
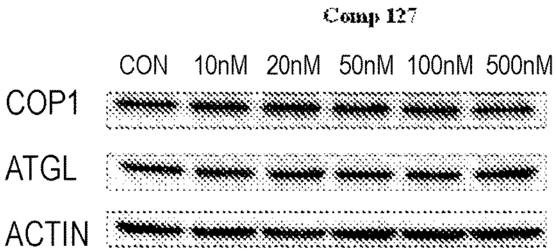
Figure 1N:
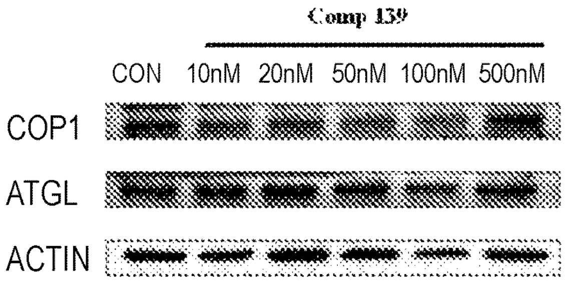
Figure 1O:
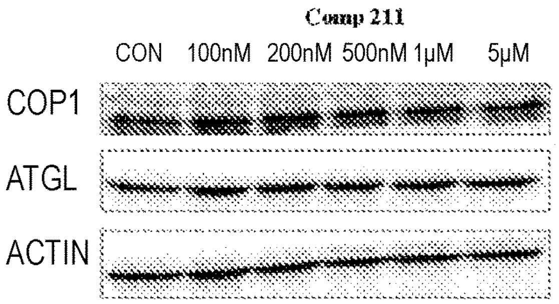
Figure 1P:
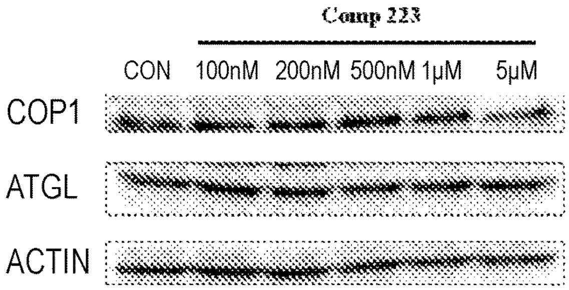
Figure 1Q:
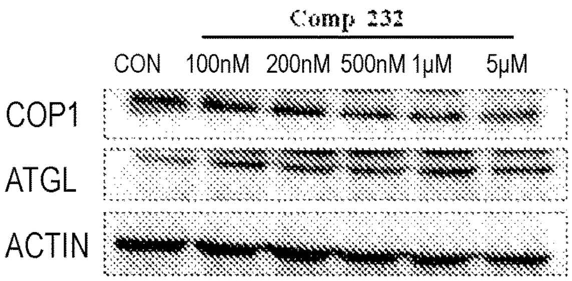
Figure 1R:
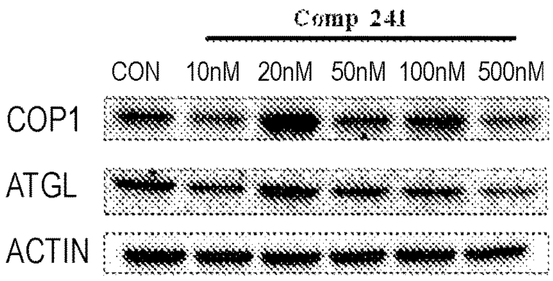
Figure 1S:
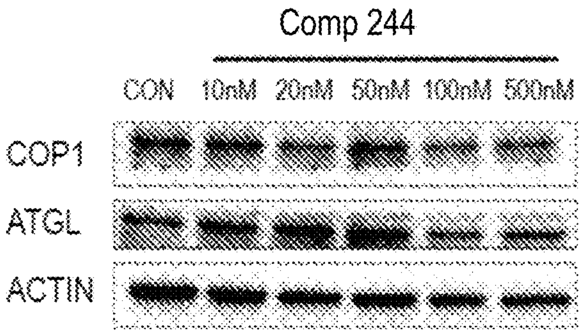
Figure 1T:
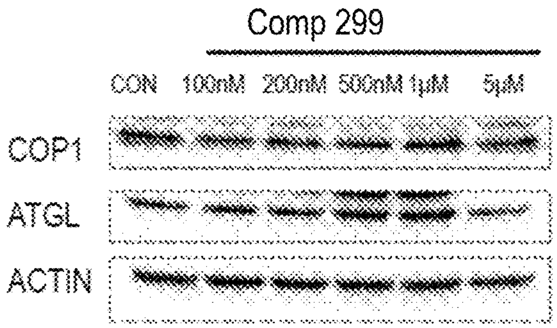
Figure 1U:
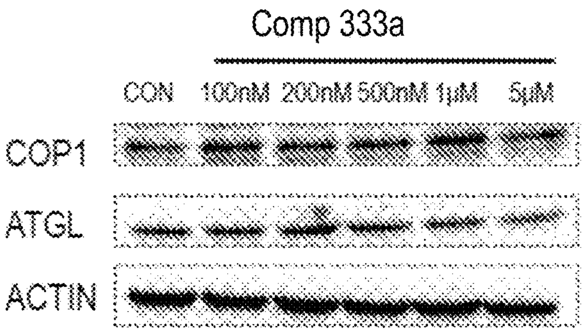
Figure 1V:
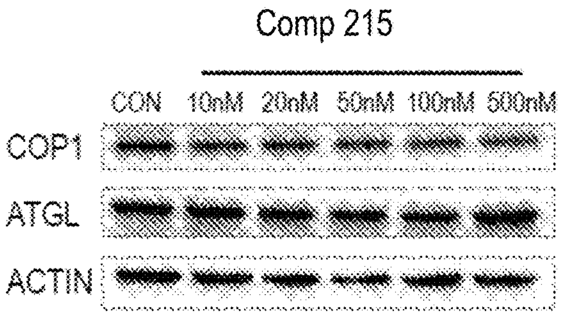
Figure 1W:
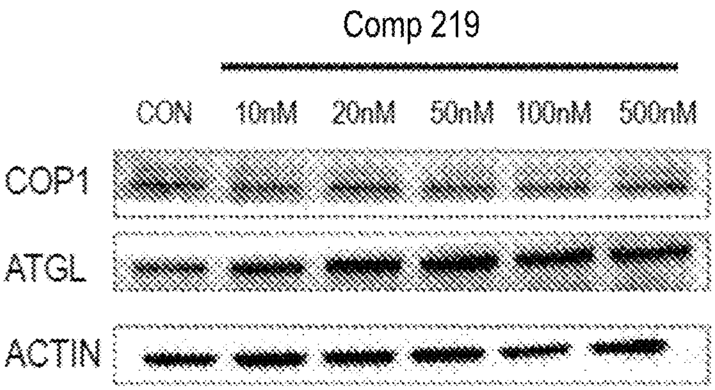
Figure 1X:
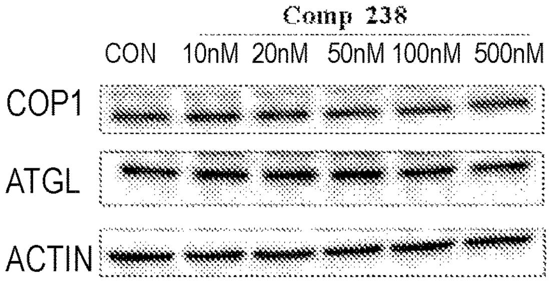

The present disclosure relates to a compound having Structure I or salts thereof:

Structure I

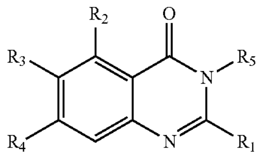

wherein $R_1$ is independently selected from the group consisting of:

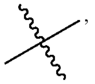,
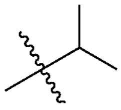,
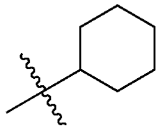,
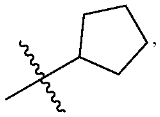,
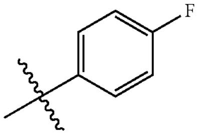,
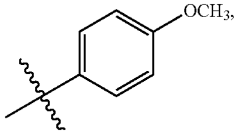
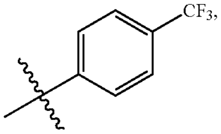
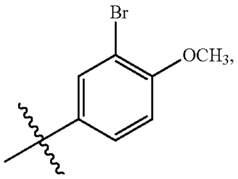,
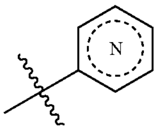,
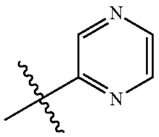,
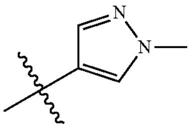,
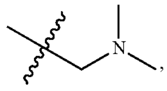,
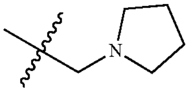,
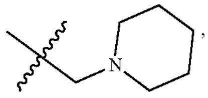,
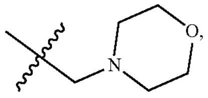
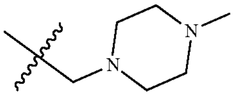,
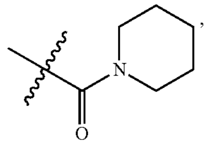

-continued
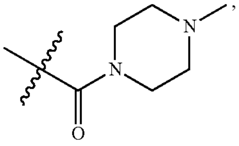
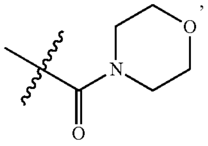
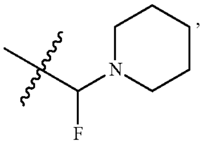
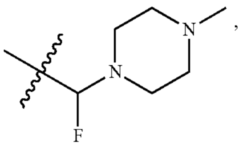
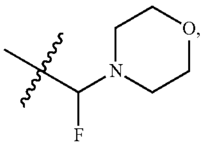
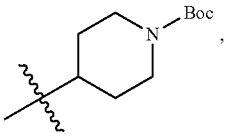
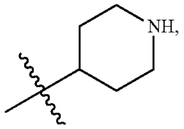
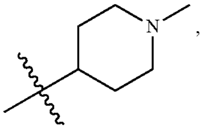
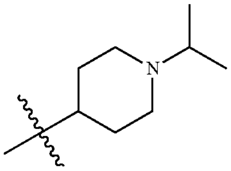 [SMILES: *C1CCN(C(C)C)CC1]
$R_2$ is independently selected from the group consisting of:
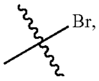
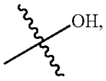
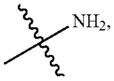
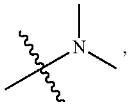
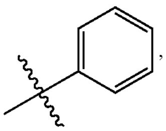
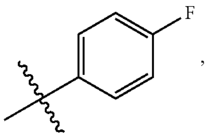
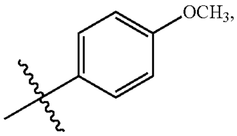
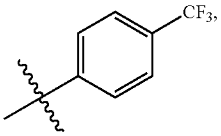
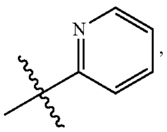
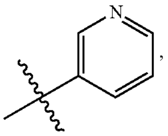
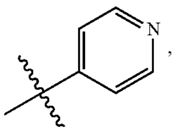
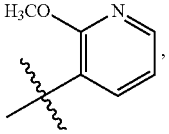
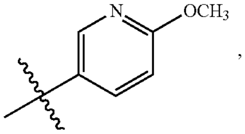
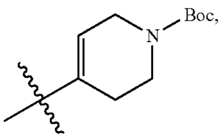
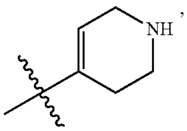
-continued
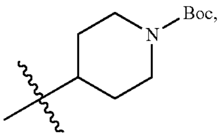
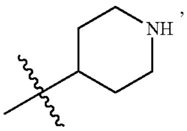
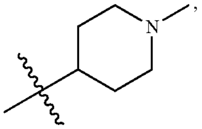
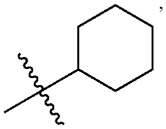
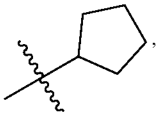
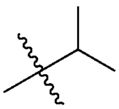
$R_3$ is independently selected from the group consisting of:
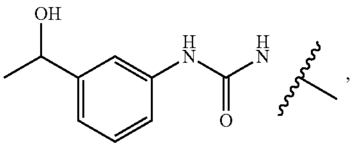
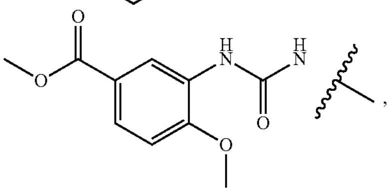
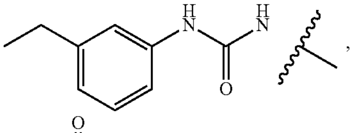
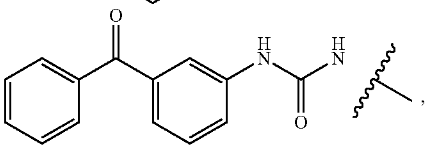
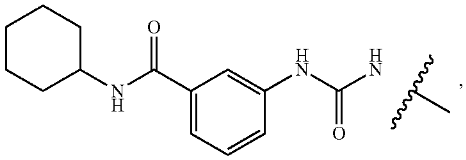
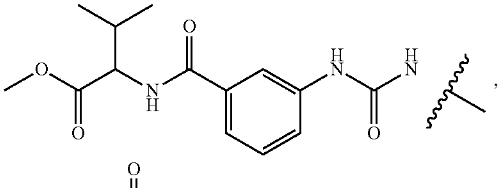
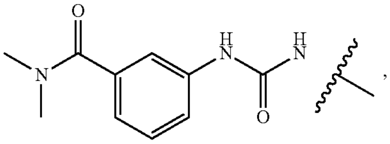
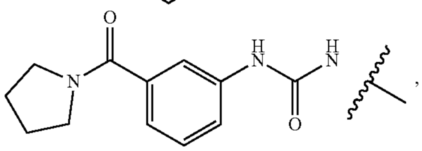

-continued
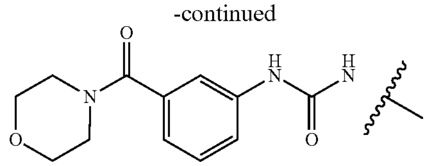
,
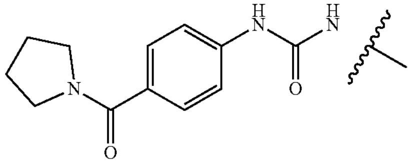
,
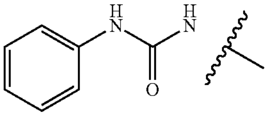
,
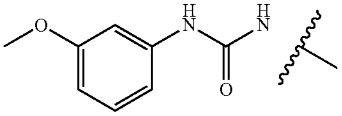
,
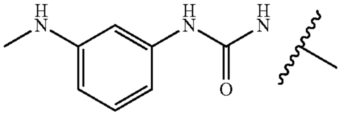
,
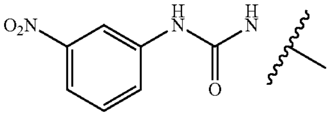
,
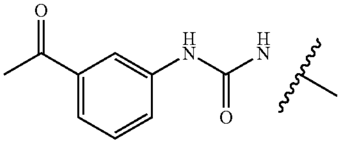
,
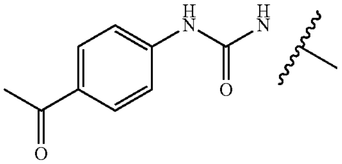
,
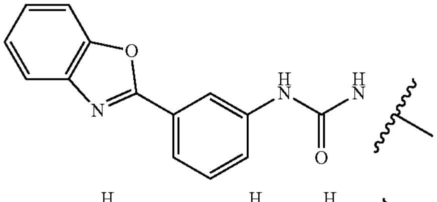
,
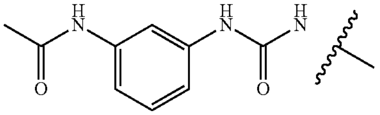
,
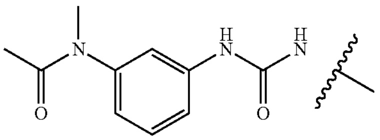
,
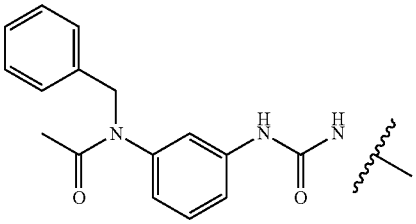
,
-continued
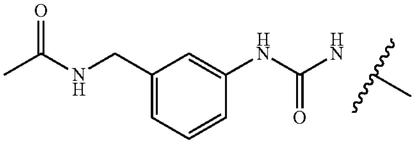
,
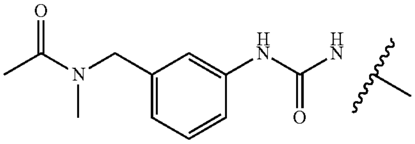
,
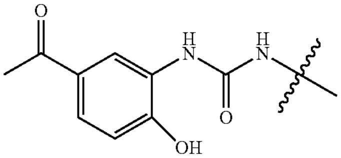
,
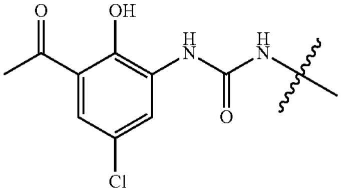
,
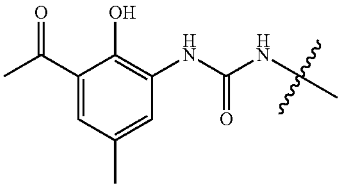
,
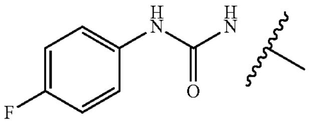
,
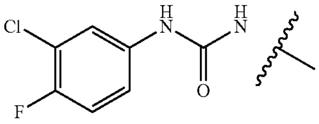
,
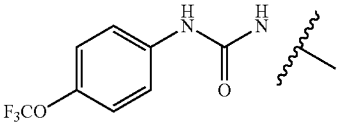
,
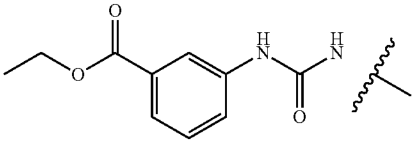
,
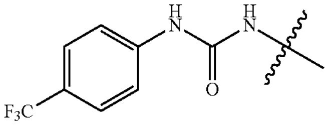
,
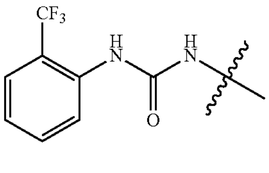
, -continued
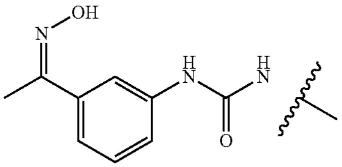,
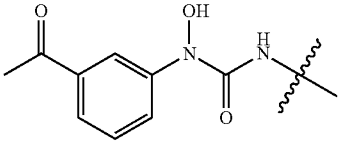,
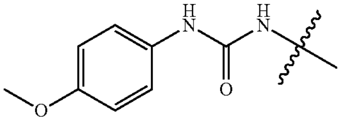,
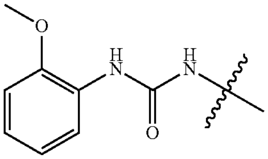,
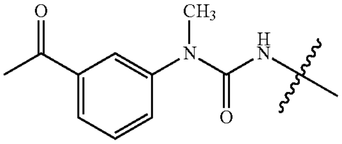
$R_4$ is independently selected from the group consisting of:
H, 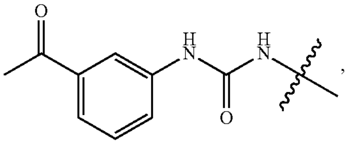,
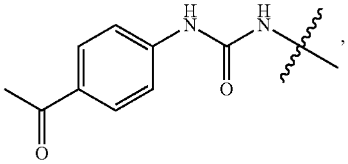,
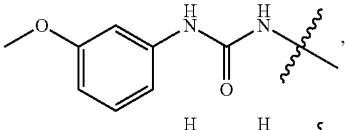,
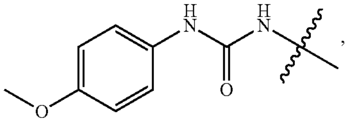,
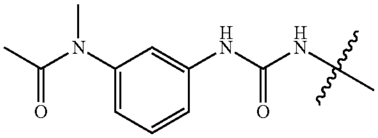
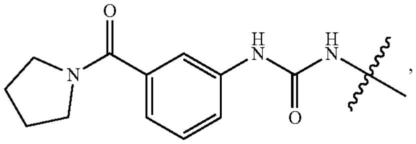,
-continued
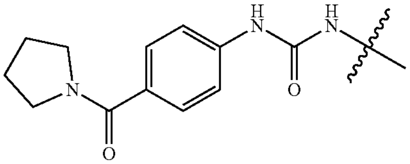
$R_5$ is independently selected from the group consisting of:
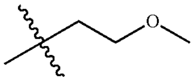, 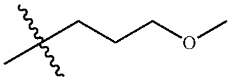,
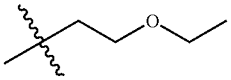, 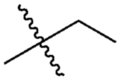,
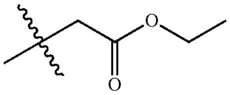, 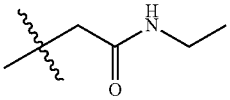,
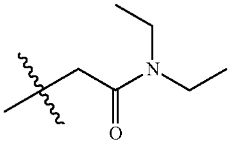, 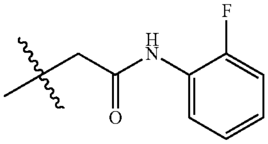,
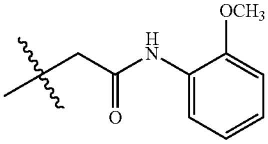, 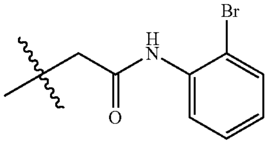,
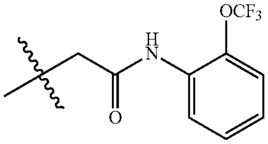, 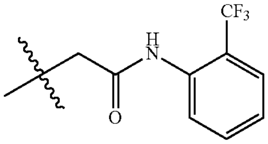,
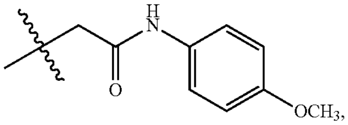
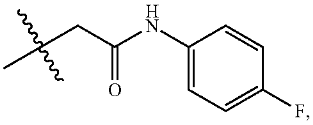
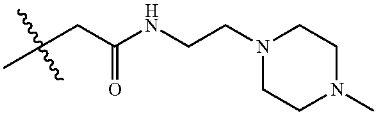,
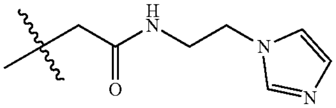,
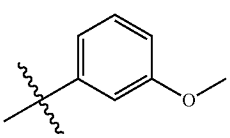, 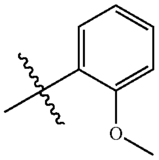, -continued

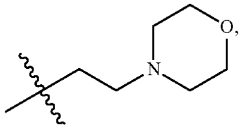, 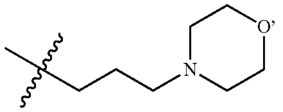, 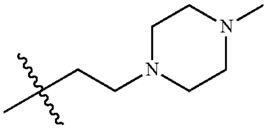, 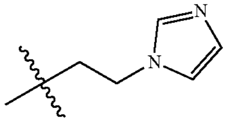, 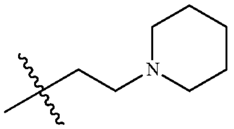, 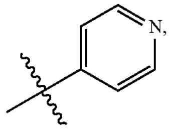, 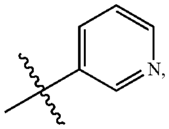, 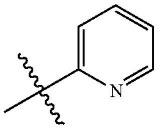, 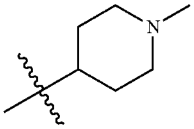, 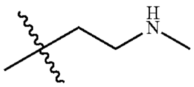, 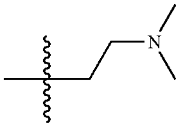, 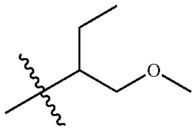, 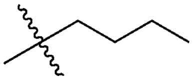, -continued

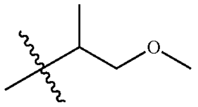, 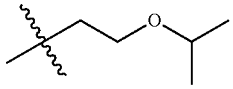,

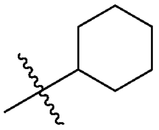

All the compounds of this disclosure having Structure I are depicted in the Table 1:

Structure I

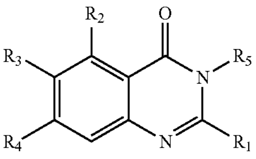

TABLE 1

| Structure of the compounds disclosed | | | |
|---|---|---|---|
| Serial No. | Compound No. | Structure | IUPAC Name |
| 1 | 5 | 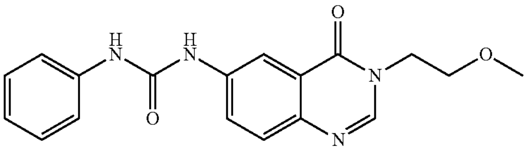 [SMILES: COCCn1cnc2ccc(NC(=O)Nc3ccccc3)cc2c1=O] | 1-(3-(2-methoxyethyl)-4-oxo-3,4-dihydroquinazolin-6-yl)-3-phenylurea |
| 2 | 6 | 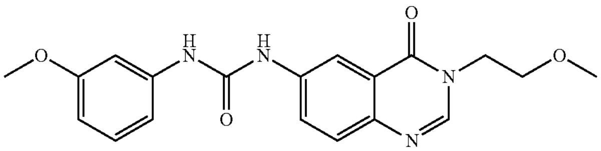 | 1-(3-(2-methoxyethyl)-4-oxo-3,4-dihydroquinazolin-6-yl)-3-(3-methoxyphenyl)urea |
| 3 | 7 | 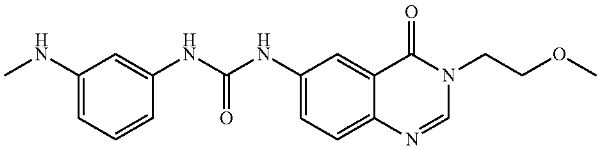 | 1-(3-(2-methoxyethyl)-4-oxo-3,4-dihydroquinazolin-6-yl)-3-(3-(methylamino)phenyl)urea |
| 4 | 8 | 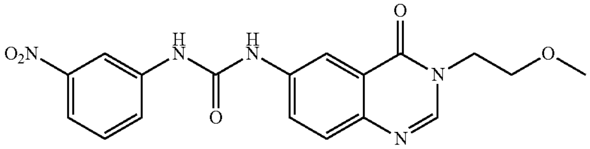 [SMILES: COCCn1cnc2ccc(NC(=O)Nc3cccc([N+](=O)[O-])c3)cc2c1=O] | 1-(3-(2-methoxyethyl)-4-oxo-3,4-dihydroquinazolin-6-yl)-3-(3-nitrophenyl)urea |

TABLE 1-continued

| Structure of the compounds disclosed | | | |
|---|---|---|---|
| Serial No. | Compound No. | Structure | IUPAC Name |
| 5 | 9 | 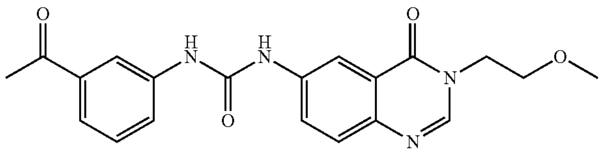 [SMILES: COCCn1cnc2ccc(NC(=O)Nc3cccc(C(C)=O)c3)cc2c1=O] | 1-(3-acetylphenyl)-3-(3-(2-methoxyethyl)-4-oxo-3,4-dihydroquinazolin-6-yl)urea |
| 6 | 10 | 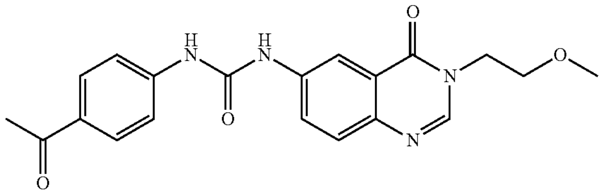 [SMILES: COCCn1cnc2ccc(NC(=O)Nc3ccc(C(C)=O)cc3)cc2c1=O] | 1-(4-acetylphenyl)-3-(3-(2-methoxyethyl)-4-oxo-3,4-dihydroquinazolin-6-yl)urea |
| 7 | 11 | 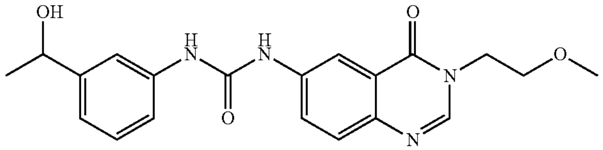 [SMILES: COCCn1cnc2ccc(NC(=O)Nc3cccc(C(C)O)c3)cc2c1=O] | 1-(3-(1-hydroxyethyl)phenyl)-3-(3-(2-methoxyethyl)-4-oxo-3,4-dihydroquinazolin-6-yl)urea |
| 8 | 12 | 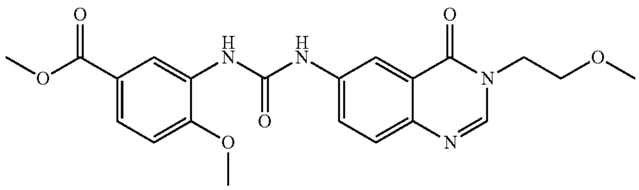 | methyl 4-methoxy-3-(3-(3-(2-methoxyethyl)-4-oxo-3,4-dihydroquinazolin-6-yl)ureido)benzoate |
| 9 | 13 | 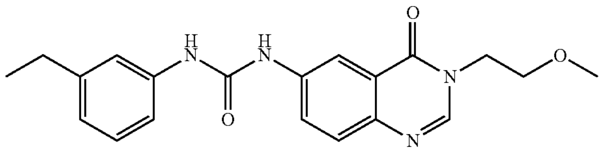 [SMILES: CCc1cccc(NC(=O)Nc2ccc3ncn(CCOC)c(=O)c3c2)c1] | 1-(3-ethylphenyl)-3-(3-(2-methoxyethyl)-4-oxo-3,4-dihydroquinazolin-6-yl)urea |
| 10 | 14 | 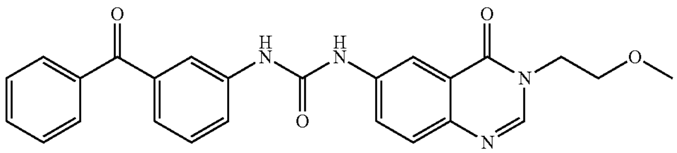 [SMILES: COCCn1cnc2ccc(NC(=O)Nc3cccc(C(=O)c4ccccc4)c3)cc2c1=O] | 1-(3-benzoylphenyl)-3-(3-(2-methoxyethyl)-4-oxo-3,4-dihydroquinazolin-6-yl)urea |
| 11 | 15 | 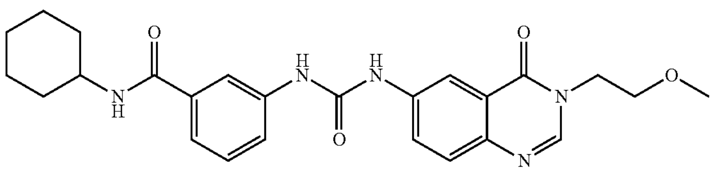 [SMILES: COCCn1cnc2ccc(NC(=O)Nc3cccc(C(=O)NC4CCCCC4)c3)cc2c1=O] | N-cyclohexyl-3-(3-(3-(2-methoxyethyl)-4-oxo-3,4-dihydroquinazolin-6-yl)ureido)benzamide |
| 12 | 16 | 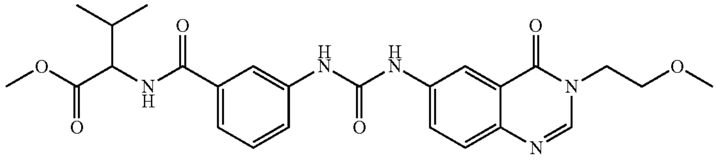 | methyl 2-(3-(3-(3-(2-methoxyethyl)-4-oxo-3,4-dihydroquinazolin-6-yl)ureido)benzamido)-3-methylbutanoate |

TABLE 1-continued

| Structure of the compounds disclosed | | | |
|---|---|---|---|
| Serial No. | Compound No. | Structure | IUPAC Name |
| 13 | 17 | 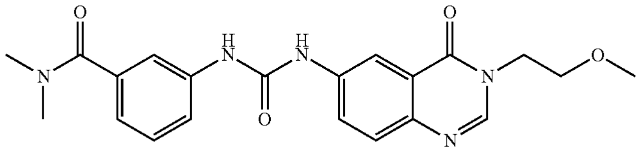 | 3-(3-(3-(2-methoxyethyl)-4-oxo-3,4-dihydroquinazolin-6-yl)ureido)-N,N-dimethylbenzamide |
| 14 | 18 | 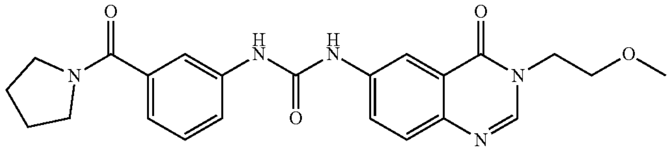 [SMILES: COCCn1cnc2ccc(NC(=O)Nc3cccc(C(=O)N4CCCC4)c3)cc2c1=O] | 1-(3-(2-methoxyethyl)-4-oxo-3,4-dihydroquinazolin-6-yl)-3-(3-(pyrrolidine-1-carbonyl)phenyl)urea |
| 15 | 19 | 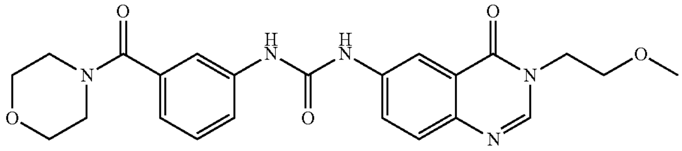 [SMILES: COCCn1cnc2ccc(NC(=O)Nc3cccc(C(=O)N4CCOCC4)c3)cc2c1=O] | 1-(3-(2-methoxyethyl)-4-oxo-3,4-dihydroquinazolin-6-yl)-3-(3-(morpholine-4-carbonyl)phenyl)urea |
| 16 | 20 | 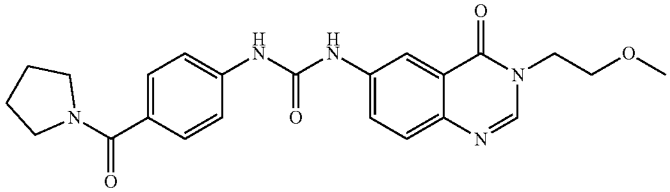 [SMILES: COCCn1cnc2ccc(NC(=O)Nc3ccc(C(=O)N4CCCC4)cc3)cc2c1=O] | 1-(3-(2-methoxyethyl)-4-oxo-3,4-dihydroquinazolin-6-yl)-3-(4-(pyrrolidine-1-carbonyl)phenyl)urea |
| 17 | 21 | 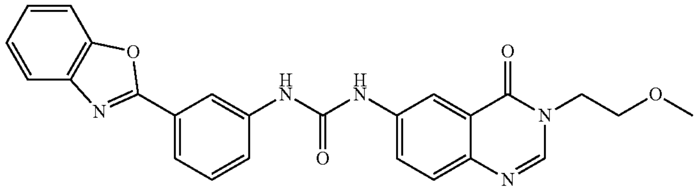 [SMILES: COCCn1cnc2ccc(NC(=O)Nc3cccc(-c4nc5ccccc5o4)c3)cc2c1=O] | 1-(3-(benzo[d]oxazol-2-yl)phenyl)-3-(3-(2-methoxyethyl-4-oxo-3,4-dihydroquinazolin-6-yl)urea |
| 18 | 22 | 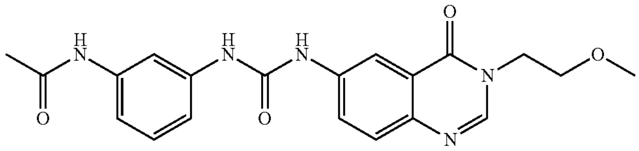 [SMILES: COCCn1cnc2ccc(NC(=O)Nc3cccc(NC(C)=O)c3)cc2c1=O] | N-(3-(3-(3-(2-methoxyethyl)-4-oxo-3,4-dihydroquinazolin-6-yl)ureido)phenyl)acetamide |
| 19 | 23 | 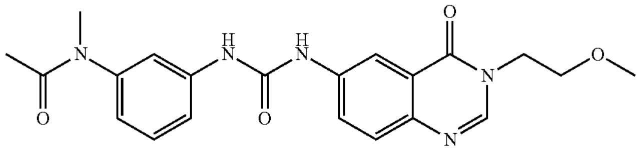 [SMILES: COCCn1cnc2ccc(NC(=O)Nc3cccc(N(C)C(C)=O)c3)cc2c1=O] | N-(3-(3-(3-(2-methoxyethyl)-4-oxo-3,4-dihydroquinazolin-6-yl)ureido)phenyl)-N-methylacetamide |
| 20 | 24 | 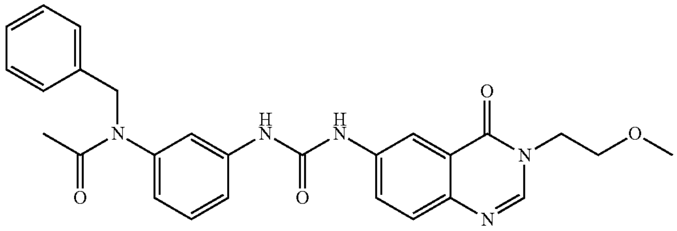 [SMILES: COCCn1cnc2ccc(NC(=O)Nc3cccc(N(Cc4ccccc4)C(C)=O)c3)cc2c1=O] | N-benzyl-N-(3-(3-(3-(2-methoxyethyl)-4-oxo-3,4-dihydroquinazolin-6-yl)ureido)phenyl)acetamide |

TABLE 1-continued

| Structure of the compounds disclosed | | | |
|---|---|---|---|
| Serial No. | Compound No. | Structure | IUPAC Name |
| 21 | 25 | 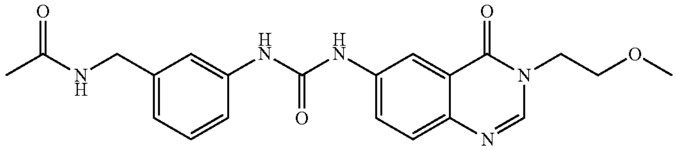 [SMILES: COCCn1cnc2ccc(NC(=O)Nc3cccc(CNC(C)=O)c3)cc2c1=O] | N-(3-(3-(3-(2-methoxyethyl)-4-oxo-3,4-dihydroquinazolin-6-yl)ureido)benzyl)acetamide |
| 22 | 26 | 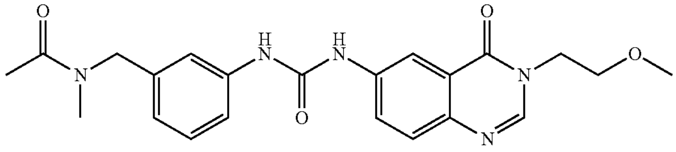 [SMILES: COCCn1cnc2ccc(NC(=O)Nc3cccc(CN(C)C(C)=O)c3)cc2c1=O] | N-(3-(3-(3-(2-methoxyethyl)-4-oxo-3,4-dihydroquinazolin-6-yl)ureido)benzyl)-N-methylacetamide |
| 23 | 32 | 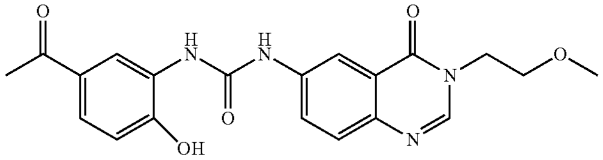 [SMILES: COCCn1cnc2ccc(NC(=O)Nc3cc(C(C)=O)ccc3O)cc2c1=O] | 1-(5-acetyl-2-hydroxyphenyl)-3-(3-(2-methoxyethyl)-4-oxo-3,4-dihydroquinazolin-6-yl)urea |
| 24 | 33 | 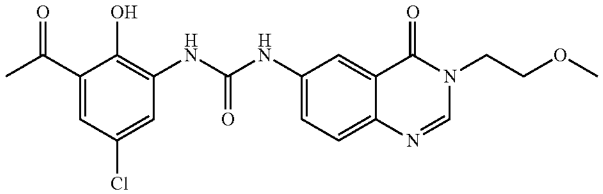 [SMILES: COCCn1cnc2ccc(NC(=O)Nc3cc(Cl)cc(C(C)=O)c3O)cc2c1=O] | 1-(3-acetyl-5-chloro-2-hydroxyphenyl)-3-(3-(2-methoxyethyl)-4-oxo-3,4-dihydroquinazolin-6-yl)urea |
| 25 | 34 | 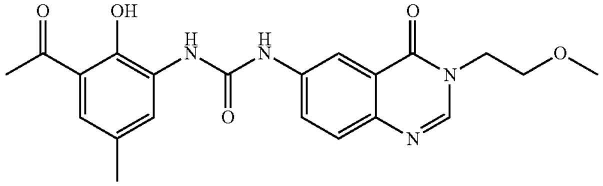 [SMILES: COCCn1cnc2ccc(NC(=O)Nc3cc(C)cc(C(C)=O)c3O)cc2c1=O] | 1-(3-acetyl-2-hydroxy-5-methylphenyl)-3-(3-(2-methoxyethyl)-4-oxo-3,4-dihydroquinazolin-6-yl)urea |
| 26 | 35 | 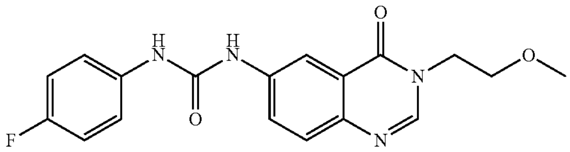 [SMILES: COCCn1cnc2ccc(NC(=O)Nc3ccc(F)cc3)cc2c1=O] | 1-(4-fluorophenyl)-3-(3-(2-methoxyethyl)-4-oxo-3,4-dihydroquinazolin-6-yl)urea |
| 27 | 36 | 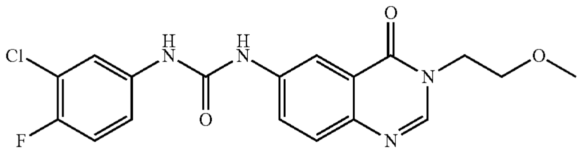 [SMILES: COCCn1cnc2ccc(NC(=O)Nc3ccc(F)c(Cl)c3)cc2c1=O] | 1-(3-chloro-4-fluorophenyl)-3-(3-(2-methoxyethyl)-4-oxo-3,4-dihydroquinazolin-6-yl)urea |
| 28 | 37 | 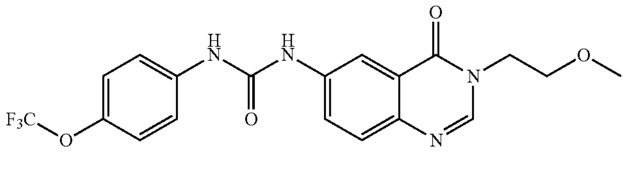 [SMILES: COCCn1cnc2ccc(NC(=O)Nc3ccc(OC(F)(F)F)cc3)cc2c1=O] | 1-(3-(2-methoxyethyl)-4-oxo-3,4-dihydroquinazolin-6-yl)-3-(4-(trifluoromethoxy)phenyl)urea |

TABLE 1-continued

Structure of the compounds disclosed

| Serial No. | Compound No. | Structure | IUPAC Name |
|---|---|---|---|
| 29 | 38 | 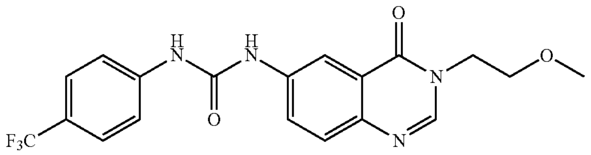 | 1-(3-(2-methoxyethyl)-4-oxo-3,4-dihydroquinazolin-6-yl)-3-(4-(trifluoromethyl)phenyl)urea |
| 30 | 39 | 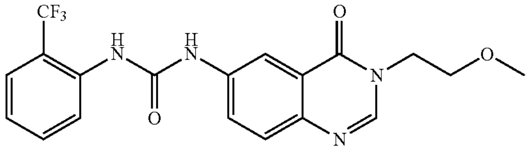 [SMILES: COCCn1cnc2ccc(NC(=O)Nc3ccccc3C(F)(F)F)cc2c1=O] | 1-(3-(2-methoxyethyl)-4-oxo-3,4-dihydroquinazolin-6-yl)-3-(2-(trifluoromethyl)phenyl)urea |
| 31 | 40 | 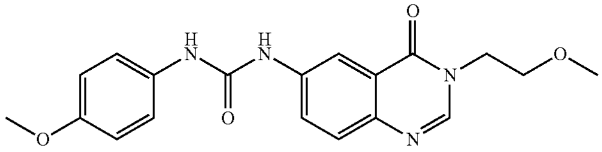 | 1-(3-(2-methoxyethyl)-4-oxo-3,4-dihydroquinazolin-6-yl)-3-(4-methoxyphenyl)urea |
| 32 | 41 | 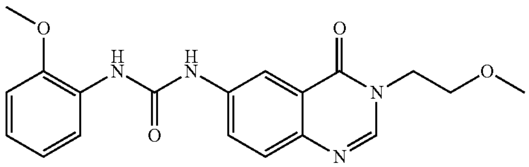 [SMILES: COCCn1cnc2ccc(NC(=O)Nc3ccccc3OC)cc2c1=O] | 1-(3-(2-methoxyethyl)-4-oxo-3,4-dihydroquinazolin-6-yl)-3-(2-methoxyphenyl)urea |
| 33 | 42 | 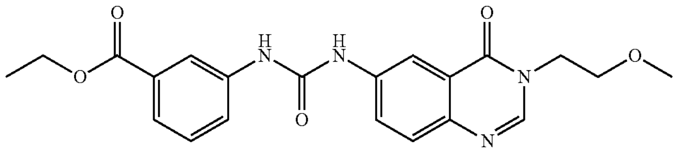 [SMILES: CCOC(=O)c1cccc(NC(=O)Nc2ccc3ncn(CCOC)c(=O)c3c2)c1] | ethyl 3-(3-(3-(2-methoxyethyl)-4-oxo-3,4-dihydroquinazolin-6-yl)ureido)benzoate |
| 34 | 42a | 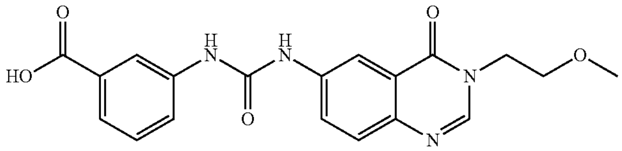 [SMILES: COCCn1cnc2ccc(NC(=O)Nc3cccc(C(=O)O)c3)cc2c1=O] | 3-(3-(3-(2-methoxyethyl)-4-oxo-3,4-dihydroquinazolin-6-yl)ureido)benzoic acid |
| 35 | 45 | 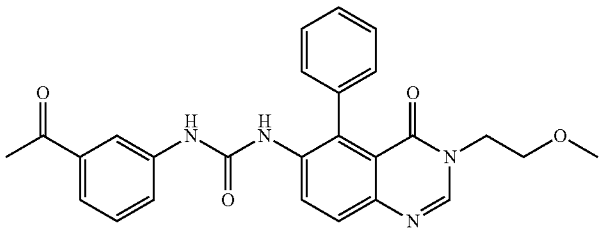 [SMILES: COCCn1cnc2ccc(NC(=O)Nc3cccc(C(C)=O)c3)c(-c3ccccc3)c2c1=O] | 1-(3-acetylphenyl)-3-(3-(2-methoxyethyl)-4-oxo-5-phenyl-3,4-dihydroquinazolin-6-yl)urea |
| 36 | 47 | 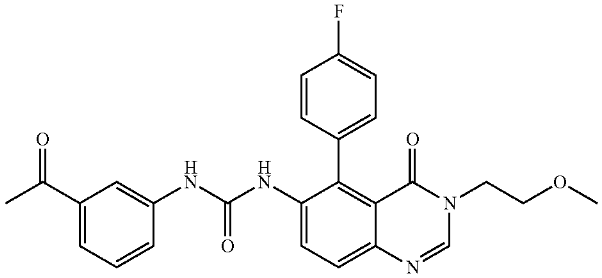 [SMILES: COCCn1cnc2ccc(NC(=O)Nc3cccc(C(C)=O)c3)c(-c3ccc(F)cc3)c2c1=O] | 1-(3-acetylphenyl)-3-(5-(4-fluorophenyl)-3-(2-methoxyethyl)-4-oxo-3,4-dihydroquinazolin-6-yl)urea |

TABLE 1-continued

| Serial No. | Compound No. | Structure | IUPAC Name |
| --- | --- | --- | --- |
| Structure of the compounds disclosed | | | |
| 37 | 49 | 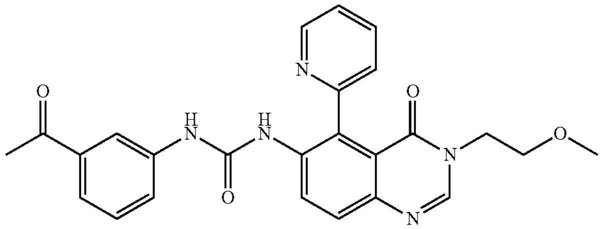 [SMILES: COCCn1cnc2ccc(NC(=O)Nc3cccc(C(C)=O)c3)c(-c3ccccn3)c2c1=O] | 1-(3-acetylphenyl)-3-(3-(2-methoxyethyl)-4-oxo-5-(pyridin-2-yl)-3,4-dihydroquinazolin-6-yl)urea |
| 38 | 51 | 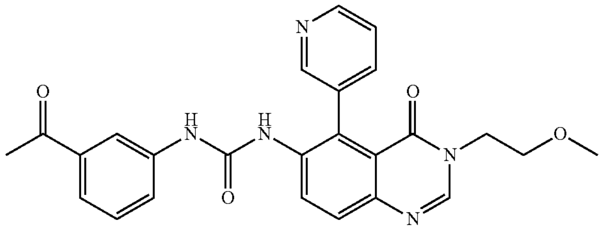 [SMILES: COCCn1cnc2ccc(NC(=O)Nc3cccc(C(C)=O)c3)c(-c3cccnc3)c2c1=O] | 1-(3-acetylphenyl)-3-(3-(2-methoxyethyl)-4-oxo-5-(pyridin-3-yl)-3,4-dihydroquinazolin-6-yl)urea |
| 39 | 53 | 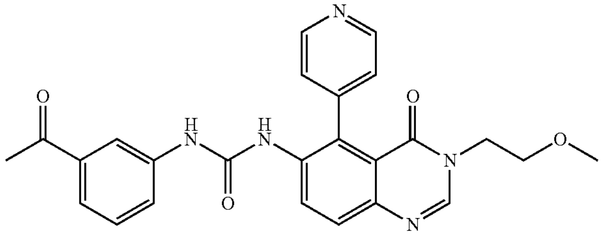 [SMILES: COCCn1cnc2ccc(NC(=O)Nc3cccc(C(C)=O)c3)c(-c3ccncc3)c2c1=O] | 1-(3-acetylphenyl)-3-(3-(2-methoxyethyl)-4-oxo-5-(pyridin-4-yl)-3,4-dihydroquinazolin-6-yl)urea |
| 40 | 55 | 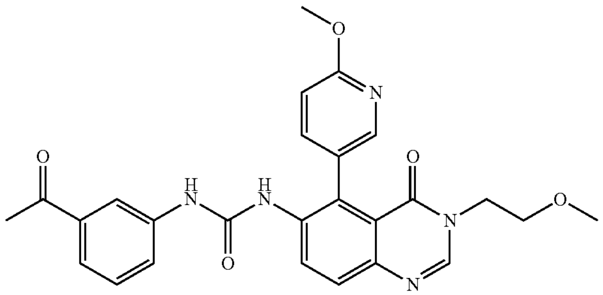 [SMILES: COCCn1cnc2ccc(NC(=O)Nc3cccc(C(C)=O)c3)c(-c3ccc(OC)nc3)c2c1=O] | 1-(3-acetylphenyl)-3-(3-(2-methoxyethyl)-5-(6-methoxypyridin-3-yl)-4-oxo-3,4-dihydroquinazolin-6-yl)urea |
| 41 | 57 | 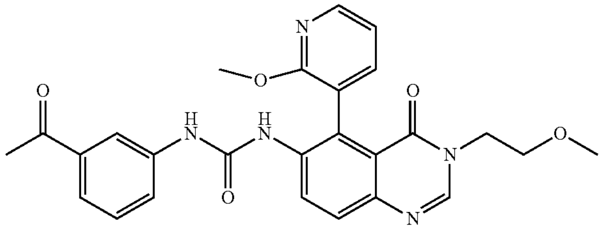 [SMILES: COCCn1cnc2ccc(NC(=O)Nc3cccc(C(C)=O)c3)c(-c3cccnc3OC)c2c1=O] | 1-(3-acetylphenyl)-3-(3-(2-methoxyethyl)-5-(2-methoxypyridin-3-yl)-4-oxo-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 42 | 59 | 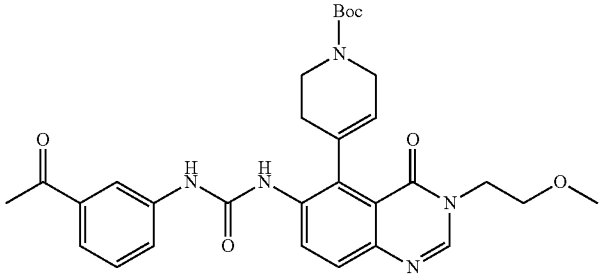 [SMILES: COCCn1cnc2ccc(NC(=O)Nc3cccc(C(C)=O)c3)c(C3=CCN(C(=O)OC(C)(C)C)CC3)c2c1=O] | tert-butyl 4-(6-(3-(3-acetylphenyl)ureido)-3-(2-methoxyethyl)-4-oxo-3,4-dihydroquinazolin-5-yl)-5,6-dihydropyridine-1(2H)-carboxylate |
| 43 | 60 | 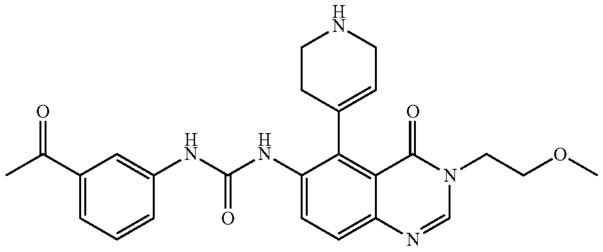 [SMILES: COCCn1cnc2ccc(NC(=O)Nc3cccc(C(C)=O)c3)c(C3=CCNCC3)c2c1=O] | 1-(3-acetylphenyl)-3-(3-(2-methoxyethyl)-4-oxo-5-(1,2,3,6-tetrahydropyridin-4-yl)-3,4-dihydroquinazolin-6-yl)urea |
| 44 | 61 | 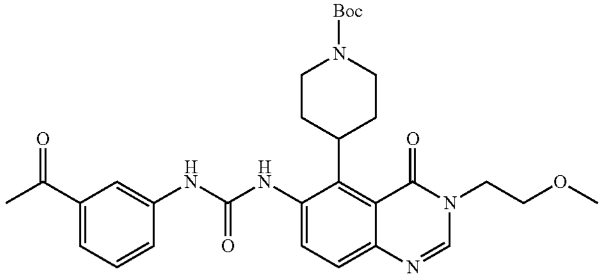 [SMILES: COCCn1cnc2ccc(NC(=O)Nc3cccc(C(C)=O)c3)c(C3CCN(C(=O)OC(C)(C)C)CC3)c2c1=O] | tert-butyl 4-(6-(3-(3-acetylphenyl)ureido)-3-(2-methoxyethyl)-4-oxo-3,4-dihydroquinazolin-5-yl)piperidine-1-carboxylate |
| 45 | 62 | 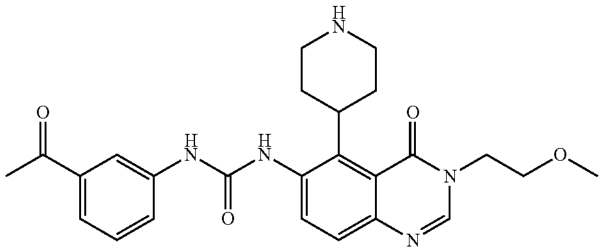 [SMILES: COCCn1cnc2ccc(NC(=O)Nc3cccc(C(C)=O)c3)c(C3CCNCC3)c2c1=O] | 1-(3-acetylphenyl)-3-(3-(2-methoxyethyl)-4-oxo-5-(piperidin-4-yl)-3,4-dihydroquinazolin-6-yl)urea |
| 46 | 64 | 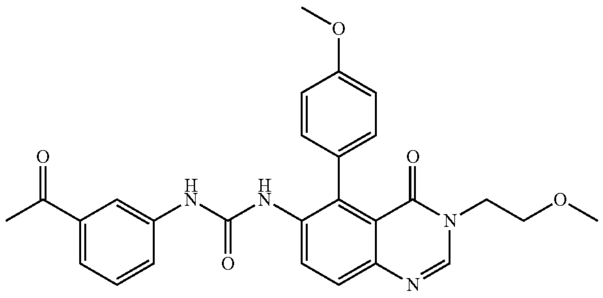 [SMILES: COCCn1cnc2ccc(NC(=O)Nc3cccc(C(C)=O)c3)c(-c3ccc(OC)cc3)c2c1=O] | 1-(3-acetylphenyl)-3-(3-(2-methoxyethyl)-5-(4-methoxyphenyl)-4-oxo-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 47 | 66 | 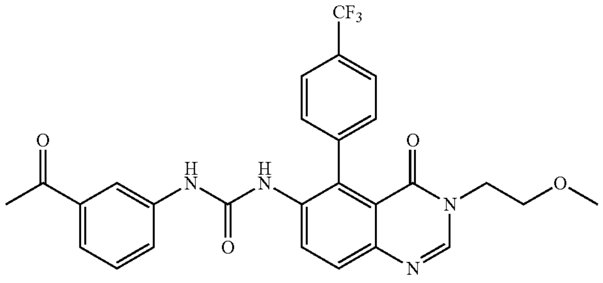 [SMILES: COCCn1cnc2ccc(NC(=O)Nc3cccc(C(C)=O)c3)c(-c3ccc(C(F)(F)F)cc3)c2c1=O] | 1-(3-acetylphenyl)-3-(3-(2-methoxyethyl)-4-oxo-5-(4-(trifluoromethyl)phenyl)-3,4-dihydroquinazolin-6-yl)urea |
| 48 | 68 | 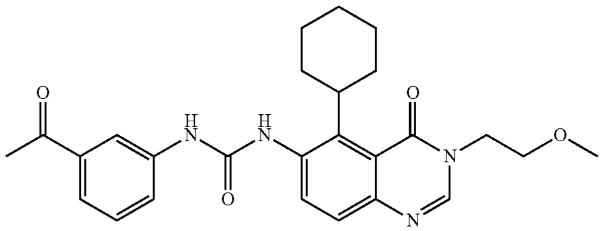 [SMILES: COCCn1cnc2ccc(NC(=O)Nc3cccc(C(C)=O)c3)c(C3CCCCC3)c2c1=O] | 1-(3-acetylphenyl)-3-(5-cyclohexyl-3-(2-methoxyethyl)-4-oxo-3,4-dihydroquinazolin-6-yl)urea |
| 49 | 70 | 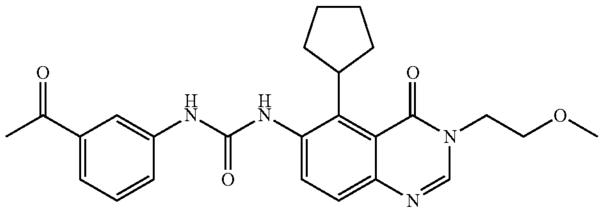 [SMILES: COCCn1cnc2ccc(NC(=O)Nc3cccc(C(C)=O)c3)c(C3CCCC3)c2c1=O] | 1-(3-acetylphenyl)-3-(5-cyclopentyl-3-(2-methoxyethy])-4-oxo-3,4-dihydroquinazolin-6-yl)urea |
| 50 | 72 | 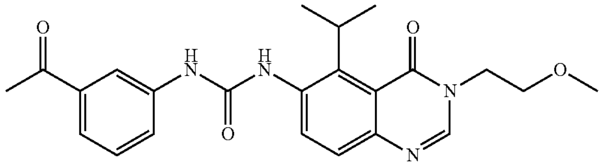 [SMILES: COCCn1cnc2ccc(NC(=O)Nc3cccc(C(C)=O)c3)c(C(C)C)c2c1=O] | 1-(3-acetylphenyl)-3-(5-isopropyl-3-(2-methoxyethyl)-4-oxo-3,4-dihydroquinazolin-6-yl)urea |
| 51 | 73 | 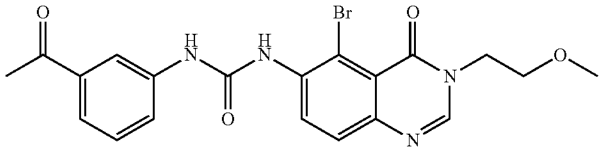 [SMILES: COCCn1cnc2ccc(NC(=O)Nc3cccc(C(C)=O)c3)c(Br)c2c1=O] | 1-(3-acetylphenyl)-3-(5-bromo-3-(2-methoxyethyl)-4-oxo-3,4-dihydroquinazolin-6-yl)urea |
| 52 | 83 | 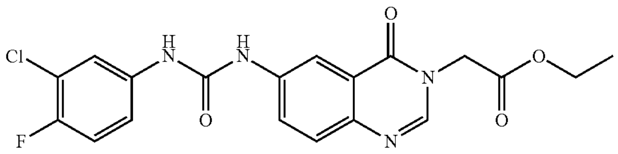 [SMILES: CCOC(=O)Cn1cnc2ccc(NC(=O)Nc3ccc(F)c(Cl)c3)cc2c1=O] | ethyl 2-(6-(3-(3-chloro-4-fluorophenyl)ureido)-4-oxoquinazolin-3(4H)-yl)acetate |
| 53 | 84 | 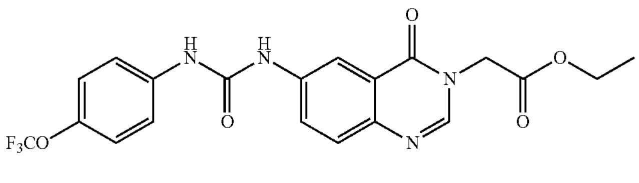 [SMILES: CCOC(=O)Cn1cnc2ccc(NC(=O)Nc3ccc(OC(F)(F)F)cc3)cc2c1=O] | ethyl 2-(4-oxo-6-(3-(4-(trifluoromethoxy)phenyl)ureido)quinazolin-3(4H)-yl)acetate |

TABLE 1-continued

Structure of the compounds disclosed

| Serial No. | Compound No. | Structure | IUPAC Name |
|---|---|---|---|
| 54 | 85 | 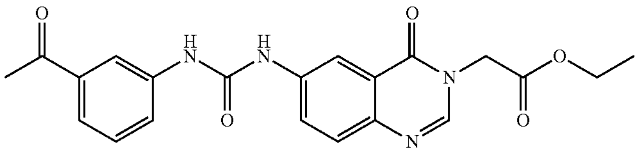 [SMILES: CCOC(=O)Cn1cnc2ccc(NC(=O)Nc3cccc(C(C)=O)c3)cc2c1=O] | ethyl 2-(6-(3-(3-acetylphenyl)ureido)-4-oxoquinazolin-3(4H)-yl)acetate |
| 55 | 85a | 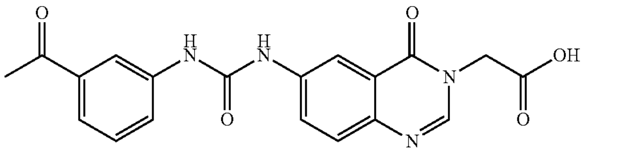 [SMILES: CC(=O)c1cccc(NC(=O)Nc2ccc3ncn(CC(=O)O)c(=O)c3c2)c1] | 2-(6-(3-(3-acetylphenyl)ureido)-4-oxoquinazolin-3(4H)-yl)acetic acid |
| 56 | 89 | 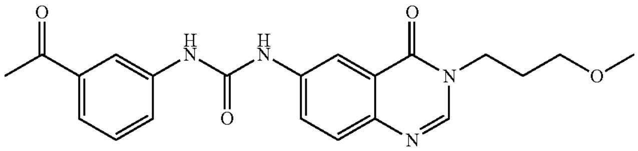 [SMILES: COCCCn1cnc2ccc(NC(=O)Nc3cccc(C(C)=O)c3)cc2c1=O] | 1-(3-acetylphenyl)-3-(3-(3-methoxypropyl)-4-oxo-3,4-dihydroquinazolin-6-yl)urea |
| 57 | 93 | 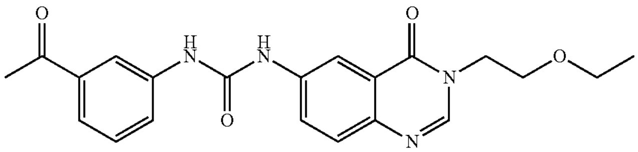 [SMILES: CCOCCn1cnc2ccc(NC(=O)Nc3cccc(C(C)=O)c3)cc2c1=O] | 1-(3-acetylphenyl)-3-(3-(2-ethoxyethyl)-4-oxo-3,4-dihydroquinazolin-6-yl)urea |
| 58 | 94 | 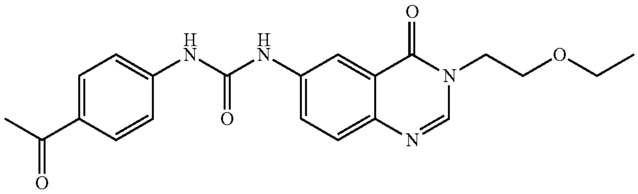 [SMILES: CCOCCn1cnc2ccc(NC(=O)Nc3ccc(C(C)=O)cc3)cc2c1=O] | 1-(4-acetylphenyl)-3-(3-(2-ethoxyethyl)-4-oxo-3,4-dihydroquinazolin-6-yl)urea |
| 59 | 98 | 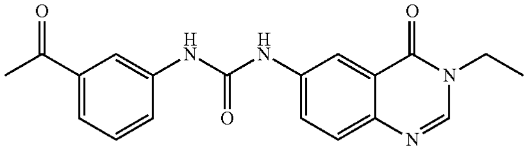 [SMILES: CCn1cnc2ccc(NC(=O)Nc3cccc(C(C)=O)c3)cc2c1=O] | 1-(3-acetylphenyl)-3-(3-ethyl-4-oxo-3,4-dihydroquinazolin-6-yl)urea |
| 60 | 99 | 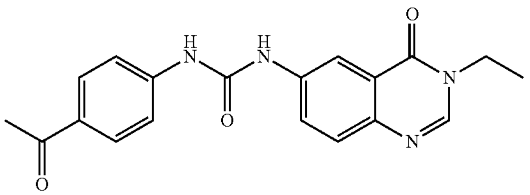 [SMILES: CCn1cnc2ccc(NC(=O)Nc3ccc(C(C)=O)cc3)cc2c1=O] | 1-(4-acetylphenyl)-3-(3-ethyl-4-oxo-3,4-dihydroquinazolin-6-yl)urea |
| 61 | 103 | 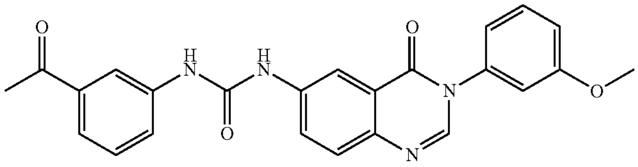 [SMILES: COc1cccc(-n2cnc3ccc(NC(=O)Nc4cccc(C(C)=O)c4)cc3c2=O)c1] | 1-(3-acetylphenyl)-3-(3-(3-methoxyphenyl)-4-oxo-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 62 | 107 | 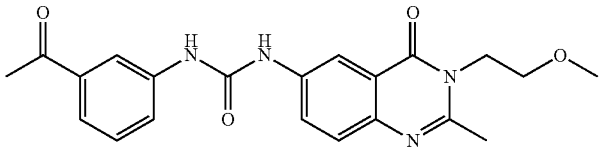 [SMILES: COCCn1c(C)nc2ccc(NC(=O)Nc3cccc(C(C)=O)c3)cc2c1=O] | 1-(3-acetylphenyl)-3-(3-(2-methoxyethyl)-2-methyl-4-oxo-3,4-dihydroquinazolin-6-yl)urea |
| 63 | 111 | 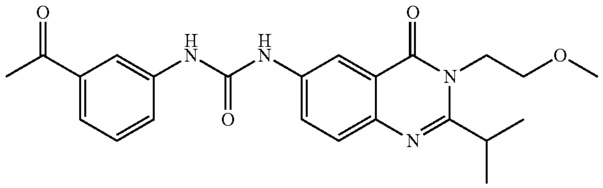 [SMILES: COCCn1c(C(C)C)nc2ccc(NC(=O)Nc3cccc(C(C)=O)c3)cc2c1=O] | 1-(3-acetylphenyl)-3-(2-isopropyl-3-(2-methoxyethyl)-4-oxo-3,4-dihydroquinazolin-6-yl)urea |
| 64 | 115 | 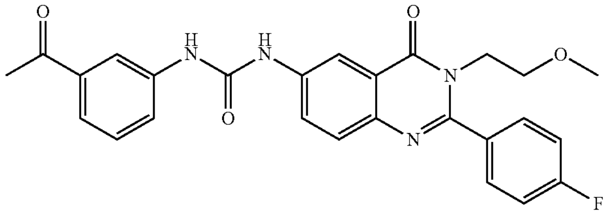 [SMILES: COCCn1c(-c2ccc(F)cc2)nc2ccc(NC(=O)Nc3cccc(C(C)=O)c3)cc2c1=O] | 1-(3-acetylphenyl)-3-(2-(4-fluorophenyl)-3-(2-methoxyethyl)-4-oxo-3,4-dihydroquinazolin-6-yl)urea |
| 65 | 119 | 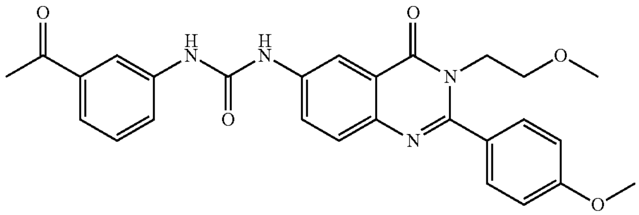 [SMILES: COCCn1c(-c2ccc(OC)cc2)nc2ccc(NC(=O)Nc3cccc(C(C)=O)c3)cc2c1=O] | 1-(3-acetylphenyl)-3-(3-(2-methoxyethyl)-2-(4-methoxyphenyl)-4-oxo-3,4-dihydroquinazolin-6-yl)urea |
| 66 | 123 | 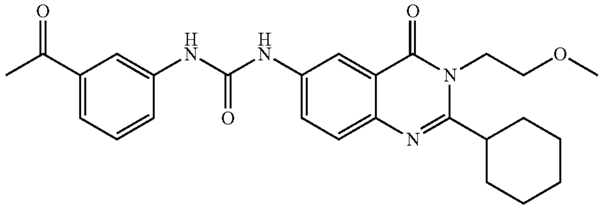 [SMILES: COCCn1c(C2CCCCC2)nc2ccc(NC(=O)Nc3cccc(C(C)=O)c3)cc2c1=O] | 1-(3-acetylphenyl)-3-(2-cyclohexyl-3-(2-methoxyethyl)-4-oxo-3,4-dihydroquinazolin-6-yl)urea |
| 67 | 127 | 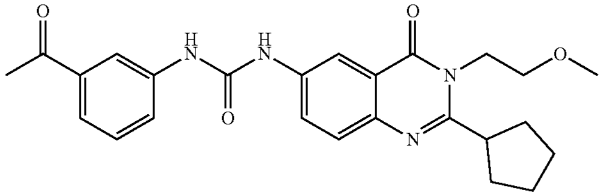 [SMILES: COCCn1c(C2CCCC2)nc2ccc(NC(=O)Nc3cccc(C(C)=O)c3)cc2c1=O] | 1-(3-acetylphenyl)-3-(2-cyclopentyl-3-(2-methoxyethyl)-4-oxo-3,4-dihydroquinazolin-6-yl)urea |
| 68 | 131 | 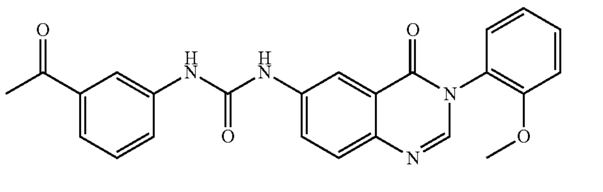 [SMILES: COc1ccccc1-n1cnc2ccc(NC(=O)Nc3cccc(C(C)=O)c3)cc2c1=O] | 1-(3-acetylphenyl)-3-(3-(2-methoxyphenyl)-4-oxo-3,4-dihydroquinazolin-6-yl)urea |

TABLE 1-continued

Structure of the compounds disclosed

| Serial No. | Compound No. | Structure | IUPAC Name |
|---|---|---|---|
| 69 | 135 | 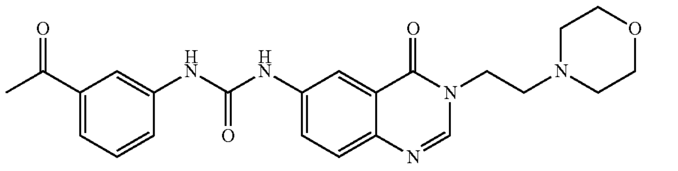 [SMILES: CC(=O)c1cccc(NC(=O)Nc2ccc3ncn(CCN4CCOCC4)c(=O)c3c2)c1] | 1-(3-acetylphenyl)-3-(3-(2-morpholinoethyl)-4-oxo-3,4-dihydroquinazolin-6-yl)urea |
| 70 | 139 | 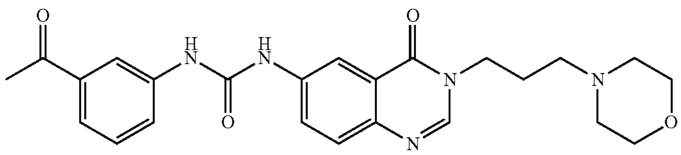 [SMILES: CC(=O)c1cccc(NC(=O)Nc2ccc3ncn(CCCN4CCOCC4)c(=O)c3c2)c1] | 1-(3-acetylphenyl)-3-(3-(3-morpholinopropyl)-4-oxo-3,4-dihydroquinazolin-6-yl)urea |
| 71 | 143 | 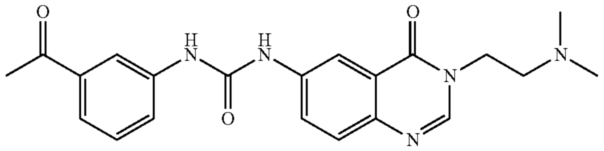 [SMILES: CC(=O)c1cccc(NC(=O)Nc2ccc3ncn(CCN(C)C)c(=O)c3c2)c1] | 1-(3-acetylphenyl)-3-(3-(2-(dimethylamino)ethyl)-4-oxo-3,4-dihydroquinazolin-6-yl)urea |
| 72 | 147 | 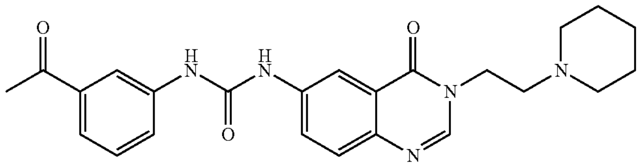 [SMILES: CC(=O)c1cccc(NC(=O)Nc2ccc3ncn(CCN4CCCCC4)c(=O)c3c2)c1] | 1-(3-acetylphenyl)-3-(4-oxo-3-(2-(piperidin-1-yl)ethyl)-3,4-dihydroquinazolin-6-yl)urea |
| 73 | 151 | 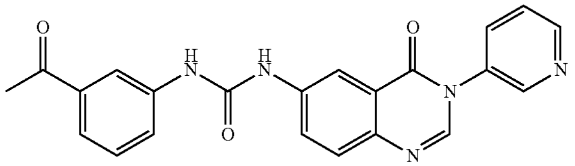 [SMILES: CC(=O)c1cccc(NC(=O)Nc2ccc3ncn(-c4cccnc4)c(=O)c3c2)c1] | 1-(3-acetylphenyl)-3-(4-oxo-3-(pyridin-4-yl)-3,4-dihydroquinazolin-6-yl)urea |
| 74 | 155 | 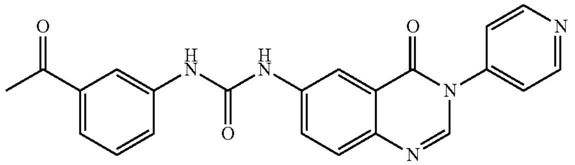 [SMILES: CC(=O)c1cccc(NC(=O)Nc2ccc3ncn(-c4ccncc4)c(=O)c3c2)c1] | 1-(3-acetylphenyl)-3-(4-oxo-3-(pyridin-3-yl)-3,4-dihydroquinazolin-6-yl)urea |
| 75 | 159 | 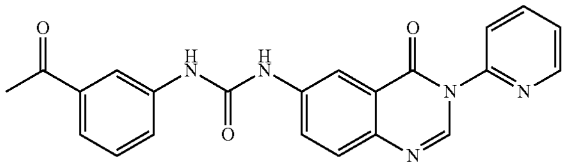 [SMILES: CC(=O)c1cccc(NC(=O)Nc2ccc3ncn(-c4ccccn4)c(=O)c3c2)c1] | 1-(3-acetylphenyl)-3-(4-oxo-3-(pyridin-2-yl)-3,4-dihydroquinazolin-6-yl)urea |
| 76 | 163 | 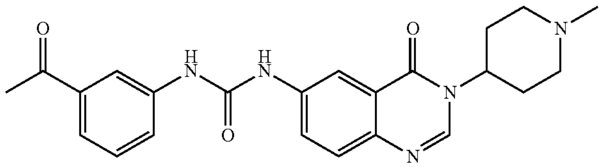 [SMILES: CC(=O)c1cccc(NC(=O)Nc2ccc3ncn(C4CCN(C)CC4)c(=O)c3c2)c1] | 1-(3-acetylphenyl)-3-(3-(1-methylpiperidin-4-yl)-4-oxo-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 77 | 167 | 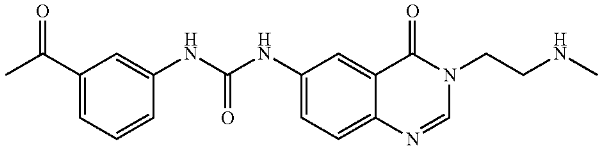 | 1-(3-acetylphenyl)-3-(3-(2-(methylamino)ethyl)-4-oxo-3,4-dihydroquinazolin-6-yl)urea |
| 78 | 171 | 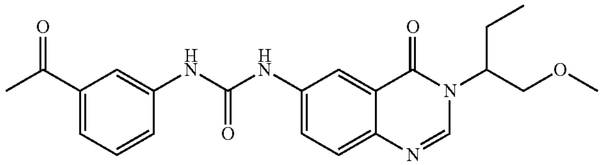 [SMILES: CCC(COC)n1cnc2ccc(NC(=O)Nc3cccc(C(C)=O)c3)cc2c1=O] | 1-(3-acetylphenyl)-3-(3-(1-methoxybutan-2-yl)-4-oxo-3,4-dihydroquinazolin-6-yl)urea |
| 79 | 175 | 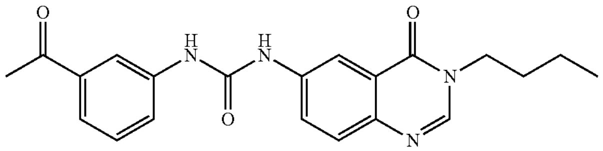 | 1-(3-acetylphenyl)-3-(3-butyl-4-oxo-3,4-dihydroquinazolin-6-yl)urea |
| 80 | 179 | 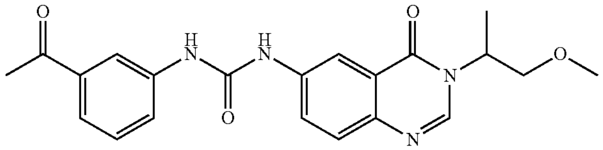 | 1-(3-acetylphenyl)-3-(3-(1-methoxypropan-2-yl)-4-oxo-3,4-dihydroquinazolin-6-yl)urea |
| 81 | 183 | 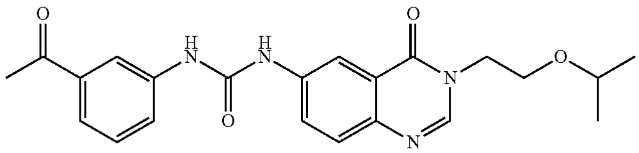 | 1-(3-acetylphenyl)-3-(3-(2-isopropoxyethyl)-4-oxo-3,4-dihydroquinazolin-6-yl)urea |
| 82 | 187 | 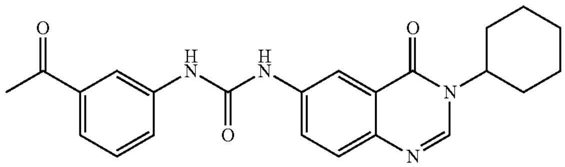 [SMILES: CC(=O)c1cccc(NC(=O)Nc2ccc3ncn(C4CCCCC4)c(=O)c3c2)c1] | 1-(3-acetylphenyl)-3-(3-cyclohexyl-4-oxo-3,4-dihydroquinazolin-6-yl)urea |
| 83 | 192 | 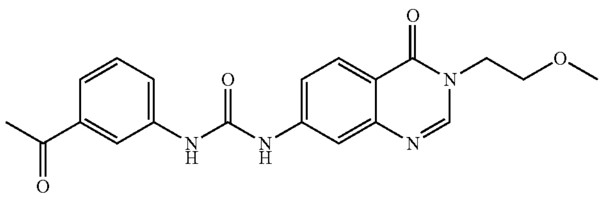 [SMILES: COCCn1cnc2cc(NC(=O)Nc3cccc(C(C)=O)c3)ccc2c1=O] | 1-(3-acetylphenyl)-3-(3-(2-methoxyethyl)-4-oxo-3,4-dihydroquinazolin-7-yl)urea |
| 84 | 193 | 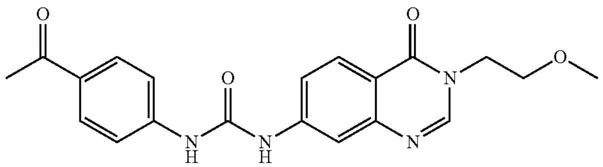 [SMILES: COCCn1cnc2cc(NC(=O)Nc3ccc(C(C)=O)cc3)ccc2c1=O] | 1-(4-acetylphenyl)-3-(3-(2-methoxyethyl)-4-oxo-3,4-dihydroquinazolin-7-yl)urea |

TABLE 1-continued

Structure of the compounds disclosed

| Serial No. | Compound No. | Structure | IUPAC Name |
| --- | --- | --- | --- |
| 85 | 194 | 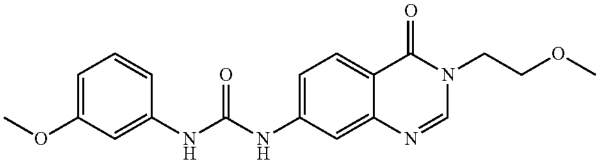 | 1-(3-(2-methoxyethyl)-4-oxo-3,4-dihydroquinazolin-7-yl)-3-(3-methoxyphenyl)urea |
| 86 | 195 | 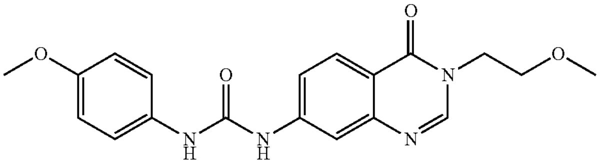 | 1-(3-(2-methoxyethyl)-4-oxo-3,4-dihydroquinazolin-7-yl)-3-(4-methoxyphenyl)urea |
| 87 | 196 | 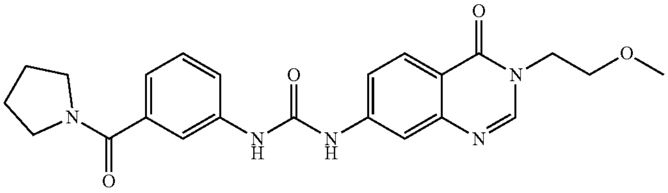 [SMILES: COCCn1cnc2cc(NC(=O)Nc3cccc(C(=O)N4CCCC4)c3)ccc2c1=O] | 1-(3-(2-methoxyethyl)-4-oxo-3,4-dihydroquinazolin-7-yl)-3-(3-(pyrrolidine-1-carbonyl)phenyl)urea |
| 88 | 197 | 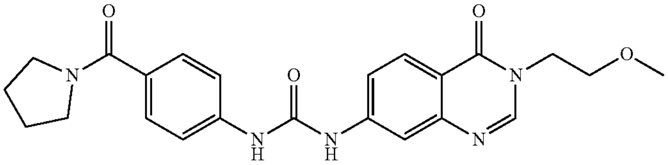 [SMILES: COCCn1cnc2cc(NC(=O)Nc3ccc(C(=O)N4CCCC4)cc3)ccc2c1=O] | 1-(3-(2-methoxyethyl)-4-oxo-3,4-dihydroquinazolin-7-yl)-3-(4-(pyrrolidine-1-carbonyl)phenyl)urea |
| 89 | 198 | 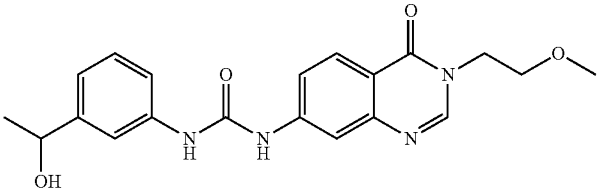 [SMILES: COCCn1cnc2cc(NC(=O)Nc3cccc(C(C)O)c3)ccc2c1=O] | 1-(3-(1-hydroxyethyl)phenyl)-3-(3-(2-methoxyethyl)-4-oxo-3,4-dihydroquinazolin-7-yl)urea |
| 90 | 199 | 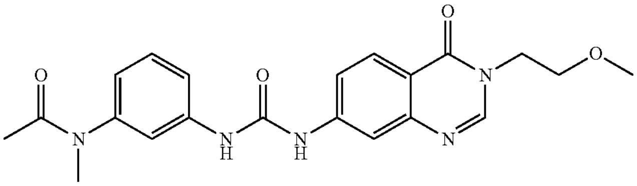 [SMILES: COCCn1cnc2cc(NC(=O)Nc3cccc(N(C)C(C)=O)c3)ccc2c1=O] | N-(3-(3-(3-(2-methoxyethyl)-4-oxo-3,4-dihydroquinazolin-7-yl)ureido)phenyl)-N-methylacetamide |
| 91 | 203 | 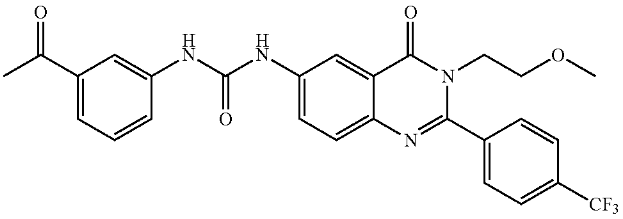 [SMILES: COCCn1c(-c2ccc(C(F)(F)F)cc2)nc2ccc(NC(=O)Nc3cccc(C(C)=O)c3)cc2c1=O] | 1-(3-acetylphenyl)-3-(3-(2-methoxyethyl)-4-oxo-2-(4-(trifluoromethyl)phenyl)-3,4-dihydroquinazolin-6-yl)urea |

TABLE 1-continued

Structure of the compounds disclosed

| Serial No. | Compound No. | Structure | IUPAC Name |
|---|---|---|---|
| 92 | 207 | 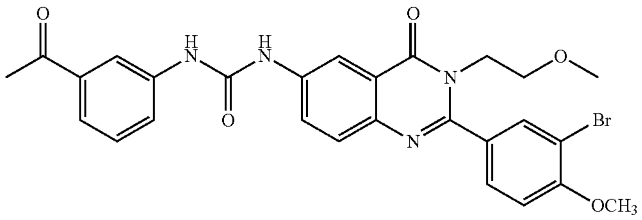 [SMILES: COCCn1c(-c2ccc(OC)c(Br)c2)nc2ccc(NC(=O)Nc3cccc(C(C)=O)c3)cc2c1=O] | 1-(3-acetylphenyl)-3-(2-(3-bromo-4-methoxyphenyl)-3-(2-methoxyethyl)-4-oxo-3,4-dihydroquinazolin-6-yl)urea |
| 93 | 211 | 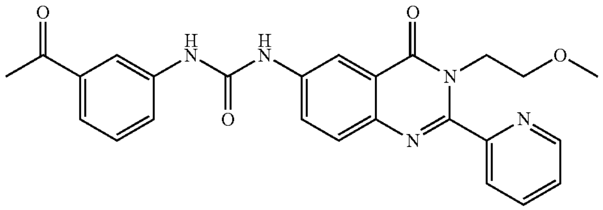 [SMILES: COCCn1c(-c2ccccn2)nc2ccc(NC(=O)Nc3cccc(C(C)=O)c3)cc2c1=O] | 1-(3-acetylphenyl)-3-(3-(2-methoxyethyl)-4-oxo-2-(pyridin-2-yl)-3,4-dihydroquinazolin-6-yl)urea |
| 94 | 215 | 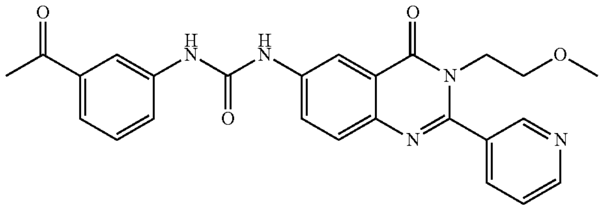 [SMILES: COCCn1c(-c2cccnc2)nc2ccc(NC(=O)Nc3cccc(C(C)=O)c3)cc2c1=O] | 1-(3-acetylphenyl)-3-(3-(2-methoxyethyl)-4-oxo-2-(pyridin-3-yl)-3,4-dihydroquinazolin-6-yl)urea |
| 95 | 219 | 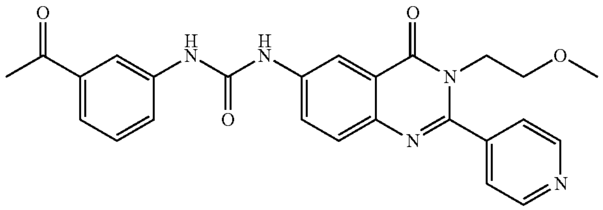 [SMILES: COCCn1c(-c2ccncc2)nc2ccc(NC(=O)Nc3cccc(C(C)=O)c3)cc2c1=O] | 1-(3-acetylphenyl)-3-(3-(2-methoxyethyl)-4-oxo-2-(pyridin-4-yl)-3,4-dihydroquinazolin-6-yl)urea |
| 96 | 223 | 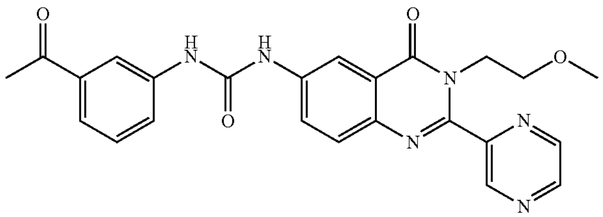 [SMILES: COCCn1c(-c2cnccn2)nc2ccc(NC(=O)Nc3cccc(C(C)=O)c3)cc2c1=O] | 1-(3-acetylphenyl)-3-(3-(2-methoxyethyl)-4-oxo-2-(pyrazin-2-yl)-3,4-dihydroquinazolin-6-yl)urea |
| 97 | 227 | 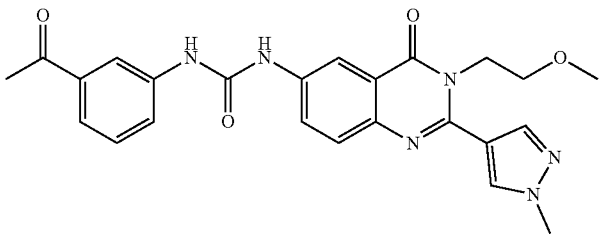 [SMILES: COCCn1c(-c2cnn(C)c2)nc2ccc(NC(=O)Nc3cccc(C(C)=O)c3)cc2c1=O] | 1-(3-acetylphenyl)-3-(3-(2-methoxyethyl)-2-(1-methyl-1H-pyrazol-4-yl)-4-oxo-3,4-dihydroquinazolin-6-yl)urea |

TABLE 1-continued

Structure of the compounds disclosed

| Serial No. | Compound No. | Structure | IUPAC Name |
|---|---|---|---|
| 98 | 232 | 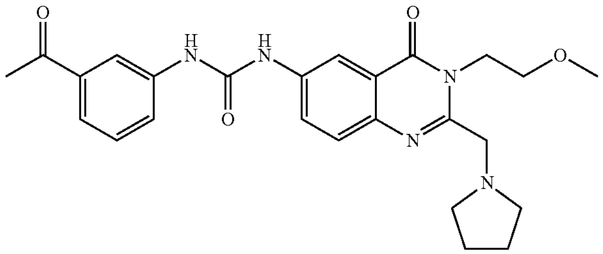 [SMILES: COCCn1c(CN2CCCC2)nc2ccc(NC(=O)Nc3cccc(C(C)=O)c3)cc2c1=O] | 1-(3-acetylphenyl)-3-(3-(2-methoxyethyl)-4-oxo-2-(pyrrolidin-1-ylmethyl)-3,4-dihydroquinazolin-6-yl)urea |
| 99 | 235 | 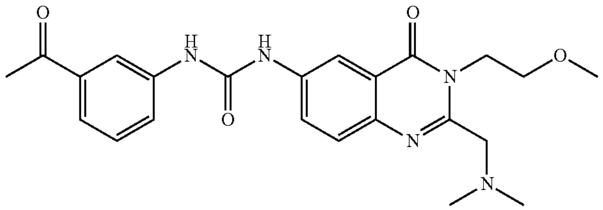 [SMILES: COCCn1c(CN(C)C)nc2ccc(NC(=O)Nc3cccc(C(C)=O)c3)cc2c1=O] | 1-(3-acetylphenyl)-3-(2-((dimethylamino)methyl)-3-(2-methoxyethyl)-4-oxo-3,4-dihydroquinazolin-6-yl)urea |
| 100 | 238 | 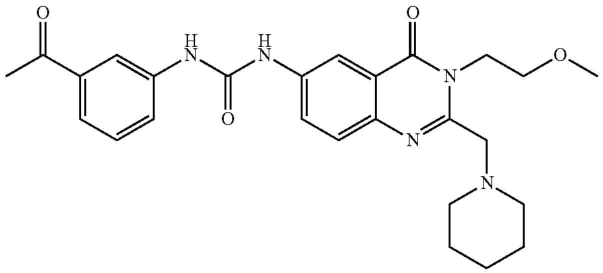 [SMILES: COCCn1c(CN2CCCCC2)nc2ccc(NC(=O)Nc3cccc(C(C)=O)c3)cc2c1=O] | 1-(3-acetylphenyl)-3-(3-(2-methoxyethyl)-4-oxo-2-(piperidin-1-ylmethyl)-3,4-dihydroquinazolin-6-yl)urea |
| 101 | 241 | 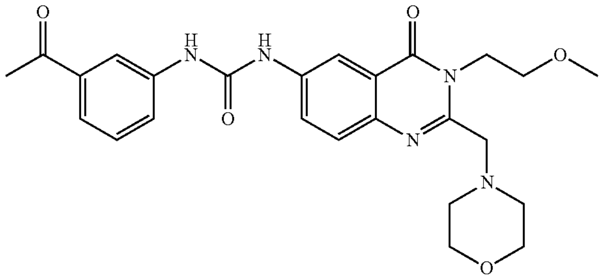 [SMILES: COCCn1c(CN2CCOCC2)nc2ccc(NC(=O)Nc3cccc(C(C)=O)c3)cc2c1=O] | 1-(3-acetylphenyl)-3-(3-(2-methoxyethyl)-2-(morpholinomethyl)-4-oxo-3,4-dihydroquinazolin-6-yl)urea |
| 102 | 244 | 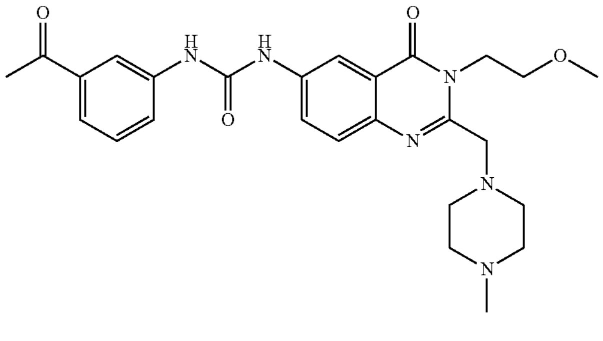 [SMILES: COCCn1c(CN2CCN(C)CC2)nc2ccc(NC(=O)Nc3cccc(C(C)=O)c3)cc2c1=O] | 1-(3-acetylphenyl)-3-(3-(2-methoxyethyl)-2-((4-methylpiperazin-1-yl)methyl)-4-oxo-3,4-dihydroquinazolin-6-yl)urea |
| 103 | 247 | 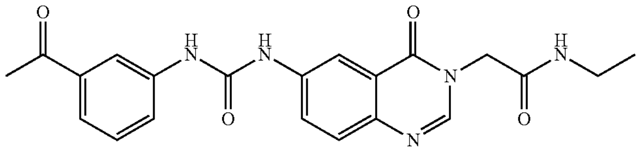 | 2-(6-(3-(3-acetylphenyl)ureido)-4-oxoquinazolin-3(4H)-yl)-N-ethylacetamide |

TABLE 1-continued

| Serial No. | Compound No. | Structure | IUPAC Name |
|---|---|---|---|
| 104 | 250 | 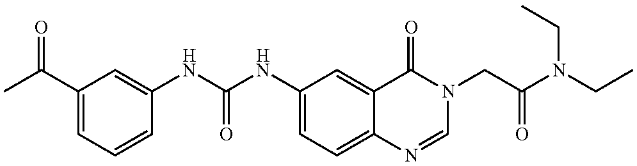 [SMILES: CCN(CC)C(=O)Cn1cnc2ccc(NC(=O)Nc3cccc(C(C)=O)c3)cc2c1=O] | 2-(6-(3-(3-acetylphenyl)ureido)-4-oxoquinazolin-3(4H)-yl)-N,N-diethylacetamide |
| 105 | 253 | 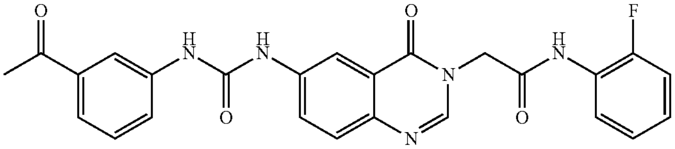 [SMILES: CC(=O)c1cccc(NC(=O)Nc2ccc3ncn(CC(=O)Nc4ccccc4F)c(=O)c3c2)c1] | 2-(6-(3-(3-acetylphenyl)ureido)-4-oxoquinazolin-3(4H)-yl)-N-(2-fluorophenyl)acetamide |
| 106 | 256 | 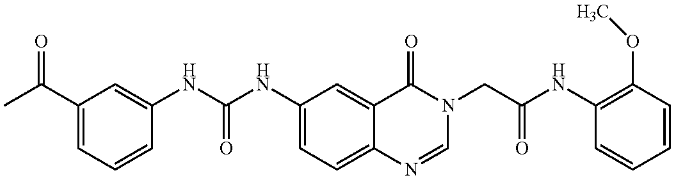 [SMILES: COc1ccccc1NC(=O)Cn1cnc2ccc(NC(=O)Nc3cccc(C(C)=O)c3)cc2c1=O] | 2-(6-(3-(3-acetylphenyl)ureido)-4-oxoquinazolin-3(4H)-yl)-N-(2-methoxyphenyl)acetamide |
| 107 | 259 | 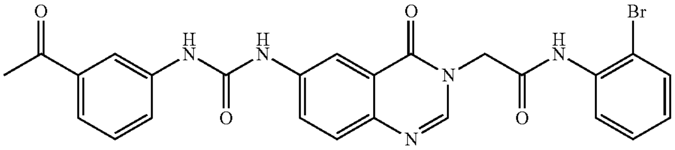 [SMILES: CC(=O)c1cccc(NC(=O)Nc2ccc3ncn(CC(=O)Nc4ccccc4Br)c(=O)c3c2)c1] | 2-(6-(3-(3-acetylphenyl)ureido)-4-oxoquinazolin-3(4H)-yl)-N-(2-bromophenyl)acetamide |
| 108 | 262 | 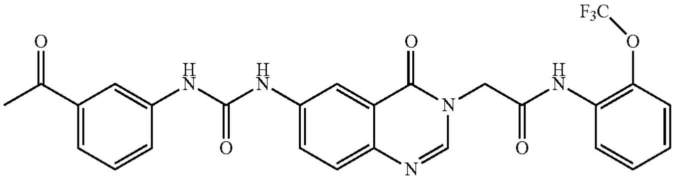 [SMILES: CC(=O)c1cccc(NC(=O)Nc2ccc3ncn(CC(=O)Nc4ccccc4OC(F)(F)F)c(=O)c3c2)c1] | 2-(6-(3-(3-acetylphenyl)ureido)-4-oxoquinazolin-3(4H)-yl)-N-(2-(trifluoromethoxy)phenyl)acetamide |
| 109 | 265 | 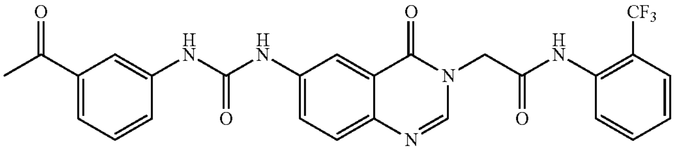 [SMILES: CC(=O)c1cccc(NC(=O)Nc2ccc3ncn(CC(=O)Nc4ccccc4C(F)(F)F)c(=O)c3c2)c1] | 2-(6-(3-(3-acetylphenyl)ureido)-4-oxoquinazolin-3(4H)-yl)-N-(2-(trifluoromethyl)phenyl)acetamide |
| 110 | 268 | 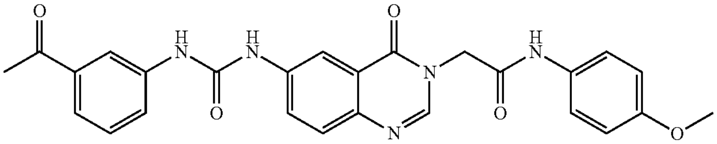 [SMILES: COc1ccc(NC(=O)Cn2cnc3ccc(NC(=O)Nc4cccc(C(C)=O)c4)cc3c2=O)cc1] | 2-(6-(3-(3-acetylphenyl)ureido)-4-oxoquinazolin-3(4H)-yl)-N-(4-methoxyphenyl)acetamide |
| 111 | 271 | 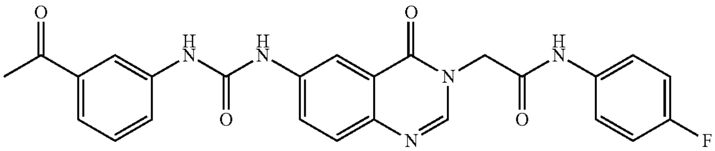 [SMILES: CC(=O)c1cccc(NC(=O)Nc2ccc3ncn(CC(=O)Nc4ccc(F)cc4)c(=O)c3c2)c1] | 2-(6-(3-(3-acetylphenyl)ureido)-4-oxoquinazolin-3(4H)-yl)-N-(4-fluorophenyl)acetamide |

TABLE 1-continued

| Structure of the compounds disclosed | | | |
|---|---|---|---|
| Serial No. | Compound No. | Structure | IUPAC Name |
| 112 | 274 | 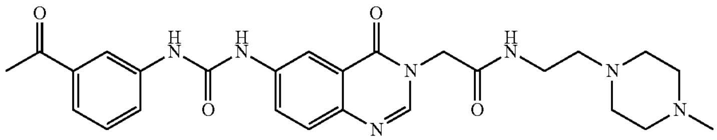 [SMILES: CC(=O)c1cccc(NC(=O)Nc2ccc3ncn(CC(=O)NCCN4CCN(C)CC4)c(=O)c3c2)c1] | 2-(6-(3-(3-acetylphenyl)ureido)-4-oxoquinazolin-3(4H)-yl)-N-(2-(4-methylpiperazin-1-yl)ethyl)acetamide |
| 113 | 277 | 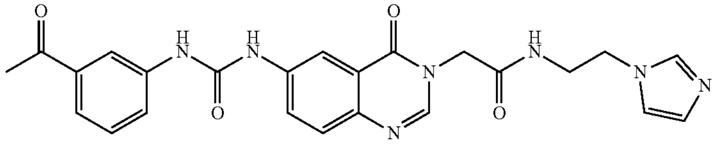 [SMILES: CC(=O)c1cccc(NC(=O)Nc2ccc3ncn(CC(=O)NCCn4ccnc4)c(=O)c3c2)c1] | N-(2-(1H-imidazol-1-yl)ethyl)-2-(6-(3-(3-acetylphenyl)ureido)-4-oxoquinazolin-3(4H)-yl)acetamide |
| 114 | 281 | 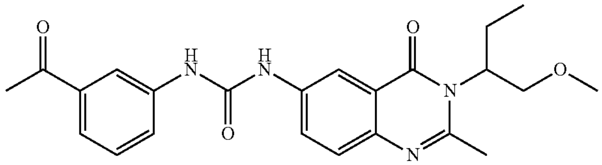 [SMILES: CCC(COC)n1c(C)nc2ccc(NC(=O)Nc3cccc(C(C)=O)c3)cc2c1=O] | 1-(3-acetylphenyl)-3-(3-(1-methoxybutan-2-yl)-2-methyl-4-oxo-3,4-dihydroquinazolin-6-yl)urea |
| 115 | 285 | 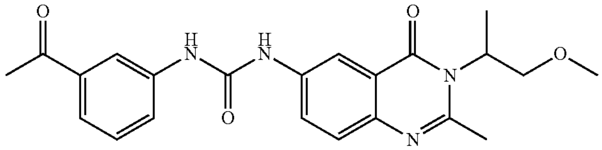 [SMILES: COCC(C)n1c(C)nc2ccc(NC(=O)Nc3cccc(C(C)=O)c3)cc2c1=O] | 1-(3-acetylphenyl)-3-(3-(1-methoxypropan-2-yl)-2-methyl-4-oxo-3,4-dihydroquinazolin-6-yl)urea |
| 116 | 289 | 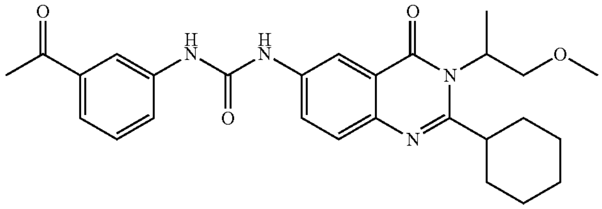 | 1-(3-acetylphenyl)-3-(2-cyclohexyl-3-(1-methoxypropan-2-yl)-4-oxo-3,4-dihydroquinazolin-6-yl)urea |
| 117 | 292 | 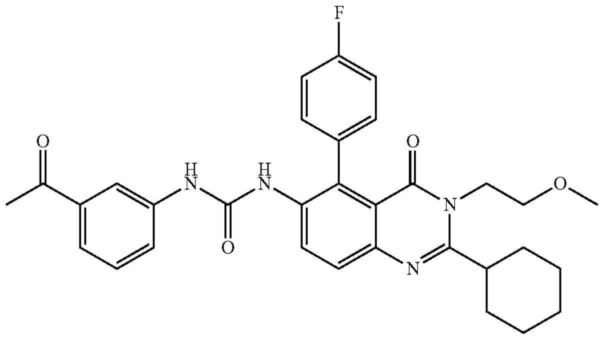 [SMILES: COCCn1c(C2CCCCC2)nc2ccc(NC(=O)Nc3cccc(C(C)=O)c3)c(-c3ccc(F)cc3)c2c1=O] | 1-(3-acetylphenyl)-3-(2-cyclohexyl-5-(4-fluorophenyl)-3-(2-methoxyethyl)-4-oxo-3,4-dihydroquinazolin-6-yl)urea |
| 118 | 295 | 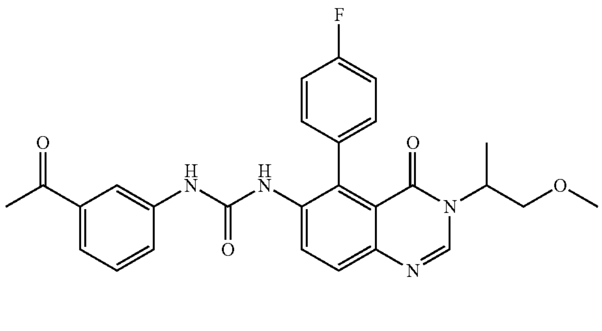 | 1-(3-acetylphenyl)-3-(5-(4-fluorophenyl)-3-(1-methoxypropan-2-yl)-4-oxo-3,4-dihydroquinazolin-6-yl)urea |

TABLE 1-continued

| Serial No. | Compound No. | Structure | IUPAC Name |
|---|---|---|---|
| | | Structure of the compounds disclosed | |
| 119 | 299 | 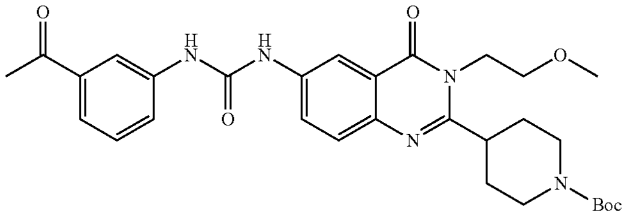 [SMILES: COCCn1c(C2CCN(C(=O)OC(C)(C)C)CC2)nc2ccc(NC(=O)Nc3cccc(C(C)=O)c3)cc2c1=O] | tert-butyl 4-(6-(3-(3-acetylphenyl)ureido)-3-(2-methoxyethyl)-4-oxo-3,4-dihydroquinazolin-2-yl)piperidine-1-carboxylate |
| 120 | 300 | 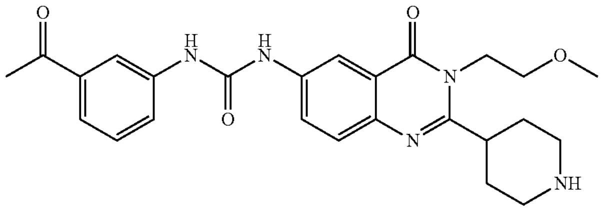 [SMILES: COCCn1c(C2CCNCC2)nc2ccc(NC(=O)Nc3cccc(C(C)=O)c3)cc2c1=O] | 1-(3-acetylphenyl)-3-(3-(2-methoxyethyl)-4-oxo-2-(piperidin-4-yl)-3,4-dihydroquinazolin-6-yl)urea |
| 121 | 304 | 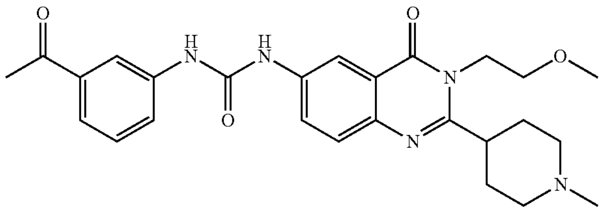 [SMILES: COCCn1c(C2CCN(C)CC2)nc2ccc(NC(=O)Nc3cccc(C(C)=O)c3)cc2c1=O] | 1-(3-acetylphenyl)-3-(3-(2-methoxyethyl)-2-(1-methylpiperidin-4-yl)-4-oxo-3,4-dihydroquinazolin-6-yl)urea |
| 122 | 307 | 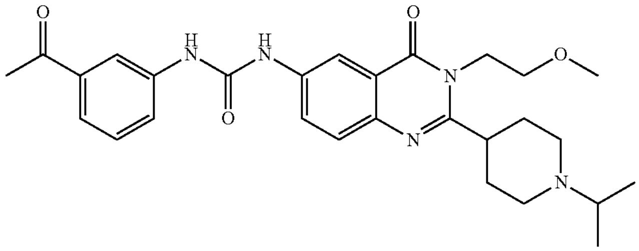 [SMILES: COCCn1c(C2CCN(C(C)C)CC2)nc2ccc(NC(=O)Nc3cccc(C(C)=O)c3)cc2c1=O] | 1-(3-acetylphenyl)-3-(2-(1-isopropylpiperidin-4-yl)-3-(2-methoxyethyl)-4-oxo-3,4-dihydroquinazolin-6-yl)urea |
| 123 | 308 | 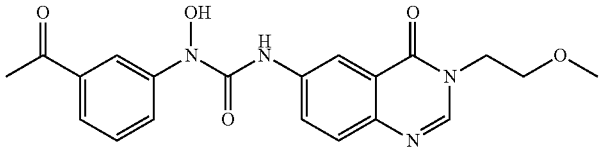 [SMILES: COCCn1cnc2ccc(NC(=O)N(O)c3cccc(C(C)=O)c3)cc2c1=O] | 1-(3-acetylphenyl)-1-hydroxy-3-(3-(2-methoxyethyl)-4-oxo-3,4-dihydroquinazolin-6-yl)urea |
| 124 | 309 | 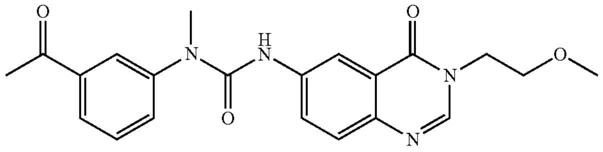 | 1-(3-acetylphenyl)-3-(3-(2-methoxyethyl)-4-oxo-3,4-dihydroquinazolin-6-yl)-1-methylurea |

TABLE 1-continued

Structure of the compounds disclosed

| Serial No. | Compound No. | Structure | IUPAC Name |
|---|---|---|---|
| 125 | 310 | 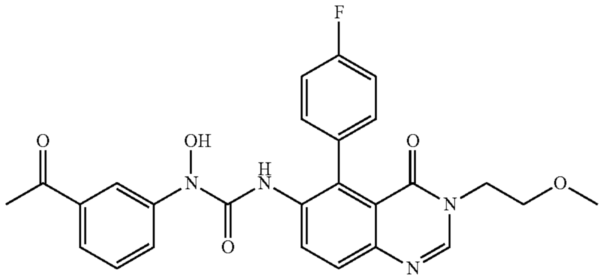 [SMILES: COCCn1cnc2ccc(NC(=O)N(O)c3cccc(C(C)=O)c3)c(-c3ccc(F)cc3)c2c1=O] | 1-(3-acetylphenyl)-3-(5-(4-fluorophenyl)-3-(2-methoxyethyl)-4-oxo-3,4-dihydroquinazolin-6-yl)-1-hydroxyurea |
| 126 | 311 | 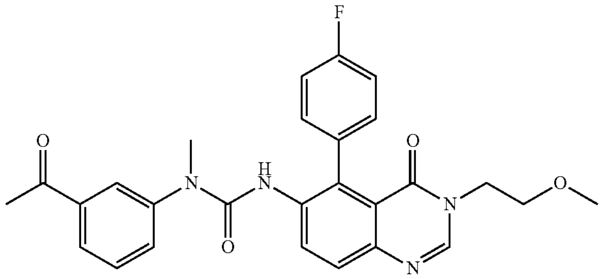 [SMILES: COCCn1cnc2ccc(NC(=O)N(C)c3cccc(C(C)=O)c3)c(-c3ccc(F)cc3)c2c1=O] | 1-(3-acetylphenyl)-3-(5-(4-fluorophenyl)-3-(2-methoxyethyl)-4-oxo-3,4-dihydroquinazolin-6-yl)-1-methylurea |
| 127 | 312 | 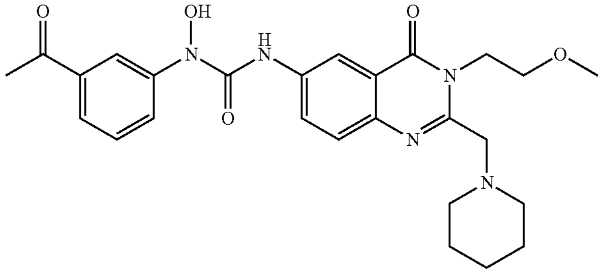 [SMILES: COCCn1c(CN2CCCCC2)nc2ccc(NC(=O)N(O)c3cccc(C(C)=O)c3)cc2c1=O] | 1-(3-acetylphenyl)-1-hydroxy-3-(3-(2-methoxyethyl)-4-oxo-2-(piperidin-1-ylmethyl)-3,4-dihydroquinazolin-6-yl)urea |
| 128 | 313 | 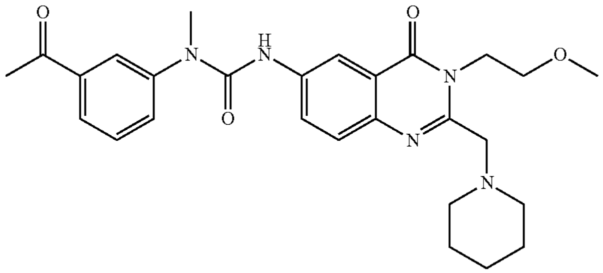 [SMILES: COCCn1c(CN2CCCCC2)nc2ccc(NC(=O)N(C)c3cccc(C(C)=O)c3)cc2c1=O] | 1-(3-acetylphenyl)-3-(3-(2-methoxyethyl)-4-oxo-2-(piperidin-1-ylmethyl)-3,4-dihydroquinazolin-6-yl)-1-methylurea |
| 129 | 314 | 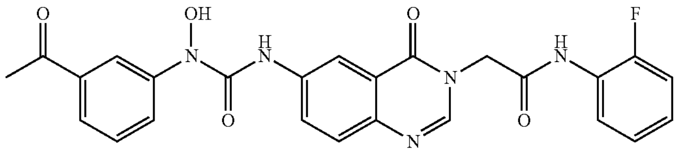 [SMILES: CC(=O)c1cccc(N(O)C(=O)Nc2ccc3ncn(CC(=O)Nc4ccccc4F)c(=O)c3c2)c1] | 2-(6-(3-(3-acetylphenyl)-3-hydroxyureido)-4-oxoquinazolin-3(4H)-yl)-N-(2-fluorophenyl)acetamide |
| 130 | 315 | 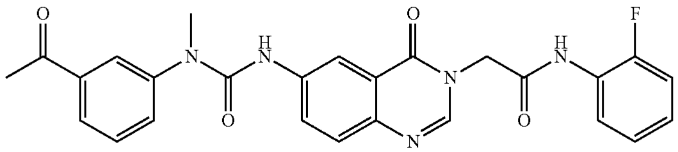 [SMILES: CC(=O)c1cccc(N(C)C(=O)Nc2ccc3ncn(CC(=O)Nc4ccccc4F)c(=O)c3c2)c1] | 2-(6-(3-(3-acetylphenyl)-3-methylureido)-4-oxoquinazolin-3(4H)-yl)-N-(2-fluorophenyl)acetamide |

TABLE 1-continued

Structure of the compounds disclosed

| Serial No. | Compound No. | Structure | IUPAC Name |
| --- | --- | --- | --- |
| 131 | 316 | 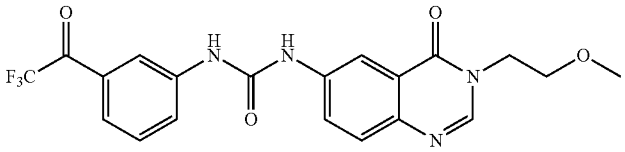 [SMILES: COCCn1cnc2ccc(NC(=O)Nc3cccc(C(=O)C(F)(F)F)c3)cc2c1=O] | 1-(3-(2-methoxyethyl)-4-oxo-3,4-dihydroquinazolin-6-yl)-3-(3-(2,2,2-trifluoroacetyl)phenyl)urea |
| 132 | 317 | 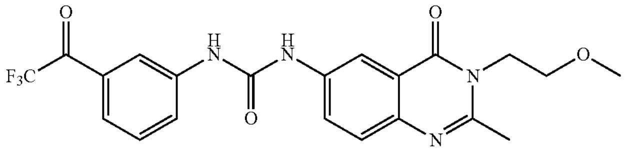 [SMILES: COCCn1c(C)nc2ccc(NC(=O)Nc3cccc(C(=O)C(F)(F)F)c3)cc2c1=O] | 1-(3-(2-methoxyethyl)-2-methyl-4-oxo-3,4-dihydroquinazolin-6-yl)-3-(3-(2,2,2-trifluoroacetyl)phenyl)urea |
| 133 | 318 | 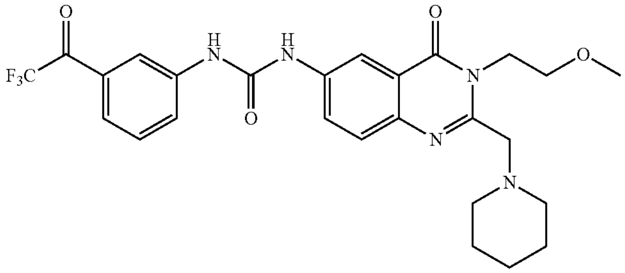 [SMILES: COCCn1c(CN2CCCCC2)nc2ccc(NC(=O)Nc3cccc(C(=O)C(F)(F)F)c3)cc2c1=O] | 1-(3-(2-methoxyethyl)-4-oxo-2-(piperidin-1-ylmethyl)-3,4-dihydroquinazolin-6-yl)-3-(3-(2,2,2-trifluoroacetyl)phenyl)urea |
| 134 | 319 | 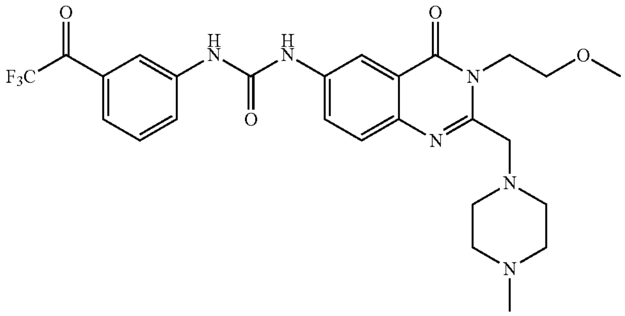 [SMILES: COCCn1c(CN2CCN(C)CC2)nc2ccc(NC(=O)Nc3cccc(C(=O)C(F)(F)F)c3)cc2c1=O] | 1-(3-(2-methoxyethyl)-2-((4-methylpiperazin-1-yl)methyl)-4-oxo-3,4-dihydroquinazolin-6-yl)-3-(3-(2,2,2-trifluoroacetyl)phenyl)urea |
| 135 | 320 | 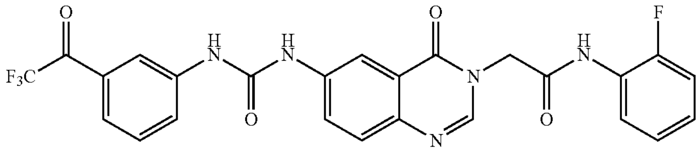 [SMILES: O=C(Cn1cnc2ccc(NC(=O)Nc3cccc(C(=O)C(F)(F)F)c3)cc2c1=O)Nc1ccccc1F] | N-(2-fluorophenyl)-2-(4-oxo-6-(3-(3-(2,2,2-trifluoroacetyl)phenyl)ureido) quinazolin-3(4H)-yl)acetamide |
| 136 | 321 | 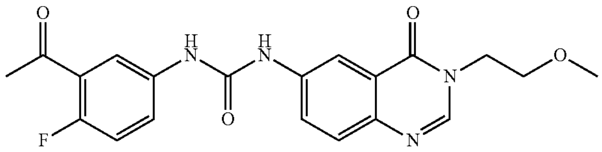 [SMILES: COCCn1cnc2ccc(NC(=O)Nc3ccc(F)c(C(C)=O)c3)cc2c1=O] | 1-(3-acetyl-4-fluorophenyl)-3-(3-(2-methoxyethyl)-4-oxo-3,4-dihydroquinazolin-6-yl)urea |
| 137 | 322 | 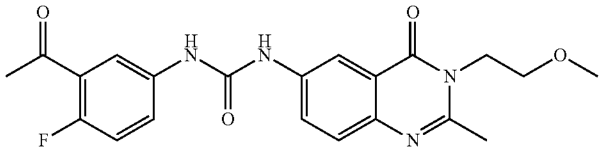 [SMILES: COCCn1c(C)nc2ccc(NC(=O)Nc3ccc(F)c(C(C)=O)c3)cc2c1=O] | 1-(3-acetyl-4-fluorophenyl)-3-(3-(2-methoxyethyl)-2-methyl-4-oxo-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 138 | 323 | 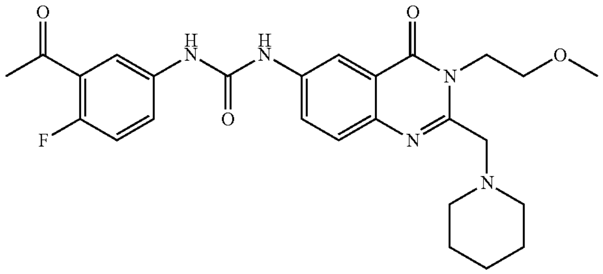 [SMILES: COCCn1c(CN2CCCCC2)nc2ccc(NC(=O)Nc3ccc(F)c(C(C)=O)c3)cc2c1=O] | 1-(3-acetyl-4-fluorophenyl)-3-(3-(2-methoxyethyl)-4-oxo-2-(piperidin-1-ylmethyl)-3,4-dihydroquinazolin-6-yl)urea |
| 139 | 324 | 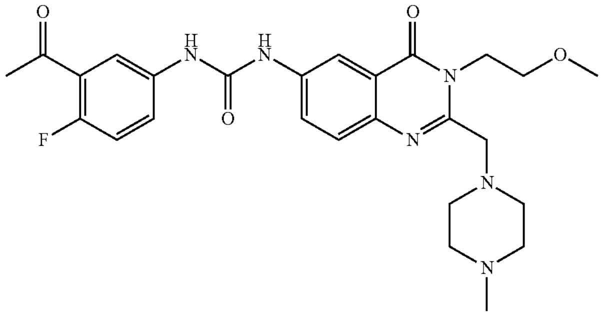 [SMILES: COCCn1c(CN2CCN(C)CC2)nc2ccc(NC(=O)Nc3ccc(F)c(C(C)=O)c3)cc2c1=O] | 1-(3-acetyl-4-fluorophenyl)-3-(3-(2-methoxyethyl)-2-((4-methylpiperazin-1-yl)methyl)-4-oxo-3,4-dihydroquinazolin-6-yl)urea |
| 140 | 325 | 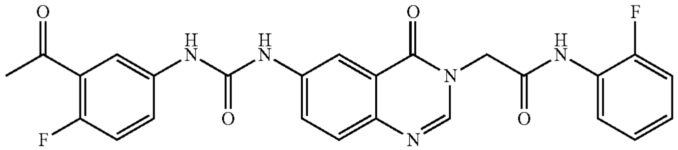 [SMILES: CC(=O)c1cc(NC(=O)Nc2ccc3ncn(CC(=O)Nc4ccccc4F)c(=O)c3c2)ccc1F] | 2-(6-(3-(3-acetyl-4-fluorophenyl)ureido)-4-oxoquinazolin-3(4H)-yl)-N-(2-fluorophenyl)acetamide |
| 141 | 330 | 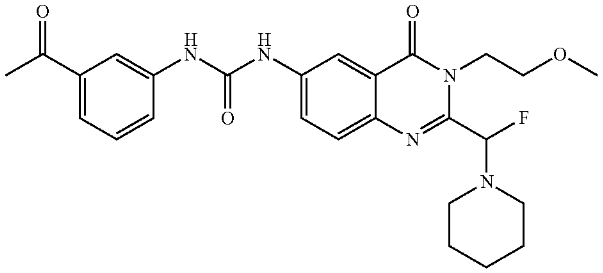 [SMILES: COCCn1c(C(F)N2CCCCC2)nc2ccc(NC(=O)Nc3cccc(C(C)=O)c3)cc2c1=O] | 1-(3-acetylphenyl)-3-(2-(fluoro(piperidin-1-yl)methyl)-3-(2-methoxyethyl)-4-oxo-3,4-dihydroquinazolin-6-yl)urea |
| 142 | 330a | 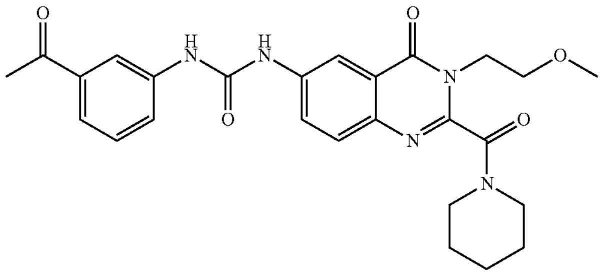 [SMILES: COCCn1c(C(=O)N2CCCCC2)nc2ccc(NC(=O)Nc3cccc(C(C)=O)c3)cc2c1=O] | 1-(3-acetylphenyl)-3-(3-(2-methoxyethyl)-4-oxo-2-(piperidine-1-carbonyl)-3,4-dihydroquinazolin-6-yl)urea |

TABLE 1-continued

| Structure of the compounds disclosed | | | |
|---|---|---|---|
| Serial No. | Compound No. | Structure | IUPAC Name |
| 143 | 333 | 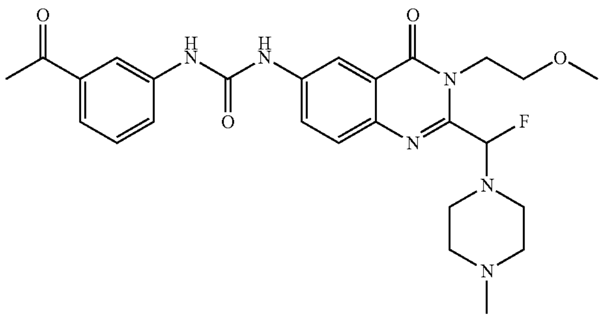 [SMILES: COCCn1c(C(F)N2CCN(C)CC2)nc2ccc(NC(=O)Nc3cccc(C(C)=O)c3)cc2c1=O] | 1-(3-acetylphenyl)-3-(2-(fluoro(4-methylpiperazin-1-yl)methyl)-3-(2-methoxyethyl)-4-oxo-3,4-dihydroquinazolin-6-yl)urea |
| 144 | 333a | 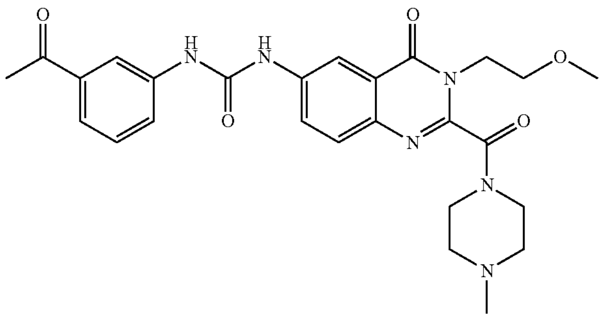 [SMILES: COCCn1c(C(=O)N2CCN(C)CC2)nc2ccc(NC(=O)Nc3cccc(C(C)=O)c3)cc2c1=O] | 1-(3-acetylphenyl)-3-(3-(2-methoxyethyl)-2-(4-methylpiperazine-1-carbonyl)-4-oxo-3,4-dihydroquinazolin-6-yl)urea |
| 145 | 336 | 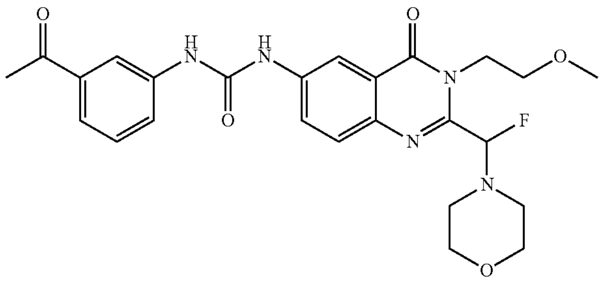 [SMILES: COCCn1c(C(F)N2CCOCC2)nc2ccc(NC(=O)Nc3cccc(C(C)=O)c3)cc2c1=O] | 1-(3-acetylphenyl)-3-(2-(fluoro(morpholino)methyl)-3-(2-methoxyethyl)-4-oxo-3,4-dihydroquinazolin-6-yl)urea |
| 146 | 336a | 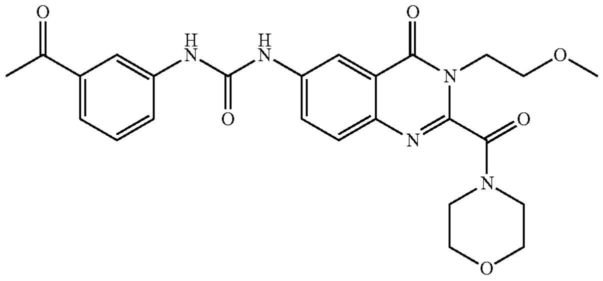 [SMILES: COCCn1c(C(=O)N2CCOCC2)nc2ccc(NC(=O)Nc3cccc(C(C)=O)c3)cc2c1=O] | 1-(3-acetylphenyl)-3-(3-(2-methoxyethyl)-2-(morpholine-4-carbonyl)-4-oxo-3,4-dihydroquinazolin-6-yl)urea |
| 147 | 340 | 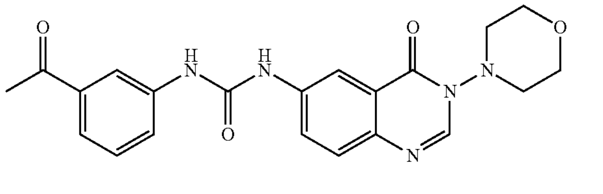 [SMILES: CC(=O)c1cccc(NC(=O)Nc2ccc3ncn(N4CCOCC4)c(=O)c3c2)c1] | 1-(3-acetylphenyl)-3-(3-morpholino-4-oxo-3,4-dihydroquinazolin-6-yl)urea |

TABLE 1-continued

Structure of the compounds disclosed

| Serial No. | Compound No. | Structure | IUPAC Name |
|---|---|---|---|
| 148 | 341 | 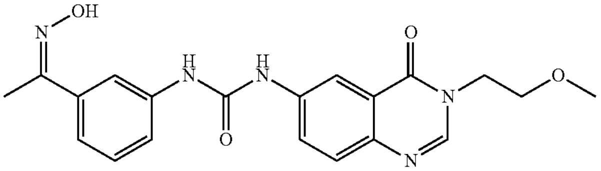 [SMILES: COCCn1cnc2ccc(NC(=O)Nc3cccc(/C(C)=N\O)c3)cc2c1=O] | (Z)-1-(3-(1-(hydroxyimino)ethyl)phenyl)-3-(3-(2-methoxyethyl)-4-oxo-3,4-dihydroquinazolin-6-yl)urea |
| 149 | 342 | 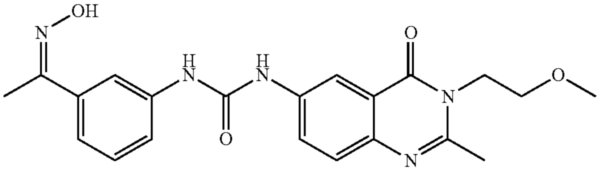 [SMILES: COCCn1c(C)nc2ccc(NC(=O)Nc3cccc(/C(C)=N\O)c3)cc2c1=O] | (Z)-1-(3-(1-(hydroxyimino)ethyl)phenyl)-3-(3-(2-methoxyethyl)-2-methyl-4-oxo-3,4-dihydroquinazolin-6-yl)urea |
| 150 | 343 | 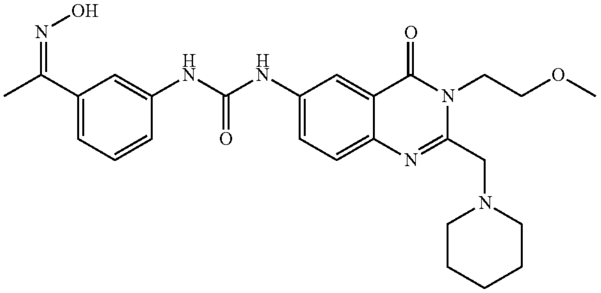 [SMILES: COCCn1c(CN2CCCCC2)nc2ccc(NC(=O)Nc3cccc(/C(C)=N\O)c3)cc2c1=O] | (Z)-1-(3-(1-(hydroxyimino)ethyl)phenyl)-3-(3-(2-methoxyethyl)-4-oxo-2-(piperidin-1-ylmethyl)-3,4-dihydroquinazolin-6-yl)urea |
| 151 | 345 | 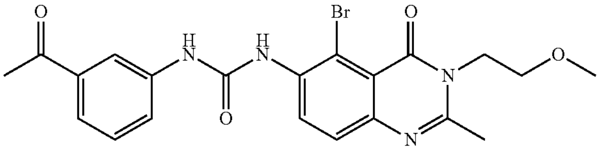 [SMILES: COCCn1c(C)nc2ccc(NC(=O)Nc3cccc(C(C)=O)c3)c(Br)c2c1=O] | 1-(3-acetylphenyl)-3-(5-bromo-3-(2-methoxyethyl)-2-methyl-4-oxo-3,4-dihydroquinazolin-6-yl)urea |

General Process for Preparation:

The process for preparation of the compound having Structure I as given in Table 1 comprises the following steps:

(i) reacting 2-amino-5-nitrobenzoic acid (compound 1) with an aliphatic or an aromatic amine selected from the group consisting of 2-methoxyethylamine, glycineethylester hydrochloride, 3-methoxypropylamine, 2-ethoxyethylamine, ethylamine 2M in THF, 4-(2-aminoethyl)morpholine, 3-(4-morpholinyl)propylamine, N,N-dimethylethylenediamine, 1-(2-aminoethyl)piperidine, 4-amino-1-methylpiperidine, N-methylethylenediamine, 2-amino-1-methoxybutane, 1-butylamine, 1-methoxy-2-propylamine, 2-aminoethyl isopropyl ether, cyclohexylamine, 4-aminomorpholine, m-anisidine, o-anisidine, 4-aminopyridine, 3-aminopyridine, and 2-aminopyridine in presence of HATU/DMF followed by TEA as a base at room temperature for 1-3 hours to obtain an amide compound selected from the group consisting of 2, 80, 86, 90, 95, 132, 136, 140, 144, 160, 164, 168, 172, 176, 180, 184, 337, 100, 128, 148, 152, and 156;

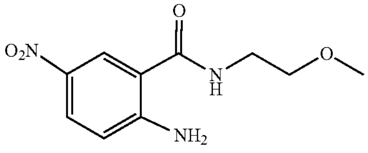
2

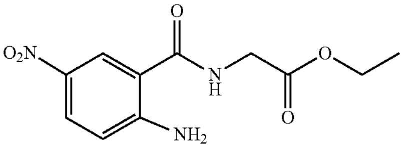
80

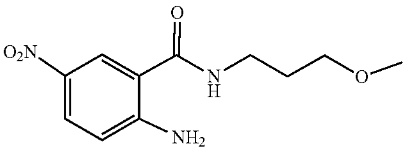
86

-continued
90
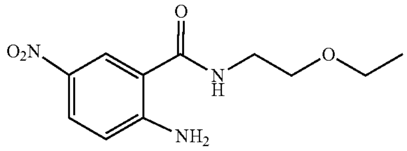
95
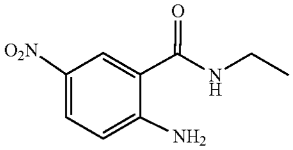
132
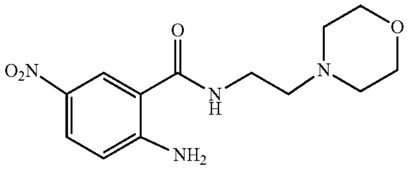
136
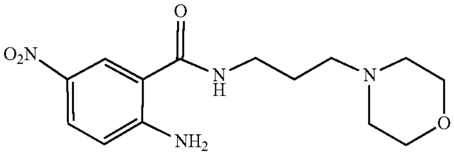
140
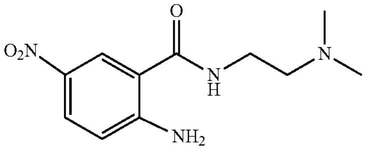
144
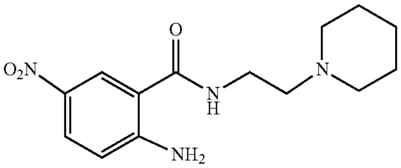
160
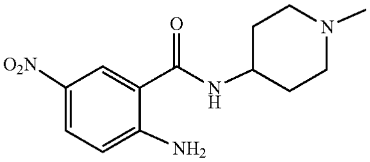
164
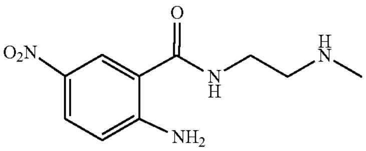
168
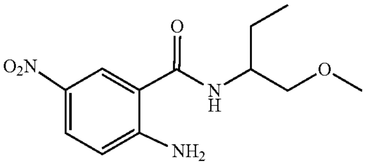
-continued
172
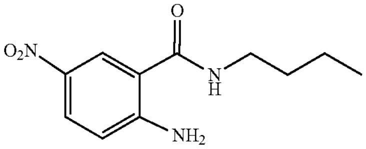
176
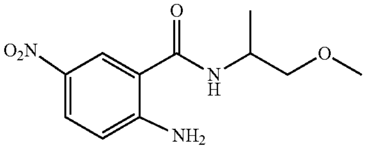
180
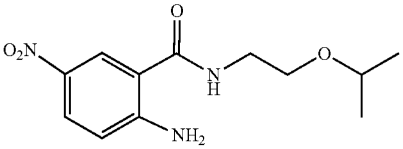
184
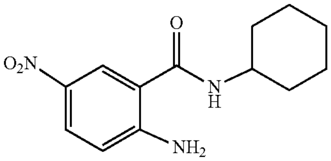
337
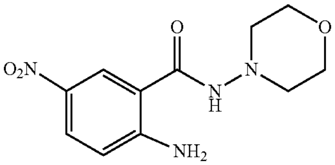
100
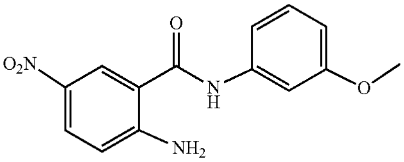
128
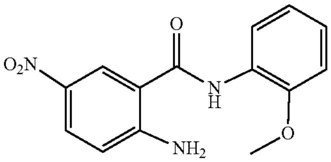
148
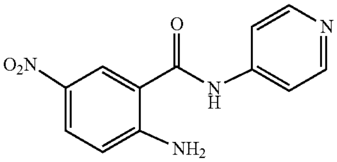
152
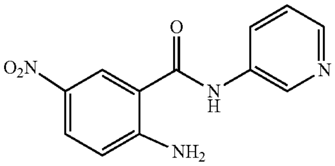

-continued

156

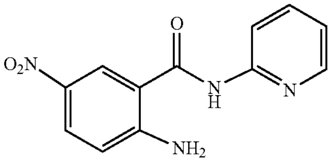

(ii) separately, reacting 2-amino-4-nitrobenzoic acid (compound 188) with 2-methoxyethylamine in presence of HATU/DMF followed by TEA as a base at room temperature for 1 hour to obtain a compound 189;

188

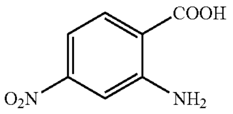

189

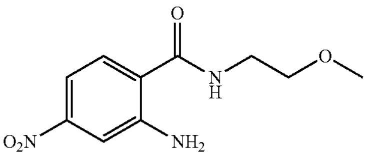

(iii) adding an acid chloride selected from the group consisting of acetyl chloride, isopropyl chloride, 4-fluorobenzoyl chloride, 4-methoxybenzoyl chloride, cyclohexanecarbonyl chloride, cyclopentanecarbonyl chloride, 4-(trifluoromethyl)benzoyl chloride, 3-Bromo-4-methoxybenzoyl chloride, Picolinoyl chloride, Nicotinoyl chloride, Isonicotinoyl chloride, Pyrazinecarbonyl chloride, 1-methyl-1H-pyrazole-4-carbonyl chloride, and 2-chloroacetyl chloride to compound 2 obtained in step (i) in DCM at a temperature range from 0° C. to room temperature for 1-8 hours to obtain a compound selected from the group consisting of 104, 108, 112, 116, 120, 124, 200, 204, 208, 212, 216, 220, 224, and 228;

104

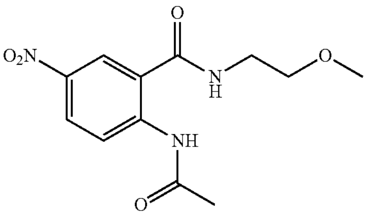

108

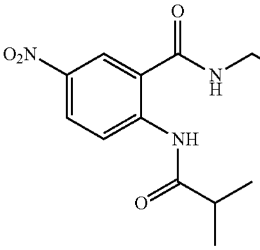

-continued

112

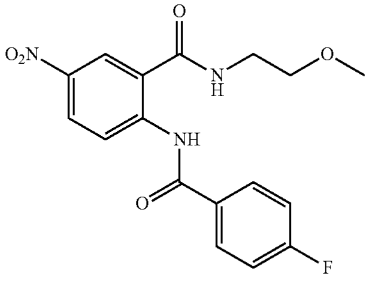

116

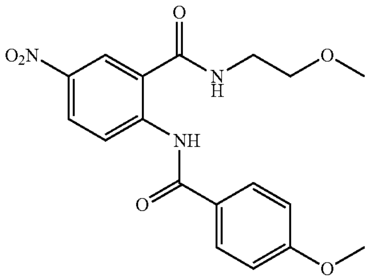

120

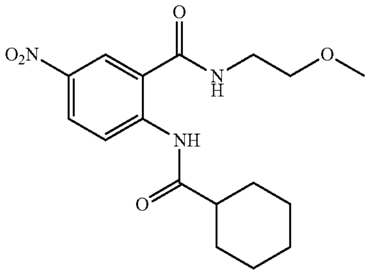

124

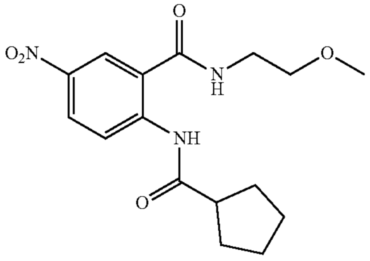

200

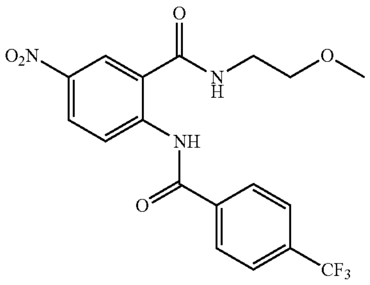

-continued
204
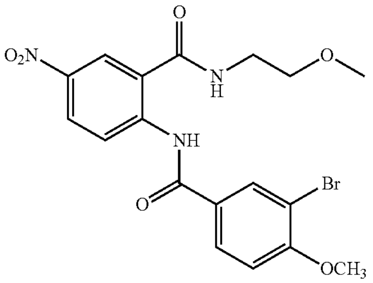
208
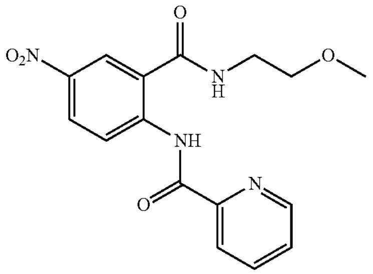
212
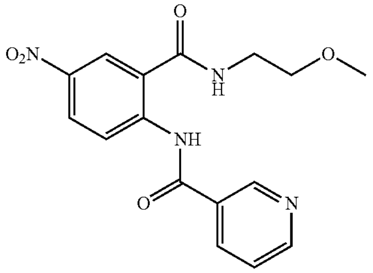
216
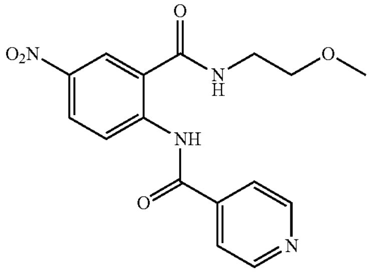
220
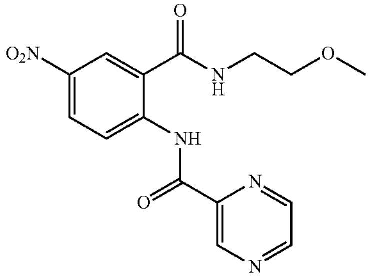
-continued
224
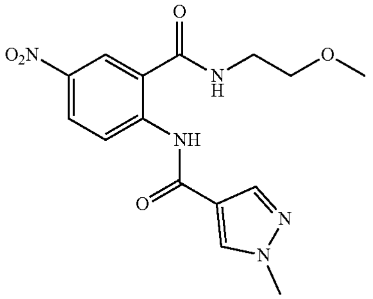
228
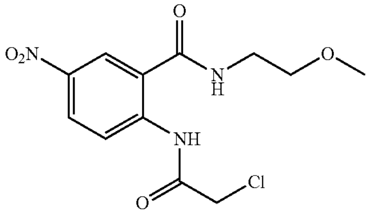
(iv) acetylating a compound selected from the group consisting of 168, and 176 obtained in step (i) using acetyl chloride and triethylamine (TEA) as a base in DCM at a temperature range of 0° C. to room temperature for 8 hours to obtain a compound selected from the group consisting of 278 and 282;
168
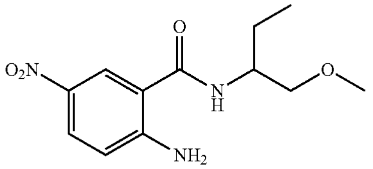
176
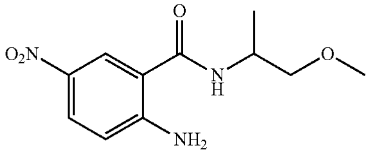
278
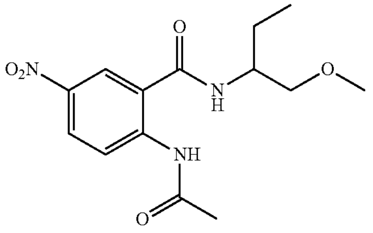
282
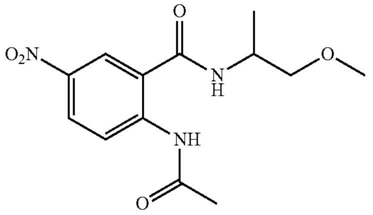

(v) alternatly, adding cyclohexanecarbonyl chloride to compound 176 obtained in step (i) to obtain a compound 286;

286

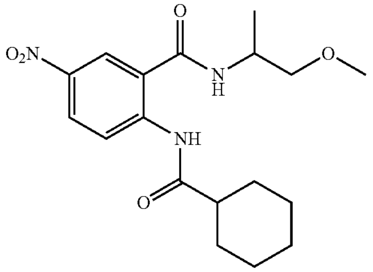

(vi) alternatly, adding tert-butyl 4-(chlorocarbonyl)piperidine-1-carboxylate to compound 2 obtained in step (i) to obtain a compound 296;

296

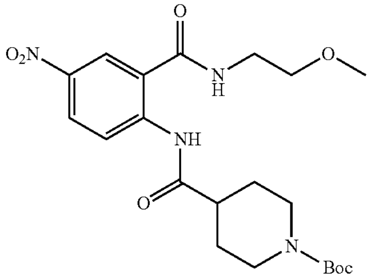

(vii) alternately, treating compound 2 obtained in step (i) with 2-chloro-2-fluoroacetic acid or 2-chloro-2-difluoroacetic acid along with $POCl_3$ in pyridine solvent to obtain a compound selected from the group consisting of 326 and 326a;

326

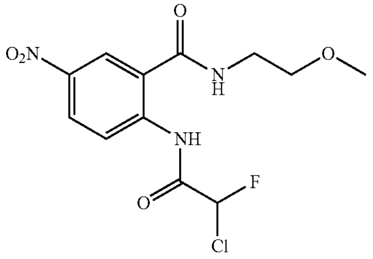

326a

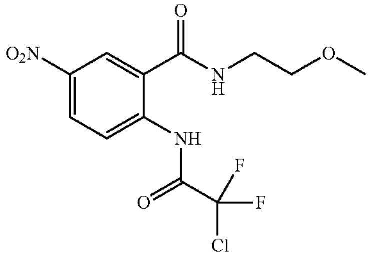

(viii) cyclizing the compound selected from the group consisting of 2, 80, 86, 90, 95, 100, 128, 132, 136, 140, 144, 148, 152, 156, 160, 164, 168, 172, 176, 180, 184, 189, and 337 obtained in step (i) and (ii) using a cyclizing agent selected from trimethylorthoformate or triethylorthoformate at 100° C. for 12-16 hours to obtain a compound selected from the group consisting of 3, 81, 87, 91, 96, 101, 129, 133, 137, 141, 145, 149, 153, 157, 161, 165, 169, 173, 177, 181, 185, 190 and 338;

3

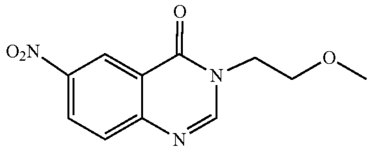

81

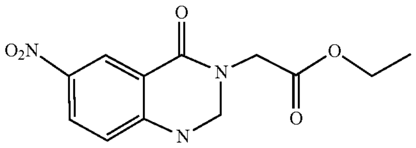

87

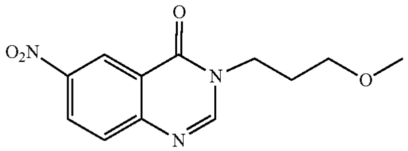

91

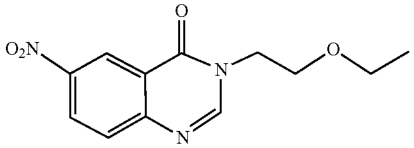

96

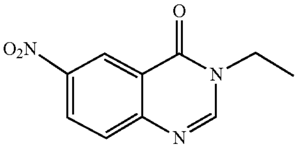

101

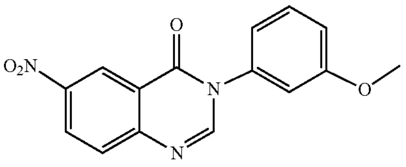

129

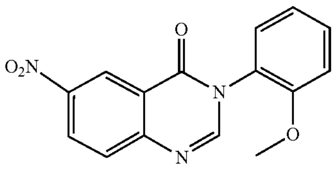

133

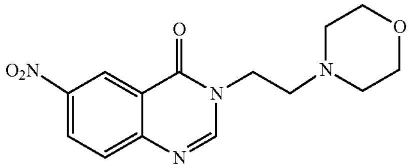

-continued
137
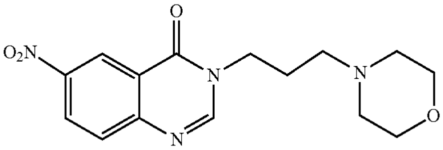
141
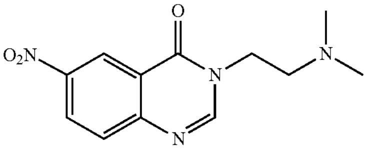
145
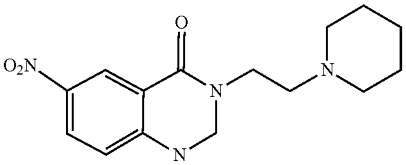
149
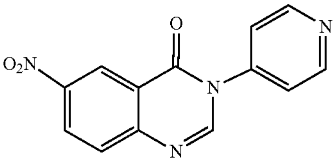
153
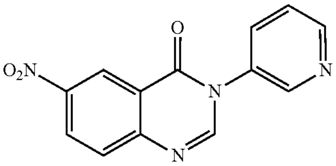
157
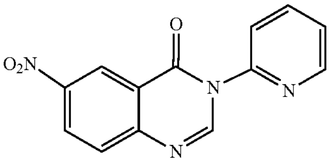
161
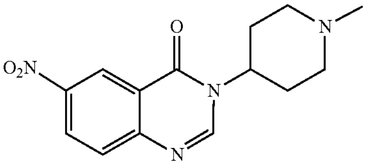
165
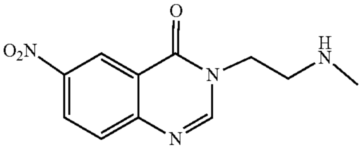
169
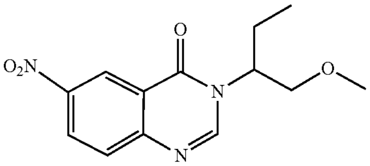
-continued
173
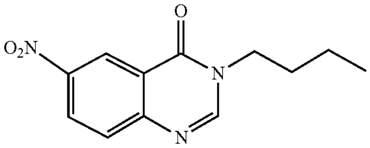
177
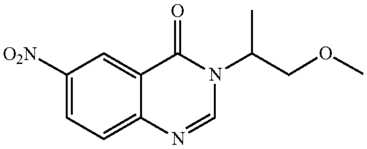
181
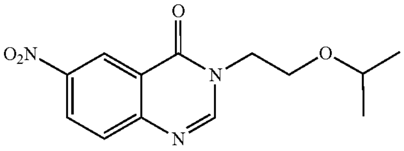
185
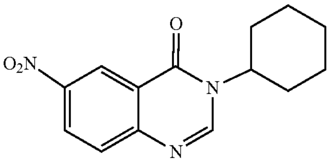
190
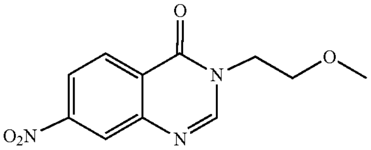
338
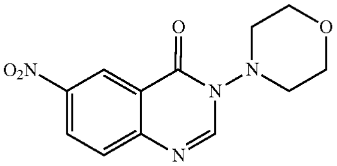
(ix) cyclizing the compound selected from the group consisting of 104, 108, 112, 116, 120, 124, 200, 204, 208, 212, 216, 220, 224, 228, 278, 282, 286, 296, 326, and 326a obtained in step (iii), (iv), (v), (vi) and (vii) using a cyclizing agent $ZnCl_2$ and hexamethyldisilazane (HMDS) in DMF at 100° C. for 12-16 hours to obtain a compound selected from the group consisting of 105, 109, 113, 117, 121, 125, 201, 205, 209, 213, 217, 221, 225, 229, 279, 283, 287, 297, 327 and 327a;
105
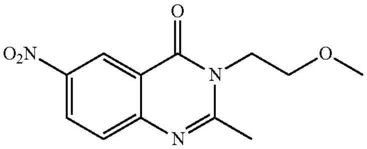

-continued
109
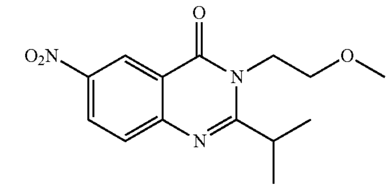
113
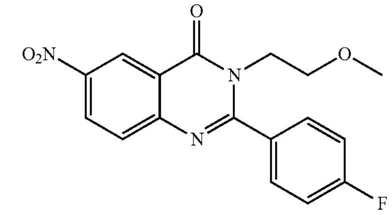
117
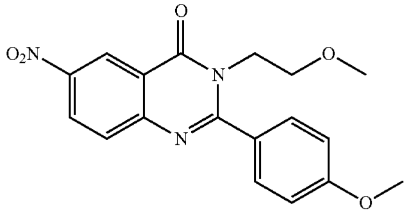
121
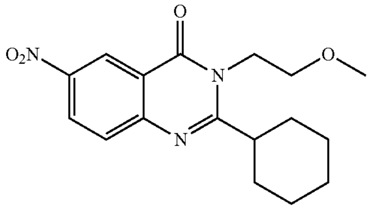
125
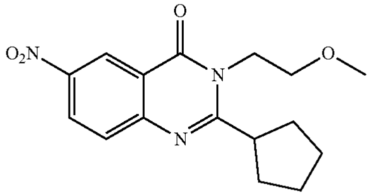
201
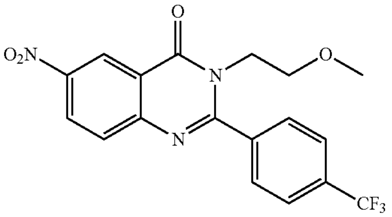
205
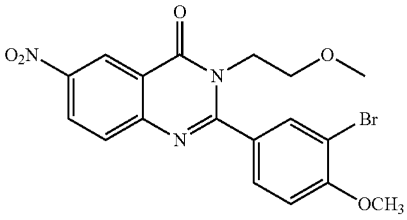
-continued
209
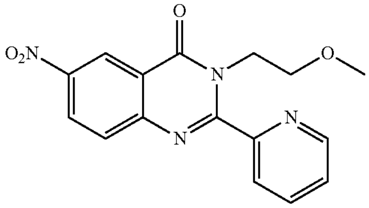
213
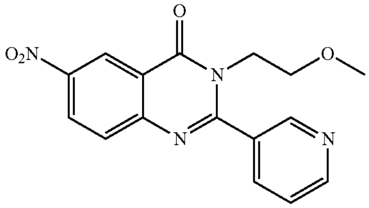
217
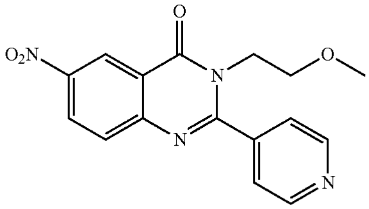
221
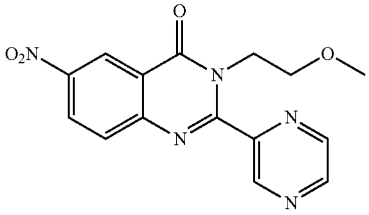
225
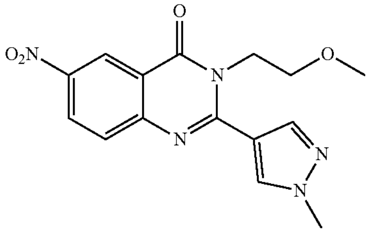
229
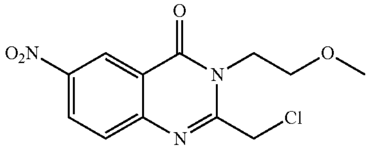
279
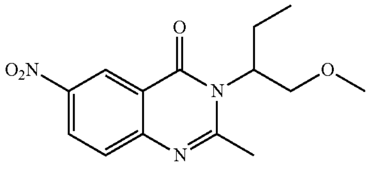
283
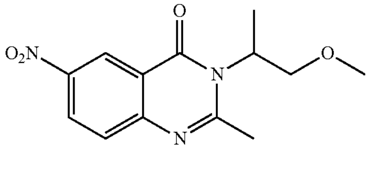

-continued

287

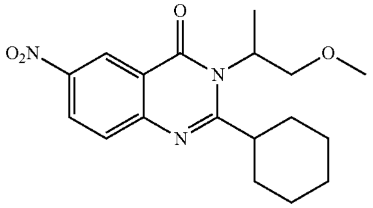

297

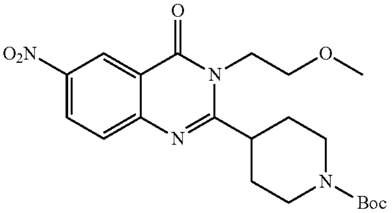

327

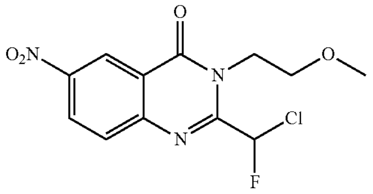

327a

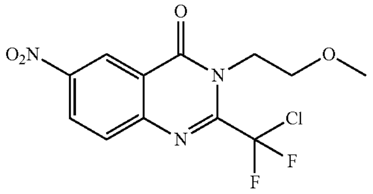

(x) reacting the compound 81 obtained in step (viii) with an amine selected from the group consisting of ethyl amine, diethylamine, 2-fluroaniline, o-anisidine, 2-bromoaniline, 2-(trifluoromethoxy)aniline, 2-(trifluoromethyl)aniline, p-anisidine, 4-fluoroaniline, 1-(2-aminoethyl)-4-methylpiperizine, and 1H-Imidazole-1-ethanamine in presence of anhydrous $AlCl_3$ in toluene at a temperature range from room temperature to 110° C. to obtain a compound selected from the group consisting of 245, 248, 251, 254, 257, 260, 263, 266, 269, 272 and 275;

245

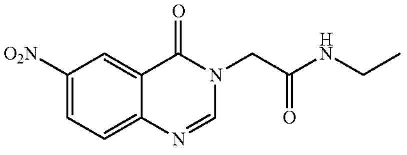

248

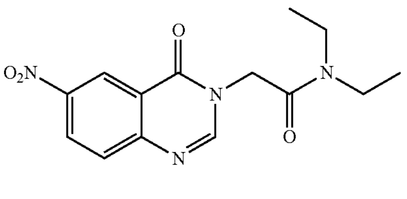

-continued

251

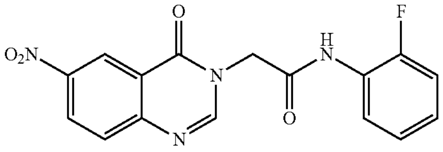

254

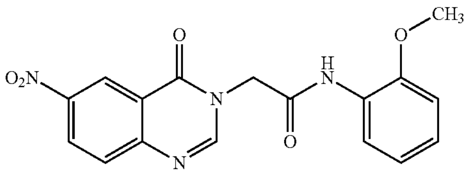

257

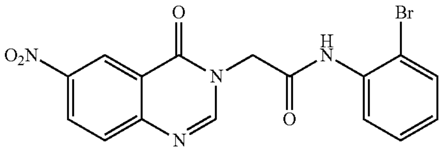

260

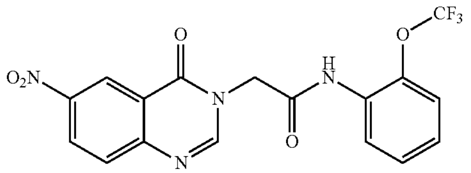

263

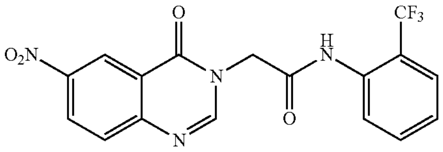

266

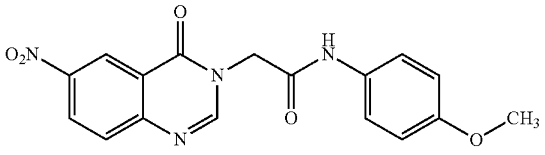

269

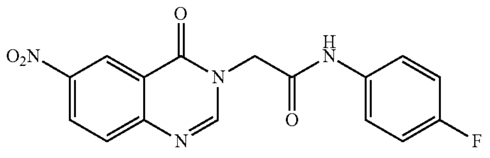

272

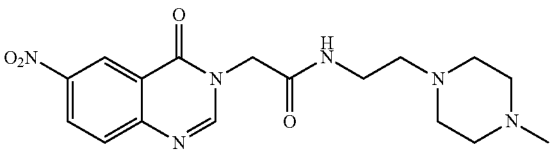

275

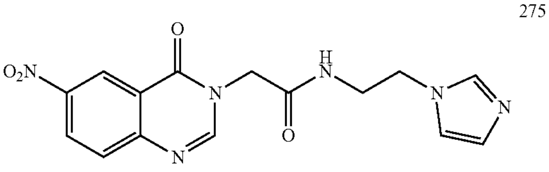

(xi) reacting the compound 229 obtained in step (ix) with an amine selected from the group consisting of pyrrolidine, dimethylamine, piperidine, morpholine, and 1-methylpiperazine in toluene at 100° C. for 2 hours to obtain a compound selected from the group consisting of 230, 233, 236, 239, and 242;

230

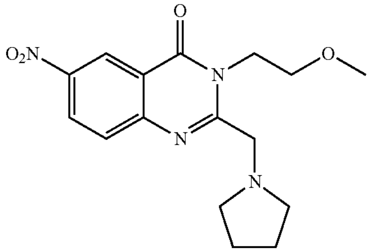

233

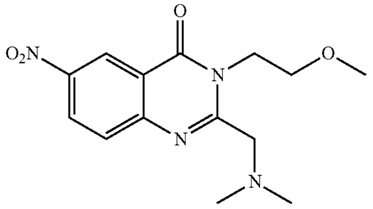

236

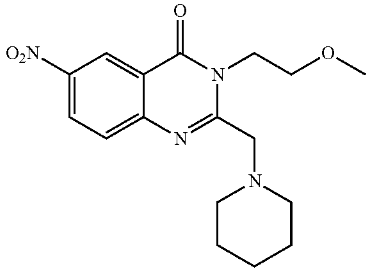

239

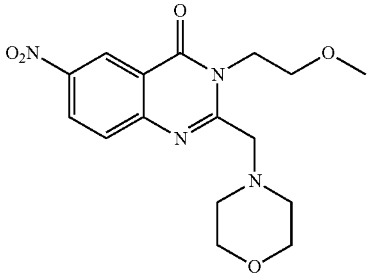

242

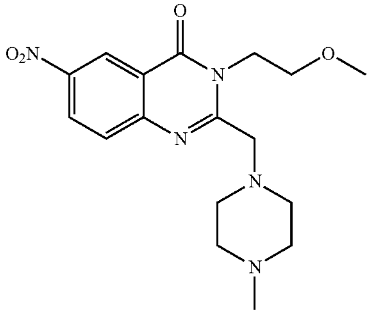

(xii) reacting the compound 327 obtained in step (ix) with an amine selected from the group consisting of piperidine, 1-methylpiperazine, and morpholine in presence of toluene to obtain a compound selected from the group consisting of 328, 331, and 334;

328

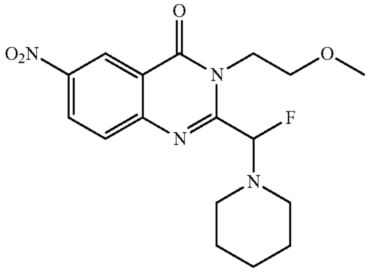

331

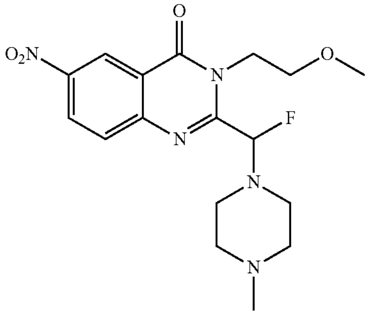

334

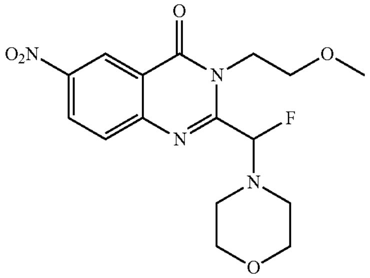

(xiii) reacting the compound 327a obtained in step (ix) with an amine selected from the group consisting of piperidine, 1-methylpiperazine, and morpholine in presence of a solvent selected from the group consisting of toluene, DMF, and THF in absence or presence of a base seleted from $K_2CO_3$, or N,N-diethylaniline to obtain a compound seleted from the group consisting of 328a, 331a, and 334a;

328a

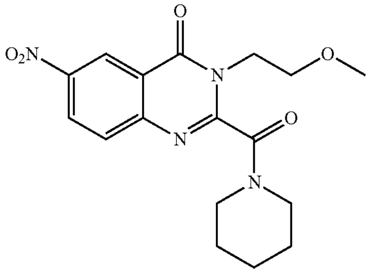

-continued

331a

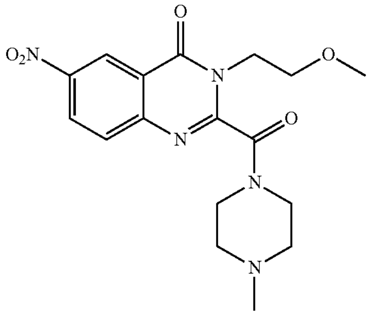

334a

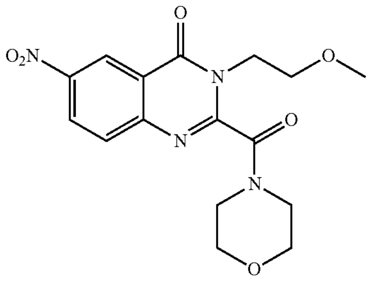

(xiv) separately reacting the compound 297 obtained in step (ix) with trifluoroacetic acid (TFA) in DCM at a temperature range of 0° C. to room temperature for 2 hours to obtain a compound 301;

301

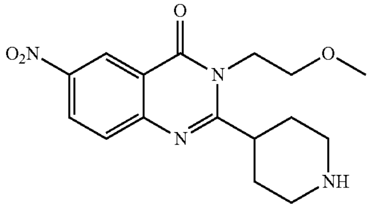

(xv) reacting the compound 301 obtained in step (xiv) with sodium hydride (NaH) in DMF at a temperature range of 0° C. to room temperature for 3 hours with methyl iodide and 2-chloropropane, respectively to obtain a compound selected from the group consisting of 302 and 305;

302

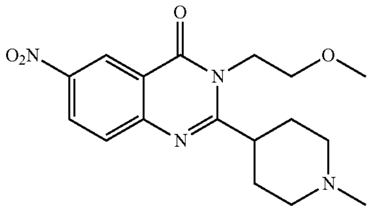

-continued

305

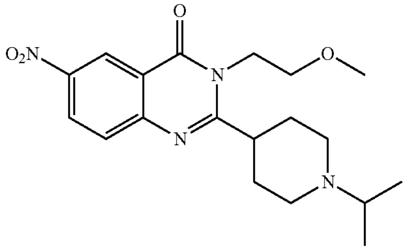

(xvi) reducing the compound selected from the group consisting of 3, 81, 87, 91, 96, 101, 105, 109, 113, 117, 121, 125, 129, 133, 137, 141, 145, 149, 153, 157, 161, 165, 169, 173, 177, 181, 185, 190, 201, 209, 213, 217, 221, 225, 230, 233, 236, 239, 242, 245, 248, 251, 254, 260, 263, 266, 269, 272, 275, 279, 283, 287, 297, 302, 305, 328, 328a, 331, 331a, 334, 334a and 338 obtained in steps (viii), (ix), (x), (xi), (xii), (xiii) and (xv) using Palladium-Charcoal (5% or 10% wet) at room temperature for 3-5 hours in presence of $H_2$ to obtain an amine compound selected from the group consisting of 4, 82, 88, 92, 97, 102, 106, 110, 114, 118, 122, 126, 130, 134, 138, 142, 146, 150, 154, 158, 162, 166, 170, 174, 178, 182, 186, 191, 202, 210, 214, 218, 222, 226, 231, 234, 237, 240, 243, 246, 249, 252, 255, 261, 264, 267, 270, 273, 276, 280, 284, 288, 298, 303, 306, 329, 329a, 332, 332a, 335, 335a, and 339;

4

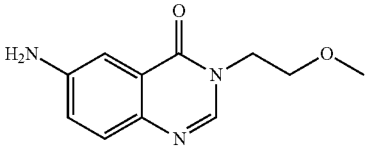

82

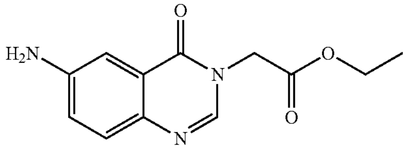

88

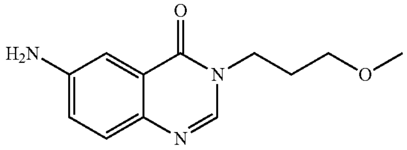

92

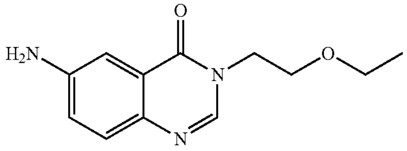

97

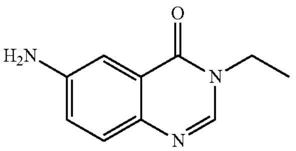

-continued
102
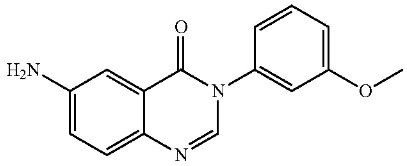
106
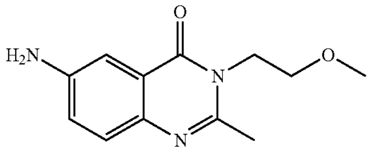
110
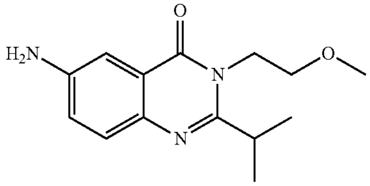
114
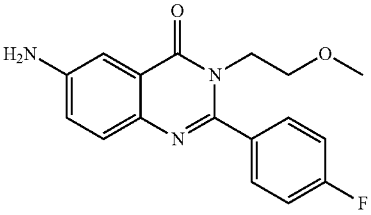
118
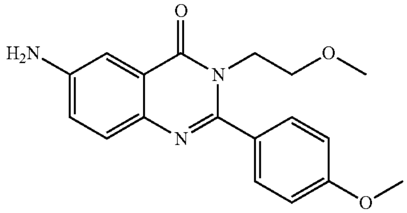
122
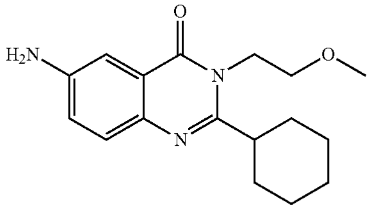
126
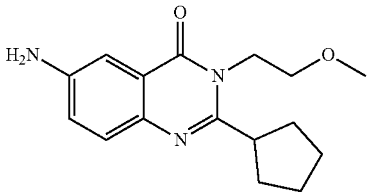
130
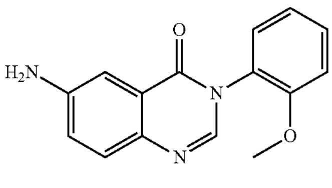
-continued
134
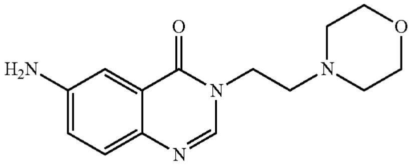
138
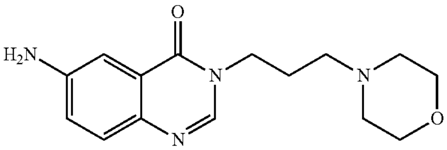
142
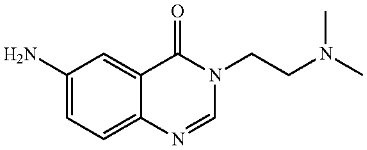
146
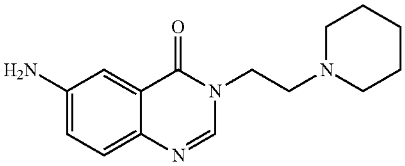
150
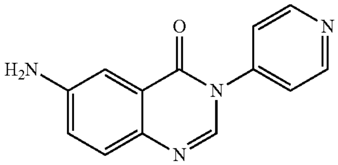
154
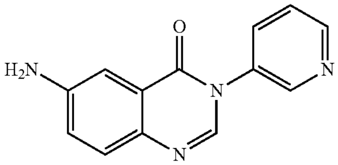
158
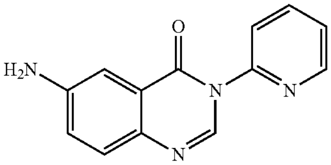
162
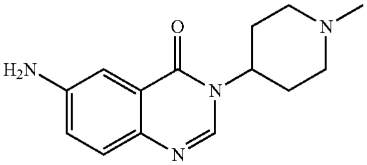
166
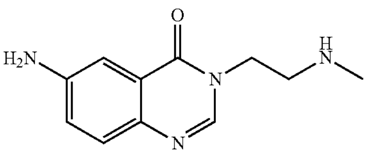

-continued
170
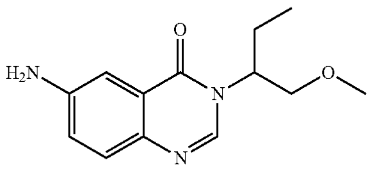
174
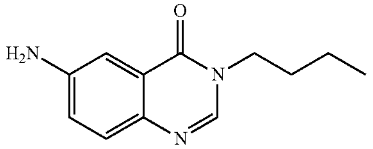
178
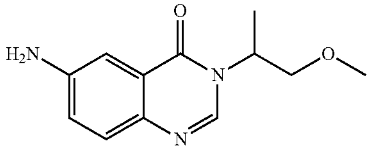
182
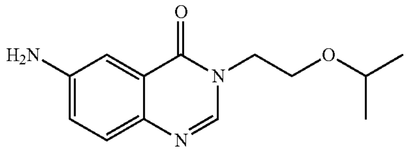
186
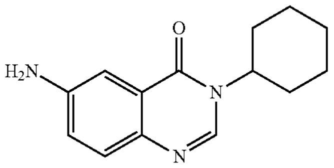
191
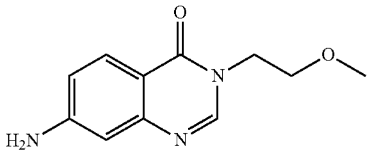
202
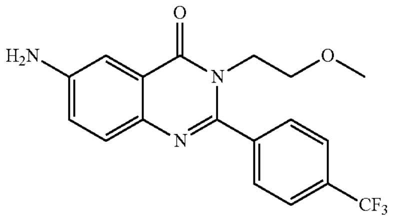
210
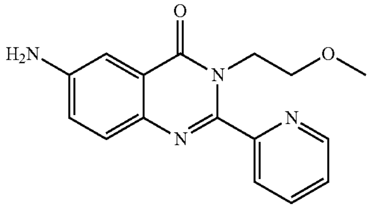
-continued
214
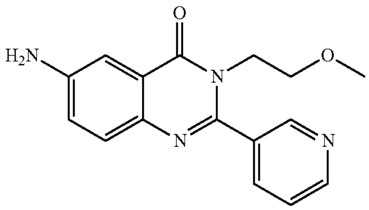
218
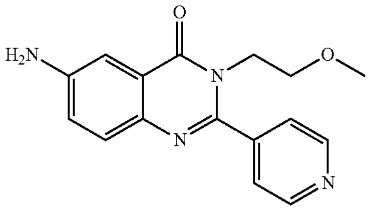
222
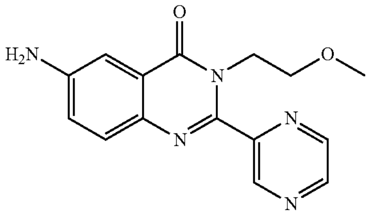
226
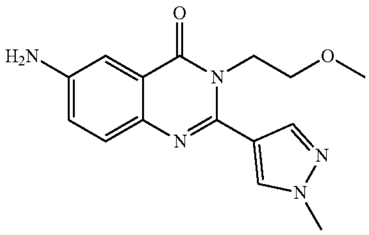
231
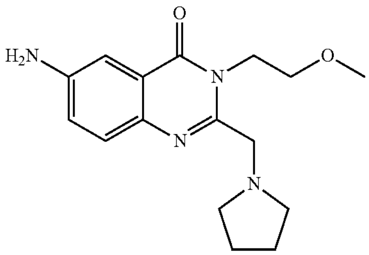
234
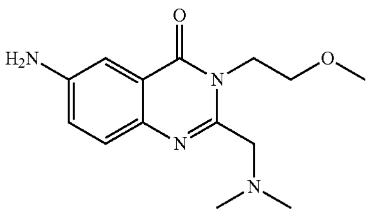

-continued
237
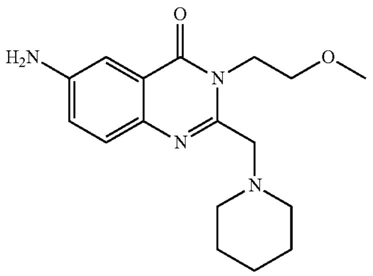
240
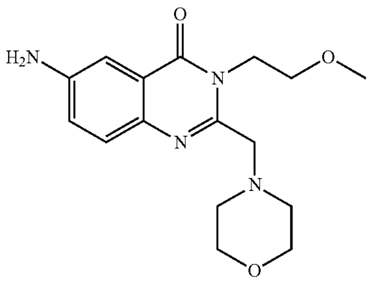
243
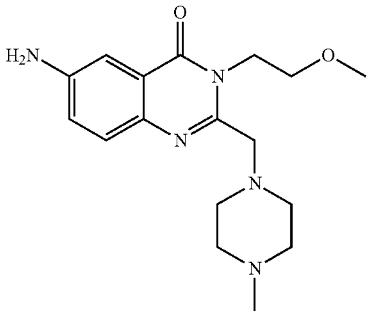
246
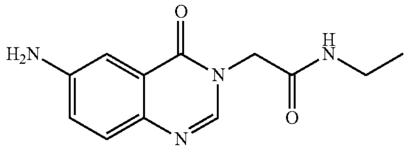
249
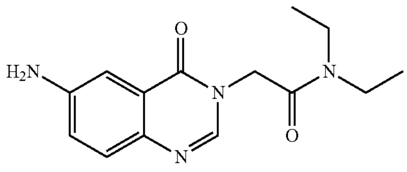
252
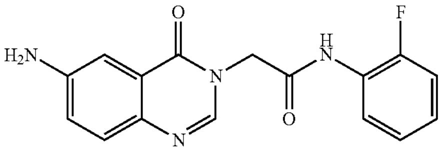
255
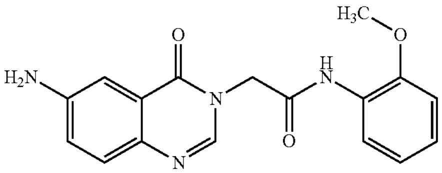
-continued
261
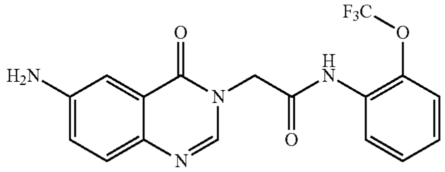
264
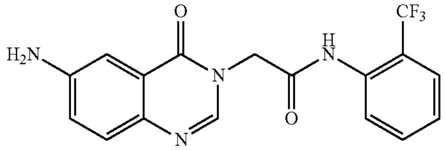
267
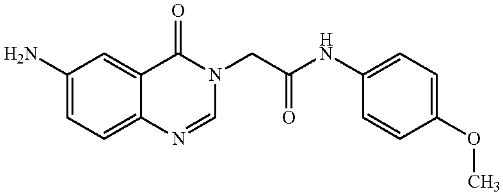
270
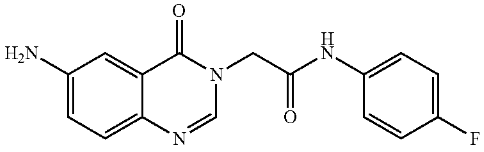
273
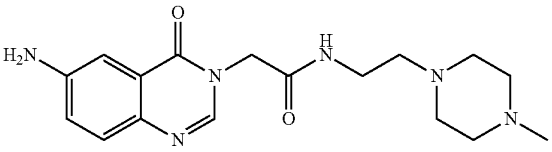
276
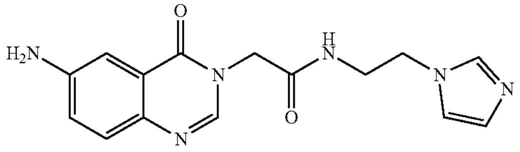
280
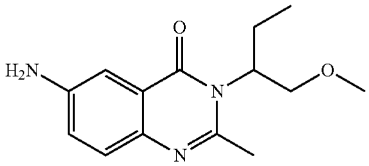
284
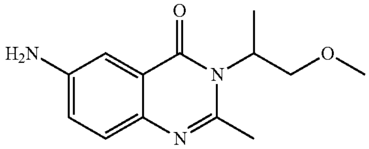
288
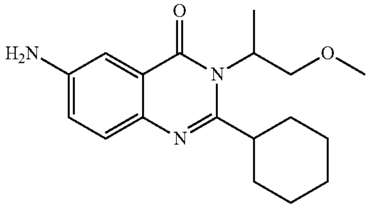

-continued
298
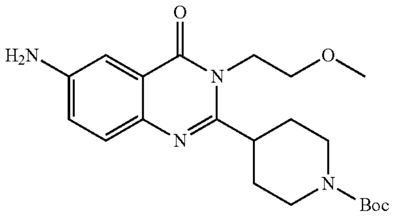
303
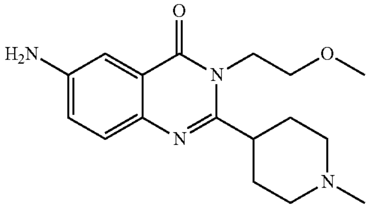
306
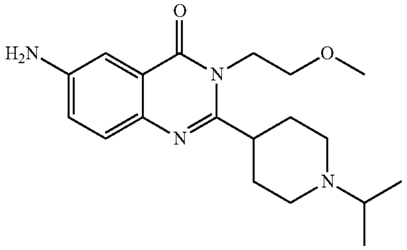
329
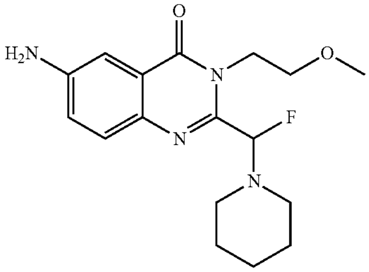
329a
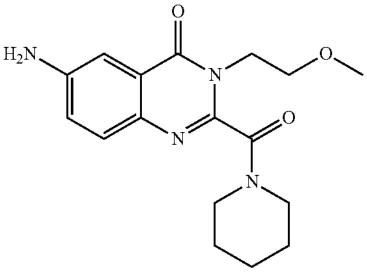
332
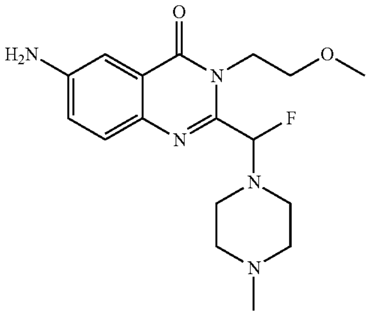
-continued
332a
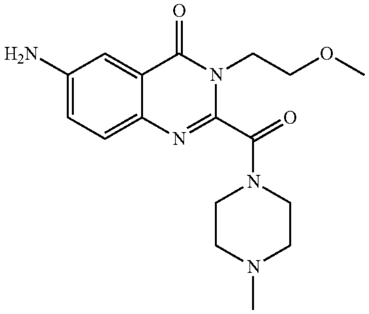
335
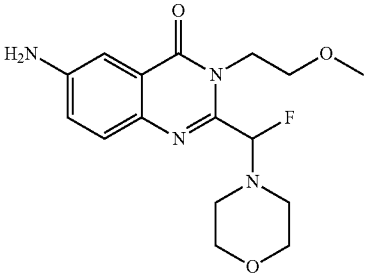
335a
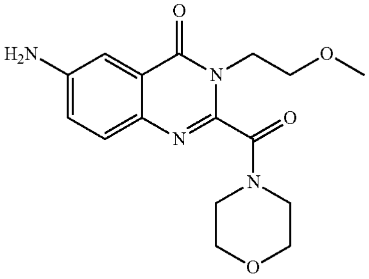
339
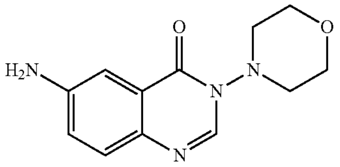
(xvii) reducing the compound selected from 205 or, 257 obtained in step (ix) and (x) using $SnCl_2 \cdot 2H_2O$ to obtain the compound selected from 206 or 258;
206
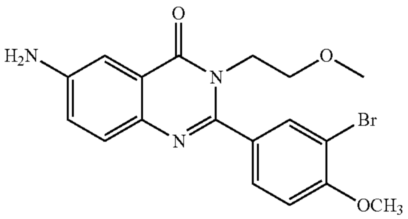
258
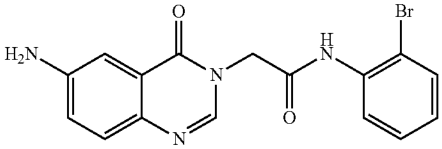

(xviii) brominating the compound selected from the group consisting of 4, 106, 122, and 178 obtained in step (xvi) diluted in dichloromethane or chloroform solution by carrying out reaction in acetic acid medium followed by dropwise addition of liquid bromine on the compound at room temperature for 3-4 hours to obtain a compound selected from the group consisting of 43, 344, 290, and 293;

43

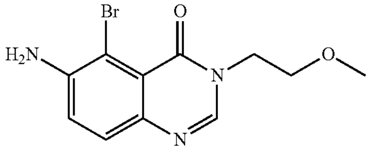

344

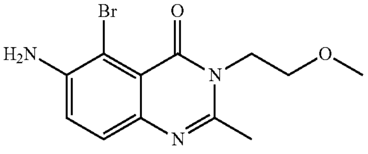

290

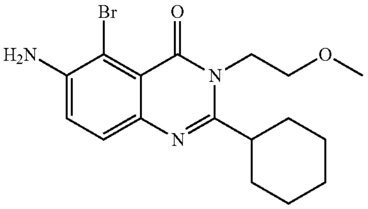

293

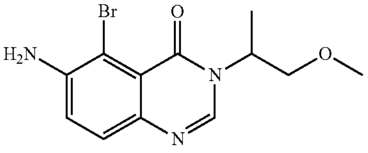

(xix) carrying out Suzuki reaction on a compound selected from the group consisting of 43, 290, and 293 obtained in step (xviii) by $Pd_2(dba)_3$ or $Pd(PPh_3)_4$ in presence of $Cs_2CO_3$ or 2M $Na_2CO_3$ solution in dioxane and X-Phos as a ligand at 100° C. over a period of 10-12 hours along with a boronic acid selected from the group consisting of benzeneboronic acid, 4-fluorobenzeneboronic acid, pyridine-2-boronic acid, pyridine-3-boronic acid, pyridine-4-boronic acid, 6-methoxypyridine-3-boronic acid, 2-methoxypyridine-3-boronic acid, (1-(tert-butoxycarbonyl)-1,2,3,6-tetrahydropyridin-4-yl)boronic acid, 4-methoxybenzeneboronic acid, 4-trifluoromethylbenzeneboronic acid, cyclohexylboronic acid, cyclopentyl boronic acid, and isopropylboronic acid to obtain a compound selected from the group consisting of 44, 46, 48, 50, 52, 54, 56, 58, 63, 65, 67, 69, 71, 291, and 294 which is treated with 4-nitrophenylchloroformate in presence of TEA as a base followed by reaction with 3-aminoacetophenone in dry THF at room temperature for 5-8 hours to obtain the compound having Structure I selected from the group consisting of 45, 47, 49, 51, 53, 55, 57, 59, 64, 66, 68, 70, 72, 292, and 295;

44

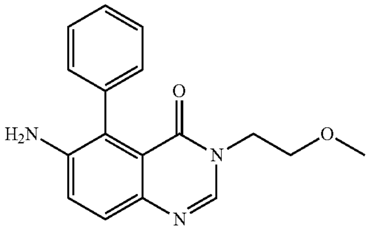

45

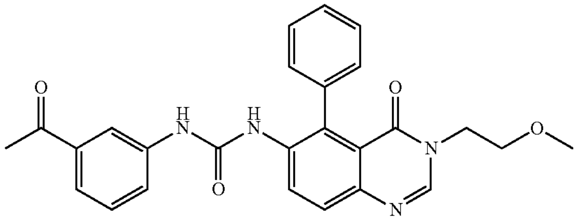

46

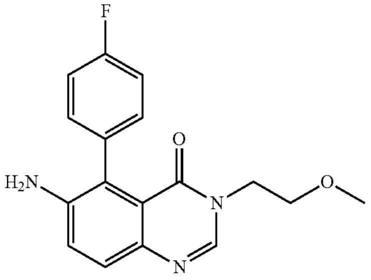

47

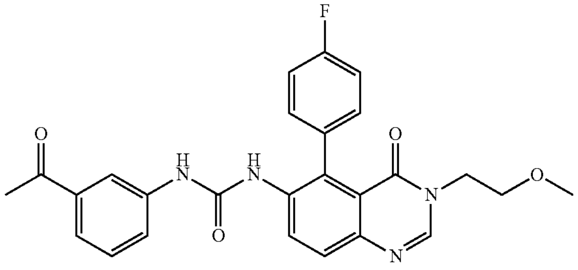

48

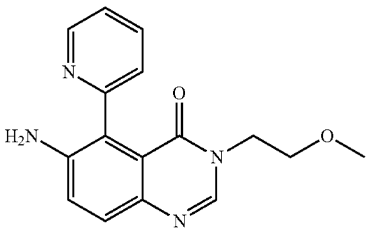

49

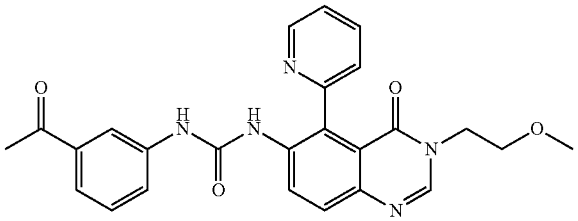

-continued
50
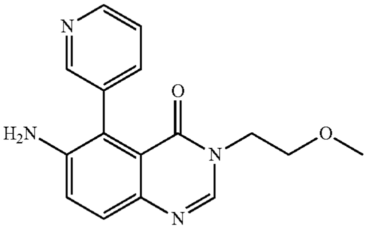
51
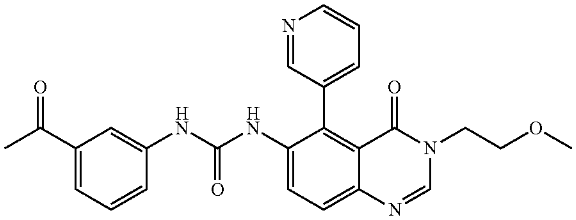
52
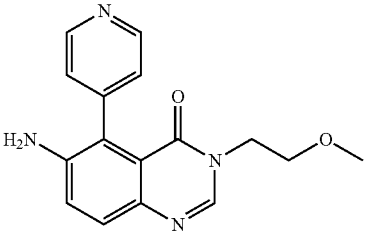
53
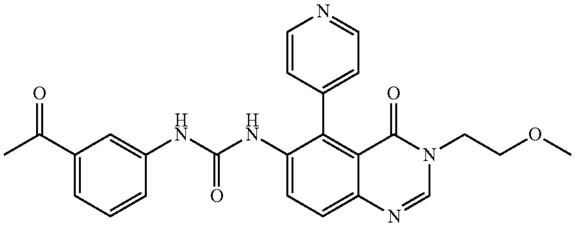
54
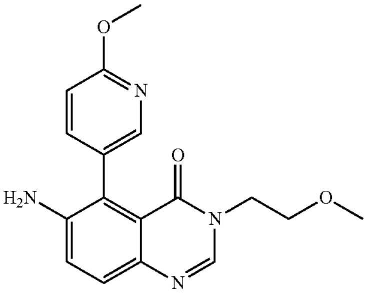
55
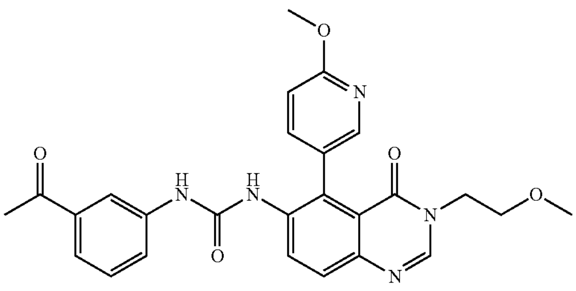
-continued
56
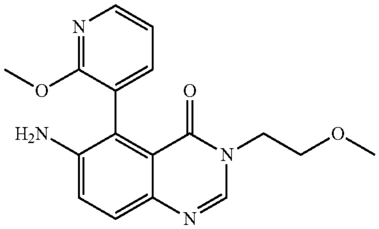
57
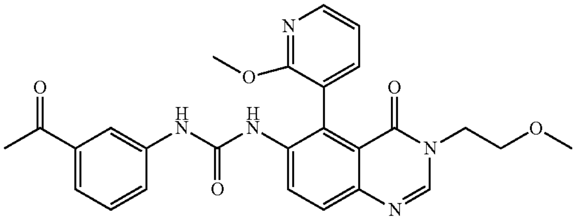
58
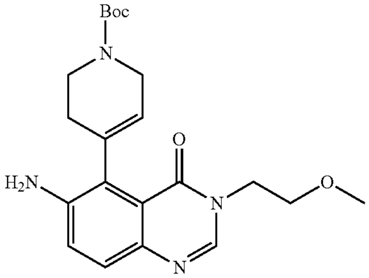
59
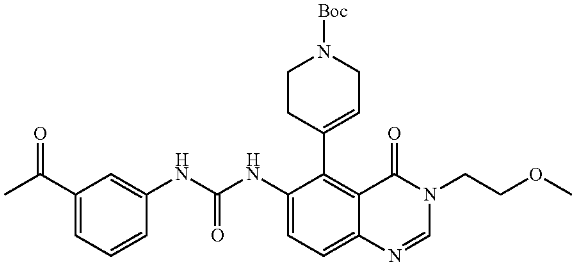
63
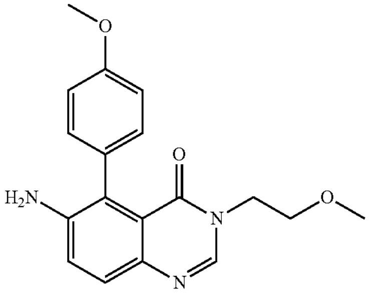

-continued
64
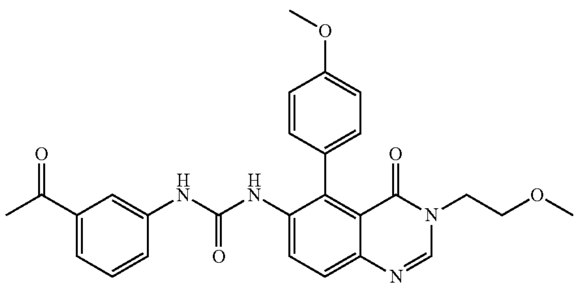
65
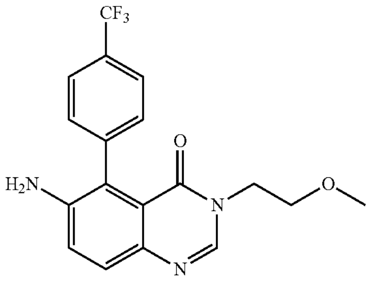
66
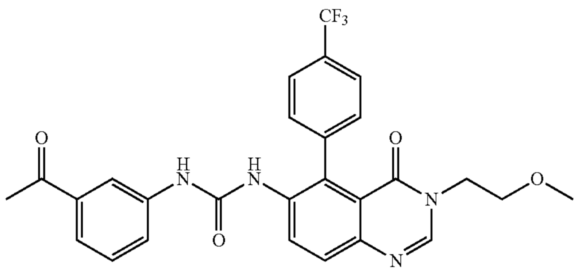
67
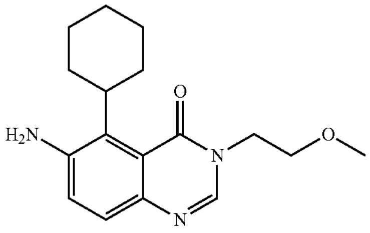
68
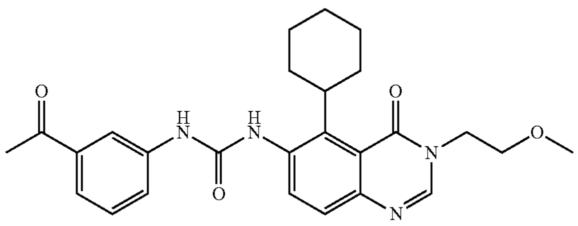
69
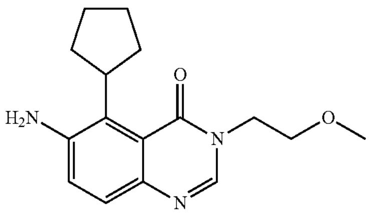
-continued
70
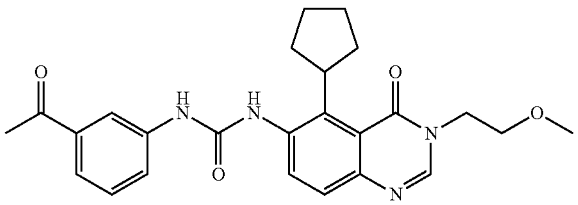
71
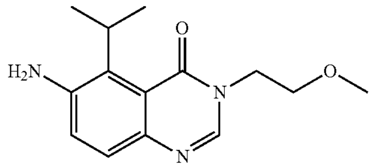
72
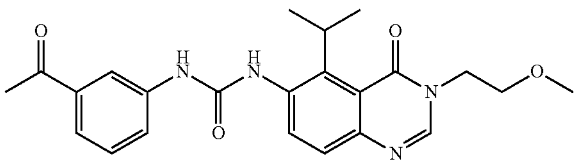
291
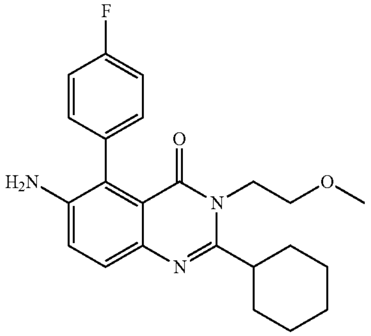
292
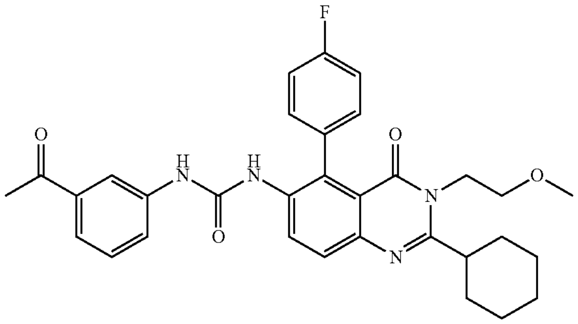
294
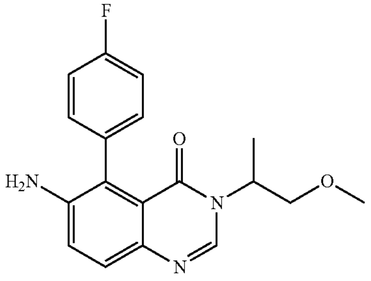

-continued

295

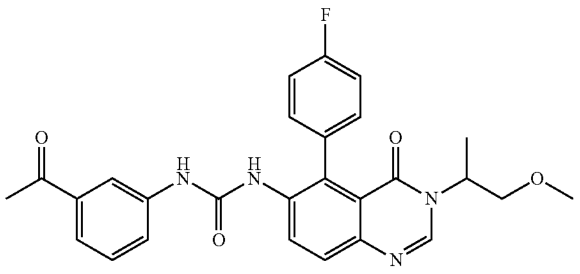

(xx) alternately, treating compound 4 obtained in step (xvi) with 4-nitrophenylchloroformate in presence of TEA as a base followed by reaction with an amine selected from the group consisting of aniline, m-anisidine, N1-methylbenzene-1,3-diamine, m-nitroaniline, 3-aminoacetophenone, 4-aminoacetophenone, 1-(3-aminophenyl)ethanol, methyl 3-amino-4-methoxybenzoate, 3-ethylaniline, 3'-aminobenzophenone, 3-amino-N-cyclohexylbenzamide, methyl 2-(3-aminobenzamido)-3-methylbutanoate, 3-amino-N,N-dimethylbenzamide, (3-aminophenyl)(pyrrolidin-1-yl) methanone, (3-aminophenyl)(pyrrolidin-1-yl) methanone, (4-aminophenyl)(pyrrolidin-1-yl) methanone, 3-(benzo[d]oxazol-2-yl)aniline, N-(3-aminophenyl)acetamide, N-(3-aminophenyl)-N-methylacetamide, N-(3-aminophenyl)-N-benzylacetamide, N-(3-aminobenzyl)acetamide, N-(3-aminobenzyl)-N-methylacetamide, dimethylamine, piperdine, 4-amino-1-methylpiperdine, 4-benzylpiperidine, 1-benzylpiperidin-4-amine, 1-(3-amino-4-hydroxyphenyl)ethanone, 1-(3-amino-5-chloro-2-hydroxyphenyl)ethanone, 1-(3-amino-2-hydroxy-5-methylphenyl)ethanone, 1-(3-aminophenyl)-2,2,2-trifluoroethanol in dry THF at room temperature for 3-8 hours to obtain the compound having Structure I selected from the group consisting of 5, 6, 7, 8, 9, 10, 11, 12, 13, 14, 15, 16, 17, 18, 19, 20, 21, 22, 23, 24, 25, 26, 27, 28, 29, 30, 31, 32, 33, and 34;

5

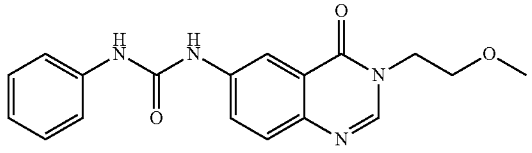

6

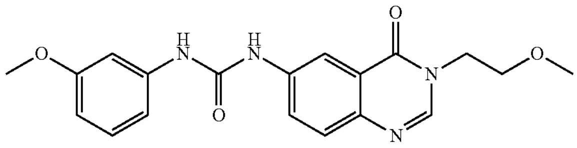

7

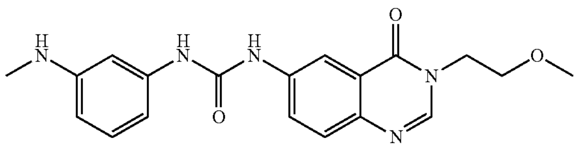

-continued

8

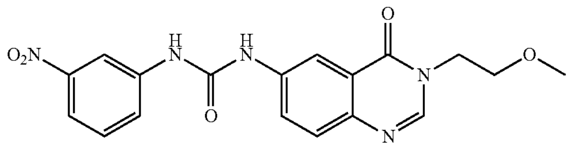

9

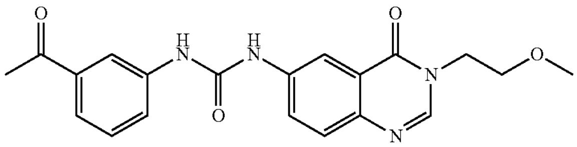

10

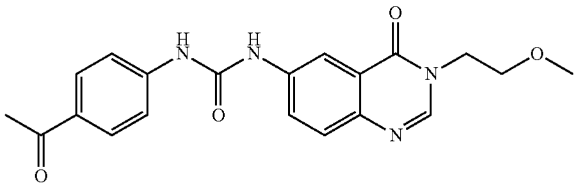

11

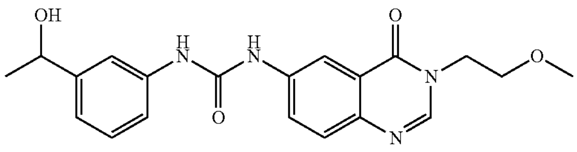

12

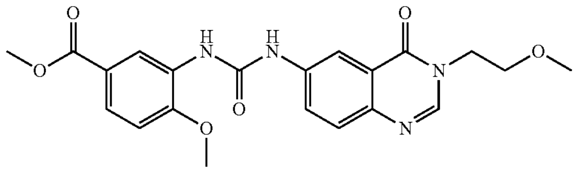

13

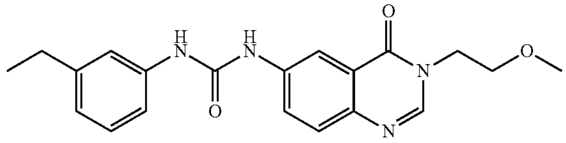

14

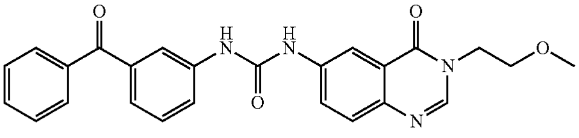

15

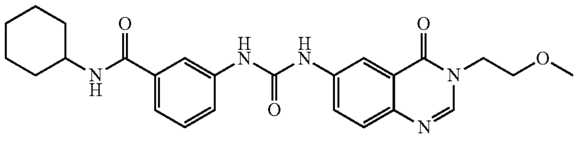

16

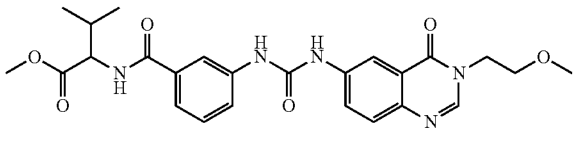

-continued
17
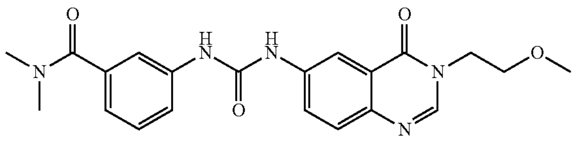
18
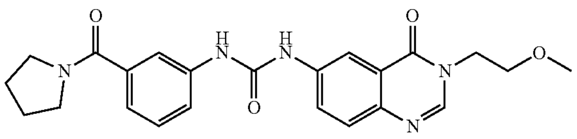
19
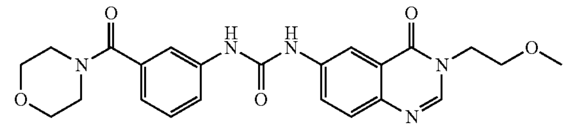
20
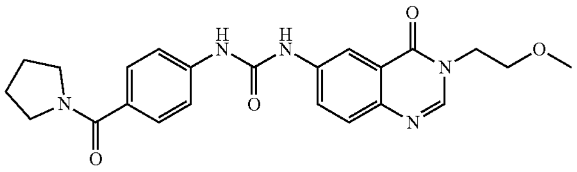
21
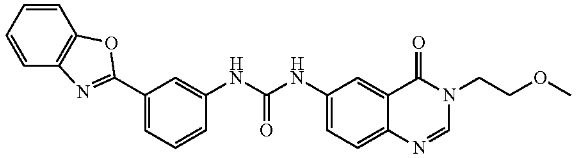
22
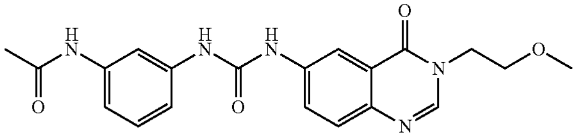
23
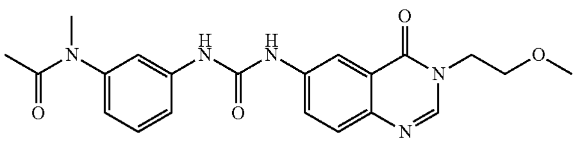
24
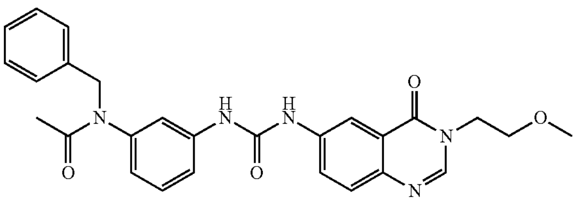
25
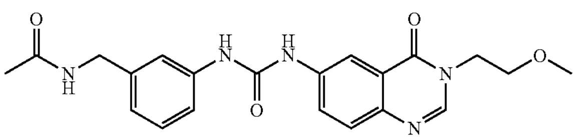
-continued
26
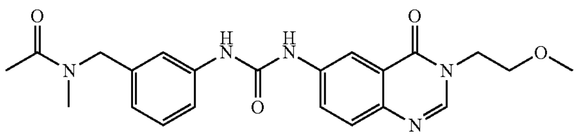
27
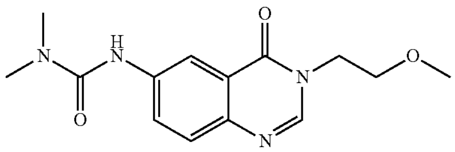
28
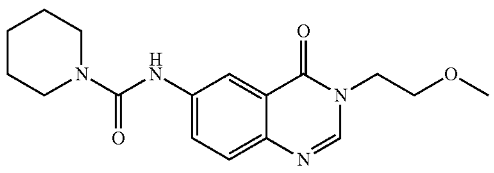
29
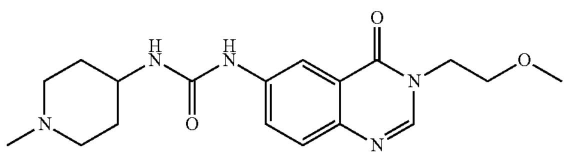
30
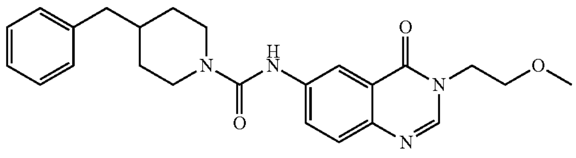
31
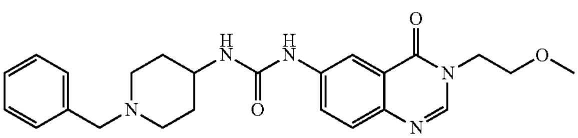
32
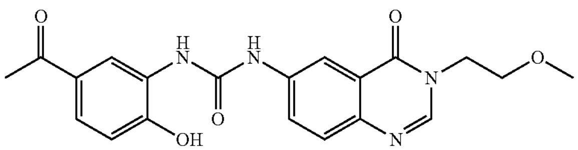
33
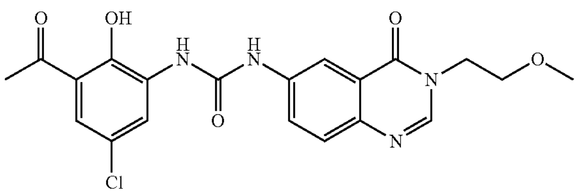

-continued

34

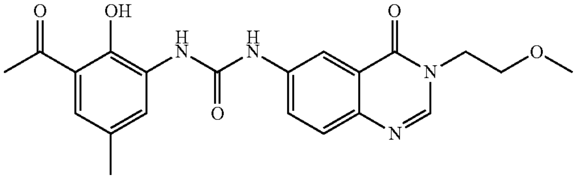

(xxi) alternately, treating the compound selected from the group consisting of 43, 88, 106, 110, 114, 118, 122, 126, 130, 138, 150, 154, 158, 162, 166, 170, 174, 178, 182, 186, 191, 202, 206, 210, 214, 218, 222, 226, 231, 234, 237, 240, 243, 246, 249, 252, 255, 258, 261, 264, 267, 270, 273, 276, 280, 284, 288, 298, 303, 306, 329, 329a, 332, 332a, 335, 335a, 339, and 344 obtained in step (xvi), (xvii) and (xviii) with 4-nitrophenylchloroformate in presence of TEA as a base followed by reaction with 3-aminoacetophenone in dry THF at room temperature for 3-8 hours to obtain the compound having Structure I selected from the group consisting of 73, 89, 107, 111, 115, 119, 123, 127, 131, 139, 151, 155, 159, 163, 167, 171, 175, 179, 183, 187, 192, 193, 194, 195, 196, 197, 198, 199, 203, 207, 211, 215, 219, 223, 227, 232, 235, 238, 241, 244, 247, 253, 256, 259, 262, 268, 274, 277, 281, 285, 289, 304, 307, 330, 330a, 333, 333a, 336, 336a, 340, and 345;

73

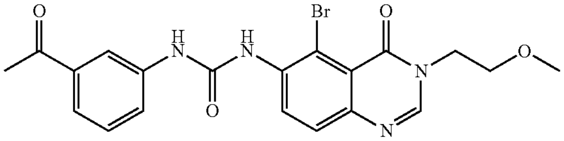

89

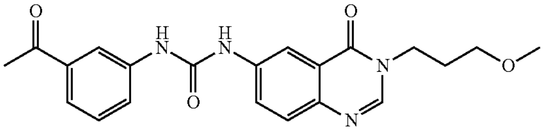

107

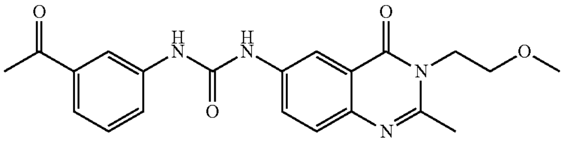

111

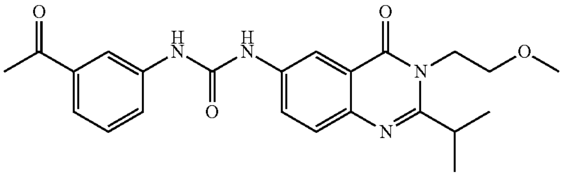

115

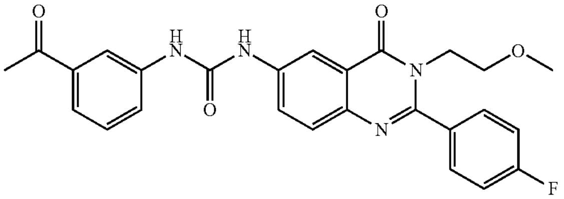

119

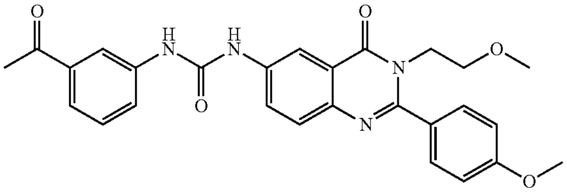

123

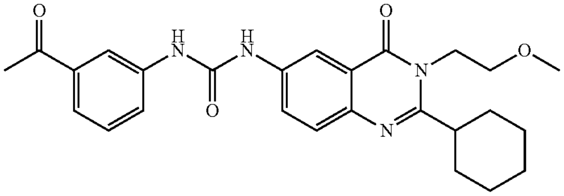

127

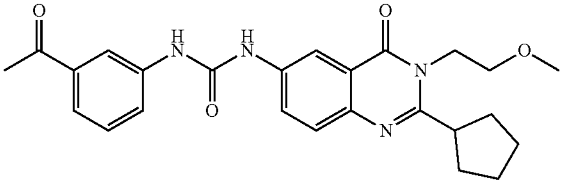

131

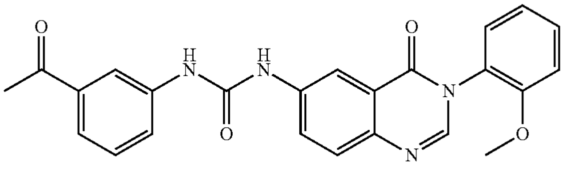

139

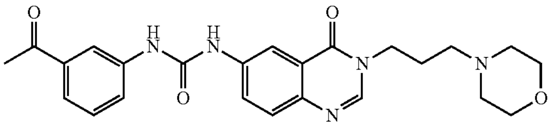

151

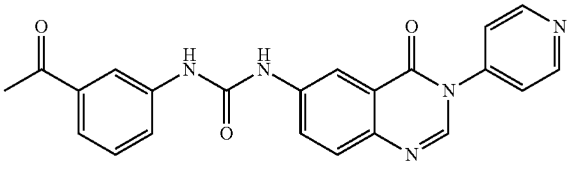

155

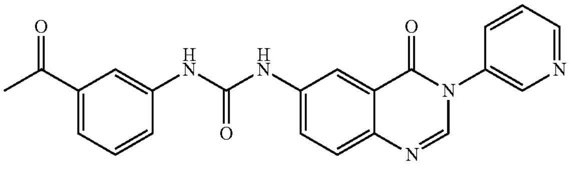

-continued
159
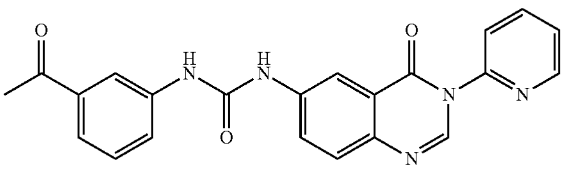
163
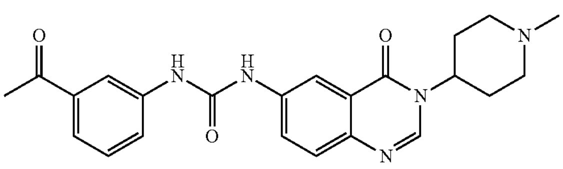
167
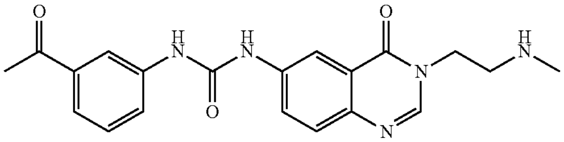
171
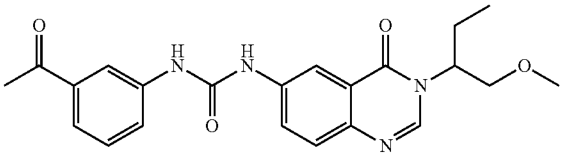
175
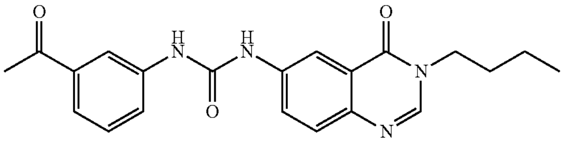
179
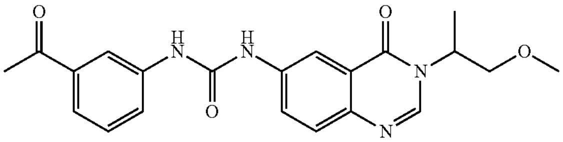
183
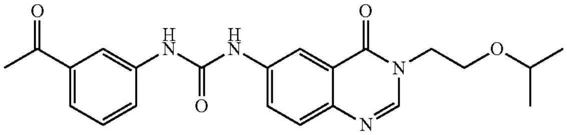
187
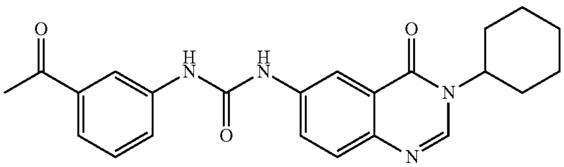
192
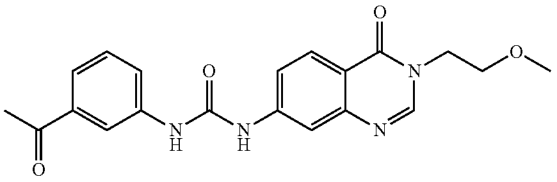
193
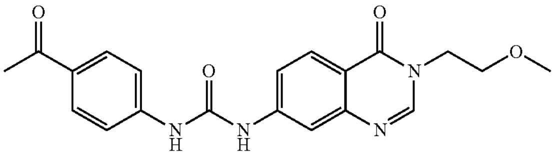
194
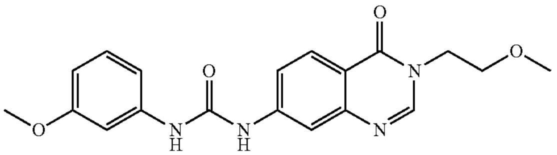
195
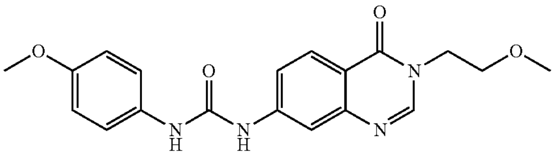
196
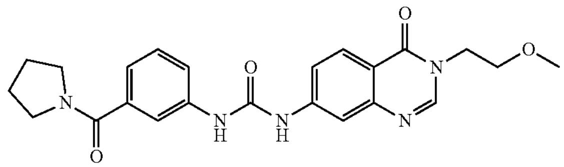
197
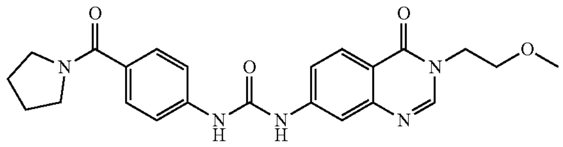
198
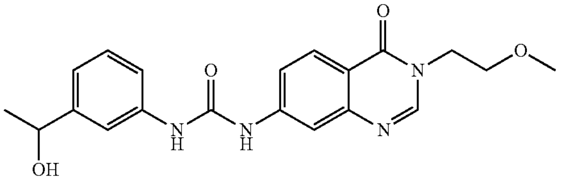
199
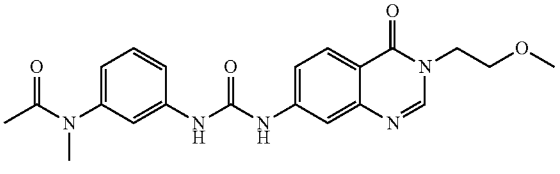

-continued
203
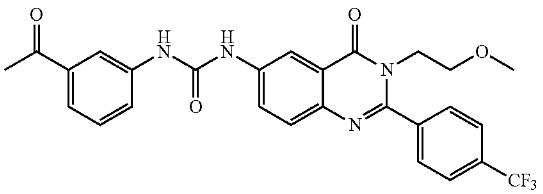
207
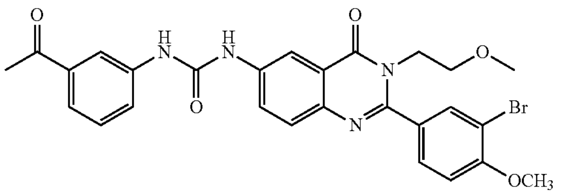
211
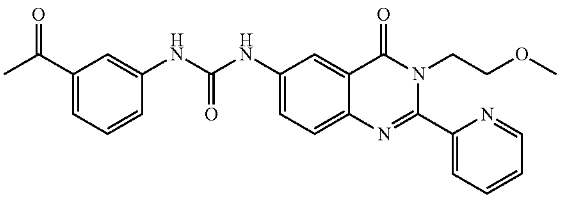
215
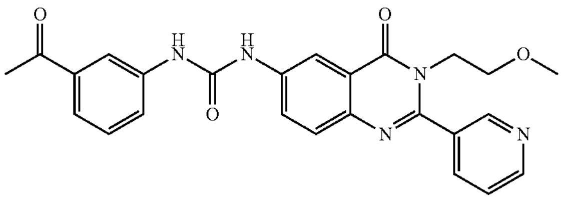
219
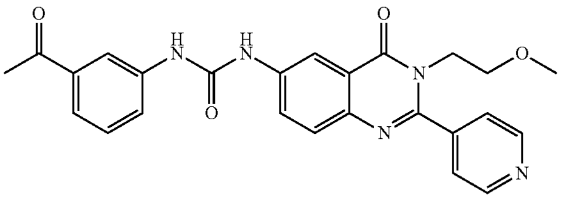
223
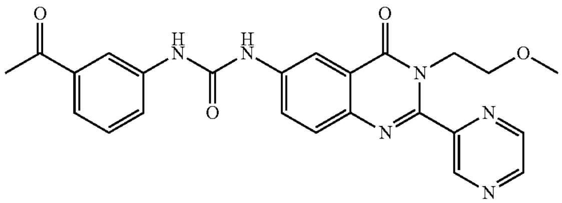
227
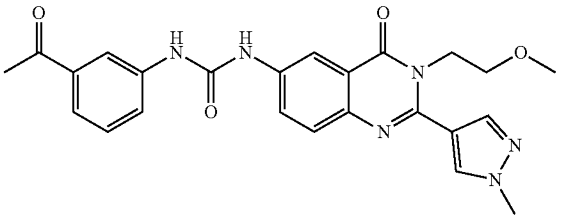
232
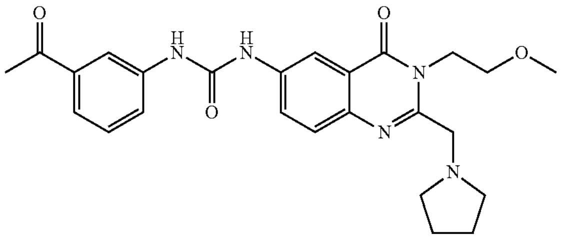
235
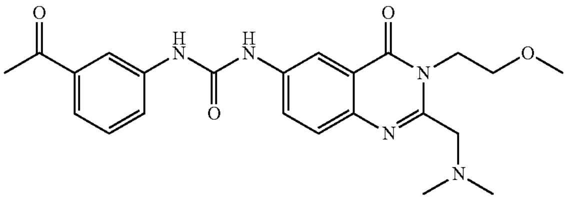
238
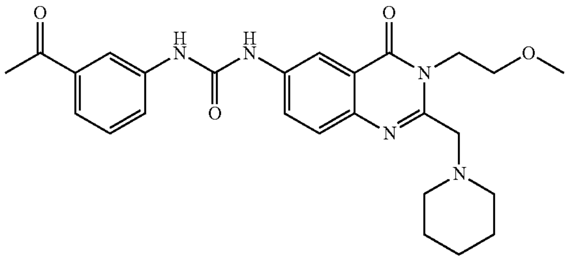
241
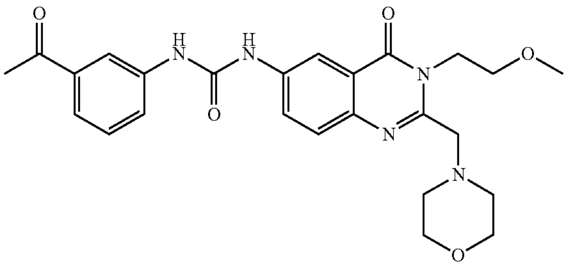
244
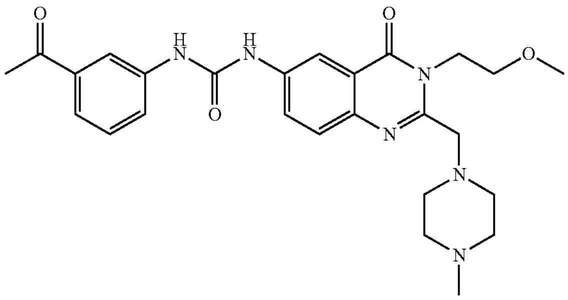

-continued
247
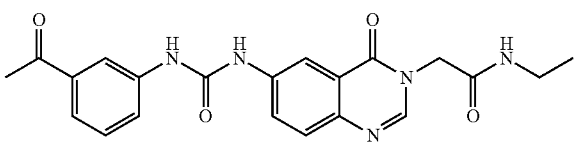
253
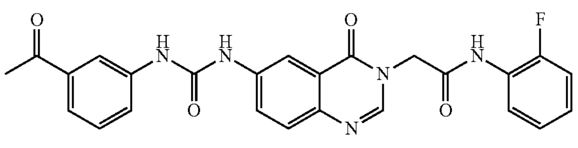
256
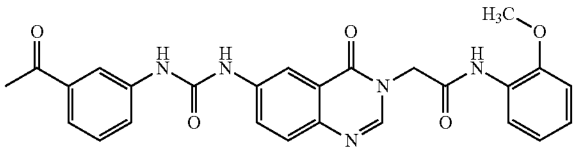
259
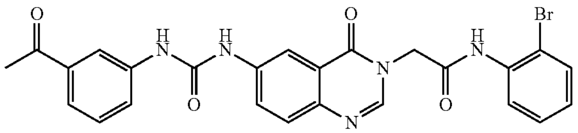
262
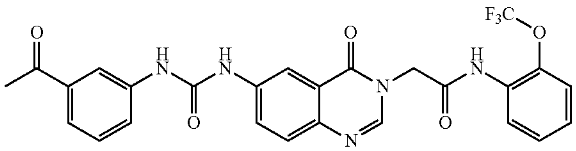
268
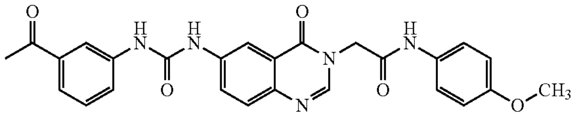
274
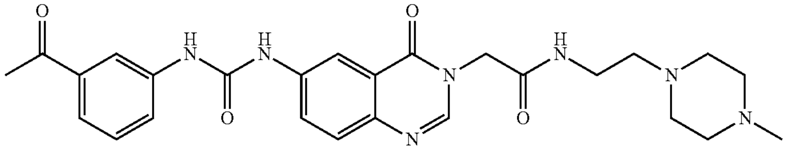
277
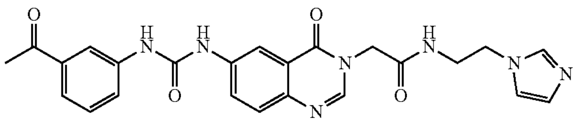
281
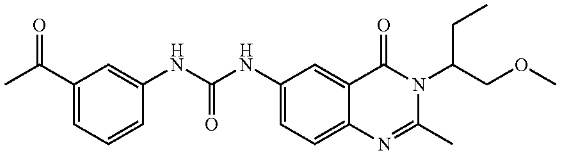
285
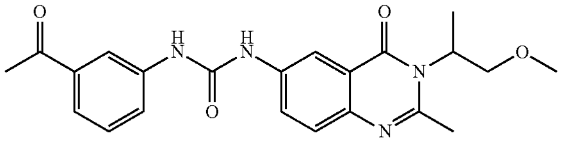
289
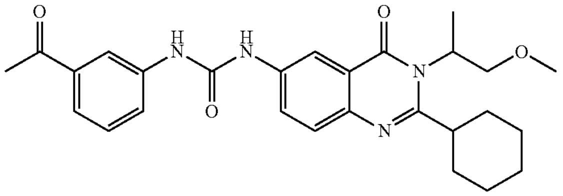
304
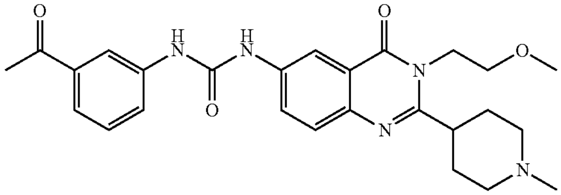
307
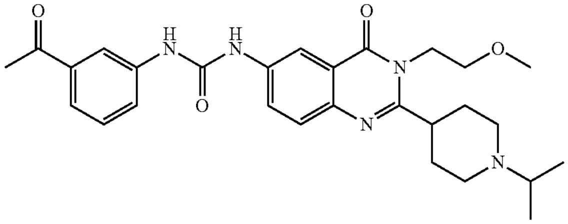
330
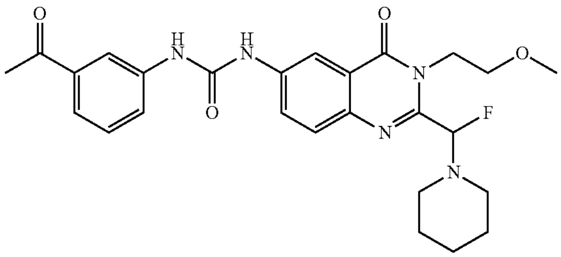
330a
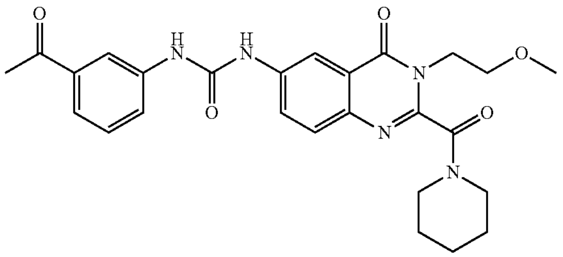

-continued

333

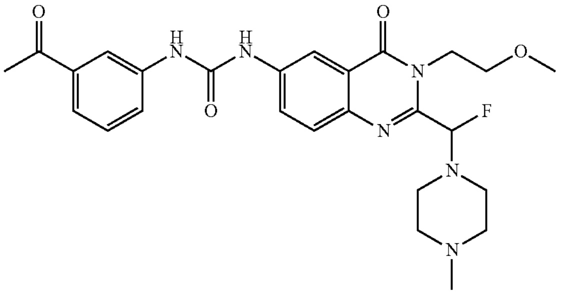

333a

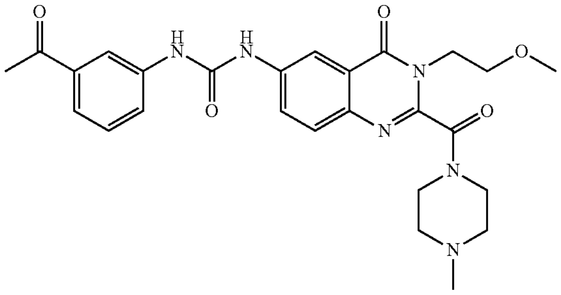

336

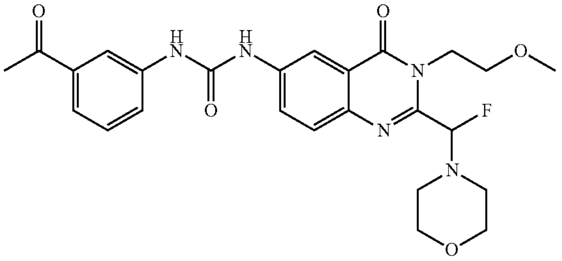

336a

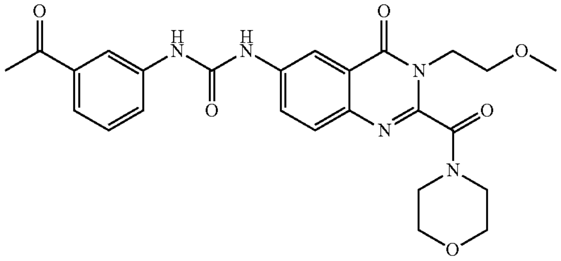

340

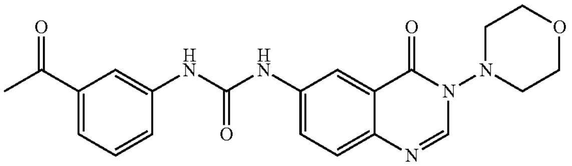

345

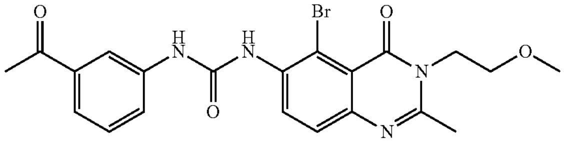

(xxii) alternately, treating the compound selected from the group consisting of 4, 82, 92, 97, 102, 134, 142, and 146 obtained in step (xvi) with a substituted aromatic isocyanate selected from the group consisting of 4-fluorophenylisocyanate, 3-chloro-4-fluorophenylisocyanate, (4-trifluoromethoxy)phenylisocyanate, (4-trifluoromethyl)phenylisocyanate, (2-trifluoromethyl) phenylisocyanate, 4-methoxyphenylisocyanate, 2-methoxyphenylisocyanate, ethyl 3-isocyanatobenzoate, 3-acetylphenylisocyanate, and 4-acetylphenylisocyanate in presence of TEA as a base in dry THF at room temperature for 3-8 hours to obtain the compound having Structure I selected from the group consisting of 35, 36, 37, 38, 39, 40, 41, 42, 83, 84, 85, 93, 94, 98, 99, 103, 135, 143, and 147;

35

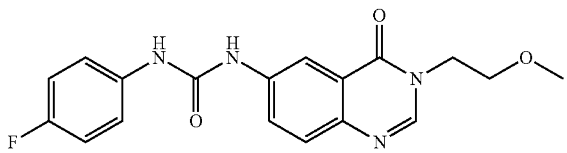

36

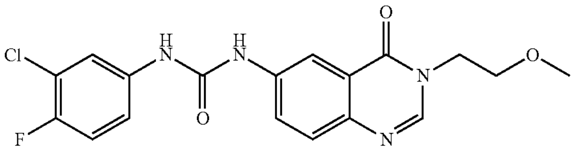

-continued

37

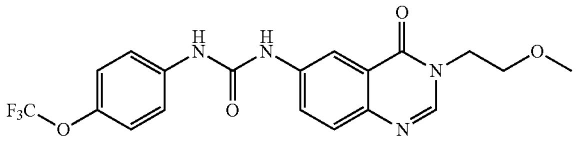

38

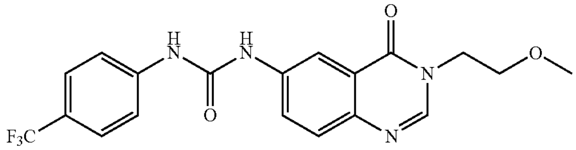

39

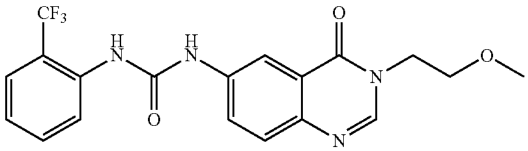

40

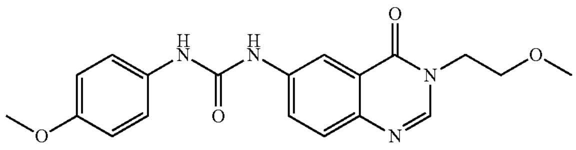

-continued

41

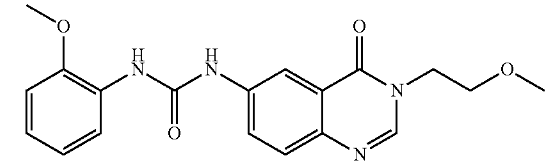

42

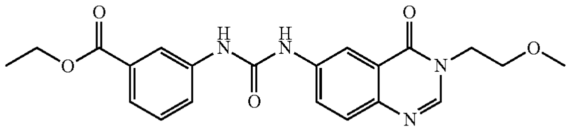

83

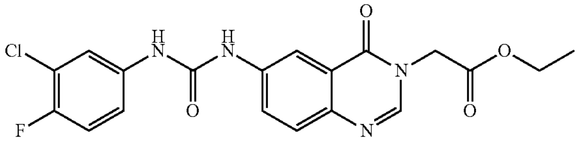

84

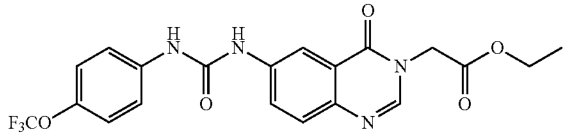

85

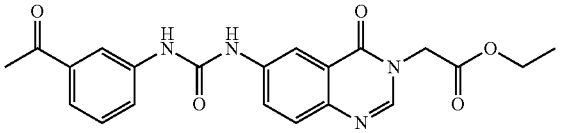

93

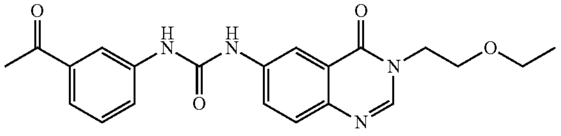

94

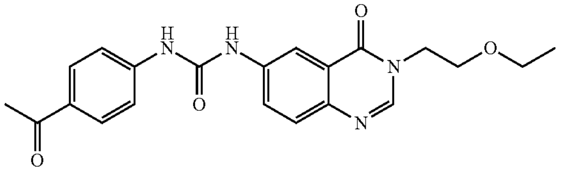

98

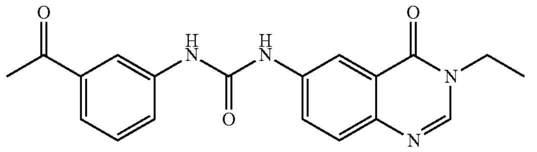

99

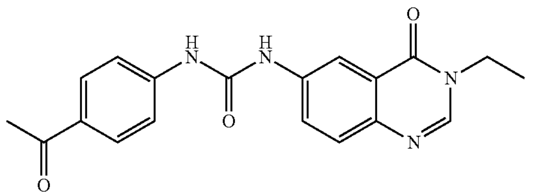

-continued

103

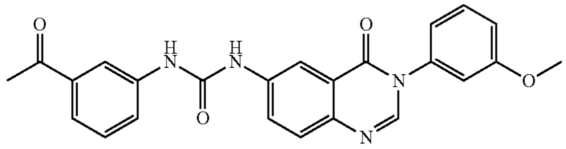

135

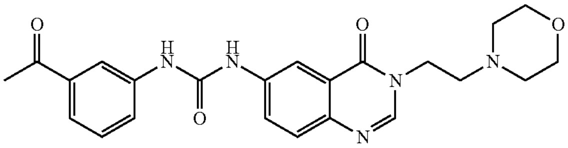

143

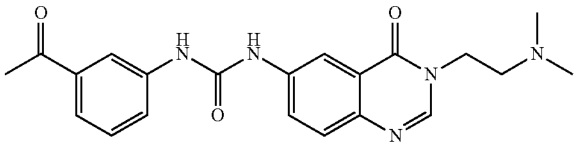

147

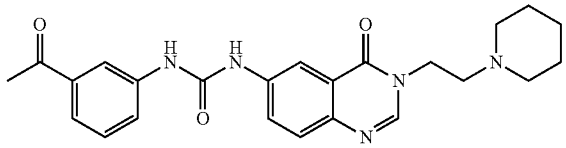

(xxiii) alternately, reacting compound 4 obtained in step (xvi) with HATU/TEA in DMF at room temperature with 5 hours of stirring to obtain a compound 74;

74

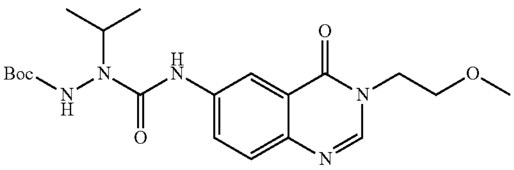

(xxiv) separately adding 3-nitrobenzoyl chloride (3-nitrobenzoic acid and Oxalyl Chloride) at 0° C. in DCM and TEA and stirring for 5 hours at room temperature to obtain a compound 77;

77

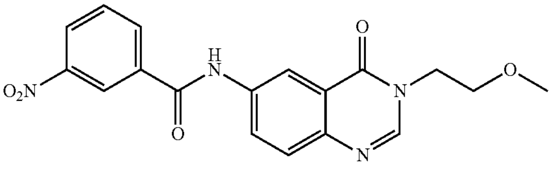

(xxv) separately Boc deprotecting the compound 59 obtained in step (xix) and the compound 74 obtained in step (xxiii) by TFA at room temperature for 2 hours to obtain a compound selected from 60 or 75;

60

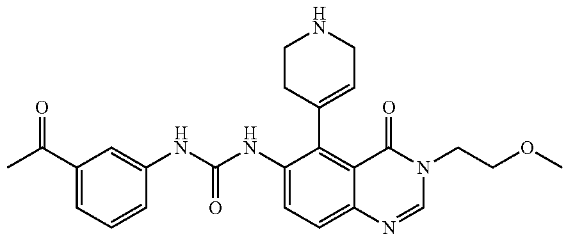

75

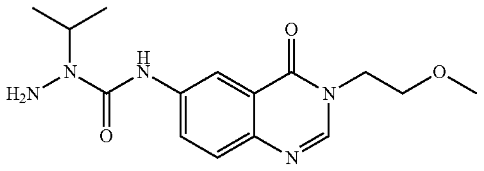

(xxvi) treating the compound 59 obtained in step (xix) and compound 60 obtained in step (xxv) with $H_2$/Pd—C (5% wet) to obtain the compound having Structure I selected from the group consisting of 61 and 62;

61

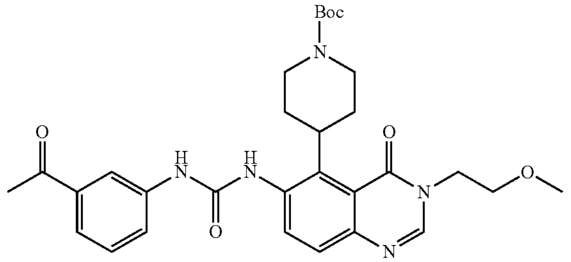

62

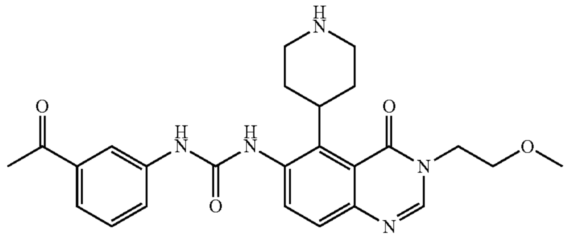

(xxvii) alternately, treating the compound selected from the group consisting of 191, 4, 46, 237, 249, 106, 243, and 252 obtained in step (xvi) and (xix) with 4-nitrophenylchloroformate in presence of TEA as a base followed by reaction with an amine selected from the group consisting of 3-aminoacetophenone, 4-aminoacetophenone, m-anisidine, p-anisidine, (3-aminophenyl)(pyrrolidin-1-yl)methanone, (4-aminophenyl)(pyrrolidin-1-yl)methanone, 1-(3-aminophenyl)-2,2,2-trifluoroethanol, -(3-aminophenyl)-N-methylacetamide, 1-(3-(hydroxyamino)phenyl) ethanone, 1-(3-(methylamino)phenyl)ethanone, and 1-(3-aminophenyl)-2,2,2-trifluoroethanone in dry THF at room temperature for 3-8 hours to obtain the compound having Structure I selected from the group consisting of 194, 195, 196, 197, 198, 199, 308, 309, 310, 311, 312, 313, 314, 315, 316, 317, 318, 319, 320, 321, 322, 323, 324, and 325;

194

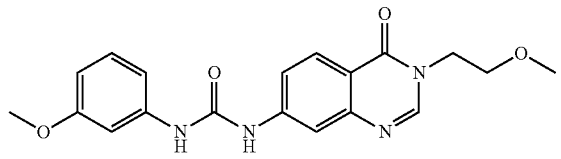

195

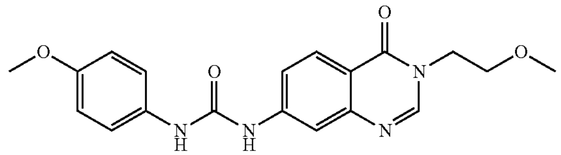

196

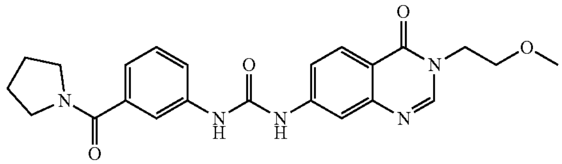

197

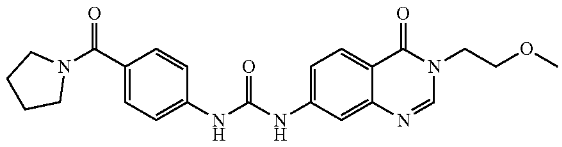

198

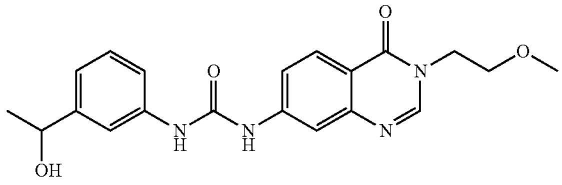

199

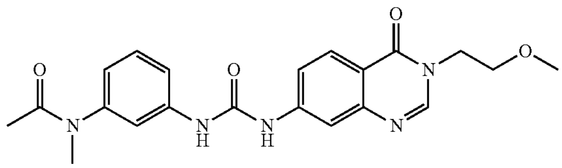

308

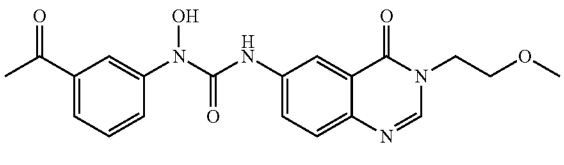

309

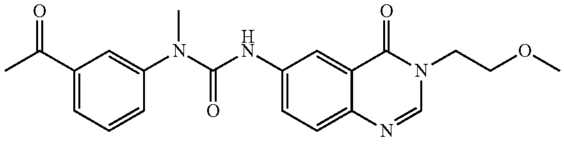

-continued
310
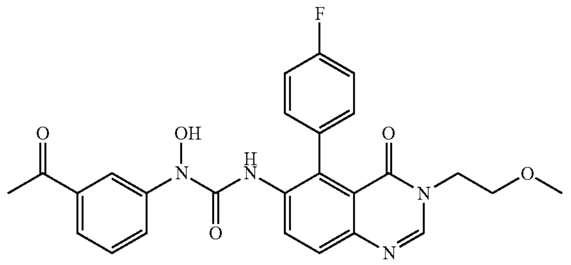
311
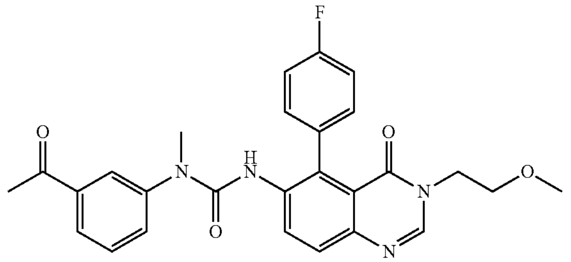
312
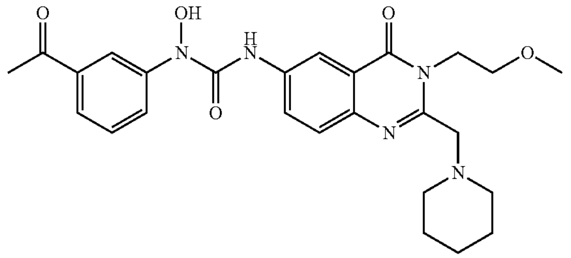
313
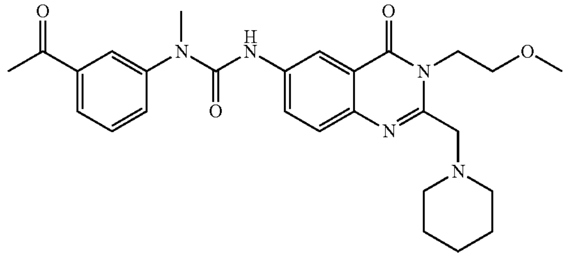
314
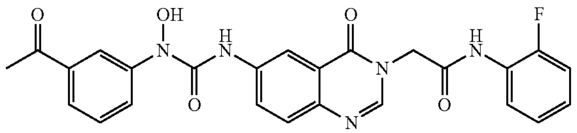
315
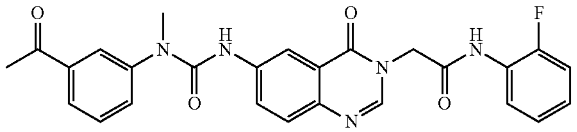
316
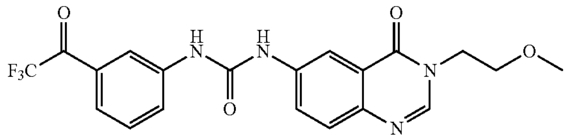
-continued
317
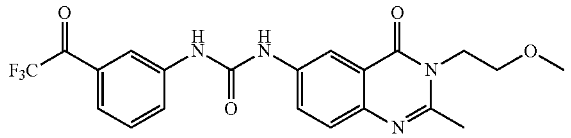
318
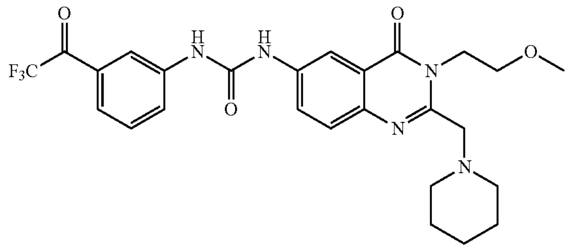
319
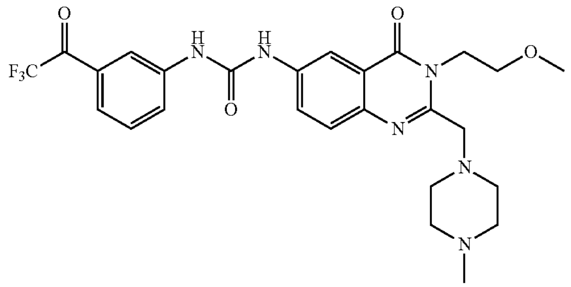
320
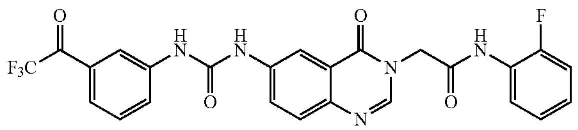
321
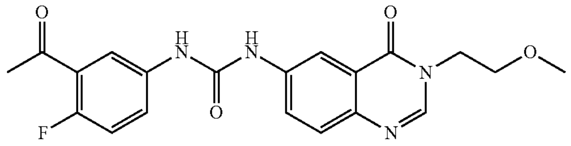
322
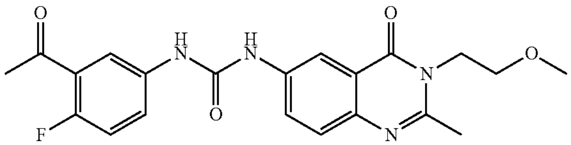
323
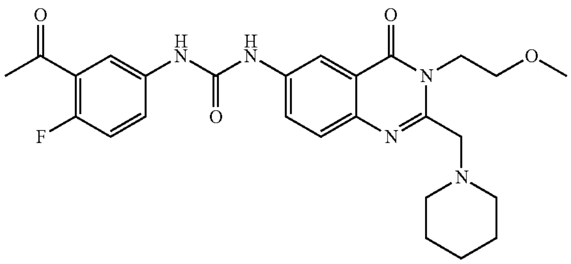

-continued

324

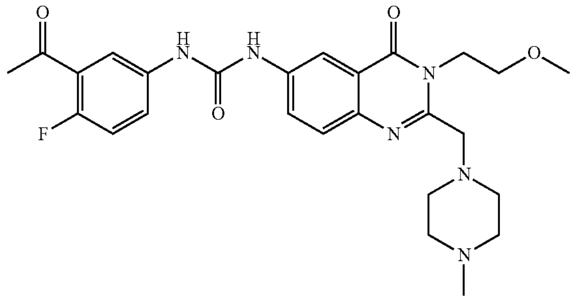

325

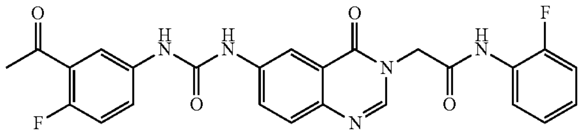

(xxviii) subjecting the compound selected from 42 and 85 obtained in step (xxii) to ester hydrolysis by LiOH monohydrate in presence of THF:EtOH:Water (3:2:1) proportion at room temperature for 1-2 hours to obtain the compound having Structure I selected from the group consisting of 42a and 85a;

42a

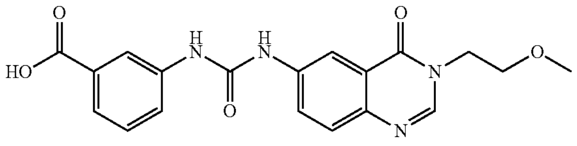

85a

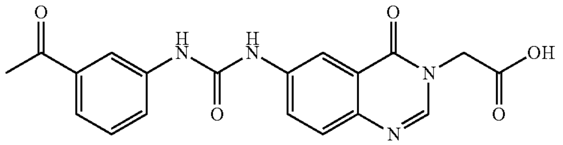

(xxix) reacting the compound 238 obtained in step (xxi) with 1M HCl in dioxane to obtain the compound having Structure I 238a; and 283a

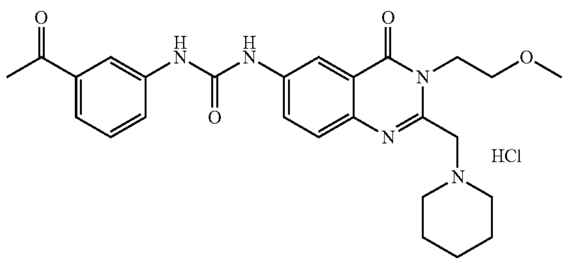

(xxx) reacting the compound selected from the group consisting of 9, 107, and 238 obtained in step (xx) and (xxi) with hydroxylamine hydrochloride ($NH_2OH \cdot HCl$) in ethanol (EtOH) at 80° C. for 12-16 hours to obtain the compound having Structure I selected from the group consisting of 341, 342 and 343

341

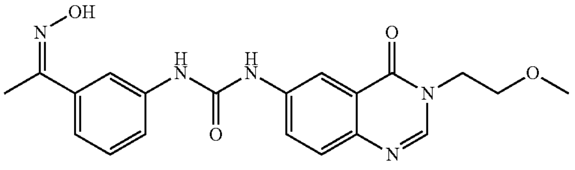

342

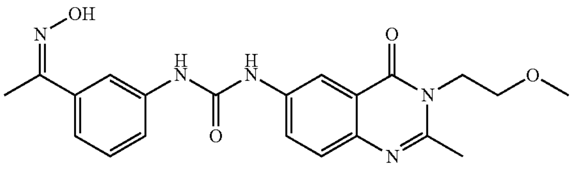

343

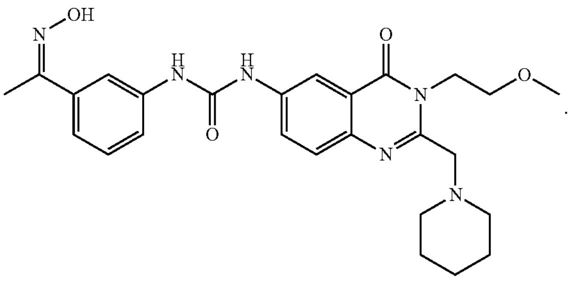

General Procedure for Urea Formation Via Chloroformate Intermediate

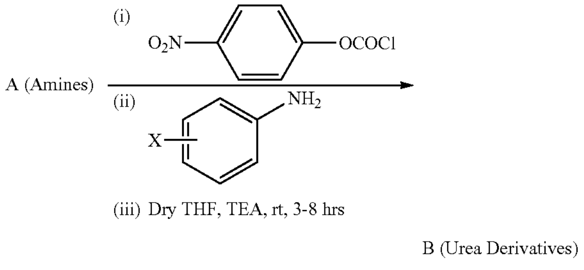

Table 2 provides the structures of reactants and products obtained with reaction via chloroformate intermediates:

TABLE 2
| Serial No. | Amine (A) | 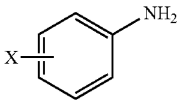 |
|---|---|---|
| 1 | 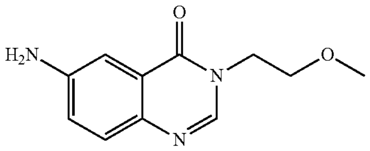 4 | 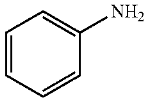 |
| 2 | 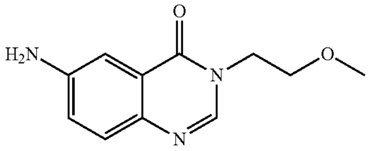 4 | 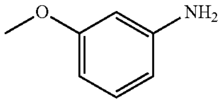 |
| 3 | 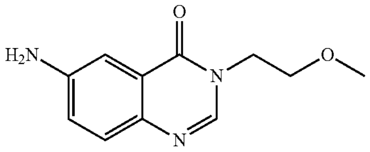 4 | 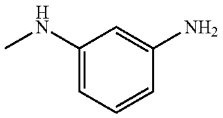 |
| 4 | 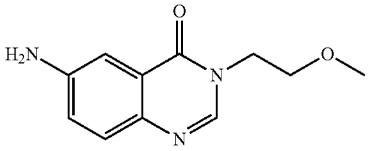 4 | 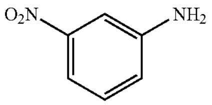 |
| 5 | 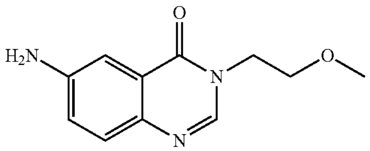 4 | 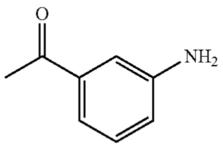 |
| 6 | 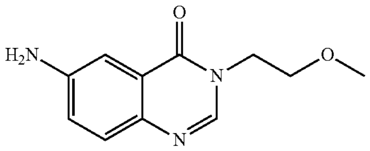 4 | 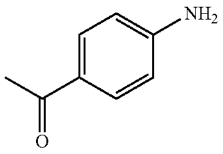 |
| 7 | 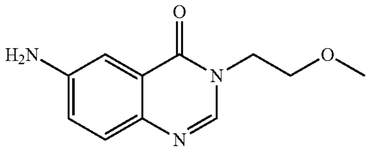 4 | 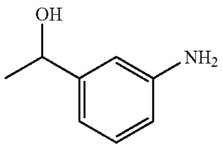 |

TABLE 2-continued
| | | |
|---|---|---|
| 8 | 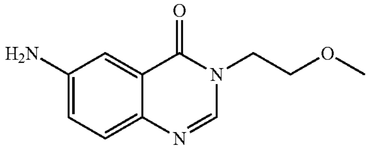<br>4 | 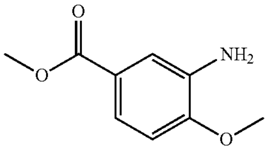 |
| 9 | 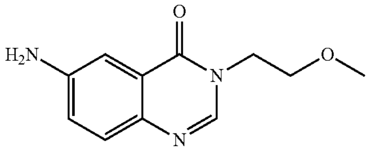<br>4 | 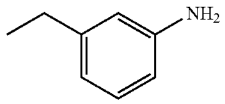 |
| 10 | 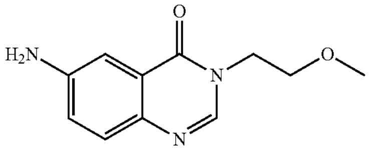<br>4 | 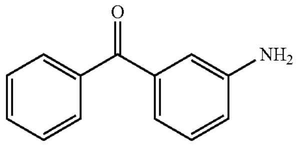 [SMILES: Nc1cccc(C(=O)c2ccccc2)c1] |
| 11 | 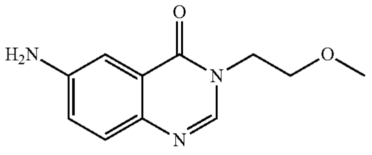<br>4 | 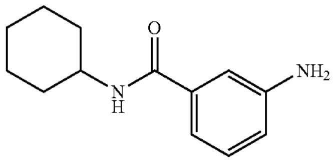 [SMILES: Nc1cccc(C(=O)NC2CCCCC2)c1] |
| 12 | 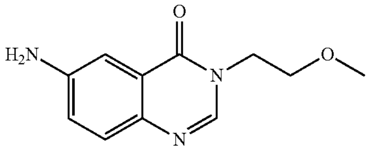<br>4 | 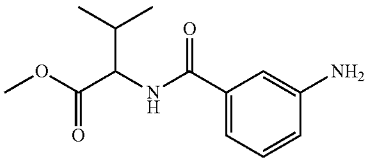 [SMILES: COC(=O)C(NC(=O)c1cccc(N)c1)C(C)C] |
| 13 | 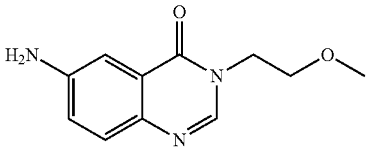<br>4 | 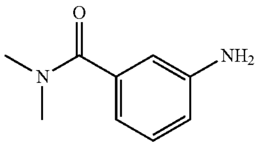 |
| 14 | 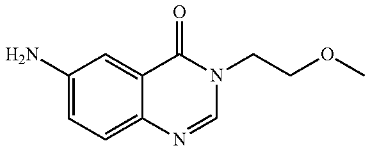<br>4 | 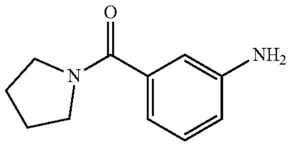 [SMILES: Nc1cccc(C(=O)N2CCCC2)c1] |
| 15 | 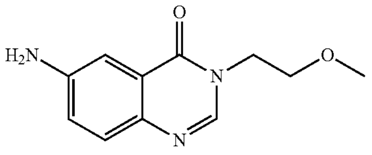<br>4 | 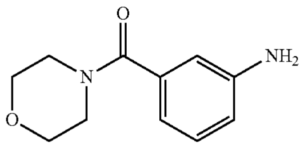 [SMILES: Nc1cccc(C(=O)N2CCOCC2)c1] |

TABLE 2-continued
| | | |
|---|---|---|
| 16 | 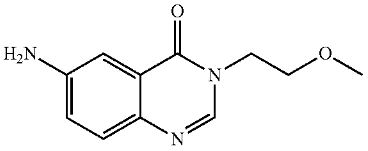 4 | 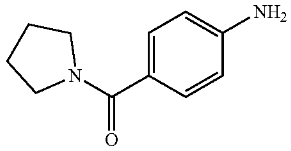 [SMILES: Nc1ccc(C(=O)N2CCCC2)cc1] |
| 17 | 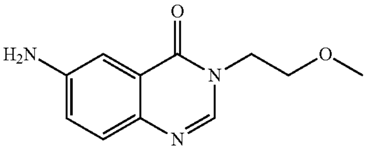 4 | 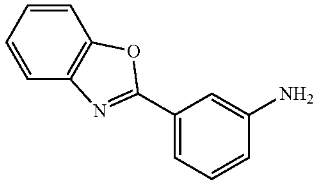 [SMILES: Nc1cccc(-c2nc3ccccc3o2)c1] |
| 18 | 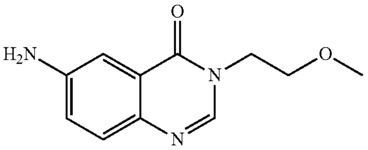 4 | 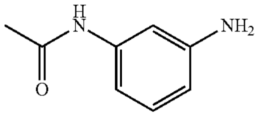 |
| 19 | 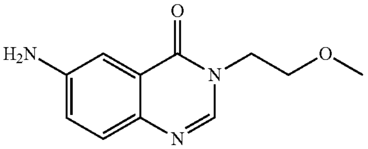 4 | 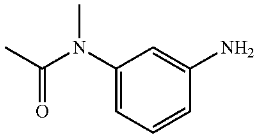 |
| 20 | 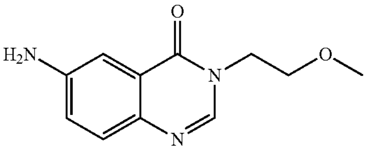 4 | 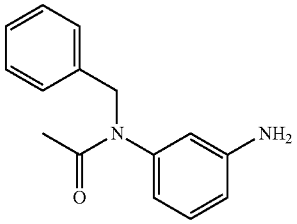 [SMILES: CC(=O)N(Cc1ccccc1)c1cccc(N)c1] |
| 21 | 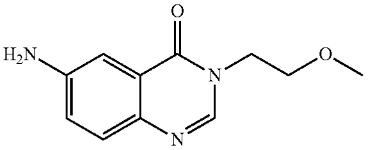 4 | 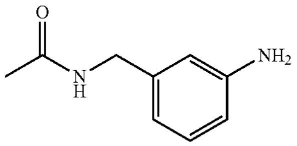 |
| 22 | 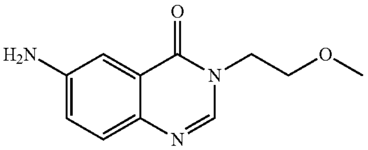 4 | 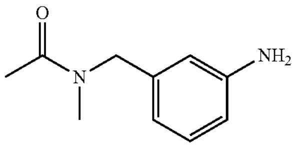 |
| 23 | 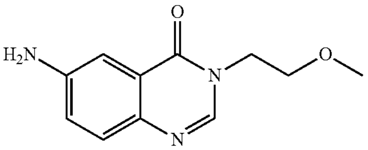 4 | 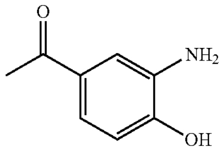 |

TABLE 2-continued
| | | |
|---|---|---|
| 24 | 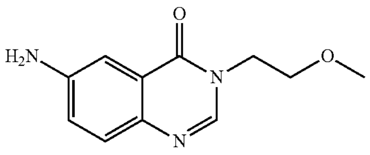 4 | 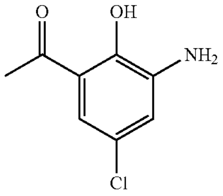 |
| 25 | 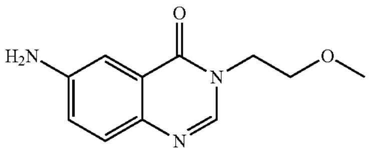 4 | 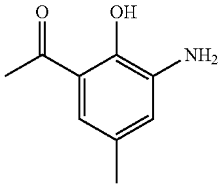 |
| 26 | 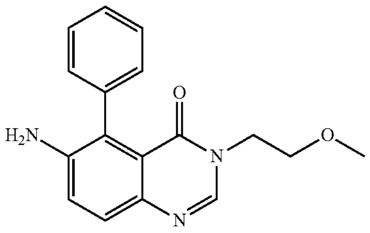 44 | 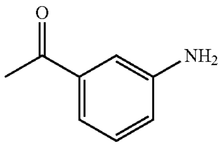 |
| 27 | 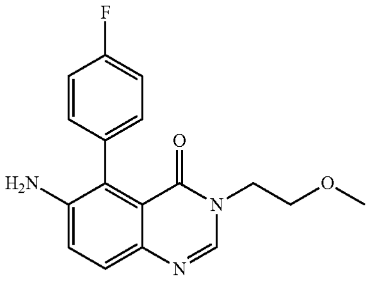 46 | 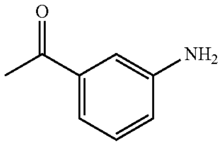 |
| 28 | 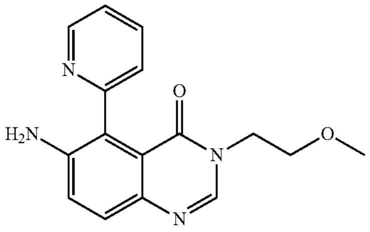 48 | 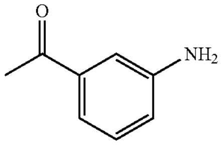 |
| 29 | 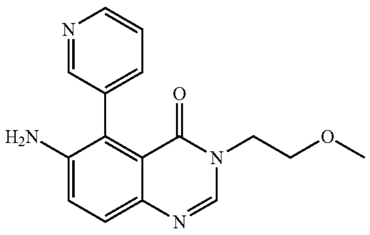 50 | 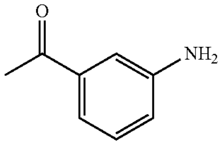 |

TABLE 2-continued
| | | |
|---|---|---|
| 30 | 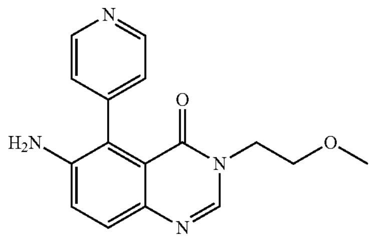 52 | 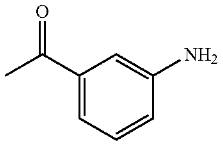 |
| 31 | 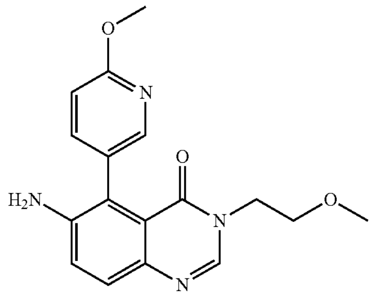 54 | 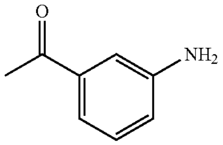 |
| 32 | 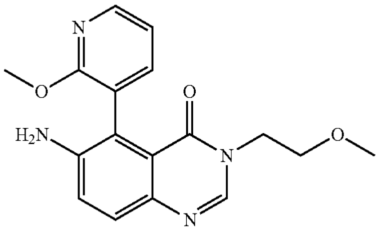 56 | 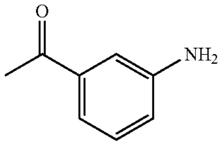 |
| 33 | 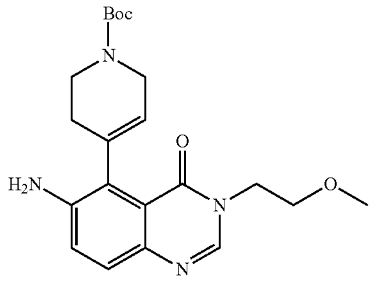 58 | 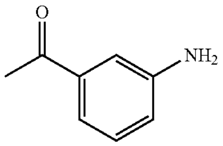 |
| 34 | 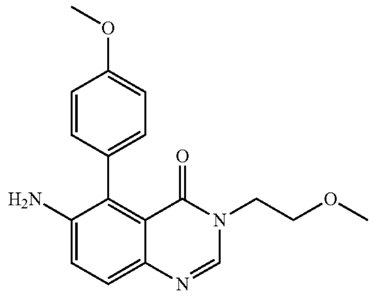 63 | 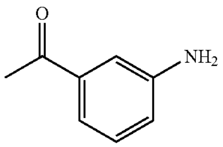 |

TABLE 2-continued
| | | |
|---|---|---|
| 35 | 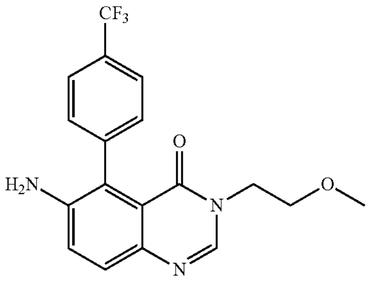<br>65 | 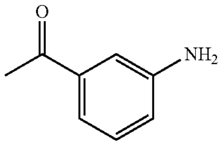 |
| 36 | 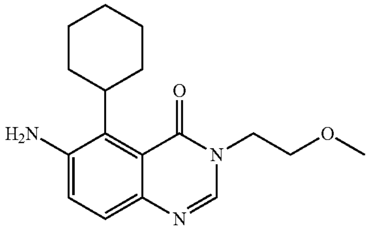<br>67 | 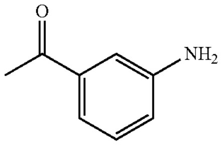 |
| 37 | 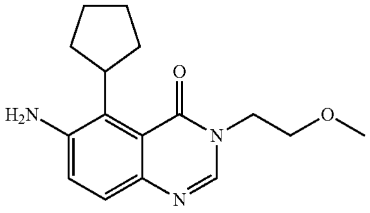<br>69 | 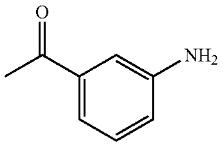 |
| 38 | 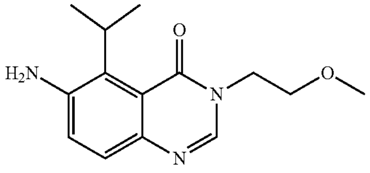<br>71 | 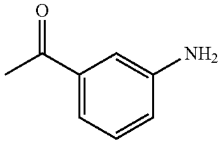 |
| 39 | 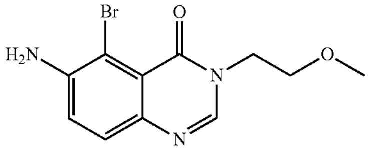<br>43 | 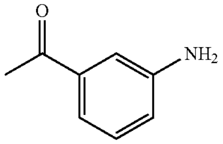 |
| 40 | 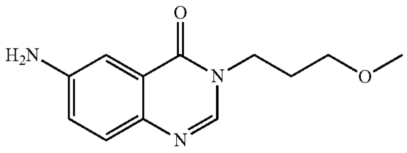<br>88 | 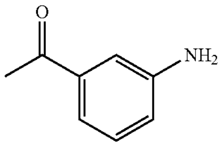 |

TABLE 2-continued
| | | |
|---|---|---|
| 41 | 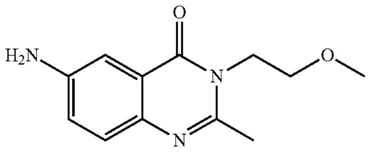<br>106 | 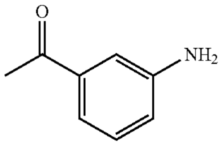 |
| 42 | 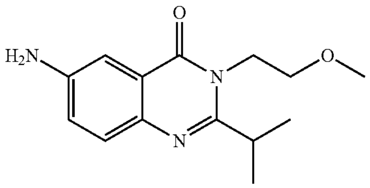<br>110 | 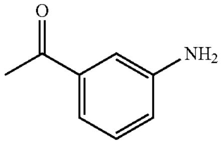 |
| 43 | 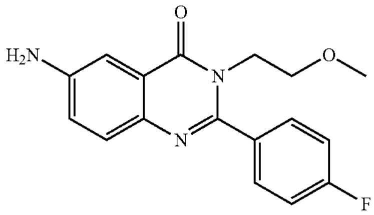<br>114 | 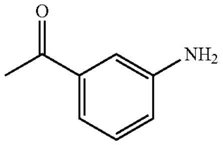 |
| 44 | 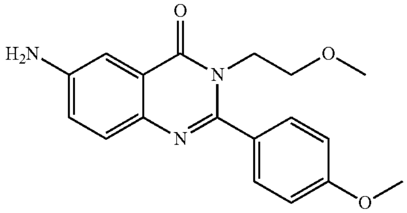<br>118 | 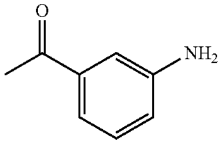 |
| 45 | 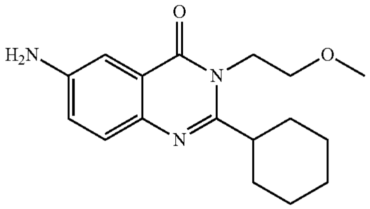<br>122 | 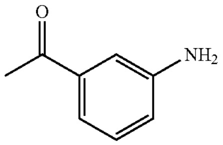 |
| 46 | 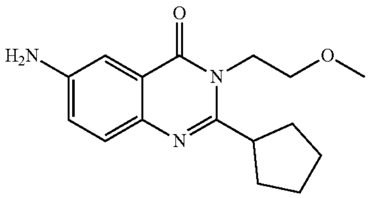<br>126 | 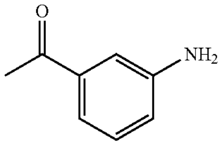 |

TABLE 2-continued
| | | |
|---|---|---|
| 47 | 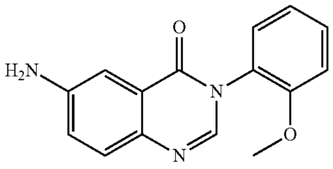 130 | 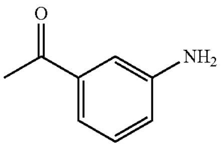 |
| 48 | 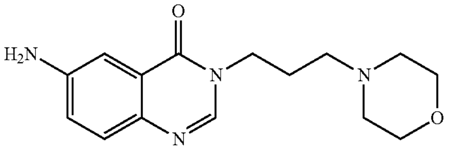 138 | 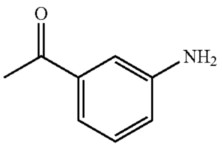 |
| 49 | 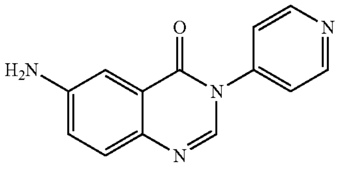 150 | 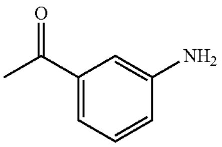 |
| 50 | 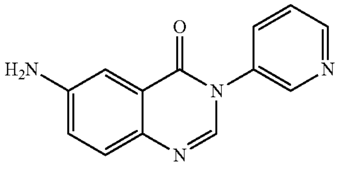 154 | 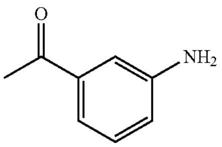 |
| 51 | 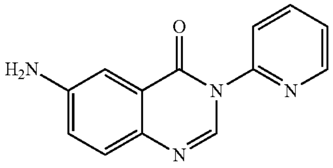 158 | 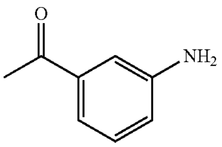 |
| 52 | 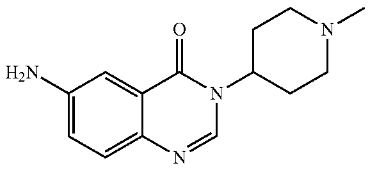 162 | 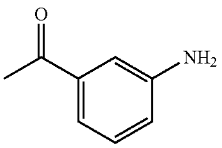 |
| 53 | 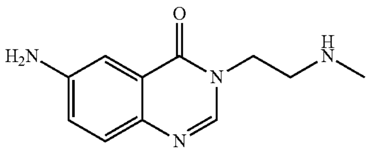 166 | 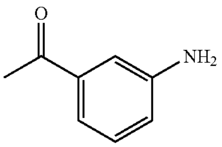 |

TABLE 2-continued
| | | |
|---|---|---|
| 54 | 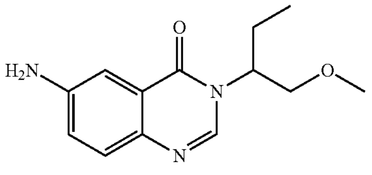 170 | 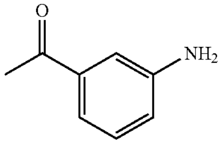 |
| 55 | 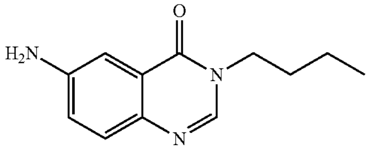 174 | 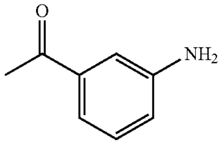 |
| 56 | 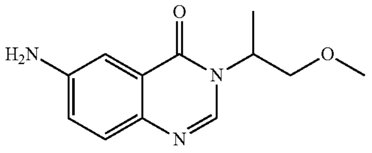 178 | 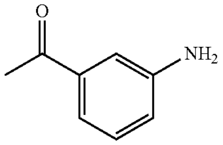 |
| 57 | 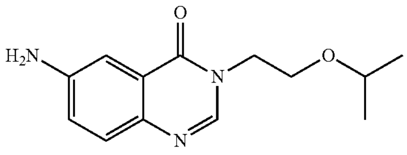 182 | 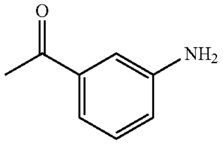 |
| 58 | 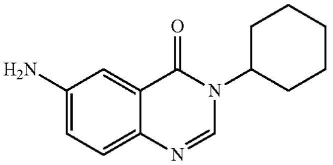 186 | 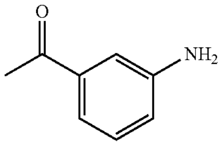 |
| 59 | 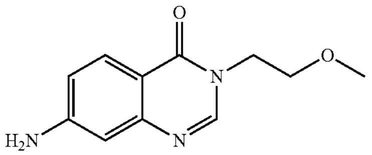 191 | 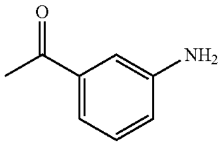 |
| 60 | 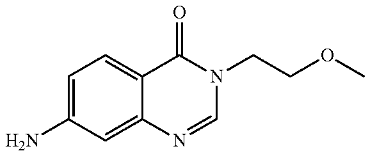 191 | 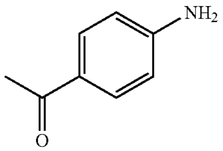 |
| 61 | 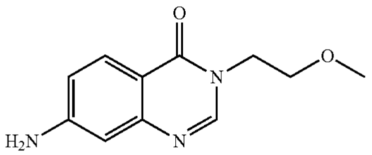 191 | 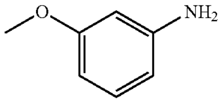 |

TABLE 2-continued
| | | |
|---|---|---|
| 62 | 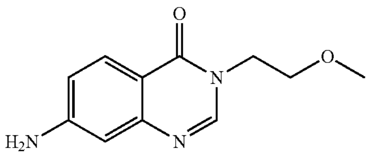 191 | 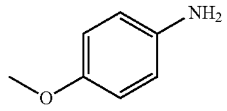 |
| 63 | 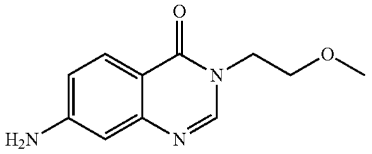 191 | 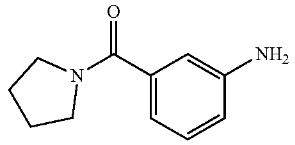 [SMILES: Nc1cccc(C(=O)N2CCCC2)c1] |
| 64 | 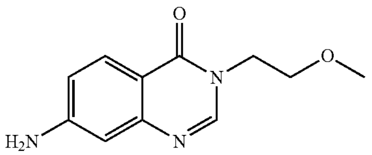 191 | 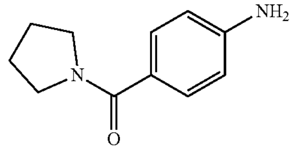 [SMILES: Nc1ccc(C(=O)N2CCCC2)cc1] |
| 65 | 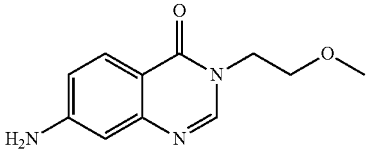 191 | 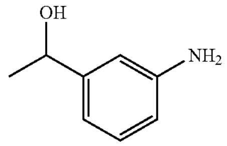 |
| 66 | 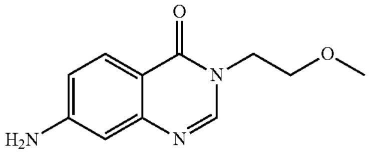 191 | 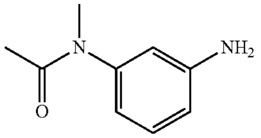 |
| 67 | 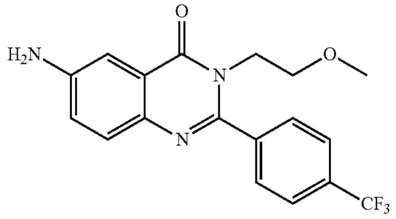 202 | 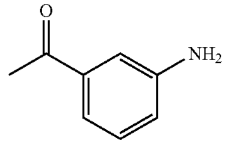 |
| 68 | 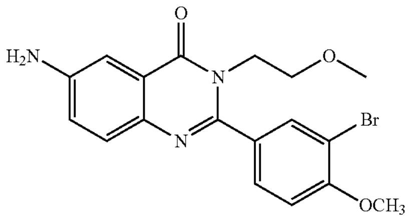 206 | 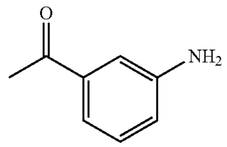 |

TABLE 2-continued
| | | |
|---|---|---|
| 69 | 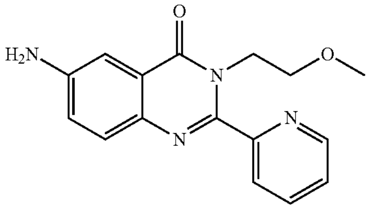<br>210 | 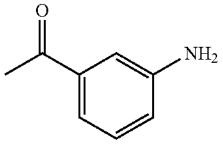 |
| 70 | 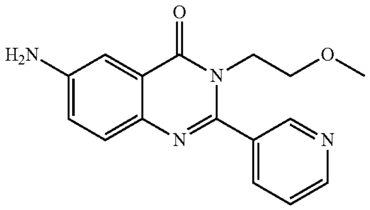<br>214 | 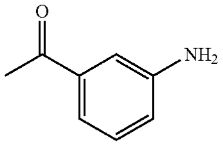 |
| 71 | 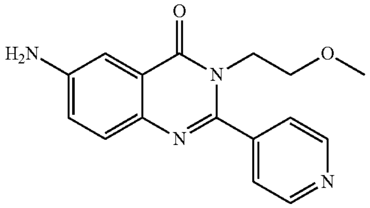<br>218 | 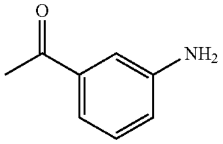 |
| 72 | 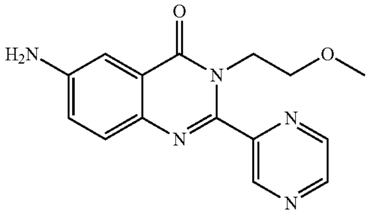<br>222 | 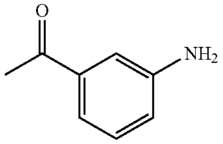 |
| 73 | 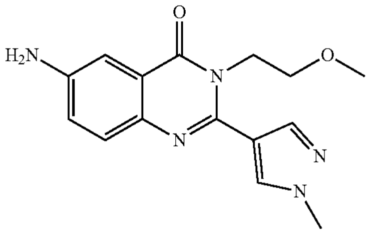<br>226 | 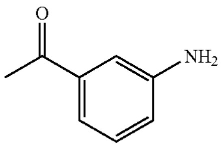 |
| 74 | 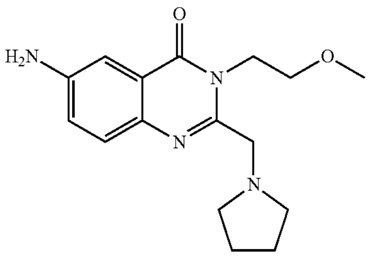<br>231 | 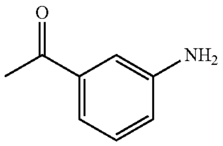 |

TABLE 2-continued
| | | |
|---|---|---|
| 75 | 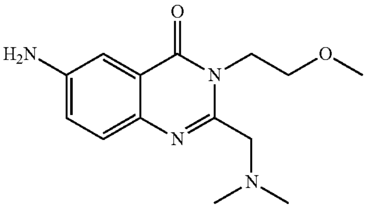<br>234 | 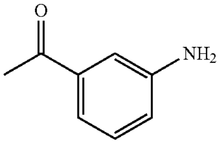 |
| 76 | 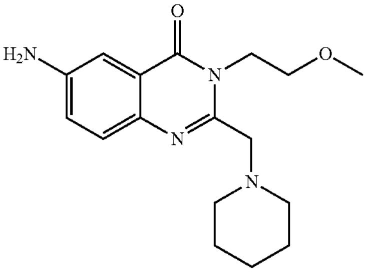<br>237 | 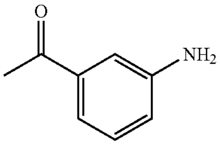 |
| 77 | 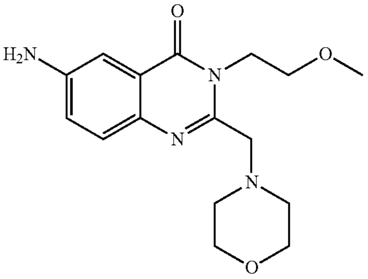<br>240 | 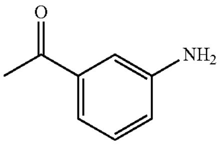 |
| 78 | 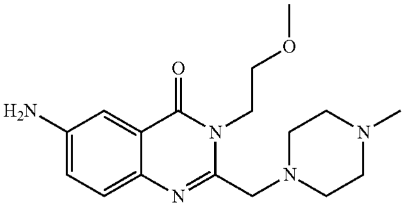 [SMILES: COCCn1c(CN2CCN(C)CC2)nc2ccc(N)cc2c1=O] | 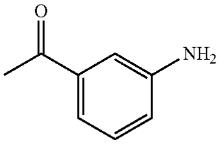 |
| 79 | 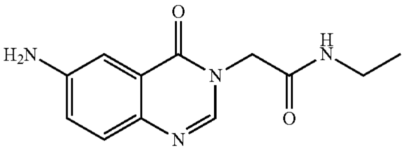<br>246 | 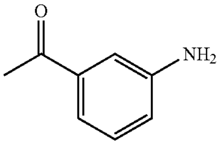 |
| 80 | 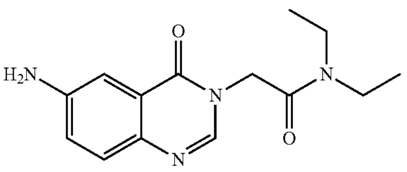<br>249 | 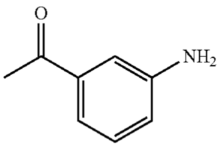 |

TABLE 2-continued
| | | |
|---|---|---|
| 81 | 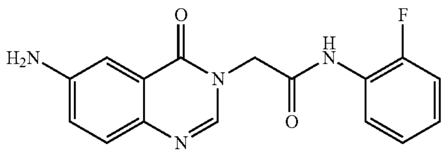 252 | 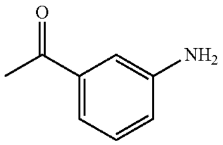 |
| 82 | 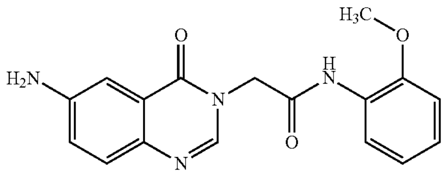 255 | 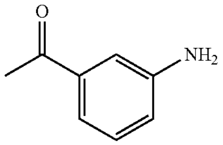 |
| 83 | 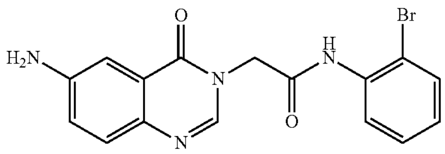 258 | 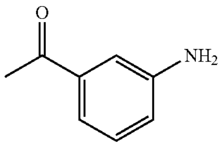 |
| 84 | 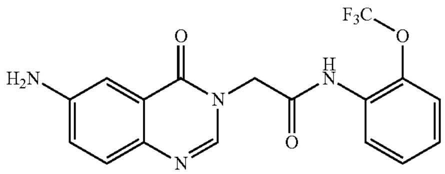 261 | 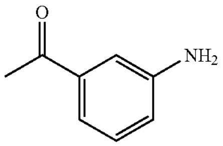 |
| 85 | 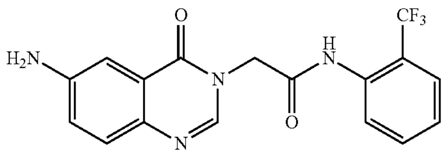 264 | 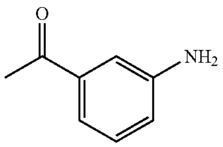 |
| 86 | 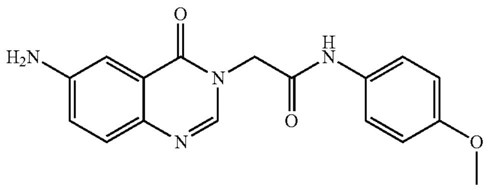 [SMILES: Nc1ccc2ncn(CC(=O)Nc3ccc(F)cc3)c(=O)c2c1] 267 | 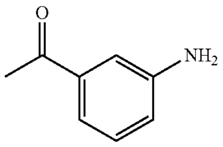 |
| 87 | 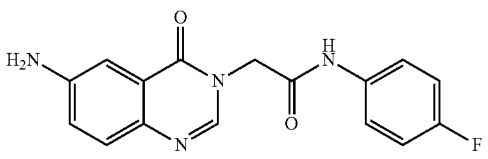 272 | 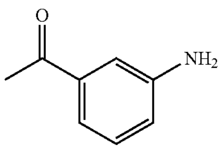 |

TABLE 2-continued
| | | |
|---|---|---|
| 88 | 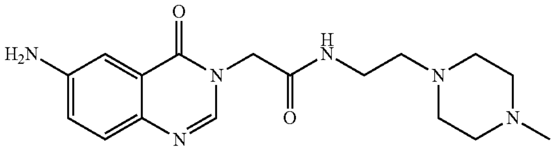 273 | 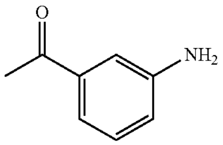 |
| 89 | 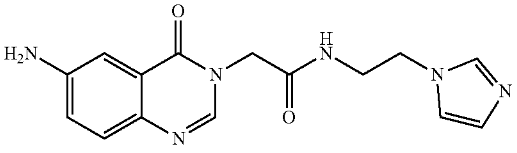 276 | 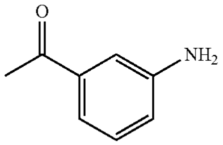 |
| 90 | 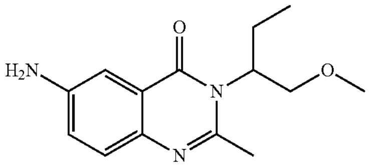 280 | 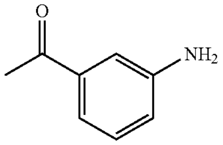 |
| 91 | 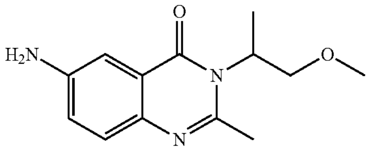 284 | 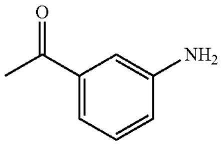 |
| 92 | 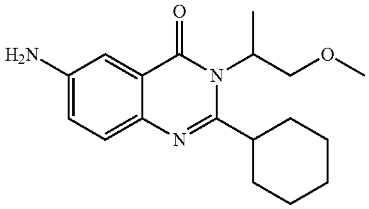 288 | 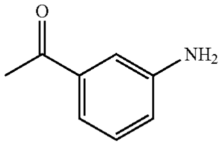 |
| 93 | 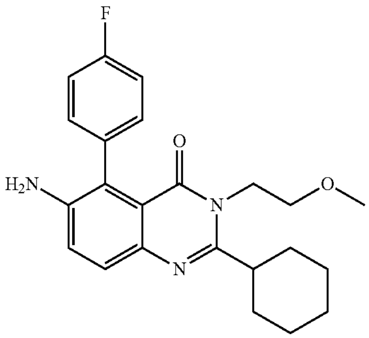 291 | 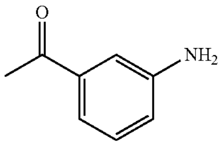 |

TABLE 2-continued
| | | |
|---|---|---|
| 94 | 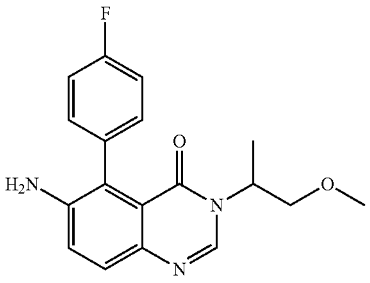 294 | 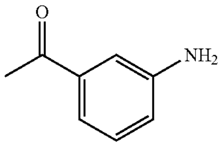 |
| 95 | 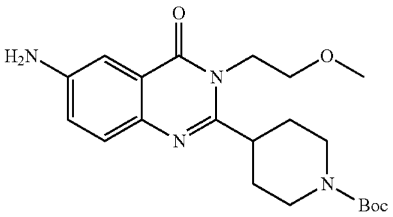 298 | 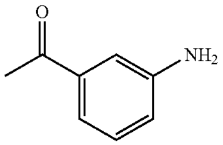 |
| 96 | 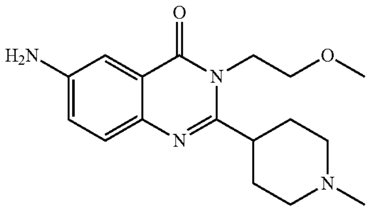 303 | 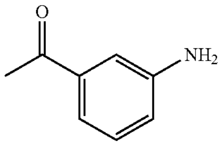 |
| 97 | 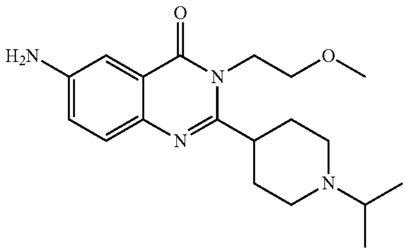 306 | 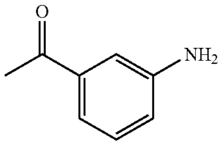 |
| 98 | 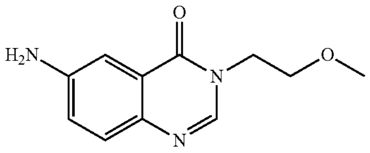 4 | 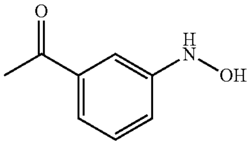 |
| 99 | 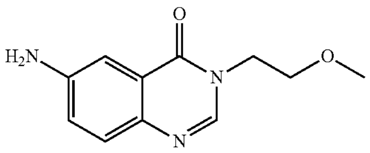 4 | 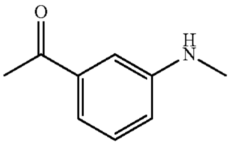 |

TABLE 2-continued
| | | |
|---|---|---|
| 100 | 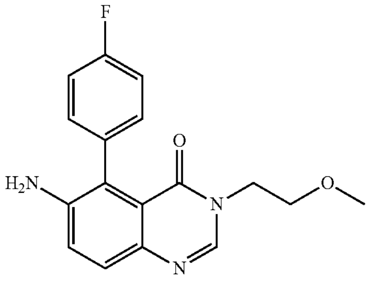 46 | 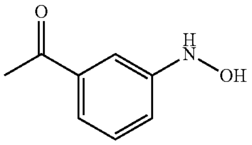 |
| 101 | 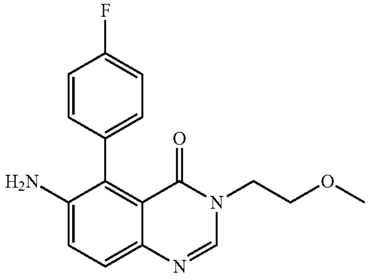 46 | 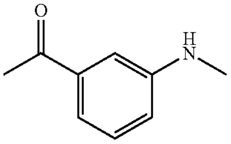 |
| 102 | 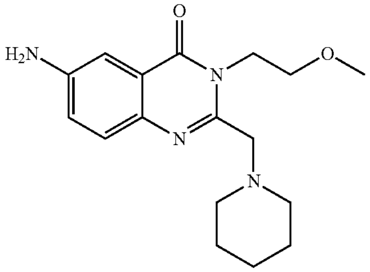 237 | 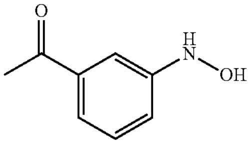 |
| 103 | 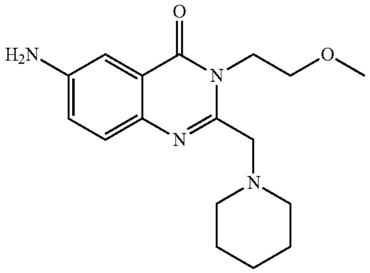 237 | 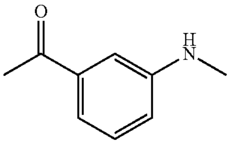 |
| 104 | 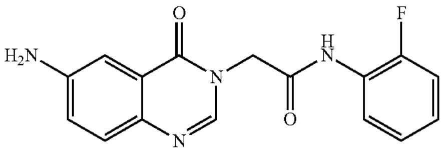 252 | 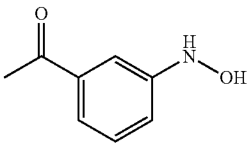 |

TABLE 2-continued
| | | |
|---|---|---|
| 105 | 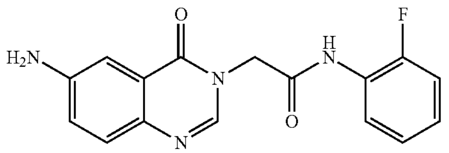<br>252 | 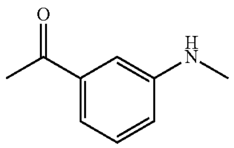 |
| 106 | 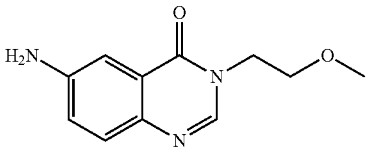<br>4 | 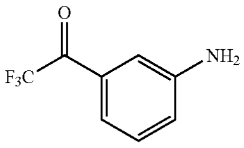 |
| 107 | 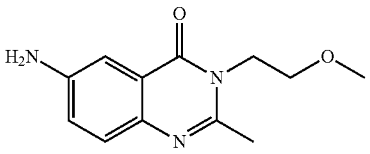<br>106 | 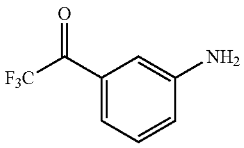 [SMILES: Nc1cccc(C(=O)C(F)(F)F)c1] |
| 108 | 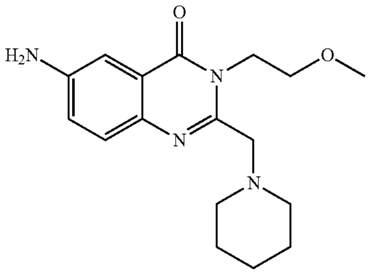<br>237 | 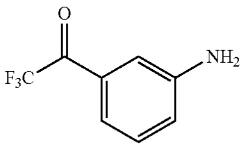 [SMILES: Nc1cccc(C(=O)C(F)(F)F)c1] |
| 109 | 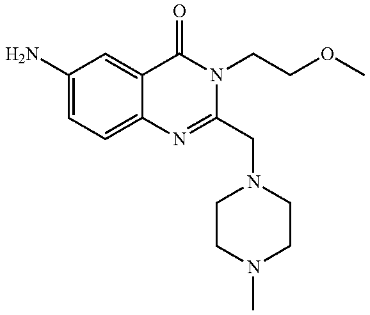<br>243 | 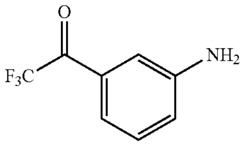 [SMILES: Nc1cccc(C(=O)C(F)(F)F)c1] |
| 110 | 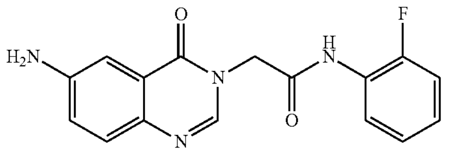<br>252 | 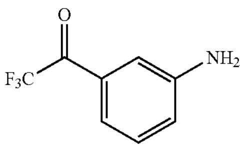 [SMILES: Nc1cccc(C(=O)C(F)(F)F)c1] |

TABLE 2-continued
| | | |
|---|---|---|
| 111 | 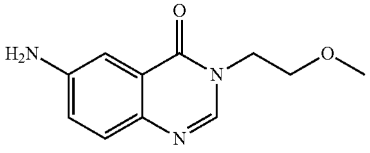 4 | 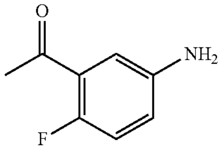 |
| 112 | 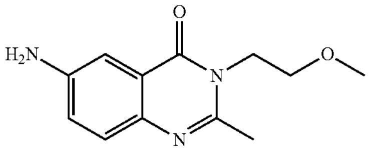 106 | 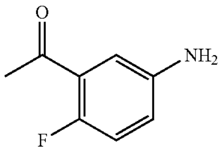 |
| 113 | 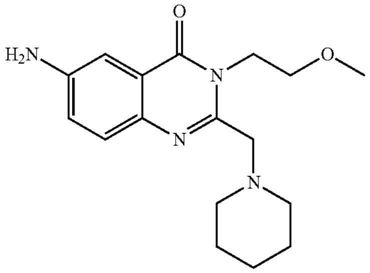 237 | 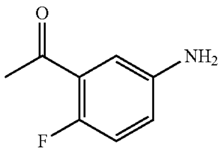 |
| 114 | 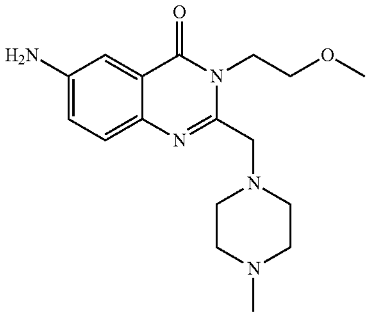 243 | 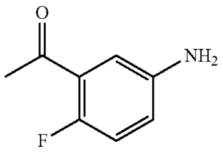 |
| 115 | 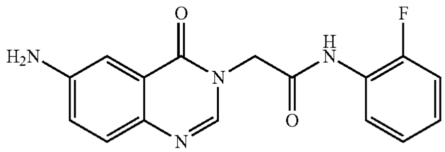 252 | 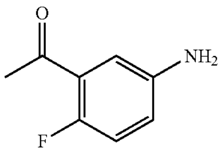 |
| 116 | 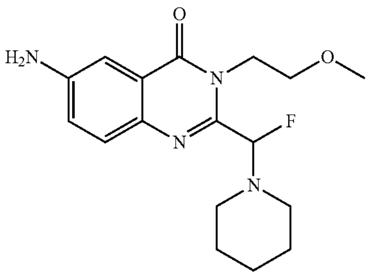 329 | 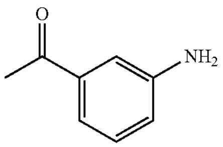 |

TABLE 2-continued
| | | |
|---|---|---|
| 117 | 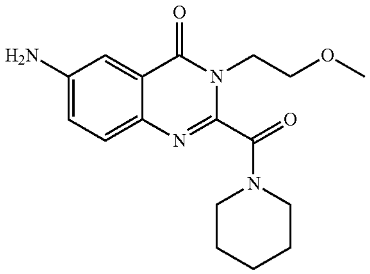<br>329a | 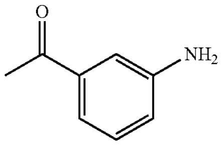 |
| 118 | 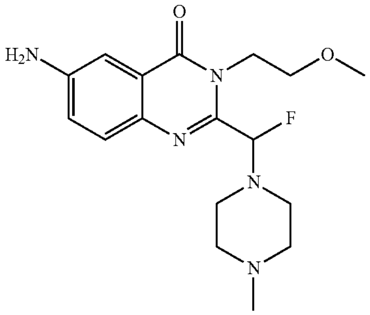 [SMILES: COCCn1c(C(F)N2CCOCC2)nc2ccc(N)cc2c1=O]<br>332 | 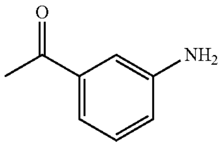 |
| 119 | 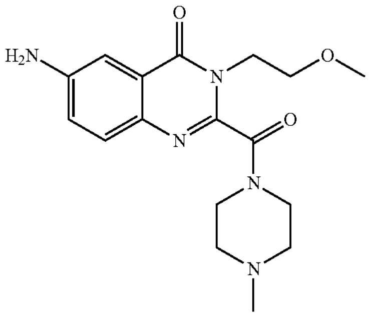 [SMILES: COCCn1c(C(=O)N2CCOCC2)nc2ccc(N)cc2c1=O]<br>332a | 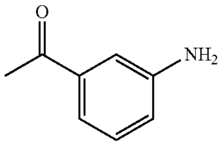 |
| 120 | 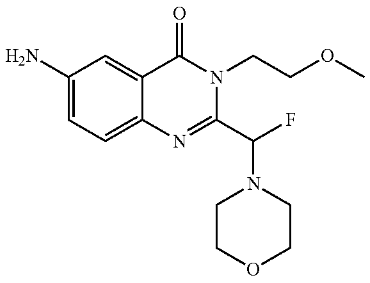<br>335 | 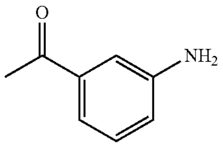 |

TABLE 2-continued
| | | |
|---|---|---|
| 121 | 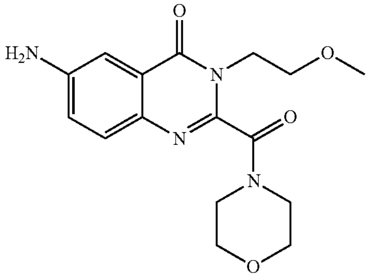<br>335a | 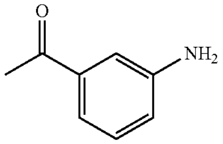 |
| 122 | 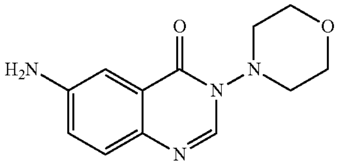<br>339 | 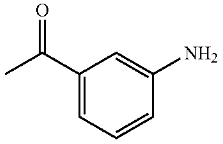 |
| 123 | 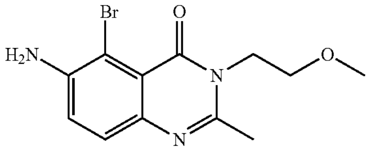<br>344 | 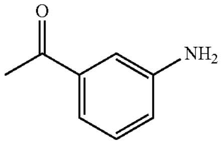 |
| Serial No. | B (Urea derivatives) |
|---|---|
| 1 | 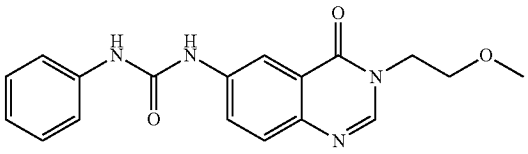<br>5 |
| 2 | 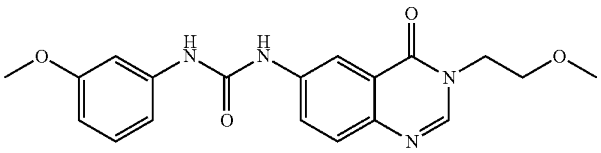<br>6 |
| 3 | 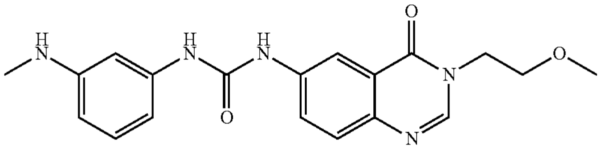<br>7 |
| 4 | 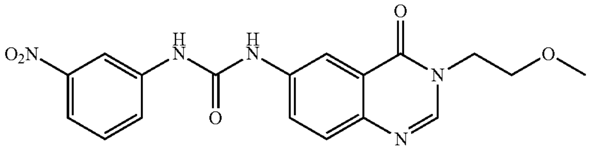<br>8 |

TABLE 2-continued
| | |
|---|---|
| 5 | 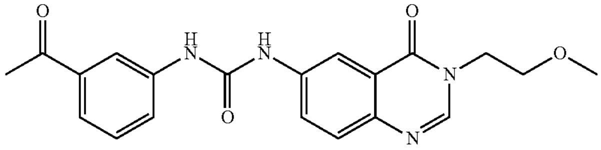<br>9 |
| 6 | 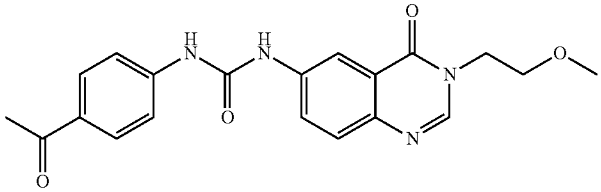<br>10 |
| 7 | 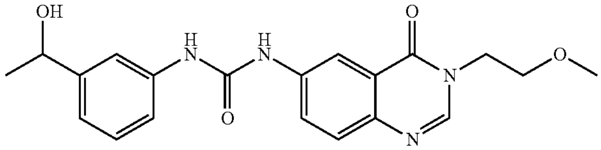<br>11 |
| 8 | 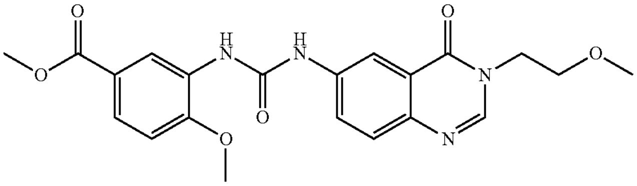<br>12 |
| 9 | 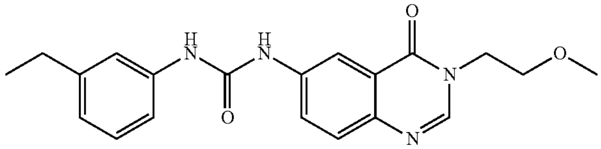<br>13 |
| 10 | 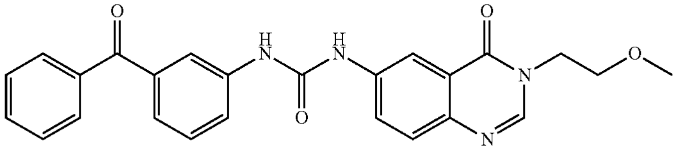<br>14 |
| 11 | 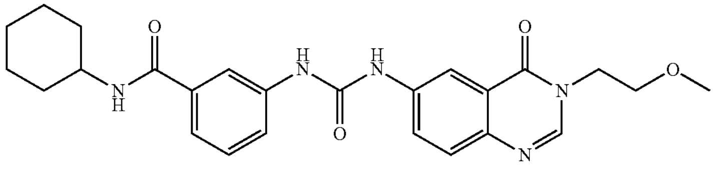<br>15 |

TABLE 2-continued
| | |
|---|---|
| 12 | 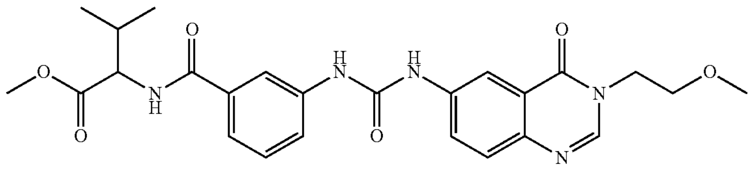 16 |
| 13 | 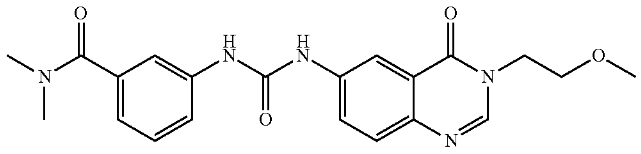 17 |
| 14 | 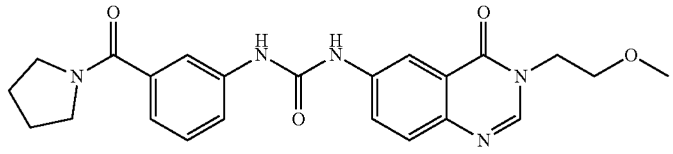 18 |
| 15 | 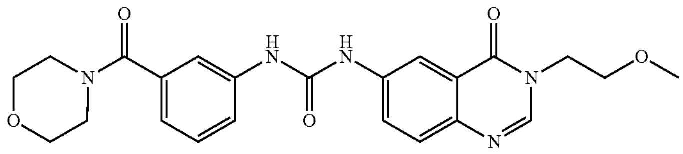 19 |
| 16 | 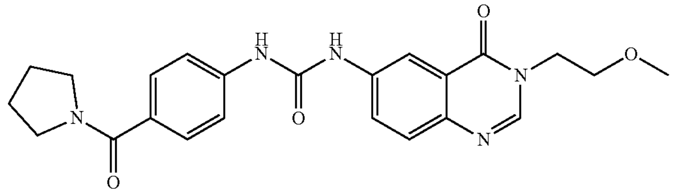 20 |
| 17 | 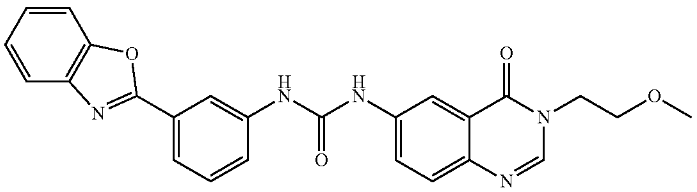 21 |
| 18 | 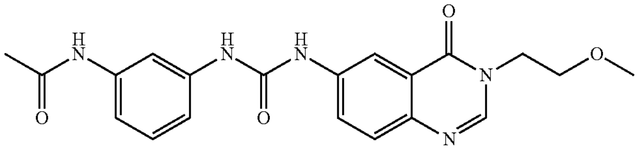 22 |

TABLE 2-continued
| | | |
|---|---|---|
| 19 | 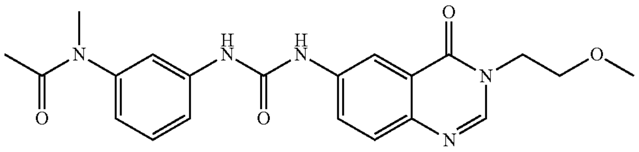 | 23 |
| 20 | 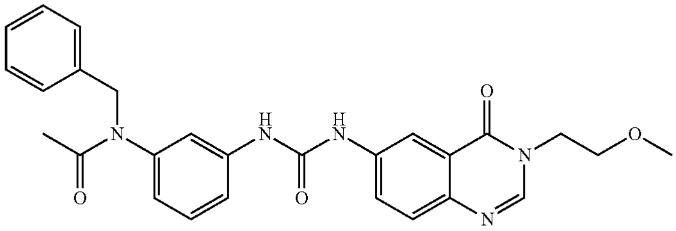 | 24 |
| 21 | 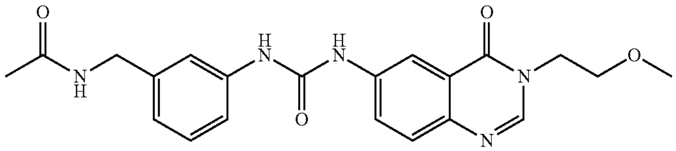 | 25 |
| 22 | 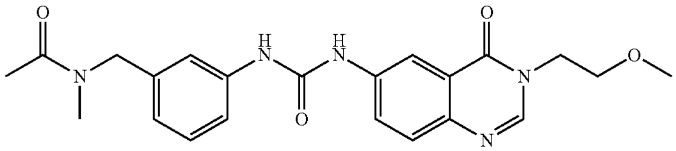 | 26 |
| 23 | 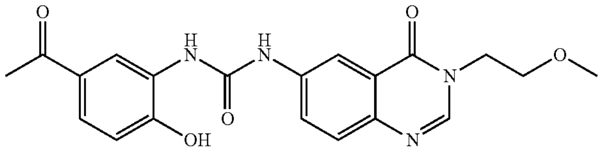 | 32 |
| 24 | 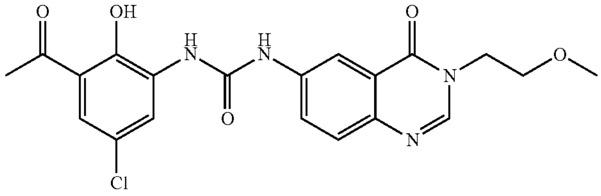 | 33 |
| 25 | 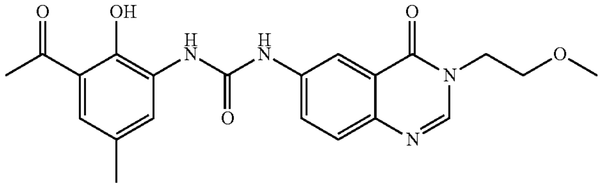 | 34 |

TABLE 2-continued
26
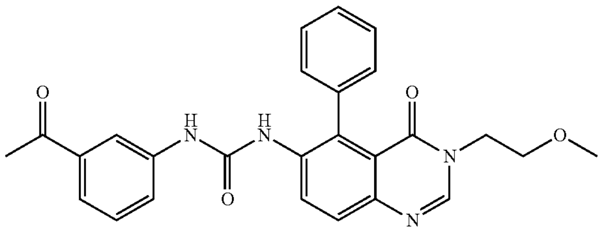
45
27
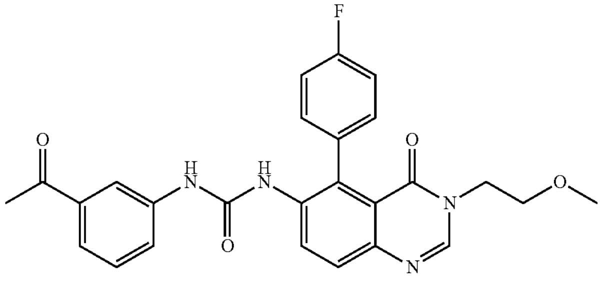
47
28
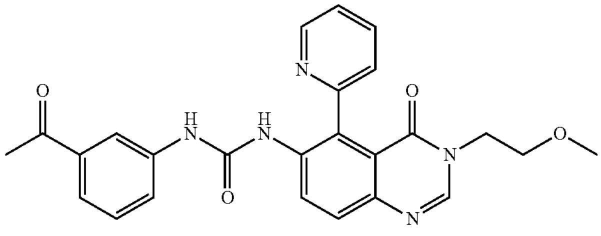
49
29
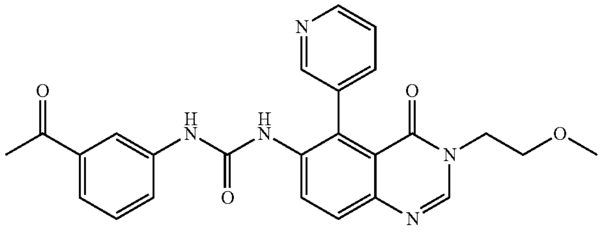
51
30
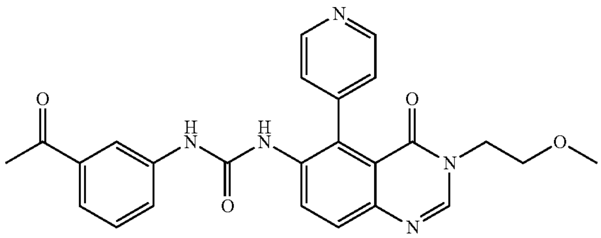
53

TABLE 2-continued
31
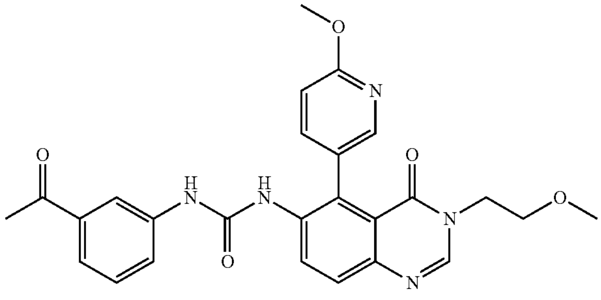
55
32
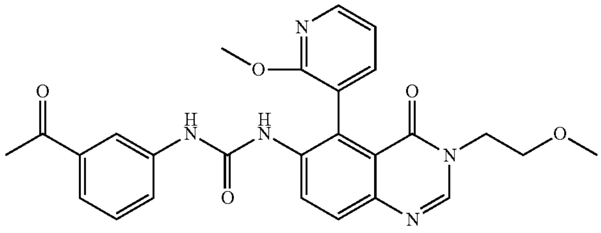
57
33
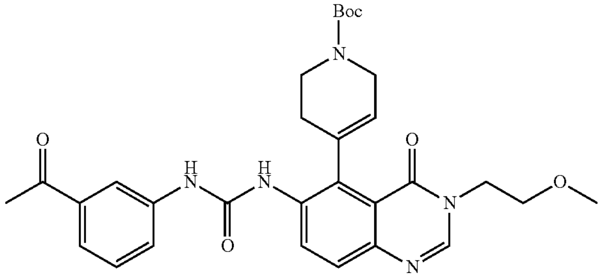
59
34
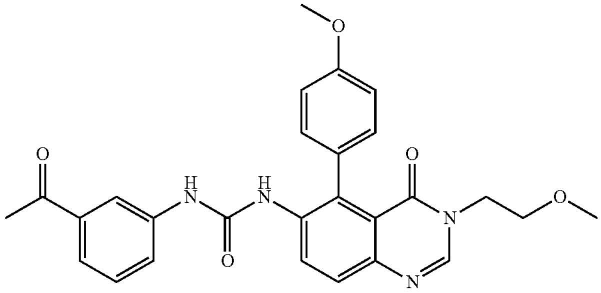
64
35
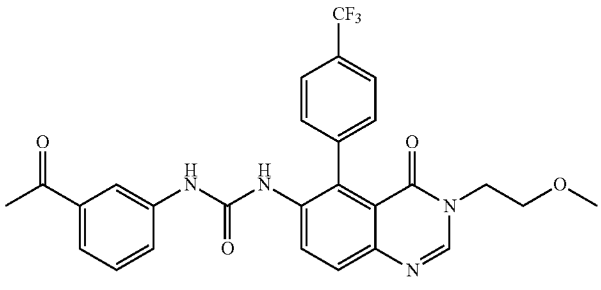
66

TABLE 2-continued
36
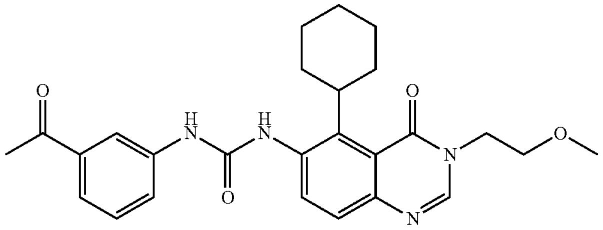
68
37
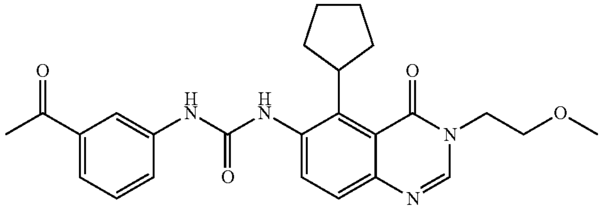
70
38
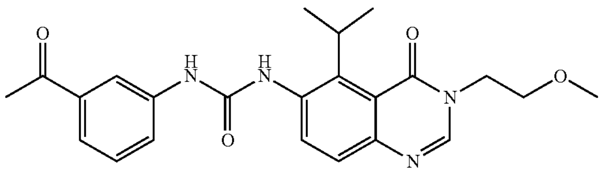
72
39
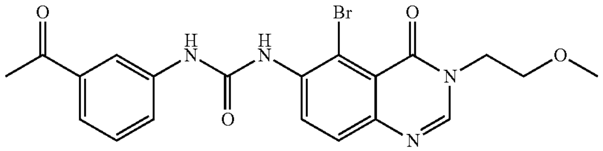
73
40
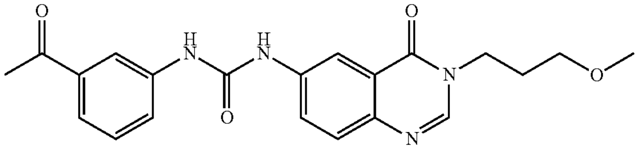
89
41
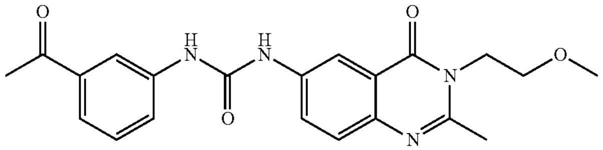
107
42
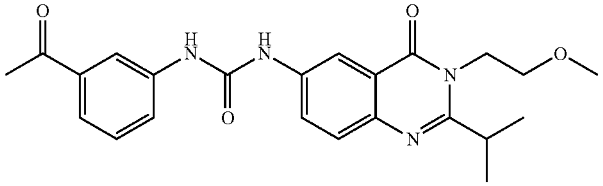
111

TABLE 2-continued
43
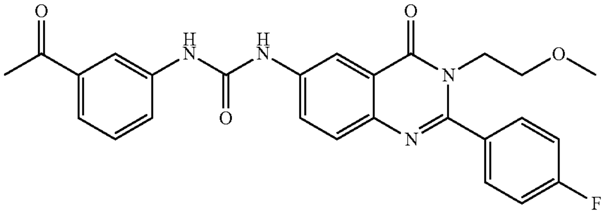
115
44
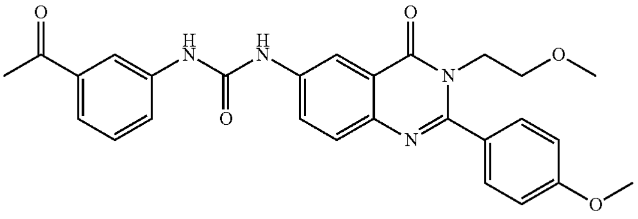
119
45
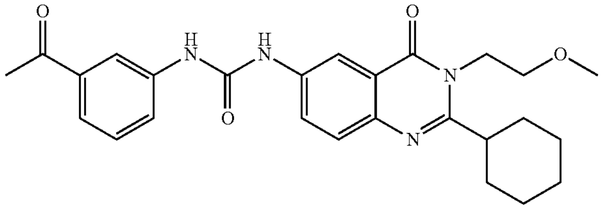
123
46
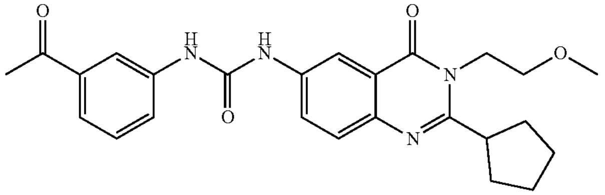
127
47
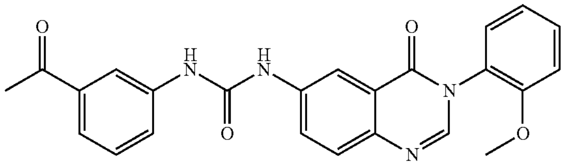
131
48
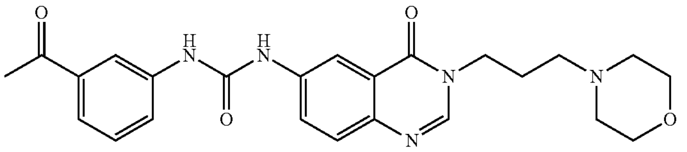
139

TABLE 2-continued
49
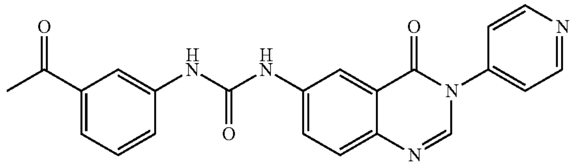
151
50
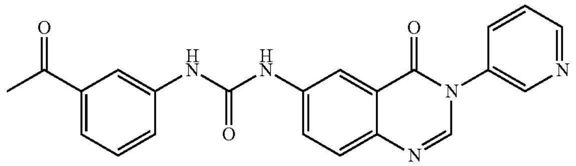
155
51
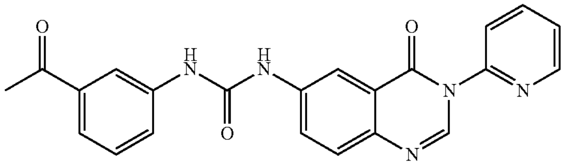
159
52
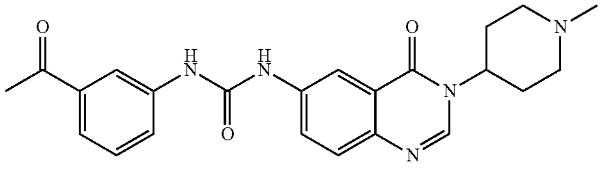
163
53
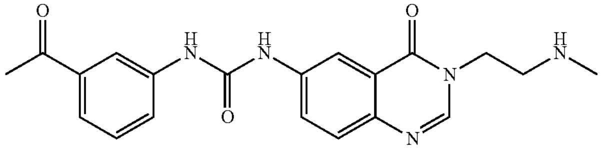
167
54
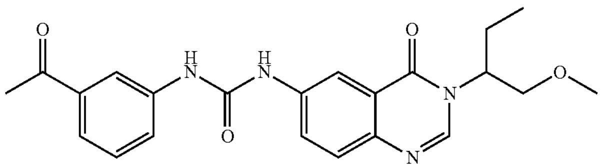
171
55
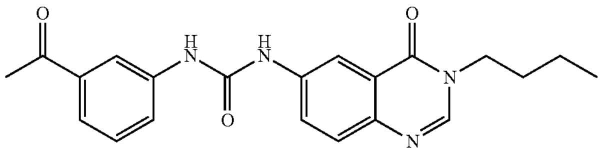
175

TABLE 2-continued
56
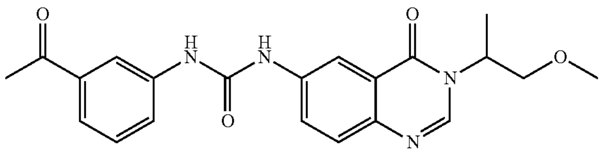
179
57
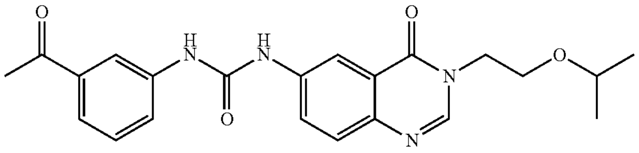
183
58
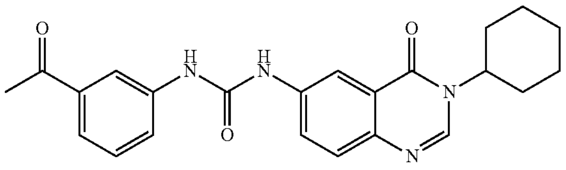
187
59
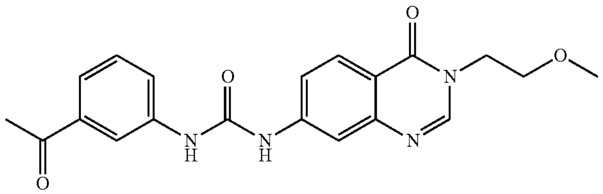
192
60
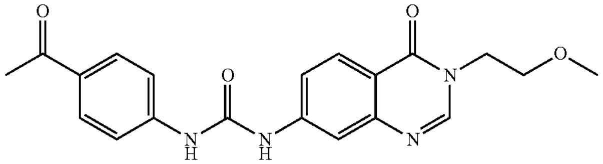
193
61
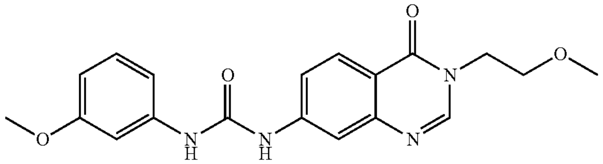
194
62
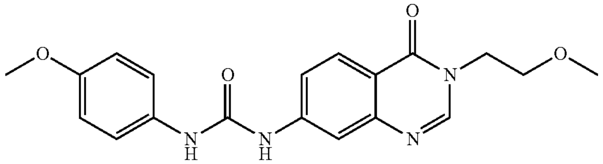
195

TABLE 2-continued
63
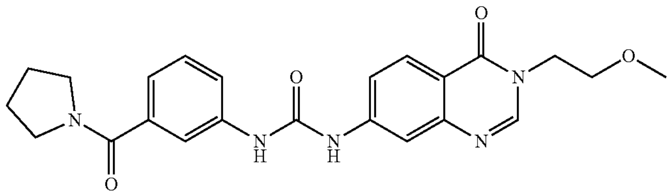
196
64
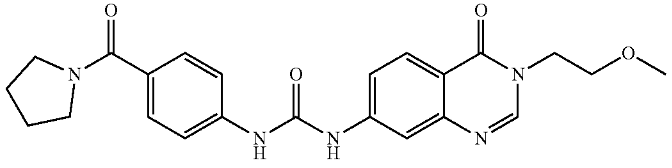
197
65
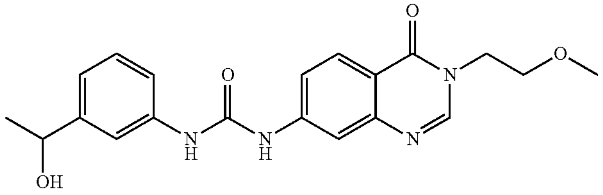
198
66
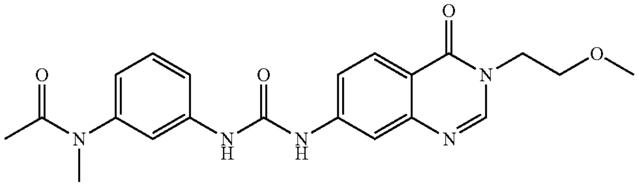
199
67
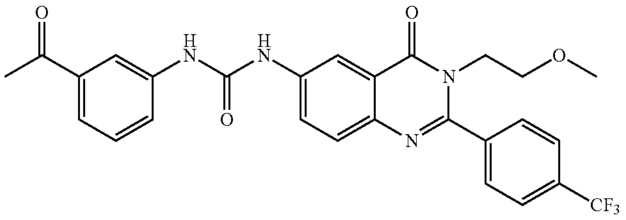
203
68
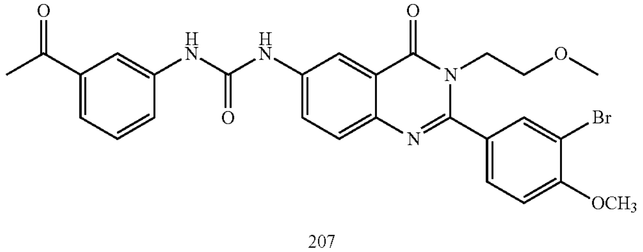 [SMILES: COCCn1c(-c2ccc(OC)c(Br)c2)nc2ccc(NC(=O)Nc3cccc(C(C)=O)c3)cc2c1=O]
207

TABLE 2-continued
69
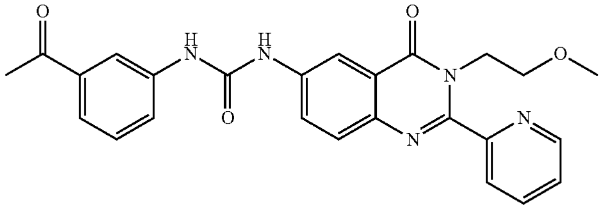
211
70
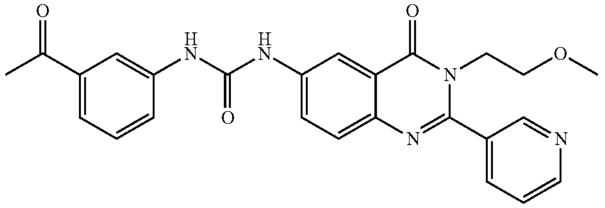
215
71
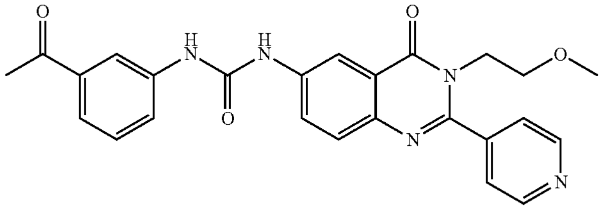
219
72
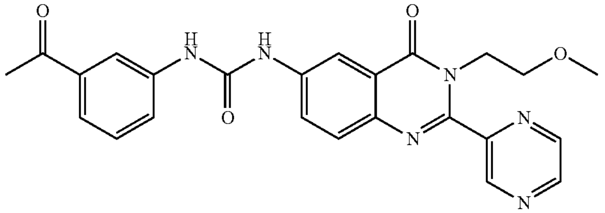
223
73
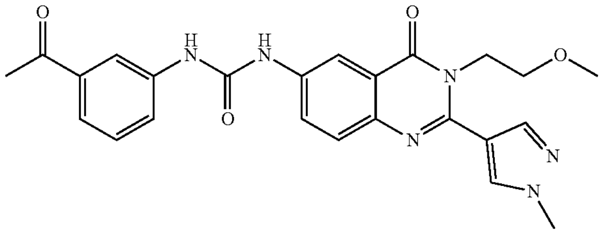
227
74
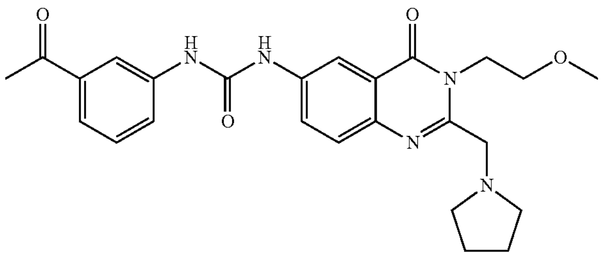
232

TABLE 2-continued
75
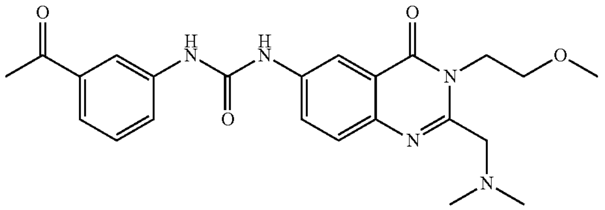
235
76
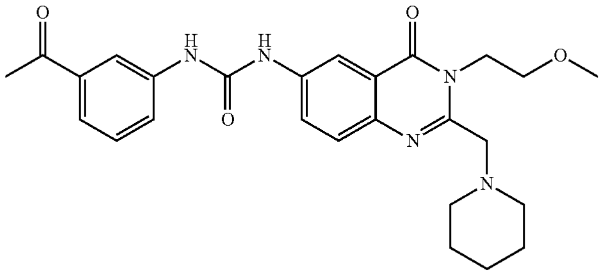
238
77
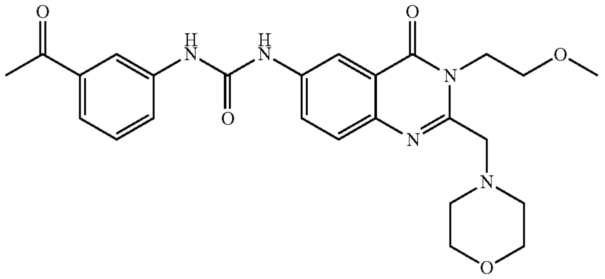
241
78
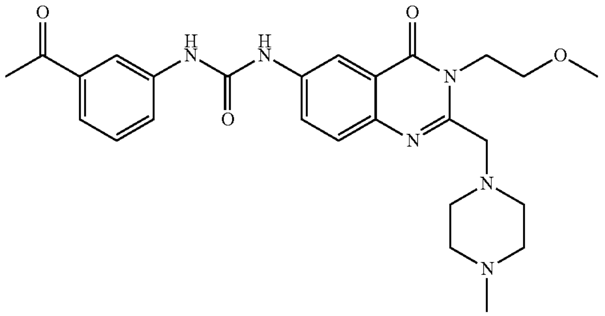
244
79
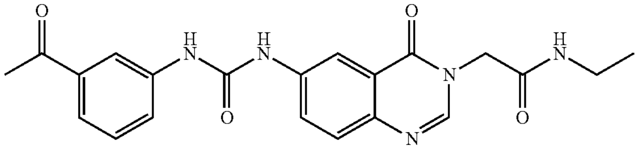
247

TABLE 2-continued
80
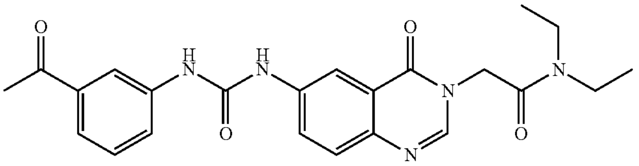
250
81
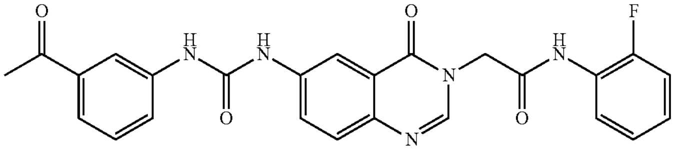
253
82
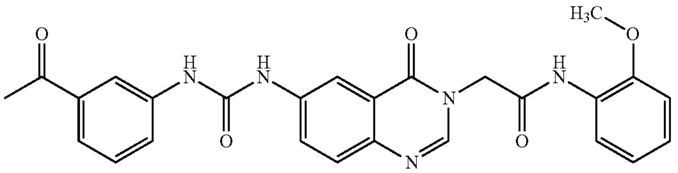
256
83
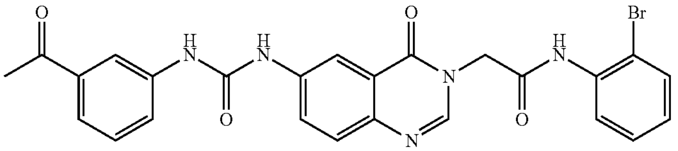
259
84
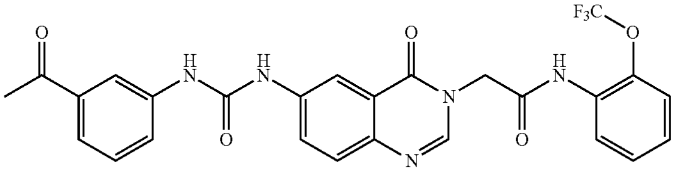
262
85
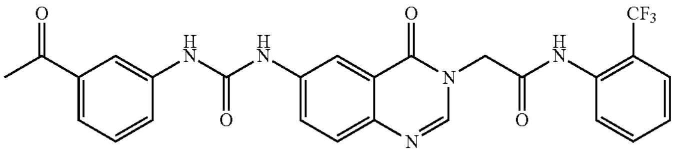
265
86
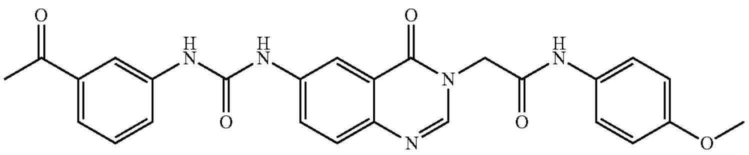
268
87
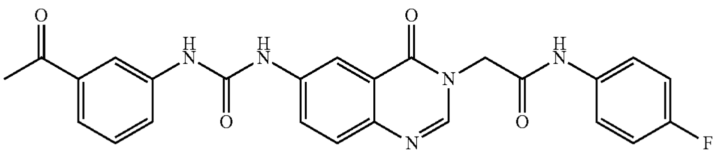
271

TABLE 2-continued
88
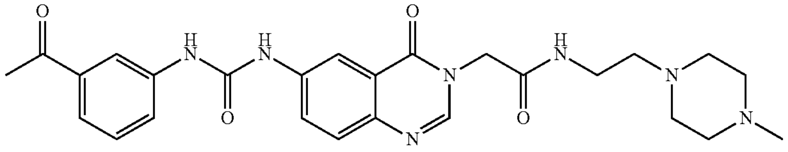
274
89
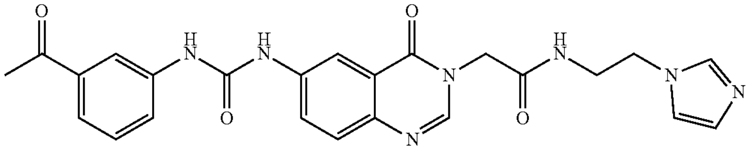
277
90
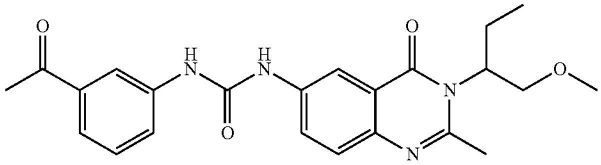
281
91
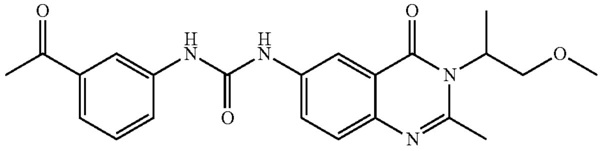
285
92
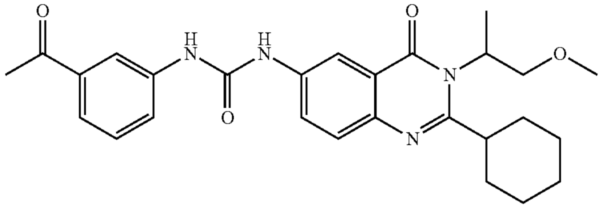
289
93
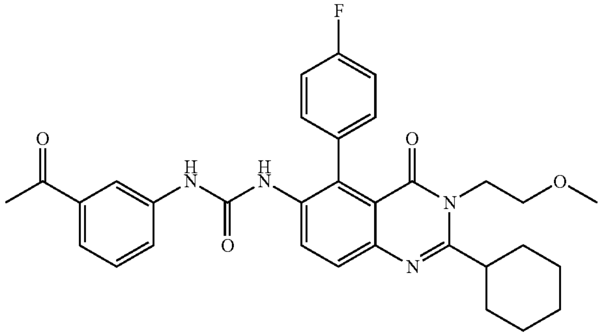
292

TABLE 2-continued
94
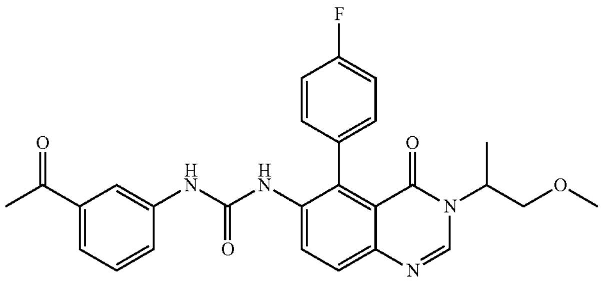
295
95
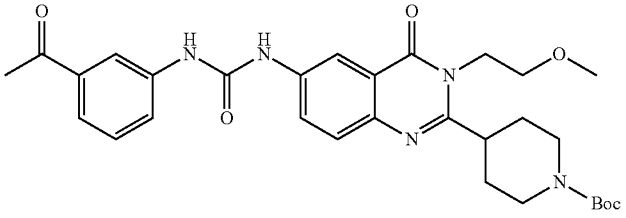
299
96
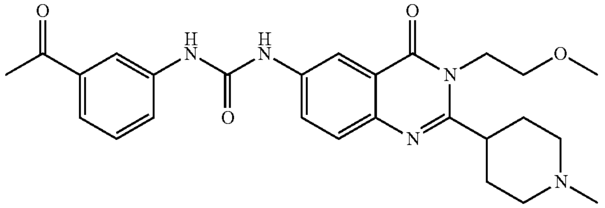
304
97
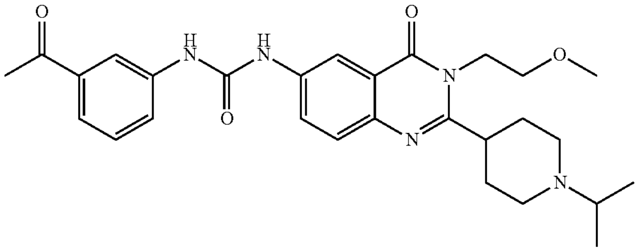
307
98
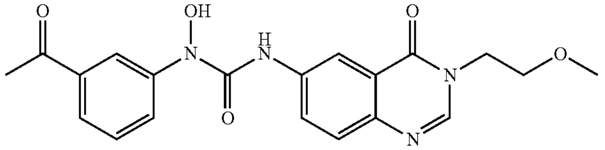
308
99
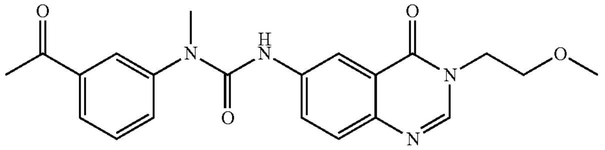
309

TABLE 2-continued
100
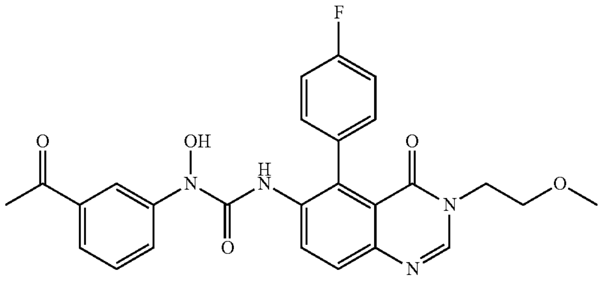
310
101
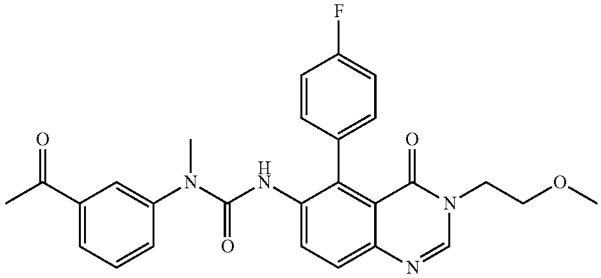
311
102
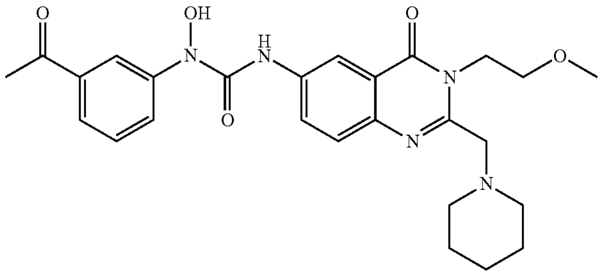
312
103
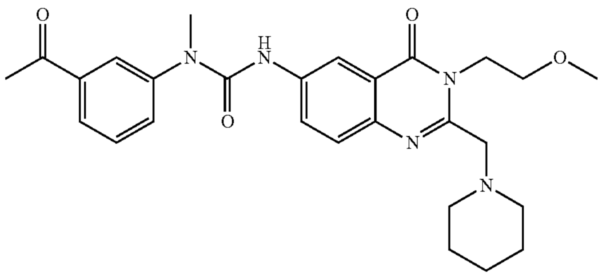
313
104
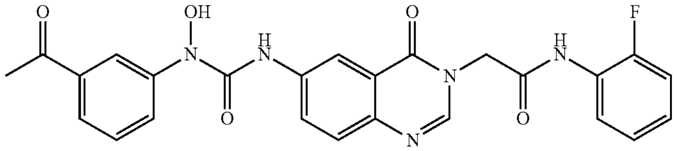
314

TABLE 2-continued
105
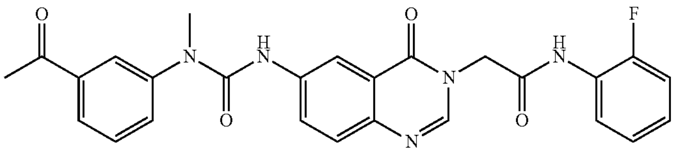
315
106
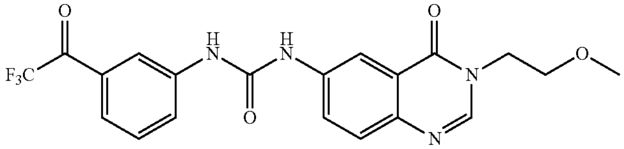
316
107
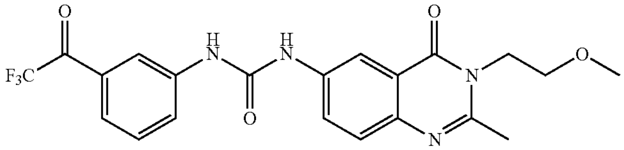
317
108
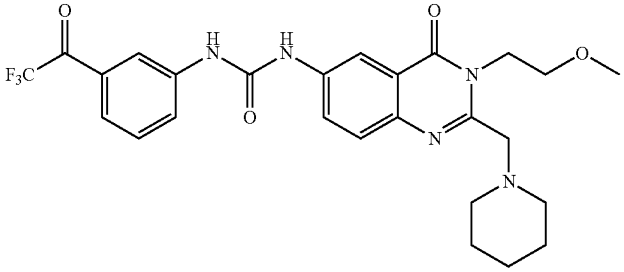
318
109
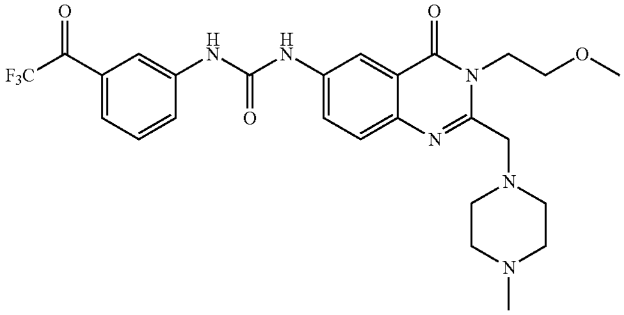
319
110
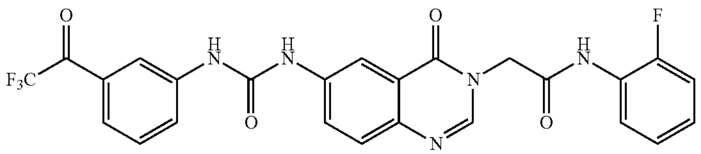
320

TABLE 2-continued
| | | |
|---|---|---|
| 111 | 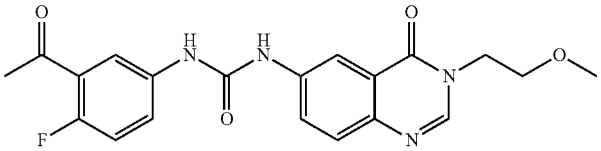 | 321 |
| 112 | 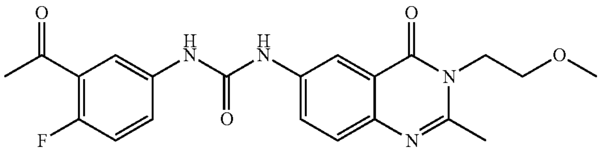 | 322 |
| 113 | 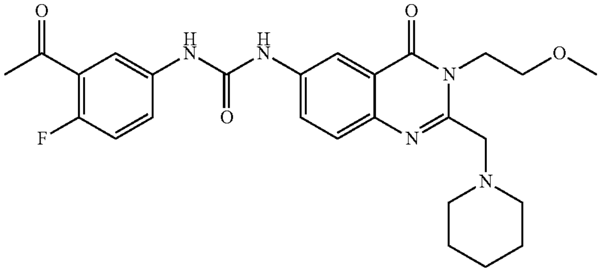 | 323 |
| 114 | 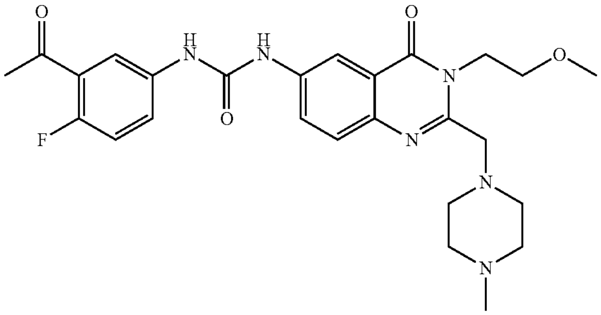 | 324 |
| 115 | 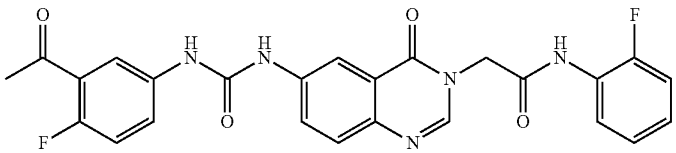 | 325 |
| 116 | 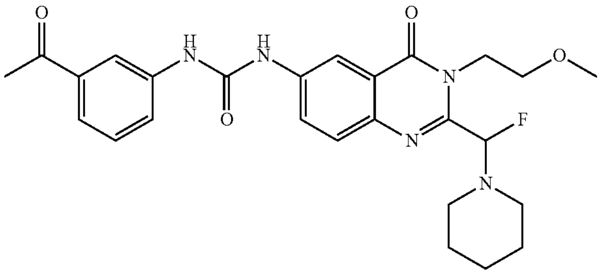 | 330 |

TABLE 2-continued
117
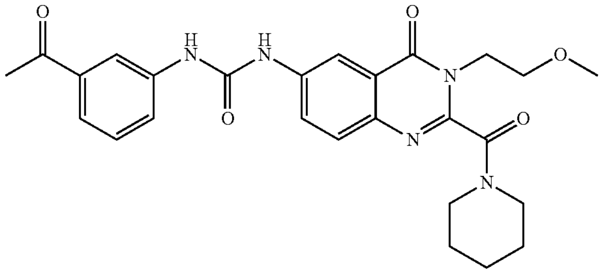
330a
118
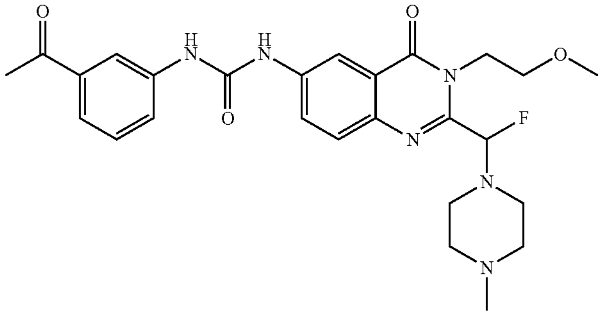
333
119
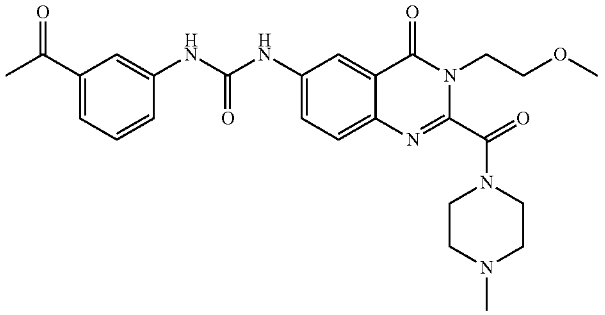
333a
120
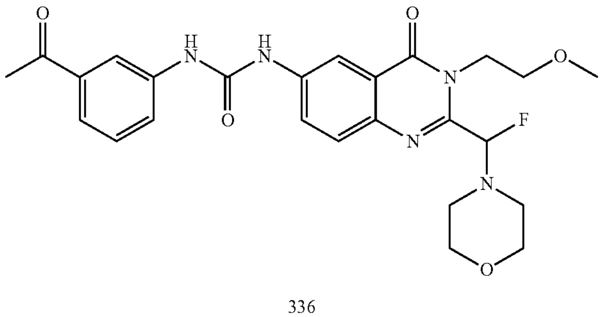 [SMILES: COCCn1c(C(F)N2CCOCC2)nc2ccc(NC(=O)Nc3cccc(C(C)=O)c3)cc2c1=O]
336

TABLE 2-continued
| | | |
|---|---|---|
| 121 | 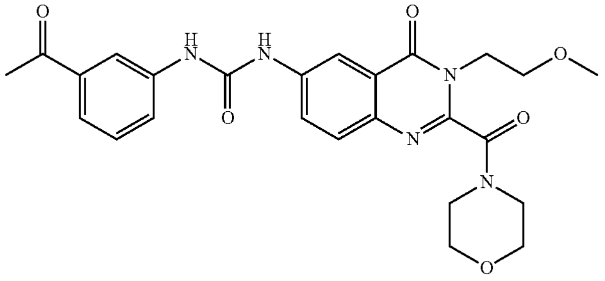 | 336a |
| 122 | 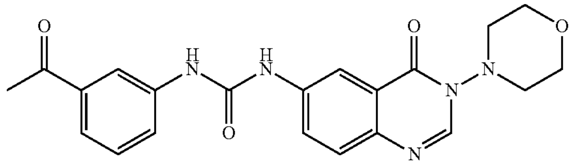 | 340 |
| 123 | 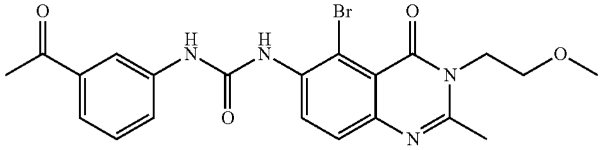 | 345 |
General Procedure of Urea Formation from Isocyanates
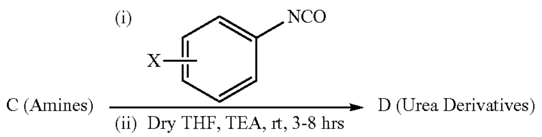
Table 3 provides the structures of reactants and products obtained with reaction with isocyanates:

TABLE 3
| Serial No. | Amine (C) | 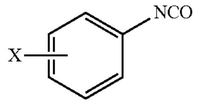 | D (Urea derivatives) |
|---|---|---|---|
| 01 | 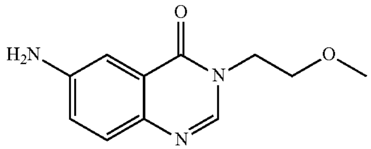 4 | 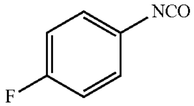 | 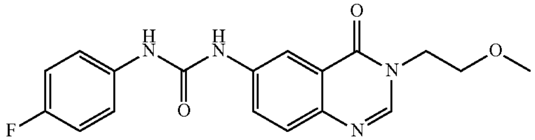 35 |
| 02 | 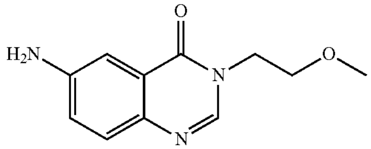 4 | 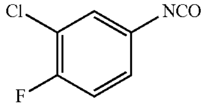 | 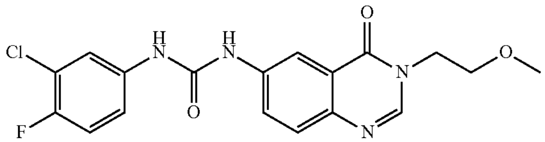 36 |
| 03 | 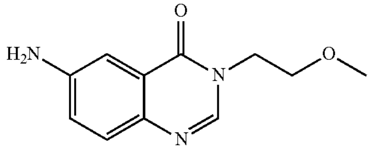 4 | 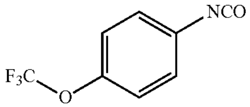 | 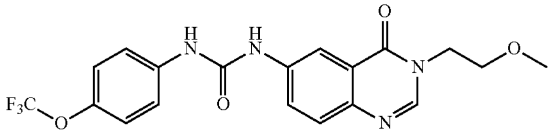 37 |
| 04 | 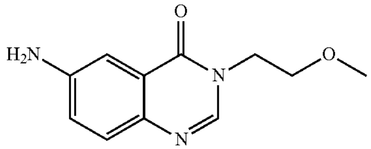 4 | 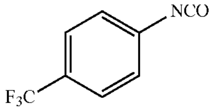 | 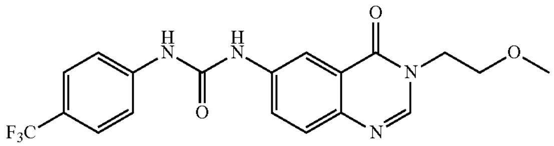 38 |

TABLE 3-continued
| Serial No. | Amine (C) | 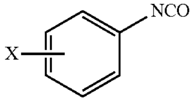 | D (Urea derivatives) |
|---|---|---|---|
| 05 | 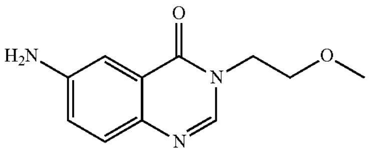 4 | 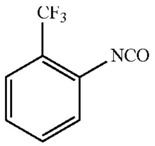 | 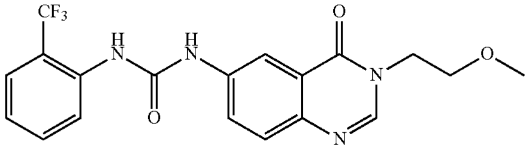 39 |
| 06 | 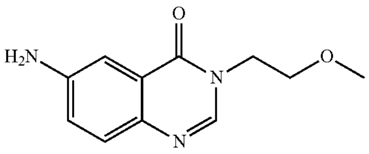 4 | 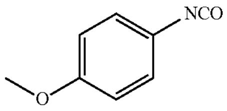 | 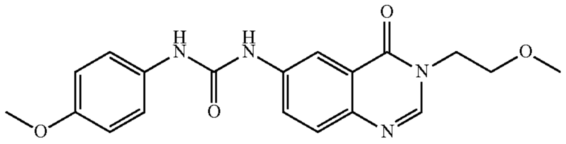 40 |
| 07 | 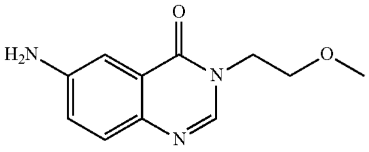 4 | 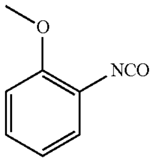 | 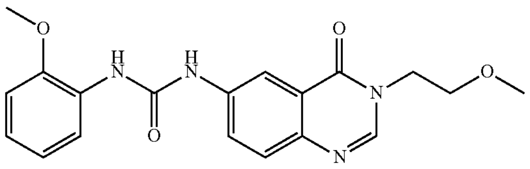 41 |
| 08 | 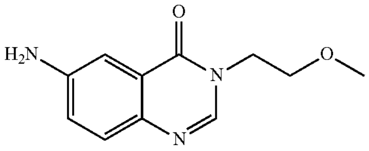 4 | 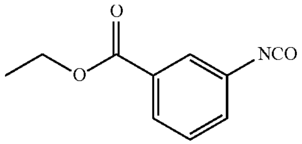 | 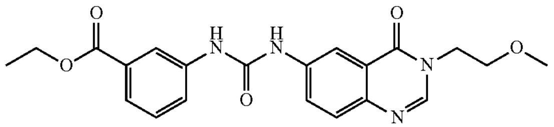 42 |

TABLE 3-continued
| Serial No. | Amine (C) | 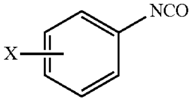 | D (Urea derivatives) |
|---|---|---|---|
| 09 | 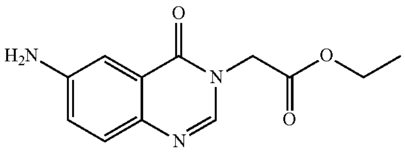 82 | 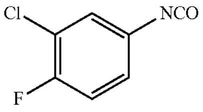 | 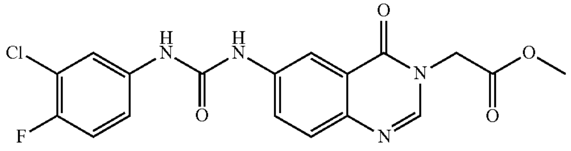 83 |
| 10 | 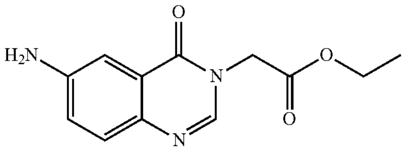 82 | 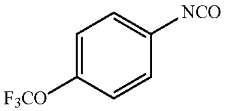 | 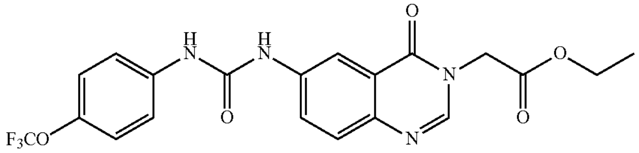 84 |
| 11 | 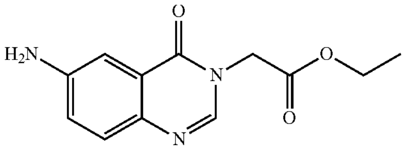 82 | 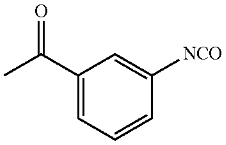 | 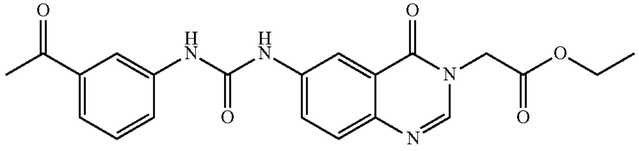 85 |
| 12 | 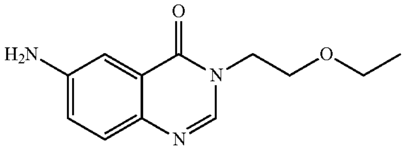 92 | 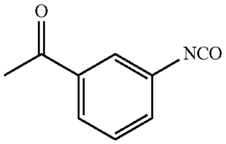 | 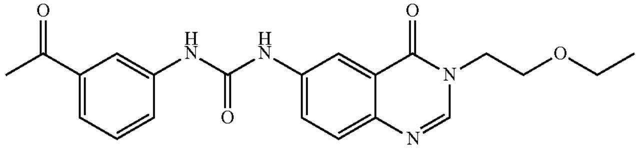 93 |

TABLE 3-continued
| Serial No. | Amine (C) | 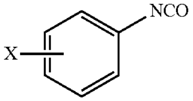 | D (Urea derivatives) |
|---|---|---|---|
| 13 | 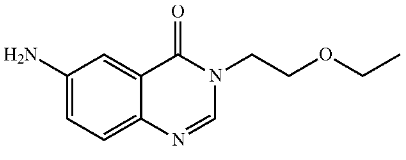 92 | 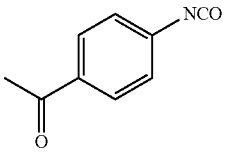 | 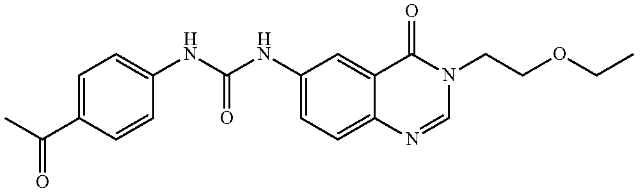 94 |
| 14 | 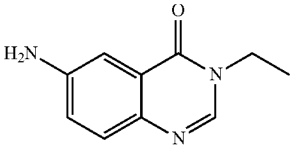 97 | 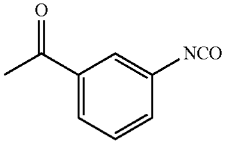 | 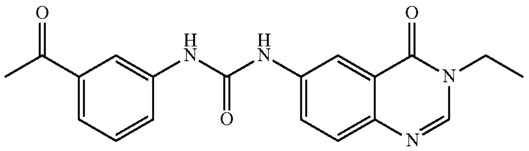 98 |
| 15 | 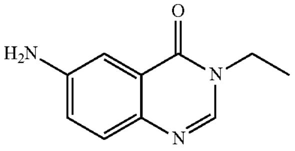 97 | 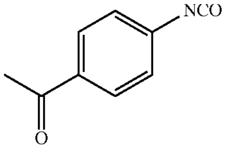 | 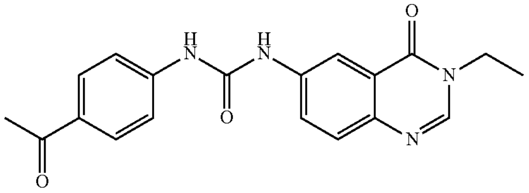 99 |
| 16 | 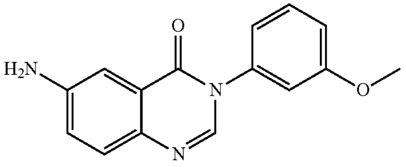 102 | 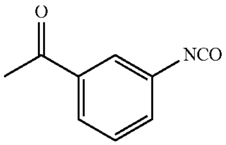 | 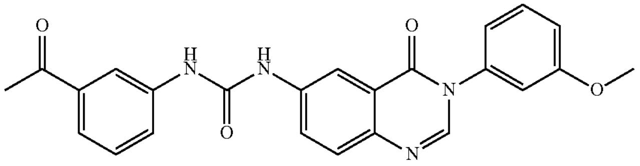 103 |

TABLE 3-continued
| Serial No. | Amine (C) | 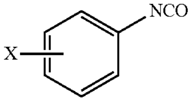 | D (Urea derivatives) |
| --- | --- | --- | --- |
| 17 | 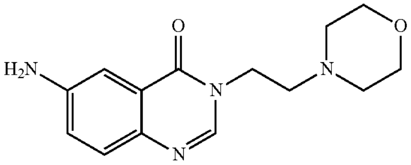 134 | 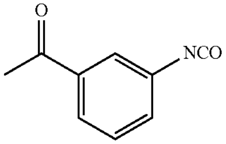 | 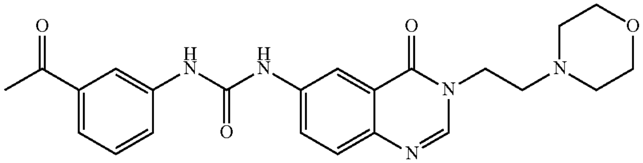 135 |
| 18 | 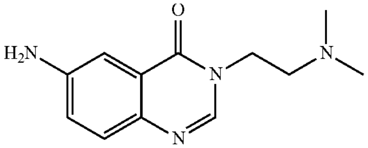 142 | 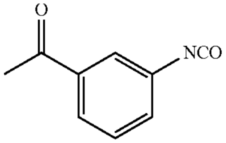 | 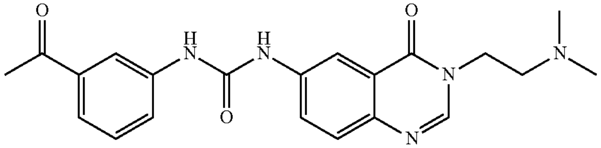 143 |
| 19 | 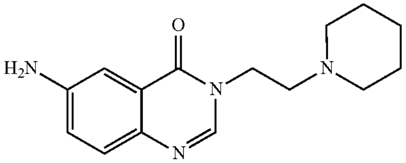 146 | 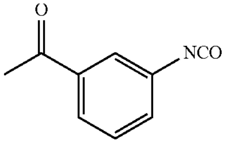 | 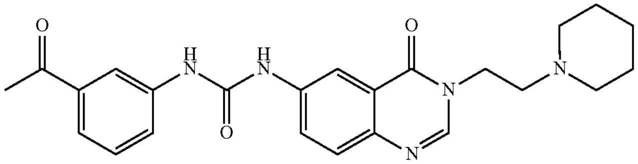 147 |

General Procedure of Suzuki Coupling Reaction
E (Bromo Heterocycles)
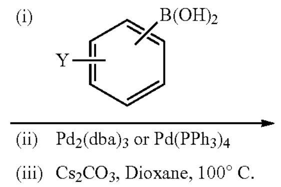
F (Suzuki coupling reaction derived derivatives)
Table 4 provides the structures of reactants and products obtained for Suzuki reaction:
TABLE 4
| Serial No. | Bromo Heterocycles (E) | 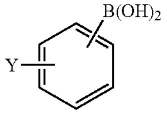 | F (Suzuki coupled Product) |
|---|---|---|---|
| 1 | 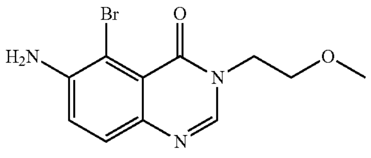 43 | 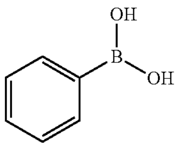 | 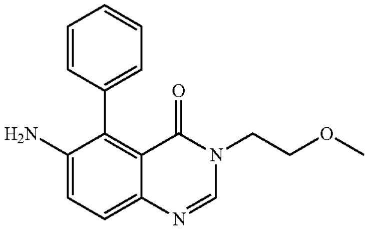 44 |
| 2 | 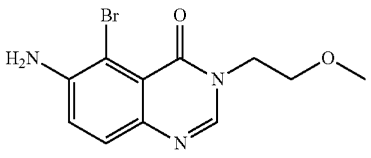 43 | 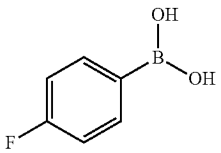 | 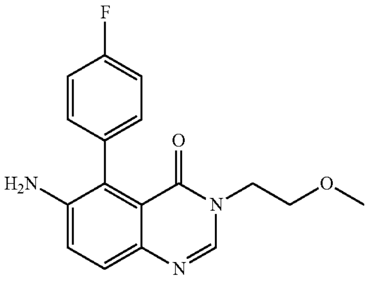 46 |
| 3 | 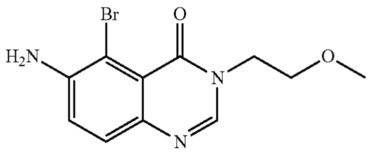 43 | 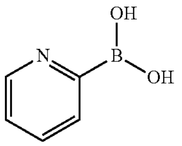 | 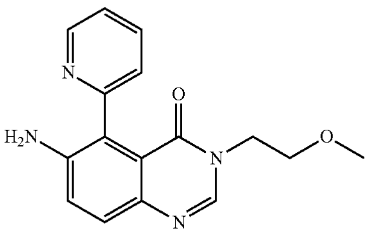 48 |

TABLE 4-continued
| Serial No. | Bromo Heterocycles (E) | 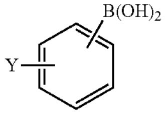 | F (Suzuki coupled Product) |
|---|---|---|---|
| 4 | 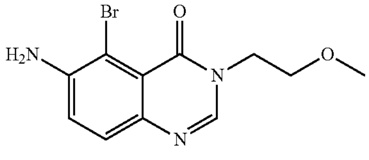 43 | 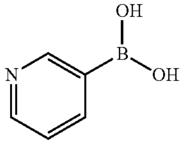 | 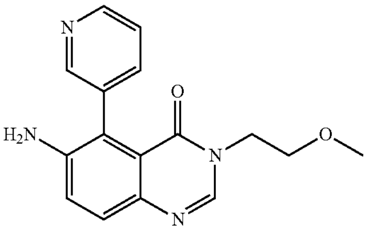 50 |
| 5 | 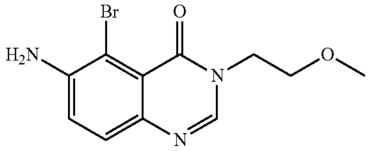 43 | 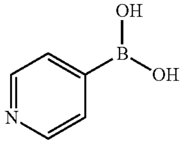 | 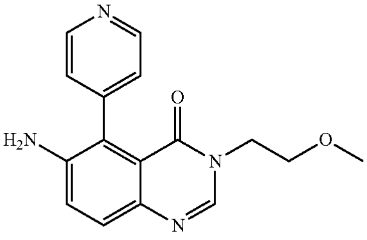 52 |
| 6 | 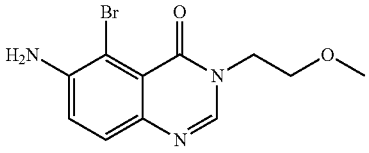 43 | 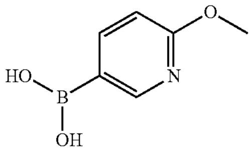 | 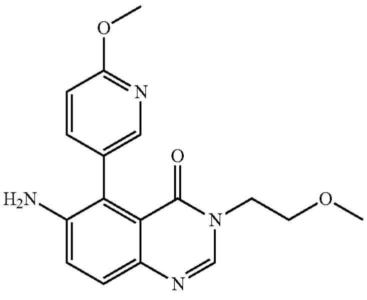 54 |
| 7 | 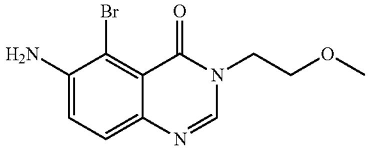 43 | 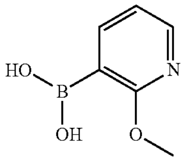 | 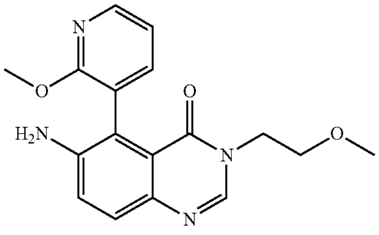 56 |
| 8 | 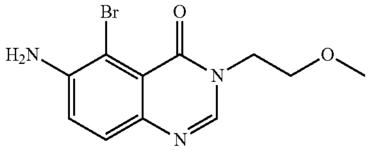 43 | 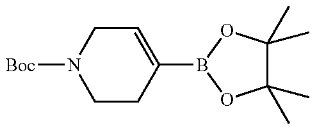 [SMILES: CC(C)(C)OC(=O)N1CC=C(B2OC(C)(C)C(C)(C)O2)CC1] | 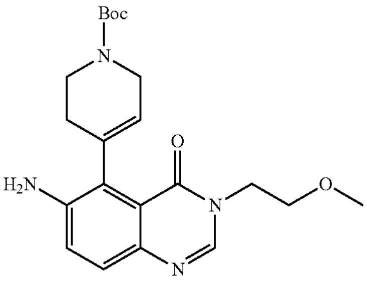 58 |

TABLE 4-continued
| Serial No. | Bromo Heterocycles (E) | 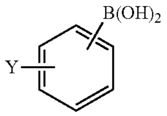 | F (Suzuki coupled Product) |
|---|---|---|---|
| 9 | 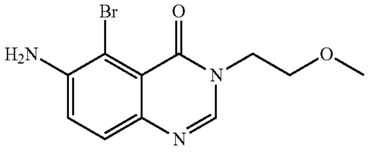 43 | 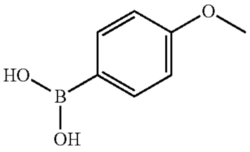 | 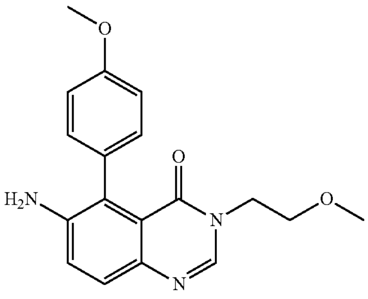 63 |
| 10 | 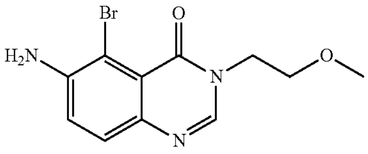 43 | 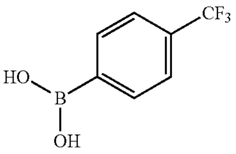 [SMILES: OB(O)c1ccc(C(F)(F)F)cc1] | 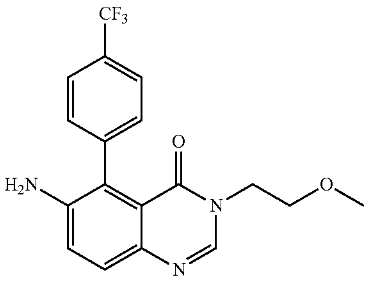 65 |
| 11 | 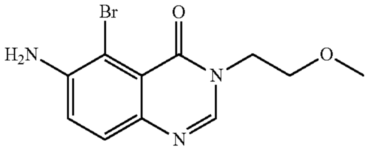 43 | 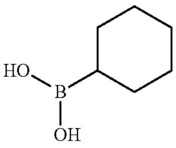 | 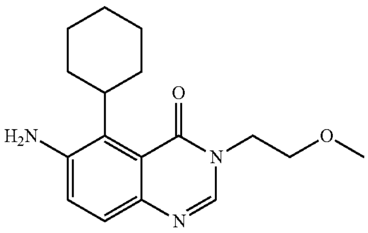 67 |
| 12 | 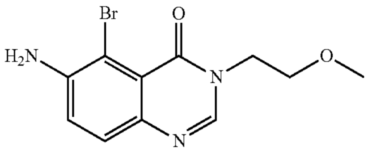 43 | 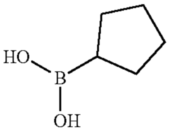 | 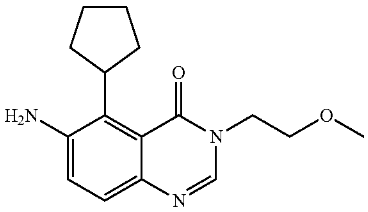 69 |
| 13 | 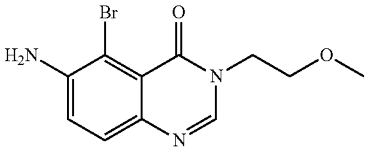 43 | 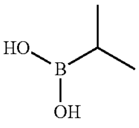 | 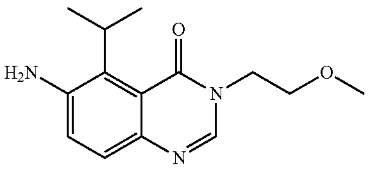 71 |

TABLE 4-continued

| Serial No. | Bromo Heterocycles (E) | 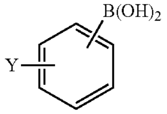 | F (Suzuki coupled Product) |
| --- | --- | --- | --- |
| 14 | 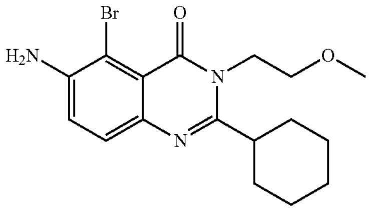 290 | 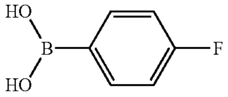 | 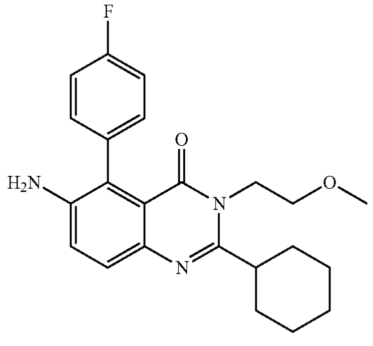 291 |
| 15 | 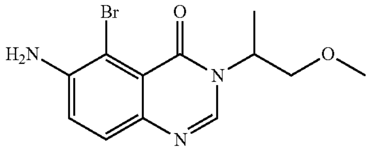 293 | 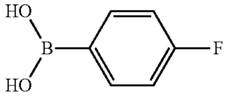 | 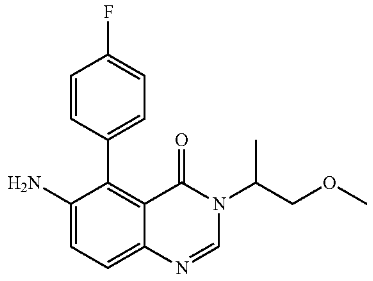 294 |

Abbreviations

DMF N,N-dimethylformamide
HATU 1-[Bis(dimethylamino)methylene]-1H-1,2,3-triazolo[4,5-b]pyridinium 3-oxidehexafluorophosphate
TEA Triethylamine
MeOH Methanol
HMDS Hexamethyldisilazane
$CHCl_3$ Chloroform
$Br_2$ Bromine
$ZnCl_2$ Zinc chloride
$Cs_2CO_3$ Cesium carbonate
$Pd_2(dba)_3$ Tris(dibenzylideneacetone)dipalladium(0)
$CH(OMe)_3$ Trimethylorthoformate (TMOF)
$Pd(PPh_3)_4$ Tetrakis(triphenylphosphine)palladium(0)
THF Tetrahydrofuran
$LiOH \cdot H_2O$ Lithium hydroxide monohydrate
Ar Argon Provided below are the schemes for preparing the compounds disclosed in the present application.

Scheme 1

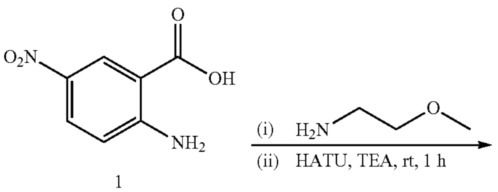

1

-continued

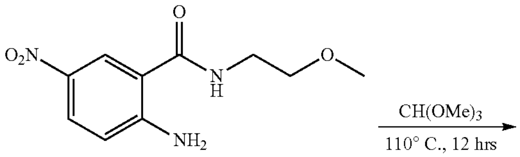

2

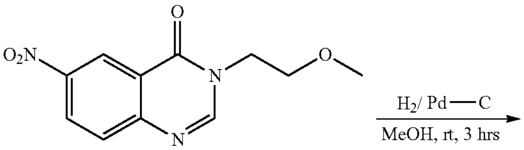

3

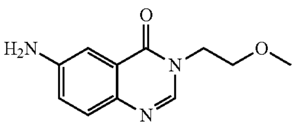

4

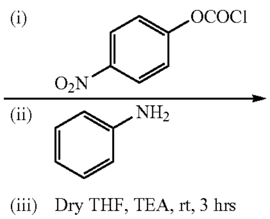

-continued
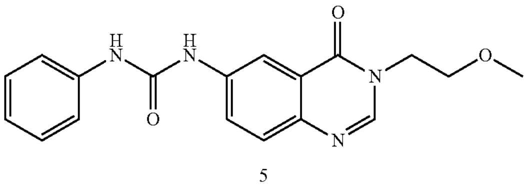
5
4
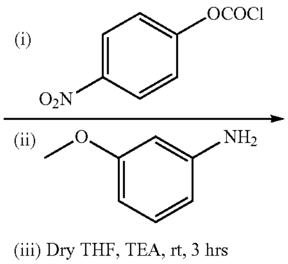
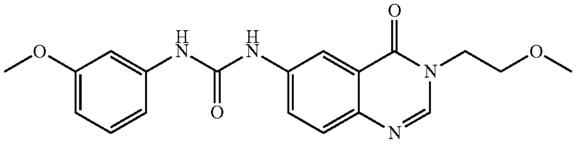
6
4
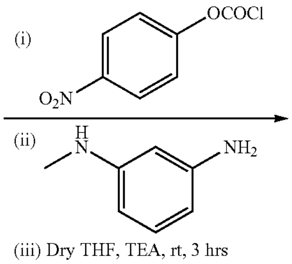
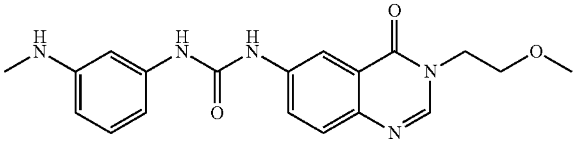
7
4
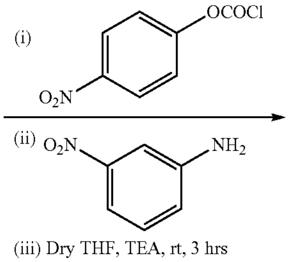
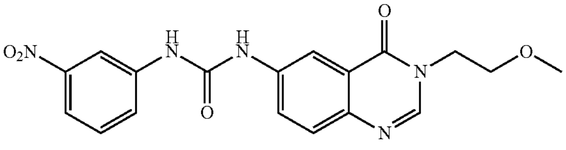
8
-continued
4
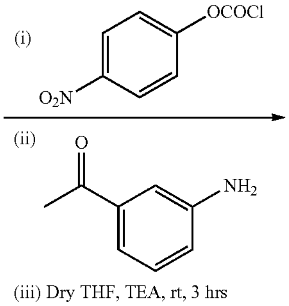
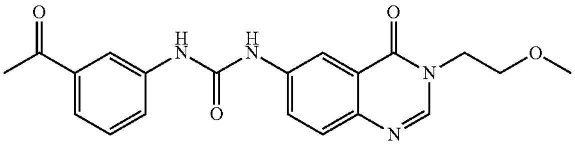
9
4
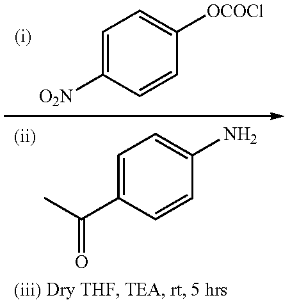
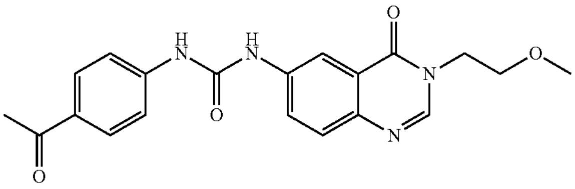
10
4
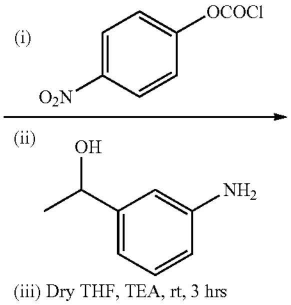
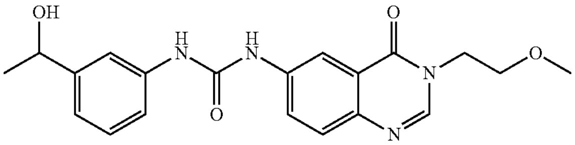
11

-continued
4
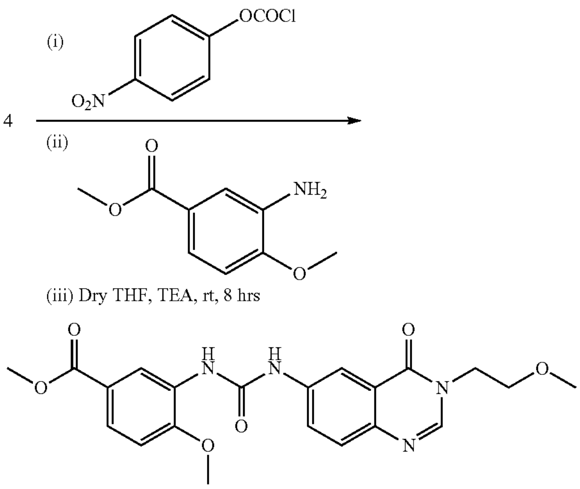
12
4
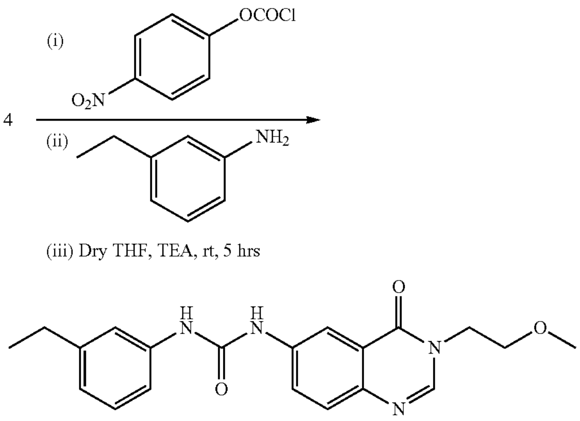
13
4
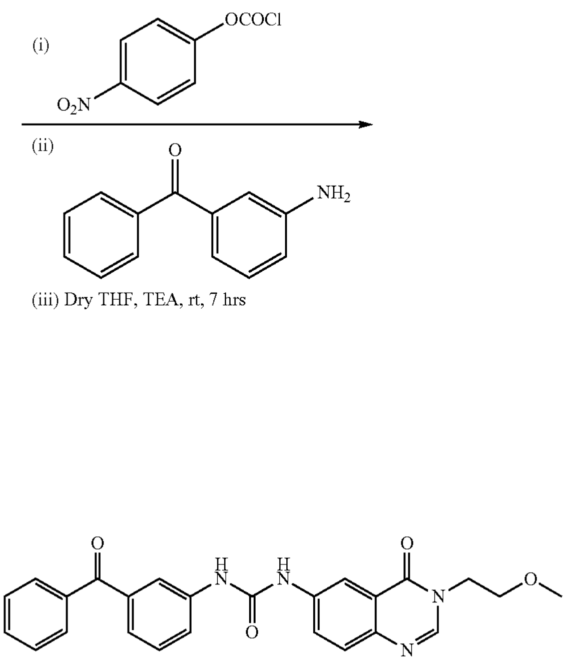
14
-continued
4
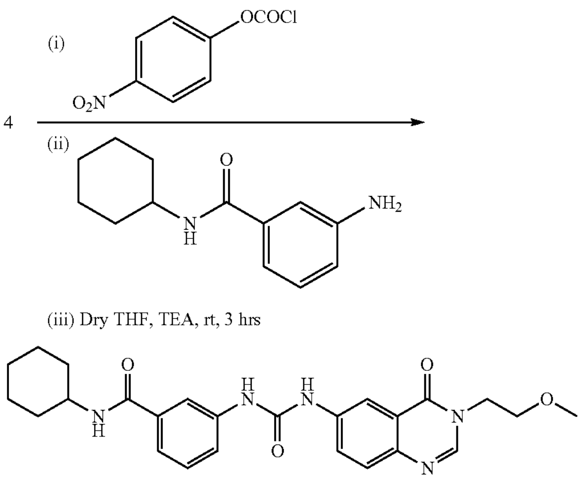
15
4
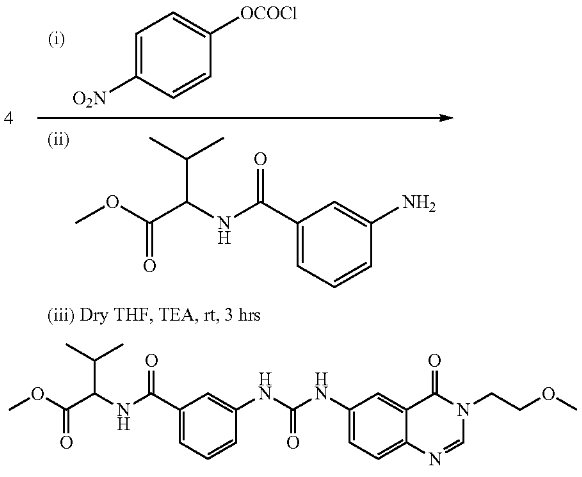
16
4
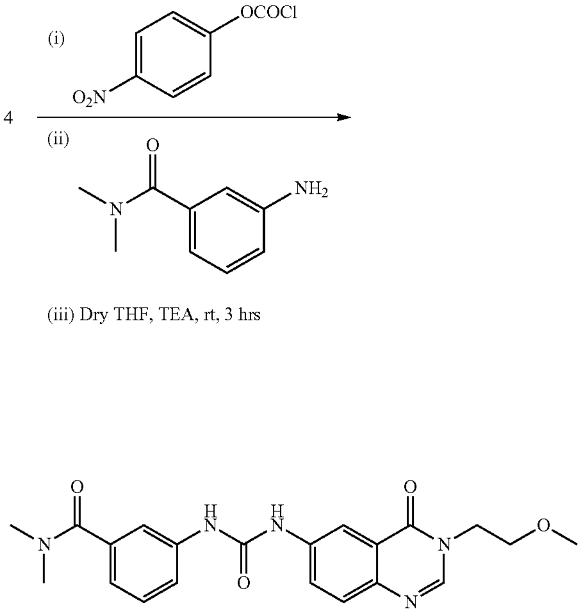
17

-continued
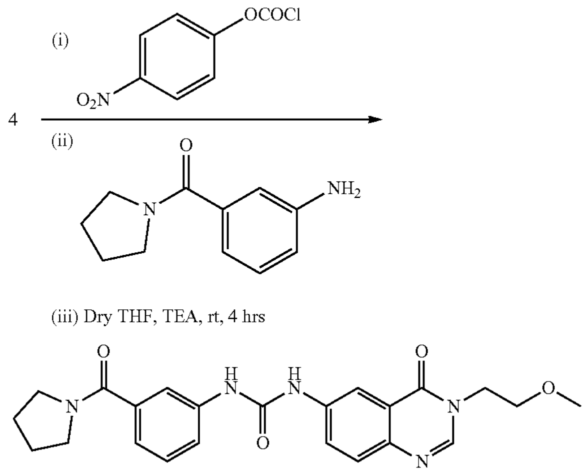
18
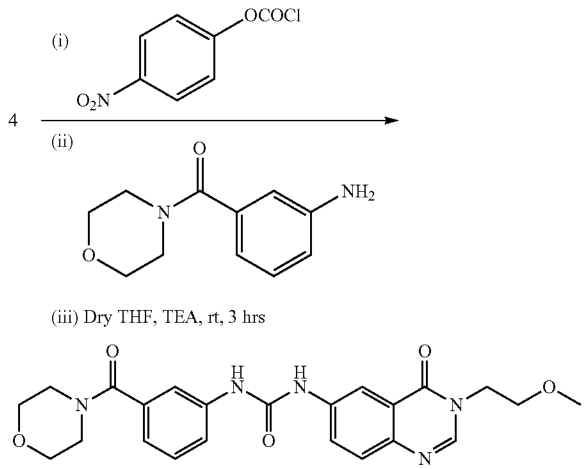
19
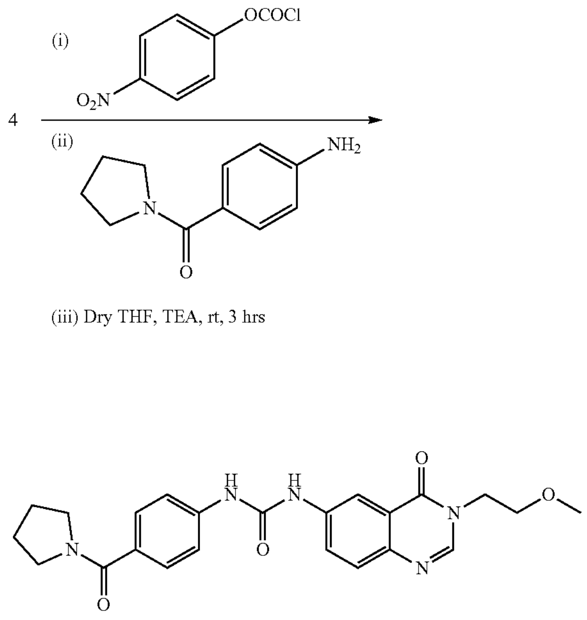
20
-continued
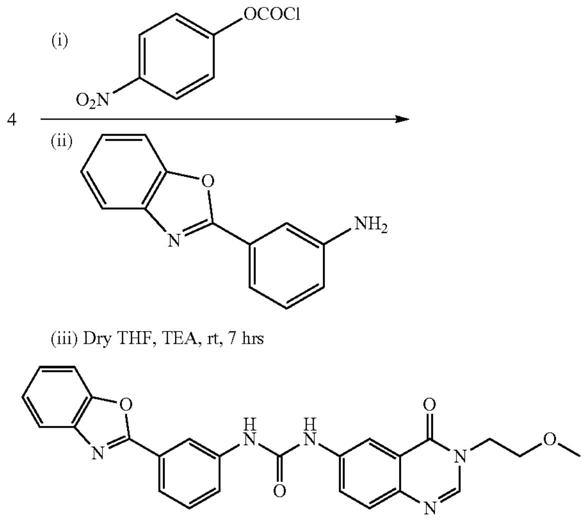
21
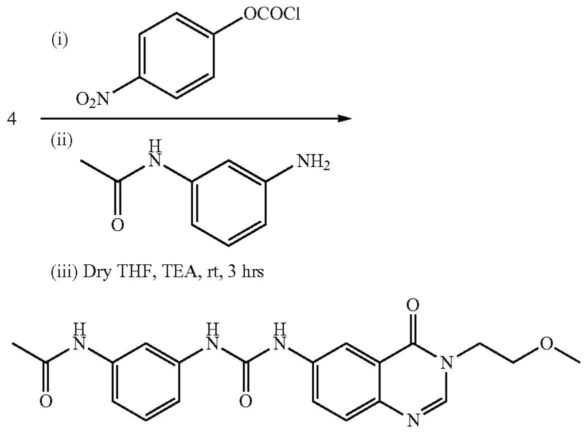
22
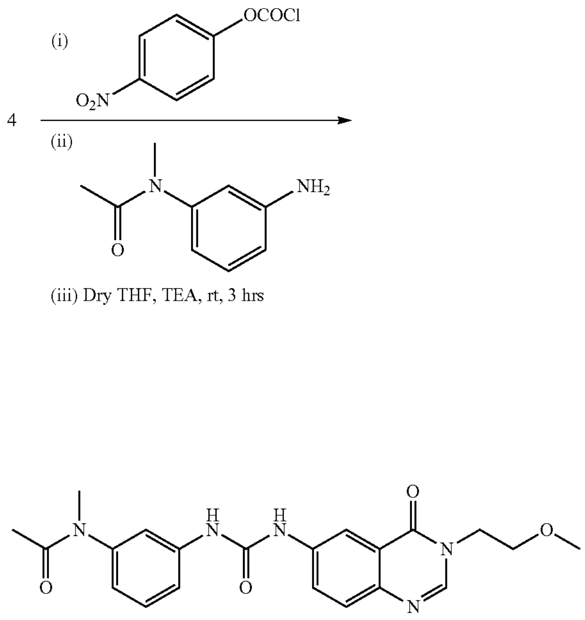
23

-continued
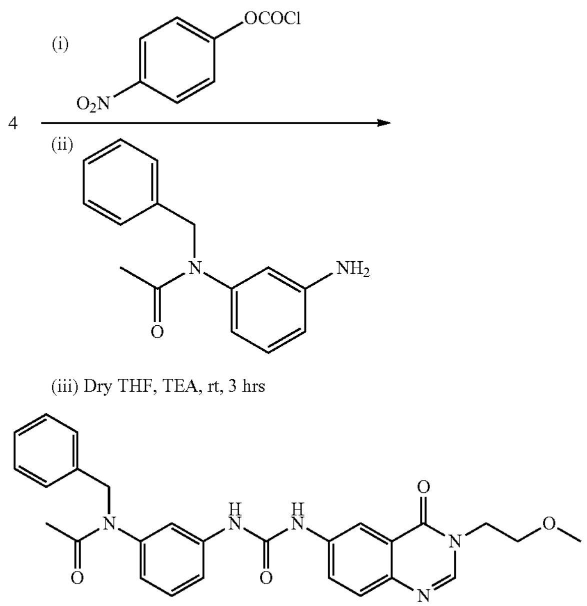
24
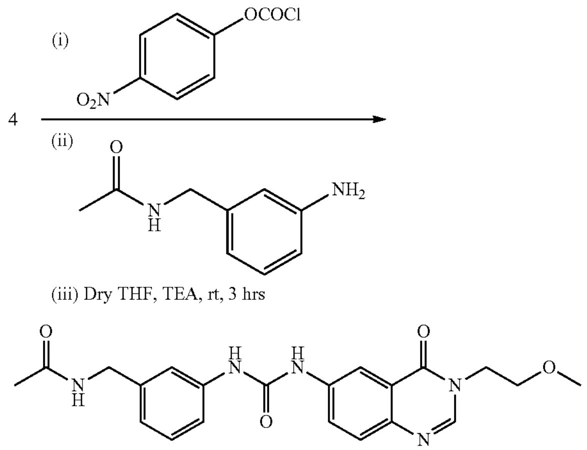
25
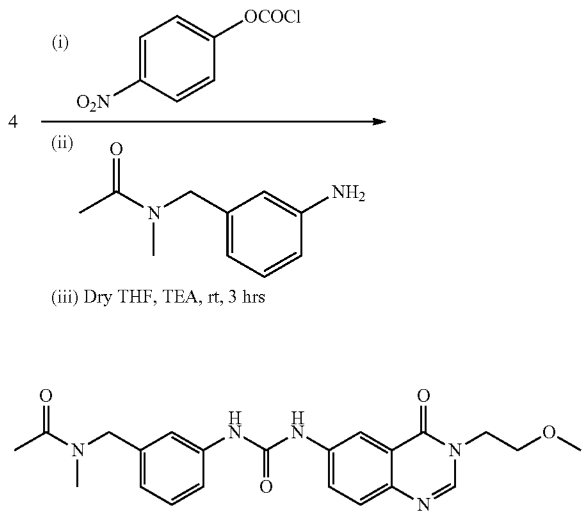
26
-continued
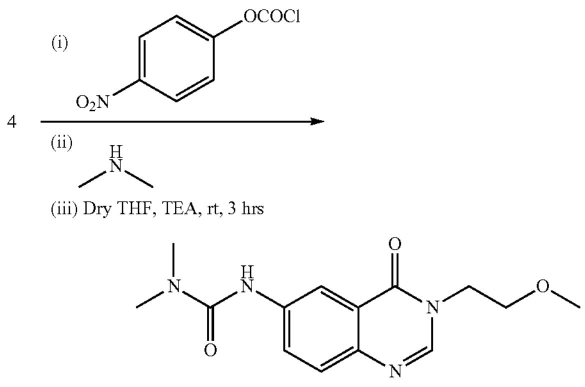
27
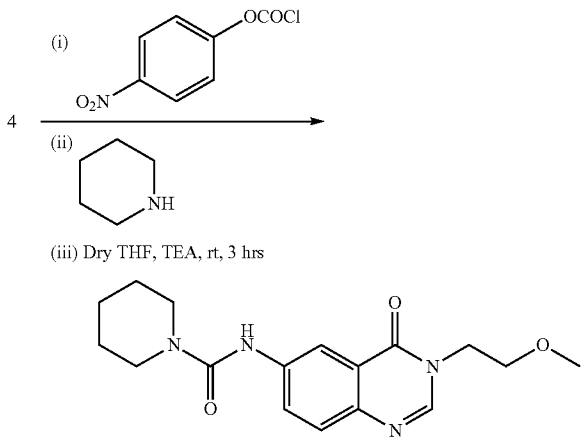
28
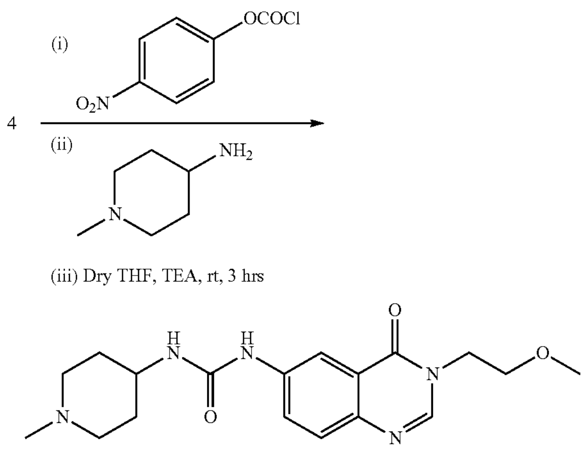
29
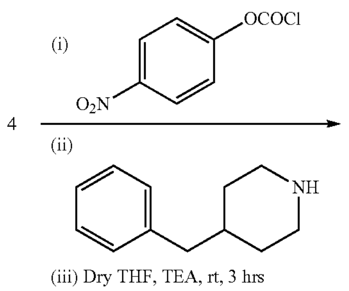

-continued
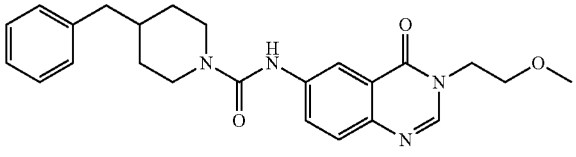
30
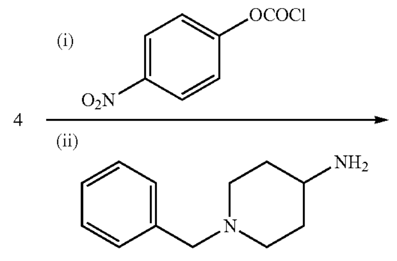
(iii) Dry THF, TEA, rt, 3 hrs
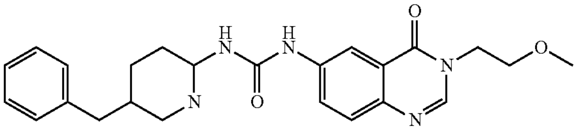
31
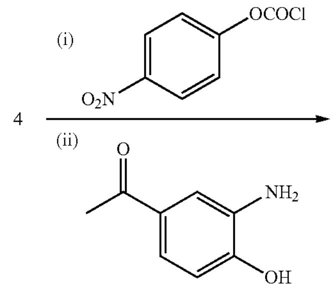
(iii) Dry THF, TEA, rt, 3 hrs
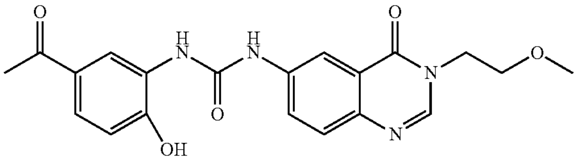
32
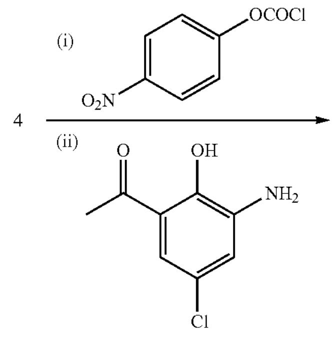
(iii) Dry THF, TEA, rt, 3 hrs
-continued
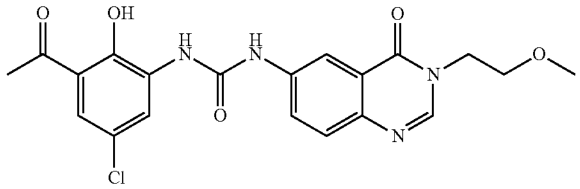
33
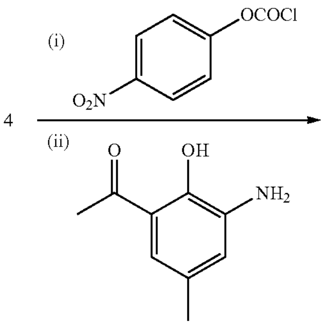
(iii) Dry THF, TEA, rt, 3 hrs
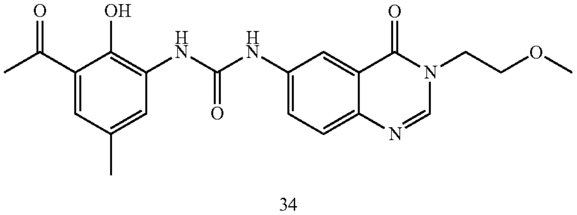
34
Scheme 2
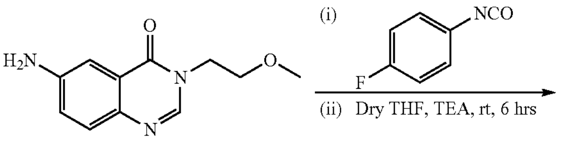
4
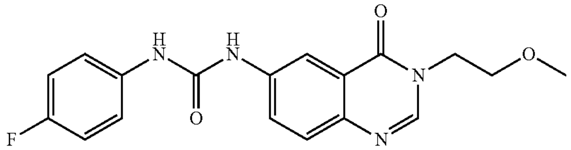 [SMILES: COCCn1cnc2ccc(NC(=O)Nc3ccc(F)cc3)cc2c1=O]
35
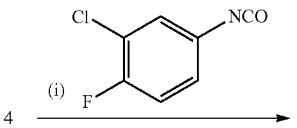
(iii) Dry THF, TEA, rt, 6 hrs -continued
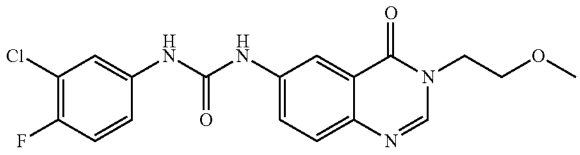
36
4 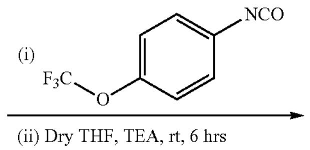
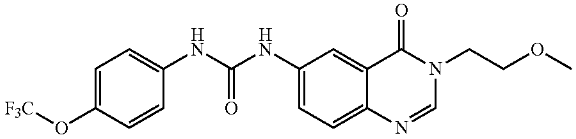
37
4 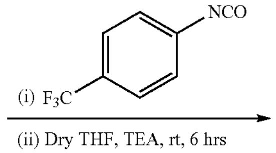
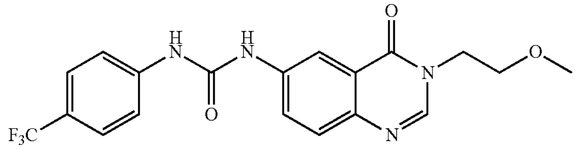
38
4 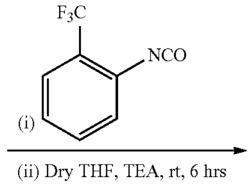
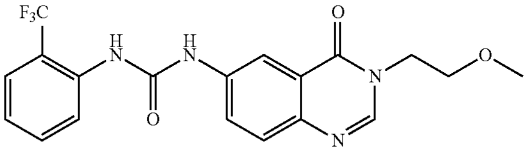
39
4 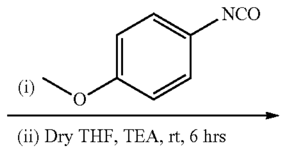
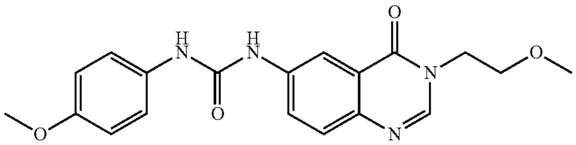
40
-continued
4 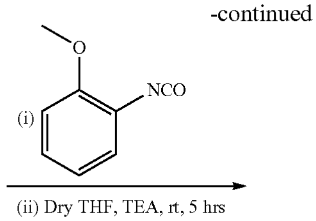
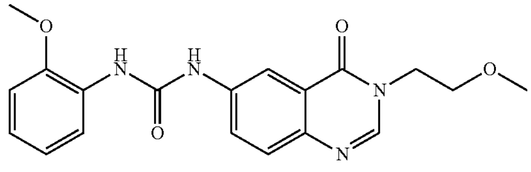
41
4 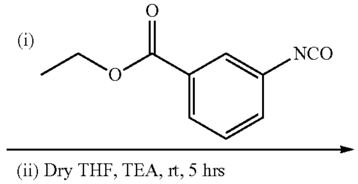
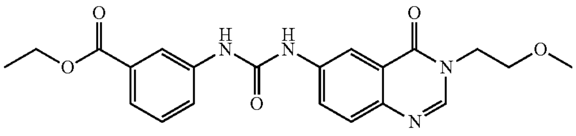
42
42 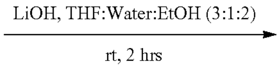
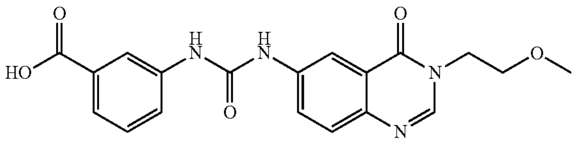
42 a
Scheme 3
4 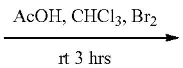
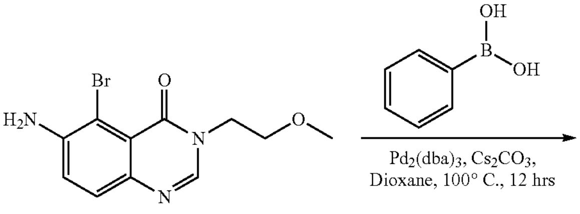
43
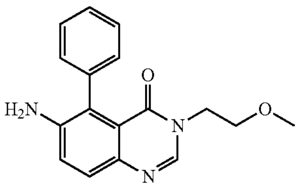
44
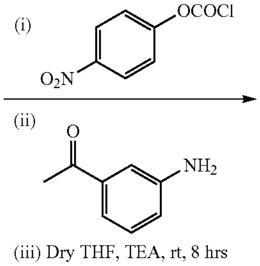

-continued
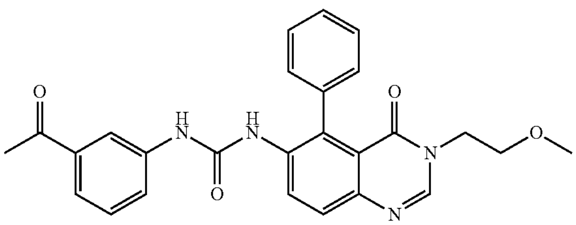
45
43 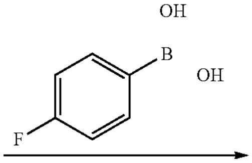
Pd$_2$(dba)$_3$, Cs$_2$CO$_3$,
Dioxane, 100° C., 12 hrs
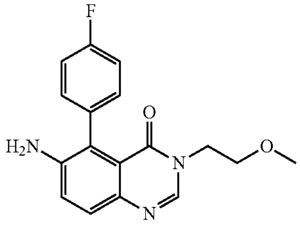
46
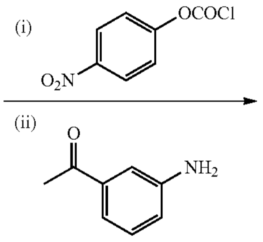
(iii) Dry THF, TEA, rt, 8 hrs
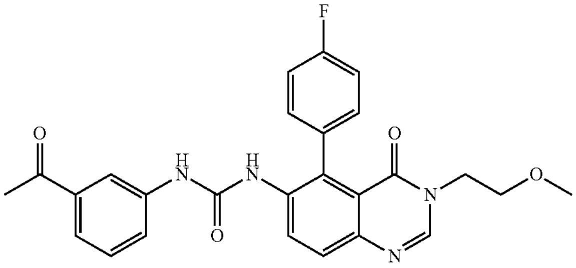
47
43 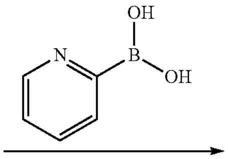
Pd$_2$(dba)$_3$, Cs$_2$CO$_3$,
Dioxane, 100° C., 12 hrs
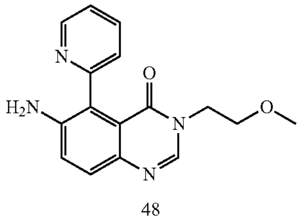
48
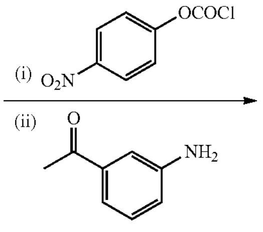
(iii) Dry THF, TEA, rt, 8 hrs
-continued
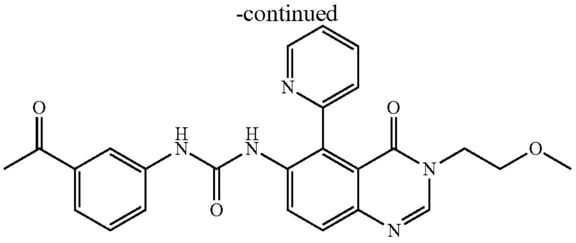
49
43 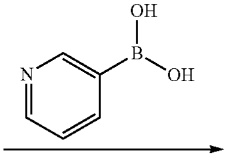
Pd$_2$(dba)$_3$, Cs$_2$CO$_3$,
Dioxane, 100° C., 12 hrs
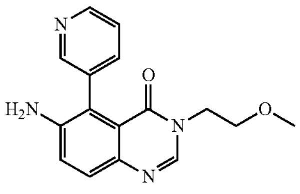
50
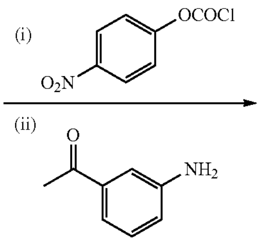
(iii) Dry THF, TEA, rt, 8 hrs
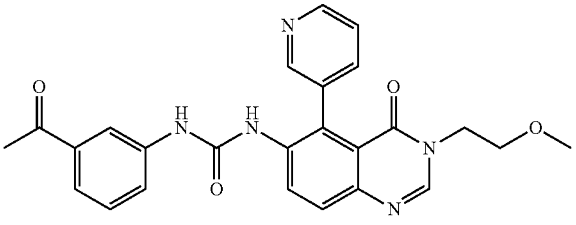
51
43 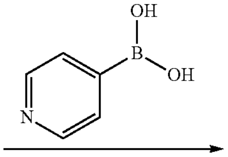
Pd$_2$(dba)$_3$, Cs$_2$CO$_3$,
Dioxane, 100° C., 12 hrs
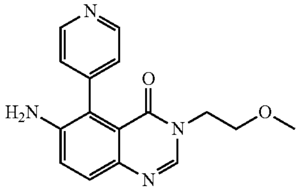
52
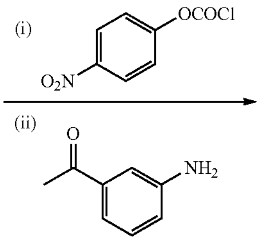
(iii) Dry THF, TEA, rt, 8 hrs
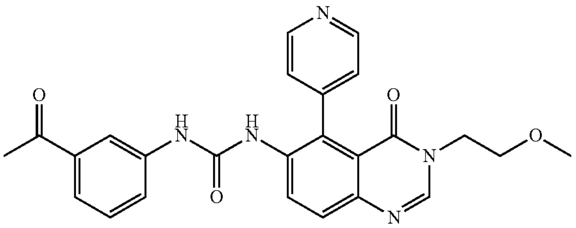
53

-continued
43
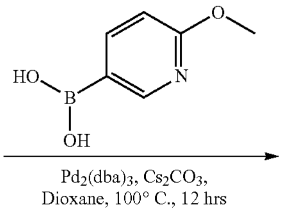
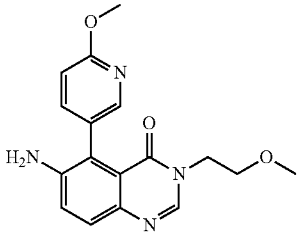
54
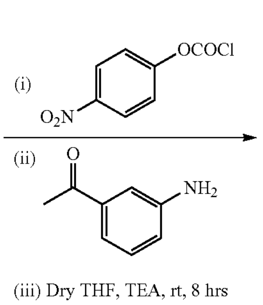
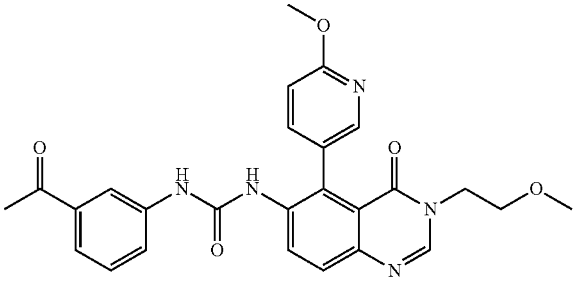
55
43
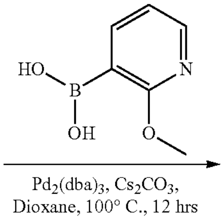
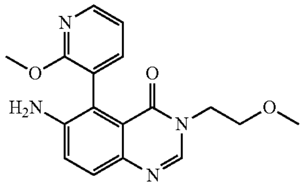
56
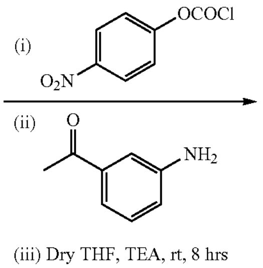
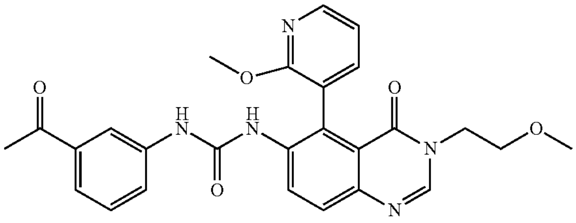
57
-continued
43
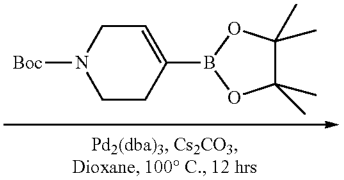
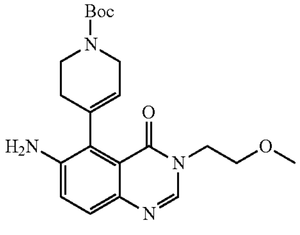
58
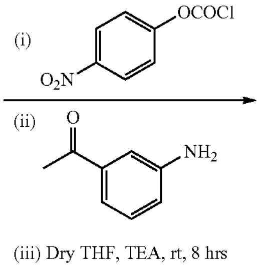
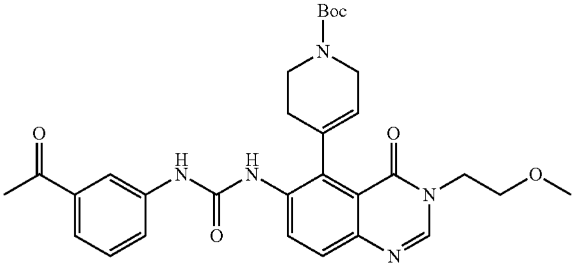
59
59
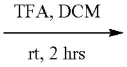
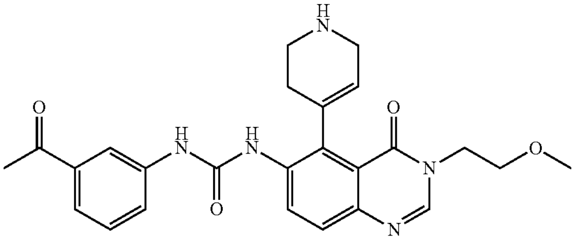
60
59
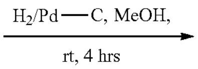
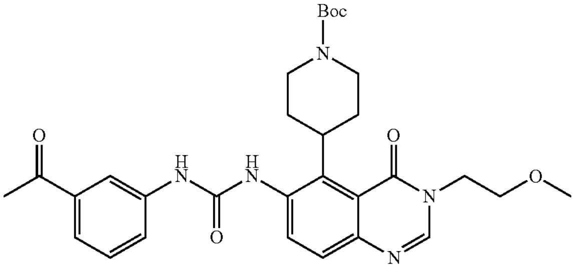
61
60
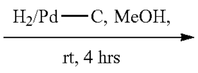

-continued
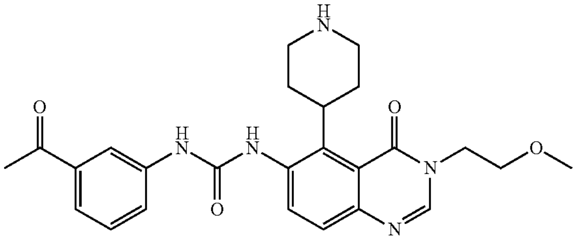
62
43
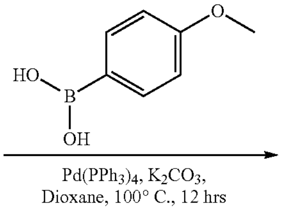
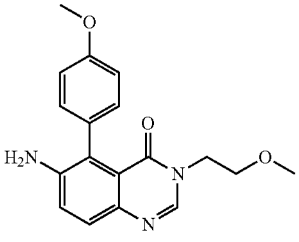
63
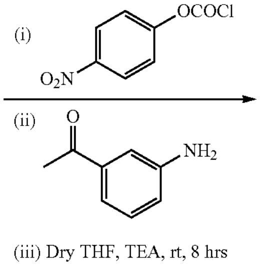
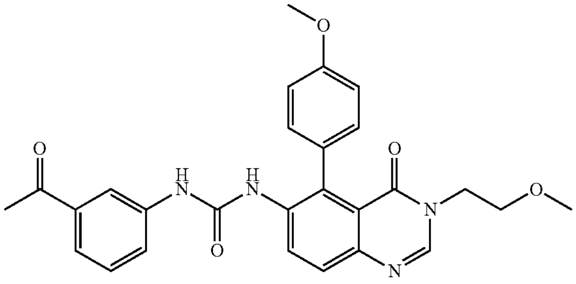
64
43
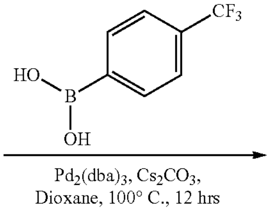
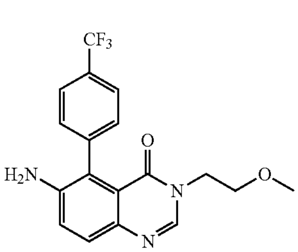
65
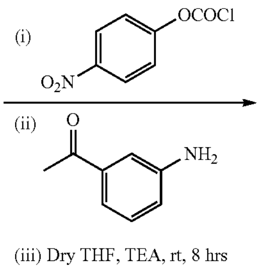
-continued
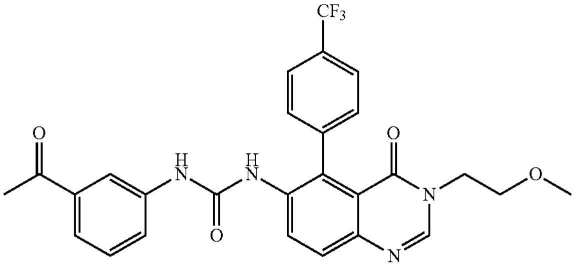
66
43
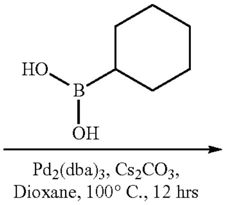
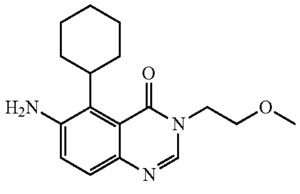
67
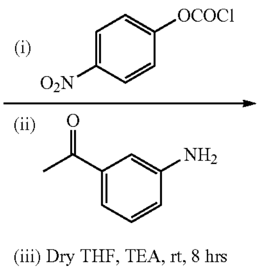
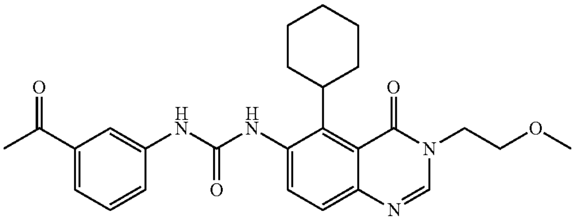
68
43
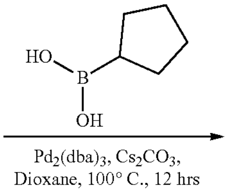
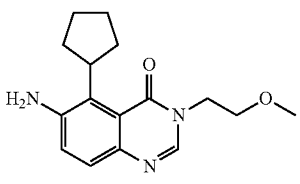
69
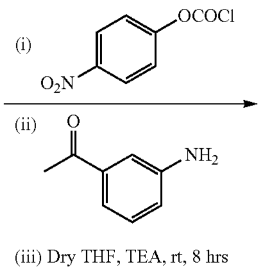

-continued
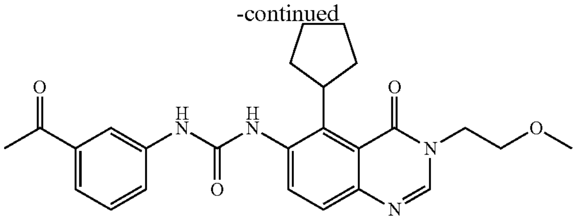
70
43
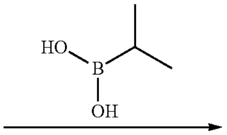
Pd$_2$(dba)$_3$, Cs$_2$CO$_3$,
Dioxane, 100° C., 12 hrs
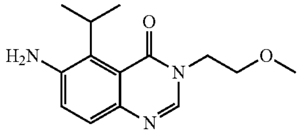
71
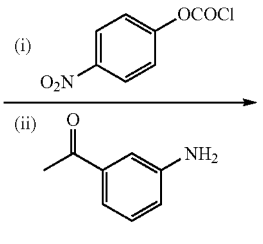
(iii) Dry THF, TEA, rt, 8 hrs
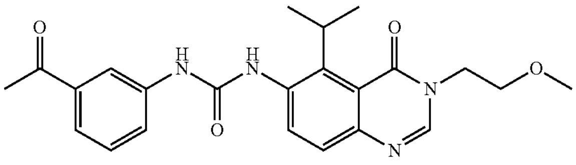
72
Scheme 4
43
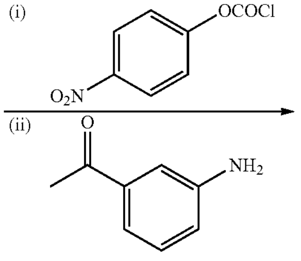
(iii) Dry THF, TEA, rt, 3 hrs
-continued
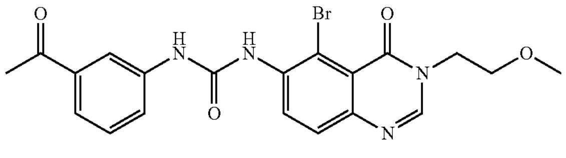
73
Scheme 5
4
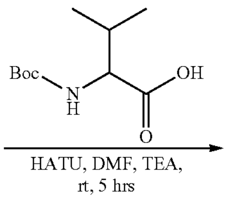
HATU, DMF, TEA,
rt, 5 hrs
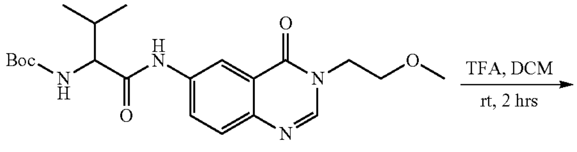
74
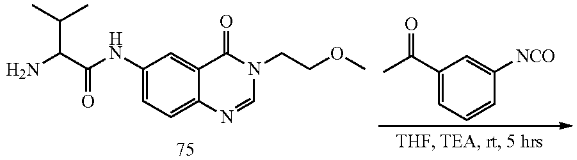
75
THF, TEA, rt, 5 hrs
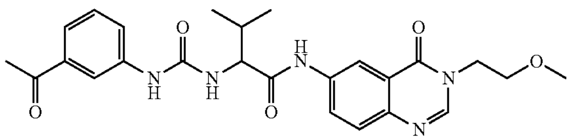
76
Scheme 6
4
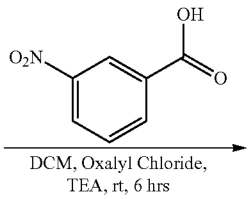
DCM, Oxalyl Chloride,
TEA, rt, 6 hrs
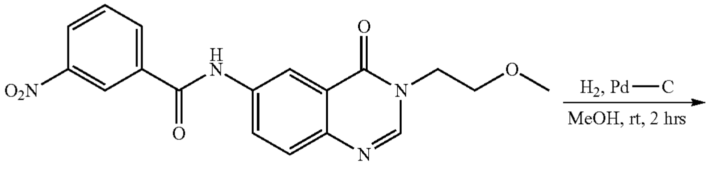
77

-continued
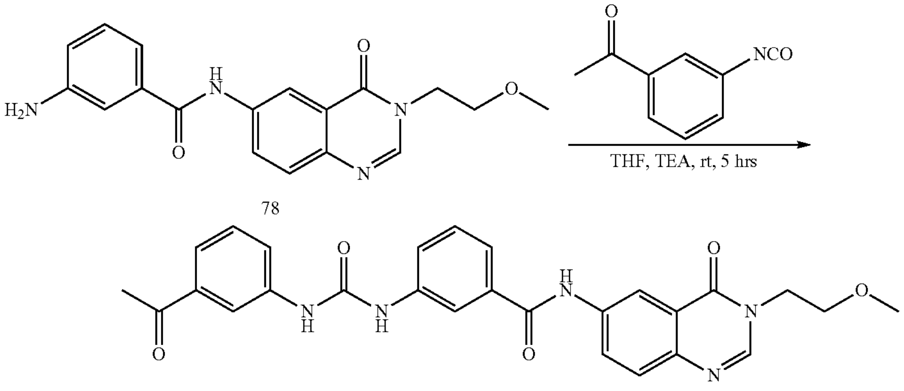
78
79
Scheme 7
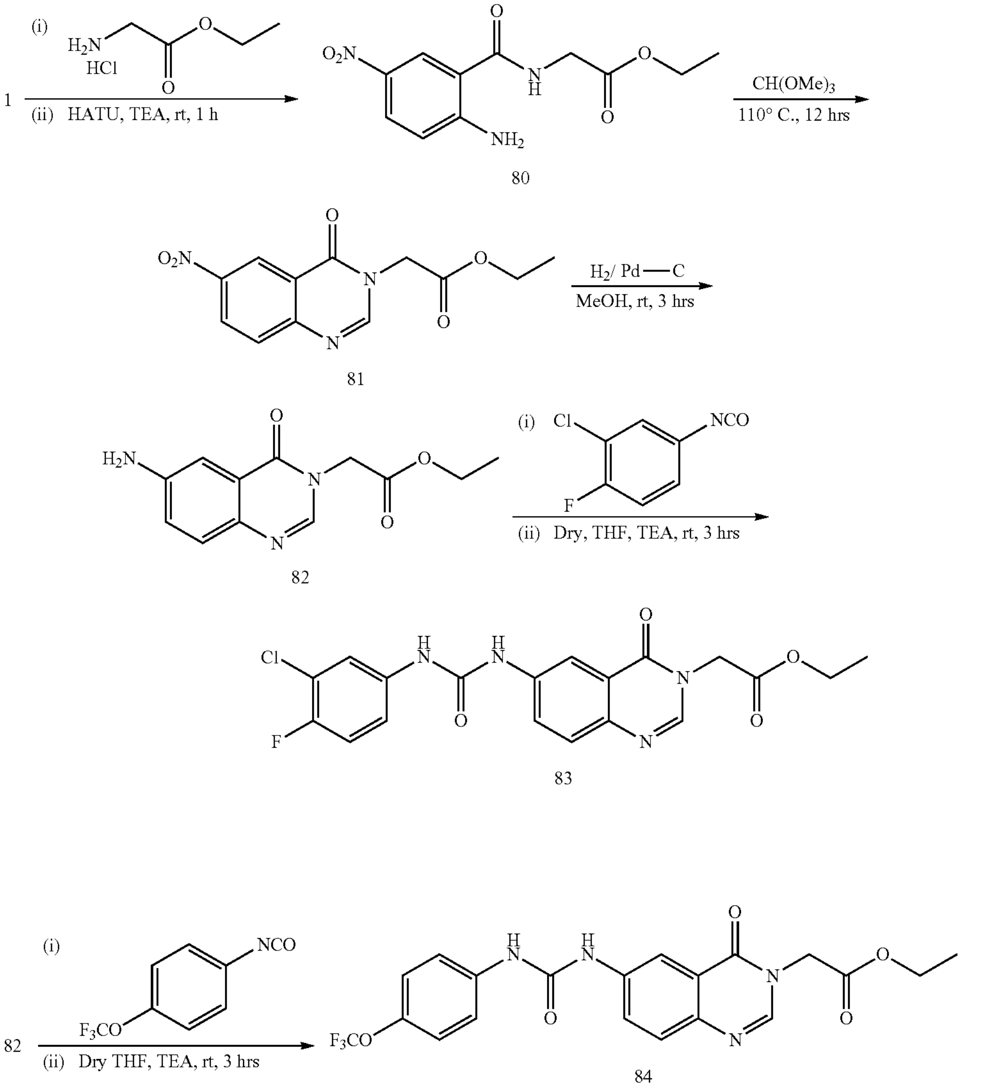
80
81
82
83
84

-continued
82
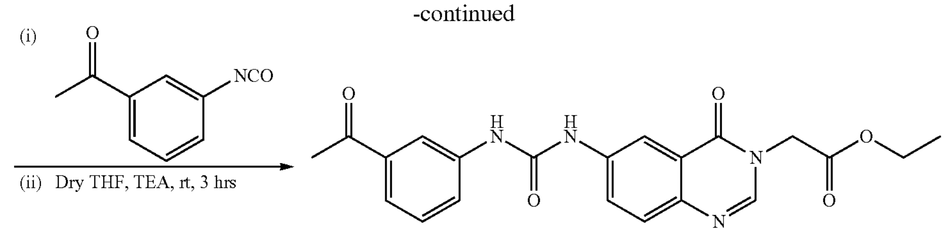
85
85
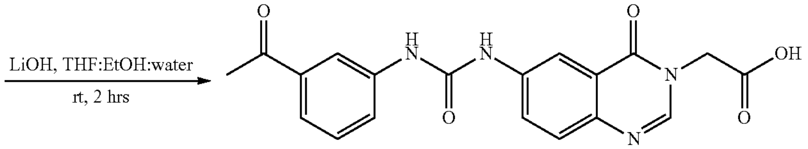
85 a
Scheme 8
1
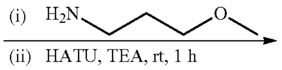
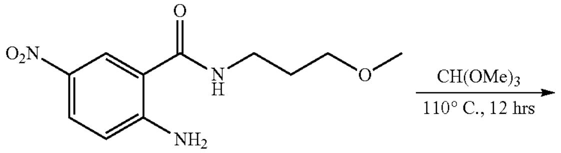
86
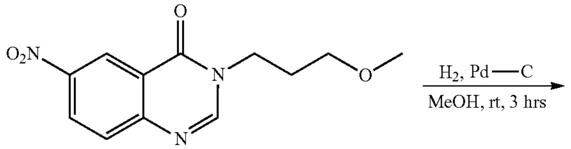
87
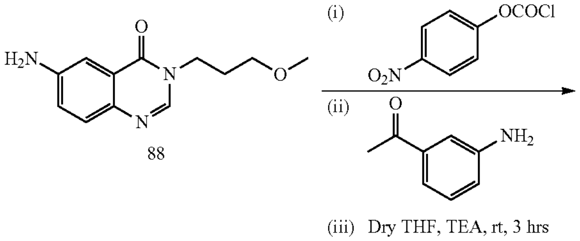
88
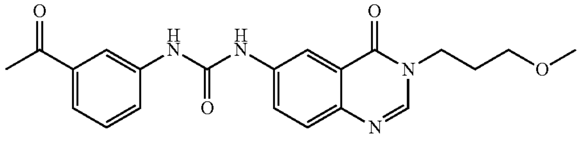
89
Scheme 9
1
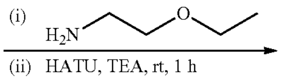
-continued
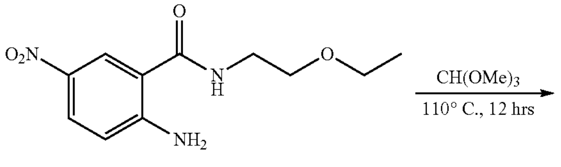
90
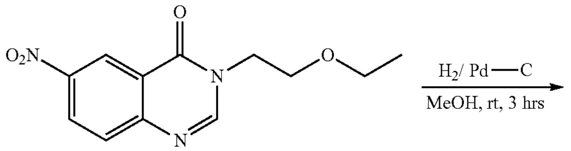
91
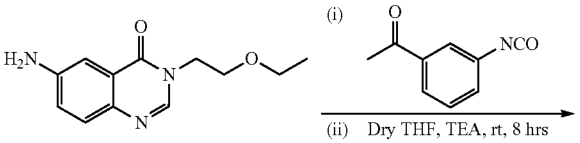
92
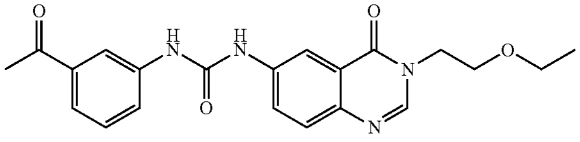
93
92
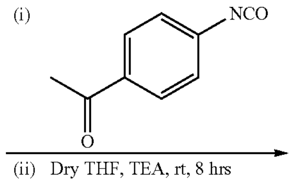
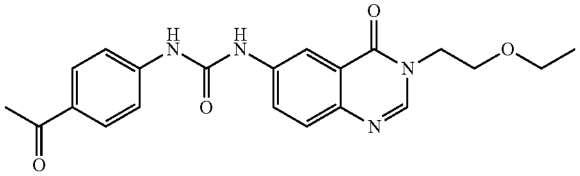
94

Scheme 10
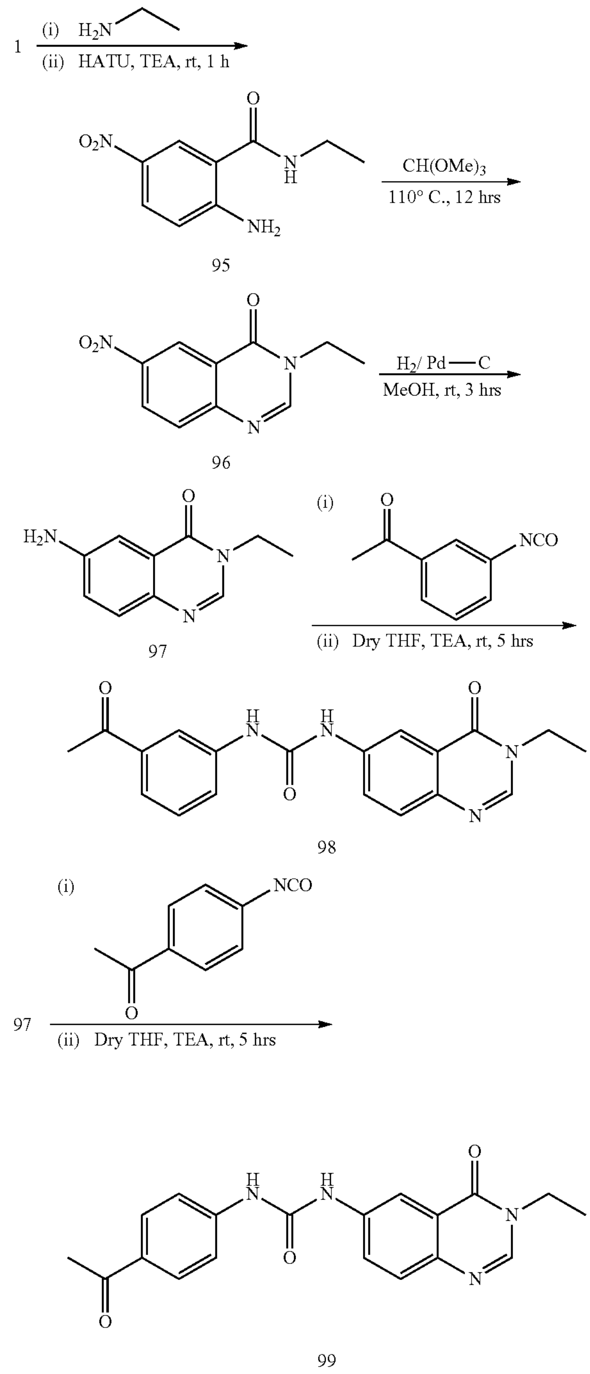
Scheme 11
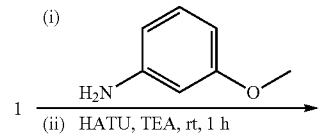
-continued
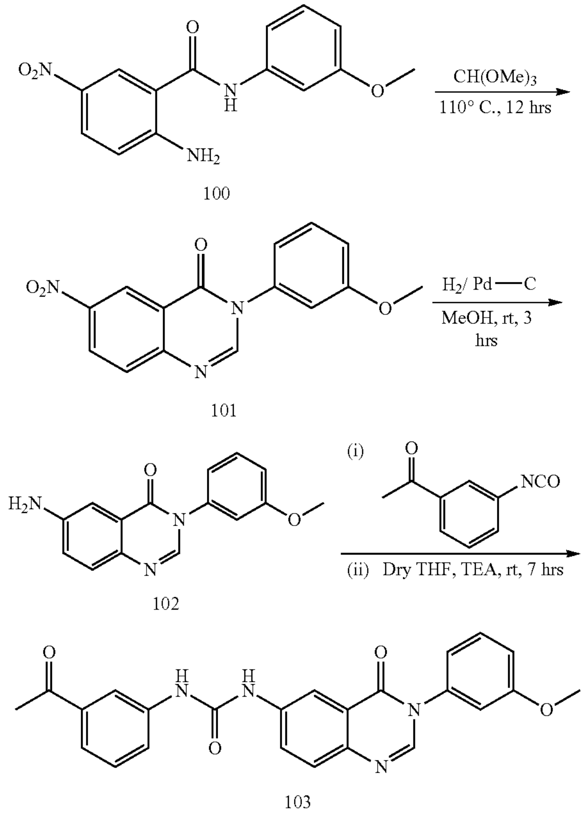
Scheme 12
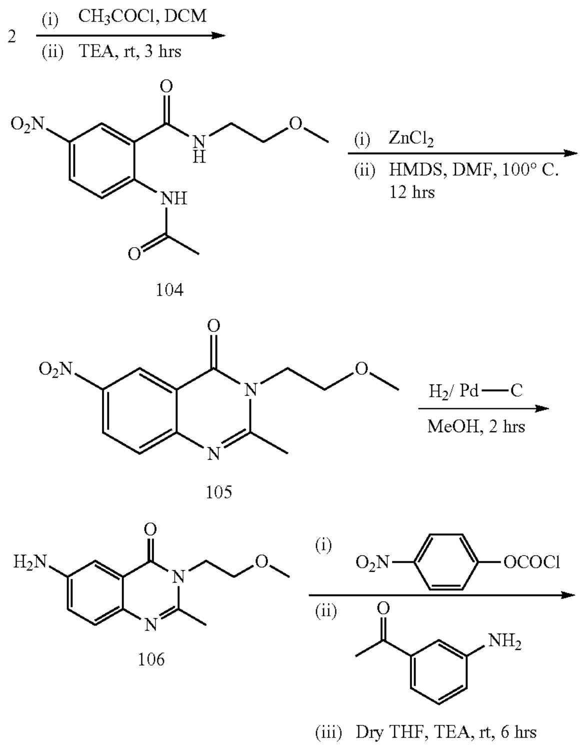

-continued
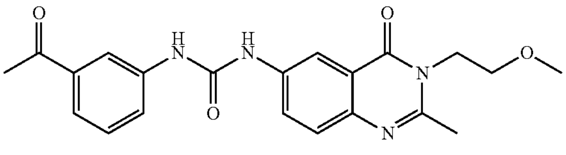
107
Scheme 13
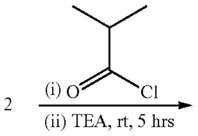
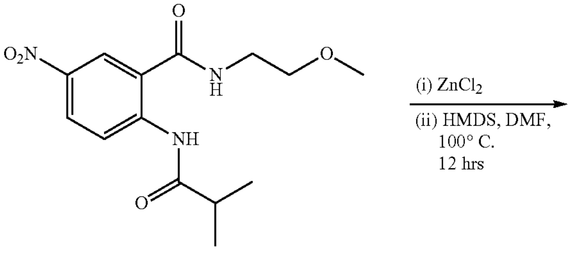
108
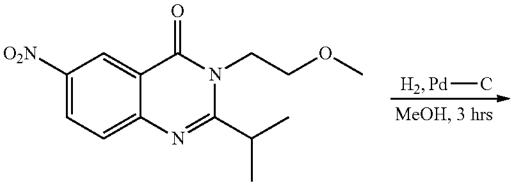
109
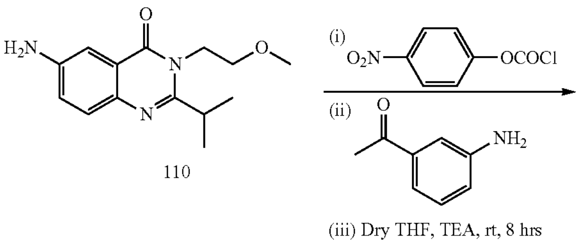
110
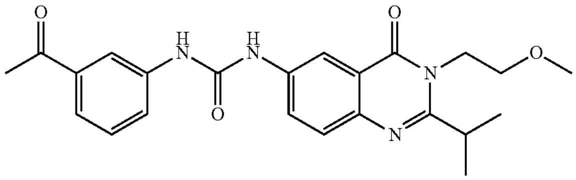
111
Scheme 14
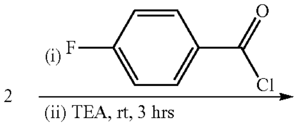
-continued
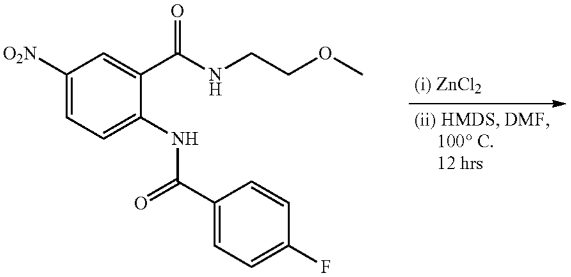
112
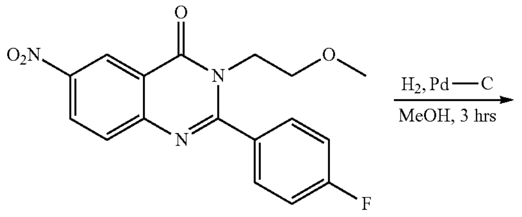
113
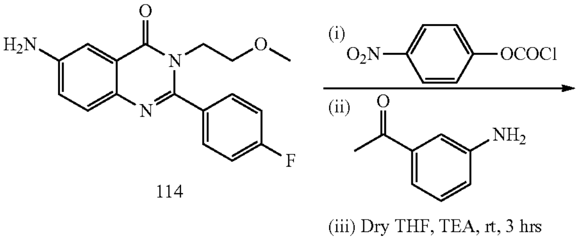
114
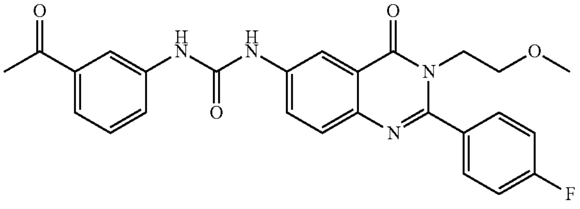
115
Scheme 15
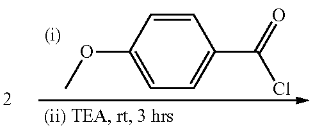
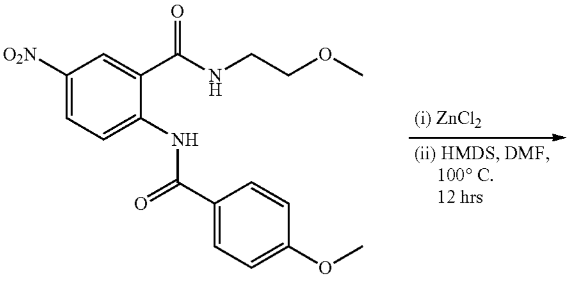
116

-continued
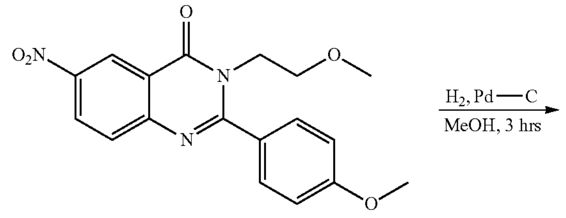
117
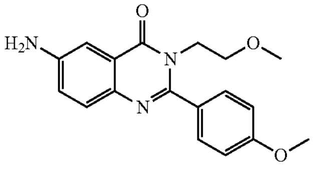
118
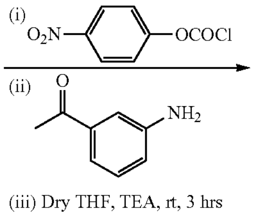
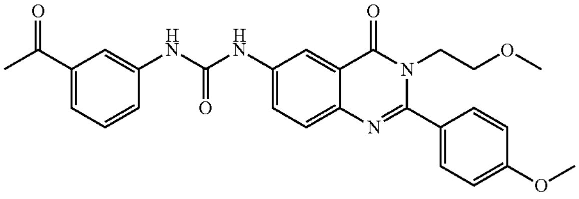
119
Scheme 16
2
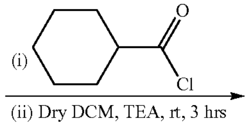
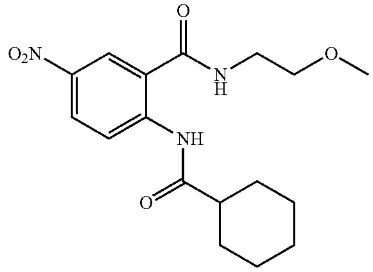
120
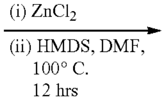
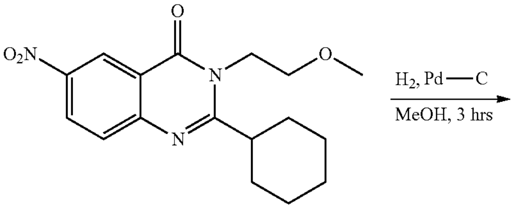
121
-continued
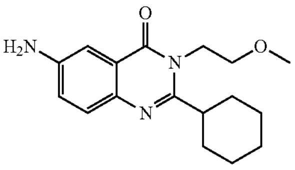
122
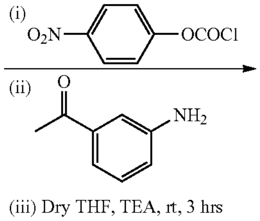
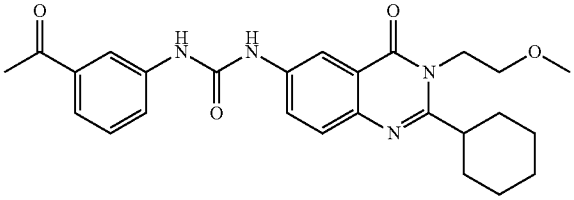
123
Scheme 17
2
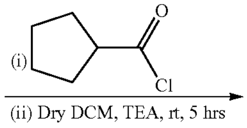
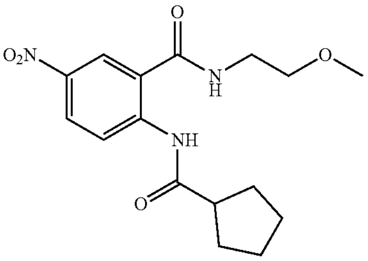
124
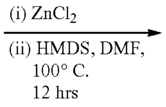
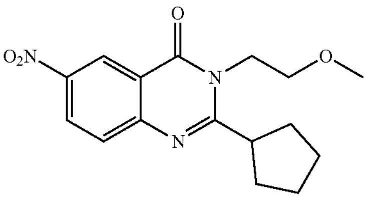
125
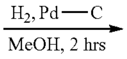
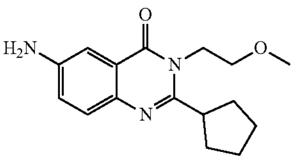
126
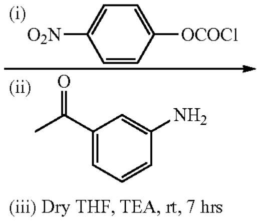

-continued
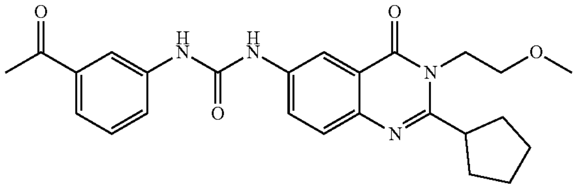
127
Scheme 18
1 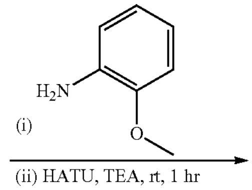
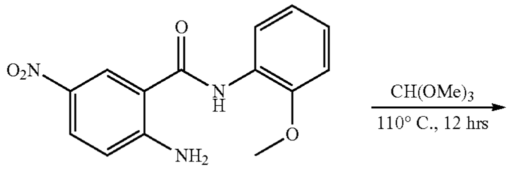
128
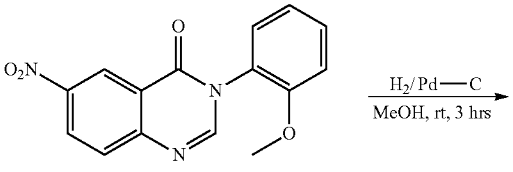
129
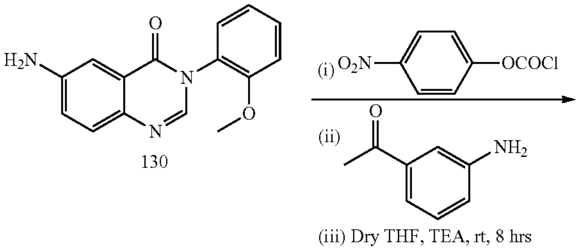
130
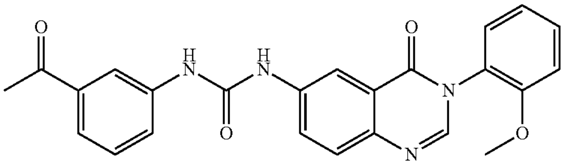
131
Scheme 19
1 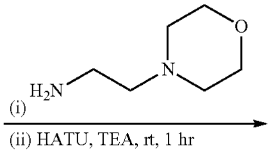
-continued
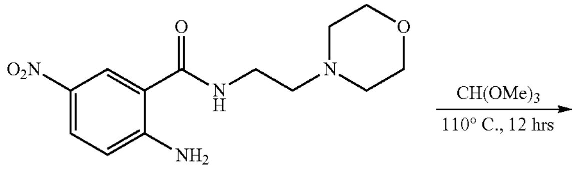
132
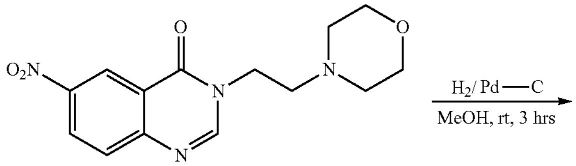
133
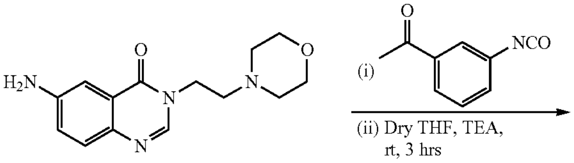
134
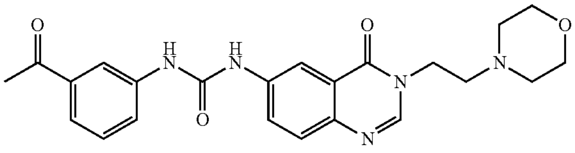
135
Scheme 20
1 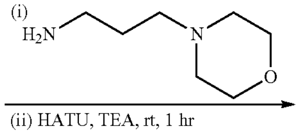
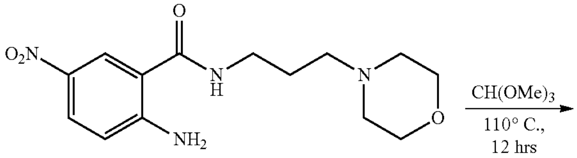
136
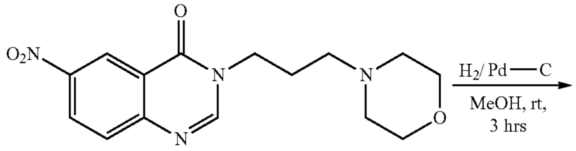
137
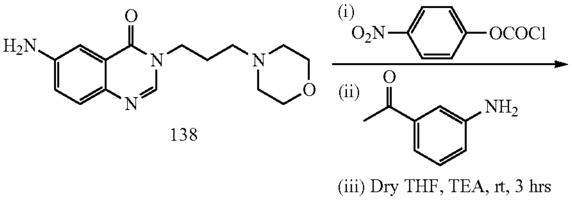
138

-continued
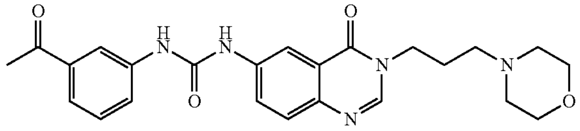
139
Scheme 21
1 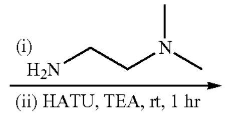
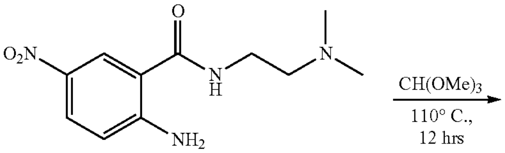
140
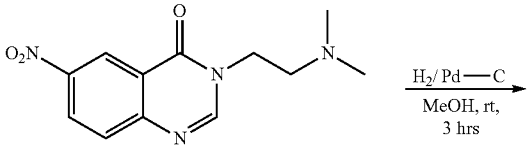
141
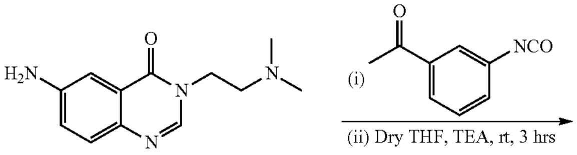
142
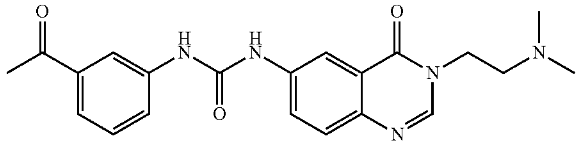
143
Scheme 22
1 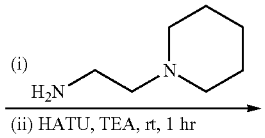
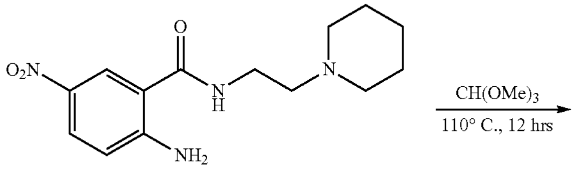
144
-continued
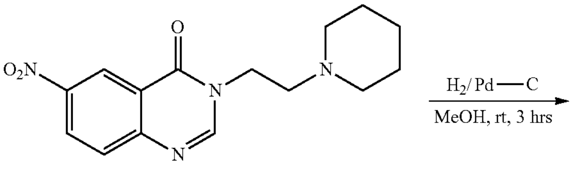
145
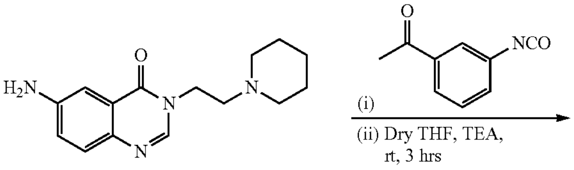
146
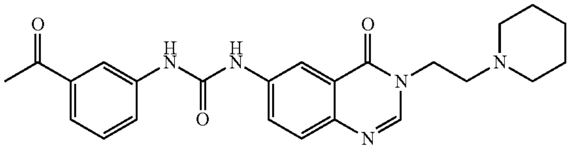
147
Scheme 23
1 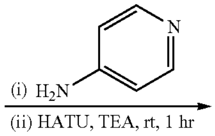
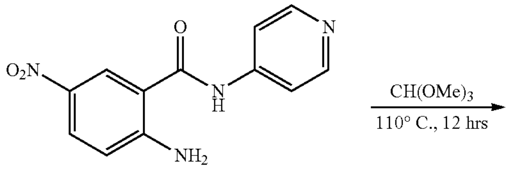
148
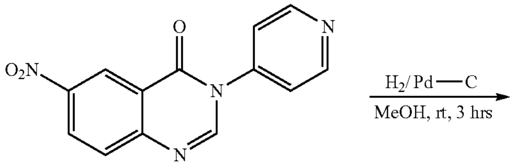
149
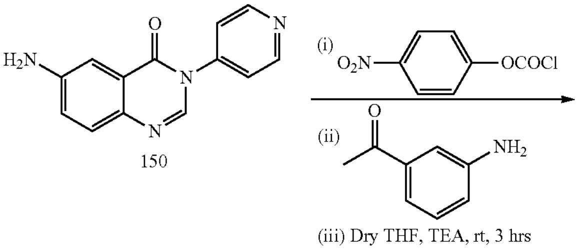
150
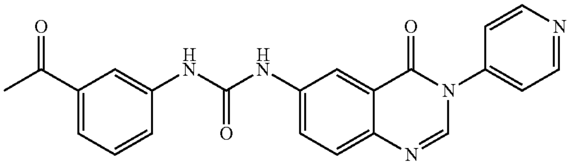
151

Scheme 24
1
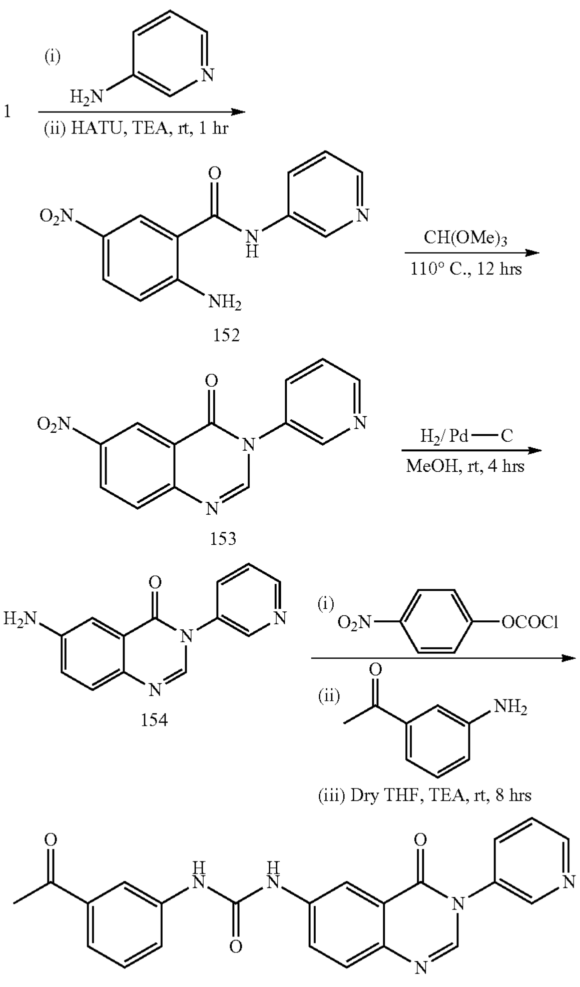
152
153
154
155
Scheme 25
1
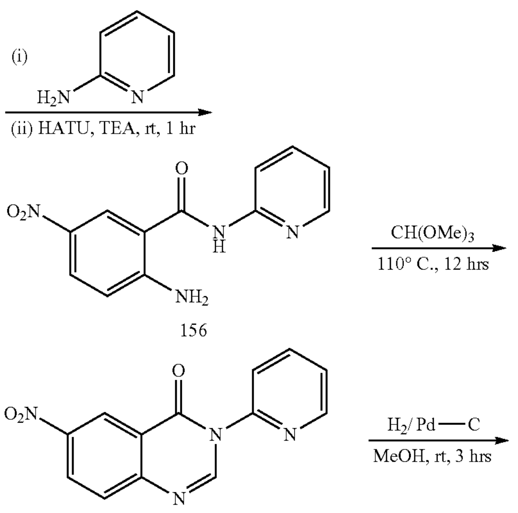
156
157
-continued
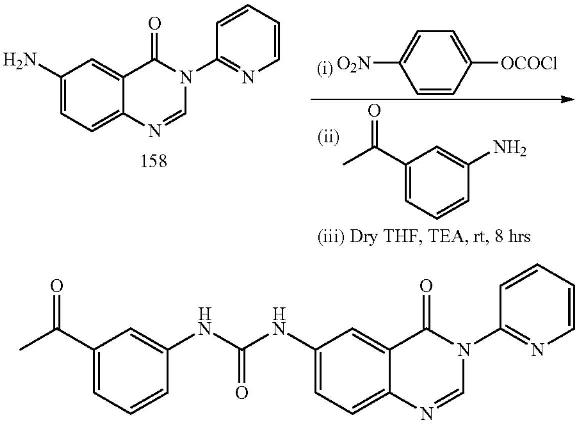
158
159
Scheme 26
1
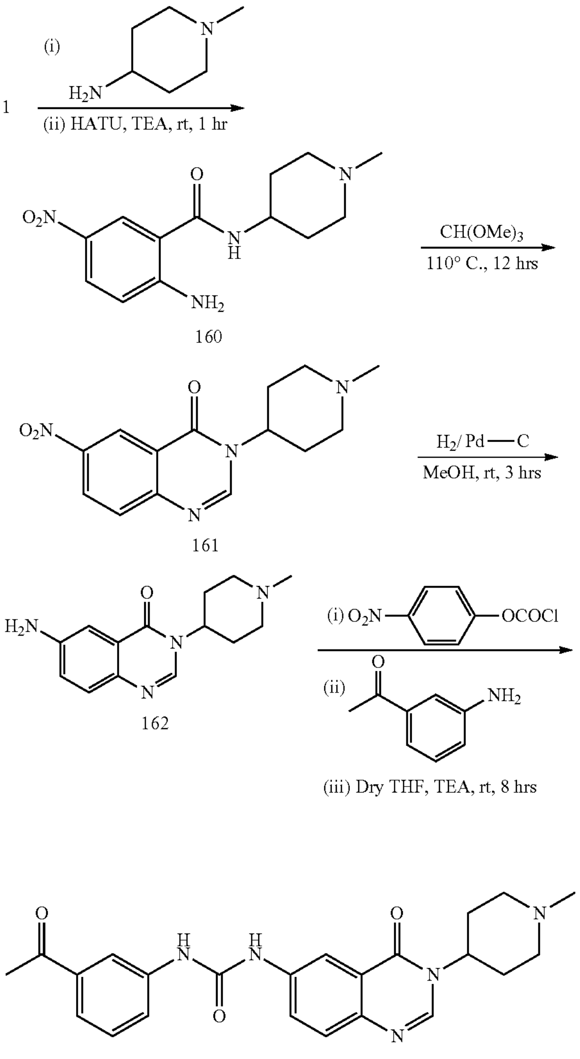
160
161
162
163

Scheme 27
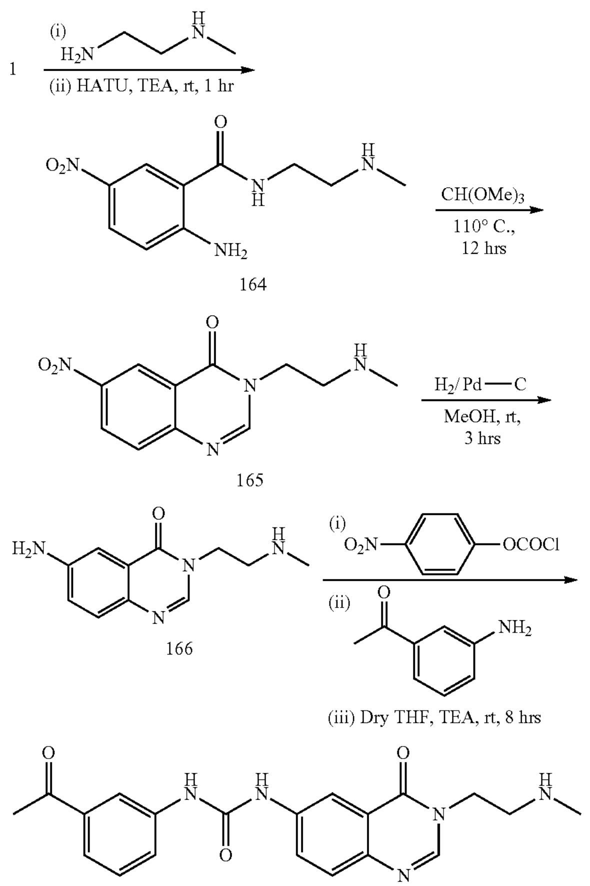
164
165
166
167
Scheme 28
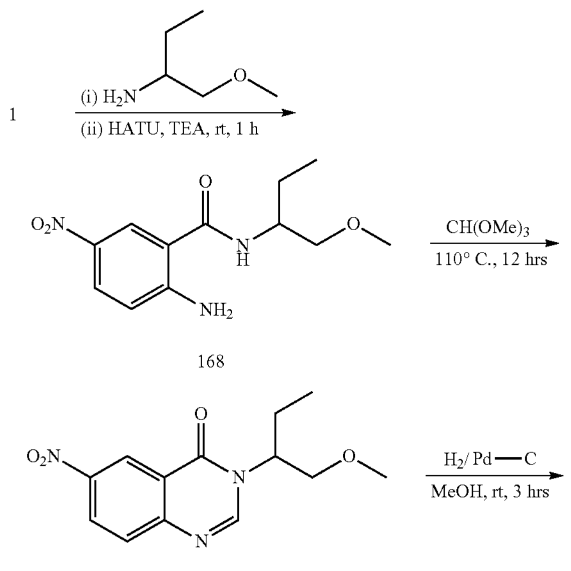
168
169
-continued
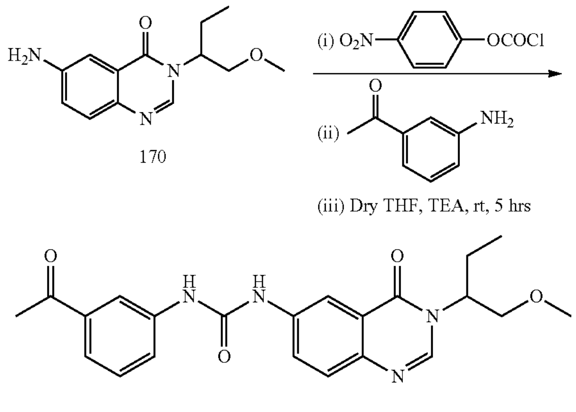
170
171
Scheme 29
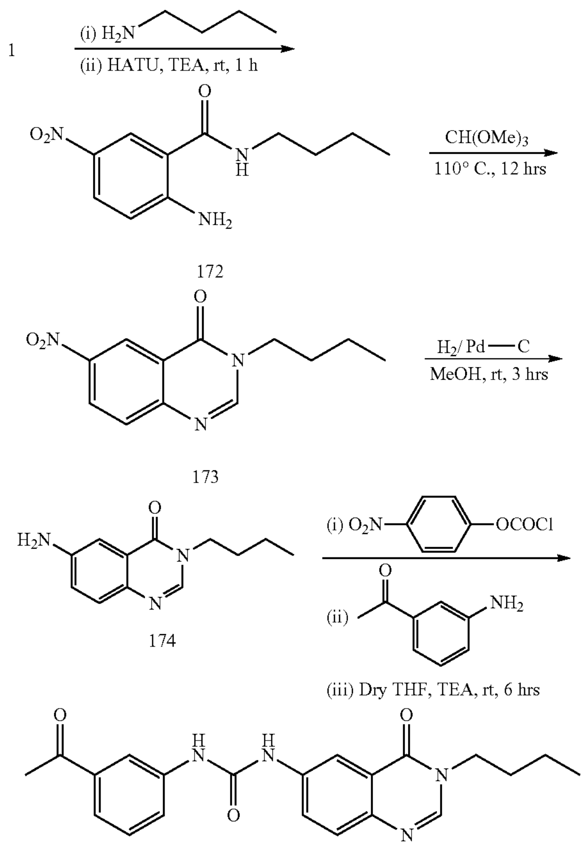
172
173
174
175
Scheme 30
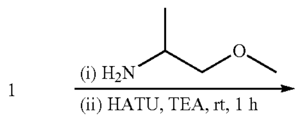

-continued
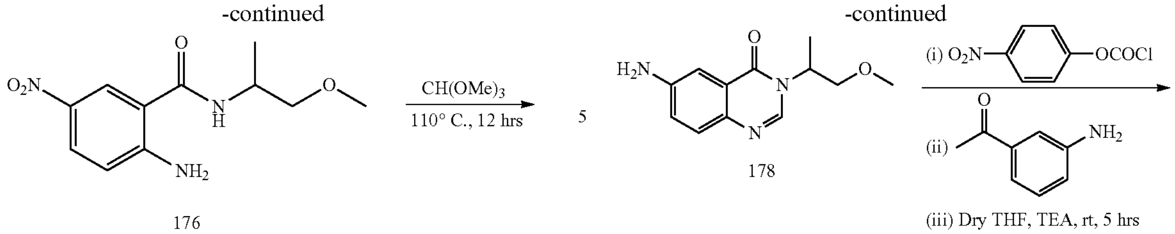
176
178
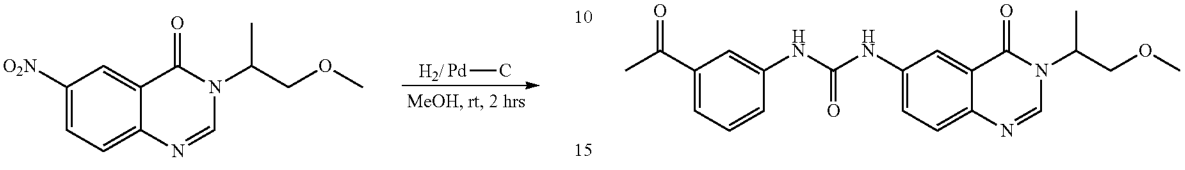
177
179
Scheme 31
1
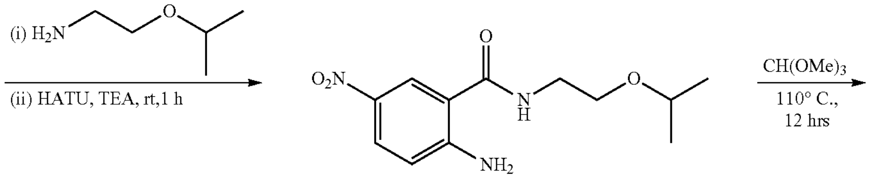
180
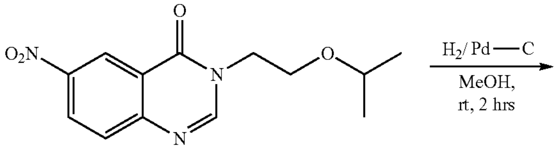
181
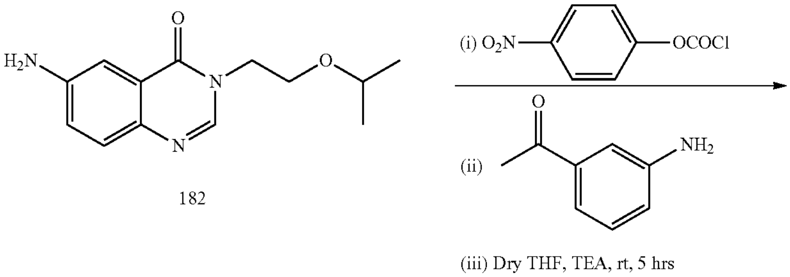
182
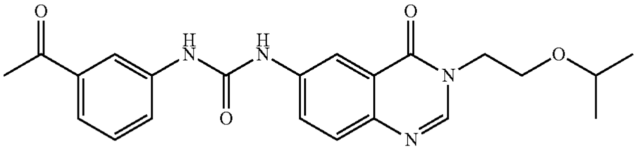
183

Scheme 32
1
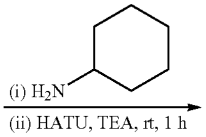
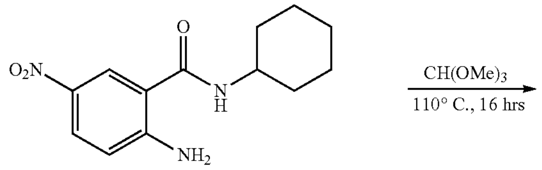
184
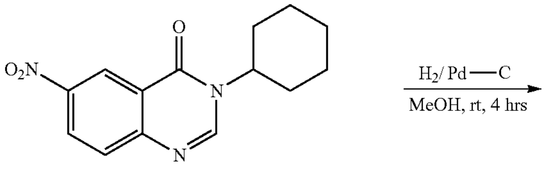
185
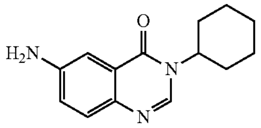
186
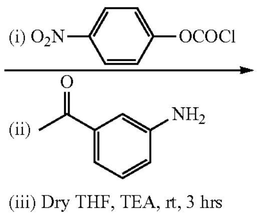
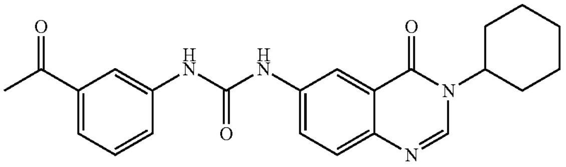
187
Scheme 33
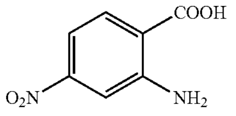
188
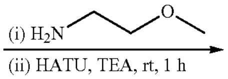
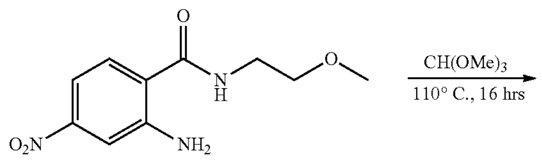
189
-continued
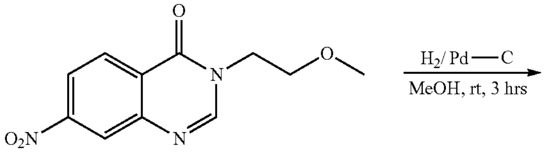
190
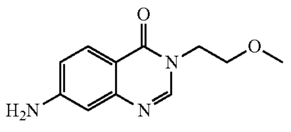
191
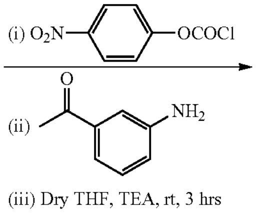
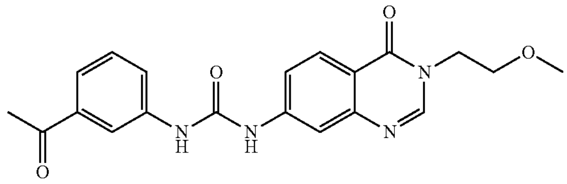
192
191
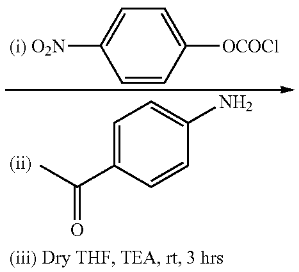
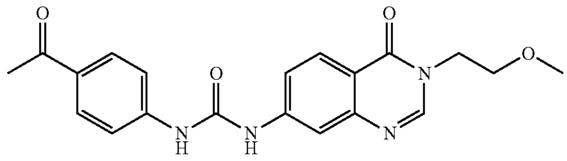
193
191
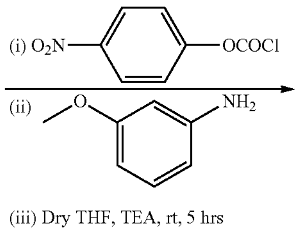
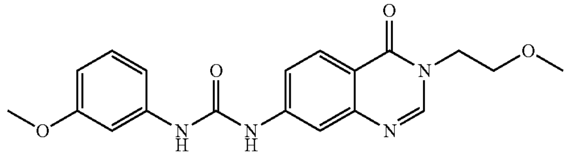
194

-continued
191 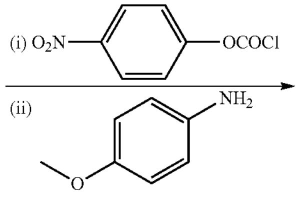
(iii) Dry THF, TEA, rt, 5 hrs
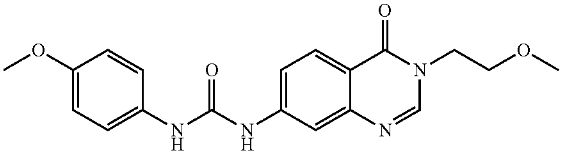
195
191 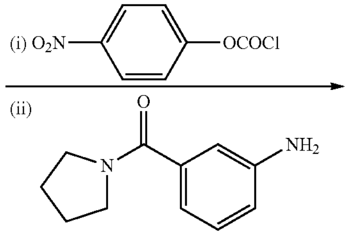
(iii) Dry THF, TEA, rt, 8 hrs
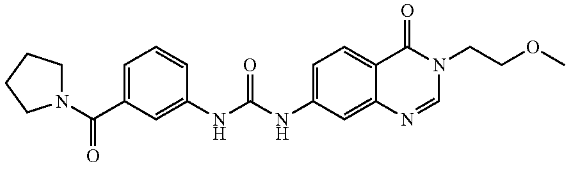
196
191 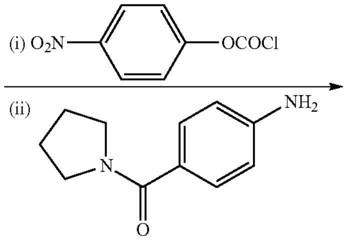
(iii) Dry THF, TEA, rt, 8 hrs
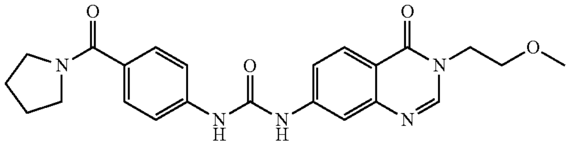
197
191 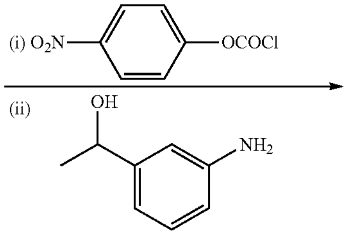
(iii) Dry THF, TEA, rt, 7 hrs
-continued
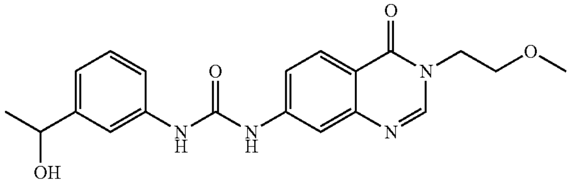
198
191 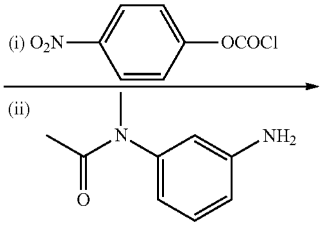
(iii) Dry THF, TEA, rt, 8 hrs
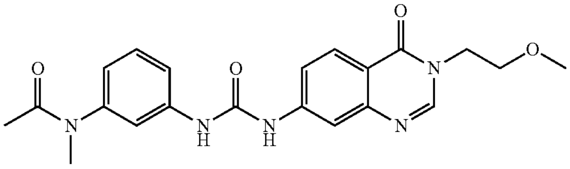
199
Scheme 34
2 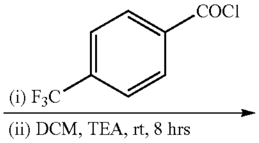
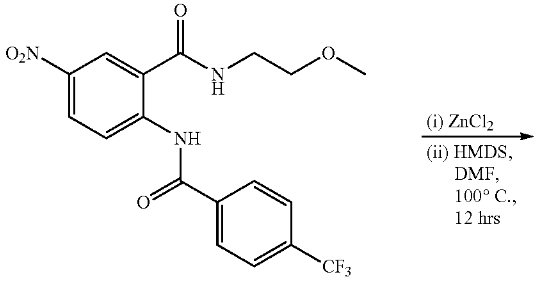
200
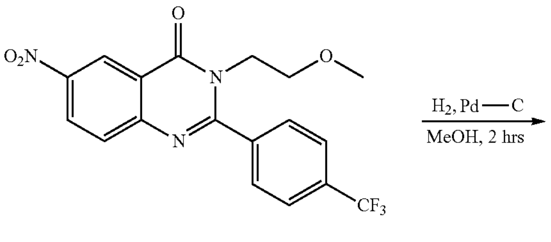
201

-continued
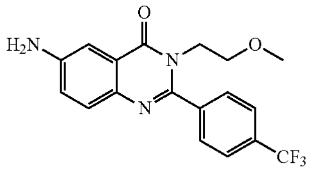
202
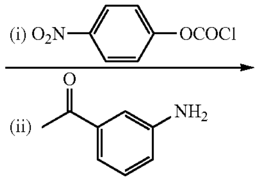
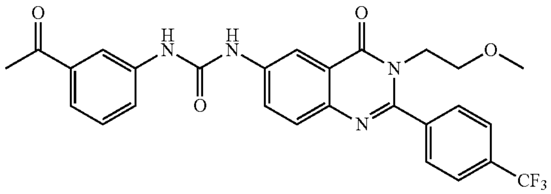
203
Scheme 35
2
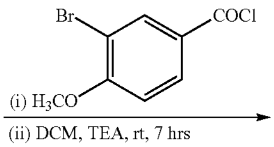
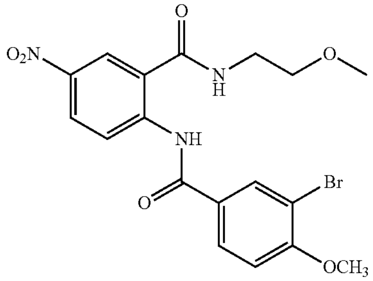
204
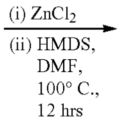
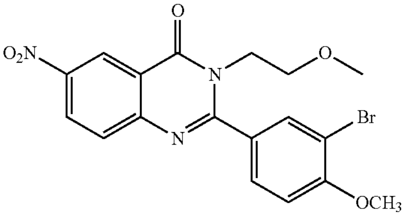
205
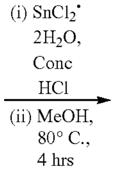
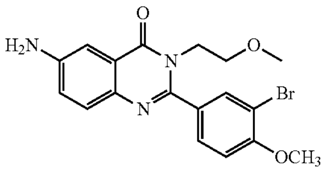
206
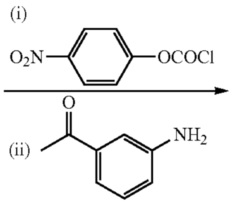
-continued
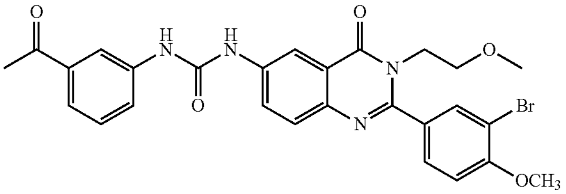
207
Scheme 36
2
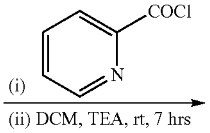
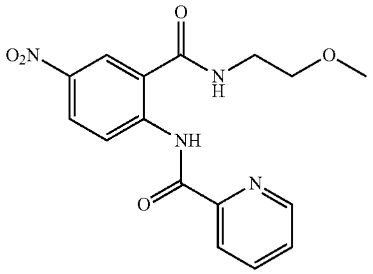
208
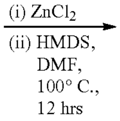
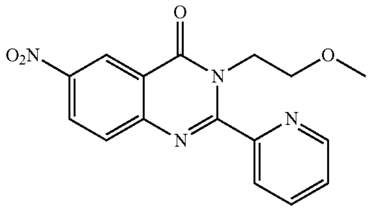
209
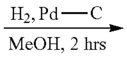
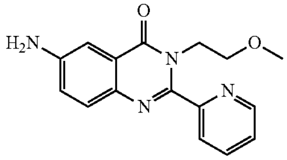
210
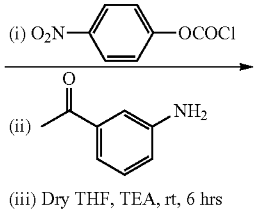
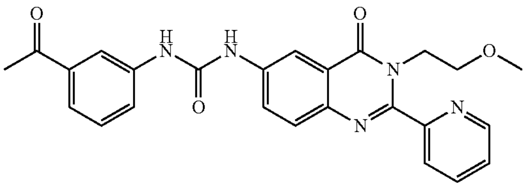
211

Scheme 37
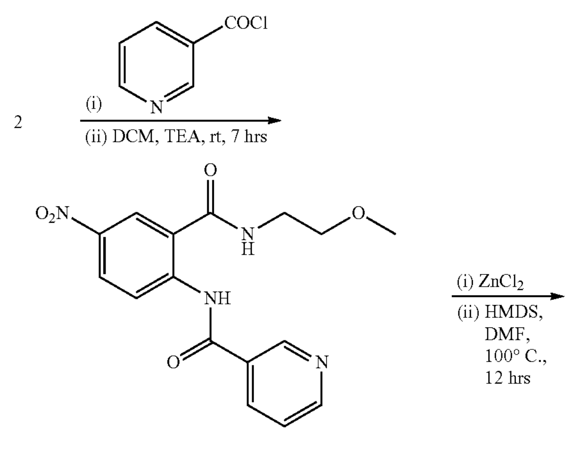
212
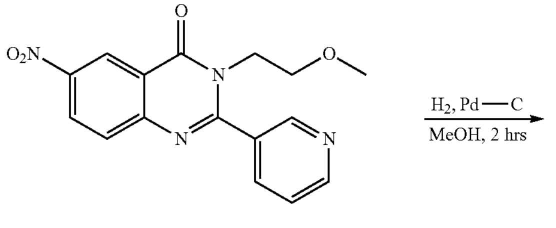
213
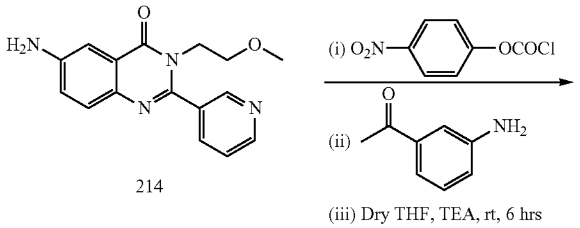
214
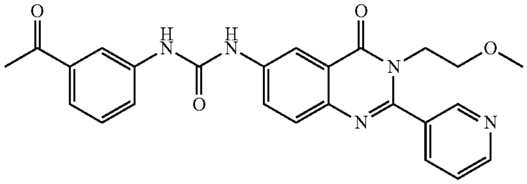
215
Scheme 38
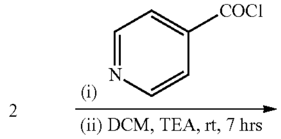
-continued
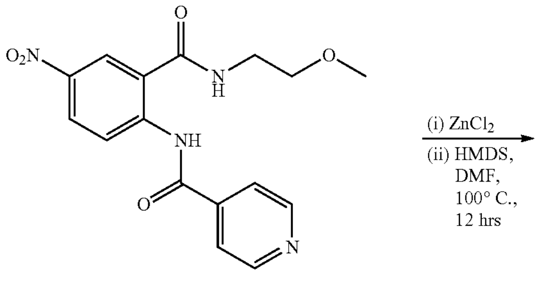
216
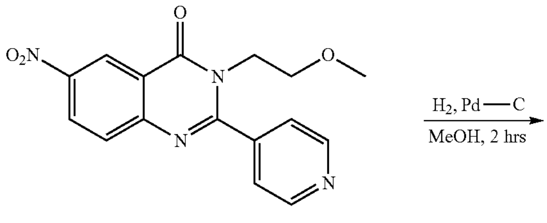
217
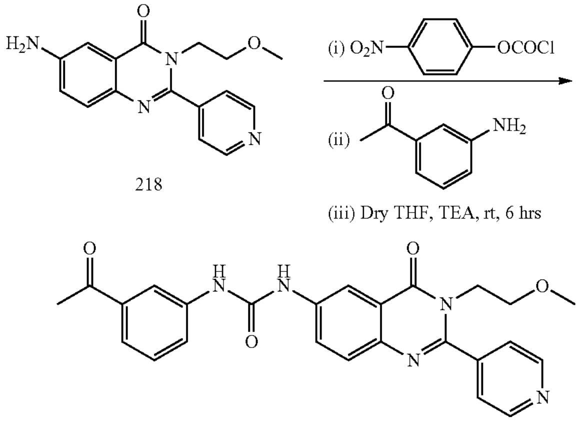
218
219
Scheme 39
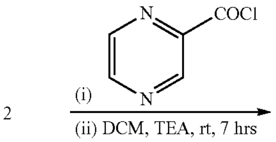
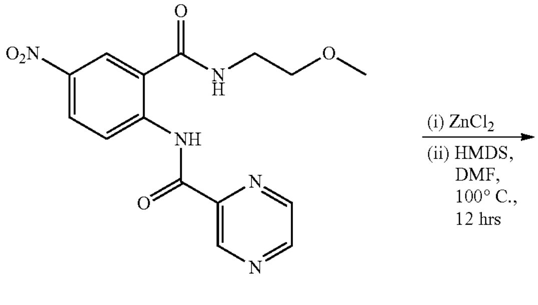
220

-continued
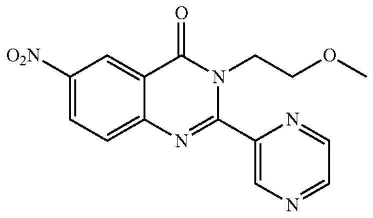
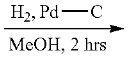
221
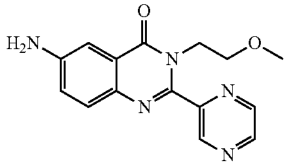
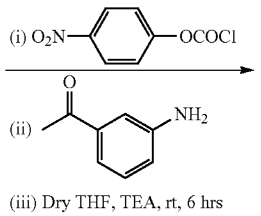
222
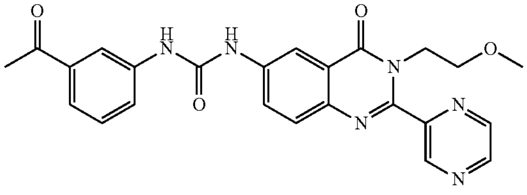
223
Scheme 40
2
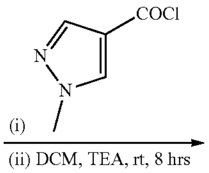
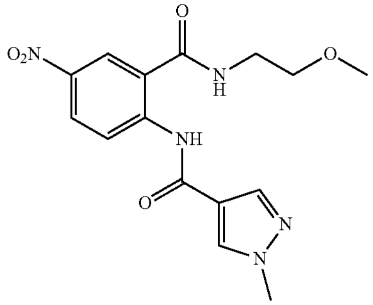
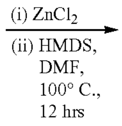
224
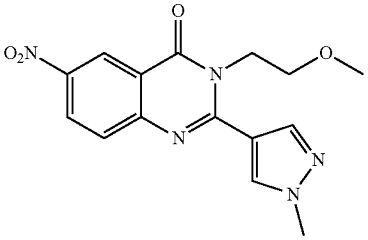
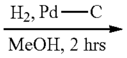
225
-continued
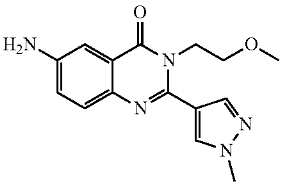
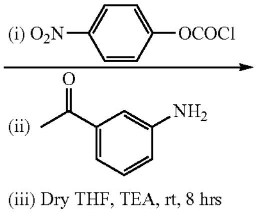
226
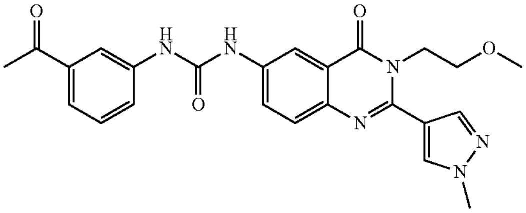
227
Scheme 41
2
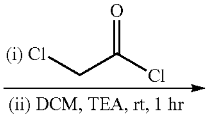
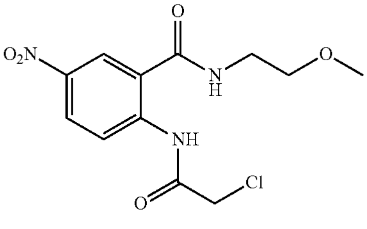
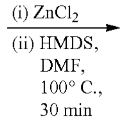
228
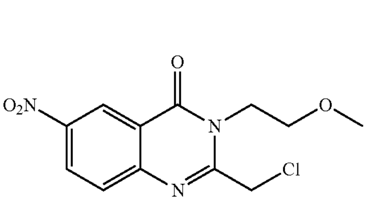
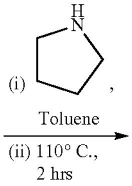
229
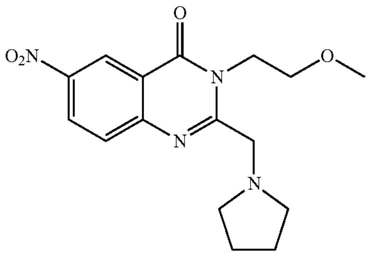
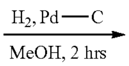
230

-continued
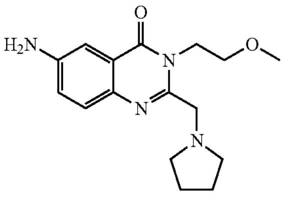
231
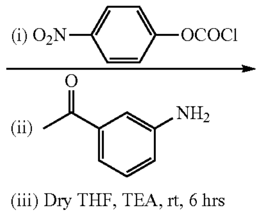
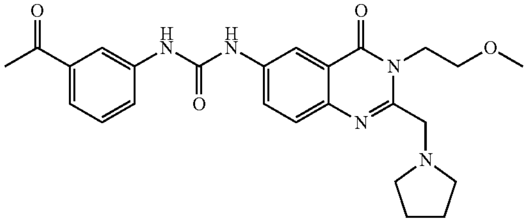
232
Scheme 42
229
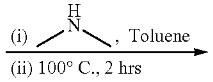
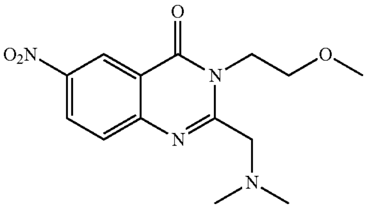
233
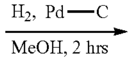
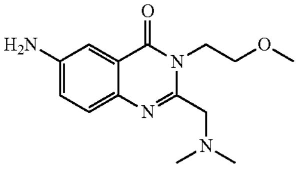
234
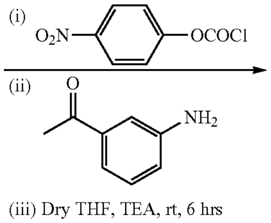
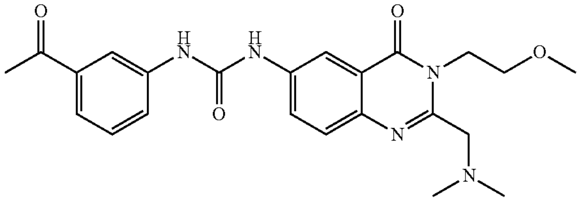
235
Scheme 43
229
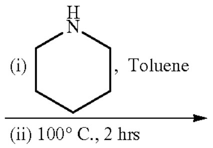
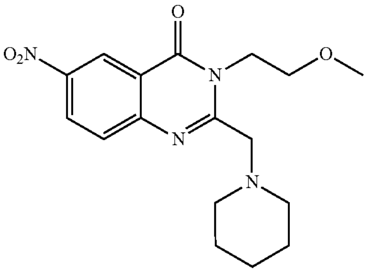
236
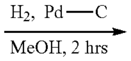
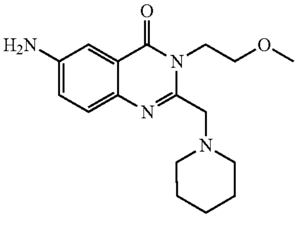
237
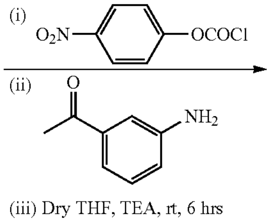
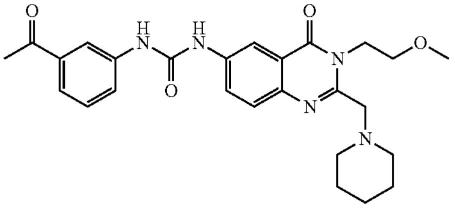
238
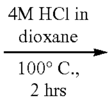
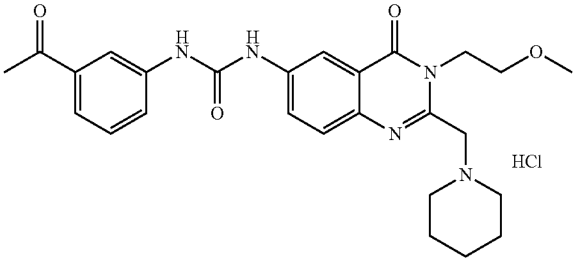
238a
229
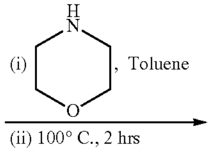

-continued
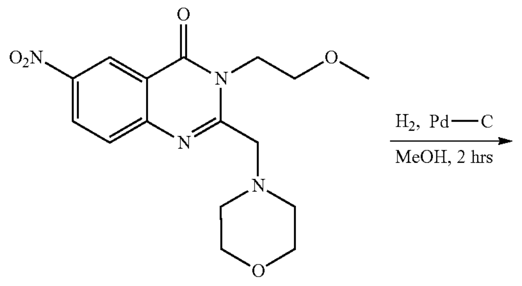
239
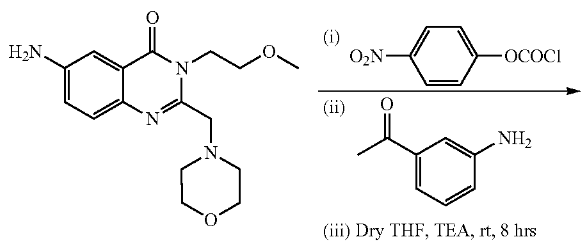
240
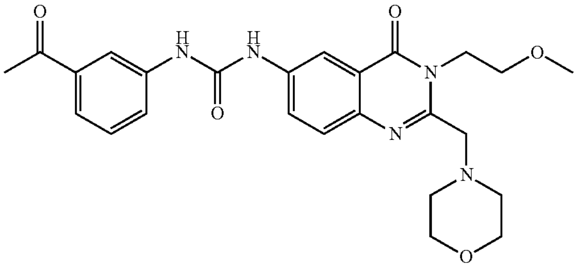
241
Scheme 45
229
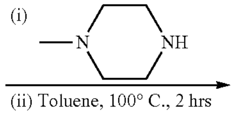
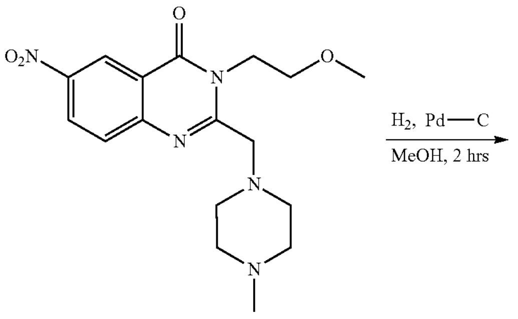
242
-continued
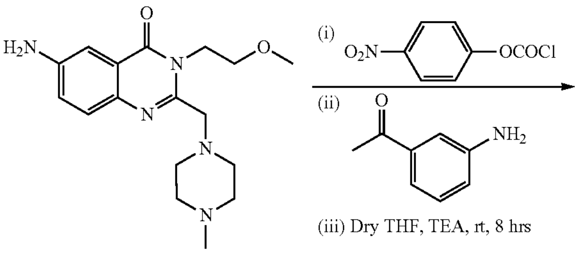
243
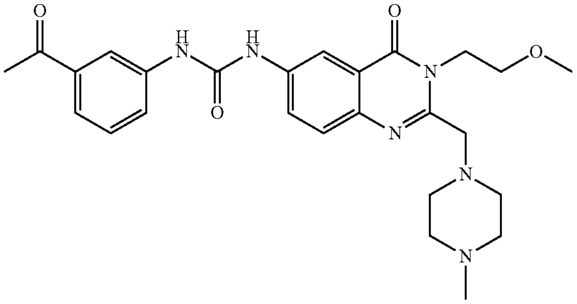
244
Scheme 46
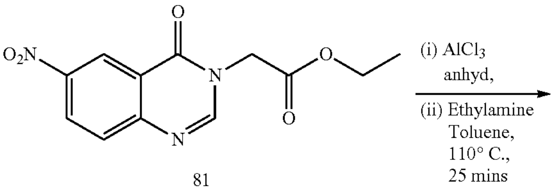
81
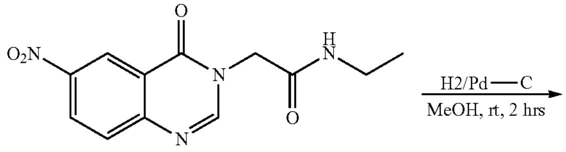
245
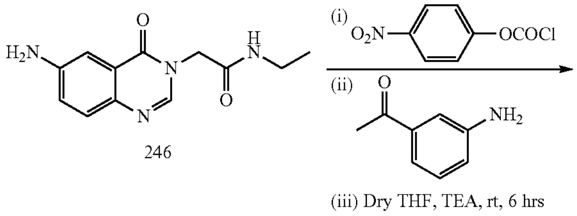
246
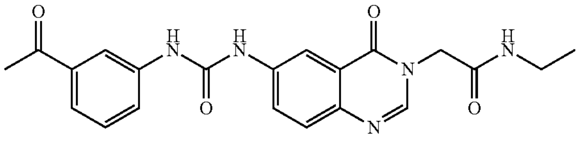
247

Scheme 47
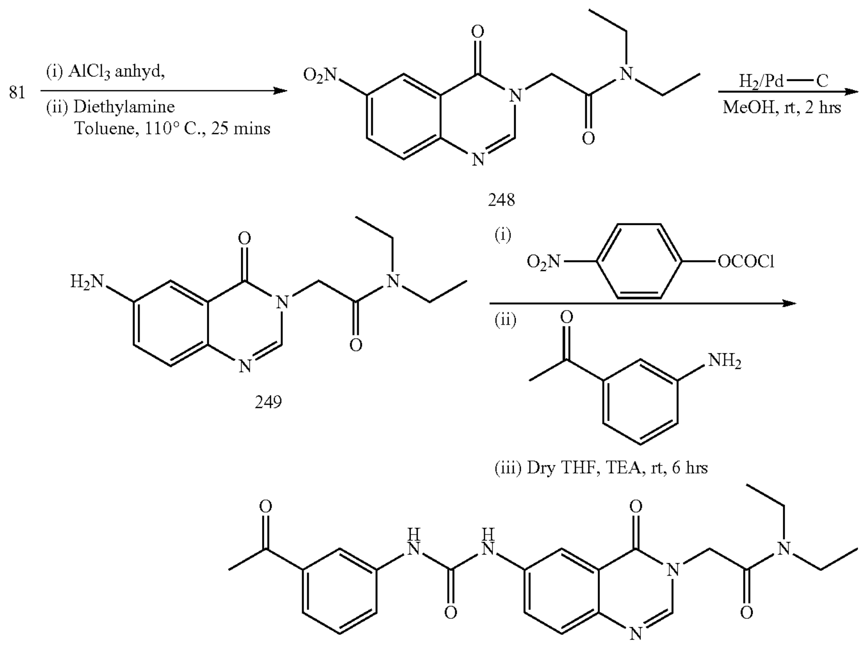
250
Scheme 48
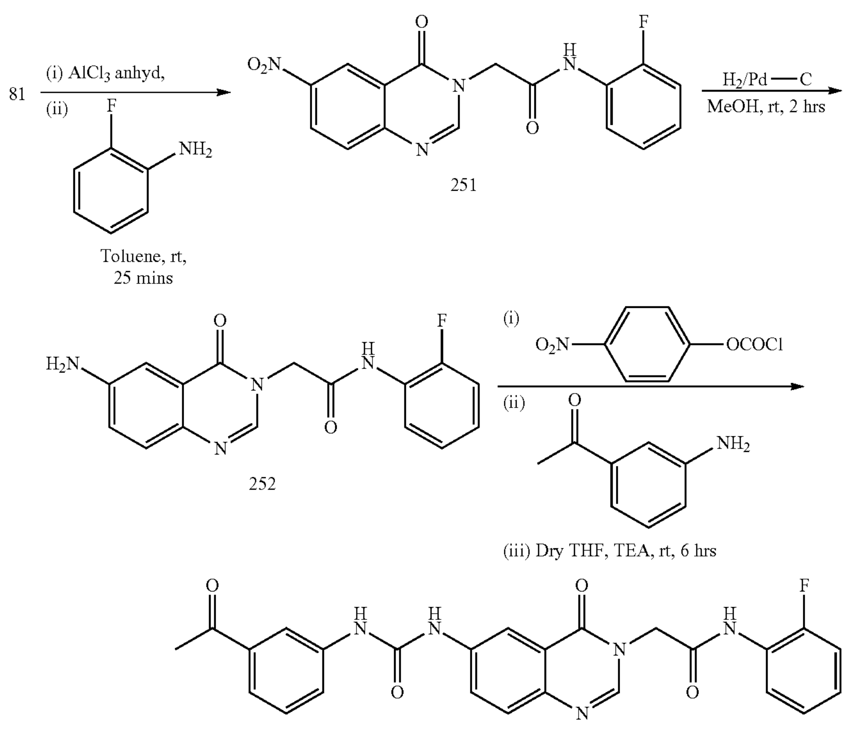
253

Scheme 49
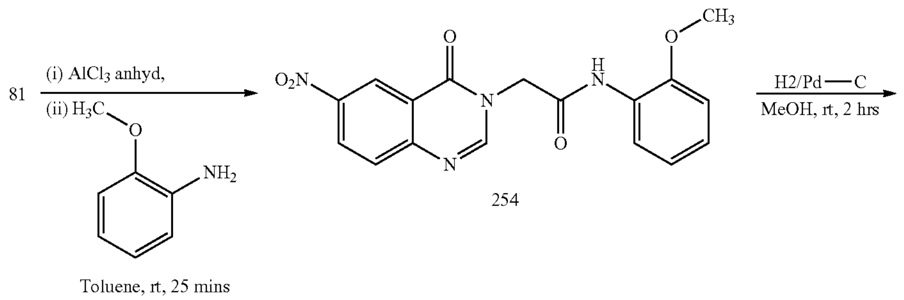
254
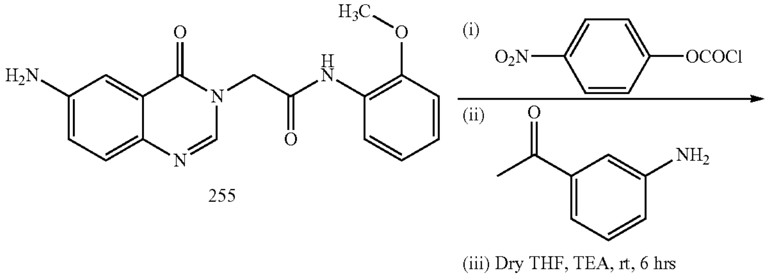
255
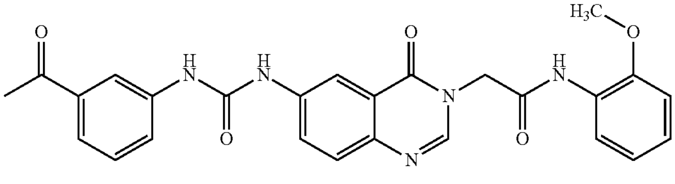
256
Scheme 50
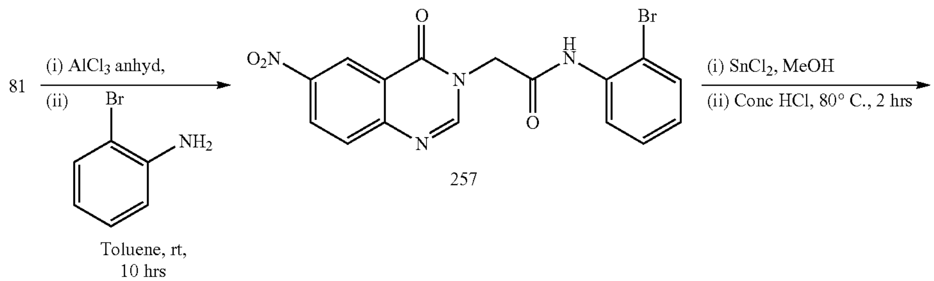
257
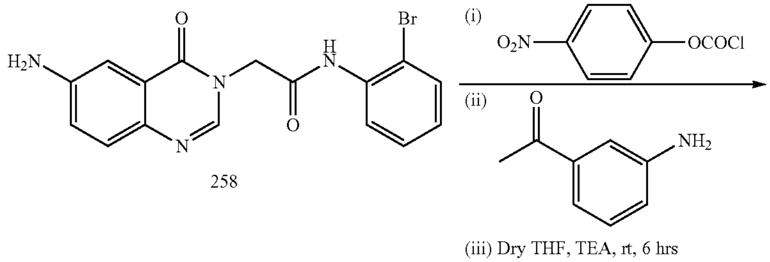
258

-continued
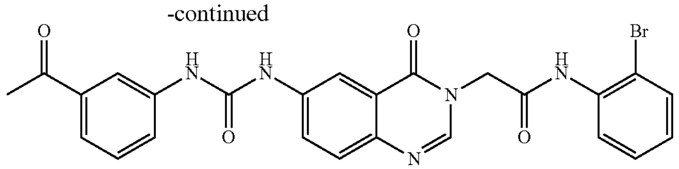
259
Scheme 51
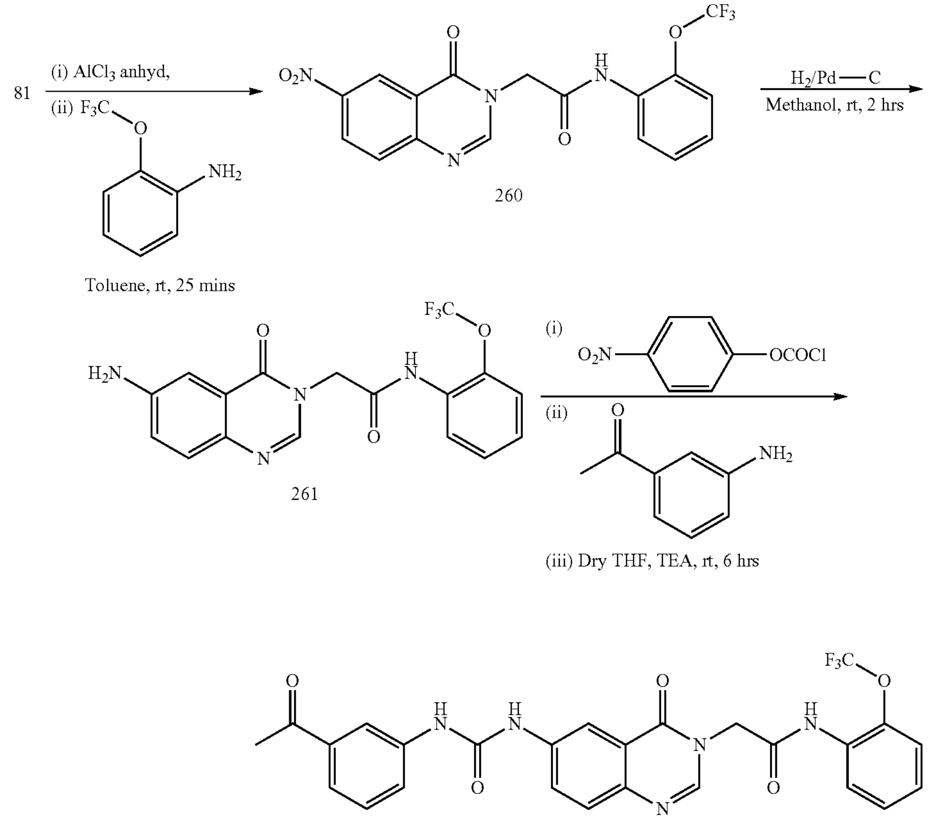
260
261
262
Scheme 52
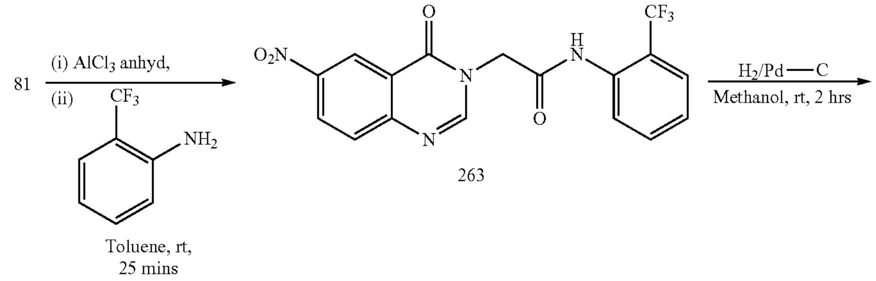
263

-continued
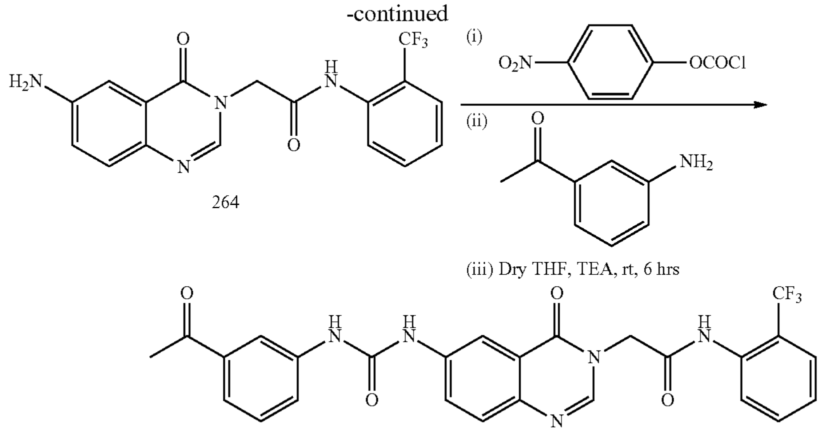
264
265
Scheme 53
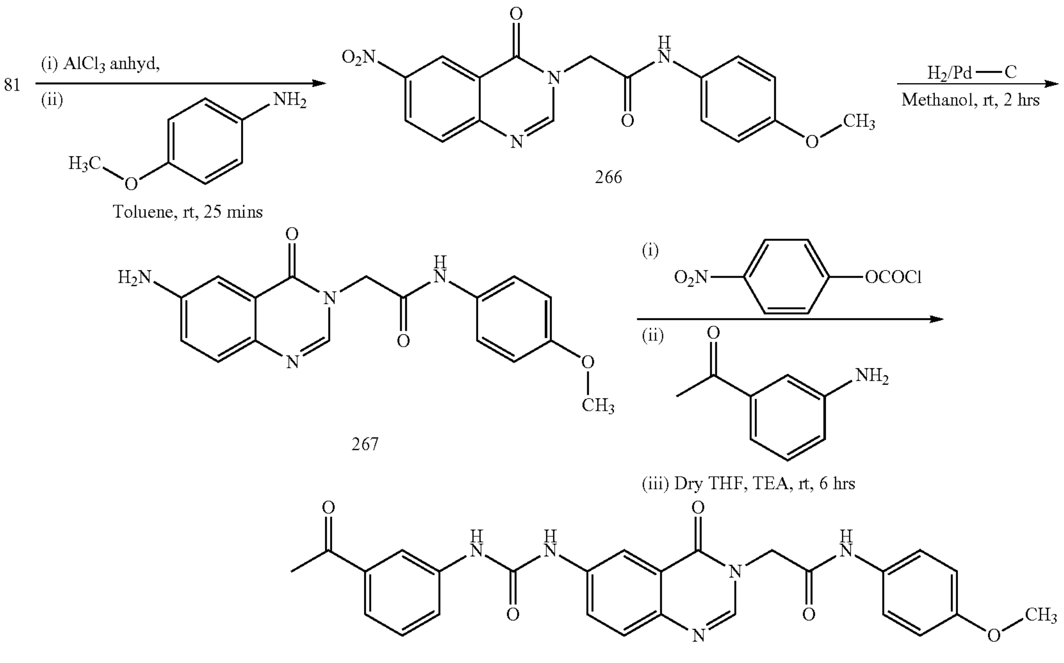
266
267
268
Scheme 54
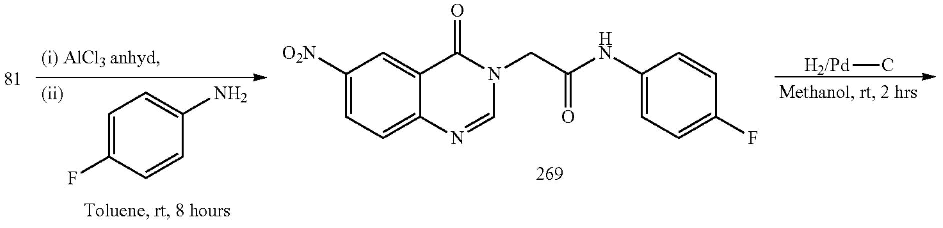
269

-continued
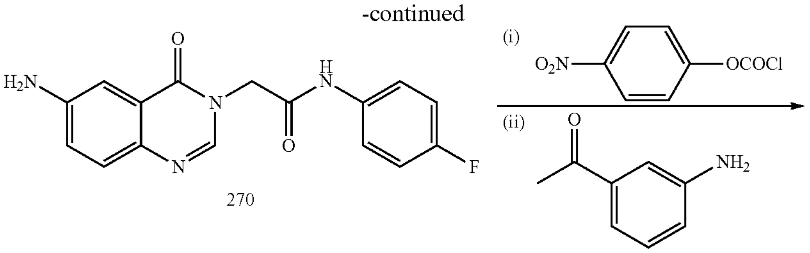
270
(iii) Dry THF, TEA, rt, 6 hrs
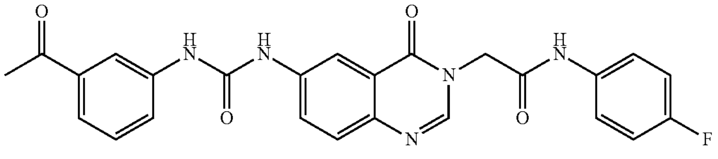
271
Scheme 55
81
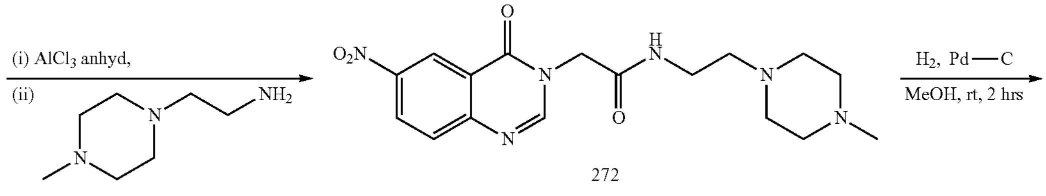
272
Toluene, 110° C., 25 mins
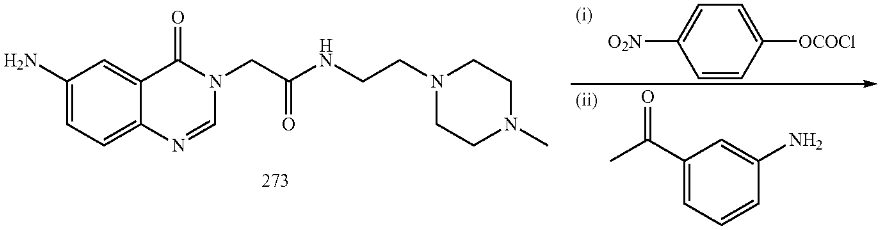
273
(iii) Dry THF, TEA, rt, 6 hrs
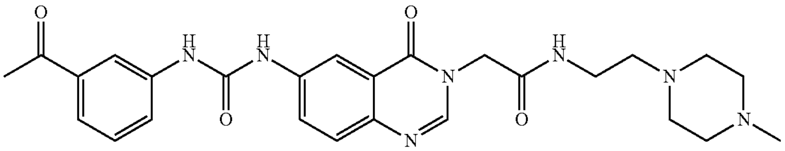
274
Scheme 56
81
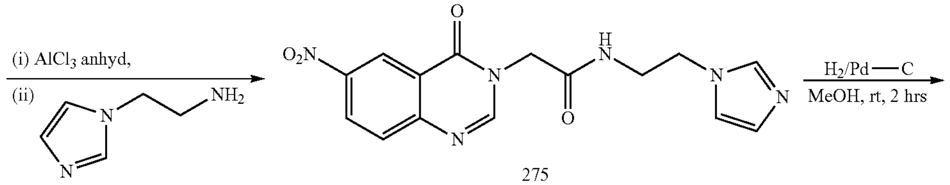
275
Toluene, 110° C., 25 mins -continued
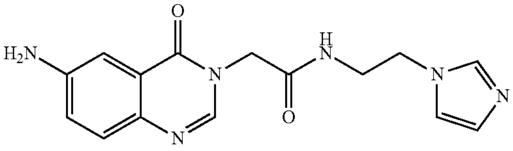
276
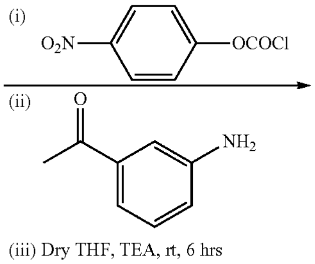
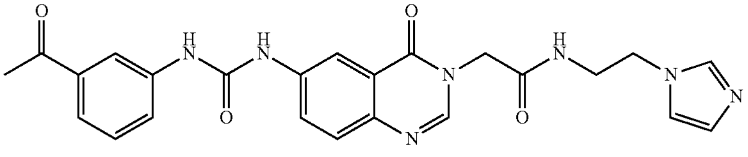
277
Scheme 57
168 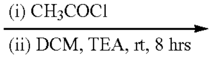
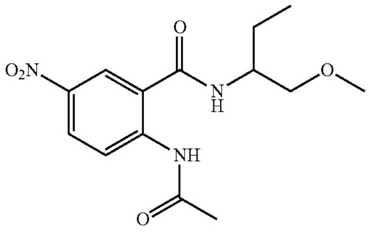
278
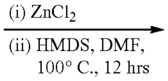
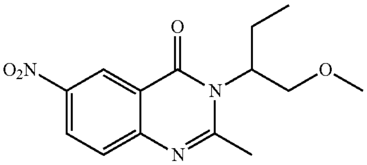
279
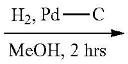
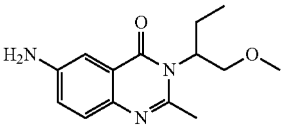
280
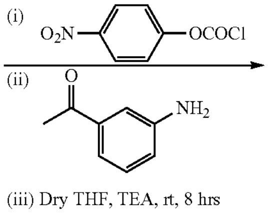
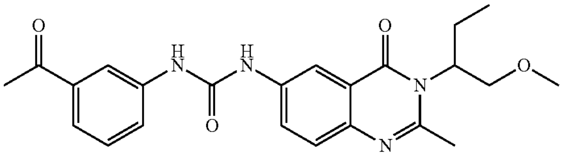
281
Scheme 58
176 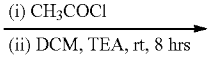
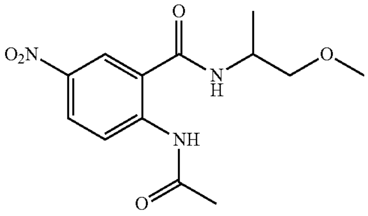
282
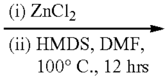
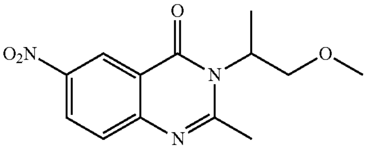
283
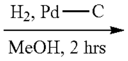
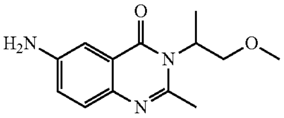
284
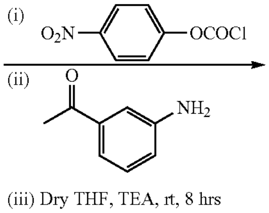
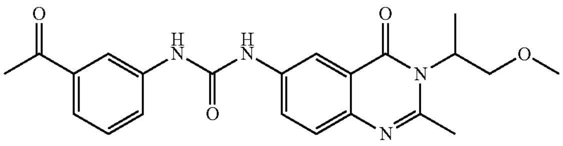
285

Scheme 59
176 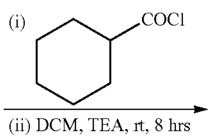
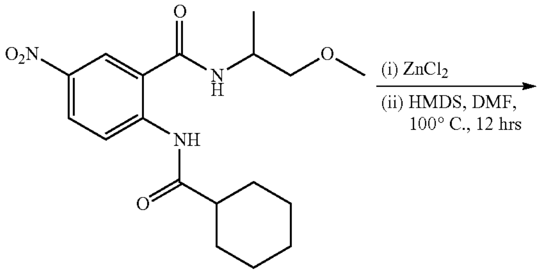
286
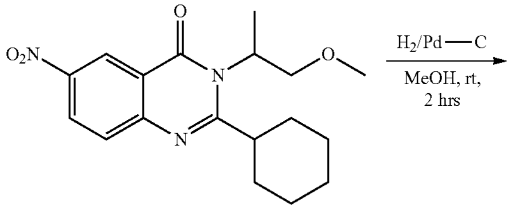
287
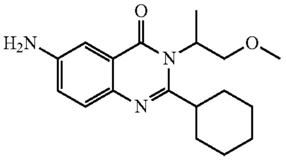
288
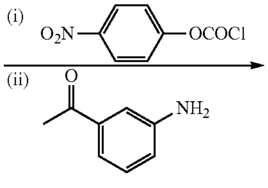
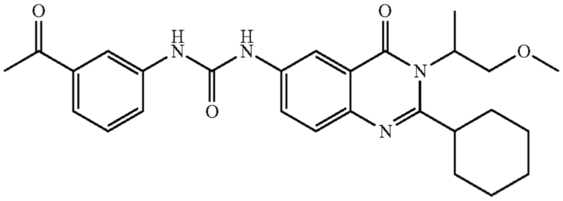
289
Scheme 60
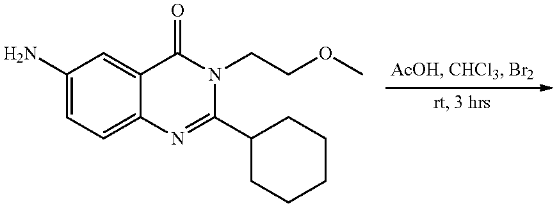
122
-continued
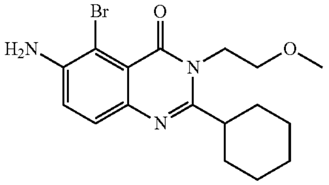
290
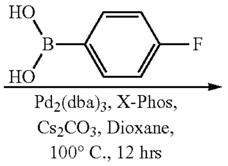
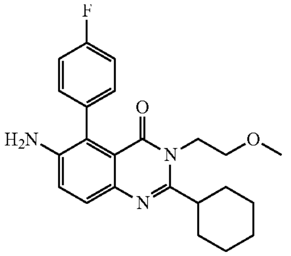
291
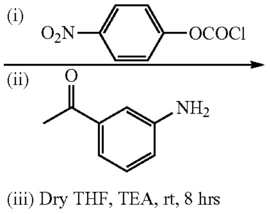
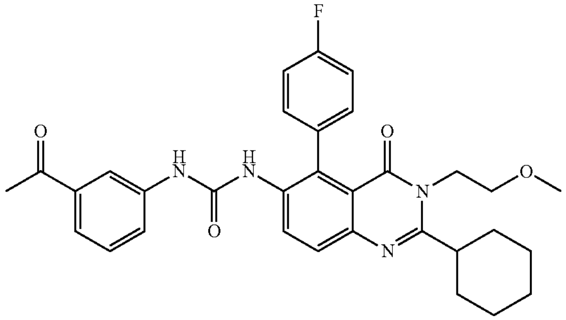
292
Scheme 61
178 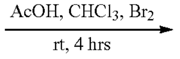
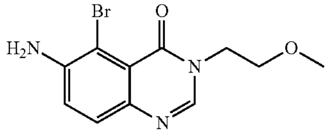
293
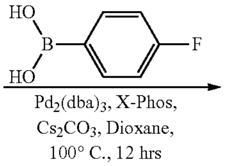
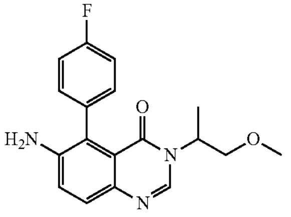
294
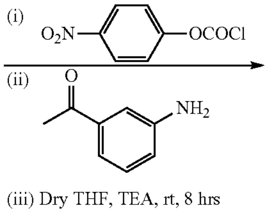

-continued
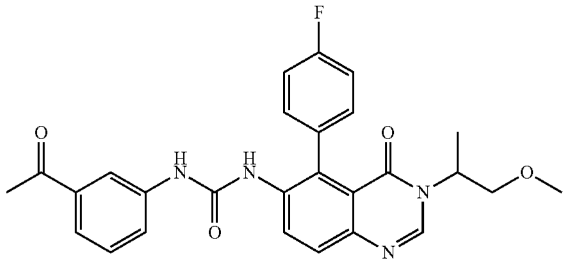
295
Scheme 62
2
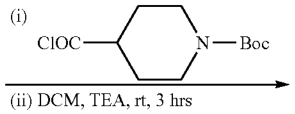
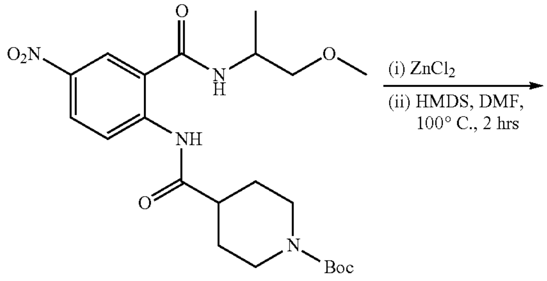
296
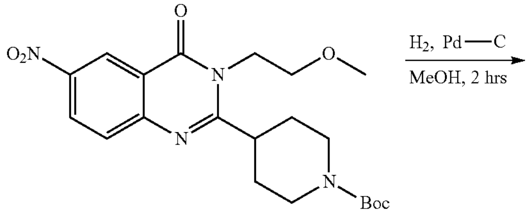
297
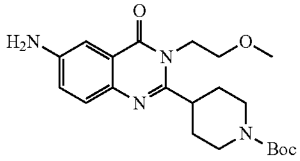
298
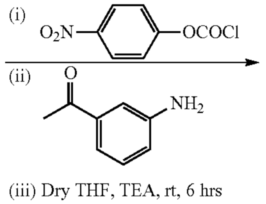
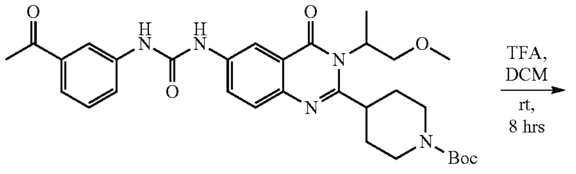
299
-continued
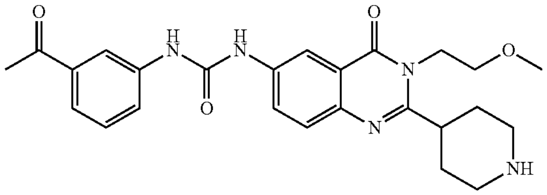
300
Scheme 63
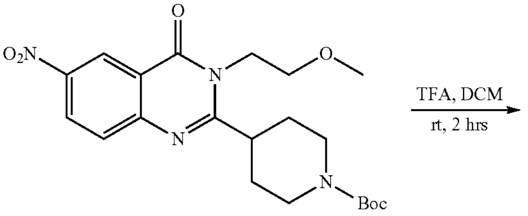
297
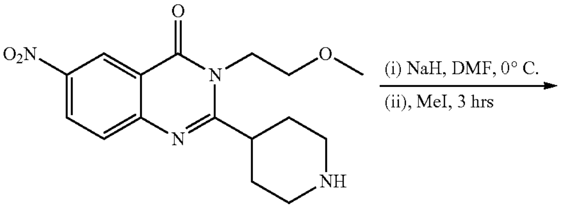
301
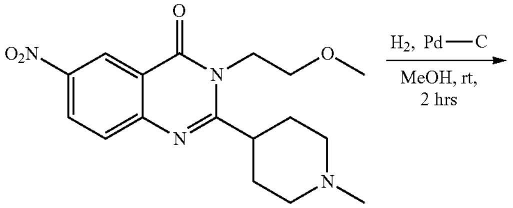
302
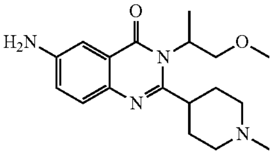
303
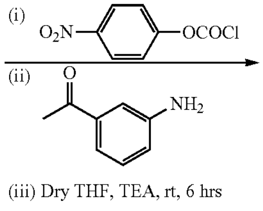
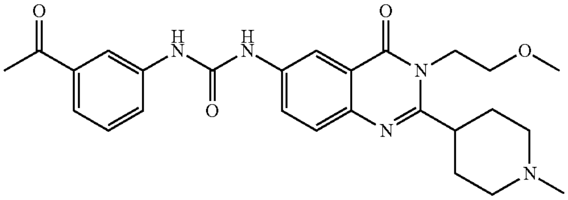
304

Scheme 64
301
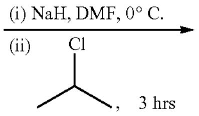
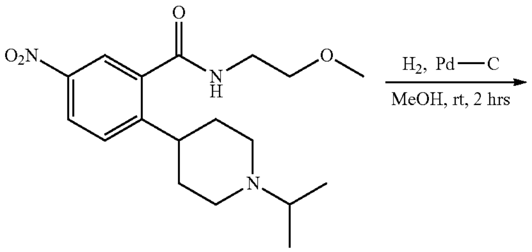
305
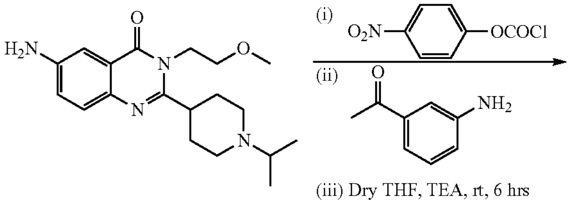
306
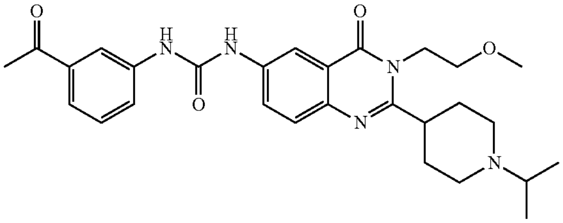
307
Scheme 65
4
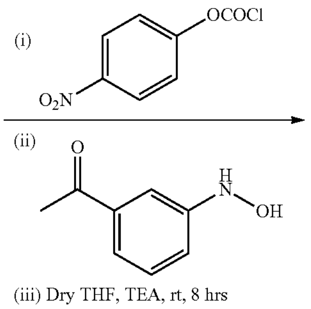
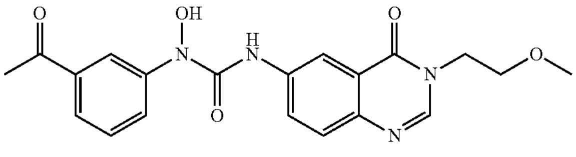
308
-continued
4
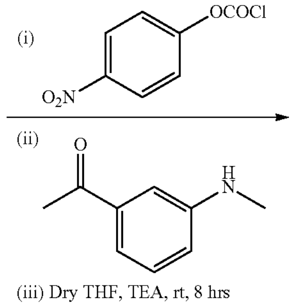
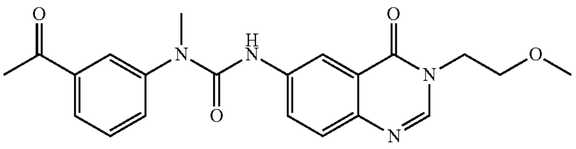
309
46
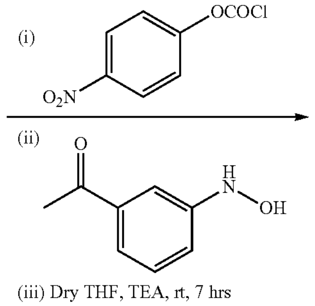
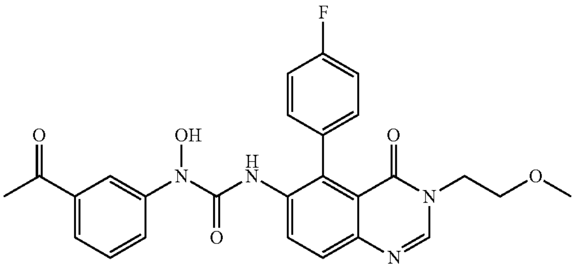
310
46
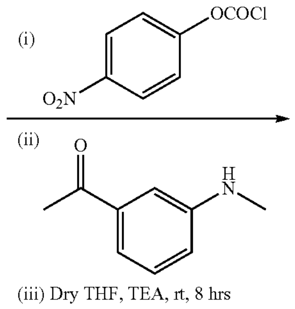
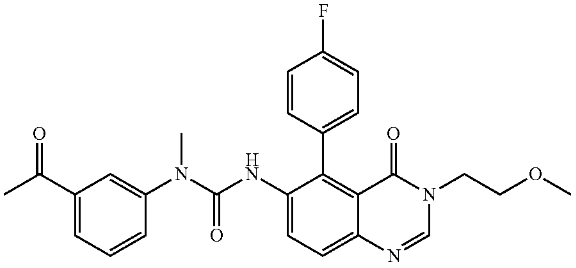
311

-continued
237
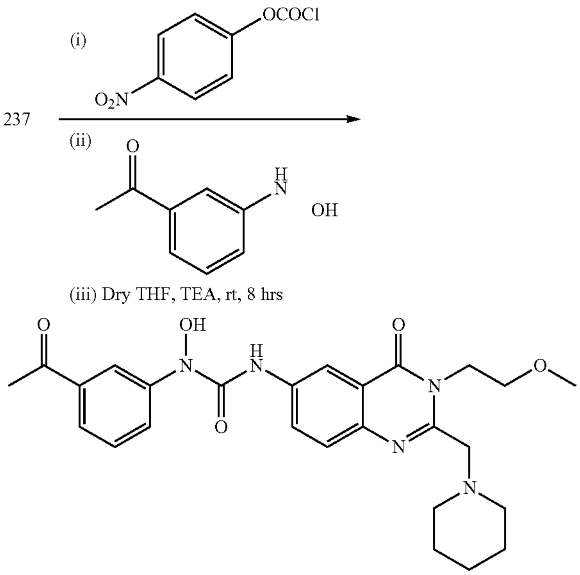
312
237
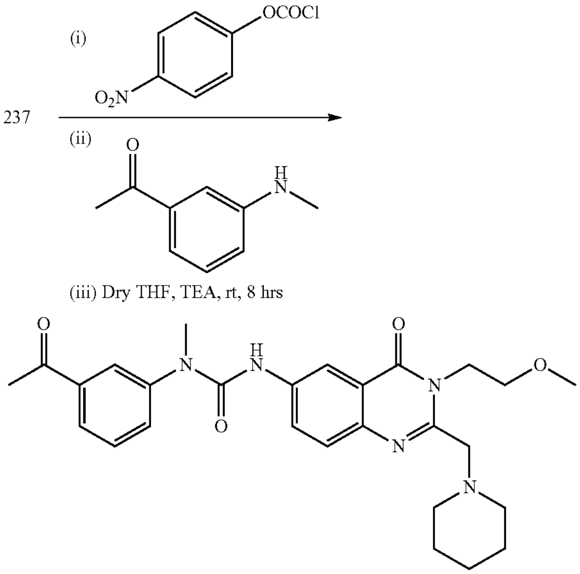
313
252
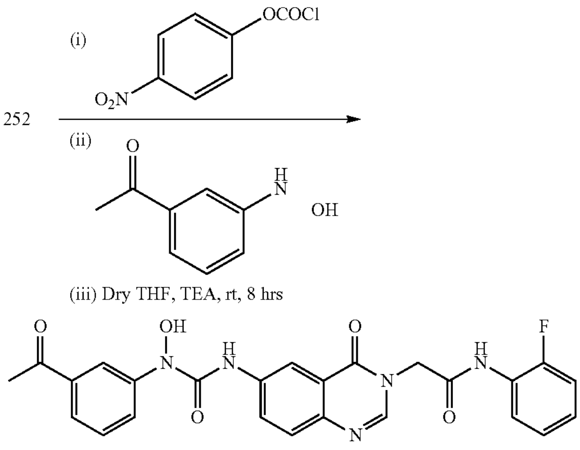
314
-continued
252
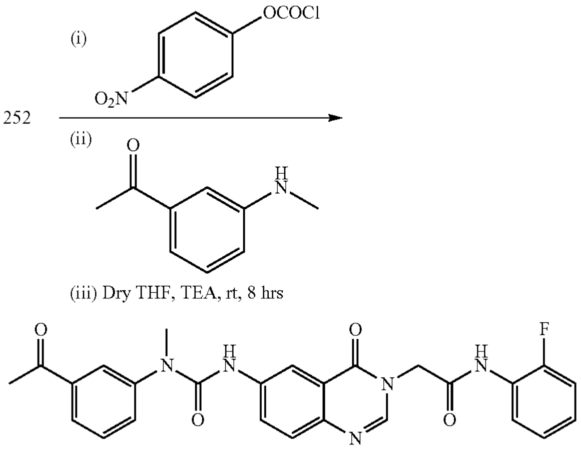
315
Scheme 66
4
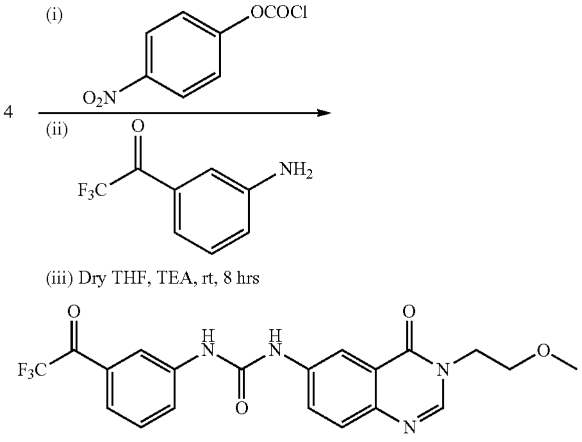
316
106
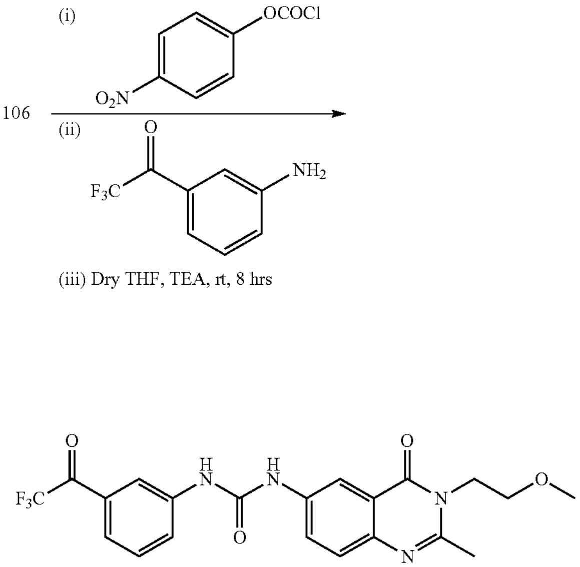
317

-continued
237
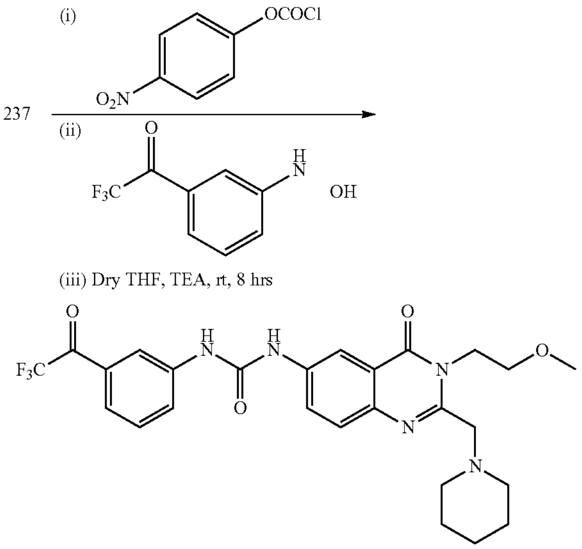
318
243
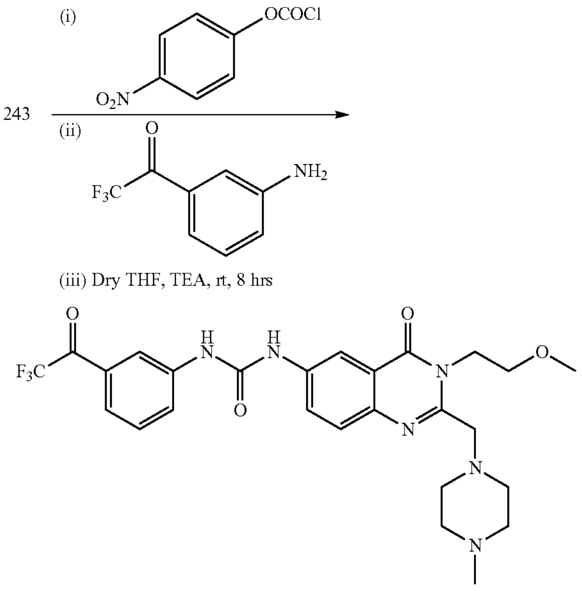
319
252
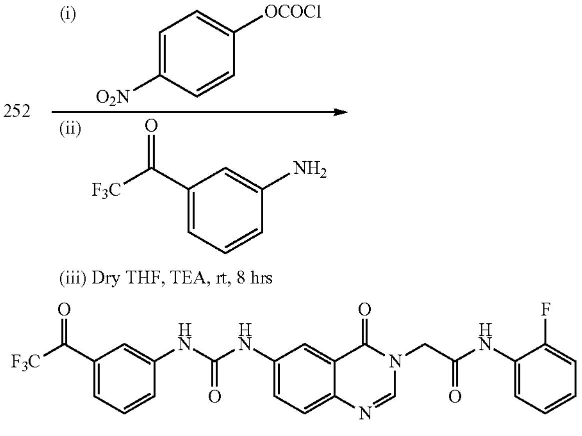
320
Scheme 67
4
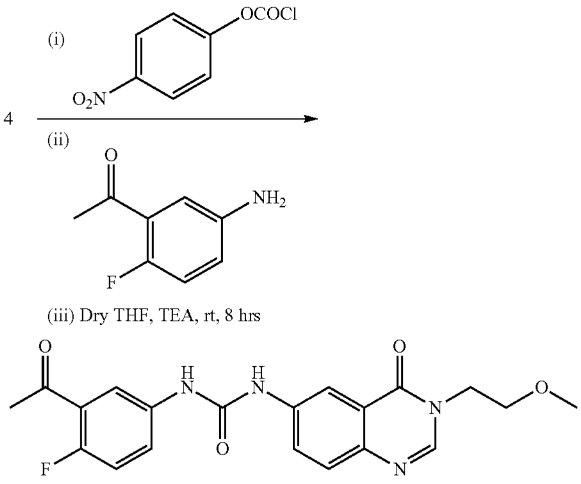
321
106
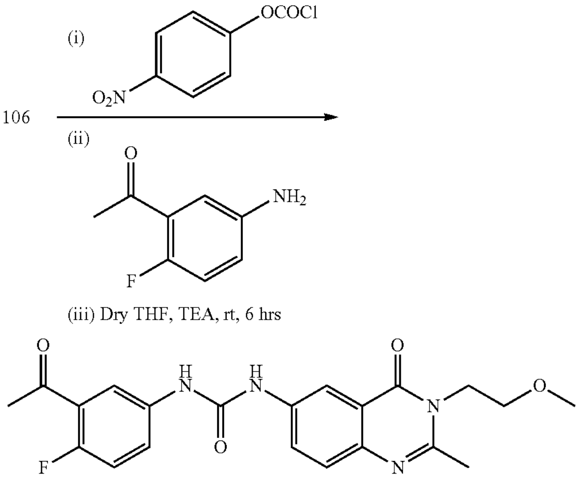
322
237
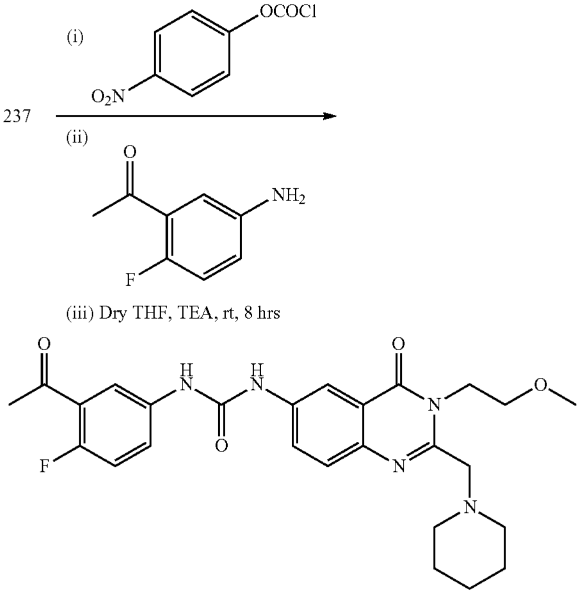
323

-continued
243
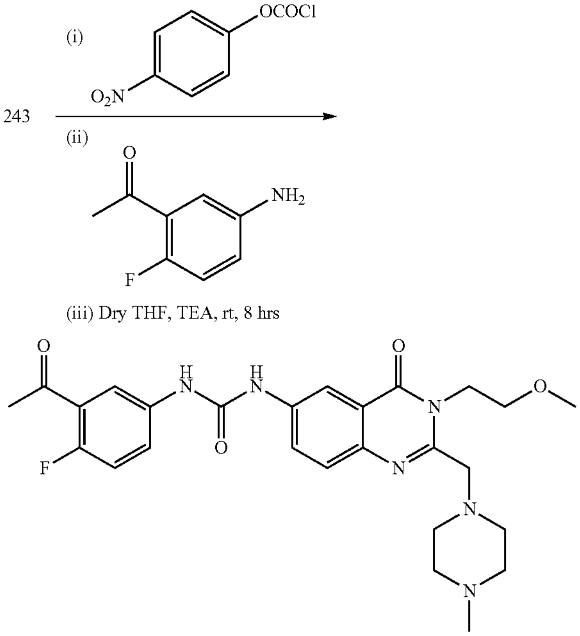
324
252
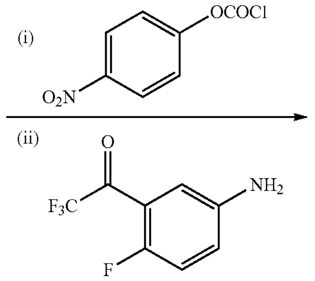
(iii) Dry THF, TEA, rt, 7 hrs
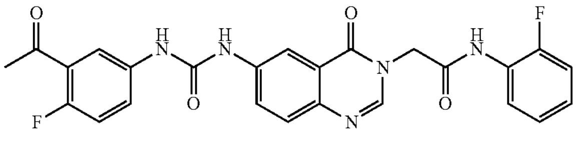
325
Scheme 68
2
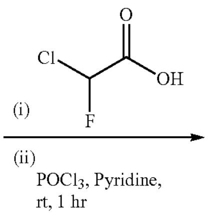
-continued
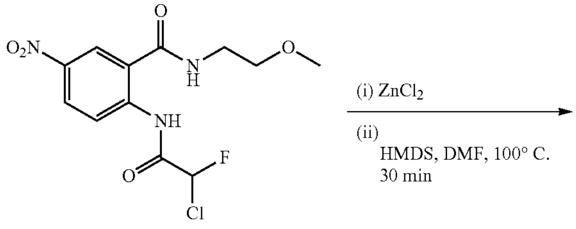
326
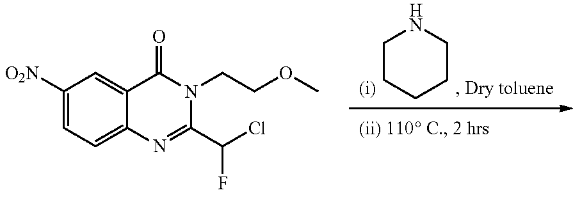
327
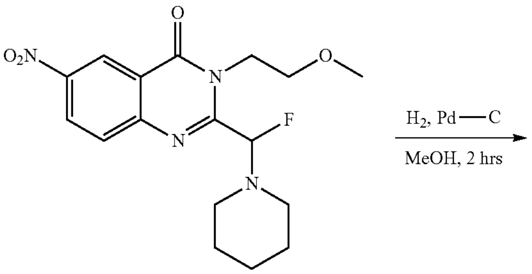
328
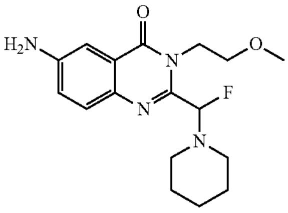
329
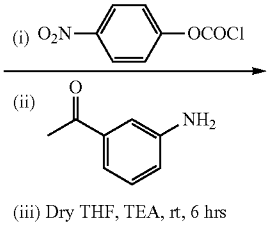
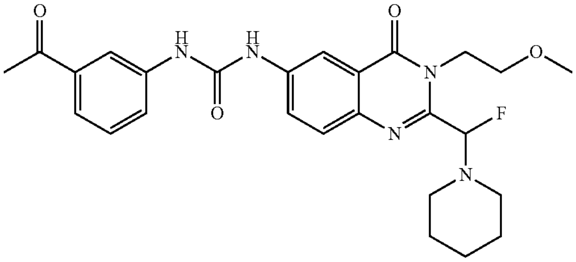
330
2
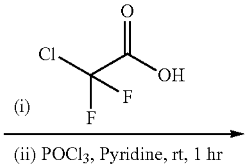

-continued
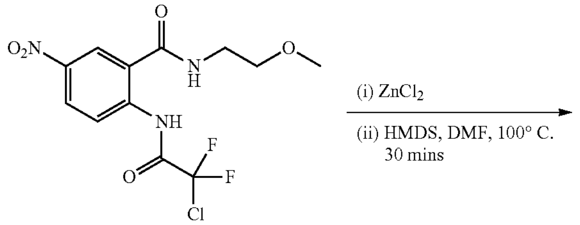
326 a
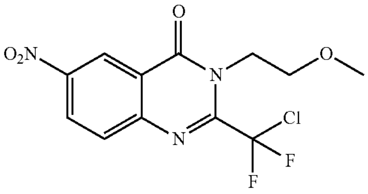
327 a
327 a
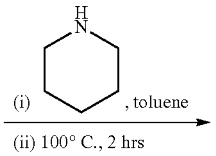
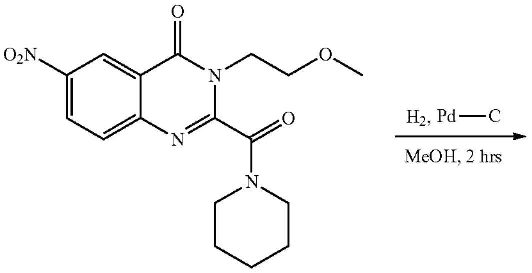
328 a
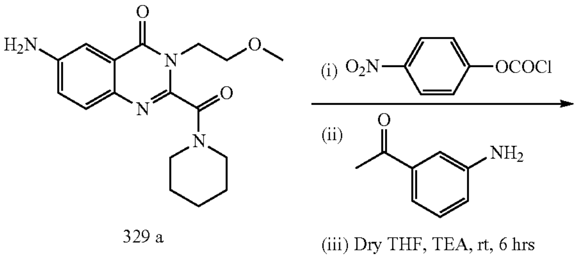
329 a
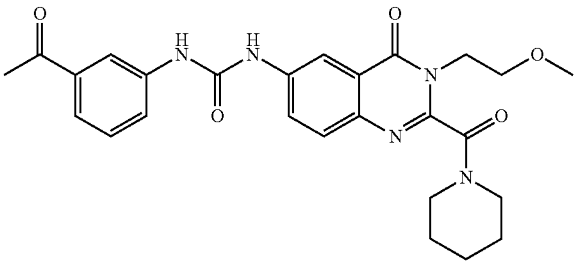
330 a
Scheme 69
327
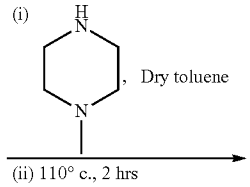
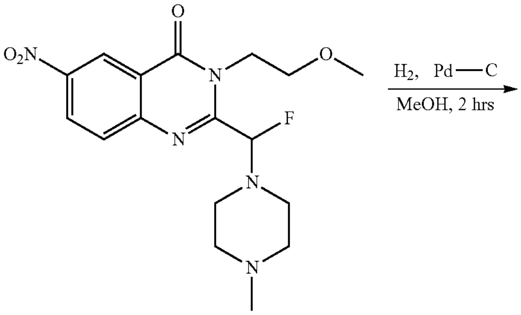
331
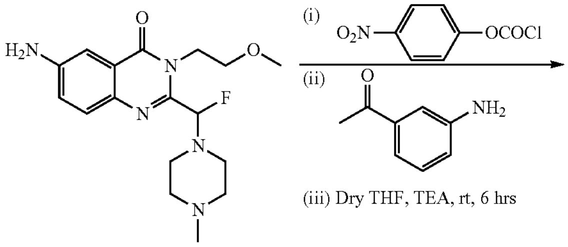
332
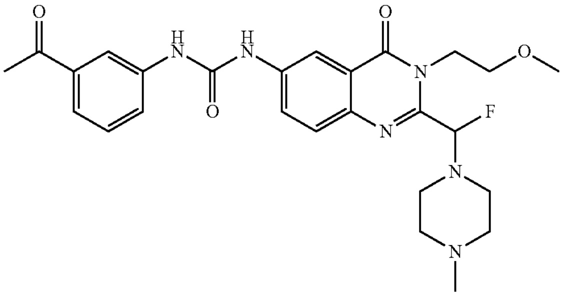
333
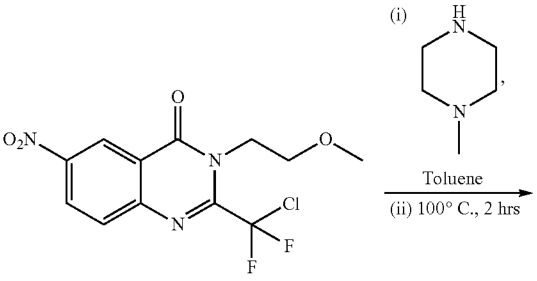
327a -continued
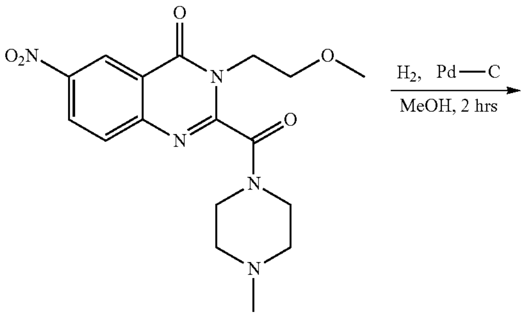
331 a
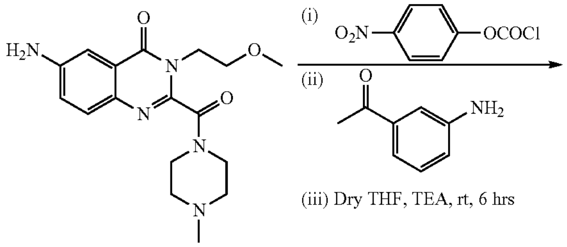
332 a
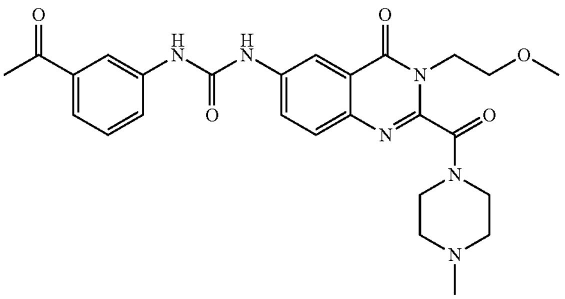
333 a
Scheme 70
327
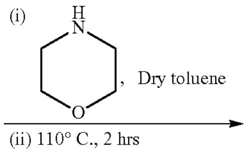
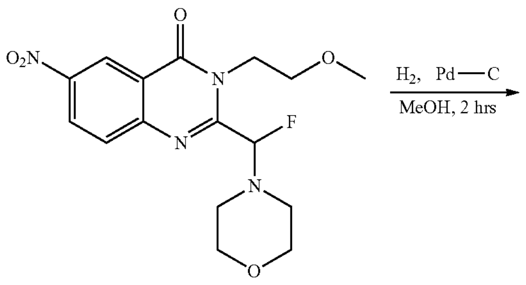
334
-continued
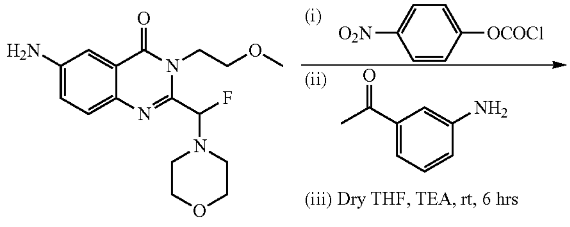
335
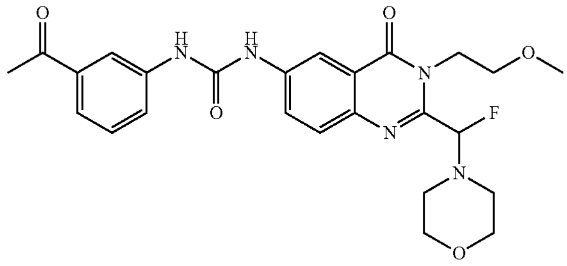
336
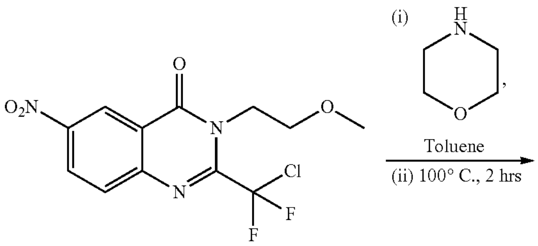
327a
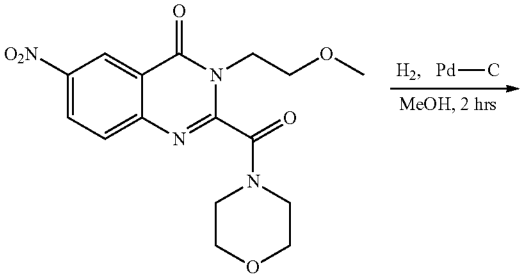
334 a
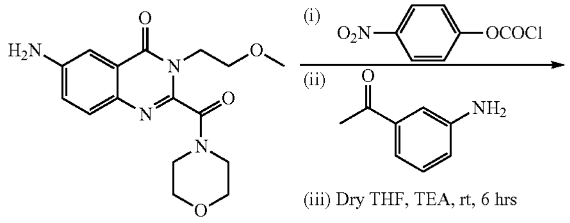
335 a -continued

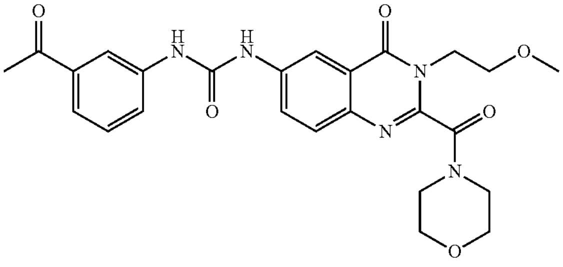

336 a

Scheme 71

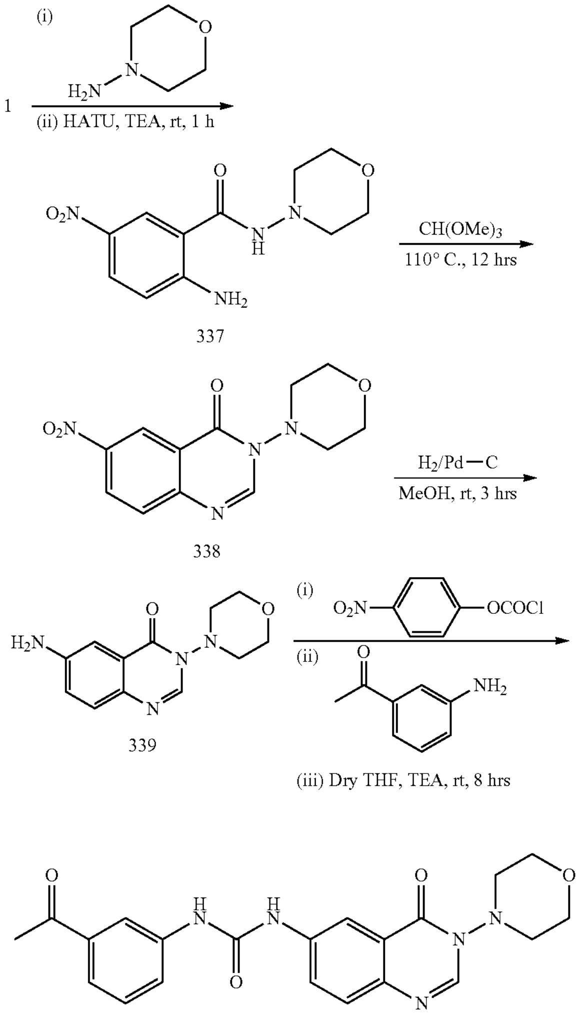

337

338

339

340

Scheme 72

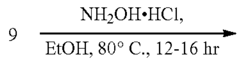

-continued

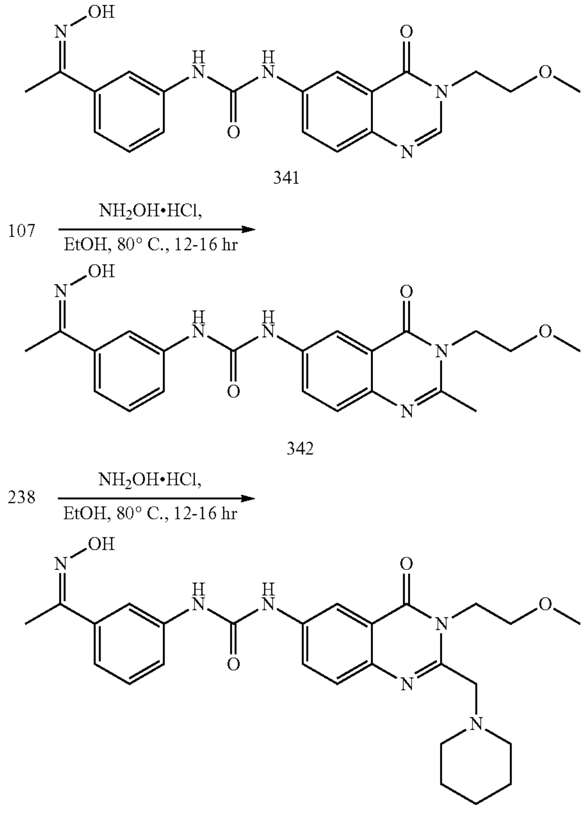

341

342

343

Scheme 73

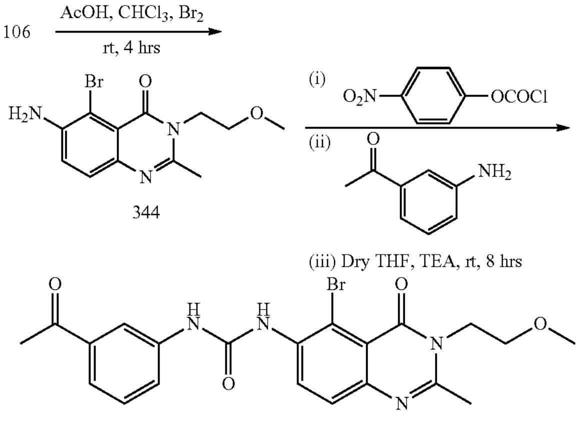

344

345

In an embodiment of the present disclosure, there is provided a compound having Structure I for use in treating diseases and disorders related to modulation of COP1 enzyme through its stabilization or modulation of ATGL.

In another embodiment of the present disclosure, there is provided a compound having Structure I for use in decreasing the level of triglycerides in hepatocytes.

In yet another embodiment of the present disclosure, there is provided a compound having Structure I for use in treatment of disease selected from Non-Alcoholic Fatty Liver Disease (NAFLD) or Non-Alcoholic Steatohepatitis (NASH).

In still another embodiment of the present disclosure, there is provided a composition comprising the compound having Structure I along with pharmaceutically acceptable excipients.

Another embodiment of the present disclosure provides a method of modulation COP1 enzyme through its stabilization by the compound having Structure I.

Yet another embodiment of the present disclosure provides a method of increasing the level of ATGL by the compound having Structure I.

EXAMPLES

Following examples are given by way of illustration and therefore should not be construed to limit the scope of the present disclosure.

Temperatures are given in degree Celsius. The structures of final products, intermediates and starting materials are confirmed by standard analytical methods, spectroscopic characterization e.g., MS, NMR. Abbreviations used are those conventional in the art.

All starting materials, reagents, catalysts, building blocks, acids, bases, dehydrating agents and solvents utilized to synthesize the compounds of the present disclosure are either commercially available or can be produced by known organic synthesis methods in the art.

Example 1

General Procedure A: Amide Formation Reaction

Suitable carboxylic acid (1 mmol) was taken in DMF (1-2 mL) and HATU (1-1.2 equivalent) was added followed by stirring for 15 min-1 hour to obtain a reaction mixture. Suitable substituted aliphatic or aromatic amine was added dropwise (1-1.5 equivalent) to the reaction mixture followed by TEA (2.5-3 equivalent) and the contents of the reaction mixture were stirred for another 45 min. Reaction was monitored by checking TLC. Upon completion, the reaction mixture was washed thoroughly with ice cold water to remove DMF and extracted with EtOAc. Column chromatography was performed to get the pure product.

Example 2

General Procedure B: Cyclization Using Trimethylorthoformate

An amide compound (1 mmol) prepared by general procedure A provided in Example 1 was taken in trimethylorthoformate (TMOF) (5-10 equivalent) and heated at 110° C. for 12-18 hrs. Reaction was monitored by checking TLC. Upon completion, the reaction mixture was evaporated in vacuum to remove excess TMOF and washed with water followed by extraction with EtOAc. Column chromatography was performed to get the pure product.

Example 3

General Procedure C: Reduction

A compound prepared by general procedure B (1 mmol) provided in example 2 was dissolved in methanol (2-5 mL) and a pinch of 10% wet Pd—C was added. The reaction mixture was degassed by passing nitrogen and $H_2$ gas for 2-5 hours to get fully reduced compound. Reaction was thoroughly monitored by checking TLC. Upon completion of the reaction, Pd—C was filtered through celite bed and methanol was evaporated in vacuum to get the desired compound. Column chromatography was performed to get the pure product.

Example 4

General Procedure D: Urea Derivative Formation Via Chloroformate Intermediate A compound prepared by general procedure C (1 mmol) provided in example 3 was dissolved in dry THF (5-10 mL). 4-nitrophenylchloroformate (1-1.5 equivalent) was added portion wise and reaction mixture was stirred for 15 min-3 hour till the amine got consumed. Reaction was monitored by checking TLC. Further, suitable amine (1-1.5 equivalent) was added to the reaction mixture followed by TEA (2-4 equivalent) and reaction mixture was stirred for another 2-8 hours. Upon completion of the reaction, reaction mass was evaporated in vacuum to remove THF and washed with satd. $NaHCO_3$ solution and extracted with EtOAc. Column chromatography was performed to get the pure product.

Example 5

General Procedure E: Urea Derivative Formation Via Isocyante

A compound prepared by general procedure C (1 mmol) provided in example 3 was taken in dry THF (5-10 mL) and suitable aromatic substituted isocyanate (1-1.5 equivalent) was added followed by TEA (2-4 equivalent). The reaction mixture was stirred for 2-8 hours. Reaction was monitored by checking TLC. Upon completion of the reaction, reaction mass was evaporated in vacuum to remove THF and washed with satd. $NaHCO_3$ solution and extracted with EtOAc. Column chromatography was performed to get the pure product.

Example 6

General Procedure F: Suzuki Coupling

Suzuki reaction was performed with suitable halo compound (1 mmol), an aliphatic or aromatic (substituted) boronic acid (1-2 equivalent) in presence of $Cs_2CO_3$ or 2M $Na_2CO_3$ or 2M $K_2CO_3$ (2-4 equivalent) solution taken in a pressure tube and dissolved in dioxane: $H_2O$ (9:1) (8 mL). The reaction mixture was purged with Ar-gas for 15 minutes. $Pd_2(dba)_3$ or $Pd(PPh_3)_4$ (10 mol %) and ligands such as X-phos (20 mol %) were added and the reaction mixture was stirred at 100° C.-110° C. for 10-16 hours. Reaction was monitored by checking TLC. After completion, reaction mass was washed with water and extracted with ethyl acetate and evaporated. Column chromatography was performed to purify the compound.

Example 7

General Procedure G: Zinc Chloride Mediated Cyclization

An uncyclized diamide compound (1 mmol) was taken in DMF (8-10 mL) and $ZnCl_2$ (4-8 equivalent) was added followed by HMDS (8-10 equivalent) and the reaction mixture was heated at 100° C.-110° C. for 30 mins-16 hours. Reaction was monitored by checking TLC. After completion; the reaction mixture was washed with ice cold water and extracted with EtOAc. Column chromatography was performed to purify the compound.

Example 8

General Procedure H: Side Chain Modification

An ester compound (1 mmol) was dissolved in toluene (5-7 mL) and anhydrous $AlCl_3$ (4-8 equivalent) was added under $N_2$ atmosphere to obtain a reaction mixture. Suitable aliphatic or aromatic or substituted aromatic amine (1-2 equivalent) was added to the reaction mixture followed by TEA (0.3 mL, 2.43 mmol) and the reaction mixture was stirred for 25 mins-10 hours at a temperature ranging from room temperature to 100° C.-110° C. The reaction was monitored by checking TLC. Upon completion of the reaction, the reaction mass was washed with water and 0.1 (N) NaOH solution and extracted with EtOAc. Compound was purified by column chromatography.

Example 9

Synthesis of 2-amino-N-(2-methoxyethyl)-5-nitrobenzamide (2): The compound was prepared by general procedure A provided in example 1 using 2-amino-5-nitrobenzoic acid 1 (4 g, 21.97 mmol), DMF (12 mL), HATU (9.1 g, 24.17 mmol), 2-methoxyethylamine (2.1 mL, 24.17 mmol) and TEA (7.6 mL, 54.93 mmol). After evaporation, the crude mass was diluted with chloroform and pet ether was added to obtain the precipitation. The precipitate was washed with pet ether to afford compound 2 (4.2 g, 80%) as yellow solid. $^1H$ NMR (400 MHz, $d_6$-DMSO) δ in ppm 8.71 (br.s, —NH), 8.46 (d, J=2.8 Hz, 1H), 7.96 (dd, J=9.4 Hz, 2.4 Hz, 1H), 7.71 (br.s, 2H), 6.75 (d, J=9.2 Hz, 1H), 3.43-3.40 (m, 2H), 3.37-3.33 (m, 2H), 3.23 (s, 3H). ESI-HRMS m/z 240.0995 ($M+H^+$). Melting Point: 168° C.

Example 10

Synthesis of 3-(2-methoxyethyl)-6-nitroquinazolin-4(3H)-one (3): The compound was prepared by general procedure B provided in example 2 using compound 2 (2 g, 8.63 mmol), (TMOF) (9 mL, 86.3 mmol) to obtain compound 3 (1.8 g, 87%) as pale yellow solid. $^1H$ NMR (400 MHz, $d_6$-DMSO) δ in ppm 8.78 (d, J=2.4 Hz, 1H), 8.50 (dd, J=9 Hz, 2.8 Hz, 1H), 8.45 (s, 1H), 7.82 (d, J=9.2 Hz, 1H), 4.16 (t, J=5.2 Hz, 2H), 3.59 (t, J=4.8 Hz, 2H), 3.21 (s, 3H). ESI-HRMS m/z 250.0834 ($M+H^+$). Melting Point: 152° C.

Example 11

Synthesis of 6-amino-3-(2-methoxyethyl)quinazolin-4(3H)-one (4): The compound was prepared by general procedure C provided in example 3 using compound 3 (1 g, 4.01 mmol), methanol (10 mL) to obtain compound 4 (0.8 g, 91%) as brown solid. $^1H$ NMR (300 MHz, $d_6$-DMSO) δ in ppm 7.94 (s, 1H), 7.37 (d, J=8.7 Hz, 1H), 7.21 (d, J=2.4 Hz, 1H), 7.07 (dd, J=8.5 Hz, 2.7 Hz, 1H), 5.66 (br.s, 2H), 4.09 (t, J=5.4 Hz, 2H), 3.58 (t, J=5.1 Hz, 2H), 3.24 (s, 3H). ESI-HRMS m/z 220.1095 ($M+H^+$). Melting Point: 172° C.

Example 12

Synthesis of 1-(3-(2-methoxyethyl)-4-oxo-3,4-dihydroquinazolin-6-yl)-3-phenylurea (5): The compound was prepared by general procedure D provided in example 4 using compound 4 (0.14 g, 0.63 mmol), dry THF (8 mL), 4-nitrophenylchloroformate (0.16 g, 0.79 mmol), aniline (0.07 mL, 0.79 mmol), TEA (0.4 mL, 2.63 mmol) to obtain compound 5 (0.075 g, 35%) as off white solid. $^1H$ NMR (300 MHz, $d_6$-DMSO) δ in ppm 9.09 (s, 1H), 8.78 (s, 1H), 8.35 (d, J=2.4 Hz, 1H), 8.17 (s, 1H), 7.79 (dd, J=8.7 Hz, J=2.4 Hz, 1H), 7.62 (d, J=8.7 Hz, 1H), 7.48 (d, J=7.8 Hz, 2H) 7.32-7.27 (m, 2H), 7.01-6.96 (m, 1H), 4.15 (t, J=5.7 Hz, 2H), 3.61 (t, J=5.1 Hz, 2H), 3.25 (s, 3H). ESI-MS m/z 339.0 ($M+H^+$). Melting Point: 218° C.

Example 13

Synthesis of 1-(3-(2-methoxyethyl)-4-oxo-3,4-dihydroquinazolin-6-yl)-3-(3-methoxyphenyl)urea (6): The compound was prepared by general procedure D provided in example 4 using compound 4 (0.12 g, 0.54 mmol), dry THF (8 mL), 4-nitrophenylchloroformate (0.137 g, 0.68 mmol), m-anisidine (0.076 mL, 0.68 mmol), TEA (0.3 mL, 2.25 mmol) to obtain compound 6 (0.066 g, 33%) as white solid. $^1H$ NMR (400 MHz, $d_6$-DMSO) δ in ppm 9.01 (s, 1H), 8.71 (s, 1H), 8.30 (d, J=2.4 Hz, 1H), 8.10 (d, J=1.2 Hz, 1H), 7.73 (dd, J=8 Hz, J=2.8 Hz, 1H), 7.56 (d, J=8.4 Hz, 1H), 7.17-7.11 (m, 2H) 6.90 (d, J=8.1 Hz, 1H), 6.51 (d, J=10.8 Hz, 1H), 4.09 (t, J=4.8 Hz, 2H), 3.68 (s, 3H), 3.56 (t, J=5.2 Hz, 2H), 3.19 (s, 3H). ESI-MS m/z 369.0 ($M+H^+$). Melting Point: 150° C.

Example 14

Synthesis of 1-(3-(2-methoxyethyl)-4-oxo-3,4-dihydroquinazolin-6-yl)-3-(3-(methylamino)phenyl)urea (7): The compound was prepared by general procedure D provided in example 4 using compound 4 (0.12 g, 0.54 mmol), dry THF (8 mL), 4-nitrophenylchloroformate (0.137 g, 0.68 mmol), $N^1$-methylbenzene-1,3-diamine (0.083 g, 0.68 mmol), TEA (0.3 mL, 2.25 mmol) to obtain compound 7 (0.05 g, 25%) as light yellow solid.

Example 15

Synthesis of 1-(3-(2-methoxyethyl)-4-oxo-3,4-dihydroquinazolin-6-yl)-3-(3-nitrophenyl)urea (8): The compound was prepared by general procedure D provided in example 4 using compound 4 (0.12 g, 0.54 mmol), dry THF (8 mL), 4-nitrophenylchloroformate (0.137 g, 0.68 mmol), 3-nitroaniline (0.094 g, 0.68 mmol), TEA (0.3 mL, 2.25 mmol) to obtain compound 8 (0.07, 33%) as yellow solid. $^1H$ NMR (300 MHz, $d_6$-DMSO) δ in ppm 9.31 (d, J=16.2 Hz, 2H), 8.57 (s, 1H), 8.37 (d, J=2.1 Hz, 1H), 8.18 (s, 1H), 7.86-7.75 (m, 3H), 7.65-7.55 (m, 2H), 4.16 (t, J=5.1 Hz, 2H), 3.62 (t, J=4.8 Hz, 2H), 3.25 (s, 3H). ESI-MS m/z 384.07 ($M+H^+$). Melting Point: 208° C.

Example 16

Synthesis of 1-(3-acetylphenyl)-3-(3-(2-methoxyethyl)-4-oxo-3,4-dihydroquinazolin-6-yl)urea (9): The compound was prepared by general procedure D provided in example 4 using compound 4 (0.1 g, 0.45 mmol), dry THF (6 mL), 4-nitrophenylchloroformate (0.114 g, 0.57 mmol), 3'-aminoacetophenone (0.077 g, 0.57 mmol), TEA (0.3 mL, 1.88 mmol) to obtain compound 9 (0.08, 46%) as off white solid. $^1H$ NMR (300 MHz, $d_6$-DMSO) δ in ppm 9.15 (s, 1H), 9.02 (s, 1H), 8.37 (d, J=1.5 Hz, 1H), 8.17 (s, 1H), 8.10 (s, 1H), 7.82 (dd, J=8.7 Hz, J=1.8 Hz, 1H), 7.70 (d, J=7.8 Hz, 1H), 7.64-7.59 (m, 2H), 7.48-7.43 (m, 1H), 4.15 (t, J=4.8 Hz, 2H), 3.61 (t, J=4.8 Hz, 2H), 3.25 (s, 3H), 2.57 (s, 3H). ESI-MS m/z 381.03 (M+H$^+$). Melting Point: 210° C.

Example 17

Synthesis of 1-(4-acetylphenyl)-3-(3-(2-methoxyethyl)-4-oxo-3,4-dihydroquinazolin-6-yl)urea (10): The compound was prepared by general procedure D provided in example 4 using compound 4 (0.12 g, 0.54 mmol), dry THF (8 mL), 4-nitrophenylchloroformate (0.137 g, 0.68 mmol), 4'-aminoacetophenone (0.092 g, 0.68 mmol), TEA (0.3 mL, 2.25 mmol) to obtain compound 10 (0.08, 46%) as off white solid. $^1$H NMR (300 MHz, $d_6$-DMSO) δ in ppm 9.26 (s, 1H), 9.24 (s, 1H), 8.37 (d, J=2.4 Hz, 1H), 8.17 (s, 1H), 7.92 (s, 1H), 7.89 (s, 1H), 7.81 (dd, J=8.8 Hz, 2.7 Hz, 1H), 7.64-7.60 (m, 3H), 4.15 (t, J=5.1 Hz, 2H), 3.61 (t, J=5.1 Hz, 2H), 3.24 (s, 3H), 2.51 (s, 3H). ESI-MS m/z 381.07 (M+H$^+$). Melting Point: 202° C.

Example 18

Synthesis of 1-(3-(1-hydroxyethyl)phenyl)-3-(3-(2-methoxyethyl)-4-oxo-3,4-dihydroquinazolin-6-yl)urea (11): The compound was prepared by general procedure D provided in example 4 using compound 4 (0.12 g, 0.54 mmol), dry THF (8 mL), 4-nitrophenylchloroformate (0.137 g, 0.68 mmol), 1-(3-aminophenyl)ethanol (0.093 g, 0.68 mmol), TEA (0.3 mL, 2.25 mmol) to obtain compound 11 (0.08 g, 38%) as light yellow solid. $^1$H NMR (300 MHz, $d_6$-DMSO) δ in ppm 9.02 (s, 1H), 8.73 (s, 1H), 8.34 (d, J=2.4 Hz, 1H), 8.14 (s, 1H), 7.77 (dd, J=9 Hz, 2.4 Hz, 1H), 7.59 (d, J=9 Hz, 1H), 7.44 (s, 1H), 7.32 (d, J=7.8 Hz, 1H), 7.23-7.17 (m, 1H), 6.94 (d, J=7.5 Hz, 1H), 5.14 (d, J=3.9 Hz, 1H), 4.70-4.62 (m, 1H), 4.13 (t, J=5.1 Hz, 2H), 3.59 (t, J=4.8 Hz, 2H), 3.23 (s, 3H), 1.29 (d, J=6.6 Hz, 3H). ESI-MS m/z 383.02 (M+H$^+$). Melting Point: 168° C.

Example 19

Synthesis of methyl 4-methoxy-3-(3-(3-(2-methoxyethyl)-4-oxo-3,4-dihydroquinazolin-6-yl)ureido)benzoate (12): The compound was prepared by general procedure D provided in example 4 using compound 4 (0.13 g, 0.593 mmol), dry THF (8 mL), 4-nitrophenylchloroformate (0.15 mg, 0.74 mmol), methyl 3-amino-4-methoxybenzoate (0.134 g, 0.74 mmol), TEA (0.3 mL, 2.44 mmol) to obtain compound 12 (0.08 g, 32%) as off white solid. $^1$H NMR (300 MHz, $d_6$-DMSO) δ in ppm 9.75 (s, 1H), 8.84 (s, 1H), 8.43 (s, 1H), 8.39 (d, J=2.1 Hz, 1H), 8.17 (s, 1H), 7.77 (dd, J=8.7 Hz, 2.1 Hz, 1H), 7.66-7.61 (m, 2H), 7.15 (d, J=8.4 Hz, 1H), 4.16 (t, J=4.8 Hz, 2H), 3.98 (s, 3H), 3.83 (s, 3H) 3.62 (t, J=4.8 Hz, 2H), 3.25 (s, 3H). ESI-MS m/z 427.1 (M+H$^+$). Melting Point: 224° C.

Example 20

Synthesis of 1-(3-ethylphenyl)-3-(3-(2-methoxyethyl)-4-oxo-3,4-dihydroquinazolin-6-yl)urea (13): The compound was prepared by general procedure D provided in example 4 using compound 4 (0.12 g, 0.54 mmol), dry THF (8 mL), 4-nitrophenylchloroformate (0.137 g, 0.68 mmol), 3-ethylaniline (0.085 g, 0.68 mmol), TEA (0.3 mL, 2.25 mmol) to obtain compound 13 (0.07 g, 35%) as off white solid. $^1$H NMR (400 MHz, $d_6$-DMSO) δ in ppm 9.00 (s, 1H), 8.63 (s, 1H), 8.30 (d, J=2.4 Hz, 1H), 8.10 (s, 1H), 7.73 (dd, J=8.8 Hz, 2.4 Hz, 1H), 7.56 (d, J=8.8 Hz, 1H), 7.30-7.29 (m, 1H), 7.21 (d, J=8.8 Hz, 1H), 7.15-7.12 (m, 1H), 6.78 (d, J=7.6 Hz, 1H), 4.09 (t, J=5.2 Hz, 2H), 3.56 (t, J=5.32 Hz, 2H), 3.19 (s, 3H), 2.52 (q, J=Hz, 2H), 1.12 (t, J=Hz, 3H). ESI-MS m/z 367.3 (M+H$^+$). Melting Point: 182° C.

Example 21

Synthesis of 1-(3-benzoylphenyl)-3-(3-(2-methoxyethyl)-4-oxo-3,4-dihydroquinazolin-6-yl)urea (14): The compound was prepared by general procedure D provided in example 4 using compound 4 (0.12 g, 0.54 mmol), dry THF (8 mL), 4-nitrophenylchloroformate (0.137 g, 0.68 mmol), (3-aminophenyl)(phenyl)methanone (0.135 g, 0.68 mmol), TEA (0.3 mL, 2.25 mmol) to obtain compound 14 (0.065 g, 27%) as off white solid. $^1$H NMR (300 MHz, $d_6$-DMSO) δ in ppm 9.17 (s, 1H), 9.10 (s, 1H), 8.34 (d, J=2.4 Hz, 1H), 8.16 (s, 1H), 7.93 (s, 1H), 7.82-7.77 (m, 4H), 7.68 (d, J=7.2 Hz, 1H), 7.63-7.55 (m, 3H), 7.52-7.46 (m, 1H), 7.35 (d, J=7.8 Hz, 1H), 4.15 (t, J=5.1 Hz, 2H), 3.61 (t, J=5.1 Hz, 2H), 3.24 (s, 3H). ESI-MS m/z 443.2 (M+H$^+$). Melting Point: 136° C.

Example 22

Synthesis of N-cyclohexyl-3-(3-(3-(2-methoxyethyl)-4-oxo-3,4-dihydroquinazolin-6-yl)ureido)benzamide (15): The compound was prepared by general procedure D provided in example 4 using compound 4 (0.12 g, 0.54 mmol), dry THF (8 mL), 4-nitrophenylchloroformate (0.137 g, 0.68 mmol), 3-amino-N-cyclohexylbenzamide (0.15 g, 0.68 mmol), TEA (0.3 mL, 2.25 mmol) to obtain compound 15 (0.085 g, 33%) as off white solid. $^1$H NMR (300 MHz, $d_6$-DMSO) δ in ppm 9.12 (s, 1H), 8.94 (s, 1H), 8.37 (d, J=2.4 Hz, 1H), 8.20 (s, 1H), 8.17 (s, 1H), 7.85 (s, 1H), 7.81 (dd, J=9 Hz, 2.7 Hz, 1H), 7.66-7.61 (m, 2H), 7.44 (d, J=7.8 Hz, 1H), 7.38-7.33 (m, 1H), 4.15 (t, J=5.1 Hz, 2H), 3.77-3.70 (m, 1H), 3.61 (t, J=5.1 Hz, 2H), 3.25 (s, 3H), 1.83-1.79 (m, 2H), 1.75-1.71 (m, 2H), 1.64-1.57 (m, 1H), 1.38-1.23 (m, 4H), 1.17-1.1 (m, 1H). ESI-MS m/z 464.2 (M+H$^+$). Melting Point: 206° C.

Example 23

Synthesis of methyl 2-(3-(3-(3-(2-methoxyethyl)-4-oxo-3,4-dihydroquinazolin-6-yl)ureido)benzamido)-3-methylbutanoate (16): The compound was prepared by general procedure D provided in example 4 using compound 4 (0.12 g, 0.54 mmol), dry THF (8 mL), 4-nitrophenylchloroformate (0.137 g, 0.68 mmol), methyl 2-(3-aminobenzamido)-3-methylbutanoate (0.17 g, 0.68 mmol), TEA (0.3 mL, 2.25 mmol) to obtain compound 16 (0.08 g, 30%) as off white solid. $^1$H NMR (300 MHz, $d_6$-DMSO) δ in ppm 9.14 (s, 1H), 8.94 (s, 1H), 8.60 (d, J=7.8 Hz, 1H), 8.36 (d, J=2.1 Hz, 1H), 8.17 (s, 1H), 7.86 (s, 1H), 7.81 (dd, J=9 Hz, 2.1 Hz, 1H), 7.71 (d, J=8.1 Hz, 1H), 7.62 (d, J=8.7 Hz, 1H), 7.50 (d, J=7.8 Hz, 1H), 7.42-7.37 (m, 1H), 4.29 (t, J=7.5 Hz, 1H), 4.15 (t, J=4.8 Hz, 2H), 3.66 (s, 3H), 3.61 (t, J=5.1 Hz, 2H), 3.25 (s, 3H), 2.24-2.13 (m, 1H), 0.965 (q, J=6.9 Hz, 6H). ESI-HRMS m/z 496.2181 (M+H$^+$). Melting Point: 198° C.

Example 24

Synthesis of 3-(3-(3-(2-methoxyethyl)-4-oxo-3,4-dihydroquinazolin-6-yl)ureido)-N,N-dimethylbenzamide (17): The compound was prepared by general procedure D provided in example 4 using compound 4 (0.06 g, 0.27 mmol), dry THF (6 mL), 4-nitrophenylchloroformate (0.069 g, 0.34 mmol), 3-amino-N,N-dimethylbenzamide (0.056 g, 0.34 mmol), TEA (0.1 mL, 1.12 mmol) to obtain compound 17 (0.056 g, 50%) as off white solid. $^1$H NMR (300 MHz, $d_6$-DMSO) δ in ppm 9.32 (d, J=18.3 Hz, 1H), 9.02 (d, J=18.3 Hz, 1H), 8.36 (s, 1H), 8.17 (s, 1H), 7.86-7.79 (m, 1H), 7.65-7.57 (m, 2H), 7.47-7.30 (m, 2H), 7.00-6.96 (m, 1H), 4.15 (t, J=4.5 Hz, 2H), 3.61 (t, J=4.8 Hz, 2H), 3.25 (s, 3H), 2.98 (s, 3H), 2.92 (s, 3H). ESI-HRMS m/z 410.1837 (M+H$^+$). Melting Point: 182° C.

Example 25

Synthesis of 1-(3-(2-methoxyethyl)-4-oxo-3,4-dihydroquinazolin-6-yl)-3-(3-(pyrrolidine-1-carbonyl)phenyl)urea (18): The compound was prepared by general procedure D provided in example 4 using compound 4 (0.12 g, 0.54 mmol), dry THF (8 mL), 4-nitrophenylchloroformate (0.137 mg, 0.68 mmol), (3-aminophenyl)(pyrrolidin-1-yl)methanone (0.13 g, 0.68 mmol), TEA (0.3 mL, 2.25 mmol) to obtain compound 18 (0.052 g, 22%) as light yellow solid. $^1$H NMR (300 MHz, $d_6$-DMSO) δ in ppm 9.19 (s, 1H), 8.95 (s, 1H), 8.36 (d, J=2.1 Hz, 1H), 8.17 (s, 1H), 7.80 (dd, J=9 Hz, 2.4 Hz, 1H), 7.70 (s, 1H), 7.62 (d, J=8.7 Hz, 1H), 7.47-7.41 (m, 1H), 7.37-7.33 (m, 1H), 7.12-7.08 (m, 1H), 4.15 (t, J=4.2 Hz, 2H), 3.61 (t, J=4.8 Hz, 2H), 3.46 (t, J=4.8 Hz, 4H), 3.25 (s, 3H), 1.89-1.79 (m, 4H). ESI-MS m/z 435.8 (M+H$^+$). Melting Point: 198° C.

Example 26

Synthesis of 1-(3-(2-methoxyethyl)-4-oxo-3,4-dihydroquinazolin-6-yl)-3-(3-(morpholine-4-carbonyl)phenyl)urea (19): The compound was prepared by general procedure D provided in example 4 using compound 4 (0.10 g, 0.45 mmol), dry THF (8 mL) and 4-nitrophenylchloroformate (0.137 g, 0.68 mmol), (3-aminophenyl)(morpholino)methanone (0.12 g, 0.54 mmol), TEA (0.3 mL, 1.88 mmol) to obtain compound 19 (0.05 g, 24%) as light yellow solid. $^1$H NMR (400 MHz, $d_6$-DMSO) δ in ppm 9.09 (s, 1H), 8.86 (s, 1H), 8.30 (s, 1H), 8.10 (s, 1H), 7.74 (d, J=8.8 Hz, 1H), 7.55-7.51 (m, 2H), 7.43-7.37 (m, 1H), 7.32-7.29 (m, 1H), 6.96-6.92 (m, 1H), 4.09 (t, J=4.4 Hz, 2H), 3.58-3.53 (m, 8H), 3.34-3.31 (m, 2H), 3.19 (s, 3H). ESI-MS m/z 452.3 (M+H$^+$). Melting Point: 102° C.

Example 27

Synthesis of 1-(3-(2-methoxyethyl)-4-oxo-3,4-dihydroquinazolin-6-yl)-3-(4-(pyrrolidine-1-carbonyl)phenyl)urea (20): The compound was prepared by general procedure D provided in example 4 using compound 4 (0.12 g, 0.54 mmol), dry THF (8 mL), 4-nitrophenylchloroformate (0.137 g, 0.68 mmol), (4-aminophenyl)(pyrrolidin-1-yl)methanone (0.13 g, 0.68 mmol), TEA (0.3 mL, 2.25 mmol) to obtain compound 20 (0.075 g, 31%) as light yellow solid. H NMR (300 MHz, $d_6$-DMSO) δ in ppm 9.21 (d, J=14.4 Hz, 1H), 8.99 (d, J=12.9 Hz, 1H), 8.37 (d, J=2.4 Hz, 1H), 8.17 (s, 1H), 7.80 (dd, J=9 Hz, 2.7 Hz, 1H), 7.62 (d, J=8.7 Hz, 1H), 7.55-7.47 (m, 4H), 4.15 (t, J=4.5 Hz, 2H), 3.61 (t, J=4.8 Hz, 2H), 3.47-3.42 (m, 4H) 3.25 (s, 3H), 1.88-1.79 (m, 4H). ESI-HRMS m/z 436.1987 (M+H$^+$). Melting Point: 202° C.

Example 28

Synthesis of 1-(3-(benzo[d]oxazol-2-yl)phenyl)-3-(3-(2-methoxyethyl)-4-oxo-3,4-dihydroquinazolin-6-yl)urea (21): The compound was prepared by general procedure D provided in example 4 using compound 4 (0.08 g, 0.36 mmol), dry THF (8 mL), 4-nitrophenylchloroformate (0.092 g, 0.45 mmol), 3-(benzo[d]oxazol-2-yl)aniline (0.096 g, 0.45 mmol), TEA (0.2 mL, 1.50 mmol) to obtain compound 21 (0.042 g, 25%) as off white solid. $^1$H NMR (300 MHz, $d_6$-DMSO) δ in ppm 9.06 (s, 1H), 8.81 (s, 1H), 8.33 (s, 1H), 8.16 (s, 1H), 7.76 (dd, J=8.8 Hz, 2.7 Hz, 1H), 7.60 (d, J=8.7 Hz, 1H), 7.46 (d, J=8.4 Hz, 1H), 7.33-7.29 (m, 4H), 7.26-7.20 (m, 2H), 6.87 (d, J=7.8 Hz, 1H), 4.15 (t, J=4.8 Hz, 2H), 3.61 (t, J=5.1 Hz, 2H), 3.25 (s, 3H). Melting Point: 176° C.

Example 29

Synthesis of N-(3-(3-(3-(2-methoxyethyl)-4-oxo-3,4-dihydroquinazolin-6-yl)ureido)phenyl)acetamide (22): The compound was prepared by general procedure D provided in example 4 using compound 4 (0.13 g, 0.59 mmol), dry THF (8 mL), 4-nitrophenylchloroformate (0.149 g, 0.74 mmol), N-(3-aminophenyl)acetamide (0.111 g, 0.74 mmol), TEA (0.4 mL, 2.44 mmol) to obtain compound 22 (0.05 g, 21%) as light yellow solid. $^1$H NMR (300 MHz, $d_6$-DMSO) δ in ppm 9.93 (s, 1H), 9.09 (s, 1H), 8.89 (s, 1H), 8.38 (d, J=2.4 Hz, 1H), 8.16 (s, 1H), 7.80-7.75 (m, 2H), 7.61 (d, J=8.7 Hz, 1H), 7.24-7.16 (m, 3H), 4.15 (t, J=5.1 Hz, 2H), 3.61 (t, J=5.1 Hz, 2H), 3.25 (s, 3H), 2.04 (s, 3H). ESI-HRMS m/z 396.1689 (M+H$^+$). Melting Point: 162° C.

Example 30

Synthesis of N-(3-(3-(3-(2-methoxyethyl)-4-oxo-3,4-dihydroquinazolin-6-yl)ureido)phenyl)-N-methylacetamide (23): The compound was prepared by general procedure D provided in example 4 using compound 4 (0.130 g, 0.59 mmol), dry THF (8 mL), 4-nitrophenylchloroformate (0.149 g, 0.74 mmol), N-(3-aminophenyl)-N-methylacetamide (0.12 g, 0.74 mmol), TEA (0.4 mL, 2.44 mmol) to obtain compound 23 (0.052 g, 21%) as off white solid. $^1$H NMR (300 MHz, $d_6$-DMSO) δ in ppm 9.25 (s, 1H), 8.96 (s, 1H), 8.36 (s, 1H), 8.17 (s, 1H), 7.80 (d, J=9.3 Hz, 1H), 7.62 (d, J=8.4 Hz, 1H), 7.51 (s, 1H), 7.37-7.32 (m, 2H), 6.94 (s, 1H), 4.15 (t, J=4.5 Hz, 2H), 3.61 (t, J=4.8 Hz, 2H), 3.25 (s, 3H), 3.15 (s, 3H), 1.80 (s, 3H). ESI-MS m/z 410.4 (M+H$^+$). Melting Point: 98° C.

Example 31

Synthesis of N-benzyl-N-(3-(3-(3-(2-methoxyethyl)-4-oxo-3,4-dihydroquinazolin-6-yl)ureido)phenyl)acetamide (24): The compound was prepared by general procedure D provided in example 4 using compound 4 (0.15 g, 0.68 mmol), dry THF (8 mL), 4-nitrophenylchloroformate (0.172 g, 0.85 mmol), N-(3-aminophenyl)-N-benzylacetamide (0.20 g, 0.85 mmol), TEA (0.4 mL, 2.82 mmol) to obtain compound 24 (0.08 g, 24%) as light yellow solid. $^1$H NMR (300 MHz, $d_6$-DMSO) δ in ppm 9.13 (s, 1H), 8.86 (s, 1H), 8.34 (s, 1H), 8.16 (s, 1H), 7.77 (dd, J=8.7 Hz, 1.5 Hz, 1H), 7.61 (d, J=8.7 Hz, 1H), 7.38-7.35 (m, 2H), 7.31-7.27 (m, 3H), 7.24-7.19 (m, 3H), 6.80 (d, J=7.5 Hz, 1H), 4.85 (s, 2H), 4.15 (t, J=4.8 Hz, 2H), 3.61 (t, J=4.8 Hz, 2H), 3.24 (s, 3H), 1.88 (s, 3H). ESI-MS m/z 486.2 (M+H$^+$). Melting Point: 184° C.

Example 32

Synthesis of N-(3-(3-(3-(2-methoxyethyl)-4-oxo-3,4-dihydroquinazolin-6-yl)ureido)benzyl)acetamide (25): The compound was prepared by general procedure D provided in example 4 using compound 4 (0.10 g, 0.45 mmol), dry THF (6 mL), 4-nitrophenylchloroformate (0.137 g, 0.68 mmol), N-(3-aminobenzyl)acetamide (0.089 g, 0.54 mmol), TEA (0.3 mL, 1.88 mmol) to obtain compound 25 (0.08 g, 43%) as off white solid. $^1$H NMR (300 MHz, $d_6$-DMSO) δ in ppm 9.08 (s, 1H), 8.81 (s, 1H), 8.37 (s, 1H), 8.36 (s, 1H), 8.16 (s, 1H), 7.78 (dd, J=8.7 Hz, J=1.2 Hz, 1H), 7.61 (d, J=8.7 Hz, 1H), 7.39-7.31 (m, 2H), 7.26-7.21 (m, 1H), 6.88 (d, J=7.5 Hz, 1H), 4.17 (t, J=4.8 Hz, 2H), 4.15 (t, J=4.8 Hz, 2H), 3.61 (t, J=4.8 Hz, 2H), 3.25 (s, 3H), 1.88 (s, 3H). ESI-HRMS m/z 410.1827 (M+H$^+$). Melting Point: 202° C.

Example 33

Synthesis of N-(3-(3-(3-(2-methoxyethyl)-4-oxo-3,4-dihydroquinazolin-6-yl)ureido)benzyl)-N-methylacetamide (26): The compound was prepare by general procedure D provided in example 4 using compound 4 (0.10 g, 0.45 mmol), dry THF (6 mL) and 4-nitrophenylchloroformate (0.114 g, 0.68 mmol), N-(3-aminobenzyl)-N-methylacetamide (0.097 g, 0.54 mmol), TEA (0.3 mL, 1.88 mmol) to obtain compound 26 (0.075 g, 39%) as off white solid.

Example 34

Synthesis of 3-(3-(2-methoxyethyl)-4-oxo-3,4-dihydroquinazolin-6-yl)-1,1-dimethylurea (27): The compound was prepared by general procedure D provided in example 4 using compound 4 (0.10 g, 0.45 mmol), dry THF (6 mL), 4-nitrophenylchloroformate (0.114 g, 0.57 mmol), dimethylamine 2M in THF solution (1.1 mL, 0.57 mmol), TEA (0.3 mL, 1.88 mmol) to obtain compound 27 (0.047 g, 35%) as off white solid. $^1$H NMR (300 MHz, $d_6$-DMSO) δ in ppm 8.86 (s, 1H), 8.29 (d, J=2.1 Hz, 1H), 8.13 (s, 1H), 7.97 (dd, J=8.8 Hz, 2.1 Hz, 1H), 7.55 (d, J=9 Hz, 1H), 4.13 (t, J=5.1 Hz, 2H), 3.60 (t, J=5.1 Hz, 2H), 3.24 (s, 3H), 2.95 (s, 6H). ESI-MS m/z 291.2 (M+H$^+$). Melting Point: 182° C.

Example 35

Synthesis of N-(3-(2-methoxyethyl)-4-oxo-3,4-dihydroquinazolin-6-yl)piperidine-1-carboxamide (28): The compound was prepared by general procedure D provided in example 4 using compound 4 (0.08 g, 0.36 mmol), dry THF (6 mL), 4-nitrophenylchloroformate (0.092 g, 0.45 mmol), piperidine (0.04 mL, 0.45 mmol), TEA (0.2 mL, 1.50 mmol) to obtain compound 28 (0.052 g, 43%) as off white solid. $^1$H NMR (300 MHz, $d_6$-DMSO) δ in ppm 8.84 (s, 1H), 8.27 (d, J=2.1 Hz, 1H), 8.13 (s, 1H), 7.95 (dd, J=8.8 Hz, 2.4 Hz, 1H), 7.55 (d, J=9 Hz, 1H), 4.13 (t, J=5.1 Hz, 2H), 3.60 (t, J=5.1 Hz, 2H), 3.44 (t, J=4.2 Hz, 4H), 3.24 (s, 3H), 1.61-1.56 (m, 2H), 1.51-1.48 (m, 4H). ESI-HRMS m/z 331.1769 (M+H$^+$). Melting Point: 162° C.

Example 36

Synthesis of 1-(3-(2-methoxyethyl)-4-oxo-3,4-dihydroquinazolin-6-yl)-3-(1-methylpiperidin-4-yl)urea (29): The compound was prepared by general procedure D provided in example 4 using compound 4 (0.10 g, 0.45 mmol), dry THF (6 mL), 4-nitrophenylchloroformate (0.114 g, 0.57 mmol), 4-amino-1-methylpiperidine (0.07 mL, 0.57 mmol), TEA (0.3 mL, 1.88 mmol) to obtain compound 29 (0.072, 44%)) as light yellow solid. $^1$H NMR (300 MHz, $d_6$-DMSO) δ in ppm 8.94 (s, 1H), 8.26 (d, J=2.1 Hz, 1H), 8.11 (s, 1H), 7.73 (dd, J=8.7 Hz, 2.1 Hz, 1H), 7.54 (d, J=8.7 Hz, 1H), 6.45 (d, J=7.5 Hz, 1H), 4.14-4.07 (m, 3H), 3.60 (t, J=5.1 Hz, 2H), 3.24 (s, 3H), 2.66-2.63 (m, 2H), 2.15 (s, 3H), 2.02-1.96 (m, 2H), 1.80-1.76 (m, 2H), 1.46-1.35 (m, 2H). ESI-HRMS m/z 360.2032 (M+H$^+$). Melting Point: 142° C.

Example 37

Synthesis of 4-benzyl-N-(3-(2-methoxyethyl)-4-oxo-3,4-dihydroquinazolin-6-yl)piperidine-1-carboxamide (30): The compound was prepared by general procedure D provided in example 4 using compound 4 (0.10 g, 0.45 mmol), dry THF (8 mL), 4-nitrophenylchloroformate (0.114 g, 0.57 mmol), 4-benzylpiperidine (0.1 mL, 0.57 mmol), TEA (0.3 mL, 1.88 mmol) to obtain compound 30 (0.066 g, 35%) as light yellow solid. $^1$H NMR (300 MHz, $d_6$-DMSO) δ in ppm 8.85 (s, 1H), 8.27 (d, J=1.2 Hz, 1H), 8.13 (s, 1H), 7.94 (dd, J=8.7 Hz, 1.5 Hz, 1H), 7.55 (d, J=8.7 Hz, 1H), 7.31-7.26 (m, 2H), 7.19-7.17 (m, 3H), 4.15-4.10 (m, 4H), 3.60 (t, J=4.5 Hz, 2H), 3.24 (s, 3H), 2.78-2.70 (m, 2H), 2.54-2.52 (m, 2H), 1.76-1.70 (m, 1H), 1.61-1.57 (m, 2H), 1.19-1.06 (m, 2H). ESI-HRMS m/z 421.2242 (M+H$^+$). Melting Point: 146° C.

Example 38

Synthesis of 1-(1-benzylpiperidin-4-yl)-3-(3-(2-methoxyethyl)-4-oxo-3,4-dihydroquinazolin-6-yl)urea (31): The compound was prepared by general procedure D provided in example 4 using compound 4 (0.10 g, 0.45 mmol), dry THF (8 mL), 4-nitrophenylchloroformate (0.114 g, 0.57 mmol), 4-amino-1-benzylpiperidine (0.1 mL, 0.57 mmol), TEA (0.3 mL, 1.88 mmol) to obtain compound 31 (0.059 g, 30%) as light brown solid. ESI-HRMS m/z 436.2340 (M+H$^+$).

Example 39

Synthesis of 1-(5-acetyl-2-hydroxyphenyl)-3-(3-(2-methoxyethyl)-4-oxo-3,4-dihydroquinazolin-6-yl)urea (32): The compound was prepared by general procedure D provided in example 4 using compound 4 (0.1 g, 0.45 mmol), THF (6 mL), 4-nitrophenylchloroformate (0.114 g, 0.57 mmol), 1-(3-amino-4-hydroxyphenyl)ethanone (0.103 g, 0.68 mmol), TEA (0.3 mL, 1.88 mmol) to obtain compound 32 (0.0, 38%) as off white solid.

Example 40

Synthesis of 1-(3-acetyl-5-chloro-2-hydroxyphenyl)-3-(3-(2-methoxyethyl)-4-oxo-3,4-dihydroquinazolin-6-yl) urea (33): The compound was prepared by general procedure D provided in example 4 using compound 4 (0.1 g, 0.45 mmol), dry THF (6 mL), 4-nitrophenylchloroformate (0.114 g, 0.57 mmol), 1-(3-amino-5-chloro-2-hydroxyphenyl)ethanone (0.126 g, 0.68 mmol), TEA (0.3 mL, 1.88 mmol) to obtain compound 33 (0.065, 33%) as white solid.

Example 41

Synthesis of 1-(3-acetyl-2-hydroxy-5-methylphenyl)-3-(3-(2-methoxyethyl)-4-oxo-3,4-dihydroquinazolin-6-yl) urea (34): The compound was prepared by general procedure D provided in example 4 using compound 4 (0.1 g, 0.45 mmol), dry THF (6 mL), 4-nitrophenylchloroformate (0.114 g, 0.57 mmol), 1-(3-amino-2-hydroxy-5-methylphenyl) ethanone (0.113 g, 0.68 mmol), TEA (0.3 mL, 1.88 mmol) to obtain compound 34 (0.07, 37%) as yellow solid.

Example 42

Synthesis of 1-(4-fluorophenyl)-3-(3-(2-methoxyethyl)-4-oxo-3,4-dihydroquinazolin-6-yl)urea (35): The compound was prepared by general procedure E provided in example 5 using compound 4 (0.085 g, 0.38 mmol), dry THF (5 mL), 4-fluorophenyl isocyanate (0.05 mL, 0.48 mmol), TEA (0.1 mL, 0.81 mmol) to obtain compound 35 (0.056 g, 43%) as white solid. $^1$H NMR (400 MHz, $d_6$-DMSO) δ in ppm 9.04 (s, 1H), 8.75 (s, 1H), 8.29 (d, J=2.4 Hz, 1H), 8.11 (s, 1H), 7.75 (dd, J=8.8 Hz, 2.4 Hz, 1H), 7.56 (d, J=8.8 Hz, 1H), 7.46-7.42 (m, 2H), 7.11-7.06 (m, 2H), 4.10 (t, J=5.2 Hz, 2H), 3.56 (t, J=5.2 Hz, 2H), 3.20 (s, 3H). ESI-MS m/z 357.03 (M+H$^+$). Melting Point: 206° C.

Example 43

Synthesis of 1-(3-chloro-4-fluorophenyl)-3-(3-(2-methoxyethyl)-4-oxo-3,4-dihydroquinazolin-6-yl)urea (36): The compound was prepared by general procedure E provided in example 5 using compound 4 (0.10 g, 0.45 mmol), dry THF (5 mL), 3-chloro-4-fluorophenyl isocyanate (0.085 mL, 0.68 mmol), TEA (0.2 mL, 1.36 mmol) to obtain compound 36 (0.052 g, 29%) as white solid. $^1$H NMR (300 MHz, $d_6$-DMSO) δ in ppm 9.19 (s, 1H), 8.98 (s, 1H), 8.34 (d, J=2.4 Hz, 1H), 8.17 (s, 1H), 7.82-7.78 (m, 2H), 7.62 (d, J=9 Hz, 1H), 7.36-7.33 (m, 2H), 4.15 (t, J=5.1 Hz, 2H), 3.61 (t, J=4.8 Hz, 2H), 3.24 (s, 3H). ESI-MS m/z 390.99 (M+H$^+$). Melting Point: 202° C.

Example 44

Synthesis of 1-(3-(2-methoxyethyl)-4-oxo-3,4-dihydroquinazolin-6-yl)-3-(4-(trifluoromethoxy)phenyl)urea (37): The compound was prepared by general procedure E provided in example 5 using compound 4 (0.10 g, 0.45 mmol), dry THF (6 mL), 4-(trifluoromethoxy)phenyl isocyanate (0.1 mL, 0.68 mmol), TEA (0.2 mL, 1.36 mmol) to obtain compound 37 (0.06 g, 31%) as off white solid. $^1$H NMR (300 MHz, $d_6$-DMSO) δ in ppm 9.31 (s, 1H), 9.15 (s, 1H), 8.35 (d, J=2.4 Hz, 1H), 8.17 (s, 1H), 7.81 (dd, J=8.8 Hz, 2.4 Hz, 1H), 7.63-7.57 (m, 3H), 7.31 (s, 1H), 7.29 (s, 1H), 4.15 (t, J=4.8 Hz, 2H), 3.61 (t, J=4.8 Hz, 2H), 3.24 (s, 3H). ESI-MS m/z 423.0 (M+H$^+$). Melting Point: 182° C.

Example 45

Synthesis of 1-(3-(2-methoxyethyl)-4-oxo-3,4-dihydroquinazolin-6-yl)-3-(4-(trifluoromethyl)phenyl)urea (38): The compound was prepared by general procedure E provided in example 5 using compound 4 (0.10 g, 0.45 mmol), dry THF (5 mL), 4-(trifluoromethyl)phenyl isocyanate (0.1 mL, 0.68 mmol), TEA (0.2 mL, 1.36 mmol) to obtain compound 38 (0.07 g, 38%) as white solid. $^1$H NMR (300 MHz, $d_6$-DMSO) δ in ppm 9.25 (d, J=6.3 Hz, 2H), 8.37 (d, J=2.4 Hz, 1H), 8.18 (s, 1H), 7.82 (dd, J=9 Hz, 2.4 Hz, 1H), 7.71-7.62 (m, 5H), 4.15 (t, J=5.1 Hz, 2H), 3.61 (t, J=5.1 Hz, 2H), 3.25 (s, 3H). ESI-MS m/z 407.2 (M+H$^+$). Melting Point: 196° C.

Example 46

Synthesis of 1-(3-(2-methoxyethyl)-4-oxo-3,4-dihydroquinazolin-6-yl)-3-(2-(trifluoromethyl)phenyl)urea (39): The compound was prepared by general procedure E provided in example 5 using compound 4 (0.10 g, 0.45 mmol), dry THF (5 mL), 2-(Trifluoromethyl)phenyl isocyanate (0.1 mL, 0.68 mmol), TEA (0.2 mL, 1.36 mmol) to obtain compound 39 (0.066 g, 37%) as white solid. $^1$H NMR (300 MHz, $d_6$-DMSO) δ in ppm 9.79 (s, 1H), 8.38 (d, J=2.4 Hz, 1H), 8.19 (s, 1H), 8.17 (s, 1H), 7.96 (d, J=8.1 Hz, 1H), 7.78 (dd, J=9 Hz, J=2.7 Hz, 1H), 7.71-7.62 (m, 3H), 7.33-7.28 (m, 1H), 4.15 (t, J=5.1 Hz, 2H), 3.61 (t, J=5.1 Hz, 2H), 3.25 (s, 3H). ESI-MS m/z 407.2 (M+H$^+$). Melting Point: 220° C.

Example 47

Synthesis of 1-(3-(2-methoxyethyl)-4-oxo-3,4-dihydroquinazolin-6-yl)-3-(4-methoxyphenyl)urea (40): The compound was prepared by general procedure E provided in example 5 using compound 4 (0.10 g, 0.45 mmol), dry THF (5 mL), 4-methoxyphenylisocyanate (0.083 mL, 0.68 mmol), TEA (0.2 mL, 1.36 mmol) to obtain compound 40 (0.072 g, 43%) as off white solid. $^1$H NMR (300 MHz, $d_6$-DMSO) δ in ppm 9.02 (s, 1H), 8.58 (s, 1H), 8.33 (s, 1H), 8.15 (s, 1H), 7.79 (dd, J=8.7 Hz, J=1.2 Hz, 1H), 7.60 (d, J=9 Hz, 1H), 7.38 (d, J=8.7 Hz, 2H), 6.88 (d, J=8.7 Hz, 2H), 4.14 (t, J=5.1 Hz, 2H), 3.72 (s, 3H), 3.61 (t, J=5.1 Hz, 2H), 3.24 (s, 3H). ESI-HRMS m/z 369.1 (M+H$^+$). Melting Point: 206° C.

Example 48

Synthesis of 1-(3-(2-methoxyethyl)-4-oxo-3,4-dihydroquinazolin-6-yl)-3-(2-methoxyphenyl)urea (41): The compound was prepared by general procedure E provided in example 5 using compound 4 (0.10 g, 0.45 mmol), dry THF (5 mL), 2-methoxyphenylisocyanate (0.083 mL, 0.68 mmol), TEA (0.2 mL, 1.36 mmol) to obtain compound 41 (0.070 g, 41%) as off white solid. $^1$H NMR (300 MHz, $d_6$-DMSO) δ in ppm 9.71 (s, 1H), 8.37 (d, J=2.4 Hz, 1H), 8.29 (s, 1H), 8.17 (s, 1H), 8.14 (d, J=1.8 Hz, 1H), 7.76 (dd, J=8.8 Hz, 2.7 Hz, 1H), 7.62 (d, J=8.7 Hz, 1H), 7.05-6.88 (m, 3H), 4.15 (t, J=4.8 Hz, 2H), 3.89 (s, 3H), 3.61 (t, J=5.1 Hz, 2H), 3.25 (s, 3H). ESI-MS m/z 369.3 (M+H$^+$). Melting Point: 192° C.

Example 49

Synthesis of ethyl 3-(3-(3-(2-methoxyethyl)-4-oxo-3,4-dihydroquinazolin-6-yl)ureido)benzoate (42): The compound was prepared by general procedure E provided in example 5 using compound 4 (0.12 g, 0.54 mmol), dry THF (8 mL), 3-(Ethoxycarbonyl)phenyl isocyanate (0.1 mL, 0.65 mmol), TEA (0.2 mL, 1.36 mmol) to obtain compound 41 (0.080 g, 36%) as off white solid. $^1$H NMR (300 MHz, $d_6$-DMSO) δ in ppm 9.14 (s, 1H), 9.07 (s, 1H), 8.36 (s, 1H), 8.17 (s, 2H), 7.81 (d, J=7.2 Hz, 1H), 7.69-7.57 (m, 3H), 7.46-7.41 (m, 1H), 4.32 (q, J=4.5 Hz, 2H), 4.15 (t, J=4.8 Hz, 2H), 3.61 (t, J=5.1 Hz, 2H), 3.25 (s, 3H), 1.31 (t, J=7.2 Hz, 3H). ESI-MS m/z 411.2 (M+H$^+$). Melting Point: 170° C.

Example 50

Synthesis of 6-amino-5-bromo-3-(2-methoxyethyl) quinazolin-4 (3H)-one (43): Compound 4 (2 g, 6.73 mmol) was dissolved in acetic acid (15 mL). Liq. bromine (0.56 mL, 1.2 equiv.) was added in DCM (4 mL) and then the resultant solution was added dropwise at 0° C. to the reaction mixture over a period for 15 minutes. Then, the reaction mixture was allowed to stir at room temperature for 3 hrs. After completion of reaction, it was worked up with ethyl acetate and aqueous $NaHCO_3$ soln. Then, it was purified by column chromatography (Silica gel, mesh size 100-200) eluting (70% EtOAc/Pet ether) to obtain compound 43 as light brown solid at 66% yield. $^1$H NMR (400 MHz, $CDCl_3$) δ in ppm 7.90 (s, 1H), 7.48 (d, J=8.8 Hz, 1H), 7.15 (d, J=8.8 Hz, 1H), 4.56 (s, 2H), 4.11 (t, J=4.4 Hz, 2H), 3.65 (t, J=4.4 Hz, 2H), 3.30 (s, 3H). ESI-HRMS m/z 298.0184 (M+H$^+$). Melting Point: 132° C.

Example 51

Synthesis of 6-amino-3-(2-methoxyethyl)-5-phenylquinazolin-4 (3H)-one (44): The compound was prepared by general procedure F provided in example 6 using compound 43 (0.20 g, 0.67 mmol), benzene boronic acid (0.099 g, 0.80 mmol), cesium carbonate (0.44 g, 1.34 mmol), solution of dioxane, $H_2O$ (9:1) (10 mL), $Pd_2(dba)_3$ (0.061 g, 0.06 mmol), X-phos (0.064 g, 0.13 mmol) to obtain compound 44 (0.125 g, 63%) as light yellow solid. $^1H$ NMR (400 MHz, $CDCl_3$) δ in ppm 7.88 (s, 1H), 7.55 (d, J=8.8 Hz, 1H), 7.48-7.45 (m, 2H), 7.40-7.36 (m, 1H), 7.24-7.22 (m, 2H), 7.15 (d, J=8.4 Hz, 1H), 3.97 (t, J=4.4 Hz, 2H), 3.68 (br.s., 2H), 3.49 (t, J=4.4 Hz, 2H), 3.26 (s, 3H). ESI-HRMS m/z 296.1410 (M+H$^+$).

Example 52

Synthesis of 1-(3-acetylphenyl)-3-(3-(2-methoxyethyl)-4-oxo-5-phenyl-3,4-dihydroquinazolin-6-yl)urea (45): The compound was prepared by general procedure D provided in example 4 using compound 44 (0.10 g, 0.33 mmol), dry THF (5 mL), 4-nitrophenylchloroformate (0.096 g, 0.47 mmol), 3'-aminoacetophenone (0.051 g, 0.37 mmol), TEA (0.19 mL, 1.35 mmol) to obtain compound 45 (0.07 g, 45%) as yellow solid. $^1H$ NMR (400 MHz, $d_6$-DMSO) δ in ppm 9.35 (s, 1H), 8.32 (d, J=8.8 Hz, 1H), 8.13 (s, 1H), 7.88 (s, 1H), 7.62 (d, J=8.8 Hz, 1H), 7.57 (d, J=8.4 Hz, 1H), 7.50 (d, J=7.6 Hz, 1H), 7.42-7.32 (m, 5H), 7.12 (s, 1H), 7.11 (s, 1H), 3.90 (t, J=5.2 Hz, 2H), 3.39 (t, J=5.2 Hz, 2H), 3.16 (s, 3H), 2.48 (s, 3H). ESI-HRMS m/z 457.1876 (M+H$^+$).

Example 53

Synthesis of 6-amino-5-(4-fluorophenyl)-3-(2-methoxyethyl)quinazolin-4 (3H)-one (46): The compound was prepared by general procedure F provided in example 6 using compound 43 (0.20 g, 0.67 mmol), 4-fluorophenylboronic acid (0.112 g, 0.80 mmol), cesium carbonate (0.437 g, 1.34 mmol), dioxane/$H_2O$ (9:1) (10 mL), $Pd_2(dba)_3$ (0.062 g, 0.06 mmol), X-phos (0.064 g, 0.13 mmol) to obtain compound 46 (0.094 g, 45%) as yellow solid. $^1H$ NMR (600 MHz, $d_6$-DMSO) δ in ppm 7.93 (s, 1H), 7.42 (d, J=9 Hz, 1H), 7.23 (d, J=9 Hz, 1H), 7.19-7.16 (m, 2H), 7.12-7.09 (m, 2H), 4.77 (s, 2H), 3.89 (t, J=4.8 Hz, 2H), 3.41 (t, J=2.7 Hz, 2H), 3.19 (s, 3H). ESI-MS m/z 314.1 (M+H$^+$).

Example 54

Synthesis of 1-(3-acetylphenyl)-3-(5-(4-fluorophenyl)-3-(2-methoxyethyl)-4-oxo-3,4-dihydroquinazolin-6-yl)urea (47): The compound was prepared by general procedure D provided in example 4 using compound 46 (0.08 g, 0.25 mmol), dry THF (4 mL), 4-nitrophenylchloroformate (0.072 g, 0.35 mmol), 3'-aminoacetophenone (0.037 g, 0.28 mmol), TEA (0.17 mL, 1.22 mmol) to obtain compound 47 (0.049 g, 41%) as yellow solid. $^1H$ NMR (300 MHz, $CDCl_3$) δ in ppm 8.66 (d, J=9 Hz, 1H), 8.02 (s, 1H), 7.77 (d, J=9 Hz, 1H), 7.71-7.67 (m, 2H), 7.46-7.43 (m, 1H), 7.37-7.32 (m, 1H), 7.13-7.09 (m, 2H), 7.05-6.99 (m, 2H), 6.86 (s, 1H), 6.43 (s, 1H), 3.99 (t, J=4.5 Hz, 2H), 3.50 (t, J=4.8 Hz, 2H), 3.28 (s, 3H), 2.58 (s, 3H). ESI-MS m/z 475.1 (M+H$^+$).

Example 55

Synthesis of 6-amino-3-(2-methoxyethyl)-5-(pyridin-2-yl)quinazolin-4 (3H)-one (48): The compound was prepared by general procedure F provided in example 6 using compound 43 (0.20 g, 0.67 mmol), 2-pyridineboronic acid (0.98 g, 0.80 mmol), cesium carbonate (0.437 g, 1.34 mmol) dioxane/$H_2O$ (9:1) (10 mL), $Pd_2(dba)_3$ (0.062 g, 0.06 mmol), X-phos (0.064 g, 0.13 mmol) to obtain compound 48 (0.103 g, 52%) as yellow solid.

Example 56

Synthesis of 1-(3-acetylphenyl)-3-(3-(2-methoxyethyl)-4-oxo-5-(pyridin-2-yl)-3,4-dihydroquinazolin-6-yl)urea (49): The compound was prepared by general procedure D provided in example 4 using compound 48 (0.08 g, 0.25 mmol), dry THF, 4-nitrophenylchloroformate (0.072 g, 0.35 mmol). 3'-aminoacetophenone (0.037 g, 0.28 mmol), TEA (0.17 mL, 1.22 mmol) to obtain compound 49 (0.046 g, 38%) as yellow solid.

Example 57

Synthesis of 6-amino-3-(2-methoxyethyl)-5-(pyridin-3-yl)quinazolin-4 (3H)-one (50): The compound was prepared by general procedure F provided in example 6 using compound 43 (0.20 g, 0.67 mmol), 3-pyridineboronic acid (0.98 g, 0.80 mmol), cesium carbonate (0.437 g, 1.34 mmol), dioxane/$H_2O$ (9:1) (10 mL), $Pd_2(dba)_3$ (0.062 g, 0.06 mmol), (0.064 g, 0.13 mmol) to obtain compound 50 (0.115 g, 58%) as yellow solid. $^1H$ NMR (600 MHz, $d_6$-DMSO) δ in ppm 8.49 (dd, J=3.6 Hz, 1.2 Hz, 1H), 8.27 (d, J=1.8 Hz, 1H), 7.95 (s, 1H), 7.54-7.52 (m, 1H), 7.46 (d, J=9 Hz, 1H), 7.40-7.38 (m, 1H), 7.26 (d, J=9 Hz, 1H), 4.91 (s, 2H), 3.90 (t, J=4.8 Hz, 2H), 3.42 (t, J=5.4 Hz, 2H), 3.18 (s, 3H). ESI-MS m/z 297.2 (M+H$^+$).

Example 58

Synthesis of 1-(3-acetylphenyl)-3-(3-(2-methoxyethyl)-4-oxo-5-(pyridin-3-yl)-3,4-dihydroquinazolin-6-yl)urea (51): The compound was prepared by general procedure D provided in example 4 using compound 50 (0.08 g, 0.25 mmol), dry THF (4 mL) and 4-nitrophenylchloroformate (0.072 g, 0.35 mmol), 3'-aminoacetophenone (0.037 g, 0.28 mmol), TEA (0.17 mL, 1.22 mmol) to obtain compound 51 (0.046 g, 38%) as yellow solid. ESI-MS m/z 458.3 (M+H$^+$).

Example 59

Synthesis of 6-amino-3-(2-methoxyethyl)-5-(pyridin-4-yl)quinazolin-4 (3H)-one (52): The compound was prepared by general procedure F provided in example 6 using compound 43 (0.20 g, 0.67 mmol), 4-pyridineboronic acid (0.98 g, 0.80 mmol), cesium carbonate (0.437 g, 1.34 mmol), dioxane/$H_2O$ (9:1) (10 mL), $Pd_2(dba)_3$ (0.062 g, 0.06 mmol), X-phos (0.064 g, 0.13 mmol) to obtain compound 52 (0.103 g, 52%) as yellow solid. $^1H$ NMR (600 MHz, $CDCl_3$) δ in ppm 8.73 (d, J=3.6 Hz, 2H), 7.92 (s, 1H), 7.62 (d, J=8.4 Hz, 1H), 7.23 (d, J=6 Hz, 2H), 7.18 (d, J=8.4 Hz, 1H), 4.00 (t, J=4.8 Hz, 2H), 3.68 (s, 2H), 3.53 (t, J=4.8 Hz, 2H), 3.29 (s, 3H). ESI-MS m/z 297.2 (M+H$^+$).

Example 60

Synthesis of 1-(3-acetylphenyl)-3-(3-(2-methoxyethyl)-4-oxo-5-(pyridin-4-yl)-3,4-dihydroquinazolin-6-yl)urea (53):

The compound was prepared by general procedure D provided in example 4 using compound 52 (0.08 g, 0.25 mmol), dry THF (4 mL), 4-nitrophenylchloroformate (0.072 g, 0.35 mmol), 3'-aminoacetophenone (0.037 g, 0.28 mmol), TEA (0.17 mL, 1.22 mmol) to obtain compound 53 (0.039 g, 32%) as yellow solid.

Example 61

Synthesis of 6-amino-3-(2-methoxyethyl)-5-(6-methoxypyridin-3-yl)quinazolin-4 (3H)-one (54): The compound was prepared by general procedure F provided in example 6 using compound 43 (0.20 g, 0.67 mmol), 2-methoxypyridine-5-boronic acid pinacol ester (0.19 g, 0.80 mmol), cesium carbonate (0.437 g, 1.34 mmol), dioxane/$H_2O$ (9:1) (10 mL), $Pd_2(dba)_3$ (0.062 g, 0.06 mmol), X-phos (0.064 g, 0.13 mmol) to obtain compound 54 (0.1 g, 46%) as yellow solid. $^1H$ NMR (300 MHz, $d_6$-DMSO) δ in ppm 7.95 (s, 1H), 7.86 (d, J=2.1 Hz, 1H), 7.46-7.42 (m, 2H), 7.25 (d, J=8.7 Hz, 1H), 6.83 (d, J=8.4 Hz, 1H), 4.95 (s, 2H), 3.92 (t, J=5.1 Hz, 2H), 3.89 (s, 3H), 3.44 (t, J=5.1 Hz, 2H), 3.20 (s, 3H). ESI-HRMS m/z 327.1470 ($M+H^+$).

Example 62

Synthesis of 1-(3-acetylphenyl)-3-(3-(2-methoxyethyl)-5-(6-methoxypyridin-3-yl)-4-oxo-3,4-dihydroquinazolin-6-yl)urea (55): The compound was prepared by general procedure D provided in example 4 using compound 54 (0.10 g, 0.30 mmol), dry THF (4 mL), 4-nitrophenylchloroformate (0.087 g, 0.42 mmol), 3'-aminoacetophenone (0.046 g, 0.33 mmol), TEA (0.17 mL, 1.22 mmol) to obtain compound 55 (0.075 g, 46%) as yellow solid. $^1H$ NMR (400 MHz, $d_6$-DMSO) δ in ppm 9.30 (s, 1H), 8.41 (d, J=8.8 Hz, 1H), 8.13 (s, 1H), 7.90-7.88 (m, 2H), 7.64 (d, J=9.2 Hz, 1H), 7.58 (d, J=6.0 Hz, 1H), 7.51 (d, J=8.0 Hz, 1H), 7.46 (dd, J=8.4 Hz, 1H), 7.39-7.36 (m, 2H), 6.85 (d, J=8.4 Hz, 1H), 3.92 (t, J=5.2 Hz, 2H), 3.88 (s, 3H), 3.40 (t, J=5.2 Hz, 2H), 3.16 (s, 3H), 2.49 (s, 3H). ESI-MS m/z 488.1 ($M+H^+$).

Example 63

Synthesis of 6-amino-3-(2-methoxyethyl)-5-(2-methoxypyridin-3-yl)quinazolin-4 (3H)-one (56): The compound was prepared by general procedure F provided in example 6 using compound 43 (0.20 g, 0.67 mmol), 2-methoxy-3-pyridinylboronic acid (0.123 g, 0.80 mmol), cesium carbonate (0.437 g, 1.34 mmol), dioxane/$H_2O$ (9:1) (10 mL), $Pd_2(dba)_3$ (0.062 g, 0.06 mmol), X-phos (0.064 g, 0.13 mmol) to obtain compound 56 (0.12 g, 58%) as yellow solid.

Example 64

Synthesis of 1-(3-acetylphenyl)-3-(3-(2-methoxyethyl)-5-(2-methoxypyridin-3-yl)-4-oxo-3,4-dihydroquinazolin-6-yl)urea (57): The compound was prepared by general procedure D provided in example 4 using compound 56 (0.10 g, 0.30 mmol), dry THF (4 mL), 4-nitrophenylchloroformate (0.087 g, 0.42 mmol), 3'-aminoacetophenone (0.046 g, 0.33 mmol), TEA (0.17 mL, 1.22 mmol) to obtain compound 57 (0.075 g, 46%) as yellow solid.

Example 65

Synthesis of tert-butyl 4-(6-amino-3-(2-methoxyethyl)-4-oxo-3,4-dihydroquinazolin-5-yl)-5,6-dihydropyridine-1 (2H)-carboxylate (58): The compound was prepared by general procedure F provided in example 6 using compound 43 (0.2 g, 0.67 mmol), tert-butyl 5-(4,4,5,5-tetramethyl-1,3,2-dioxaborolan-2-yl)-3,6-dihydropyridine-1 (2H)-carboxylate (0.25 g, 0.80 mmol), cesium carbonate (0.437 g, 1.34 mmol), dioxane, $H_2O$ (9:1) (10 mL), $Pd_2(dba)_3$ (0.062 g, 0.06 mmol), X-phos (0.064 g, 0.13 mmol) to obtain compound 58 (0.12 g, 47%) as light brown solid. $^1H$ NMR (300 MHz, $d_6$-DMSO) δ in ppm 7.93 (s, 1H), 7.32 (d, J=8.7 Hz, 1H), 7.19 (d, J=8.7 Hz, 1H), 5.36 (s, 1H), 5.18 (s, 1H), 4.12-4.09 (m, 2H), 4.03 (t, J=4.8 Hz, 2H), 3.80-3.73 (m, 2H), 3.53 (t, J=5.1 Hz, 2H), 3.23 (s, 3H), 2.82-2.31 (m, 1H), 2.09-2.03 (m, 1H), 1.45 (s, 9H). ESI-MS m/z 401.2185 ($M+H^+$).

Example 66

Synthesis of tert-butyl 4-(6-(3-(3-acetylphenyl)ureido)-3-(2-methoxyethyl)-4-oxo-3,4-dihydroquinazolin-5-yl)-5,6-dihydropyridine-1 (2H)-carboxylate (59): The compound was prepared by general procedure D provided in example 4 using compound 58 (0.1 g, 0.25 mmol), dry THF (3 mL), 4-nitrophenylchloroformate (0.071 g, 0.35 mmol), 3'-aminoacetophenone (0.037 g, 0.27 mmol), TEA (0.07 mL, 0.50 mmol) to obtain compound 59 (0.07 g, 53%) as off white solid. $^1H$ NMR (400 MHz, $CDCl_3$), δ in ppm 8.55 (d, J=9.2 Hz, 1H), 8.36 (brs, 1H), 8.07 (s, 1H), 8.00 (s, 1H), δ 7.71 (d, J=8.4 Hz, 1H), 7.67 (d, J=9.2 Hz, 1H), 7.62 (d, J=6.4 Hz, 2H), 7.38 (t, J=7.6 Hz, 1H), 5.55 (brs, 1H), 4.38 (d, J=11.4 Hz, 1H), 4.10 (t, J=4.8 Hz, 2H), 4.38 (d, J=15.4 Hz, 1H), 3.61 (t, J=5.2 Hz, 2H), 3.50-3.43 (m, 1H), 3.31 (s, 3H), 2.58 (s, 3H), 2.27 (brs, 3H), 1.45 (s, 9H). ESI-HRMS m/z 562.2667 ($M+H^+$).

Example 67

Synthesis of 1-(3-acetylphenyl)-3-(3-(2-methoxyethyl)-4-oxo-5-(1,2,3,6-tetrahydropyridin-4-yl)-3,4-dihydroquinazolin-6-yl)urea (60): Compound 59 (0.10 g, 0.17 mmol) was dissolved in dry DCM (2 mL) and TFA (0.5 mL) was added dropwise at 0° C. and reaction mixture was stirred at room temperature for 2 hours. After completion of reaction, it was washed with ethyl acetate and aq. $NaHCO_3$ solution and purified by column chromatography (Silica gel, mesh size 100-200, Merck) eluting (5% MeOH—$CHCl_3$) to obtain compound 60 (0.05 g, 61%) as off white solid. $^1H$ NMR (300 MHz, $CDCl_3$), δ in ppm 8.71 (d, J=9.0 Hz, 1H), 8.10 (s, 1H), 7.94 (s, 1H), 7.68 (d, J=8.1 Hz, 1H), 7.58 (d, J=9.0 Hz, 1H), 7.51 (d, J=7.5 Hz, 1H), 7.31 (d, J=8.1 Hz, 1H), 5.52 (s, 1H), 4.02 (t, J=4.5 Hz, 2H), 3.68-3.62 (m, 2H), 3.54 (t, J=4.5 Hz, 2H), 3.37-3.30 (m, 2H), 3.24 (s, 3H), 2.73-2.66 (m, 1H), 2.52 (s, 3H), 2.38-2.33 (m, 1H). ESI-HRMS m/z 462.2142 ($M+H^+$).

Example 68

Synthesis of tert-butyl 4-(6-(3-(3-acetylphenyl)ureido)-3-(2-methoxyethyl)-4-oxo-3,4-dihydroquinazolin-5-yl)piperidine-1-carboxylate (61): The compound was prepared by general procedure C provided in example 3 using compound 59 (0.10 g, 0.17 mmol), MeOH (5 mL), a pinch of Pd/C under hydrogen atmosphere to obtain compound 61 (0.032 g, 32%) as off white solid. $^1H$ NMR (300 MHz, $d_6$-DMSO), δ in ppm 9.41 (s, 1H), 8.38-8.32 (m, 1H), 8.17 (s, 1H), 7.77 (s, 1H), 7.57 (d, J=9.0 Hz, 1H), 7.38 (d, J=7.5 Hz, 2H), 7.22 (t, J=7.8 Hz, 1H), 6.94 (d, J=7.5 Hz, 1H), 5.47 (s, 1H), 5.14 (s, 1H), 4.69-4.67 (m, 1H), 4.17 (d, J=18.0 Hz, 1H), 4.08 (t, J=4.8 Hz, 2H), 3.86-3.80 (m, 2H), 3.56 (t, J=4.8 Hz, 2H), 3.25 (s, 3H), 2.24-2.15 (m, 3H), 1.45 (s, 9H), 1.30 (d, J=6.3 Hz, 3H). ESI-HRMS m/z 564.2819 (M+H+).

Example 69

Synthesis of 1-(3-acetylphenyl)-3-(3-(2-methoxyethyl)-4-oxo-5-(piperidin-4-yl)-3,4-dihydroquinazolin-6-yl)urea (62): The compound was prepared by general procedure C provided in example 3 using compound 60 (0.10 g, 0.21 mmol), MeOH (8 mL), pinch of Pd/C was added under nitrogen hydrogen atmosphere to obtain compound 62 (0.023 g, 23%) as off white solid. $^1$H NMR (300 MHz, $d_6$-DMSO) δ in ppm 8.74 (d, J=9.3 Hz, 1H), 7.96 (br.s, 2H), 7.62 (d, J=9.3 Hz, 1H), 7.44 (s, 1H), 7.36 (d, J=8.1 Hz, 1H), 7.16-7.10 (m, 1H), 6.79 (d, J=7.5 Hz, 1H), 5.55 (s, 1H), 4.05 (t, J=4.5 HZ, 2H), 3.91-3.86 (m, 1H), 3.72-3.66 (m, 1H), 3.57 (t, J=4.5 Hz, J=4.5 Hz, 2H), 3.43-3.40 (m, 2H), 3.28 (s, 3H), 3.08 (s, 3H), 3.01-2.95 (m, 3H), 2.60-2.43 (m, 3H). ESI-MS m/z 464.2 (M+H+).

Example 70

Synthesis of 6-amino-3-(2-methoxyethyl)-5-(4-methoxyphenyl)quinazolin-4 (3H)-one (63): The compound was prepared by general procedure F provided in example 6 using compound 43 (0.150 g, 0.50 mmol), 4-methoxyphenylboronic acid (0.1 g, 0.60 mmol, dioxane/$H_2O$ (9:1) (5 mL) and $K_2CO_3$ (0.2 mL, 2 M) solution, $Pd(PPh_3)_4$ (0.058 g, 0.05 mmol) to obtain compound 63 (0.1 g, 61%) as brown solid. $^1$H NMR (600 MHz, $d_6$-DMSO) δ in ppm 7.92 (s, 1H), 7.40 (d, J=9 Hz, 1H), 7.22 (d, J=9 Hz, 1H), 7.00 (d, J=9 Hz, 2H), 6.94 (d, J=9 Hz, 2H), 4.70 (t, J=5.4 Hz, 2H), 3.89 (t, J=5.4 Hz, 2H), 3.78 (s, 3H), 3.42 (t, J=5.4 Hz, 2H), 3.19 (s, 3H). ESI-MS m/z 326.1 (M+H+).

Example 71

Synthesis of 1-(3-acetylphenyl)-3-(3-(2-methoxyethyl)-5-(4-methoxyphenyl)-4-oxo-3,4-dihydroquinazolin-6-yl)urea (64): The compound was prepared by general procedure D provided in example 4 using compound 63 (0.1 g, 0.30 mmol), dry THF (3 mL), 4-nitrophenylchloroformate (0.093 g, 0.46 mmol), 3'-Aminoacetophenone (0.06 g, 0.46 mmol), TEA (0.1 mL, 0.75 mmol) to obtain compound 64 (0.06 g, 40%) as off white solid. $^1$H NMR (300 MHz, $CDCl_3$) δ in ppm 8.68 (d, J=9 Hz, 1H), 7.99 (s, 1H), 7.74 (d, J=9 Hz, 1H), 7.63 (d, J=7.8 Hz, 1H), 7.49 (d, J=7.8 Hz, 1H), 7.33-7.30 (m, 1H), 7.05 (d, J=8.1 Hz, 3H), 6.85 (d, J=8.4 Hz, 2H), 6.58 (s, 1H), 3.97 (t, J=4.8 Hz, 2H), 3.76 (s, 3H), 3.49 (t, J=4.8 Hz, 2H), 3.26 (s, 3H), 2.56 (s, 3H). ESI-MS m/z 487.2003 (M+H+).

Example 72

Synthesis of 6-amino-3-(2-methoxyethyl)-5-(4-(trifluoromethyl)phenyl)quinazolin-4 (3H)-one (65): The compound was prepared by general procedure F provided in example 6 using compound 43 (0.20 g, 0.67 mmol), 4-(trifluoromethyl)phenylboronic acid (0.153 g, 0.80 mmol), cesium carbonate (0.437 g, 1.34 mmol), dioxane/$H_2O$ (9:1) (8 mL), $Pd_2(dba)_3$ (0.062 g, 0.06 mmol), X-phos (0.064 g, 0.13 mmol) to obtain compound 65 (0.146 g, 60%) as yellow solid. ESI-HRMS m/z 364.1281 (M+H+).

Example 73

Synthesis of 1-(3-acetylphenyl)-3-(3-(2-methoxyethyl)-4-oxo-5-(4-(trifluoromethyl)phenyl)-3,4-dihydroquinazolin-6-yl)urea (66): The compound was prepared by general procedure D provided in example 4 using compound 65 (0.1 g, 0.27 mmol), dry THF (3 mL), 4-nitrophenylchloroformate (0.081 g, 0.40 mmol), 3'-Aminoacetophenone (0.054 g, 0.40 mmol), TEA (0.1 mL, 0.65 mmol) to obtain compound 66 (0.054 g, 38%) as off white solid. $^1$H NMR (300 MHz, $d_6$-DMSO) δ in ppm 9.29 (s, 1H), 8.37 (d, J=9 Hz, 1H), 8.21 (s, 1H), 7.94 (brs, 1H), 7.80 (d, J=8.1 Hz, 2H), 7.72 (d, J=9 Hz, 1H), 7.62-7.55 (m, 3H), 7.43 (d, J=2.7 Hz, 1H), 7.41 (d, J=3 Hz, 1H), 7.27 (s, 1H), 3.96 (t, J=4.5 Hz, 2H), 3.44 (t, J=4.8 Hz, 2H), 3.21 (s, 3H), 2.54 (s, 3H). ESI-HRMS m/z 525.1769 (M+H+).

Example 74

Synthesis of 6-amino-5-cyclohexyl-3-(2-methoxyethyl) quinazolin-4 (3H)-one (67): The compound was prepared by general procedure F provided in example 6 using compound 43 (0.20 g, 0.67 mmol), cyclohexylboronic acid (0.102 g, 0.80 mmol), cesium carbonate (0.437 g, 1.34 mmol), dioxane/$H_2O$ (9:1) (8 mL), $Pd_2(dba)_3$ (0.062 g, 0.06 mmol), X-phos (0.064 g, 0.13 mmol) to obtain compound 67 (0.121 g, 60%) as yellow solid.

Example 75

Synthesis of 1-(3-acetylphenyl)-3-(5-cyclohexyl-3-(2-methoxyethyl)-4-oxo-3,4-dihydroquinazolin-6-yl)urea (68): The compound was prepared by general procedure D provided in example 4 using compound 67 (0.1 g, 0.33 mmol), dry THF (3 mL), 4-nitrophenylchloroformate (0.100 g, 0.49 mmol), 3'-Aminoacetophenone (0.066 g, 0.49 mmol), TEA (0.11 mL, 0.82 mmol) to obtain compound 68 (0.053 g, 35%) as off white solid.

Example 76

Synthesis of 6-amino-5-cyclopentyl-3-(2-methoxyethyl) quinazolin-4 (3H)-one (69): The compound was prepared by general procedure F provided in example 6 using compound 43 (0.20 g, 0.67 mmol), cyclopentylboronic acid (0.091 g, 0.80 mmol), cesium carbonate (0.437 g, 1.34 mmol), dioxane/$H_2O$ (9:1) (8 mL), $Pd_2(dba)_3$ (0.062 g, 0.06 mmol), X-phos (0.064 g, 0.13 mmol) to obtain compound 69 (0.116 g, 60%) as yellow solid.

Example 77

Synthesis of 1-(3-acetylphenyl)-3-(5-cyclopentyl-3-(2-methoxyethyl)-4-oxo-3,4-dihydroquinazolin-6-yl)urea (70): The compound was prepared by general procedure D provided in example 4 using compound 69 (0.1 g, 0.34 mmol), dry THF (3 mL), 4-nitrophenylchloroformate (0.102 g, 0.51 mmol), 3'-Aminoacetophenone (0.068 g, 0.51 mmol), TEA (0.10 mL, 0.85 mmol) to obtain compound 70 (0.065 g, 42%) as off white solid.

Example 78

Synthesis of 6-amino-5-isopropyl-3-(2-methoxyethyl) quinazolin-4 (3H)-one (71): The compound was prepared by general procedure F provided in example 6 using compound 43 (0.20 g, 0.67 mmol), isopropylboronic acid (0.070 g, 0.80 mmol), cesium carbonate (0.437 g, 1.34 mmol), dioxane/$H_2O$ (9:1) (8 mL), $Pd_2(dba)_3$ (0.062 g, 0.06 mmol), X-phos (0.064 g, 0.13 mmol) to obtain compound 71 (0.126 g, 72%) as yellow solid.

Example 79

Synthesis of 1-(3-acetylphenyl)-3-(5-isopropyl-3-(2-methoxyethyl)-4-oxo-3,4-dihydroquinazolin-6-yl)urea (72): The compound was prepared by general procedure D provided in example 4 using compound 71 (0.1 g, 0.38 mmol), dry THF (3 mL) and 4-Nitrophenylchloroformate (0.114 g, 0.57 mmol), 3'-Aminoacetophenone (0.07 g, 0.57 mmol), TEA (0.13 mL, 0.85 mmol) to obtain compound 72 (0.072 g, 45%) as off white solid.

Example 80

Synthesis of 1-(3-acetylphenyl)-3-(5-bromo-3-(2-methoxyethyl)-4-oxo-3,4-dihydroquinazolin-6-yl)urea (73): The compound was prepared by general procedure D provided in example 4 using compound 43 (0.1 g, 0.33 mmol), dry THF (6 mL) and 4-nitrophenylchloroformate (0.101 g, 0.50 mmol), 3'-aminoacetophenone (0.054 g, 0.40 mmol), TEA (0.2 mL, 1.38 mmol) to obtain compound 73 (0.071 g, 46%) as off white solid. $^1$H NMR (400 MHz, $d_6$-DMSO) δ in ppm 9.80 (s, 1H), 8.46 (s, 1H), 8.41 (d, J=9.2 Hz, 1H), 8.20 (s, 1H), 8.04-8.03 (m, 1H), 7.67-7.64 (m, 1H), 7.60 (d, J=8.8 Hz, 1H), 7.56 (d, J=7.6 Hz, 1H), 7.43-7.39 (m, 1H), 4.07 (t, J=5.2 Hz, 2H), 3.55 (t, J=5.2 Hz, 2H), 3.20 (s, 3H), 2.52 (s, 3H). ESI-MS m/z 459.2 (M+H$^+$). Melting Point: 204° C.

Example 81

Synthesis of tert-butyl (1-((3-(2-methoxyethyl)-4-oxo-3,4-dihydroquinazolin-6-yl)amino)-3-methyl-1-oxobutan-2-yl)carbamate (74): N-Boc Valine (1 g, 4.60 mmol) was taken in DMF (8 mL) and HATU (2 g, 5.06 mmol) was added followed by TEA (1.5 mL, 11.41 mmol) and compound 4 (1 g, 5.06 mmol) and reaction mixture was stirred at room temperature for 5 hours. After completion of reaction, reaction mixture was washed thoroughly with cold water and extracted with EtOAc to afford reddish coloured crude mass which was then purified by column chromatography (Silica gel, mesh size 100-200) eluting (50% EtOAc/Pet ether) to obtain compound 74 (0.8 g, 42%) as brown solid. $^1$H NMR (300 MHz, $d_6$-DMSO) δ in ppm 10.36 (s, 1H), 8.52 (d, J=1.8 Hz, 1H), 8.19 (s, 1H), 7.95 (br.s, —NH), 7.64 (d, J=9 Hz, 1H), 6.98 (d, J=8.4 Hz, 1H), 4.15 (t, J=5.1 Hz, 2H), 3.93 (t, J=7.8 Hz, 1H), 3.60 (t, J=5.1 Hz, 2H), 3.24 (s, 3H), 2.04-1.96 (m, 1H), 1.38 (s, 9H), 0.90 (d, J=6.6 Hz, 6H). ESI-HRMS m/z 419.2296 (M+H$^+$). Melting Point: 120° C.

Example 82

Synthesis of 2-amino-N-(3-(2-methoxyethyl)-4-oxo-3,4-dihydroquinazolin-6-yl)-3-methylbutanamide (75): Compound 74 (0.2 g, 0.47 mmol) was taken in DCM (3 mL) and TFA (0.8 mL) was added dropwise under cooling condition. After 2 hours, the reaction was completed and reaction mixture was neutralized by $NaHCO_3$ solution and extracted with DCM; evaporated to obtain compound 75 (0.11 g, 72%) as white solid. $^1$H NMR (400 MHz, $d_6$-DMSO) δ in ppm 9.85 (s, 1H), 8.26 (d, J=7.2 Hz, 1H), 8.20 (d, J=2 Hz, 1H), 7.98 (s, 1H), 7.65 (d, J=8.8 Hz, 1H), 4.14 (t, J=4.4 Hz, 2H), 3.64 (t, J=4.4 Hz, 2H), 3.44-3.41 (m, 1H), 3.28 (s, 3H), 2.46-2.40 (m, 1H), 1.02 (d, J=6.8 Hz, 3H), 0.86 (d, J=6.8 Hz, 3H). ESI-HRMS m/z 319.1772 (M+H$^+$). Melting Point: 118° C.

Example 83

Synthesis of 2-(3-(3-acetylphenyl)ureido)-N-(3-(2-methoxyethyl)-4-oxo-3,4-dihydroquinazolin-6-yl)-3-methylbutanamide (76): The compound was prepared by general procedure E provided in example 5 using compound 75 (0.087 g, 0.27 mmol), dry THF (2 mL), 3-acetylphenyl isocyanate (0.05 mL, 0.32 mmol), TEA (0.1 mL, 0.60 mmol) to obtain compound 76 (0.062, 47%) as white solid. $^1$H NMR (300 MHz, $d_6$-DMSO) δ in ppm 10.55 (s, 1H), 8.95 (s, 1H), 8.53 (s, 1H), 8.20 (s, 1H), 8.00-7.95 (m, 2H), 7.65 (d, J=8.4 Hz, 1H), 7.59 (d, J=7.8 Hz, 1H), 7.52 (d, J=6.6 Hz, 1H), 7.41-7.36 (m, 1H), 6.57 (d, J=8.7 Hz, 1H), 4.32 (t, J=6.3 Hz, 1H), 4.14 (t, J=4.8 Hz, 2H), 3.60 (t, J=4.8 Hz, 2H), 3.24 (s, 3H), 2.53 (s, 3H), 2.13-2.02 (m, 1H), 0.95 (q, J=5.4 Hz, 6H). ESI-HRMS m/z 480.2266 (M+H$^+$). Melting Point: 202° C.

Example 84

Synthesis of N-(3-(2-methoxyethyl)-4-oxo-3,4-dihydroquinazolin-6-yl)-3-nitrobenzamide (77): 3-Nitrobenzoic acid (0.365 g, 2.19 mmol) was taken in dry DCM and oxalyl chloride (0.3 mL, 3.27 mmol) was added dropwise under cooling conditions and reaction mixture was stirred at room temperature for 1 hour. Excess oxalyl chloride was evaporated in rotavapor and diluted with DCM (5 mL). To it, compound 4 (0.4 g, 1.82 mmol) diluted with (5 mL) was added dropwise over a period of 5 minutes and the reaction mixture was kept for another 5 hours. After completion of reaction, reaction mixture was evaporated to obtain a yellow coloured crude mass which was purified by column chromatography (Silica gel, mesh size 100-200) eluting (50% EtOAc/Pet ether) to obtain compound 77 as yellow solid (0.35 g, 83% yield). $^1$H NMR (400 MHz, $d_6$-DMSO) δ in ppm 10.85 (s, 1H), 8.80 (brs, —NH), 8.62 (d, J=2.4 Hz, 1H), 8.42-8.39 (m, 2H), 8.20-8.17 (m, 2H), 7.83-7.79 (m, 1H), 7.66 (d, J=9.2 Hz, 1H), 4.13 (t, J=5.2 Hz, 2H), 3.58 (t, J=5.2 Hz, 2H), 3.21 (s, 3H). ESI-HRMS m/z 369.1214 (M+H$^+$). Melting Point: 212° C.

Example 85

Synthesis of 3-amino-N-(3-(2-methoxyethyl)-4-oxo-3,4-dihydroquinazolin-6-yl)benzamide (78): The compound was prepared by general procedure C provided in example 3 using compound 77 (0.25 g, 0.67 mmol), MeOH (8 mL) pinch of 10% wet Pd—C under hydrogen atmosphere to obtain compound 78 as yellow solid (0.2 g, 87% yield). $^1$H NMR (400 MHz, $d_6$-DMSO) δ in ppm 10.37 (s, 1H), 8.62 (d, J=2.4 Hz, 1H), 8.16 (s, 1H), 8.13 (dd, J=8.8 Hz, 2.4 Hz, 1H), 7.61 (d, J=9.2 Hz, 1H), 7.14-7.05 (m, 3H), 6.72 (d, J=9.6 Hz, 1H), 5.29 (brs, 2H), 4.12 (t, J=5.2 Hz, 2H), 3.58 (t, J=5.2 Hz, 2H), 3.21 (s, 3H). ESI-HRMS m/z 339.1214 (M+H$^+$). Melting Point: 132° C.

Example 86

Synthesis of 3-(3-(3-acetylphenyl)ureido)-N-(3-(2-methoxyethyl)-4-oxo-3,4-dihydroquinazolin-6-yl)benzamide (79): The compound was prepared by general procedure E provided in example 5 using compound 78 (0.11 g, 0.32 mmol), dry THF (8 mL), 3-acetylphenyl isocyanate (0.05 mL, 0.38 mmol), TEA (0.1 mL, 0.81 mmol) to obtain compound 79 (0.08 g, 49%) as light yellow solid. $^1$H NMR (300 MHz, $d_6$-DMSO) δ in ppm 10.62 (s 1H), 8.99 (s 1H), 8.98 (s 1H), 8.69 (d, J=2.4 Hz, 1H), 8.23-8.18 (m, 2H), 8.10-8.09 (m, 1H), 8.05-8.03 (m, 1H), 7.73-7.68 (m, 3H), 7.64-7.59 (m, 2H), 7.50-7.42 (m, 2H), 4.17 (t, J=5.1 Hz, 2H), 3.62 (t, J=5.1 Hz, 2H), 3.26 (s, 3H), 2.57 (s, 3H). ESI-HRMS m/z 500.1945 (M+H+). Melting Point: 140° C.

Example 87

Synthesis of ethyl 2-(2-amino-5-nitrobenzamido)acetate (80): The compound was prepared by general procedure A provided in example 1 using compound 1 (2 g, 10.98 mmol), DMF (12 mL), HATU (4.5 g, 12.08 mmol), Glycine ethyl ester hydrochloride (1.7 g, 12.08 mmol), TEA (4.5 mL, 32.96 mmol) to obtain compound 80 (2.5 g, 85%) as yellow solid. $^1$H NMR (400 MHz, $d_6$-DMSO) δ in ppm 9.11 (br.s, —NH), 8.52 (d, J=2.8 Hz, 1H), 7.99 (dd, J=9.2 Hz, 2.8 Hz, 1H), 7.73 (br.s, 2H), 6.77 (d, J=9.2 Hz, 1H), 4.08 (q, J=7.2 Hz, 2H), 3.92 (d, J=5.6 Hz, 2H), 1.16 (t, J=6.8 Hz, 3H). ESI-HRMS m/z 268.0941 (M+H+). Melting Point: 178° C.

Example 88

Synthesis of ethyl 2-(6-nitro-4-oxoquinazolin-3 (4H)-yl) acetate (81): The compound was prepared by general procedure B provided in example 2 using compound 80 (2.5 g, 9.36 mmol), trimethylorthoformate (TMOF) (10 mL, 93.63 mmol) to obtain compound 81 (2.3 g, 89%) as pale yellow solid. $^1$H NMR (400 MHz, $d_6$-DMSO) δ in ppm 8.82 (d, J=2.8 Hz, 1H), 8.60-8.57 (m, 2H), 7.92 (d, J=8.8 Hz, 1H), 4.87 (s, 2H), 4.17 (q, J=7.2 Hz, 2H), 1.21 (t, J=7.2 Hz, 3H). ESI-HRMS m/z 278.0785 (M+H+). Melting Point: 166° C.

Example 89

Synthesis of ethyl 2-(6-amino-4-oxoquinazolin-3 (4H)-yl)acetate (82): The compound was prepared by general procedure C provided in example 3 using compound 81 (1 g, 3.60 mmol), methanol (10 mL) pinch of 10% wet Pd—C under hydrogen atmosphere to obtain compound 82 (0.8 g, 90%) as yellow solid. $^1$H NMR (300 MHz, $d_6$-DMSO) δ in ppm 8.02 (s, 1H), 7.40 (d, J=8.7 Hz, 1H), 7.19 (d, J=2.4 Hz, 1H), 7.09 (dd, J=8.7 Hz, 2.7 Hz, 1H), 5.71 (s, 2H), 4.75 (s, 2H), 4.16 (q, J=7.2 Hz, 2H), 1.21 (t, J=7.2 Hz, 3H). ESI-HRMS m/z 248.1041 (M+H+). Melting Point: 138° C.

Example 90

Synthesis of ethyl 2-(6-(3-(3-chloro-4-fluorophenyl) ureido)-4-oxoquinazolin-3 (4H)-yl)acetate (83): The compound was prepared by general procedure E provided in example 5 using compound 82 (0.1 g, 0.40 mmol), dry THF (6 mL), 3-chloro-4-fluorophenyl isocyanate (0.08 mL, 0.68 mmol), TEA (0.2 mL, 1.36 mmol) to obtain compound 83 (0.059 g, 35%) as yellow solid. $^1$H NMR (300 MHz, $d_6$-DMSO) δ in ppm 9.23 (s, 1H), 9.00 (s, 1H), 8.33 (d, J=2.4 Hz, 1H), 8.25 (s, 1H), 7.86-7.80 (m, 2H), 7.66 (d, J=9 Hz, 1H), 7.35 (d, J=7.5 Hz, 2H), 4.81 (s, 2H), 4.17 (q, J=7.2 Hz, 2H), 1.22 (t, J=6.9 Hz, 3H). ESI-MS m/z 419.1 (M+H+). Melting Point: 220° C.

Example 91

Synthesis of ethyl 2-(4-oxo-6-(3-(4-(trifluoromethoxy) phenyl)ureido)quinazolin-3 (4H)-yl)acetate (84): The compound was prepared by general procedure E provided in example 5 using compound 82 (0.1 g, 0.40 mmol), dry THF (5 mL), 4-(trifluoromethoxy)phenyl isocyanate (0.07 mL, 0.50 mmol), TEA (0.2 mL, 1.66 mmol) to obtain compound 84 (70 mg, 43%) as white solid. $^1$H NMR (300 MHz, $d_6$-DMSO) δ in ppm 9.18 (s, 1H), 9.00 (s, 1H), 8.34 (d, J=2.1 Hz, 1H), 8.25 (s, 1H), 7.83 (dd, J=8 Hz, 2.1 Hz, 1H), 7.67-7.56 (m, 3H), 7.30 (d, J=8.4 Hz, 2H), 4.81 (s, 2H), 4.17 (q, J=7.2 Hz, 2H), 1.22 (t, J=6.9 Hz, 3H). ESI-MS m/z 451.13 (M+H+). Melting Point: 230° C.

Example 92

Synthesis of ethyl 2-(6-(3-(3-acetylphenyl)ureido)-4-oxo-quinazolin-3 (4H)-yl)acetate (85): The compound was prepared by general procedure E provided in example 5 using compound 82 (60 mg, 0.24 mmol), dry THF (5 mL), 3-acetylphenyl isocyanate (0.04 mL, 0.34 mmol), TEA (0.1 mL, 0.68 mmol) to obtain compound 85 (80 mg, 49%) as white solid. $^1$H NMR (300 MHz, $d_6$-DMSO) δ in ppm 9.21 (s, 1H), 9.05 (s, 1H), 8.36 (d, J=2.4 Hz, 1H), 8.25 (s, 1H), 8.10 (s, 1H), 7.85 (dd, J=8.8 Hz, 2.7 Hz, 1H), 7.72-7.59 (m, 3H), 7.48-7.43 (m, 1H), 4.82 (s, 2H), 4.18 (q, J=7.2 Hz, 2H), 2.57 (s, 3H), 1.22 (t, J=6.9 Hz, 3H). ESI-MS m/z 409.4 (M+H+). Melting Point: 196° C.

Example 93

Synthesis of 2-amino-N-(3-methoxypropyl)-5-nitrobenzamide (86): The compound was prepared by general procedure A provided in example 1 using compound 1 (0.8 g, 4.93 mmol), DMF (6 mL), HATU (1.8 g, 4.83 mmol), 3-methoxypropylamine (0.5 mL, 4.83 mmol), TEA (1.5 mL, 10.98 mmol) to obtain compound 86 (0.9 g, 90%) as yellow solid. $^1$H NMR (300 MHz, $d_6$-DMSO) δ in ppm 8.70 (br.s., —NH), 8.49 (d, J=2.4 Hz, 1H), 8.01 (dd, J=9.1 Hz, 2.4 Hz, 1H), 7.76 (br.s, 2H), 6.79 (d, J=9 Hz, 1H), 3.37 (t, J=6.3 Hz, 2H), 3.28 (t, J=6 Hz, 2H), 3.24 (s, 3H), 1.80-1.71 (m, 2H). ESI-HRMS m/z 254.1133 (M+H+). Melting Point: 102° C.

Example 94

Synthesis of 3-(3-methoxypropyl)-6-nitroquinazolin-4 (3H)-one (87): The compound was prepared by general procedure B provided in example 2 using compound 86 (0.6 g, 2.36 mmol), trimethylorthoformate (TMOF) (5 mL, 47.43 mmol) to obtain compound 87 (0.59 g, 95%) as pale yellow solid. $^1$H NMR (300 MHz, $d_6$-DMSO) δ in ppm 8.84 (d, J=2.4 Hz, 1H), 8.58-8.54 (m, 2H), 7.88 (d, J=9 Hz, 1H), 4.05 (t, J=7.2 Hz, 2H), 3.93 (t, J=6 Hz, 2H), 3.20 (s, 3H), 1.99-1.91 (m, 2H). ESI-MS m/z 264.2 (M+H+). Melting Point: 110° C.

Example 95

Synthesis of 6-amino-3-(3-methoxypropyl)quinazolin-4 (3H)-one (88): The compound was prepared by general procedure C provided in example 3 using compound 87 (0.3 g, 1.13 mmol), methanol (6 mL), pinch of 10% wet Pd—C under hydrogen atmosphere was added to obtain compound 88 (0.25 g, 94%) as brown solid. ESI-HRMS m/z 234.1253 (M+H+). Melting Point: 98° C.

Example 96

Synthesis of 1-(3-acetylphenyl)-3-(3-(3-methoxypropyl)-4-oxo-3,4-dihydroquinazolin-6-yl)urea (89): The compound was prepared by general procedure D provided in example 4 using compound 88 (0.12 g, 0.51 mmol), dry THF (8 mL), 4-nitrophenylchloroformate (0.124 g, 0.61 mmol), 3'-aminoacetophenone (0.084, 0.61 mmol), TEA (0.2 mL, 1.54 mmol) to obtain compound 89 (0.075 g, 37%) as off white solid. $^1$H NMR (400 MHz, $d_6$-DMSO) δ in ppm 9.08 (s, 1H), 8.95 (s, 1H), 8.30 (d, J=2.8 Hz, 1H), 8.16 (d, J=2 Hz, 1H), 8.05-8.04 (m, 1H), 7.77 (dd, J=8.8 Hz, 2.4 Hz, 1H), 7.67-7.64 (m, 1H), 7.58-7.54 (m, 2H), 7.42-7.38 (m, 1H), 3.97 (t, J=6.8 Hz, 2H), 3.31-3.30 (m, 2H) 3.17 (s, 3H), 2.52 (s, 3H), 1.91-1.85 (m, 2H). ESI-MS m/z 395.3 ($M+H^+$). Melting Point: 162° C.

Example 97

Synthesis of 2-amino-N-(2-ethoxyethyl)-5-nitrobenzamide (90): The compound was prepared by general procedure A provided in example 1 using compound 1 (0.8 g, 4.93 mmol), DMF (6 mL), HATU (1.8 g, 4.83 mmol), 2-ethoxyethylamine (0.5 mL, 4.83 mmol), TEA (1.5 mL, 10.98 mmol) to obtain compound 90 (1 g, 90%) as yellow solid. $^1H$ NMR (400 MHz, $d_6$-DMSO) δ in ppm 8.71 (br.s, —NH), 8.46 (d, J=2.8 Hz, 1H), 7.96 (dd, J=6.4 Hz, 2.8 Hz, 1H), 7.73 (s, 2H), 6.75 (d, J=9.2 Hz, 1H), 3.46-3.39 (m, 4H), 3.33 (q, J=6 Hz, 2H), 1.07 (t, J=6.8 Hz, 3H). ESI-HRMS m/z 254.1135 ($M+H^+$). Melting Point: 104° C.

Example 98

Synthesis of 3-(2-ethoxyethyl)-6-nitroquinazolin-4 (3H)-one (91): The compound was prepared by general procedure B provided in example 2 using compound 90 (0.85 g, 3.37 mmol), trimethylorthoformate (TMOF) (7 mL, 67.19 mmol) to obtain compound 91 (0.8 g, 96%) as pale yellow solid. $^1H$ NMR (400 MHz, $d_6$-DMSO) δ in ppm 8.80 (d, J=2.4 Hz, 1H), 8.51 (dd, J=6.4 Hz, 2.4 Hz, 1H), 8.45 (s, 1H), 7.83 (d, J=8.4 Hz, 1H), 4.15 (t, J=5.2 Hz, 2H), 3.62 (t, J=5.2 Hz, 2H), 3.40 (q, J=7.2 Hz, 2H), 1.00 (t, J=6.8 Hz, 3H). ESI-HRMS m/z 264.0975 ($M+H^+$). Melting Point: 138° C.

Example 99

Synthesis of 6-amino-3-(2-ethoxyethyl)quinazolin-4 (3H)-one (92): The compound was prepared by general procedure C provided in example 3 using compound 91 (0.55 g, 2.09 mmol), methanol (6 mL) and pinch of 10% wet Pd—C under hydrogen atmosphere to obtain compound 92 (0.45 g, 92%) as light brown solid. $^1H$ NMR (400 MHz, $d_6$-DMSO) δ in ppm 7.94 (s, 1H), 7.37 (d, J=8.4 Hz, 1H), 7.21 (d, J=2.4 Hz, 1H), 7.07 (dd, J=8.7 Hz, 2.7 Hz, 1H), 5.66 (s, 2H), 4.08 (t, J=5.4 Hz, 2H), 3.61 (t, J=5.4 Hz, 2H), 3.42 (q, J=6.9 Hz, 2H), 1.04 (t, J=7.2 Hz, 3H). ESI-HRMS m/z 234.1229 ($M+H^+$). Melting Point: 102° C.

Example 100

Synthesis of 1-(3-acetylphenyl)-3-(3-(2-ethoxyethyl)-4-oxo-3,4-dihydroquinazolin-6-yl)urea (93): The compound was prepared by general procedure E provided in example 5 using compound 92 (0.12 g, 0.51 mmol), THF (6 mL), 3-acetylphenyl isocyanate (0.09 mL, 0.61 mmol), TEA (0.2 mL, 1.28 mmol) to obtain compound 93 (0.06 g, 30%) as light yellow solid. $^1H$ NMR (600 MHz, $d_6$-DMSO) δ in ppm 9.12 (s, 1H), 8.99 (s, 1H), 8.35 (d, J=2.4 Hz, 1H), 8.16 (s, 1H), 8.08 (s, 1H), 7.80 (dd, J=9 Hz, 2.4 Hz, 1H), 7.70-7.68 (m, 1H), 7.62-7.58 (m, 2H), 7.45-7.42 (m, 1H), 4.12 (t, J=5.4 Hz, 2H), 3.63 (t, J=5.4 Hz, 2H), 3.42 (q, J=7.2 Hz, 2H), 2.56 (s, 3H), 1.03 (t, J=6.6 Hz, 3H). ESI-HRMS m/z 395.1728 ($M+H^+$). Melting Point: 192° C.

Example 101

Synthesis of 1-(4-acetylphenyl)-3-(3-(2-ethoxyethyl)-4-oxo-3,4-dihydroquinazolin-6-yl)urea (94): The compound was prepared by general procedure E provided in example 5 using compound 92 (0.12 g, 0.51 mmol), dry THF (6 mL), 4-acetylphenyl isocyanate, (0.09 mL, 0.61 mmol), TEA (0.2 mL, 1.28 mmol) to obtain compound 94 (0.07 g, 34%) as light yellow solid. $^1H$ NMR (600 MHz, $d_6$-DMSO) δ in ppm 9.21 (s, 1H), 9.18 (s, 1H), 8.36 (d, J=2.4 Hz, 1H), 8.16 (s, 1H), 7.90 (d, J=9 Hz, 2H), 7.79 (dd, J=8.4 Hz, 2.4 Hz, 1H), 7.62-7.59 (m, 3H), 4.12 (t, J=4.8 Hz, 2H), 3.63 (t, J=5.4 Hz, 2H), 3.42 (q, J=6.6 Hz, 2H), 2.50 (s, 3H), 1.03 (t, J=7.2 Hz, 3H). ESI-HRMS m/z 395.1727 ($M+H^+$). Melting Point: 102° C.

Example 102

Synthesis of 2-amino-N-ethyl-5-nitrobenzamide (95): The compound was prepared by general procedure A provided in example 1 using compound 1 (1 g, 5.49 mmol), DMF (6 mL), HATU (2.2 g, 6.04 mmol), ethylamine 2 M in THF (2.5 mL), TEA (1.9 mL, 13.73 mmol) to obtain compound 95 (1.1 g, 96%) as yellow solid. $^1H$ NMR (300 MHz, $CDCl_3$) δ in ppm 8.33 (d, J=2.7 Hz, 1H), 8.07 (dd, J=9 Hz, 2.4 Hz, 1H), 6.65 (d, J=9 Hz, 1H), 6.28 (br.s, —NH), 5.05 (br.s, 2H), 3.52-3.43 (m, 2H), 1.28 (t, J=7.2 Hz, 3H). ESI-HRMS m/z 210.0881 ($M+H^+$). Melting Point: 136° C.

Example 103

Synthesis of 3-ethyl-6-nitroquinazolin-4 (3H)-one (96): The compound was prepared by general procedure B provided in example 2 using compound 95 (0.80 g, 3.82 mmol), trimethylorthoformate (TMOF) (8 mL, 76.55 mmol) to obtain compound 96 (0.8 g, 95%) as pale yellow solid. $^1H$ NMR (300 MHz, $d_6$-DMSO) δ in ppm 8.82 (d, J=2.7 Hz, 1H), 8.61 (s, 1H), 8.53 (dd, J=9 Hz, 2.7 Hz, 1H), 7.86 (d, J=8.7 Hz, 1H), 4.03 (q, J=7.2 Hz, 2H), 1.29 (t, J=7.2 Hz, 3H). ESI-MS m/z 220.0728 ($M+H^+$). Melting Point: 146° C.

Example 104

Synthesis of 6-amino-3-ethylquinazolin-4 (3H)-one (97): The compound was prepared by general procedure C provided in example 3 using compound 96 (0.50 g, 2.28 mmol), methanol (6 mL) and pinch of 10% wet Pd—C under hydrogen atmosphere to obtain compound 97 (0.39 g, 90%) as light brown solid. $^1H$ NMR (400 MHz, $d_6$-DMSO) δ in ppm 8.06 (s, 1H), 7.37 (d, J=8.7 Hz, 1H), 7.21 (d, J=2.7 Hz, 1H), 7.06 (dd, J=8.7 Hz, 2.7 Hz, 1H), 5.64 (s, 2H), 3.95 (q, J=7.2 Hz, 2H), 1.25 (t, J=7.2 Hz, 3H). ESI-MS m/z 190.1 ($M+H^+$). Melting Point: 164° C.

Example 105

Synthesis of 1-(3-acetylphenyl)-3-(3-ethyl-4-oxo-3,4-dihydroquinazolin-6-yl)urea (98): The compound was prepared by general procedure E provided in example 5 using compound 97 (0.12 g, 0.63 mmol), dry THF (6 mL), 3-acetylphenyl isocyanate (0.10 mL, 0.76 mmol), TEA (0.2 mL, 1.58 mmol) to obtain compound 98 (0.08 g, 36%) as white solid. $^1H$ NMR (400 MHz, $d_6$-DMSO) δ in ppm 9.07 (s, 1H), 8.93 (s, 1H), 8.30 (d, J=2.4 Hz, 1H), 8.23 (s, 1H), 8.05-8.04 (m, 1H), 7.76 (dd, J=9 Hz, 2.4 Hz, 1H), 7.66-7.63 (m, 1H), 7.57-7.53 (m, 2H), 7.41-7.37 (m, 1H), 3.95 (q, J=7.2 Hz, 2H), 2.52 (s, 3H), 1.23 (t, J=7.2 Hz, 3H). ESI-HRMS m/z 351.1465 ($M+H^+$). Melting Point: 202° C.

Example 106

Synthesis of 1-(4-acetylphenyl)-3-(3-ethyl-4-oxo-3,4-dihydroquinazolin-6-yl)urea (99): The compound was prepared by general procedure E provided in example 5 using compound 97 (0.12 g, 0.63 mmol), dry THF (6 mL), 4-acetylphenyl isocyanate (0.10 mL, 0.76 mmol), TEA (0.2 mL, 1.58 mmol) to obtain compound 99 (0.08 g, 36%) as white solid. $^1$H NMR (400 MHz, $d_6$-DMSO) δ in ppm 9.13 (d, J=8.8 Hz, 2H), 8.31 (d, J=2.4 Hz, 1H), 8.24 (s, 1H), 7.86 (d, J=8.8 Hz, 2H), 7.75 (dd, J=6.4 Hz, 2.4 Hz, 1H), 7.58-7.55 (m, 3H), 3.95 (q, J=6.8 Hz, 2H), 2.96 (s, 3H), 1.23 (t, J=7.2 Hz, 3H). ESI-HRMS m/z 351.1464 (M+H$^+$). Melting Point: 212° C.

Example 107

Synthesis of 2-amino-N-(3-methoxyphenyl)-5-nitrobenzamide (100): The compound was prepared by general procedure A provided in example 1 using compound 1 (0.8 g, 4.93 mmol), DMF (6 mL), HATU (1.8 g, 4.83 mmol), m-anisidine (0.55 mL, 4.83 mmol), TEA (1.5 mL, 10.98 mmol) to obtain compound 100 (1.1 g, 90%) as yellow solid. $^1$H NMR (400 MHz, $d_6$-DMSO) δ in ppm 10.34 (s, 1H), 8.55 (d, J=2.4 Hz, 1H), 8.03 (dd, J=6.4 Hz, 2.8 Hz, 1H), 7.59 (s, 2H), 7.34-7.33 (m, 1H), 7.27-7.19 (m, 2H), 6.81 (d, J=9.2 Hz, 1H), 6.67-6.64 (m, 1H), 3.71 (s, 3H). ESI-HRMS m/z 288.0990 (M+H$^+$). Melting Point: 178° C.

Example 108

Synthesis of 3-(3-methoxyphenyl)-6-nitroquinazolin-4 (3H)-one (101): The compound was prepared by general procedure B provided in example 2 using compound 100 (0.80 g, 2.78 mmol), trimethylorthoformate (TMOF) (6 mL, 55.74 mmol) to obtain compound 101 (0.79 g, 96%) as light yellow solid. $^1$H NMR (400 MHz, $d_6$-DMSO) δ in ppm 8.83 (d, J=2.8 Hz, 1H), 8.57 (dd, J=6 Hz, 2.8 Hz, 1H), 8.51 (s, 1H), 7.90 (d, J=9.2 Hz, 1H), 7.47-7.43 (m, 1H), 7.16-7.15 (m, 1H), 7.10-7.06 (m, 2H), 3.76 (s, 3H). ESI-MS m/z 298.0 (M+H$^+$). Melting Point: 204° C.

Example 109

Synthesis of 6-amino-3-(3-methoxyphenyl)quinazolin-4 (3H)-one (102): The compound was prepared by general procedure C provided in example 3 using compound 101 (0.7 g, 2.35 mmol), methanol (6 mL) and pinch of 10% wet Pd—C under hydrogen atmosphere to obtain compound 102 (0.59 g, 94%) as light brown solid. $^1$H NMR (300 MHz, $d_6$-DMSO) 8.01 (s, 1H), 7.47-7.42 (m, 2H), 7.29 (d, J=2.7 Hz, 1H), 7.15-7.09 (m, 2H), 7.08-7.04 (m, 2H), 3.80 (s, 3H). ESI-MS m/z 268.1 (M+H$^+$). Melting Point: 188° C.

Example 110

Synthesis of 1-(3-acetylphenyl)-3-(3-(3-methoxyphenyl)-4-oxo-3,4-dihydroquinazolin-6-yl)urea (103): The compound was prepared by general procedure E provided in example 5 using compound 102 (0.12 g, 0.45 mmol), dry THF (7 mL), 3-acetylphenyl isocyanate (0.08 mL, 0.53 mmol), TEA (0.2 mL, 1.12 mmol) to obtain compound 103 (0.072 g, 37%) as light yellow solid. $^1$H NMR (400 MHz, $d_6$-DMSO) δ in ppm 9.13 (s, 1H), 8.95 (s, 1H), 8.34 (d, J=2.4 Hz, 1H), 8.16 (s, 1H), 8.04-8.03 (m, 1H), 7.84 (dd, J=8.8 Hz, 2.4 Hz, 1H), 7.67-7.63 (m, 2H), 7.55 (d, J=7.6 Hz, 1H), 7.43-7.38 (m, 2H), 7.10-7.09 (m, 1H), 7.05-7.01 (m, 2H), 3.75 (s, 3H), 2.52 (s, 3H). ESI-MS m/z 429.1 (M+H$^+$). Melting Point: 194° C.

Example 111

Synthesis of 2-acetamido-N-(2-methoxyethyl)-5-nitrobenzamide (104): Compound 2 (0.6 g, 2.50 mmol) was taken in dry DCM (10 mL) and TEA (0.77 mL, 5.52 mmol) was added. Acetyl chloride (0.21 mL, 3.01 mmol) was added dropwise at 0° C. and reaction mixture was allowed to stir at room temperature for 3 hours. Reaction was monitored by checking TLC. After completion of reaction, reaction mixture was washed with satd. $NaHCO_3$ solution and extracted with DCM, evaporated to afford yellow coloured mass which was further diluted with chloroform and pet ether was added to get precipitation. The precipitate was filtered and washed with 20% (EtOAc/Pet ether) solution to obtain compound 104 (0.5 g, 71%) as light yellow solid. $^1$H NMR (400 MHz, $d_6$-DMSO) δ in ppm 11.57 (s, 1H), 9.18 (br.s, —NH), 8.60 (d, J=7.6 Hz, 1H), 8.58 (d, J=1.2 Hz, 1H), 8.32 (dd, J=10.8 Hz, 2 Hz, 1H), 3.46-3.39 (m, 4H), 3.24 (s, 3H), 2.12 (s, 3H). ESI-HRMS m/z 282.1089 (M+H$^+$). Melting Point: 160° C.

Example 112

Synthesis of 3-(2-methoxyethyl)-2-methyl-6-nitroquinazolin-4 (3H)-one (105): The compound was prepared by general procedure G provided in example 7 using compound 104 (0.4 g, 1.42 mmol), DMF (6 mL), Hexamethyldisilazane (3 mL, 14.22 mmol), $ZnCl_2$ (0.96 g, 7.11 mmol) to obtain compound 105 (0.32 g, 86%) as white solid. $^1$H NMR (400 MHz, $d_6$-DMSO) δ in ppm 8.75 (d, J=2.4 Hz, 1H), 8.48 (dd, J=6 Hz, 2.8 Hz, 1H), 7.72 (d, J=9.2 Hz, 1H), 4.23 (t, J=5.2 Hz, 2H), 3.60 (t, J=5.6 Hz, 2H), 3.20 (s, 3H), 2.65 (s, 3H). ESI-MS m/z 264.1 (M+H$^+$). Melting Point: 154° C.

Example 113

Synthesis of 6-amino-3-(2-methoxyethyl)-2-methylquinazolin-4 (3H)-one (106): The compound was prepared by general procedure C provided in example 3 using compound 105 (0.22 g, 0.83 mmol), methanol (6 mL) and pinch of 10% wet Pd—C under hydrogen atmosphere to obtain compound 106 (0.18 g, 93%) as light brown solid. $^1$H NMR (600 MHz, $d_6$-DMSO) δ in ppm 7.26 (d, J=9 Hz, 1H), 7.13 (d, J=2.4 Hz, 1H), 7.02 (dd, J=8.4 Hz, 2.4 Hz, 1H), 5.52 (br.s, 2H), 4.16 (t, J=5.4 Hz, 2H), 3.56 (t, J=5.4 Hz, 2H), 3.21 (s, 3H), 2.51 (s, 3H). ESI-MS m/z 234.2 (M+H$^+$). Melting Point: 196° C.

Example 114

Synthesis of 1-(3-acetylphenyl)-3-(3-(2-methoxyethyl)-2-methyl-4-oxo-3,4-dihydroquinazolin-6-yl)urea (107): The compound was prepared by general procedure D provided in example 4 using compound 106 (0.14 g, 0.61 mmol), dry THF (8 mL), 4-nitrophenylchloroformate (0.15 g, 0.76 mmol), 3'-aminoacetophenone (0.10 g, 0.76 mmol), TEA (0.4 mL, 2.53 mmol) to obtain compound 107 (0.08 g, 33%) as light yellow solid. $^1$H NMR (300 MHz, $d_6$-DMSO) δ in ppm 9.06 (s, 1H), 8.99 (s, 1H), 8.30 (d, J=2.4 Hz, 1H), 8.09 (s, 1H), 7.77 (dd, J=8.7 Hz, J=2.4 Hz, 1H), 7.70 (d, J=9 Hz, 1H), 7.60 (d, J=7.5 Hz, 1H), 7.53 (d, J=9 Hz, 1H), 7.48-7.42 (m, 1H), 4.23 (t, J=5.4 Hz, 2H), 3.62 (t, J=5.4 Hz, 2H), 3.24 (s, 3H), 2.60 (s, 3H), 2.57 (s, 3H). ESI-MS m/z 395.3 (M+H$^+$). Melting Point: 218° C.

Example 115

Synthesis of 2-isobutyramido-N-(2-methoxyethyl)-5-nitrobenzamide (108): Compound 2 (0.6 g, 2.50 mmol) was taken in dry DCM (10 mL) and TEA (0.8 mL, 5.52 mmol) was added to it. Under cooling condition, isobutyryl chloride (0.3 mL, 3.01 mmol) was added dropwise at 0° C. and reaction was monitored by checking TLC. After 5 hours, reaction was completed and reaction mixture was diluted with DCM and washed thoroughly with $NaHCO_3$ solution and extracted to give light brown crude mass which was purified by column chromatography (Silica gel, mesh size 100-200) eluting (50% EtOAc/Pet ether) to obtain compound 108 (0.69 g, 89%) as white solid. $^1H$ NMR (400 MHz, $d_6$-DMSO) δ in ppm 11.79 (s, 1H), 9.21 (br.s, 1H), 8.64 (dd, J=9.2 Hz, 2.8 Hz, 1H), 8.61-8.60 (m, 1H), 8.31 (d, J=9.2 Hz, 1H), 3.45-3.42 (m, 4H), 3.23 (s, 3H), 2.59-2.52 (m, 1H), 1.11 (d, J=6.8 Hz, 6H). ESI-HRMS m/z 310.1390 (M+$H^+$). Melting Point: 140° C.

Example 116

Synthesis of 2-isopropyl-3-(2-methoxyethyl)-6-nitroquinazolin-4 (3H)-one (109): The compound was prepared by general procedure G provided in example 7 using compound 108 (0.5 g, 1.61 mmol), DMF (8 mL), $ZnCl_2$ (0.88 g, 6.46 mmol), HMDS (2.71 mL, 12.93 mmol) to obtain compound 109 (0.39 g, 83%) as white solid. $^1H$ NMR (400 MHz, $d_6$-DMSO) δ in ppm 8.70 (d, J=6 Hz, 1H), 8.44-8.40 (m, 1H), 7.70 (d, J=8.8 Hz, 1H), 4.27 (t, J=5.2 Hz, 2H), 3.54 (t, J=5.2 Hz, 2H), 3.44-3.36 (m, 1H), 3.17 (s, 3H), 1.21 (d, J=6.4 Hz, 6H). ESI-HRMS m/z 292.1291 (M+$H^+$). Melting Point: 136° C.

Example 117

Synthesis of 6-amino-2-isopropyl-3-(2-methoxyethyl) quinazolin-4 (3H)-one (110): The compound was prepared by general procedure C provided in example 3 using compound 109 (0.22 g, 0.75 mmol), methanol (6 mL) and pinch of 10% wet Pd—C under hydrogen atmosphere to obtain compound 110 (0.17 g, 86%) as light brown solid. $^1H$ NMR (400 MHz, $d_6$-DMSO) δ in ppm 7.26 (d, J=7.6 Hz, 1H), 7.12 (d, J=2.8 Hz, 1H), 7.01 (dd, J=6 Hz, 2.8 Hz, 1H), 5.49 (s, 2H), 4.20 (t, J=5.6 Hz, 2H), 3.51 (t, J=5.6 Hz, 2H), 3.28-3.23 (m, 1H), 3.17 (s, 3H), 1.17 (d, J=6.8 Hz, 6H). ESI-HRMS m/z 262.1541 (M+$H^+$). Melting Point: 170° C.

Example 118

Synthesis of 1-(3-acetylphenyl)-3-(2-isopropyl-3-(2-methoxyethyl)-4-oxo-3,4-dihydroquinazolin-6-yl)urea (111): The compound was prepared by general procedure D provided in example 4 using compound 110 (0.12 g, 0.45 mmol), dry THF (6 mL), 4-nitrophenylchloroformate (111 mg, 0.55 mmol), 3'-aminoacetophenone (0.075 g, 0.55 mmol), TEA (0.2 mL, 1.54 mmol) to obtain compound 111 (0.08 g, 41%) as light brown solid. $^1H$ NMR (300 MHz, $d_6$-DMSO) δ in ppm 9.09 (s, 1H), 8.99 (s, 1H), 8.31 (d, J=2.4 Hz, 1H), 8.10 (s, 1H), 7.79 (dd, J=8.7 Hz, J=2.4 Hz, 1H), 7.70 (d, J=7.8 Hz, 1H), 7.60 (d, J=7.8 Hz, 1H), 7.56 (d, J=8.7 Hz, 1H), 7.48-7.42 (m, 1H), 4.30 (t, J=5.4 Hz, 2H), 3.59 (t, J=5.4 Hz, 2H), 3.42-3.38 (m, 1H), 3.23 (s, 3H), 2.57 (s, 3H), 1.26 (d, J=6.6 Hz, 6H). ESI-MS m/z 423.3 (M+$H^+$). Melting Point: 206° C.

Example 119

Synthesis of 2-(4-fluorobenzamido)-N-(2-methoxyethyl)-5-nitrobenzamide (112): Compound 2 (0.8 g, 3.34 mmol) was taken in dry DCM (10 mL) and TEA (1.1 mL, 8.36 mmol) was added to it. Under cooling conditions, 4-fluorobenzoyl chloride (0.5 mL, 4.01 mmol) was added dropwise at 0° C. and reaction was monitored by checking TLC. After 3 hours, reaction was completed and reaction mixture was diluted with DCM and washed thoroughly with $NaHCO_3$ solution and extracted to give light brown crude mass which was purified by column chromatography (Silica gel, mesh size 100-200) eluting (50% EtOAc/Pet ether) to obtain compound 112 (1.1 g, 91%) as white solid. $^1H$ NMR (300 MHz, $d_6$-DMSO) δ in ppm 13.03 (s, 1H), 9.44 (s, 1H), 8.86 (d, J=9.3 Hz, 1H), 8.78 (s, 1H), 8.45 (d, J=9.3 Hz, 1H), 8.04-7.99 (m, 2H), 7.50-7.44 (m, 2H), 3.51 (br.s, 4H), 3.28 (s, 3H). Melting Point: 256° C.

Example 120

Synthesis of 2-(4-fluorophenyl)-3-(2-methoxyethyl)-6-nitroquinazolin-4 (3H)-one (113): The compound was prepared by general procedure G provided in example 7 using compound 112 (0.7 g, 1.93 mmol), DMF (8 mL), $ZnCl_2$ (1.3 g, 9.69 mmol), HMDS (4 mL, 19.38 mmol) to obtain compound 113 (0.59 g, 89%) as white solid. $^1H$ NMR (600 MHz, $CDCl_3$) δ in ppm 9.18 (d, J=3 Hz, 1H), 8.54 (dd, J=9 Hz, 2.4 Hz, 1H), 7.83 (d, J=9 Hz, 1H), 7.63-7.61 (m, 2H), 7.24-7.21 (m, 2H), 4.28 (t, J=4.8 Hz, 2H), 3.62 (t, J=5.4 Hz, 2H), 3.18 (s, 3H). ESI-HRMS m/z 344.1038 (M+$H^+$). Melting Point: 156° C.

Example 121

Synthesis of 6-amino-2-(4-fluorophenyl)-3-(2-methoxyethyl)quinazolin-4 (3H)-one (114): The compound was prepared by general procedure C provided in example 3 using compound 113 (0.25 g, 0.72 mmol), methanol (5 mL) and pinch of 10% wet Pd—C under hydrogen atmosphere to obtain compound 114 (0.19 g, 83%) as brown solid. $^1H$ NMR (400 MHz, $CDCl_3$) δ in ppm 7.55-7.51 (m, 3H), 7.46 (d, J=2.8 Hz, 1H), 7.17-7.13 (m, 2H), 7.09 (dd, J=8.8 Hz, 2.8 Hz, 1H), 4.17 (t, J=5.6 Hz, 2H), 3.56 (t, J=5.6 Hz, 2H), 3.15 (s, 3H). ESI-HRMS m/z 314.1304 (M+$H^+$). Melting Point: 160° C.

Example 122

Synthesis of 1-(3-acetylphenyl)-3-(2-(4-fluorophenyl)-3-(2-methoxyethyl)-4-oxo-3,4-dihydroquinazolin-6-yl)urea (115): The compound was obtained by general procedure D provided in example 4 using compound 110 (0.12 g, 0.38 mmol), dry THF (6 mL), 4-nitrophenylchloroformate (91 mg, 0.45 mmol), TEA (0.159 mL, 1.14 mmol) to obtain compound 115 (0.08 g, 44%) as white solid. $^1H$ NMR (300 MHz, $d_6$-DMSO) δ in ppm 9.18 (s, 1H), 9.04 (s, 1H), 8.43 (d, J=2.4 Hz, 1H), 8.12-8.11 (m, 1H), 7.83 (dd, J=8.7 Hz, 2.4 Hz, 1H), 7.73-7.67 (m, 3H), 7.64-7.60 (m, 2H), 7.49-7.44 (m, 1H), 7.40-7.34 (m, 2H), 4.10 (t, J=5.7 Hz, 2H), 3.45 (t, J=5.7 Hz, 2H), 3.04 (s, 3H), 2.58 (s, 3H). ESI-MS m/z 475.1 (M+$H^+$). Melting Point: 220° C.

Example 123

Synthesis of 2-(4-methoxybenzamido)-N-(2-methoxyethyl)-5-nitrobenzamide (116): Compound 2 (0.6 g, 2.50 mmol) was taken in dry DCM (10 mL) and TEA (0.77 mL, 5.52 mmol) was added to it. Under cooling conditions, 4-methoxybenzoyl chloride (0.4 mL, 3.01 mmol) was added dropwise at 0° C. and reaction was monitored by checking TLC. After 3 hours, reaction was completed and reaction mixture was diluted with DCM and washed thoroughly with $NaHCO_3$ solution and extracted to give light brown crude mass which was purified by column chromatography (Silica gel, mesh size 100-200) eluting (60% EtOAc/Pet ether) to obtain compound 116 (0.8 g, 85%) as yellow solid. $^1$H NMR (400 MHz, $d_6$-DMSO) δ in ppm 12.89 (s, 1H), 9.36 (br.s, 1H), 8.84 (d, J=8.8 Hz, 1H), 8.71 (d, J=2.4 Hz, 1H), 8.36 (q, J=6.8 Hz, 2.8 Hz, 1H), 7.87 (d, J=8.8 Hz, 2H), 7.09 (d, J=8.8 Hz, 2H), 3.80 (s, 3H), 3.49-3.45 (m, 4H), 3.24 (s, 3H). ESI-HRMS m/z 374.1329 (M+H$^+$). Melting Point: 184° C.

Example 124

Synthesis of 3-(2-methoxyethyl)-2-(4-methoxyphenyl)-6-nitroquinazolin-4 (3H)-one (117): The compound was prepared by general procedure G provided in example 7 using compound 116 (0.6 g, 1.60 mmol), DMF (8 mL), $ZnCl_2$ (1.0 g, 8.04 mmol), HMDS (3.3 mL, 16.08 mmol) to obtain compound 117 (0.59 g, 87%) as white solid. $^1$H NMR (400 MHz, $CDCl_3$) δ in ppm 9.15 (d, J=2.4 Hz, 1H), 8.50 (dd, J=9 Hz, 2.4 Hz, 1H), 7.80 (d, J=9.2 Hz, 1H), 7.54 (d, J=8.8 Hz, 2H), 7.02 (d, J=8.8 Hz, 2H), 4.32 (t, J=5.6 Hz, 2H), 3.87 (s, 3H), 3.59 (t, J=5.6 Hz, 2H), 3.16 (s, 3H). ESI-HRMS m/z 356.1225 (M+H$^+$). Melting Point: 162° C.

Example 125

Synthesis of 6-amino-3-(2-methoxyethyl)-2-(4-methoxyphenyl)quinazolin-4 (3H)-one (118): The compound was prepared by general procedure C provided in example 3 using compound 117 (0.25 g, 0.70 mmol), methanol (5 mL), pinch of 10% wet Pd—C under hydrogen atmosphere to obtain compound 118 (0.18 g, 89%) as brown solid. $^1$H NMR (400 MHz, $d_6$-DMSO) δ in ppm 7.46 (d, J=7.2 Hz, 2H), 7.31 (d, J=8.4 Hz, 1H), 7.18 (d, J=2.8 Hz, 1H), 7.05 (dd, J=6 Hz, 2.4 Hz, 1H), 6.99 (d, J=8.8 Hz, 2H), 5.62 (s, 2H), 4.05 (t, J=6 Hz, 2H), 3.78 (s, 3H), 3.36 (t, J=6 Hz, 2H), 2.99 (s, 3H). ESI-HRMS m/z 326.1478 (M+H$^+$). Melting Point: 172° C.

Example 126

Synthesis of 1-(3-acetylphenyl)-3-(3-(2-methoxyethyl)-2-(4-methoxyphenyl)-4-oxo-3,4-dihydroquinazolin-6-yl)urea (119): The compound was prepared by general procedure D provided in example 4 using compound 118 (0.12 g, 0.36 mmol), dry THF (6 mL), 4-nitrophenylchloroformate (89 mg, 0.44 mmol), 3'-aminoacetophenone (0.061 g, 0.44 mmol), TEA (0.15 mL, 1.10 mmol) to obtain compound 119 (0.075 g, 42%) as white solid. $^1$H NMR (300 MHz, $d_6$-DMSO) δ in ppm 9.16 (s, 1H), 9.03 (s, 1H), 8.40 (s, 1H), 8.11 (s, 1H), 7.81 (d, J=8.7 Hz, 1H), 7.71 (d, J=8.1 Hz, 1H), 7.62-7.55 (m, 4H), 7.49-7.43 (m, 1H), 7.07 (d, J=8.1 Hz, 2H), 4.15 (t, J=5.7 Hz, 2H), 3.83 (s, 3H), 3.46-3.42 (m, 2H) 3.04 (s, 3H), 2.58 (s, 3H). ESI-MS m/z 487.1 (M+H$^+$). Melting Point: 220° C.

Example 127

Synthesis of 2-(cyclohexanecarboxamido)-N-(2-methoxyethyl)-5-nitrobenzamide (120): Compound 2 (0.6 g, 2.50 mmol) was taken in dry DCM (10 mL) and TEA (0.9 mL, 6.27 mmol) was added to it. Cyclohexanecarbonyl chloride (0.6 mL, 5.01 mmol) was added dropwise at 0° C. and reaction was monitored by checking TLC. After 3 hours, reaction was completed and reaction mixture was diluted with DCM and washed thoroughly with $NaHCO_3$ solution and extracted to give light brown crude mass which was purified by column chromatography (Silica gel, mesh size 100-200) eluting (50% EtOAc/Pet ether) to obtain compound 120 (0.75 g, 86%) as white solid. $^1$H NMR (300 MHz, $d_6$-DMSO) δ in ppm 11.83 (s, 1H), 9.30-9.26 (m, 1H), 8.72 (d, J=9 Hz, 1H), 8.66 (d, J=2.7 Hz, 1H), 8.37 (dd, J=6.9 Hz, 2.4 Hz, 1H), 3.50-3.40 (m, 4H), 3.29 (s, 3H), 2.39-2.32 (m, 1H), 1.92-1.88 (m, 2H), 1.77-1.66 (m, 3H), 1.47-1.30 (m, 4H), 1.29-1.16 (m, 1H). ESI-HRMS m/z 350.1698 (M+H$^+$). Melting Point: 130° C.

Example 128

Synthesis of 2-cyclohexyl-3-(2-methoxyethyl)-6-nitroquinazolin-4 (3H)-one (121): The compound was prepared by general procedure G provided in example 7 using compound 120 (0.55 g, 1.57 mmol), DMF (8 mL), $ZnCl_2$ (1.07 g, 7.87 mmol), HMDS (3.3 mL, 15.75 mmol) to obtain compound 121 (0.45 g, 86%) as white solid. $^1$H NMR (300 MHz, $d_6$-DMSO) δ in ppm 8.80 (d, J=2.7 Hz, 1H), 8.51 (dd, J=6.3 Hz, 2.7 Hz, 1H), 7.79 (d, J=9 Hz, 1H), 4.34 (t, J=5.4 Hz, 2H), 3.62 (t, J=5.4 Hz, 2H), 3.24 (s, 3H), 3.15-3.08 (m, 1H), 1.92-1.88 (m, 3H), 1.82-1.78 (m, 3H), 1.74-1.66 (m, 2H), 1.46-1.33 (m, 2H). ESI-HRMS m/z 332.1614 (M+H$^+$). Melting Point: 148° C.

Example 129

Synthesis of 6-amino-2-cyclohexyl-3-(2-methoxyethyl) quinazolin-4 (3H)-one (122): The compound was prepared by general procedure C provided in example 3 using compound 121 (0.3 g, 0.90 mmol), methanol (5 mL) and pinch of 10% wet Pd—C to obtain compound 122 (0.25 g, 92%) as brown solid. $^1$H NMR (300 MHz, $d_6$-DMSO) δ in ppm 7.30 (d, J=8.7 Hz, 1H), 7.15 (d, J=2.4 Hz, 1H), 7.04 (dd, J=8.4 Hz, 2.4 Hz, 1H), 5.53 (s, 2H), 4.23 (t, J=5.4 Hz, 2H), 3.56 (t, J=5.4 Hz, 2H), 3.23 (s, 3H), 2.99-2.89 (m, 1H), 1.85-1.72 (m, 5H), 1.62-1.51 (m, 2H), 1.42-1.25 (m, 3H). ESI-HRMS m/z 302.1852 (M+H$^+$). Melting Point: 146° C.

Example 130

Synthesis of 1-(3-acetylphenyl)-3-(2-cyclohexyl-3-(2-methoxyethyl)-4-oxo-3,4-dihydroquinazolin-6-yl)urea (123): The compound was prepared by general procedure D provided in example 4 using compound 122 (0.12 g, 0.39 mmol), dry THF (7 mL), 4-nitrophenylchloroformate (0.12 g, 0.59 mmol), 3'-aminoacetophenone (0.06 g, 0.47 mmol), TEA (0.2 mL, 1.64 mmol) to obtain compound 123 (0.075 g, 41%) as white solid. $^1$H NMR (400 MHz, $d_6$-DMSO) δ in ppm 9.01 (s, 1H), 8.92 (s, 1H), 8.24 (d, J=2.8 Hz, 1H), 8.04-8.03 (m, 1H), 7.73 (dd, J=8.8 Hz, 2.4 Hz, 1H), 7.66-7.63 (m, 1H), 7.56-7.53 (m, 1H), 7.49 (d, J=8.8 Hz, 1H), 7.41-7.37 (m, 1H), 4.23 (t, J=5.6 Hz, 2H), 3.54 (t, J=5.6 Hz, 2H), 3.19 (s, 3H), 3.00-2.93 (m, 1H), 2.52 (s, 3H), 1.83-1.72 (m, 4H), 1.67-1.50 (m, 3H), 1.38-1.16 (m, 3H). ESI-MS m/z 463.3 (M+H$^+$). Melting Point: 202° C.

Example 131

Synthesis of 2-(cyclopentanecarboxamido)-N-(2-methoxyethyl)-5-nitrobenzamide (124): Compound 2 (0.6 g, 2.50 mmol) was taken in dry DCM (10 mL) and TEA (1.0 mL, 7.52 mmol) was added to it. Cyclopentanecarbonyl chloride (1 mL, 10.03 mmol) was added dropwise at 0° C. and reaction was monitored by checking TLC. After 5 hours, reaction was completed and reaction mixture was diluted with DCM and washed thoroughly with $NaHCO_3$ solution and extracted to give light brown crude mass which was purified by column chromatography (Silica gel, mesh size 100-200) eluting (50% EtOAc/Pet ether) to obtain compound 124 (0.75 g, 89%) as white solid. $^1$H NMR (300 MHz, $d_6$-DMSO) δ in ppm 11.82 (s, 1H), 9.28-9.25 (m, 1H), 8.70 (d, J=9.3 Hz, 1H), 8.66 (d, J=2.7 Hz, 1H), 8.37 (dd, J=8.4 Hz, 2.4 Hz, 1H), 3.53-3.46 (m, 4H), 3.32 (s, 3H), 2.87-2.79 (m, 1H), 1.94-1.87 (m, 2H), 1.79-1.56 (m, 6H). ESI-HRMS m/z 336.1560 (M+H$^+$). Melting Point: 126° C.

Example 132

Synthesis of 2-cyclopentyl-3-(2-methoxyethyl)-6-nitroquinazolin-4 (3H)-one (125): The compound was prepared by general procedure G provided in example 7 using compound 124 (0.6 g, 1.79 mmol), DMF (8 mL), $ZnCl_2$ (0.97 g, 7.16 mmol), HMDS (3 mL, 14.32 mmol) to obtain compound 125 (0.48 g, 84%) as white solid. $^1$H NMR (300 MHz, $d_6$-DMSO) δ in ppm 8.79 (d, J=2.4 Hz, 1H), 6.51 (dd, J=9 Hz, 2.7 Hz, 1H), 7.77 (d, J=9 Hz, 1H), 4.35 (t, J=5.4 Hz, 2H), 3.62 (q, J=5.4 Hz, 2H), 3.57-3.52 (m, 1H), 3.24 (s, 3H), 2.06-1.94 (m, 4H), 1.82-1.64 (m, 4H). ESI-HRMS m/z 318.1449 (M+H$^+$). Melting Point: 130° C.

Example 133

Synthesis of 6-amino-2-cyclopentyl-3-(2-methoxyethyl) quinazolin-4 (3H)-one (126): The compound was prepared by general procedure C provided in example 3 using compound 125 (0.3 g, 0.94 mmol), methanol (5 mL) and pinch of 10% wet Pd—C under hydrogen atmosphere to obtain compound 126 (0.22 g, 81%) as brown solid. $^1$H NMR (400 MHz, $d_6$-DMSO) δ in ppm 7.35 (d, J=8.4 Hz, 1H), 7.26 (d, J=7.2 Hz, 1H), 7.13 (dd, J=9 Hz, 2.4 Hz, 1H), 4.26 (t, J=5.7 Hz, 2H), 3.57 (t, J=5.7 Hz, 2H), 3.46-3.41 (m, 1H), 3.23 (s, 3H), 2.01-1.87 (m, 4H), 1.84-1.75 (m 2H), 1.70-1.58 (m, 2H). ESI-HRMS m/z 288.1704 (M+H$^+$). Melting Point: 142° C.

Example 134

Synthesis of 1-(3-acetylphenyl)-3-(2-cyclopentyl-3-(2-methoxyethyl)-4-oxo-3,4-dihydroquinazolin-6-yl)urea (127): The compound was prepared by general procedure D provided in example 4 using compound 126 (0.12 g, 0.41 mmol), dry THF (8 mL), 4-nitrophenylchloroformate (0.12 g, 0.62 mmol), 3'-aminoacetophenone (0.07 g, 0.52 mmol), TEA (0.2 mL, 1.72 mmol) to obtain compound 127 (0.079 g, 42%) as brown solid. $^1$H NMR (300 MHz, $d_6$-DMSO) δ in ppm 9.08 (s, 1H), 9.00 (s, 1H), 8.30 (d, J=2.4 Hz, 1H), 8.10 (s, 1H), 7.78 (dd, J=8.8 Hz, 2.7 Hz, 1H), 7.70 (d, J=9 Hz, 1H), 7.60 (d, J=7.5 Hz, 1H), 7.54 (d, J=8.7 Hz, 1H), 7.48-7.42 (m, 1H), 4.31 (t, J=5.4 Hz, 2H), 3.60 (t, J=5.4 Hz, 2H), 3.54-3.44 (m, 1H), 3.24 (s, 3H), 2.57 (s, 3H), 2.04-1.86 (m, 4H), 1.82-1.73 (m, 2H), 1.69-1.61 (m, 2H). ESI-MS m/z 449.2 (M+H$^+$). Melting Point: 204° C.

Example 135

Synthesis of 2-amino-N-(2-methoxyphenyl)-5-nitrobenzamide (128): The compound was prepared by general procedure A provided in example 1 using compound 1 (1 g, 5.49 mmol), DMF (10 mL), HATU (2.2 g, 6.04 mmol), o-anisidine (0.7 mL, 6.04 mmol), TEA (1.9 mL, 13.73 mmol) to obtain compound 128 (1.2 g, 76%) as yellow solid. $^1$H NMR (300 MHz, $d_6$-DMSO) δ in ppm 9.83 (s, 1H), 8.64 (d, J=2.4 Hz, 1H), 8.07 (dd, J=8.7 Hz, J=2.4 Hz, 1H), 7.68 (s, 2H), 7.54 (dd, J=7.8 Hz, J=1.8 Hz, 1H), 7.24-7.19 (m, 1H), 7.11-7.08 (m, 1H), 6.99-6.93 (m, 1H), 6.85 (d, J=9.3 Hz, 1H), 3.82 (s, 3H). ESI-HRMS m/z 288.0998 (M+H$^+$). Melting Point: 178° C.

Example 136

Synthesis of 3-(2-methoxyphenyl)-6-nitroquinazolin-4 (3H)-one (129): The compound was prepared by general procedure B provided in example 2 using compound 128 (1 g, 2.78 mmol), trimethylorthoformate (TMOF) (6 mL, 55.73 mmol) to obtain compound 129 (0.69 g, 83%) as pale yellow solid. $^1$H NMR (400 MHz, $CDCl_3$) δ in ppm 9.18 (d, J=2.4 Hz, 1H), 8.55 (dd, J=9.2 Hz, J=2.8 Hz, 1H), 8.08 (s, 1H), 7.87 (d, J=9.2 Hz, 1H), 7.51-7.47 (m, 2H), 7.33-7.31 (m, 1H), 7.13-7.09 (m, 1H), 3.81 (s, 3H). ESI-HRMS m/z 298.0836 (M+H$^+$). Melting Point: 164° C.

Example 137

Synthesis of 6-amino-3-(2-methoxyphenyl)quinazolin-4 (3H)-one (130): The compound was prepared by general procedure C provided in example 3 using compound 129 (0.8 g, 2.69 mmol), methanol (10 mL), pinch of 10% wet Pd—C under hydrogen atmosphere to obtain compound 130 (0.65 g, 90%) as light brown solid. $^1$H NMR (300 MHz, $d_6$-DMSO) δ in ppm 7.83 (s, 1H), 7.52-7.39 (m, 3H), 7.25-7.22 (m, 2H), 7.14-7.07 (m, 2H), 5.72 (brs, 2H), 3.76 (s, 3H). ESI-HRMS m/z 268.1096 (M+H$^+$). Melting Point: 169° C.

Example 138

Synthesis of 1-(3-acetylphenyl)-3-(3-(2-methoxyphenyl)-4-oxo-3,4-dihydroquinazolin-6-yl)urea (131): The compound was prepared by general procedure D provided in example 4 using compound 130 (0.12 g, 0.44 mmol), dry THF (6 mL) and 4-nitrophenylchloroformate (0.13 g, 0.67 mmol), 3'-aminoacetophenone (0.075 g, 0.56 mmol), TEA (0.3 mL, 1.85 mmol) to obtain compound 131 (0.05 g, 27%) as light yellow solid. $^1$H NMR (400 MHz, $d_6$-DMSO) δ in ppm 9.18 (s, 1H), 9.01 (s, 1H), 8.37 (d, J=2.8 Hz, 1H), 8.10-8.09 (m, 1H), 8.07 (s, 1H), 7.89 (dd, J=8.8 Hz, 2.8 Hz, 1H), 7.77-7.72 (m, 2H), 7.61-7.59 (m, 1H), 7.54-7.49 (m, 1H), 7.47-7.43 (m, 2H), 7.26 (dd, J=8.4 Hz, 1.2 Hz, 1H), 7.14-7.10 (m, 1H), 3.77 (s, 3H), 2.57 (s, 3H).

Example 139

Synthesis of 2-amino-N-(2-morpholinoethyl)-5-nitrobenzamide (132): The compound was prepared by general procedure A provided in example 1 using compound 1 (1 g, 5.49 mmol), DMF (10 mL), HATU (2.2 g, 6.04 mmol), 4-(2-aminoethyl)morpholine (0.8 mL, 6.04 mmol), TEA (1.9 mL, 13.73 mmol) to obtain compound 132 (0.9 g, 56%) as yellow solid. $^1$H NMR (300 MHz, $d_6$-DMSO) δ in ppm 8.64 (t, J=5.7 Hz, 1H), 8.46 (d, J=2.7 Hz, 1H), 8.02 (dd, J=9.3 Hz, J=2.4 Hz, 1H), 7.73 (s, 2H), 6.78 (d, J=9.3 Hz, 1H), 3.57 (t, J=4.5 Hz, 4H), 3.39-3.36 (m, 2H), 2.51-2.48 (m, 2H), 2.43-2.39 (m, 4H). ESI-HRMS m/z 295.1411 (M+H$^+$). Melting Point: 152° C.

Example 140

Synthesis of 3-(2-morpholinoethyl)-6-nitroquinazolin-4 (3H)-one (133): The compound was prepared by general procedure B provided in example 2 using compound 132 (0.6 g, 2.03 mmol), trimethylorthoformate (TMOF) (4 mL, 40.79 mmol) to obtain compound 133 (0.42 g, 68%) as pale yellow solid. ESI-HRMS m/z 305.1247 (M+H+). Melting Point: 142° C.

Example 141

Synthesis of 6-amino-3-(2-morpholinoethyl)quinazolin-4 (3H)-one (134): The compound was preapred by general procedure C provided in example 3 using compound 133 (0.25 g, 0.82 mmol), methanol (6 mL) and pinch of 10% wet Pd—C under hydrogen atmosphere to obtain compound 134 (0.15 g, 67%) as light brown solid. $^1$H NMR (300 MHz, $d_6$-DMSO) δ in ppm 8.72 (s, 1H), 8.63 (d, J=1.5 Hz, 1H), 8.11 (s, 1H), 7.53-7.48 (m, 2H), 7.25 (dd, J=8.7 Hz, 2.4 Hz, 1H), 4.06 (t, J=6 Hz, 2H), 3.52-3.51 (m, 4H), 2.59 (t, J=3.9 Hz, 2H), 2.43 (m, 4H). ESI-HRMS m/z 275.1513 (M+H+). Melting Point: 186° C.

Example 142

Synthesis of 1-(3-acetylphenyl)-3-(3-(2-morpholinoethyl)-4-oxo-3,4-dihydroquinazolin-6-yl)urea (135): The compound was prepared by general procedure E provided in example 5 using compound 134 (0.12 g, 0.43 mmol), dry THF (6 mL), 3-acetylphenylisocyanate (0.071 mL, 0.51 mmol), TEA (0.3 mL, 1.80 mmol) to obtain compound 135 (0.04 g, 21%) as yellow solid. $^1$H NMR (300 MHz, $d_6$-DMSO) δ in ppm 11.00 (s, 1H), 9.74 (s, 1H), 8.33 (d, J=2.4 Hz, 2H), 8.27 (s, 1H), 8.16 (dd, J=9 Hz, 4 Hz, 1H), 7.96 (d, J=8.1 Hz, 1H), 7.69-7.63 (m, 2H), 7.48-7.43 (m, 1H), 4.10 (t, J=6 Hz, 2H), 3.54-3.51 (m, 4H), 2.61 (t, J=6 Hz, 2H), 2.57 (s, 3H), 2.45-2.42 (m, 4H). ESI-HRMS m/z 436.1987 (M+H+). Melting Point: 140° C.

Example 143

Synthesis of 2-amino-N-(3-morpholinopropyl)-5-nitrobenzamide (136): The compound was prepared by general procedure A provided in example 1 using compound 1 (1 g, 5.49 mmol), DMF (10 mL), HATU (2.2 g, 6.04 mmol), 3-morpholinopropylamine (0.9 mL, 6.04 mmol), TEA (1.9 mL, 13.73 mmol) to obtain compound 136 (1 g, 59%) as yellow solid. ESI-HRMS m/z 309.1568 (M+H+). Melting Point: 126° C.

Example 144

Synthesis of 3-(3-morpholinopropyl)-6-nitroquinazolin-4 (3H)-one (137): The compound was prepared by general procedure B provided in example 2 using compound 136 (0.6 g, 1.94 mmol), trimethylorthoformate (TMOF) (4 mL, 38.94 mmol) to obtain compound 137 (0.48 g, 88%) as pale yellow solid. ESI-HRMS m/z 319.1398 (M+H+). Melting Point: 118° C.

Example 145

Synthesis of 6-amino-3-(3-morpholinopropyl)quinazolin-4 (3H)-one (138): The compound was prepared by general procedure C provided in example 3 using compound 137 (0.3 g, 0.94 mmol), methanol (8 mL) and pinch of 10% wet Pd—C under hydrogen atmosphere to obtain compound 138 (0.18 g, 66%) as light brown solid. ESI-HRMS m/z 289.1664 (M+H+). Melting Point: 148° C.

Example 146

Synthesis of 1-(3-acetylphenyl)-3-(3-(3-morpholinopropyl)-4-oxo-3,4-dihydroquinazolin-6-yl)urea (139): The compound was prepared by general procedure D provided in example 4 using compound 138 (0.12 g, 0.41 mmol), dry THF (8 mL), 4-nitrophenylchloroformate (0.13 g, 0.62 mmol), 3'-aminoacetophenone (0.07 g, 0.52 mmol), TEA (0.3 mL, 1.71 mmol) to obtain compound 139 (0.04 g, 22%) as yellow solid. $^1$H NMR (300 MHz, $d_6$-DMSO) δ in ppm 9.13 (s, 1H), 8.99 (s, 1H), 8.30 (s, 1H), 8.21 (s, 1H), 8.04 (s, 1H), 7.77-7.74 (m, 1H), 7.65-7.62 (m, 1H), 7.58-7.53 (m, 2H), 7.55 (dd, J=11.1 Hz, 6.9 Hz, 2H), 7.42-7.38 (m, 1H), 3.96 (t, J=3 Hz, 2H), 3.48-3.41 (m, 4H), 2.52 (s, 3H), 2.37-2.19 (m, 6H), 1.86-1.79 (m, 2H). ESI-HRMS m/z 450.2160 (M+H+). Melting Point: 178° C.

Example 147

Synthesis of 2-amino-N-(2-(dimethylamino)ethyl)-5-nitrobenzamide (140): The compound was prepared by general procedure A provided in example 1 using compound 1 (1 g, 5.49 mmol), DMF (10 mL), HATU (2.2 g, 6.04 mmol), N,N-dimethylethylenediamine (0.7 mL, 6.04 mmol), TEA (1.9 mL, 13.73 mmol) to obtain compound 140 (0.8 g, 56%) as yellow solid. $^1$H NMR (300 MHz, $d_6$-DMSO) δ in ppm 8.83 (d, J=2.7 Hz, 1H), 8.55 (dd, J=9 Hz, j=2.7 Hz, 1H), 8.52 (s, 1H), 7.86 (d, J=9 Hz, 1H), 4.11 (t, J=6 Hz, 2H), 2.57 (t, J=6 Hz, 2H), 2.19 (s, 6H). ESI-HRMS m/z 253.1304 (M+H+). Melting Point: 116° C.

Example 148

Synthesis of 3-(2-(dimethylamino)ethyl)-6-nitroquinazolin-4 (3H)-one (141): The compound was prepared by general procedure B provided in example 2 using compound 140 (0.6 g, 2.37 mmol), trimethylorthoformate (TMOF) (4 mL, 38.94 mmol) to obtain compound 141 (0.49 g, 86%) as pale yellow solid. $^1$H NMR (300 MHz, $d_6$-DMSO) δ in ppm 8.83 (d, J=2.7 Hz, 1H), 8.55 (dd, J=9 Hz, J=2.7 Hz, 1H), 8.52 (s, 1H), 7.86 (d, J=9 Hz, 1H), 4.11 (t, J=6 Hz, 2H), 2.58 (t, J=6 Hz, 2H), 2.20 (s, 6H). ESI-HRMS m/z 263.1154 (M+H+). Melting Point: 115° C.

Example 149

Synthesis of 6-amino-3-(2-(dimethylamino)ethyl)quinazolin-4 (3H)-one (142): The compound was prepared by general procedure C provided in example 3 using compound 141 (0.3 g, 1.14 mmol), methanol (8 mL) and pinch of 10% wet Pd—C under hydrogen atmosphere to obtain compound 142 (0.19 g, 72%) as light brown solid. Melting Point: 178° C.

Example 150

Synthesis of 1-(3-acetylphenyl)-3-(3-(2-(dimethylamino) ethyl)-4-oxo-3,4-dihydroquinazolin-6-yl)urea (143): The compound was prepared by general procedure E provided in example 5 using compound 142 (0.12 g, 0.51 mmol), dry THF (8 mL), 3-acetylphenylisocyanate (0.065 mL, 0.61 mmol), TEA (0.3 mL, 1.71 mmol) to obtain compound 143 (0.109 g, 54%) as yellow solid. $^1$H NMR (300 MHz, $d_6$-DMSO) δ in ppm 9.17 (s, 1H), 9.04 (s, 1H), 8.34 (d, J=2.4 Hz, 1H), 8.19 (s, 1H), 8.09 (brs, 1H), 7.79 (d, J=8.7 Hz, J=2.4 Hz, 1H), 7.69 (d, J=8.1 Hz, 1H), 7.62-7.57 (m, 2H), 7.46-7.41 (m, 1H), 4.06 (t, J=6 Hz, 2H), 2.60-2.56 (m, 5H), 2.20 (s, 6H). ESI-HRMS m/z 394.1879 (M+H+).

Example 151

Synthesis of 2-amino-5-nitro-N-(2-(piperidin-1-yl)ethyl) benzamide (144): The compound was prepared by general procedure E provided in example 5 using compound 1 (1 g, 5.49 mmol), DMF (10 mL), HATU (2.2 g, 6.04 mmol), 1-(2-aminoethyl)piperidine (0.83 mL, 6.04 mmol), TEA (1.9 mL, 13.73 mmol) to obtain compound 144 (0.7 g, 62%) as yellow solid. $^1$H NMR (300 MHz, $d_6$-DMSO) δ in ppm 8.58 (t, J=5.7 Hz, 1H), 8.41 (d, J=2.7 Hz, 1H), 7.99 (dd, J=9.0 Hz, J=2.4 Hz, 1H), 7.70 (s, 2H), 6.76 (d, J=9.3 Hz, 1H), 2.42-2.33 (m, 6H), 1.50-1.33 (m, 2H). ESI-HRMS m/z 293.1614 (M+H$^+$). Melting Point: 148° C.

Example 152

Synthesis of 6-nitro-3-(2-(piperidin-1-yl)ethyl)quinazolin-4 (3H)-one (145): The compound was prepared by general procedure B provided in example 2 using compound 144 (0.6 g, 2.05 mmol), trimethylorthoformate (TMOF) (4 mL, 39.56 mmol) to obtain compound 145 (0.52 g, 88%) as pale yellow solid. $^1$H NMR (400 MHz, $d_6$-DMSO) δ in ppm 8.79 (d, J=2.8 Hz, 1H), 8.50 (dd, J=9.2 Hz, J=2.8 Hz, 1H), 8.43 (s, 1H), 7.82 (d, J=9.2 Hz, 1H), 4.05 (t, J=6 Hz, 2H), 2.51 (t, J=6 Hz, 2H), 2.33 (m, 4H), 1.39-1.35 (m, 4H), 1.32-1.30 (m, 2H). ESI-HRMS m/z 303.1453 (M+H$^+$). Melting Point: 120° C.

Example 153

Synthesis of 6-amino-3-(2-(piperidin-1-yl)ethyl)quinazolin-4 (3H)-one (146): The compound was prepared by general procedure C provided in example 3 using compound 145 (0.3 g, 0.99 mmol), methanol (8 mL) and pinch of 10% wet Pd—C under hydrogen atmosphere to obtain compound 146 (0.189 g, 70%) as light brown solid.

Example 154

Synthesis of 1-(3-acetylphenyl)-3-(4-oxo-3-(2-(piperidin-1-yl)ethyl)-3,4-dihydroquinazolin-6-yl)urea (147): The compound was prepared by general procedure E provided in example 5 using compound 146 (0.130 g, 0.47 mmol), dry THF (8 mL), 3-acetylphenylisocyanate (0.065 mL, 0.61 mmol), TEA (0.3 mL, 1.71 mmol) to obtain compound 147 (0.095 g, 46%) as yellow solid. $^1$H NMR (400 MHz, $d_6$-DMSO) δ in ppm 8.53 (s, 1H), 8.35 (s, 1H), 8.20 (dd, J=8.8 Hz, 2 Hz, 1H), 8.00 (d, J=2.8 Hz, 1H), 7.96 (s, 1H), 7.90-7.87 (m, 2H), 7.61-7.56 (m, 2H), 7.38-7.34 (m, 1H), 4.07 (t, J=5.6 Hz, 2H), 2.69 (t, J=4.8 Hz, 2H), 2.59 (s, 3H), 2.45 (brs, 4H), 1.54-1.50 (m, 4H), 1.41-1.38 (m, 2H). ESI-HRMS m/z 434.2193 (M+H$^+$).

Example 155

Synthesis of 2-amino-5-nitro-N-(pyridin-4-yl)benzamide (148): The compound was prepared by general procedure A provided in example 1 using compound 1 (1 g, 5.49 mmol), DMF (10 mL), HATU (2.2 g, 6.04 mmol), 4-aminopyridine (0.62 mL, 6.04 mmol), TEA (1.9 mL, 13.73 mmol) to obtain compound 148 (1.02 g, 72%) as yellow solid. ESI-HRMS m/z 259.0833 (M+H$^+$). Melting Point: 246° C.

Example 156

Synthesis of 6-nitro-3-(pyridin-4-yl)quinazolin-4 (3H)-one (149): The compound was prepared by general procedure B provided in example 2 using compound 148 (0.6 g, 2.32 mmol), trimethylorthoformate (TMOF) (4 mL, 39.56 mmol) to obtain compound 149 (0.56 g, 90%) as pale yellow solid. $^1$H NMR (400 MHz, $d_6$-DMSO) δ in ppm 8.83 (d, J=2.4 Hz, 1H), 8.77 (dd, J=4.8 Hz, 1.2 Hz, 2H), 8.60-8.57 (m, 2H), 7.92 (d, J=8.8 Hz, 1H), 7.64 (dd, J=4.4 Hz, 1.6 Hz, 2H) Melting Point: 202° C.

Example 157

Synthesis of 6-amino-3-(pyridin-4-yl)quinazolin-4 (3H)-one (150): The compound was prepared by general procedure C provided in example 3 using compound 149 (0.3 g, 1.11 mmol), methanol (8 mL) and pinch of 10% wet Pd—C under hydrogen atmosphere to obtain compound 150 (0.191 g, 72%) as light brown solid.

Example 158

Synthesis of 1-(3-acetylphenyl)-3-(4-oxo-3-(pyridin-4-yl)-3,4-dihydroquinazolin-6-yl)urea (151): The compound was prepared by general procedure D provided in example 4 using compound 150 (0.130 g, 0.54 mmol), dry THF (8 mL), 4-nitrophenylchloroformate (0.131 g, 0.65 mmol), 3'-aminoacetophenone (0.081 g, 0.60 mmol), TEA (0.3 mL, 1.71 mmol) to obtain compound 151 (0.115 g, 53%) as yellow solid. $^1$H NMR (300 MHz, $d_6$-DMSO) δ in ppm 9.29 (s, 1H), 9.09 (s, 1H), 8.79 (d, J=6 Hz, 2H), 8.43 (d, J=2.4 Hz, 1H), 8.30 (s, 1H), 8.10 (brs, 1H), 7.91 (dd, J=9 Hz, J=2.7 Hz, 1H), 7.73 (s, 1H), 7.70-7.67 (m, 4H), 7.48-7.43 (m, 1H), 2.58 (s, 3H). ESI-HRMS m/z 400.1411 (M+H$^+$).

Example 159

Synthesis of 2-amino-5-nitro-N-(pyridin-3-yl)benzamide (152): The compound was prepared by general procedure A provided in example 1 using compound 1 (1 g, 5.49 mmol), DMF (10 mL), HATU (2.2 g, 6.04 mmol), 3-aminopyridine (0.62 mL, 6.04 mmol), TEA (1.9 mL, 13.73 mmol) to obtain compound 152 (1.02 g, 72%) as yellow solid. $^1$H NMR (300 MHz, $d_6$-DMSO) δ in ppm 9.19 (d, J=2.8 Hz, 1H), 8.78 (dd, J=4.8 Hz, J=1.6 Hz, 1H), 8.70 (d, J=2.8 Hz, 1H), 8.59 (dd, J=9.2 Hz, J=2.8 Hz, 1H), 8.22 (s, 1H), 7.91 (d, J=8.8 Hz, 1H), 7.86-7.83 (m, 1H), 7.56-7.52 (m, 1H). ESI-HRMS m/z 259.0844 (M+H$^+$). Melting Point: 266° C.

Example 160

Synthesis of 6-nitro-3-(pyridin-3-yl)quinazolin-4 (3H)-one (153): The compound was prepared by general procedure B provided in example 2 using compound 152 (0.6 g, 2.32 mmol), trimethylorthoformate (TMOF) (4 mL, 39.56 mmol) to obtain compound 153 (0.56 g, 90%) as pale yellow solid. $^1$H NMR (300 MHz, $d_6$-DMSO) δ in ppm 8.88 (d, J=2.4 Hz, 1H), 8.80 (d, J=2.1 Hz, 1H), 8.74 (dd, J=4.8 Hz, J=1.2 Hz, 1H), 8.65 (s, 1H), 8.63 (d, J=2.7 Hz, 1H), 8.10-8.06 (m, 1H), 7.98 (d, J=9 Hz, 1H). Melting Point: 263° C.

Example 161

Synthesis of 6-amino-3-(pyridin-3-yl)quinazolin-4 (3H)-one (154): The compound was prepared by general procedure C provided in example 3 using compound 153 (0.3 g, 1.11 mmol), methanol (8 mL) and pinch of 10% wet Pd—C under hydrogen atmosphere to obtain compound 154 (0.191 g, 72%) as light brown solid.

Example 162

Synthesis of 1-(3-acetylphenyl)-3-(4-oxo-3-(pyridin-3-yl)-3,4-dihydroquinazolin-6-yl)urea (155): The compound was prepared by general procedure D provided in example 4 using compound 154 (0.130 g, 0.54 mmol), dry THF (8 mL), 4-nitrophenylchloroformate (0.131 g, 0.65 mmol), 3'-aminoacetophenone (0.081 g, 0.60 mmol), TEA (0.3 mL, 1.71 mmol) to obtain compound 155 (0.093 g, 48%) as yellow solid. $^1$H NMR (300 MHz, $d_6$-DMSO) δ in ppm 8.81 (d, J=2.1 Hz, 1H), 8.71 (dd, J=4.8 Hz, J=1.5 Hz, 1H), 8.48 (s, 1H), 8.34 (d, J=2.4 Hz, 1H), 8.21-8.19 (m, 1H), 8.15-8.06 (m, 3H), 7.96 (d, J=8.7 Hz, 1H), 7.88 (d, J=8.1 Hz, 1H), 7.79-7.74 (m, 1H), 7.67-7.63 (m, 1H), 2.63 (s, 3H). ESI-HRMS m/z 400.1412 (M+H$^+$).

Example 163

Synthesis of 2-amino-5-nitro-N-(pyridin-2-yl)benzamide (156): The compound was prepared by general procedure A provided in example 1 using compound 1 (1 g, 5.49 mmol), DMF (10 mL), HATU (2.2 g, 6.04 mmol), 2-aminopyridine (0.62 mL, 6.04 mmol), TEA (1.9 mL, 13.73 mmol) to obtain compound 156 (0.98 g, 69%) as yellow solid. $^1$H NMR (400 MHz, $d_6$-DMSO) δ in ppm 10.99 (s, 1H), 8.60 (d, J=2.4 Hz, 1H), 8.36-8.34 (m, 1H), 8.04-8.00 (m, 2H), 7.81-7.77 (m, 1H), 7.59 (brs, 2H), 7.14-7.11 (m, 1H), 6.80 (d, J=9.2 Hz, 1H). ESI-HRMS m/z 281.0650 (M+Na$^+$). Melting Point: 180° C.

Example 164

Synthesis of 6-nitro-3-(pyridin-2-yl)quinazolin-4 (3H)-one (157): The compound was prepared by general procedure B provided in example 2 using compound 156 (0.6 g, 2.32 mmol), trimethylorthoformate (TMOF) (4 mL, 39.56 mmol) to obtain compound 157 (0.52 g, 89%) as pale yellow solid. $^1$H NMR (400 MHz, $d_6$-DMSO) δ in ppm 9.20 (d, J=2.8 Hz, 1H), 8.77 (s, 1H), 8.63-8.61 (m, 1H), 8.56 (dd, J=9 Hz, 2.8 Hz, 1H), 7.94-7.88 (m, 3H), 7.44-7.41 (m, 1H). ESI-HRMS m/z 269.0677 (M+H$^+$). Melting Point: 220° C.

Example 165

Synthesis of 6-amino-3-(pyridin-2-yl)quinazolin-4 (3H)-one (158): The compound was prepared by general procedure C provided in example 3 using compound 157 (0.3 g, 1.11 mmol), methanol (8 mL) and pinch of 10% wet Pd—C under hydrogen atmosphere to obtain compound 158 (0.183 g, 71%) as light brown solid. $^1$H NMR (300 MHz, $d_6$-DMSO) δ in ppm 8.64 (d, J=4.2 Hz, 1H), 8.23 (s, 1H), 8.07-8.01 (m, 1H), 7.80 (d, J=8.1 Hz, 1H), 7.56-7.51 (m, 1H), 7.46 (d, J=8.4 Hz, 1H), 7.30 (d, J=2.4 Hz, 1H), 7.13 (dd, J=8.7 Hz, 2.7 Hz, 1H), 5.79 (brs, 2H).

Example 166

Synthesis of 1-(3-acetylphenyl)-3-(4-oxo-3-(pyridin-2-yl)-3,4-dihydroquinazolin-6-yl)urea (159): The compound was prepared by general procedure D provided in example 4 using compound 158 (0.130 g, 0.54 mmol), dry THF (8 mL), 4-nitrophenylchloroformate (0.131 g, 0.65 mmol), 3'-aminoacetophenone (0.081 g, 0.60 mmol), TEA (0.3 mL, 1.71 mmol) to obtain compound 159 (0.095 g, 44%) as yellow solid. $^1$H NMR (400 MHz, $d_6$-DMSO) δ in ppm 9.21 (s, 1H), 9.02 (s, 1H), 8.66 (dd, J=4.8 Hz, 1.2 Hz, 1H), 8.46 (s, 1H), 8.45 (s, 1H), 8.10-8.05 (m, 2H), 7.91-7.83 (m, 2H), 7.71 (d, J=8.8 Hz, 2H), 7.61-7.55 (m, 2H), 7.47-7.43 (m, 1H), 2.57 (s, 3H). ESI-HRMS m/z 400.1407 (M+H$^+$).

Example 167

Synthesis of 2-amino-N-(1-methylpiperidin-4-yl)-5-nitrobenzamide (160): The compound was prepared by general procedure A provided in example 1 using compound 1 (1 g, 5.49 mmol), DMF (10 mL), HATU (2.2 g, 6.04 mmol), 1-methylpiperidin-4-amine (0.75 mL, 6.58 mmol), TEA (1.9 mL, 13.73 mmol) to obtain compound 160 (1.007 g, 66%) as yellow solid. $^1$H NMR (300 MHz, $d_6$-DMSO) δ in ppm 8.53 (d, J=7.5 Hz, 1H), 8.48 (d, J=2.7 Hz, 1H), 8.01 (dd, J=9.3 Hz, 2.7 Hz, 1H), 7.72 (s, 2H), 6.78 (d, J=9.3 Hz, 1H), 3.75-3.65 (m, 1H), 2.80-2.76 (m, 2H), 2.16 (s, 3H), 1.98-1.89 (m, 2H), 1.77-1.72 (m, 2H), 1.64-1.51 (m, 2H). ESI-HRMS m/z 279.1470 (M+H$^+$).

Example 168

Synthesis of 3-(1-methylpiperidin-4-yl)-6-nitroquinazolin-4 (3H)-one (161): The compound was preapred by general procedure B provided in example 2 using compound 160 (0.6 g, 2.32 mmol), trimethylorthoformate (TMOF) (4 mL, 38.23 mmol to obtain compound 161 (0.52 g, 89%) as pale yellow solid. $^1$H NMR (300 MHz, $CDCl_3$) δ in ppm 9.13 (d, J=2.4 Hz, 1H), 8.50 (dd, J=8.8 Hz, 2.8 Hz, 1H), 8.26 (s, 1H), 7.80 (d, J=9.2 Hz 1H), 3.04-3.01 (m, 2H), 2.34 (s, 3H) 2.24-2.18 (m, 2H), 2.02-1.97 (m, 4H).

Example 169

Synthesis of 6-amino-3-(1-methylpiperidin-4-yl)quinazolin-4 (3H)-one (162): The compound was prepared by general procedure C provided in example 3 using compound 161 (0.3 g, 1.11 mmol), methanol (8 mL) and pinch of 10% wet Pd—C under hydrogen atmosphere to obtain compound 162 (0.166 g, 62%) as light brown solid. $^1$H NMR (300 MHz, $d_6$-DMSO) δ in ppm 8.10 (s, 1H), 7.37 (d, J=8.4 Hz, 1H), 7.22 (d, J=2.4 Hz, 1H), 7.07 (dd, J=8.7 Hz, 2.7 Hz, 1H), 5.66 (brs, 2H), 4.64-4.54 (m, 1H), 2.94-2.91 (m, 2H), 2.23 (s, 3H), 2.13-2.03 (m, 4H), 1.75-1.70 (m, 2H).

Example 170

Synthesis of 1-(3-acetylphenyl)-3-(3-(1-methylpiperidin-4-yl)-4-oxo-3,4-dihydroquinazolin-6-yl)urea (163): The compound was prepared by general procedure D provided in example 4 using compound 162 (0.120 g, 0.46 mmol), dry THF (8 mL), 4-nitrophenylchloroformate (0.110 g, 0.55 mmol), 3'-aminoacetophenone (0.075 g, 0.55 mmol), TEA (0.3 mL, 1.71 mmol) to obtain compound 163 (0.062 g, 32%) as yellow solid. $^1$H NMR (300 MHz, $d_6$-DMSO) δ in ppm 9.42 (s, 1H), 9.26 (s, 1H), 8.37-8.34 (m, 2H), 8.11 (s, 1H), 7.83 (dd, J=8.5 Hz, 1.5 Hz, 1H), 7.71 (d, J=8.1 Hz, 1H), 7.63-7.58 (m, 2H), 7.47-7.42 (m, 1H), 4.62-4.55 (m, 1H), 2.92-2.89 (m, 2H), 2.57 (s, 3H), 2.21 (s, 3H), 2.07-2.04 (m, 4H), 1.79-1.76 (m, 2H). ESI-HRMS m/z 420.2036 (M+H$^+$).

Example 171

Synthesis of 2-amino-N-(2-(methylamino)ethyl)-5-nitrobenzamide (164): The compound was prepared by general procedure A provided in example 1 using compound 1 (1 g, 5.49 mmol), DMF (10 mL), HATU (2.2 g, 6.04 mmol), N-Methylethylenediamine (0.48 mL, 6.58 mmol), TEA (1.9 mL, 13.73 mmol) to obtain compound 164 (0.810 g, 62%) as yellow solid. ESI-HRMS m/z 239.1146 (M+H$^+$).

Example 172

Synthesis of 3-(2-(methylamino)ethyl)-6-nitroquinazolin-4 (3H)-one (165): The compound was prepared by general procedure B provided in example 2 using compound 164 (0.6 g, 2.51 mmol), trimethylorthoformate (TMOF) (4 mL, 38.23 mmol) to obtain compound 165 (0.48 g, 78%) as pale yellow solid.

Example 173

Synthesis of 6-amino-3-(2-(methylamino)ethyl)quinazolin-4 (3H)-one (166): The compound was prepared by general procedure C provided in example 3 using compound 165 (0.3 g, 1.37 mmol), methanol (10 mL) and pinch of 10% wet Pd—C under hydrogen atmosphere to obtain compound 166 (0.147 g, 56%) as light brown solid.

Example 174

Synthesis of 1-(3-acetylphenyl)-3-(3-(2-(methylamino) ethyl)-4-oxo-3,4-dihydroquinazolin-6-yl)urea (167): The compound was prepared by general procedure D provided in example 4 using compound 166 (0.120 g, 0.55 mmol), dry THF (8 mL), 4-nitrophenylchloroformate (0.133 g, 0.66 mmol), 3'-aminoacetophenone (0.074 g, 0.54 mmol) was added followed by TEA (0.3 mL, 1.71 mmol) to obtain compound 167 (0.048 g, 23%) as yellow solid.

Example 175

Synthesis of 2-amino-N-(1-methoxybutan-2-yl)-5-nitrobenzamide (168): The compound was prepared by general procedure A provided in example 1 using compound 1 (0.8 g, 4.39 mmol), DMF (8 mL), HATU (1.8 g, 4.83 mmol), 2-amino-1-methoxybutane (0.6 mL, 5.27 mmol), TEA (1.5 mL, 10.98 mmol) to obtain compound 168 (0.8 g, 68%) as yellow solid. $^1$H NMR (300 MHz, $d_6$-DMSO) δ in ppm 8.51 (d, J=2.4 Hz, 1H), 8.43 (d, J=8.4 Hz, 1H), 8.02 (dd, J=9.1 Hz, 2.7 Hz, 1H), 7.73 (s, 2H), 6.79 (d, J=9.3 Hz, 1H), 4.07-4.00 (m, 1H), 3.44-3.40 (m, 1H), 3.38-3.30 (m, 1H), 3.26 (s, 3H), 1.65-1.41 (m, 2H), 0.88 (t, J=4.5 Hz, 3H). ESI-HRMS m/z 268.1289 (M+H$^+$). Melting Point: 122° C.

Example 176

Synthesis of 3-(1-methoxybutan-2-yl)-6-nitroquinazolin-4 (3H)-one (169): The compound was prepared by general procedure B provided in example 2 using compound 168 (0.8 g, 2.99 mmol), trimethylorthoformate (TMOF) (6.5 mL, 59.89 mmol) to obtain compound 169 (0.70 g, 84%) as pale yellow solid. $^1$H NMR (300 MHz, $d_6$-DMSO) δ in ppm 8.84 (d, J=2.7 Hz, 1H), 8.61 (s, 1H), 8.57 (dd, J=9 Hz, 2.7 Hz, 1H), 7.89 (d, J=8.7 Hz, 1H), 4.92-4.83 (m, 1H), 3.87-3.81 (m, 1H), 3.65-3.60 (m, 1H), 3.23 (s, 3H), 1.92-1.82 (m, 2H), 0.84 (t, J=7.5 Hz, 3H). ESI-HRMS m/z 278.1138 (M+H$^+$). Melting Point: 104° C.

Example 177

Synthesis of 6-amino-3-(1-methoxybutan-2-yl)quinazolin-4 (3H)-one (170): The compound was prepared by general procedure C provided in example 3 using compound 169 (0.3 g, 1.08 mmol), methanol (8 mL) and pinch of 10% wet Pd—C under hydrogen atmosphere to obtain compound 170 (0.23 g, 86%) as light brown solid. $^1$H NMR (300 MHz, $d_6$-DMSO) δ in ppm 8.02 (s, 1H), 7.37 (d, J=8.7 Hz, 1H), 7.20 (d, J=2.7 Hz, 1H), 7.07 (dd, J=9.1 Hz, 2.4 Hz, 1H), 5.65 (s, 2H), 4.91-4.76 (m, 1H), 3.81-3.75 (m, 1H), 3.56 (q, J=6.3 Hz, 1H), 3.21 (s, 3H), 1.85-1.75 (m, 2H), 0.78 (t, J=7.2 Hz, 3H). ESI-HRMS m/z 248.1384 (M+H$^+$). Melting Point: 140° C.

Example 178

Synthesis of 1-(3-acetylphenyl)-3-(3-(1-methoxybutan-2-yl)-4-oxo-3,4-dihydroquinazolin-6-yl)urea (171): The compound was prepared by general procedure D provided in example 4 using compound 170 (0.10 g, 0.40 mmol), dry THF (6 mL), 4-nitrophenylchloroformate (0.12 g, 0.60 mmol), 3'-aminoacetophenone (0.065 g, 0.48 mmol), TEA (0.2 mL, 1.66 mmol) to obtain compound 171 (0.07 g, 42%) as off white solid. $^1$H NMR (300 MHz, $CDCl_3$) δ in ppm 9.09 (s, 1H), 8.96 (s, 1H), 8.30 (d, J=2.4 Hz, 1H), 8.21 (s, 1H), 8.06-8.05 (m, 1H), 7.79 (dd, J=8.8 Hz, 2.4 Hz, 1H), 7.67-7.65 (m, 1H), 7.59-7.54 (m, 2H), 7.43-7.39 (m, 1H), 4.86-4.80 (m, 1H), 3.80-3.75 (m, 1H), 3.57-3.53 (m, 1H), 3.19 (s, 3H), 2.53 (s, 3H), 1.83-1.76 (m, 2H), 0.77 (t, J=7.2 Hz, 3H). ESI-MS m/z 409.2 (M+H$^+$). Melting Point: 182° C.

Example 179

Synthesis of 2-amino-N-butyl-5-nitrobenzamide (172): The compound was prepared by general procedure A provided in example 1 using compound 1 (0.8 g, 4.39 mmol), DMF (8 mL), HATU (1.8 g, 4.83 mmol), 1-butylamine (0.5 mL, 5.27 mmol), TEA (1.5 mL, 10.98 mmol) to obtain compound 172 (0.82 g, 79%) as yellow solid. $^1$H NMR (400 MHz, $d_6$-DMSO) δ in ppm 8.62 (br.s, —NH), 8.43 (d, J=2.4 Hz, 1H), 7.96 (dd, J=9.2 Hz, 2.8 Hz, 1H), 7.70 (br.s, 2H), 6.74 (d, J=9.6 Hz, 1H), 3.18 (q, J=5.6 Hz, 2H), 1.50-1.42 (m, 2H), 1.33-1.25 (m, 2H), 0.86 (t, J=7.6 Hz, 3H). ESI-HRMS m/z 238.1173 (M+H$^+$). Melting Point: 128° C.

Example 180

Synthesis of 3-butyl-6-nitroquinazolin-4 (3H)-one (173): The compound was prepared by general procedure B provided in example 2 using compound 172 (0.6 g, 2.53 mmol), trimethylorthoformate (TMOF) (5.5 mL, 50.60 mmol) to obtain compound 173 (0.55 g, 88%) as pale yellow solid. $^1$H NMR (400 MHz, $d_6$-DMSO) δ in ppm 8.76 (d, J=2.4 Hz, 1H), 8.55 (s, 1H), 8.48 (dd, J=9 Hz, 2.4 Hz, 1H), 7.81 (d, J=9.6 Hz, 1H), 3.95 (t, J=7.2 Hz, 2H), 1.67-1.60 (m, 2H), 1.31-1.22 (m, 2H), 0.86 (t, J=7.2 Hz, 3H). ESI-HRMS m/z 248.1042 (M+H$^+$). Melting Point: 104° C.

Example 181

Synthesis of 6-amino-3-butylquinazolin-4 (3H)-one (174): The compound was prepared by general procedure C provided in example 3 using compound 173 (0.25 g, 1.01 mmol) was dissolved in methanol (5 mL) and pinch of 10% wet Pd—C under hydrogen atmosphere to obtain compound 174 (0.20 g, 91%) as light brown solid. $^1$H NMR (300 MHz, $d_6$-DMSO) δ in ppm 8.03 (s, 1H), 7.37 (d, J=8.7 Hz, 1H), 7.20 (d, J=2.7 Hz, 1H), 7.06 (dd, J=8.7 Hz, 2.7 Hz, 1H), 5.64 (s, 2H), 3.91 (t, J=7.2 Hz, 2H), 1.68-1.58 (m, 2H), 1.33-1.23 (m, 2H), 0.90 (t, J=7.5 Hz, 3H). ESI-HRMS m/z 218.1293 (M+H$^+$). Melting Point: 98° C.

Example 182

Synthesis of 1-(3-acetylphenyl)-3-(3-butyl-4-oxo-3,4-dihydroquinazolin-6-yl)urea (175): The compound was prepared by general procedure D provided in example 4 using compound 174 (0.12 g, 0.55 mmol), dry THF (6 mL), 4-nitrophneylchloroformate (0.133 g, 0.66 mmol), 3'-aminoacetophenone (0.090 g, 0.66 mmol), TEA (0.2 mL, 1.38 mmol) to obtain compound 175 (0.07 g, 33%) as off white solid. $^1$H NMR (400 MHz, $d_6$-DMSO) δ in ppm 9.09 (s, 1H), 8.96 (s, 1H), 8.29 (d, J=2.8 Hz, 1H), 8.22 (s, 1H), 8.05-8.04 (m, 1H), 7.77 (dd, J=6.8 Hz, 2.8 Hz, 1H), 7.66-7.64 (m, 1H), 7.58-7.53 (m, 2H), 7.41-7.37 (m, 1H), 3.91 (t, J=7.6 Hz, 2H), 2.52 (s, 3H), 1.65-1.58 (m, 2H), 1.30-1.21 (m, 2H), 0.86 (t, J=7.6 Hz, 3H). ESI-MS m/z 379.2 (M+H$^+$). Melting Point: 196° C.

Example 183

Synthesis of 2-amino-N-(1-methoxypropan-2-yl)-5-nitrobenzamide (176): The compound was prepared by general procedure A provided in example 1 using compound 1 (0.8 g, 4.39 mmol), DMF (8 mL), HATU (1.8 g, 4.83 mmol), 1-methoxy-2-propylamine (0.5 mL, 5.27 mmol), TEA (1.5 mL, 10.98 mmol) to obtain compound 176 (0.83 g, 75%) as yellow solid. $^1$H NMR (400 MHz, $d_6$-DMSO) δ in ppm 8.46 (br.s, —NH), 8.44 (d, J=2.8 Hz, 1H), 7.96 (dd, J=9.2 Hz, 2.8 Hz, 1H), 7.68 (br.s, 2H), 6.74 (d, J=9.6 Hz, 1H), 4.17-4.10 (m, 1H), 3.38-3.34 (m, 1H), 3.26-3.23 (m, 1H), 3.22 (s, 3H), 1.08 (d, J=6.8 Hz, 3H). ESI-HRMS m/z 254.1130 (M+H$^+$). Melting Point: 118° C.

Example 184

Synthesis of 3-(1-methoxypropan-2-yl)-6-nitroquinazolin-4 (3H)-one (177): The compound was prepared by general procedure B provided in example 2 using compound 176 (0.6 g, 2.37 mmol), trimethylorthoformate (TMOF) (5.1 mL, 47.41 mmol) to obtain compound 177 (0.57 g, 91%) as pale yellow solid. $^1$H NMR (300 MHz, $d_6$-DMSO) δ in ppm 8.84 (s, 1H), 8.62 (s, 1H), 8.57 (d, J=9 Hz, 1H), 7.88 (d, J=9.3 Hz, 1H), 5.11-5.00 (m, 1H), 3.83-3.77 (m, 1H), 3.62-3.57 (m, 1H) 3.24 (s, 3H), 1.43 (d, J=6.9 Hz, 3H). ESI-HRMS m/z 264.0977 (M+H$^+$). Melting Point: 100° C.

Example 185

Synthesis of 6-amino-3-(1-methoxypropan-2-yl)quinazolin-4 (3H)-one (178): The compound was prepared by general procedure C provided in example 3 using compound 177 (0.6 g, 2.28 mmol), methanol (8 mL) and pinch of 10% wet Pd—C under hydrogen atmosphere to obtain compound 178 (0.48 g, 90%) as light brown solid. ESI-HRMS m/z 234.1229 (M+H$^+$). Melting Point: 130° C.

Example 186

Synthesis of 1-(3-acetylphenyl)-3-(3-(1-methoxypropan-2-yl)-4-oxo-3,4-dihydroquinazolin-6-yl)urea (179): The compound was prepared by general procedure D provided in example 4 using compound 178 (0.12 g, 0.51 mmol), dry THF (6 mL), 4-nitrophenylchloroformate (0.15 g, 0.60 mmol), 3'-aminoacetophenone (0.087 g, 0.64 mmol), TEA (0.3 mL, 2.12 mmol) to obtain compound 179 (0.07 g, 41%) as off white solid. $^1$H NMR (300 MHz, $d_6$-DMSO) δ in ppm 9.16 (s, 1H), 9.03 (s, 1H), 8.35 (s, 1H), 8.29 (s, 1H), 8.10 (s, 1H), 7.83 (d, J=8.7 Hz, 1H), 7.71 (d, J=7.5 Hz, 1H), 7.64-7.60 (m, 2H), 7.48-7.43 (m, 1H), 5.11-5.01 (m, 1H), 3.79 (t, J=8.4 Hz, 1H), 3.60-3.55 (m, 1H), 3.24 (s, 3H), 2.58 (s, 3H), 1.40 (d, J=6.9 Hz, 3H). ESI-HRMS m/z 395.1728 (M+H$^+$). Melting Point: 146° C.

Example 187

Synthesis of 2-amino-N-(2-isopropoxyethyl)-5-nitrobenzamide (180): The compound was prepared by general procedure A provided in example 1 using compound 1 (0.8 g, 4.39 mmol), DMF (8 mL), HATU (1.8 g, 4.83 mmol), 2-aminoethyl isopropyl ether (0.6 mL, 4.83 mmol), TEA (1.5 mL, 10.98 mmol) to obtain compound 180 (0.83 g, 68%) as yellow solid. $^1$H NMR (300 MHz, $d_6$-DMSO) 8.74 (br.s, 1H), 8.49 (d, J=2.7 Hz, 1H), 8.01 (dd, J=9.3 Hz, 1H), 7.74 (br.s, 2H), 6.79 (d, J=9.3 Hz, 1H), 3.62-3.53 (m, 1H), 3.48 (t, J=6 Hz, 2H), 3.38-3.33 (m, 2H), 1.05 (d, J=6.3 Hz, 6H). (ESI-HRMS m/z 268.1304 (M+H$^+$). Melting Point: 88° C.

Example 188

Synthesis of 3-(2-isopropoxyethyl)-6-nitroquinazolin-4 (3H)-one (181): The compound was prepared by general procedure B provided in example 2 using compound 180 (0.80 g, 2.99 mmol), trimethylorthoformate (TMOF) (6.5 mL, 59.89 mmol) to obtain compound 181 (0.70 g, 84%) as pale yellow solid. $^1$H NMR (300 MHz, $d_6$-DMSO) 8.85 (d, J=2.7 Hz, 1H), 8.56 (dd, J=9 Hz, 2.7 Hz, 1H), 8.49 (s, 1H), 7.89 (d, J=9 Hz, 1H), 4.16 (t, J=5.4 Hz, 2H), 3.66 (t, J=5.4 Hz, 2H), 3.57-3.49 (m, 1H), 1.01 (d, J=6.3 Hz, 6H). ESI-HRMS m/z 278.1139 (M+H$^+$). Melting Point: 82° C.

Example 189

Synthesis of 6-amino-3-(2-isopropoxyethyl)quinazolin-4 (3H)-one (182): The compound was prepared by general procedure C provided in example 3 using compound 181 (0.6 g, 2.16 mmol), methanol (8 mL) and pinch of 10% wet Pd—C under hydrogen atmosphere to obtain compound 182 (0.40 g, 78%) as light brown solid. $^1$H NMR (300 MHz, $d_6$-DMSO) 7.93 (s, 1H), 7.37 (d, J=8.4 Hz, 1), 7.21 (d, J=2.7 Hz, 1H), 7.06 (dd, J=8.7 Hz, 2.4 Hz, 1H), 5.64 (s, 2H), 4.04 (t, J=5.4 Hz, 2H), 3.61 (t, J=5.4 Hz, 2H), 3.55-3.47 (m, 1H), 1.00 (d, J=6.3 Hz, ESI-HRMS m/z 248.1406 (M+H$^+$). Melting Point: 80° C.

Example 190

Synthesis of 1-(3-acetylphenyl)-3-(3-(2-isopropoxyethyl)-4-oxo-3,4-dihydroquinazolin-6-yl)urea (183): The compound was prepared by general procedure D provided in example 4 using compound 182 (0.12 g, 0.48 mmol), dry THF (6 mL), 4-nitrophenylchloroformate (0.15 g, 0.72 mmol), 3'-aminoacetophenone (0.082 g, 0.60 mmol), TEA (0.3 mL, 2 mmol) to obtain compound 183 (0.075 g, 37%) as off white solid. $^1$H NMR (300 MHz, $d_6$-DMSO) 9.14 (s, 1H), 9.01 (s, 1H), 8.37 (d, J=2.4 Hz, 1H), 8.16 (s, 1H), 8.10 (brs, 1H), 7.81 (dd, J=8.8 Hz, 2.7 Hz, 1H), 7.70 (d, J=7.2 Hz, 1H), 7.64-7.59 (m, 2H), 7.48-7.43 (m, 1H), 4.11 (t, J=5.1 Hz, 2H), 3.64 (t, J=5.1 Hz, 2H), 3.56-3.48 (m, 1H), 2.57 (s, 3H), 1.01 (d, J=6 Hz, 6H). ESI-HRMS m/z 409.1890 (M+H$^+$). Melting Point: 142° C.

Example 191

Synthesis of 2-amino-N-cyclohexyl-5-nitrobenzamide (184): The compound was prepared by general procedure A provided in example 1 using compound 1 (1 g, 5.49 mmol), DMF (10 mL), HATU (2.2 g, 6.04 mmol), cyclohexylamine (0.65 mL, 6.58 mmol), TEA (1.9 mL, 13.73 mmol) to obtain compound 184 (0.982 g, 68%) as yellow solid. ESI-HRMS m/z 264.1346 (M+H$^+$). Melting Point: 102° C.

Example 192

Synthesis of 3-cyclohexyl-6-nitroquinazolin-4 (3H)-one (185): The compound was prepared by general procedure B provided in example 2 using compound 184 (0.6 g, 2.28 mmol), trimethylorthoformate (TMOF) (4 mL, 38.23 mmol) to obtain compound 185 (0.49 g, 80%) as pale yellow solid. ESI-HRMS m/z 274.1200 ($M+H^+$).

Example 193

Synthesis of 6-amino-3-cyclohexylquinazolin-4 (3H)-one (186): The compound was prepared by general procedure C provided in example 3 using compound 185 (0.3 g, 1.09 mmol), methanol (10 mL) and pinch of 10% wet Pd—C under hydrogen atmosphere to obtain compound 186 (0.160 g, 60%) as light brown solid. ESI-HRMS m/z 244.1454 ($M+H^+$).

Example 194

Synthesis of 1-(3-acetylphenyl)-3-(3-cyclohexyl-4-oxo-3,4-dihydroquinazolin-6-yl)urea (187): The compound was prepared by general procedure D provided in example 4 using compound 186 (0.120 g, 0.49 mmol), dry THF (8 mL), 4-nitrophenylchloroformate (0.119 g, 0.59 mmol), 3'-aminoacetophenone (0.086 g, 0.63 mmol), TEA (0.3 mL, 1.71 mmol) to obtain compound 187 (0.091 g, 46%) as yellow solid.

Example 195

Synthesis of 2-amino-N-(2-methoxyethyl)-4-nitrobenzamide (189): The compound was prepared by general procedure A provided in example 1 using 2-amino-4-nitrobenzoic acid (compound 188) (1 g, 5.49 mmol), DMF (10 mL), HATU (2.2 g, 6.04 mmol), 2-methoxyethylamine (0.50 mL, 6.58 mmol), TEA (1.9 mL, 13.73 mmol) to obtain compound 189 (0.945 g, 72%) as yellow solid. $^1H$ NMR (300 MHz, $d_6$-DMSO) δ in ppm 8.59 (s, —NH), 7.66 (d, J=8.7 Hz, 1H), 7.57 (d, J=2.4 Hz, 1H), 7.28 (dd, J=8.4 Hz, 2.4 Hz, 1H), 6.84 (br.s, 2H), 3.45-3.38 (m, 4H), 3.26 (s, 3H). ESI-HRMS m/z 240.0996 ($M+H^+$).

Example 196

Synthesis of 3-(2-methoxyethyl)-7-nitroquinazolin-4 (3H)-one (190): The compound was prepared by general procedure B provided in example 2 using compound 189 (0.6 g, 2.28 mmol), trimethylorthoformate (TMOF) (4 mL, 38.23 mmol) to obtain compound 190 (0.49 g, 80%) as pale yellow solid. ESI-HRMS m/z 250.0834 ($M+H^+$).

Example 197

Synthesis of 7-amino-3-(2-methoxyethyl)quinazolin-4 (3H)-one (191): The compound was prepared by general procedure C provided in example 3 using compound 190 (0.3 g, 1.20 mmol), methanol (10 mL) and pinch of 10% wet Pd—C under hydrogen atmosphere to obtain compound 191 (0.158 g, 60%) as light brown solid. $^1H$ NMR (300 MHz, $d_6$-DMSO) δ in ppm 8.01 (s, 1H), 7.78 (d, J=8.7 Hz, 1H), 6.73 (dd, J=8.7 Hz, 2.1 Hz, 1H), 6.60 (d, J=2.1 Hz, 1H), 6.11 (br.s, 2H), 4.04 (t, J=5.1 Hz, 2H), 3.55 (t, J=5.1 Hz, 2H), 3.23 (s, 3H). ESI-HRMS m/z 220.1094 ($M+H^+$). Melting Point: 132° C.

Example 198

Synthesis of 1-(3-acetylphenyl)-3-(3-(2-methoxyethyl)-4-oxo-3,4-dihydroquinazolin-7-yl)urea (192): The compound was prepared by general procedure D provided in example 4 using compound 191 (0.120 g, 0.49 mmol), dry THF (8 mL), 4-nitrophenylchloroformate (0.119 g, 0.59 mmol), 3'-aminoacetophenone (0.086 g, 0.63 mmol), TEA (0.3 mL, 1.71 mmol) to obtain compound 192 (0.091 g, 46%) as yellow solid. $^1H$ NMR (400 MHz, $d_6$-DMSO) δ in ppm 9.23 (s, 1H), 9.05 (s, 1H), 8.18 (s, 1H), 8.06 (m, 1H), 8.02 (d, J=8.8 Hz, 1H), 7.83 (d, J=2 Hz, 1H), 7.68-7.65 (m, 1H), 7.59-7.57 (m, 1H), 7.49 (dd, J=8.8 Hz, 2 Hz, 1H), 7.44-7.40 (m, 1H), 4.08 (t, J=5.2 Hz, 2H), 3.56 (t, J=4.8 Hz, 2H), 3.21 (s, 3H), 2.54 (s, 3H). ESI-MS m/z 381.3 ($M+H^+$).

Example 199

Synthesis of 1-(4-acetylphenyl)-3-(3-(2-methoxyethyl)-4-oxo-3,4-dihydroquinazolin-7-yl)urea (193): The compound was prepared by general procedure E provided in example 5 using compound 191 (0.120 g, 0.49 mmol), dry THF (8 mL), 4-nitrophenylchloroformate (0.119 g, 0.59 mmol), 4'-aminoacetophenone (0.086 g, 0.63 mmol), TEA (0.3 mL, 1.71 mmol) to obtain compound 193 (0.079 g, 38%) as yellow solid. $^1H$ NMR (400 MHz, $d_6$-DMSO) δ in ppm 9.30 (s, 1H), 9.24 (s, 1H), 8.17 (s, 1H), 8.01 (d, J=8.4 Hz, 1H), 7.88-7.82 (m, 3H), 7.56 (d, J=8 Hz, 2 Hz, 2H), 7.46 (d, J=8.4 Hz, 1H), 4.06 (t, J=4.8 Hz, 2H), 3.53 (t, J=4.4 Hz, 2H), 3.20 (s, 3H), 2.47 (s, 3H). ESI-MS m/z 381.2 ($M+H^+$).

Example 200

Synthesis of N-(2-((2-methoxyethyl)carbamoyl)-4-nitrophenyl)picolinamide (208): Picolinic acid (0.64 g, 5.20 mmol) was dissolved in dry DCM (10 mL) followed by addition of one drop of DMF. Oxalyl Chloride (0.66 mL, 7.80 mmol) was added to the reaction mixture under ice cold condition and nitrogen atmosphere. The reaction was stirred for 15 mins for the formation of acid chloride. Then the reaction mass was evaporated to dryness to remove excess oxalyl chloride and DCM. The crude is kept under inert atmosphere and dissolved in DCM (20 mL). In another flask, compound 2 (0.5 g, 2.09 mmol) was dissolved in DCM (10 mL) followed by addition of TEA (0.7 mL, 5.64 mmol). In this reaction medium, the previously prepared acid chloride was added dropwise and under ice cold condition. The reaction was monitored by checking TLC. Upon completion of the reaction, reaction mass was evaporated to dryness and washed with water and extracted with EtOAc to get the crude. The product was purified by flash chromatography (Silica gel, mesh size 100-200) eluting (50% EtOAc/Pet ether) to obtain compound 208 (0.26 g, 29%) as white solid. $^1H$ NMR (400 MHz, $d_6$-DMSO) δ in ppm 13.24 (s, 1H), 9.20 (d, J=5.2 Hz, 1H), 8.94 (d, J=9.2, 1H), 8.76-8.74 (m, 1H), 8.64 (d, J=2.8 Hz, 1H), 8.42 (dd, J=9.2 Hz, 2.8 Hz, 1H), 8.19-8.16 (m, 1H), 8.08-8.04 (m, 1H), 7.69-7.06 (m, 1H), 3.51-3.44 (m, 4H), 3.25 (s, 3H). ESI-HRMS m/z 345.1201 ($M+H^+$). Melting point 224° C.

Example 201

Synthesis of 3-(2-methoxyethyl)-6-nitro-2-(pyridin-2-yl) quinazolin-4 (3H)-one (209): The compound was prepared by general procedure G provided in example 7 using compound 208 (0.25 g, 0.72 mmol), DMF (5 mL), zinc chloride (0.40 g, 2.91 mmol), HMDS (1.21 mL, 5.80 mmol) to obtain compound 209 (0.165 g, 70%) as yellow solid. $^1H$ NMR (400 MHz, $d_6$-DMSO) δ in ppm 8.84 (d, J=2.8 Hz, 1H), 8.96-8.67 (m, 1H), 8.57-8.54 (m, 1H), 8.07-8.02 (m, 1H), 7.89-7.85 (m, 2H), 7.61-7.57 (m, 1H), 4.37 (t, J=6 Hz, 2H), 3.43 (t, J=6 Hz, 2H), 3.31 (s, 3H). ESI-HRMS m/z 327.1096 (M+H+). Melting point 144° C.

Example 202

Synthesis of 6-amino-3-(2-methoxyethyl)-2-(pyridin-2-yl)quinazolin-4 (3H)-one (210): The compound was prepared by general procedure C provided in example 3 using compound 209 (0.155 g, 0.47 mmol), methanol (10 mL), pinch of Pd/C under hydrogen atmosphere to obtain compound 210 (0.075 g, 54%) as brown solid. $^1$H NMR (400 MHz, $d_6$-DMSO) δ in ppm 8.63-8.61 (m, 1H), 7.99-7.94 (m, 1H), 7.77-7.74 (m, 1H), 7.51-7.48 (m, 1H), 7.40 (d, J=8.8 Hz, 1H), 7.26 (d, J=2 Hz, 1H), 7.11 (dd, J=8 Hz, 2.4 Hz, 1H), 4.32 (t, J=6.4 Hz, 2H), 3.38 (t, J=6 Hz, 2H), 2.94 (s, 3H). ESI-HRMS m/z 297.1352 (M+H+). Melting point 138° C.

Example 203

Synthesis of 1-(3-acetylphenyl)-3-(3-(2-methoxyethyl)-4-oxo-2-(pyridin-2-yl)-3,4-dihydroquinazolin-6-yl)urea (211): The compound was prepared by general procedure D provided in example 4 using compound 210 (0.065 g, 0.21 mmol), dry THF (5 mL), 4-nitrophenyl chloroformate (0.06 g, 0.32 mmol), 3-aminoacetophenone (0.039 g, 0.26 mmol), TEA (0.073 mL, 0.52 mmol) to obtain 211 as off white solid (0.021 g, 21%). $^1$H NMR (400 MHz, $d_6$-DMSO) δ in ppm 9.17 (s, 1H), 9.01 (s, 1H), 8.66-8.64 (m, 1H), 8.39 (d, J=2.4 Hz, 1H), 8.07 (t, J=1.6 Hz, 1H), 8.02-7.98 (m, 1H), 7.83-7.79 (m, 2H), 7.69-7.66 (m, 1H), 7.63 (d, J=8.8 Hz, 1H), 7.58-7.52 (m, 2H), 7.42 (t, J=8.0 Hz, 1H), 4.34 (t, J=6 Hz, 2H), 3.41 (t, J=6 Hz, 2H), 2.93 (s, 3H), 2.50 (s, 3H). ESI-HRMS m/z 458.1841 (M+H+). Melting point 230° C.

Example 204

Synthesis of N-(2-((2-methoxyethyl)carbamoyl)-4-nitrophenyl)nicotinamide (212): Commercially available Nicotinic acid (0.64 g, 5.20 mmol) was dissolved in dry DCM (10 mL) followed by addition of one drop of DMF. Oxalyl chloride (0.66 mL, 7.80 mmol) was added to the reaction mixture under ice cold condition and nitrogen atmosphere. The reaction was stirred for 15 mins for the formation of acid chloride. Then the reaction mass was evaporated to dryness to remove excess oxalyl chloride and DCM. The crude is kept under inert atmosphere and dissolved in DCM (20 mL). In another flask, compound 2 (0.5 g, 2.09 mmol) was dissolved in DCM (10 mL) followed by addition of TEA (0.7 mL, 5.64 mmol). In this reaction medium, the previously prepared acid chloride was added dropwise and under ice cold condition. The reaction was monitored by checking TLC. Upon completion of the reaction, reaction mass was evaporated to dryness and washed with water and extracted with EtOAc to get the crude. The product was purified by flash chromatography (Silica gel, mesh size 100-200) eluting (50% EtOAc/Pet ether) to obtain compound 212 (0.213 g, 24%) as white solid. $^1$H NMR (400 MHz, $d_6$-DMSO) δ in ppm 13.03 (s, 1H), 9.37 (s, 1H), 9.07 (s, 1H), 8.80-8.73 (m, 3H), 8.41 (d, J=8 Hz, 1H), 7.63-7.59 (m, 1H), 3.49-3.45 (m, 4H), 3.24 (s, 3H). ESI-HRMS m/z 345.1201 (M+H+). Melting point 180° C.

Example 205

Synthesis of 3-(2-methoxyethyl)-6-nitro-2-(pyridin-3-yl) quinazolin-4 (3H)-one (213): The compound was prepared by general procedure G provided in example 7 using compound 212 (0.20 g, 0.58 mmol), DMF (5 mL), zinc chloride (0.40 g, 2.91 mmol), HMDS (1 mL, 4.65 mmol) to obtain compound 213 (0.163 g, 86%) as yellow solid. $^1$H NMR (400 MHz, $d_6$-DMSO) δ in ppm 8.85 (d, J=2.4 Hz, 1H), 8.81 (dd, J=2.4 Hz, J=0.8 Hz, 1H), 8.72 (dd, J=5 Hz, J=1.6 Hz, 1H), 8.57-8.54 (m, 1H), 8.09-8.06 (m, 1H), 7.80 (d, J=8.8 Hz, 1H), 7.58-7.55 (m, 1H), 4.09 (t, J=5.6 Hz, 2H), 3.44 (t, J=5.6 Hz, 2H), 3.01 (s, 3H). ESI-HRMS m/z 327.1097 (M+H+). Melting point 170° C.

Example 206

Synthesis of 6-amino-3-(2-methoxyethyl)-2-(pyridin-3-yl)quinazolin-4 (3H)-one (214): The compound was prepared by general procedure C provided in example 3 using compound 213 (0.150 g, 0.45 mmol), methanol (10 mL) to obtain compound 214 (0.06 g, 33%) as brown solid. $^1$H NMR (400 MHz, $d_6$-DMSO) δ in ppm 8.72 (dd, J=2.2 Hz, J=0.8 Hz, 1H), 8.64 (dd, J=4.8 Hz, J=1.6 Hz, 1H), 8.00-7.97 (m, 1H), 7.51-7.47 (m, 1H), 7.35 (d, J=8.8 Hz, 1H), 7.20 (d, J=2.4 Hz, 1H), 7.06 (dd, J=8.4 Hz, J=2.4 Hz, 1H), 5.69 (brs, 2H), 4.00 (t, J=6 Hz, 2H), 3.391 (t, J=6 Hz, 2H), 2.98 (s, 3H). Melting point 152° C.

Example 207

Synthesis of 1-(3-acetylphenyl)-3-(3-(2-methoxyethyl)-4-oxo-2-(pyridin-3-yl)-3,4-dihydroquinazolin-6-yl)urea (215): The compound was prepared by general procedure D provided in example 4 using compound 214 (0.05 g, 0.16 mmol), dry THF (5 mL), 4-nitrophenyl chloroformate (0.06 g, 0.26 mmol), 3'-aminoacetophenone (0.030 g, 0.26 mmol), (0.059 mL, 0.42 mmol) to obtain compound 215 (0.037 g, 48%) as off white solid. $^1$H NMR (400 MHz, $d_6$-DMSO) δ in ppm 9.15 (s, 1H), 8.99 (s, 1H), 8.77 (d, J=1.6 Hz, 1H), 8.68 (dd, J=4.8 Hz, J=1.6 Hz, 1H), 8.40 (d, J=2.4 Hz, 1H), 8.07-8.02 (m, 2H), 7.79 (dd, J=8.8 Hz, J=2.8 Hz, 1H) 7.69-7.66 (m, 1H), 7.62-7.55 (m, 2H) 7.54-7.55 (m, 1H), 7.44-7.40 (m, 1H), 4.05 (t, J=5.6 Hz, 2H), 3.42 (t, J=5.6 Hz, 2H) 3.00 (s, 3H), 2.53 (s, 3H). ESI-HRMS m/z 458.184 (M+H+). Melting point 218° C.

Example 208

Synthesis of N-(2-((2-methoxyethyl)carbamoyl)-4-nitrophenyl)isonicotinamide (216): Commercially available Isonicotinic acid (0.64 g, 5.20 mmol) was dissolved in dry DCM (10 mL) followed by addition of one drop of DMF. Oxalyl Chloride (0.66 mL, 7.80 mmol) was added to the reaction mixture under ice cold condition and nitrogen atmosphere. The reaction was stirred for 15 mins for the formation of acid chloride. Then the reaction mass was evaporated to dryness to remove excess oxalyl chloride and DCM. The crude is kept under inert atmosphere and dissolved in DCM (20 mL). In another flask, compound 2 (0.5 g, 2.09 mmol) was dissolved in DCM (10 mL) followed by addition of TEA (0.7 mL, 5.64 mmol). In this reaction medium, the previously prepared acid chloride was added dropwise under ice cold condition. The reaction was monitored by checking TLC. Upon completion of the reaction, reaction mass was evaporated to dryness and washed with water and extracted with EtOAc to get the crude. The product was purified by flash chromatography (Silica gel, mesh size 100-200) eluting (50% EtOAc/Pet ether) to obtain compound 216 (0.313 g, 33%) as white solid. $^1$H NMR (400 MHz, $d_6$-DMSO) δ in ppm 13.10 (s, 1H), 9.40 (d, J=4.8 Hz, 1H), 8.84-8.79 (m, 3H), 8.75 (d, J=2.4 Hz, 1H) 8.43 (dd, J=5.4 Hz, J=2.4 Hz, 1H), 7.79 (dd, J=4.4 Hz, J=1.6 Hz, 2H), 3.49-3.46 (m, 4H), 3.24 (s, 3H). Melting point 206° C.

Example 209

Synthesis of 3-(2-methoxyethyl)-6-nitro-2-(pyridin-4-yl) quinazolin-4 (3H)-one (217): The compound was prepared by general procedure G provided in example 7 using compound 216 (0.30 g, 0.87 mmol), DMF (5 mL), zinc chloride (0.48 g, 3.48 mmol), HMDS (1.5 mL, 6.96 mmol) to obtain compound 217 (0.210 g, 73%) as yellow solid. $^1$H NMR (400 MHz, $d_6$-DMSO) δ in ppm 8.85-8.85 (m, 1H), 8.75 (dd, J=4.4 Hz, J=1.6 Hz, 2H), 8.56 (dd, J=10 Hz, J=2.8 Hz, 1H), 7.86 (dd, J=9.0 Hz, J=0.4 Hz, 1H), 7.63 (dd, J=4.4 Hz, J=1.6 Hz, 2H), 4.05 (t, J=5.6 Hz, 2H), 3.43 (t, J=5.6 Hz, 2H), 3.01 (s, 3H). Melting point 200° C.

Example 210

Synthesis of 6-amino-3-(2-methoxyethyl)-2-(pyridin-4-yl)quinazolin-4 (3H)-one (218): The compound was prepared by general procedure C provided in example 3 using compound 217 (0.200 g, 0.61 mmol), methanol (10 mL), pinch of 10% Pd/C under hydrogen atmosphere to obtain compound 218 (0.065 g, 34%) as brown solid. $^1$H NMR (400 MHz, $d_6$-DMSO) δ in ppm 8.69-8.67 (m, 2H), 7.56-7.55 (m, 2H), 7.35 (d, J=8.8 Hz, 1H), 7.20 (d, J=2.4 Hz, 1H), 7.06 (dd, J=8.8 Hz, J=2.4 Hz, 1H), 5.71 (brs, 2H), 4.00 (t, J=6 Hz, 2H), 3.83 (t, J=5.6 Hz, 2H), 2.98 (s, 3H). Melting point 42° C.

Example 211

Synthesis of 1-(3-acetylphenyl)-3-(3-(2-methoxyethyl)-4-oxo-2-(pyridin-4-yl)-3,4-dihydroquinazolin-6-yl)urea (219): The compound was prepared by general procedure D provided in example 4 using compound 218 (0.059 g, 0.19 mmol), dry THF (5 mL), 4-nitrophenyl chloroformate (0.06 g, 0.29 mmol), 3'-aminoacetophenone (0.032 g, 0.26 mmol), TEA (0.07 mL, 0.49 mmol) to obtain compound 219 (0.018 g, 20%) as off white solid. $^1$H NMR (400 MHz, $d_6$-DMSO) δ in ppm 9.16 (s, 1H), 8.99 (s, 1H), 8.71 (dd, J=4.4 Hz, J=1.6 Hz, 2H), 8.40 (d, J=2.4 Hz, 1H), 8.06 (t, J=2 Hz, 1H), 7.79 (dd, J=8.8 Hz, J=2.8 Hz, 1H), 7.68-7.66 (m, 1H), 7.61-7.59 (m, 3H), 7.58-7.56 (m, 1H), 7.44-7.40 (m, 1H), 4.04 (t, J=5.6 Hz, 2H), 3.41 (t, J=5.6 Hz, 2H), 3.00 (s, 3H), 2.53 (s, 3H). ESI-HRMS m/z 458.1828 (M+H$^+$). Melting point 240° C.

Example 212

Synthesis of N-(2-((2-methoxyethyl)carbamoyl)-4-nitrophenyl)pyrazine-2-carboxamide (220): Commercially available pyrazine-2-carboxylic acid (0.649 g, 5.22 mmol) was dissolved in dry DCM (10 mL) followed by addition of one drop of DMF. Oxalyl Chloride (0.66 mL, 7.80 mmol) was added to the reaction mixture under ice cold condition and nitrogen atmosphere. The reaction was stirred for 15 mins for the formation of acid chloride. Then the reaction mass was evaporated to dryness to remove excess oxalyl chloride and DCM. The crude is kept under inert atmosphere and dissolved in DCM (20 mL). In another flask, compound 2 (0.5 g, 2.09 mmol) was dissolved in DCM (10 mL) followed by addition of TEA (0.7 mL, 5.64 mmol) and allowed to stir at room temperature for 7 hours. In this reaction medium, the previously prepared acid chloride was added dropwise under ice cold condition. The reaction was monitored by checking TLC. Upon completion of the reaction, reaction mass was evaporated to dryness and washed with water and extracted with EtOAc to get the crude. The product was purified by flash chromatography (Silica gel, mesh size 100-200) eluting (50% EtOAc/Pet ether) to obtain compound 220 (0.175 g, 49%) as white solid.

Example 213

Synthesis of 3-(2-methoxyethyl)-6-nitro-2-(pyrazin-2-yl) quinazolin-4 (3H)-one (221): The compound was prepared by general procedure G provided in example 7 using compound 220 (0.165 g, 0.47 mmol), DMF (5 mL), zinc chloride (0.26 g, 1.91 mmol), HMDS (0.83 mL, 3.89 mmol) to obtain compound 221 (0.125 g, 49%) as white solid.

Example 214

Synthesis of 6-amino-3-(2-methoxyethyl)-2-(pyrazin-2-yl)quinazolin-4 (3H)-one (222): The compound was prepared by general procedure C provided in example 3 using compound 221 (0.118 g, 0.39 mmol), methanol (10 mL), a pinch of 10% Pd/C under hydrogen atmosphere to obtain compound 222 (0.08 mg, 78%) as dark green solid.

Example 215

Synthesis of 1-(3-acetylphenyl)-3-(3-(2-methoxyethyl)-4-oxo-2-(pyrazin-2-yl)-3,4-dihydroquinazolin-6-yl)urea (223): The compound was prepared by general procedure D provided in example 4 using compound 222 (0.70 g, 0.23 mmol), dry THF (5 mL), 4-nitrophenyl chloroformate (0.072 g, 0.35 mmol), 3'-aminoacetophenone (0.039 g, 0.28 mmvol), TEA (0.082 mL, 0.58 mmol) to obtain compound 223 as off white solid (0.04 g, 39%).

Example 216

Synthesis of 2-(2-chloroacetamido)-N-(2-methoxyethyl)-5-nitrobenzamide (228): Compound 2 (1 gm, 4.18 mmol) was dissolved in dry DCM and TEA (1.16 mL, 8.36 mmol) was added followed by chloroacetyl chloride (0.39 ml, 5.01 mmole) dropwise at cooling and the reaction mixture was allowed to stir at room temperature for 1 hour. After completion of the reaction, it was worked up with ethyl acetate and water and purified by column chromatography (Silica gel, mesh size 100-200) eluting (50% EtOAc/Pet Ether) to obtain compound 228 (0.800 g, 60%) as white solid. $^1$H NMR (400 MHz, $d_6$-DMSO) δ in ppm 12.26 (s, 1H), 9.26-9.24 (m, 1H), 8.64-8.62 (m, 2H), 8.36 (dd, J=9.2 Hz, 2.8 Hz, 1H), 4.44 (s, 2H), 3.48-3.40 (m, 4H), 3.24 (s, 3H). ESI-HRMS m/z 316.0703 (M+H$^+$).

Example 217

Synthesis of 2-(chloromethyl)-3-(2-methoxyethyl)-6-nitroquinazolin-4 (3H)-one (229): The compound was prepared by general procedure G provided in example 7 using compound 228 (0.8 g, 2.53 mmol), DMF (10 mL), $ZnCl_2$ (1.4 g, 10.12 mmol), HMDS (4.24 mL, 20.24 mmol) to obtain compound 229 (0.60 g, 79%) as white solid. $^1$H NMR (400 MHz, $d_6$-DMSO) δ in ppm 8.78-8.75 (m, 1H), 8.55-8.50 (m, 1H), 7.86-7.82 (m, 1H), 4.92 (s, 2H), 4.31 (t, J=5.2 Hz, 2H), 3.61 (t, J=5.2 Hz, 2H), 3.20 (s, 3H). ESI-HRMS m/z 298.0595 (M+H$^+$).

Example 218

Synthesis of 3-(2-methoxyethyl)-6-nitro-2-(pyrrolidin-1-ylmethyl)quinazolin-4 (3H)-one (230): Compound 229 (0.2 g, 0.74 mmol) and pyrrolidine (0.125 mL, 1.48 mmol) were dissolved in toluene and reaction mixture was refluxed for 2 hours. After completion of the reaction, it was washed with water and extracted with ethyl acetate to obtain light yellow crude mass which was then purified by column chromatography (Silica gel, mesh size 100-200) eluting (80% EtOAc/Pet Ether) to obtain compound 230 (0.159 g, 64%) as white solid. $^1$H NMR (400 MHz, $d_6$-DMSO) δ in ppm 8.76 (d, J=2.8 Hz, 1H), 8.48 (dd, J=8.8 Hz, 2.8 Hz, 1H), 7.80 (d, J=9.2 Hz, 1H), 4.45 (t, J=6 Hz, 2H), 3.83 (s, 2H), 3.59 (t, J=5.6 Hz, 2H), 3.20 (s, 3H), 2.54-2.49 (m, 4H), 1.69-1.65 (m, 4H). ESI-HRMS m/z 333.1572 (M+H$^+$).

Example 219

Synthesis of 6-amino-3-(2-methoxyethyl)-2-(pyrrolidin-1-ylmethyl)quinazolin-4 (3H)-one (231): The compound was prepared by general procedure C provided in example 3 using compound 230 (0.150 g, 0.42 mmol), methanol (10 mL), pinch of 10% wet Pd—C under hydrogen atmosphere to obtain compound 231 (0.158 g, 60%) as light brown solid. $^1$H NMR (400 MHz, $d_6$-DMSO) δ in ppm 7.30 (d, J=8.8 Hz, 1H), 7.12 (d, J=2.8 Hz, 1H), 7.01 (dd, J=8.4 Hz, 2.4 Hz, 1H), 5.57 (s, 2H), 4.36 (t, J=6 Hz, 2H), 3.68 (s, 2H), 3.54 (t, J=5.6 Hz, 2H), 3.18 (s, 3H), 2.45-2.42 (m, 4H), 1.67-1.62 (m, 4H). ESI-HRMS m/z 303.1826 (M+H$^+$).

Example 220

Synthesis of 1-(3-acetylphenyl)-3-(3-(2-methoxyethyl)-4-oxo-2-(pyrrolidin-1-ylmethyl)-3,4-dihydroquinazolin-6-yl) urea (232): The compound was prepared by general procedure D provided in example 4 using compound 231 (0.120 g, 0.39 mmol), dry THF (8 mL), 4-nitrophenylchloroformate (0.094 g, 0.46 mmol), 3'-aminoacetophenone (0.062 g, 0.46 mmol), TEA (0.14 mL, 0.78 mmol) to obtain compound 232 (0.077 g, 42%) as yellow solid. $^1$H NMR (400 MHz, $d_6$-DMSO) δ in ppm 9.09 (s, 1H), 8.97 (s, 1H), 8.29 (d, J=2.8 Hz, 1H), 8.06-8.05 (m, 1H), 7.75 (dd, J=8.8 Hz, 2.4 Hz, 1H), 7.67-7.65 (m, 1H), 7.56 (d, J=8.8 Hz, 2H), 7.43-7.39 (m, 1H), 4.42 (t, J=5.6 Hz, 2H), 3.76 (s, 2H), 3.58 (t, J=5.6 Hz, 2H), 3.20 (s, 3H), 2.53 (s, 3H), 2.51-2.49 (m, 4H), 1.69-1.64 (m, 4H). ESI-HRMS m/z 464.2317 (M+H$^+$).

Example 221

Synthesis of 2-((dimethylamino)methyl)-3-(2-methoxyethyl)-6-nitroquinazolin-4 (3H)-one (233): Compound 229 (0.2 g, 0.74 mmol) and dimethylamine (0.1 mL, 1.48 mmol) were dissolved in toluene and reaction mixture was refluxed for 2 hours. After completion of the reaction, it was washed with water and extracted with ethyl acetate to get yellow crude mass which was then purified by column chromatography (Silica gel, mesh size 100-200) eluting (5% $CHCl_3$-MeOH) to obtain compound 233 (0.154 g, 75%) as yellow gummy product. $^1$H NMR (400 MHz, $d_6$-DMSO) δ in ppm 8.77 (d, J=2.4 Hz, 1H), 8.49 (dd, J=9.2 Hz, 2.8 Hz, 1H), 7.82 (d, J=8.8 Hz, 1H), 4.47 (t, J=5.6 Hz, 2H), 3.63 (s, 2H), 3.59 (t, J=5.6 Hz, 2H), 3.20 (s, 3H), 2.20 (s, 6H). ESI-HRMS m/z 307.1405 (M+H$^+$).

Example 222

Synthesis of 6-amino-2-((dimethylamino)methyl)-3-(2-methoxyethyl)quinazolin-4 (3H)-one (234): The compound was prepared by general procedure C provided in example 3 using compound 233 (0.120 g, 0.39 mmol), methanol (5 mL) and pinch of 10% wet Pd—C under hydrogen atmosphere to obtain compound 234 (0.086 g, 80%) as light brown gummy product. $^1$H NMR (400 MHz, $d_6$-DMSO) δ in ppm 7.31 (d, J=8.4 Hz, 1H), 7.13 (d, J=2.8 Hz, 1H), 7.01 (dd, J=8.4 Hz, 2.4 Hz, 1H), 5.59 (s, 2H), 4.37 (t, J=5.6 Hz, 2H), 3.54 (t, J=5.6 Hz, 2H), 3.49 (s, 2H), 3.18 (s, 3H), 2.15 (s, 6H). ESI-HRMS m/z 277.1667 (M+H$^+$).

Example 223

Synthesis of 1-(3-acetylphenyl)-3-(2-((dimethylamino) methyl)-3-(2-methoxyethyl)-4-oxo-3,4-dihydroquinazolin-6-yl)urea (235): The compound was prepared by general procedure D provided in example 4 using compound 234 (0.060 g, 0.21 mmol), dry THF (3 mL), 4-nitrophenylchloroformate (0.053 g, 0.26 mmol), 3'-aminoacetophenone (0.035 g, 0.26 mmol), TEA (0.14 mL, 0.52 mmol) to obtain compound 235 (0.062 g, 54%) as off white solid. $^1$H NMR (400 MHz, $d_6$-DMSO) δ in ppm 9.10 (s, 1H), 8.98 (s, 1H), 8.29 (d, J=2.4 Hz, 1H), 8.06-8.05 (m, 1H), 7.76 (dd, J=8.8 Hz, 2.4 Hz, 1H), 7.67-7.65 (m, 1H), 7.57-7.54 (m, 2H), 7.42-7.39 (m, 1H), 4.43 (t, J=5.6 Hz, 2H), 3.59-3.56 (m, 4H), 3.20 (s, 3H), 2.53 (s, 3H), 2.18 (s, 6H). ESI-HRMS m/z 438.2140 (M+H$^+$).

Example 224

Synthesis of 3-(2-methoxyethyl)-6-nitro-2-(piperidin-1-ylmethyl)quinazolin-4 (3H)-one (236): Compound 229 (0.2 g, 0.74 mmol) and piperidine (0.15 mL, 1.48 mmol) were dissolved in toluene and reaction mixture was refluxed for 2 hours. After completion of the reaction, it was washed with water and extracted with ethyl acetate to get light brown crude mass which was then purified by column chromatography (Silica gel, mesh size 100-200) eluting (50% EtOAc/Pet Ether) to obtain compound 233 (0.220 g, 85%) as white solid. $^1$H NMR (400 MHz, $d_6$-DMSO) δ in ppm 8.76 (d, J=2.8 Hz, 1H), 8.48 (dd, J=9.2 Hz, 2.8 Hz, 1H), 7.80 (d, J=8.8 Hz, 1H), 4.45 (t, J=6.0 Hz, 2H), 3.66 (s, 2H), 3.61 (t, J=6.0 Hz, 2H), 3.21 (s, 3H), 2.42-2.37 (m, 4H), 1.48-1.42 (m, 4H), 1.37-1.309 m, 2H). ESI-HRMS m/z 347.1716 (M+H$^+$).

Example 225

Synthesis of 6-amino-3-(2-methoxyethyl)-2-(piperidin-1-ylmethyl)quinazolin-4 (3H)-one (237): The compound was prepared by general procedure C provided in example 3 using compound 236 (0.150 g, 0.47 mmol), methanol (10 mL) and pinch of 10% wet Pd—C under hydrogen atmosphere to obtain compound 237 (0.089 g, 65%) as light brown solid. $^1$H NMR (400 MHz, $d_6$-DMSO) δ in ppm 7.30 (d, J=8.8 Hz, 1H), 7.12 (d, J=2.8 Hz, 1H), 7.01 (dd, J=8.4 Hz, 2.4 Hz, 1H), 5.57 (s, 2H), 4.36 (t, J=6 Hz, 2H), 3.68 (s, 2H), 3.54 (t, J=5.6 Hz, 2H), 3.18 (s, 3H), 2.45-2.42 (m, 4H), 1.67-1.62 (m, 4H). ESI-HRMS m/z 317.1976 (M+H$^+$).

Example 226

Synthesis of 1-(3-acetylphenyl)-3-(3-(2-methoxyethyl)-4-oxo-2-(piperidin-1-ylmethyl)-3,4-dihydroquinazolin-6-yl) urea (238): The compound was prepared by general procedure D provided in example 4 using compound 237 (0.080 g, 0.25 mmol), dry THF (3 mL), 4-nitrophenylchloroformate (0.060 g, 0.30 mmol), 3'-aminoacetophenone (0.040 g, 0.30 mmol), TEA (0.07 mL, 0.50 mmol) to obtain compound 238 (0.077 g, 42%) as yellow solid. $^1$H NMR (400 MHz, $d_6$-DMSO) δ in ppm 9.08 (s, 1H), 8.96 (s, 1H), 8.29 (d, J=2.4 Hz, 1H), 8.06-8.05 (m, 1H), 7.75 (dd, J=9.2 Hz, 2.8 Hz, 1H), 7.67-7.64 (m, 1H), 7.55 (d, J=8.4 Hz, 2H), 7.42-7.38 (m, 1H), 4.41 (t, J=6.0 Hz, 2H), 3.61-3.58 (m, 4H), 3.21 (s, 3H), 2.53 (s, 3H), 2.39-2.34 (m, 4H), 1.47-1.41 (m, 4H), 1.37-1.30 (m, 2H). ESI-HRMS m/z 478.2463 ($M+H^+$).

Example 227

Synthesis of 1-(3-acetylphenyl)-3-(3-(2-methoxyethyl)-4-oxo-2-(piperidin-1-ylmethyl)-3,4-dihydroquinazolin-6-yl) urea hydrochloride (238a): Compound 238 (0.05 g, 0.104 mmol) was taken in dioxane (1 mL) and 4 M HCl in dioxane (0.8 mL) was added under ice cold condition and reaction was heated at 100° C. for 2 hour. During heating, at first compound dissolved to obtain a clear solution and then slowly solidified after 2 hours of constant heating. Reaction mass was cooled and evaporated in rotary evaporator to obtain compound 238 a (53 mg, 98%) as pale yellow solid. $^1$H NMR (400 MHz, $d_6$-DMSO) δ in ppm 10.04 (s, 1H), 9.77 (s, 1H), 9.56 (s, 1H), 8.35 (d, J=2.4 Hz, 1H), 8.07-8.07 (m, 1H), 7.86 (dd, J=8.8 Hz, 2.4 Hz, 1H), 7.66 (d, J=8.8 Hz, 2H), 7.56 (d, J=7.6 Hz, 1H), 7.43-7.39 (m, 1H), 4.64 (d, J=3.6 Hz, 2H), 4.16 (t, J=4.8 Hz, 2H), 3.62-3.56 (m, 4H), 3.21 (s, 3H), 3.15-3.05 (m, 2H), 2.53 (s, 3H), 1.85-1.79 (m, 4H), 1.70-1.63 (m, 1H), 1.51-1.40 (m, 1H). The crystal structure of compound 238a is provided in FIG. 11. CCDC Deposition no 1988445.

Example 228

Synthesis of 3-(2-methoxyethyl)-2-(morpholinomethyl)-6-nitroquinazolin-4 (3H)-one (239): Compound 229 (0.2 g, 0.74 mmol) and morpholine (0.13 mL, 1.48 mmol) were dissolved in toluene and reaction mixture was refluxed for 2 hours. After completion of the reaction, it was washed with water and extracted with ethyl acetate to obtain light yellow crude mass which was then purified by column chromatography (Silica gel, mesh size 100-200) eluting (50% EtOAc/Pet Ether) to obtain compound 239 (0.195 g, 75%) as white solid. $^1$H NMR (400 MHz, $d_6$-DMSO) δ in ppm 8.76 (d, J=2.4 Hz, 1H), 8.49 (dd, J=9.2 Hz, 2.8 Hz, 1H), 7.81 (d, J=8.4 Hz, 1H), 4.46 (t, J=5.6 Hz, 2H) 3.72 (s, 2H), 3.62 (t, J=5.6 Hz, 2H), 3.54-3.52 (m, 4H), 3.28-3.27 (m, 4H), 3.21 (s, 3H). ESI-HRMS m/z 349.1513 ($M+H^+$).

Example 229

Synthesis of 6-amino-3-(2-methoxyethyl)-2-(morpholinomethyl)quinazolin-4 (3H)-one (240): The compound was prepared by general procedure C provided in example 3 using compound 239 (0.150 g, 0.43 mmol), methanol (10 mL) and pinch of 10% wet Pd—C under hydrogen atmosphere to obtain compound 240 (0.089 g, 65%) as light brown solid. $^1$H NMR (400 MHz, $d_6$-DMSO) δ in ppm 7.30 (d, J=8.8 Hz, 1H), 7.13 (d, J=2.8 Hz, 1H), 7.01 (dd, J=8.8 Hz, 2.8 Hz, 1H), 5.59 (s, 2H), 4.36 (t, 5.6 Hz, 2H), 3.58-3.55 (m, 4H), 3.52-3.50 (m, 4H), 3.20 (s, 3H), 2.39-2.35 (m, 4H). ESI-HRMS m/z 319.1773 ($M+H^+$).

Example 230

Synthesis of 1-(3-acetylphenyl)-3-(3-(2-methoxyethyl)-2-(morpholinomethyl)-4-oxo-3,4-dihydroquinazolin-6-yl) urea (241): The compound was prepared by general procedure D provided in example 4 using compound 240 (0.070 g, 0.22 mmol), dry THF (3 mL), 4-nitrophenylchloroformate (0.053 g, 0.26 mmol), 3'-aminoacetophenone (0.035 g, 0.26 mmol), TEA (0.14 mL, 0.52 mmol) to obtain compound 241 (0.055 g, 53%) as yellow solid. $^1$H NMR (400 MHz, $d_6$-DMSO) δ in ppm 9.08 (s, 1H), 8.95 (s, 1H), 8.28 (d, J=2.4 Hz, 1H), 8.05-8.04 (m, 1H), 7.75 (dd, J=8.8 Hz, 2.4 Hz, 1H), 7.67-7.64 (m, 1H), 7.56 (d, J=8.8 Hz, 2H), 7.43-7.39 (m, 1H), 4.42 (t, J=5.6 Hz, 2H), 3.64 (s, 2H), 3.60 (t, J=5.6 Hz, 2H), 3.54-3.52 (m, 4H), 3.21 (s, 3H), 2.53 (s, 3H), 2.43-2.39 (m, 4H). ESI-HRMS m/z 480.2246 ($M+H^+$).

Example 231

Synthesis of 3-(2-methoxyethyl)-2-((4-methylpiperazin-1-yl)methyl)-6-nitroquinazolin-4 (3H)-one (242): Compound 229 (0.2 g, 0.74 mmol) and 1-methylpiperazine (0.142 mL, 1.48 mmol) were dissolved in toluene and reaction mixture was refluxed for 2 hours. After completion of the reaction, it was washed with water and extracted with ethyl acetate to obtain light yellow crude mass which was then purified by column chromatography (Silica gel, mesh size 100-200) eluting (5% $CHCl_3$-MeOH) to obtain compound 242 (0.202 g, 75%) as white solid. $^1$H NMR (400 MHz, $d_6$-DMSO) δ in ppm 8.76 (s, 1H), 8.48 (d, J=8.8 Hz, 1H), 7.80 (d, J=8.8 Hz, 1H), 4.43 (d, J=5.6 Hz, 2H), 3.70 (s, 2H), 3.61 (t, J=5.6 Hz, 2H), 3.27-3.21 (m, 3H), 2.36-2.18 (m, 4H), 2.10 (s, 3H). ESI-HRMS m/z 362.1821 ($M+H^+$).

Example 232

Synthesis of 6-amino-3-(2-methoxyethyl)-2-((4-methylpiperazin-1-yl)methyl)quinazolin-4 (3H)-one (243): The compound was prepared by general procedure C provided in example 3 using compound 242 (0.150 g, 0.41 mmol), methanol (10 mL) and pinch of 10% wet Pd—C under hydrogen atmosphere to obtain compound 243 (0.110 g, 80%) as light brown solid. $^1$H NMR (400 MHz, d6-DMSO) δ in ppm 7.31 (d, J=8.8 Hz, 1H), 7.12 (d, J=2.8 Hz, 1H), 7.01 (dd, J=8.8 Hz, 2.8 Hz, 1H), 5.59 (s, 2H), 4.34 (t, J=6 Hz, 2H), 3.55 (t, J=6 Hz, 4H), 3.20 (s, 3H), 2.42-2.34 (m, 4H), 2.31-2.16 (m, 4H), 2.09 (s, 3H). ESI-HRMS m/z 332.2090 ($M+H^+$).

Example 233

Synthesis of 1-(3-acetylphenyl)-3-(3-(2-methoxyethyl)-2-((4-methylpiperazin-1-yl)methyl)-4-oxo-3,4-dihydroquinazolin-6-yl)urea (244): The compound was prepared by general procedure D provided in example 4 using compound 243 (0.070 g, 0.21 mmol), dry THF (3 mL), 4-nitrophenylchloroformate (0.053 g, 0.26 mmol), 3'-aminoacetophenone (0.035 g, 0.26 mmol), TEA (0.14 mL, 0.52 mmol) to obtain compound 244 (0.062 g, 54%) as yellow solid. $^1$H NMR (400 MHz, d6-DMSO) δ in ppm 9.17 (s, 1H), 9.04 (s, 1H), 8.28 (d, J=2.4 Hz, 1H), 8.06-8.04 (m, 1H), 7.75 (dd, J=8.8 Hz, 2.8 Hz, 1H), 7.56 (d, J=8.6 Hz, 1H), 7.43-7.39 (m, 1H), 4.39 (t, J=6 Hz, 2H), 3.63 (s, 2H), 3.59 (t, J=6 Hz, 2H), 3.21 (s, 3H), 2.53 (s, 3H), 2.44-2.40 (m, 4H), 2.34-2.26 (m, 4H), 2.11 (s, 3H). ESI-HRMS m/z 493.2566 ($M+H^+$).

Example 234

Synthesis of N-(2-fluorophenyl)-2-(6-nitro-4-oxoquinazolin-3 (4H)-yl)acetamide (251): The compound was prepared by general procedure H provided in example 8 using compound 81 (0.25 g, 0.90 mmol), toluene (5 mL), anhydrous $AlCl_3$ (0.481 g, 3.6 mmol), 2-fluoroaniline (0.120 g, 1.08 mmol), triethylamine (0.3 mL, 2.43 mmol) to obtain compound 251 (0.184 g, 49%) as bright white crystal. ESI-HRMS m/z 343.0844 (M+H$^+$).

Example 235

Synthesis of 2-(6-amino-4-oxoquinazolin-3 (4H)-yl)-N-(2-fluorophenyl)acetamide (252): The compound was prepared by general procedure C provided in example 3 using compound 251 (0.34 g, 0.99 mmol), methanol (10 mL), pinch of Pd/C under hydrogen atmosphere to obtain compound 252 (0.182 g, 43%) as light brown solid. ESI-HRMS m/z 313.1101 (M+H$^+$).

Example 236

Synthesis of 2-(6-(3-(3-acetylphenyl)ureido)-4-oxoquinazolin-3 (4H)-yl)-N-(2-fluorophenyl)acetamide (253): The compound was prepared by general procedure D provided in example 4 using compound 252 (0.140 g, 0.44 mmol), dry THF (5 mL), 4-nitrophenyl chloroformate (0.14 g, 0.67 mmol), 3'-aminoacetophenone (0.073 g, 0.53 mmol), TEA (0.16 mL, 1.12 mmol) to obtain compound 253 as white amorphous solid (0.064 g, 30%). ESI-HRMS m/z 474.1580 (M+H$^+$).

Example 237

Synthesis of N-(2-methoxyphenyl)-2-(6-nitro-4-oxoquinazolin-3 (4H)-yl)acetamide (254): The compound was prepared by general procedure H provided in example 8 using compound 81 (0.25 g, 0.90 mmol), toluene (5 mL), anhydrous $AlCl_3$ (0.481 g, 3.61 mmol), o-anisidine (0.134 g, 1.08 mmol), TEA (0.3 mL, 2.43 mmol) to obtain compound 254 (0.140 g, 44%) as white crystal. ESI-HRMS m/z 355.1045 (M+H$^+$).

Example 238

Synthesis of 2-(6-amino-4-oxoquinazolin-3 (4H)-yl)-N-(2-methoxyphenyl)acetamide (255): The compound was prepared by general procedure C provided in example 3 using compound 254 (0.12 g, 0.34 mmol), methanol (10 mL), pinch of Pd/C under hydrogen atmosphere to obtain compound 255 (0.1 g, 78%) as light brown solid. ESI-HRMS m/z 325.1304 (M+H$^+$).

Example 239

Synthesis of 2-(6-(3-(3-acetylphenyl)ureido)-4-oxoquinazolin-3 (4H)-yl)-N-(2-methoxyphenyl)acetamide (256): The compound was prepared by general procedure D provided in example 4 using compound 255 (0.085 g, 0.26 mmol), dry THF (4 mL), 4-nitrophenyl chloroformate (0.08 g, 0.39 mmol), 3'-aminoacetophenone (0.05 g, 0.31 mmol), TEA (0.1 mL, 0.65 mmol) to obtain compound 256 (0.054 g, 39%) as off white solid.

Example 240

Synthesis of N-(2-bromophenyl)-2-(6-nitro-4-oxoquinazolin-3 (4H)-yl)acetamide (257): The compound was prepared by general procedure H provided in example 8 using compound 81 (0.25 g, 0.90 mmol), toluene (5 mL), anhydrous $AlCl_3$ (0.481 g, 3.6 mmol), 2-bromoaniline (0.186 g, 1.08 mmol), TEA (0.3 mL, 2.43 mmol) to obtain compound 257 (0.180 g, 49%) as white solid. ESI-HRMS m/z 403.0037 (M+H$^+$).

Example 241

Synthesis of 2-(6-amino-4-oxoquinazolin-3 (4H)-yl)-N-(2-bromophenyl)acetamide (258): Compound 257 (0.160 g, 0.39 mmol) was dissolved in methanol and $SnCl_2 \cdot 2H_2O$ (0.716 g, 3.17 mmol) was added. Two drops of concentrated HCl was added and reaction mixture was heated at 80° C. for 2 hours. The reaction was monitored by checking TLC. Upon completion of the reaction, reaction mass was evaporated to dryness and washed with saturated $NaHCO_3$ solution, and extracted with EtOAc to afford the yellow coloured crude mass. The compound was dissolved in DCM (5 mL) and pet ether was added dropwise to get precipitation which was filtered under vacuum to obtain compound 258 (0.075 g, 50%) as light yellow solid.

Example 242

Synthesis of 2-(6-(3-(3-acetylphenyl)ureido)-4-oxoquinazolin-3 (4H)-yl)-N-(2-bromophenyl)acetamide (259): The compound was prepared by general procedure D provided in example 4 using compound 258 (0.040 g, 0.11 mmol), dry THF (4 mL), 4-nitrophenyl chloroformate (0.04 g, 0.17 mmol), 3'-aminoacetophenone (0.018 g, 0.13 mmol), TEA (0.037 mL, 0.27 mmol) to obtain compound 259 (0.015 g, 26%) as off white solid. ESI-HRMS m/z 534.0797 (M+H$^+$).

Example 243

Synthesis of 2-(6-nitro-4-oxoquinazolin-3 (4H)-yl)-N-(2-(trifluoromethoxy)phenyl)acetamide (260): The compound was prepared by general procedure H provided in example 8 using compound 81 (0.1 g, 0.36 mmol), toluene (5 mL), anhydrous $AlCl_3$ (0.192 g, 1.44 mmol), 2-(trifluoromethoxy) aniline (0.077 g, 0.43 mmol), TEA (0.13 mL, 0.97 mmol) to obtain compound 260 (0.072 g, 49%) as white solid. ESI-HRMS m/z 409.0755 (M+H$^+$).

Example 244

Synthesis of 2-(6-amino-4-oxoquinazolin-3 (4H)-yl)-N-(2-(trifluoromethoxy)phenyl)acetamide (261): The compound was prepared by general procedure C provided in example 3 using compound 260 (0.12 g, 0.29 mmol), methanol (10 mL), pinch of Pd/C under hydrogen atmosphere to obtain compound 261 (0.059 g, 50%).

Example 245

Synthesis of 2-(6-(3-(3-acetylphenyl)ureido)-4-oxoquinazolin-3 (4H)-yl)-N-(2-(trifluoromethoxy)phenyl)acetamide (262): The compound was prepared by general procedure D provided in example 4 using compound 261 (0.05 g, 0.15 mmol), dry THF (5 mL), 4-nitrophenyl chloroformate (0.04 g, 0.19 mmol), 3'-aminoacetophenone (0.022 g, 0.15 mmol), TEA (0.05 mL, 0.33 mmol) to obtain 262 (0.06 g, 84%) as white solid. ESI-HRMS m/z 540.1500 (M+H$^+$).

Example 246

Synthesis of 2-(6-nitro-4-oxoquinazolin-3 (4H)-yl)-N-(2-(trifluoromethyl)phenyl)acetamide (263): The compound was prepared by general procedure H provided in example 8 using compound 81 (0.25 g, 0.9 mmol), toluene (5 mL), anhydrous $AlCl_3$ (0.481 g, 3.6 mmol), 2-(trifluoromethyl) aniline (0.174 g, 1.08 mmol) to obtain compound 263 (0.160 g, 45%) as white solid.

Example 247

Synthesis of 2-(6-amino-4-oxoquinazolin-3 (4H)-yl)-N-(2-(trifluoromethyl)phenyl)acetamide (264): The compound was prepared by general procedure C provided in example 3 using compound 263 (0.08 g, 0.20 mmol), methanol (10 mL), one pinch of Pd/C under hydrogen atmosphere to obtain compound 264 (0.50 g, 68%) as light yellow solid.

Example 248

Synthesis of 2-(6-(3-(3-acetylphenyl)ureido)-4-oxoquinazolin-3 (4H)-yl)-N-(2-(trifluoromethyl)phenyl)acetamide (265): The compound was prepared by general procedure D provided in example 4 using compound 264 (0.04 g, 0.11 mmol), dry THF (4 mL), 4-nitrophenyl chloroformate (0.04 g, 0.16 mmol), 3'-aminoacetophenone (0.02 g, 0.13 mmol), TEA (0.04 mL, 0.27 mmol) to obtain compound 265 as off white solid (0.015 g, 26%).

Example 249

Synthesis of N-(4-methoxyphenyl)-2-(6-nitro-4-oxoquinazolin-3 (4H)-yl)acetamide (266): The compound was prepared by general procedure H provided in example 8 using compound 81 (0.25 g, 0.90 mmol), toluene (5 mL), anhydrous $AlCl_3$ (0.481 g, 3.61 mmol), p-anisidine (0.134 g, 1.08 mmol), TEA (0.3 mL, 2.43 mmol) to obtain compound 266 (0.142 g, 45%) as white crystal. ESI-HRMS m/z 355.1045 ($M+H^+$).

Example 250

Synthesis of 2-(6-amino-4-oxoquinazolin-3 (4H)-yl)-N-(4-methoxyphenyl)acetamide (267): The compound was prepared by general procedure C provided in example 3 using compound 266 (0.21 g, 0.59 mmol), methanol (10 mL), pinch of Pd/C under hydrogen atmosphere to obtain compound 267 (0.15 g, 78%) as light brown solid. ESI-HRMS m/z 325.1304 ($M+H^+$).

Example 251

Synthesis of 2-(6-(3-(3-acetylphenyl)ureido)-4-oxoquinazolin-3 (4H)-yl)-N-(4-methoxyphenyl)acetamide (268): The compound was prepared by general procedure D provided in example 4 using compound 267 (0.085 g, 0.26 mmol), dry THF (4 mL), 4-nitrophenyl chloroformate (0.08 g, 0.39 mmol), 3'-aminoacetophenone (0.05 g, 0.31 mmol), TEA (0.1 mL, 0.65 mmol) to obtain compound 268 (0.054 g, 39%) as off white solid.

Example 252

Synthesis of 2-acetamido-N-(1-methoxybutan-2-yl)-5-nitrobenzamide (278): Compound 168 (0.5 g, 1.87 mmol) was dissolved in DCM (10 mL). Then TEA (0.522 mL, 3.74 mmol) was added. Then acetyl chloride (0.267 mL, 3.74 mmol) was added dropwise under cooling conditions and the reaction mass was stirred for 8 hours. After completion of the reaction, DCM was evaporated out and washed with water and extracted with ethyl acetate and purified by column chromatography (Silica gel, mesh size 100-200) eluting (30% Ethyl acetate-Pet ether) to obtain compound 278 (0.462 g, 80%) as off white solid. ESI-HRMS m/z 310.1402 ($M+H^+$).

Example 253

Synthesis of 3-(1-methoxybutan-2-yl)-2-methyl-6-nitroquinazolin-4 (3H)-one (279): The compound was prepared by general procedure G provided in example 7 using compound 278 (0.4 g, 1.29 mmol), DMF (4 mL), $ZnCl_2$ (0.703 g, 5.16 mmol), HMDS (2.16 mL, 10.32 mmol) to obtain compound 279 (0.278 g, 74%) as off white solid. $^1H$ NMR (400 MHz, $d_6$-DMSO) δ in ppm 8.73 (d, J=2.4 Hz, 1H), 8.47 (dd, J=9.2 Hz, 2.8 Hz, 1H), 7.72 (d, J=8.8 Hz, 1H), 4.49-4.41 (m, 1H), 4.07-4.02 (m, 1H), 3.62-3.58 (m, 1H), 3.17 (s, 3H), 2.62 (s, 3H), 2.21-2.11 (m, 1H), 1.87-1.76 (m, 1H), 0.79 (t, J=7.6 Hz, 3H). ESI-HRMS m/z 292.1292 ($M+H^+$).

Example 254

Synthesis of 6-amino-3-(1-methoxybutan-2-yl)-2-methylquinazolin-4 (3H)-one (280): The compound was prepared by general procedure C provided in example 3 using compound 279 (0.150 g, 0.51 mmol), methanol (5 mL) and pinch of 10% wet Pd—C under hydrogen atmosphere to obtain compound 280 (0.102 g, 76%) as light brown solid. $^1H$ NMR (400 MHz, $d_6$-DMSO) δ in ppm 7.22 (d, J=8.4 Hz, 1H), 7.06 (d, J=2.8 Hz, 1H), 6.99 (dd, J=8.4 Hz, 2.4 Hz, 1H), 5.49 (brs, 2H), 4.31-4.23 (m, 1H), 3.57-3.54 (m, 1H), 3.16 (s, 3H), 2.45 (s, 3H), 2.23-2.11 (m, 1H), 1.80-1.68 (m, 1H), 0.74 (t, J=7.2 Hz, 3H). ESI-HRMS m/z 262.1559 ($M+H^+$).

Example 255

Synthesis of 1-(3-acetylphenyl)-3-(3-(1-methoxybutan-2-yl)-2-methyl-4-oxo-3,4-dihydroquinazolin-6-yl)ureae (281): The compound was prepared by general procedure D provided in example 4 using compound 280 (0.080 g, 0.30 mmol), dry THF (3 mL), 4-nitrophenylchloroformate (0.073 g, 0.36 mmol), 3'-aminoacetophenone (0.048 g, 0.36 mmol), TEA (0.083 mL, 0.60 mmol) to obtain compound 281 (0.069 g, 54%) as off white solid. $^1H$ NMR (400 MHz, $d_6$-DMSO) δ in ppm 9.03 (s, 1H), 8.97 (s, 1H), 8.21 (d, J=2.4 Hz, 1H), 8.06-8.05 (m, 1H), 7.73 (dd, J=8.8 Hz, 2.4 Hz, 1H), 7.66-7.63 (m, 1H), 7.56-7.54 (m, 1H), 7.47 (d, J=8.8 Hz, 1H), 7.42-7.38 (m, 1H), 4.39-4.31 (m, 1H), 4.08 (t, J=9.6 Hz, 1H), 3.60-3.56 (m, 1H), 3.17 (s, 3H, 2.53 (s, 6H), 2.24-2.15 (m, 1H), 1.82-1.73 (m, 1H), 0.77 (t, J=7.6 Hz, 3H). ESI-HRMS m/z 423.2030 ($M+H^+$).

Example 256

Synthesis of 2-acetamido-N-(1-methoxypropan-2-yl)-5-nitrobenzamide (282): Compound 176 (0.5 g, 1.97 mmol) was dissolved in DCM (10 mL). Then TEA (0.551 mL, 3.95 mmol) was added. Then Acetyl chloride (0.281 mL, 3.95 mmol) was added dropwise under cooling conditions and the reaction mass was stirred for 8 hours. After completion of the reaction, DCM was evaporated out and worked up with ethyl acetate and water and purified by column chromatography (Silica gel, mesh size 100-200) eluting (30% Ethyl acetate-Pet ether) to obtain compound 282 (0.437 g, 75%) as off white solid. $^1H$ NMR (300 MHz, $d_6$-DMSO) δ in ppm 11.55 (s, 1H), 8.97 (d, 7.85 Hz, 1H), 8.64-8.59 (m, 2H), 8.36 (dd, J=9.3 Hz, 2.7 Hz, 1H), 3.47-3.42 (m, 2H), 3.29 (s, 3H), 2.17 (s, 3H), 1.17 (d, J=6.6 Hz, 3H). ESI-HRMS m/z 318.1074 ($M+H^+$).

Example 257

Synthesis of 3-(1-methoxypropan-2-yl)-2-methyl-6-nitroquinazolin-4 (3H)-one (283): The compound was prepared by general procedure G provided in example 7 using compound 282 (0.4 g, 1.35 mmol), DMF (4 mL), $ZnCl_2$ (0.738 g, 5.42 mmol), HMDS (2.26 mL, 10.84 mmol) to obtain compound 283 (0.255 g, 68%) as off white solid. $^1H$ NMR (300 MHz, $d_6$-DMSO) δ in ppm 8.72 (d, J=2.7 Hz, 1H), 8.45 (dd, J=9 Hz, 2.7 Hz, 1H), 7.72 (d, 9 Hz, 1H), 4.72-4.59 (m, 1H), 4.10-4.04 (m, 1H), 3.62-3.57 (m, 1H), 3.20 (s, 3H), 2.65 (s, 3H), 1.50 (d, J=3.9 Hz, 3H). ESI-HRMS m/z 278.1151 ($M+H^+$).

Example 258

Synthesis of 6-amino-3-(1-methoxypropan-2-yl)-2-methylquinazolin-4 (3H)-one (284): The compound was prepared by general procedure C provided in example 3 using compound 283 (0.150 g, 0.54 mmol), methanol (5 mL), pinch of 10% wet Pd—C under hydrogen atmosphere to obtain compound 284 (0.086 g, 76%) as light brown solid. $^1H$ NMR (300 MHz, $d_6$-DMSO) δ in ppm 7.26 (d, J=8.7 Hz, 1H), 7.10 (d, J=2.4 Hz, 1H), 7.02 (dd, J=8.7 Hz, 2.7 Hz, 1H), 5.52 (s, 2H), 4.60-4.42 (m, 1H), 4.10-4.04 (m, 1H), 3.63-3.57 (m, 1H), 3.21 (s, 3H), 2.50 (s, 3H), 1.47 (d, J=6.6 Hz, 3H). ESI-HRMS m/z 248.1400 ($M+H^+$).

Example 259

Synthesis of 1-(3-acetylphenyl)-3-(3-(1-methoxypropan-2-yl)-2-methyl-4-oxo-3,4-dihydroquinazolin-6-yl)urea (285): The compound was prepared by general procedure D provided in example 4 using compound 284 (0.070 g, 0.28 mmol), dry THF (3 mL), 4-nitrophenylchloroformate (0.068 g, 0.34 mmol), 3'-aminoacetophenone (0.046 g, 0.34 mmol), TEA (0.083 mL, 0.56 mmol) to obtain compound 285 (0.069 g, 54%) as off white solid. $^1H$ NMR (300 MHz, $d_6$-DMSO) δ in ppm 9.06 (s, 1H), 6.99 (s, 1H), 8.25 (d, J=2.4 Hz, 1H), 8.10 (brs, 1H), 7.76 (dd, J=8.7 Hz, 2.4 Hz, 1H), 7.70 (dd, J=8.1 Hz, 0.9 Hz, 1H), 7.60 (d, J=7.8 Hz, 1H), 7.50 (d, J=9 Hz, 1H), 7.48-7.42 (m, 1H), 4.57 (s, 1H), 4.12 (t, J=9.3 Hz, 1H), 3.63-3.59 (m, 1H), 3.22 (s, 3H), 2.57 (s, 6H), 1.50 (d, J=6.9 Hz, 3H). ESI-HRMS m/z 409.1877 ($M+H^+$).

Example 260

Synthesis of 2-(cyclohexanecarboxamido)-N-(1-methoxypropan-2-yl)-5-nitrobenzamide (286): Compound 176 (0.5 g, 1.97 mmol) was dissolved in DCM (10 mL). Then TEA (0.6 mL, 3.95 mmol) was added. Then cyclohexanecarbonyl chloride (0.57 g, 3.95 mmol) was added dropwise under cooling conditions and the reaction mass was stirred for 8 hours. After completion of the reaction, DCM was evaporated out and worked up with ethyl acetate and water and purified by column chromatography (Silica gel, mesh size 100-200) eluting (30% Ethyl acetate-Pet ether) to obtain compound 286 (0.446 g, 75%) as off white solid.

Example 261

Synthesis of 2-cyclohexyl-3-(1-methoxypropan-2-yl)-6-nitroquinazolin-4 (3H)-one (287): The compound was prepared by general procedure G provided in example 7 using compound 286 (0.4 g, 1.35 mmol), DMF (4 mL), $ZnCl_2$ (0.73 g, 5.42 mmol), HMDS (2.26 mL, 10.84 mmol) to obtain compound 287 (0.285 g, 75%) as off white solid. $^1H$ NMR (400 MHz, $d_6$-DMSO) δ in ppm 8.72 (d, J=2.8 Hz, 1H), 8.44 (dd, J=8.8 Hz, 2.8 Hz, 1H), 7.70 (d, J=9.2 Hz, 1H), 4.68 (s, 1H), 4.10-4.01 (m, 1H), 3.64-3.60 (m, 1H), 3.17 (s, 3H), 3.00-2.93 (m, 1H), 1.93-1.80 (m, 2H), 1.78-1.72 (m, 2H), 1.70-1.55 (m, 3H), 1.49 (d, J=6.8 Hz, 3H), 1.44-1.33 (m, 2H), 1.33-1.28 (m, 1H). ESI-HRMS m/z 346.1772 ($M+H^+$).

Example 262

Synthesis of 6-amino-2-cyclohexyl-3-(1-methoxypropan-2-yl)quinazolin-4 (3H)-one (288): The compound was prepared by general procedure C provided in example 3 using compound 287 (0.200 g, 0.58 mmol), methanol (5 mL) and pinch of 10% wet Pd—C under hydrogen atmosphere to obtain compound 288 (0.127 g, 70%) as light brown solid. $^1H$ NMR (400 MHz, $d_6$-DMSO) δ in ppm 7.22d, J=8.4 Hz, 1H), 7.07 (d, J=2.8 Hz, 1H), 6.98 (dd, J=8.8 Hz, 2.8 Hz, 1H), 5.46 (s, 2H), 4.48 (brs, 1H), 4.06-3.99 (m, 1H), 3.65-3.61 (m, 1H), 3.16 (s, 3H), 2.83-2.75 (m, 1H), 1.87-1.84 (m, 1H), 1.79-1.71 (m, 3H), 1.66-1.63 (m, 1H), 1.58-1.52 (m, 2H), 1.45 (d, J=6.8 Hz, 3H), 1.38-1.30 (m, 2H), 1.24-1.16 (m 1H). ESI-HRMS m/z 316.2027 ($M+H^+$).

Example 263

Synthesis of 1-(3-acetylphenyl)-3-(2-cyclohexyl-3-(1-methoxypropan-2-yl)-4-oxo-3,4-dihydroquinazolin-6-yl) urea (289): The compound was prepared by general procedure D provided in example 4 using compound 288 (0.080 g, 0.25 mmol), dry THF (3 mL), 4-nitrophenylchloroformate (0.061 g, 0.30 mmol), 3'-aminoacetophenone (0.040 g, 0.30 mmol), TEA (0.069 mL, 0.50 mmol) to obtain compound 289 (0.062 g, 52%) as off white solid. ESI-HRMS m/z 477.2504 ($M+H^+$).

Example 264

Synthesis of tert-butyl 4-((2-((2-methoxyethyl)carbamoyl)-4-nitrophenyl)carbamoyl)piperidine-1-carboxylate (296): Commercially available N-Boc piperidine-4-carboxylic acid (1.2 g, 5.22 mmol) was dissolved in dry DCM (10 mL) followed by addition of one drop of DMF. Oxalyl chloride (0.66 mL, 7.80 mmol) was added to the reaction mixture at ice cold condition and under nitrogen atmosphere. The reaction is stirred for 15 mins for the formation of corresponding acid chloride. Then, the reaction mass was evaporated to dryness to remove excess oxalyl chloride and DCM. The crude was kept at nitrogen atmosphere and dissolved in measured amount of DCM (20 mL). In another vessel, compound 2 (0.50 g, 2.09 mmol) was dissolved in DCM (10 mL) followed by addition of TEA (0.7 mL, 5.64 mmol) and dropwise addition of prepared acid chloride. The reaction was stirred for another 3 hours. The reaction was monitored by checking TLC. Upon completion of the reaction, reaction mass was evaporated to dryness and washed with saturated $NaHCO_3$ and extracted with EtOAc to get the crude. The product was purified by flash chromatography (Silica gel, mesh size 100-200) eluting (60% EtOAc/Pet ether) to obtain compound 296 (0.31 g, 48.88%) as a white solid. ESI-HRMS m/z 451.219 ($M+H^+$). Melting point 102° C.

Example 265

Synthesis of tert-butyl 4-(3-(2-methoxyethyl)-6-nitro-4-oxo-3,4-dihydroquinazolin-2-yl)piperidine-1-carboxylate (297): The compound was prepared by general procedure G provided in example 7 using compound 296 (0.30 g, 0.66 mmol), DMF (5 mL), zinc chloride (0.63 g, 4.66 mmol), HMDS (0.83 mL, 3.99 mmol) to obtain compound 297 (0.17 g, 49%) as yellow solid. ESI-HRMS m/z 433.2090 (M+H+). Melting point 170° C.

Example 266

Synthesis of tert-butyl 4-(6-amino-3-(2-methoxyethyl)-4-oxo-3,4-dihydroquinazolin-2-yl)piperidine-1-carboxylate (298): The compound was prepared by general procedure C provided in example 3 using compound 297 (0.16 g, 0.38 mmol), methanol (10 mL), a pinch of Pd—C under hydrogen atmosphere to obtain compound 298 (0.15 g, 78%) as light brown solid. ESI-HRMS m/z 403.2349 (M+H+). Melting point 174° C.

Example 267

Synthesis of tert-butyl 4-(6-(3-(3-acetylphenyl)ureido)-3-(2-methoxyethyl)-4-oxo-3,4-dihydroquinazolin-2-yl)piperidine-1-carboxylate (299): The compound was prepared by general procedure D provided in example 4 using compound 298 (0.14 g, 0.34 mmol), dry THF (5 mL), 4-nitrophenylchloroformate (0.10 g, 0.52 mmol), 3'-aminoacetophenone (0.043 g, 0.31 mmol), TEA (0.06 mL, 0.41 mmol) to obtain compound 299 (0.09 g, 39%) as off white solid. ESI-HRMS m/z 564.2821 (M+H+). Melting point 196° C.

Example 268

Synthesis of 1-(3-acetylphenyl)-3-(3-(2-methoxyethyl)-4-oxo-2-(piperidin-4-yl)-3,4-dihydroquinazolin-6-yl)urea (300): Compound 299 (0.068 g, 0.12 mmol) was dissolved in DCM (3 mL) and TFA (0.05 mL, 0.60 mmol) was added dropwise under ice cold condition at inert atmosphere. The reaction was stirred for 8 hrs. The reaction was neutralised by saturated $NaHCO_3$ solution and extracted with EtOAc. The product was then purified by column chromatography (Silica gel, mesh size 100-200) eluting (70% EtOAc/Pet ether) to obtain compound 300 (0.009 g, 39.2%) as off white amorphous solid. ESI-HRMS m/z 464.2296 (M+H+).

Example 269

Synthesis of 2-(2-chloro-2,2-difluoroacetamido)-N-(2-methoxyethyl)-5-nitrobenzamide (326a): Compound 2 (0.6 g, 2.50 mmol) was dissolved in dry pyridine (6 mL), Chlorodifluoroacetic acid (0.360 g, 2.75 mmol) was added and then $POCl_3$ (0.281 mL, 2.75 mmol) was added dropwise under cooling conditions and the reaction mixture was allowed to stir at room temperature for 1 hour. After completion of the reaction, workup was done with EtOAc and 1(N) HCl soln. The product was then purified by column chromatography (Silica gel, mesh size 100-200) eluting (30% EtOAc/Pet ether) to obtain compound 326a as off white amorphous solid (0.634 g, 72%). $^1H$ NMR (400 MHz, $d_6$-DMSO) δ in ppm 13.56 (s, 1H), 9.48 (s, 1H), 8.81 (d, J=2.4 Hz, 1H), 8.54 (d, J=8.8 Hz, 1H), 8.46 (dd, J=9.2 Hz, 2.4 Hz, 1H), 3.48-3.43 (m, 4H), 3.24 (s, 3H).

Example 270

Synthesis of 2-(chlorodifluoromethyl)-3-(2-methoxyethyl)-6-nitroquinazolin-4 (3H)-one (327a): The compound was prepared by general procedure G provided in example 7 using compound 326a (0.4 g, 1.14 mmol), DMF (5 mL), zinc chloride (0.621 g, 4.56 mmol), HMDS (1.9 mL, 9.12 mmol) to obtain compound 327a as off white amorphous solid (0.303 g, 80%). $^1H$ NMR (400 MHz, DMSO-d6) δ in ppm 8.80 (d, J=2.4 Hz, 1H), 8.60 (dd, J=8.8 Hz, 3.2 Hz, 1H), 8.00 (d, J=8.8 Hz, 1H), 4.29 (t, J=6.8 Hz, 2H), 3.60 (t, J=6.8 Hz, 2H), 3.24 (s, 3H).

Example 271

Synthesis of 3-(2-methoxyethyl)-6-nitro-2-(piperidine-1-carbonyl)quinazolin-4 (3H)-one (328a): Compound 327a (0.25 g, 0.75 mmol) and piperidine (0.15 mL, 1.50 mmol) were dissolved in dry toluene and refluxed for 2 hrs. After completion of the reaction, workup was done with EtOAc and water. The product was then purified by column chromatography (Silica gel, mesh size 100-200) eluting (40% EtOAc/Pet ether) to obtain compound 328a as off white amorphous solid (0.232 g, 86%). $^1H$ NMR (400 MHz, CDCl3) δ in ppm 9.12 (d, J=2.8 Hz, 1H), 8.51 (dd, J=8.8 Hz, 2.8 Hz, 1H), 7.77 (d, J=8.8 Hz, 1H), 4.34 (t, J=5.2 Hz, 2H), 3.78-3.66 (m, 2H), 3.26 (s, 3H), 1.75-1.66 (m, 6H).

Example 272

Synthesis of 6-amino-3-(2-methoxyethyl)-2-(piperidine-1-carbonyl)quinazolin-4 (3H)-one (329a): The compound was prepared by general procedure C provided in example 3 using compound 328a (0.200 g, 0.55 mmol), methanol (10 mL), a pinch of Pd—C under hydrogen atmosphere to obtain compound 329a (0.113 g, 62%) as light brown solid. $^1H$ NMR (400 MHz, CDCl3) δ in ppm 7.48 (d, J=8.8 Hz, 1H), 7.43 (d, J=2.8 Hz, 1H), 7.06 (dd, J=8.8 Hz, 1H), 4.29 (t, J=5.6 Hz, 2H), 4.02 (brs, 2H), 3.72-3.68 (m, 2H), 3.26 (s, 3H), 1.71-1.63 (m, 6H).

Example 273

Synthesis of 1-(3-acetylphenyl)-3-(3-(2-methoxyethyl)-4-oxo-2-(piperidine-1-carbonyl)-3,4-dihydroquinazolin-6-yl) urea (330a): The compound was prepared by general procedure D provided in example 4 using compound 329a (0.07 g, 0.14 mmol), dry THF (5 mL), 4-nitrophenylchloroformate (0.048 g, 0.16 mmol), 3'-aminoacetophenone (0.032 g, 0.16 mmol), TEA (0.06 mL, 0.28 mmol) to obtain compound 330a (0.04 g, 39%) as off white solid. $^1H$ NMR (400 MHz, CDCl3) δ in ppm 8.31 (s, 1H), 8.22 (s, 1H), 8.04 (dd, J=8.8 Hz, 2.4 Hz, 1H), 7.94-7.93 (m, 1H), 7.83 (dd, J=8.4 Hz, 2.4 Hz, 1H), 7.70 (d, J=2.4 Hz, 1H), 7.59-7.55 (m, 1H), 7.43 (d, J=8.8 Hz, 1H), 7.37-7.33 (m, 1H), 4.27 (t, J=4.8 Hz, 2H), 3.81-3.73 (m, 2H), 3.67 (t, J=4.8 Hz, 2H), 3.42-3.35 (m, 2H), 3.25 (s, 3H), 2.59 (s, 3H), 1.88-1.65 (m, 6H).

Example 274

Synthesis of 3-(2-methoxyethyl)-2-(4-methylpiperazine-1-carbonyl)-6-nitroquinazolin-4 (3H)-one (331a): Compound 327a (0.25 g, 0.75 mmol) and 1-methylpiperazine (0.16 mL, 1.50 mmol) were dissolved in dry toluene (5 mL) and refluxed for 2 hrs. After completion of the reaction, workup was done with EtOAc and water. The product was then purified by column chromatography (Silica gel, mesh size 100-200) eluting (40% EtOAc/Pet ether) to obtain compound 331a as off white amorphous solid (0.232 g, 82%).

Example 275

Synthesis of 6-amino-3-(2-methoxyethyl)-2-(4-methylpiperazine-1-carbonyl)quinazolin-4 (3H)-one (332a): The compound was prepared by general procedure C provided in example 3 using compound 331a (0.200 g, 0.55 mmol), methanol (10 mL), a pinch of Pd—C under hydrogen atmosphere to obtain compound 332a (0.120 g, 58%) as light brown solid.

Example 276

Synthesis of 1-(3-acetylphenyl)-3-(3-(2-methoxyethyl)-2-(4-methylpiperazine-1-carbonyl)-4-oxo-3,4-dihydroquinazolin-6-yl)urea (333a): The compound was prepared by general procedure D provided in example 4 using compound 332a (0.07 g, 0.14 mmol), dry THF (5 mL), 4-nitrophenylchloroformate (0.049 g, 0.16 mmol), 3'-aminoacetophenone (0.033 g, 0.16 mmol), TEA (0.06 mL, 0.28 mmol) to obtain compound 333a (0.043 g, 42%) as off white solid. $^1$H NMR (400 MHz, DMSO-d6) δ in ppm 9.19 (s, 1H), 9.01 (s, 1H), 8.35 (d, J=2.8 Hz, 1H), 8.07-8.05 (m, 1H), 7.81 (dd, J=8.8 Hz, 2.4 Hz, 1H), 7.68-7.65 (m, 1H), 7.59 (d, J=8.8 Hz, 1H), 4.10 (t, J=6.0 Hz, 2H), 3.64-3.58 (m, 2H), 3.53 (t, J=6.0 Hz, 2H), 3.40-3.35 (m, 2H), 3.18 (s, 3H), 2.53 (s, 3H), 2.40-2.37 (m, 2H), 2.35-2.30 (m, 2H), 2.20 (s, 3H).

Example 277

Synthesis of 2-amino-N-morpholino-5-nitrobenzamide (337): The compound was prepared by general procedure A provided in example 1 using compound 1 (0.3 g, 1.64 mmol), DMF (6 mL), HATU (0.7 g, 1.81 mmol), 4-aminomorpholine (0.18 mL, 1.81 mmol), TEA (0.57 mL, 4.12 mmol) to obtain compound 337 (0.38 g, 86%) as yellow solid. $^1$H NMR (400 MHz, $d_6$-DMSO) δ in ppm 9.69 (s, 1H), 8.38 (d, J=2 Hz, 1H), 8.02 (dd, J=9.4 Hz, 2.8 Hz, 1H), 7.58 (brs, 2H), 6.79 (d, J=9.6 Hz, 1H), 3.67-3.65 (m, 4H), 2.88-2.85 (m, 4H).

Example 278

Synthesis of 3-morpholino-6-nitroquinazolin-4 (3H)-one (338): The compound was prepared by general procedure B provided in example 2 using compound 337 (0.35 g, 1.31 mmol), trimethylorthoformate (TMOF) (1.5 mL, 13.15 mmol) to obtain compound 338 (0.3 g, 83%) as pale yellow solid. $^1$H NMR (400 MHz, $d_6$-$CDCl_3$) δ in ppm 9.13 (d, J=2.4 Hz, 1H), 8.50 (dd, J=8.8 Hz, 2.8 Hz, 1H), 8.26 (s, 1H), 7.80 (d, J=9.2 Hz, 1H), 3.04-3.01 (m, 2H), 2.24-2.18 (m, 2H), 2.02-1.97 (m, 4H).

Example 279

Synthesis of 6-amino-3-morpholinoquinazolin-4 (3H)-one (339): The compound was prepared by general procedure C provided in example 3 using compound 338 (0.250 g, 0.90 mmol), methanol (5 mL) and pinch of 10% wet Pd—C under hydrogen atmosphere to obtain compound 339 (0.19 g, 86%) as brown solid. $^1$H NMR (300 MHz, $d_6$-DMSO) δ in ppm 7.91 (s, 1H), 7.38 (d, J=8.7 Hz, 1H), 7.21 (d, J=2.4 Hz, 1H), 7.06 (dd, J=8.4 Hz, 2.4 Hz, 1H), 5.72 (brs, 2H), 3.75-3.67 (m, 6H), 3.18-3.15 (m, 2H).

Example 280

Synthesis of 1-(3-acetylphenyl)-3-(3-morpholino-4-oxo-3,4-dihydroquinazolin-6-yl)urea (340): The compound was prepared by general procedure D provided in example 4 using compound 339 (0.14 g, 0.56 mmol), dry THF (8 mL), 4-nitrophenylchloroformate (0.18 g, 0.85 mmol), 3'-aminoacetophenone (0.093 mg, 0.68 mmol), TEA (0.2 mL, 1.42 mmol) to obtain compound 340 (0.09 g, 39%) as off white solid. $^1$H NMR (400 MHz, $d_6$-DMSO) δ in ppm 9.11 (s, 1H), 8.95 (s, 1H), 8.31 (d, J=2.8 Hz, 1H), 8.09 (s, 1H), 8.06-8.05 (m, 1H), 7.80 (dd, J=8.8 Hz, 2.4 Hz, 1H), 7.66 (dd, J=8.2 Hz, 2 Hz, 1H), 7.59-7.55 (m, 2H), 7.42-7.39 (m, 1H), 3.73-3.65 (m, 8H), 2.53 (s, 3H).

Example 281

Synthesis of 6-amino-5-bromo-3-(2-methoxyethyl)-2-methylquinazolin-4 (3H)-one (344): Compound 106 (0.300 g, 1.28 mmol) was dissolved in AcOH (4 mL). Solution of bromine (0.079 mL, 1.53 mmol) in chloroform (2 mL) was added dropwise in the reaction mixture at 0° C. and reaction mass was allowed to stir at room temperature for 4 hrs. After completion of the reaction, reaction mass was washed with aq. NaSCN soln and extracted with ethyl acetate and purified by column chromatography (Silica gel, mesh size 100-200) eluting (70% EA-PE) to obtain compound 344 (0.280 g, 70%) as off white solid. ESI-HRMS m/z 312.0351 (M+H$^+$).

Example 282

Synthesis of 1-(3-acetylphenyl)-3-(5-bromo-3-(2-methoxyethyl)-2-methyl-4-oxo-3,4-dihydroquinazolin-6-yl) urea (345): The compound was prepared by general procedure D provided in example 4 using compound 344 (0.080 g, 0.25 mmol), dry THF (3 mL), 4-nitrophenylchloroformate (0.062 g, 0.30 mmol), 3'-aminoacetophenone (0.040 g, 0.30 mmol), TEA (0.094 mL, 0.68 mmol) to obtain compound 345 (0.048 g, 40%) as light brown solid. ESI-HRMS m/z 473.0829 (M+H$^+$).

Biological Assay

To select the compounds capable of inhibiting the ubiquitination of ATGL by COP1 by targeting the VP motif, confocal microscopy was performed with the provided molecules. If the compound was effective in inhibiting the interaction, there would be a reduction in the number of fat droplets in the cells after treatment. This is because the increased ATGL levels would hydrolyze the accumulated TAG in oleate induced HepG2 cells and bring about the aforementioned reduction. With this rationale in mind, HepG2 cells were induced to accumulate lipid droplets after treatment with 250 M of oleate and 10 μM of the specific compounds were added. The potential of the compounds to bring about a reduction in the number of fat droplets was then checked by comparison with oleate induced cells by counting number of droplets of approximately 20 cells from each treatment and calculating the average number of lipid droplets of each cell. The selected compounds were then subjected to dose dependent treatments and the ones which could maintain its potency to reduce fat droplets at lower doses were then selected for western blot analysis. The compound which could reduce the number of fat droplets in the cells are expected to raise the levels of ATGL since they are likely to deter COP1 from ubiquitinating ATGL. This increase will be visible only in the protein level and gene expression is likely to remain unchanged since ubiquitination is a post transcriptional modification. Thus, western blot was performed to check ATGL levels in the cells with the selected molecules.

Example 283

Western Blotting

HepG2 cells were treated with the compounds 9, 10, 11, 17, 18, 23, 24, 115, 123, 127, 139,107, 171, 179, 73, 187, 211, 215, 219, 223, 232, 238, 241, 244, 258, 299, 308, and 333a, (10 μM for initial screening and 50 nM, 100 nM, 200 nM, 500 nM, 1 μM and 5 μM for dose dependent assays) for 24 hours. After removing media from the cells, the wells were washed with 1×PBS twice to remove any remnant media. Cells were then lysed in lysis buffer containing 50 mM Tris-HCl (pH 7.4), 100 mM NaCl, 1 mM EDTA, 1 mM EGTA, 1% Triton X-100 and protease inhibitor cocktail (Millipore, Billierica, MA, USA). Following centrifugation at 20,000 g for 20 minutes, the protein solution was extracted from the cells. Protein was estimated using Bradford assay. Bradford's reagent (BioRad) was diluted in 1:4 ratio in double distilled water. 2 μl of protein sample was added to 100 μl of the reagent and absorbance was measured at 595 nm. 30 g of protein was diluted in lysis buffer. 1× loading buffer diluted from 5× stock containing 250 mM Tris-HCl (pH 6.8), 10% SDS, 50% glycerol, 0.1% bromophenol Blue and 10% β-mercaptoethanol was added. The protein samples were then heated at 95° C. for 10 minutes, cooled and centrifuged at 12,000 g for 2 minutes prior to loading.

For western blotting, the proteins were resolved in 10% SDS PAGE (discontinuous buffer system). 1× running buffer containing SDS, Tris Base and Glycine was used to run the gel at 80V for approximately 2 hours. Transfer was done using PVDF membrane (Millipore) having pore size of 0.45 μm. 1× transfer buffer containing Tris-Base, Glycine and 20% methanol was used for wet transfer. Transfer was done at 90V for 3 hours. Following transfer, the PVDF membrane containing the proteins were washed in 1×PBST comprising of 1×PBS and 1% Tween 20 (Sigma Aldrich). The membrane was then incubated for 1 hour at room temperature in 5% skim milk powder to block the non-specific sites. Following multiple washes with 1×PBST to wash away any remaining blocking buffer, the required primary antibody (COP1 [Bethyl Laboraties], ATGL [Cell Signalling Technology] or Actin[Cell Signalling Technology]) prepared with 1×PBST, 1% Bovine Serum Albumin and 0.04% Sodium Azide was added to the membrane and incubated overnight at 4° C. The next day, the membrane was again washed multiple times with 1×PBST to remove any unbound primary antibody. The membrane was then incubated with goat anti-rabbit secondary antibody (Genei) for 1 hour at room temperature and washed again for multiple times with 1×PBST. The membrane was then developed using Clarity™ ECL Western Blotting Substrate (BioRad) and viewed in ChemiDoc (BioRad). The $EC_{50}$ values of compounds 127, 139, 211, 215, 219, 223, 232, 238 and 299 are described in Table 6.

Figure 1Y:
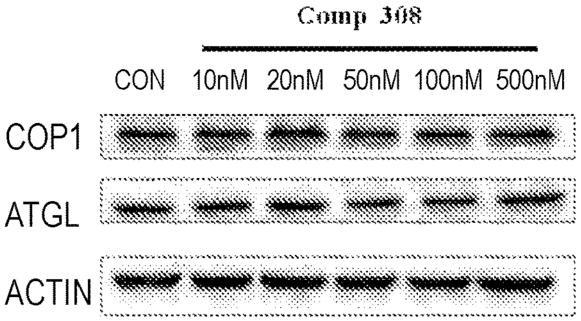

FIGS. 1A-1Y illustrate results of Western Blot Analysis in HepG2 cells after treatment with compounds 9, 10, 107, 171, 179, 73, 232, 238, 211 and 340. The figure also describes the dose dependant Western Blot analysis of following compounds 9, 11, 17, 18, 23, 24, 123, 127, 139, 211, 223, 232, 241, 244, 299, 333a, 215, 219, 238 and 308. These compounds showed increased ATGL level irrespective of the treated doses.

Example 284

Confocal Microscopy

HepG2 cells were plated in confocal dishes (SPL, Genetix Biotech Asia Pvt. Ltd.). The cells were allowed to adhere and divide for 16 hours. 10 μM for initial screening and 10 nM, 20 nM, 50 nM, 100 nM, 200 nM, 500 nM, 1 μM and 5 μM for dose dependent assays of the compounds 9 and 107 were dissolved in DMSO and added to the cells. 250 μM of oleate was used for induction. BSA (Sigma Aldrich) was used as a negative control. Post 24 hours of treatment, media was decanted from the cells and washed with 1×PBS solution to remove any remnant. 200 μl of staining solution containing 200 ng/ml BODIPY (Invitrogen) and 25 g/ml HOECKST342 (Invitrogen) were added to the cells and incubated at 37° C. for 30 minutes under dark conditions. Cells were washed 3 times with 1×PBS to remove excess stain. FLUOVIEW FV10i (Olympus) was used to visualise the cells.

Figure 2:
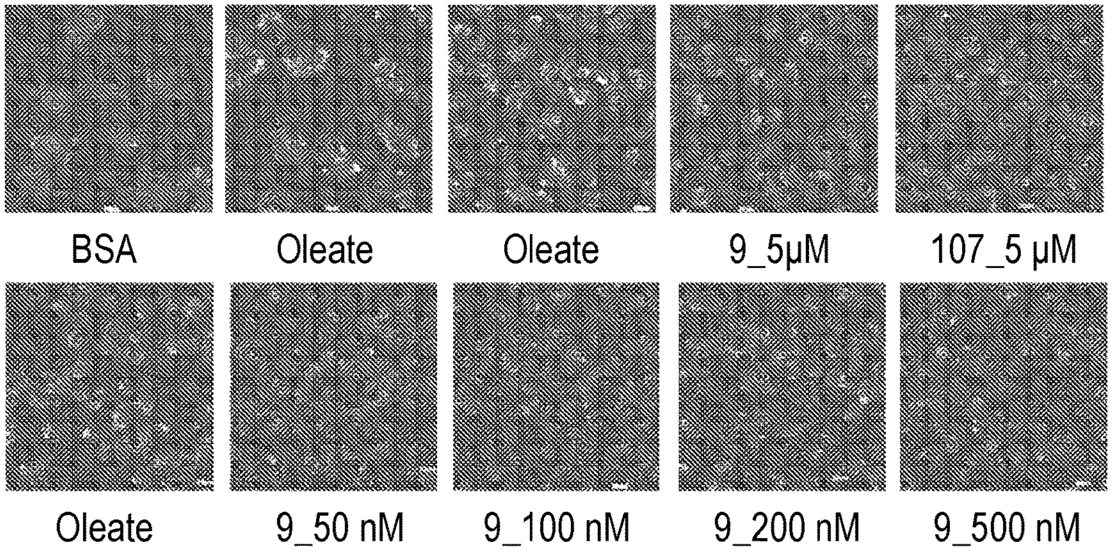
FIG. 2 illustrates images of compound screening on HepG2 cells using confocal microscopy. The white foci in the cells denote lipid droplets. Increase or decrease in the number of white foci therefore indicate the corresponding status of lipid droplets in the cells. Oleate induction resulted in an increase in lipid droplets wheareas treatment with compounds 9 and 10 caused a decrease in the number of lipid droplets upon oleate induction.

FIG. 2 illustrates images of compound 9 and 107 screening on HepG2 cells using confocal microscopy.

Example 285

The Effect of the Compounds in Primary Mouse Hepatocytes and Adipose Explant Cultures To further strengthen the efficiency of the compounds 9 and 107, primary hepatocytes were isolated from mice and these compounds were treated in a dose dependent manner for 24 hours. Primary hepatocytes and adipose tissue explants were isolated from mice and subjected to compound treatment for 24 hours at the doses of 100 nM, 500 nM and 1 μM. Post cell harvesting, western blot was carried out with the lysate to check the ATGL level. ATGL and COP1 antibodies were used. Actin served the purpose of a loading control.

Culture of Primary Mouse Hepatocytes and Adipocytes

1. Hepatocytes—2-4 months old chow-fed black male mouse (C57bl/6) was sacrificed using chloroform (SRL) and was cleaned with 70% ethanol. Under aseptic conditions, the ventral side of the mouse was cut open, until the liver, portal vein (PV) and inferior vena cava (IVC) were sufficiently exposed. Blood was drawn from the heart in order to prevent backflow into liver while perfusion. The butterfly cannula was inserted into the PV and 20 ml of HBSS (Hank's Balanced Salt Solution; 5 mM KCl, 0.4 mM $KH_2PO_4$, 4 mM $NaHCO_3$, 140 mM NaCl, 0.3 mM $Na_2HPO_4$, 6 mM Glucose, HEPES, 0.5 mM $MgCl_2 \cdot 6H_2O$, 0.4 mM $MgSO_4 \cdot 7H_2O$, 0.5 mM EDTA; not containing 1 mM $CaCl_2$)) was allowed to pass through the liver (Perfusion) at a constant flow rate of 3 ml/min, maintained by Masterflex digital peristaltic pump (Cole-Parmer). The IVC was cut as soon as the passage of the buffer through the liver began, so that blood and perfusate from liver is drained through the IVC. The liver blanched and became pale in color upon this treatment.

After the passage of HBSS, 25 ml of Collagenase (Roche) solution (1 mg/ml) in HBSS (containing 1 mM $CaCl_2$)) was allowed to pass through the liver at a constant flow rate of 2 ml/min. After this digestion, the flow was stopped, the cannula removed and the pale and soggy lobes of the liver were gently excised from the body. The gall bladder was removed from the isolated liver. The pieces of digested liver tissue were then minced on a 10 cm culture plate in HBSS (containing 1 mM $CaCl_2$)). The resulting suspension was then passed through a 100 cell strainer (SPL) to allow hepatocytes to pass through to the filtrate and retain cellular clumps and undigested tissue. The filtrate was centrifuged at 50 g for 2 minutes at 4° C. The supernatant was discarded and the cellular pellet was carefully resuspended in DMEM. The resulting suspension was centrifuged at 50 g for 2 minutes at 4° C. The supernatant was discarded and the cellular pellet was carefully resuspended in required volume of DMEM for plating. The hepatocytes were plated according to experimental requirements and were maintained in an incubator at 37° C. with 5% $CO_2$. Cells were washed once with HBSS and DMEM 6-7 hours after plating and the adhered hepatocytes were maintained and subjected to requisite treatments.

2. Adipocytes—2-4 months old chow-fed black male mouse (C57bl/6) was sacrificed using chloroform (SRL) and was cleaned with 70% ethanol. Under aseptic conditions, the ventral side of the mouse was cut open, and gonadal (epididymal) white adipose tissue were excised using scissors and suspended in 1×PBS supplemented with 0.1% BSA in a 10 cm culture plate. The attached blood vessels were removed and the adipose tissue was minced as much as possible. The suspension was centrifuged at 50 g for 2 minutes at 4° C. After centrifugation, the adipose tissue pieces suspended at the uppermost layer of the supernatant as emulsion were carefully extracted and plated in DMEM in 35 mm culture dishes. The explant tissue thus obtained was treated with different concentrations of compounds after 6-7 hours.

Figure 3A:
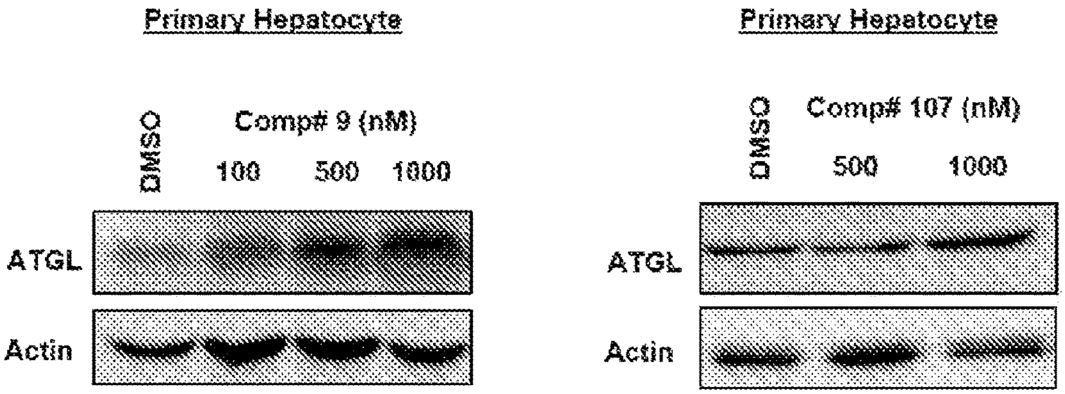
FIGS. 3A, 3B, and 3C illustrate ATGL protein status in mouse primary hepatocytes and adipose explants after compound treatment. Compounds 9 and 107 could increase ATGL level in primary mouse hepatocytes as evidenced by increase in intensity of the corresponding band with respect to control in Western blot analysis. While in adipose explants no such changes were observed.
Figure 3B:
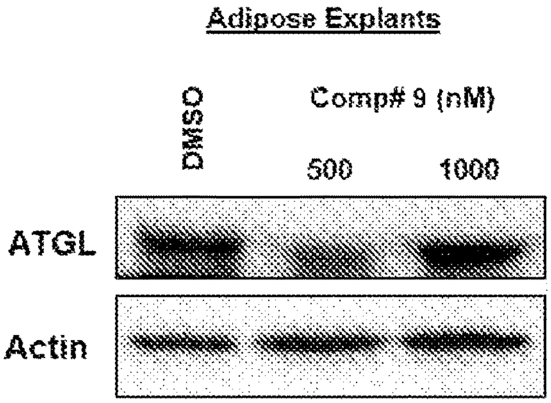
Figure 3C:
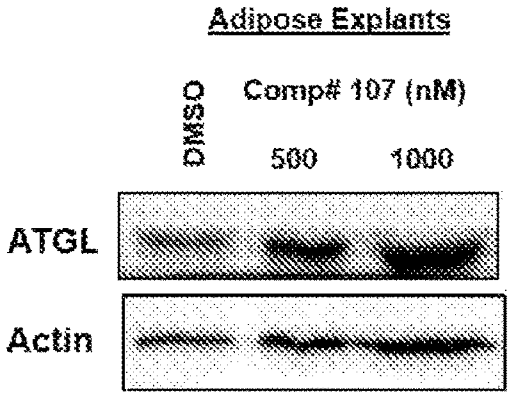

FIGS. 3A, 3B, and 3C illustrate ATGL protein status in mouse primary hepatocytes and adipose explants after compound treatment. The level of ATGL was found to be increased in a dose-dependent manner. This provides a more profound and direct evidence of the effectiveness of the compounds. As is evident, in primary hepatocytes, compounds 9 and 107 had a subtle inclination towards increasing ATGL level whereas this effect was absent in adipose tissue explants.

The major source of ATGL is the adipose tissue and, therefore, it is fitting to check if the compounds had any effect on the ATGL protein level in adipose tissue. Both 9 and 107 did not show any significant changes in ATGL protein in cultures mouse adipose explants after 24 hours of compound treatment. This partly hints at a lack of a striking regulation of ATGL turnover by COP1.

Example 286

In Vitro Ubiquitination

Purification of ATGL protein and obtaining COP1 overexpressing cell lysate: Myc-ATGL plasmid and Myc-DDK-COP1 plasmid (2 g each) were transfected separately in cultured HEK293A cells with the help of Lipofectamine2000 (Invitrogen). Cells were harvested in Lysis Buffer and protein solution was extracted as described previously. The Lysis Buffer used to harvest COP1 overexpressing cells had 0.1% SDS supplemented in it. The concentration of protein was estimated using Bradford assay. For source of E3 ligase, the total cell lysate from COP1 overexpressing HEK293A cells were used.

For purification of Myc-ATGL: 1 ml of $Ni^{2+}$-NTA resin (Roche) was taken in a 15 ml centrifuge tube and centrifuged at 2000 RPM for 5 minutes. The upper ethanol layer was discarded and the pellet was washed in 1×PBS twice to remove any remaining traces of ethanol. The pellet was finally washed once with Lysis Buffer for equilibration. 15 mg of protein was used for affinity purification reaction in a reaction volume of 10 ml with Lysis Buffer (containing protease inhibitor cocktail). The tube was incubated overnight at 4° C. in a rotary shaker.

The next day, the solution was centrifuged at 2000 RPM for 10 minutes and the supernatant collected. Lysis Buffer (containing protease inhibitor cocktail twice the previous concentration) was used for washing the beads twice to remove non-specific and unattached reactants in a stringent condition. The beads were finally washed once with 1×PBS containing the same amount of protease inhibitor for equilibration. 300 μl of 500 mM Imidazole (Sigma Aldrich) solution in 1×PBS was added to the resin for elution of ATGL and centrifuged at 2000 RPM for 30 minutes and the eluted protein was collected. To the separated resin, 300 μl of 1M Imidazole solution was added and centrifuged at 2000 RPM for 30 minutes and the second elute was collected. 201 of eluted protein from each elution was boiled with 5 μl of Laemmli's buffer at 95° C. for 10 minutes and run in 10% SDS-PAGE gel. The supernatant collected before elution of ATGL and the proteins still attached to the $Ni^{2+}$-NTA resin were also run in the SDS-PAGE. The resolved proteins were subsequently transferred on PVDF membranes and probed with anti-myc primary antibody to check the presence of purified ATGL in the elute. Also to check the yield of the purified protein, 40 μl of the elute was run in 10% SDS page and stained with Coomassie Brilliant Blue solution followed by destaining with methanol, glacial acetic acid and water in a 50:40:10 ratio.

For identifying the E2 ubiquitin-conjugating enzyme responsible for ATGL ubiquitination by COP1, an in vitro ubiquitinylation kit (Enzo Life Sciences) was used. The assay was reconstituted as per manufacturer's protocol with the panel of E2 conjugating enzymes provided and other required components at the mentioned concentrations. The reaction was carried out for 6 hours following which it was quenched as per directions with the provided 2× non-reducing gel buffer and then analysed by western blotting.

Figure 4:
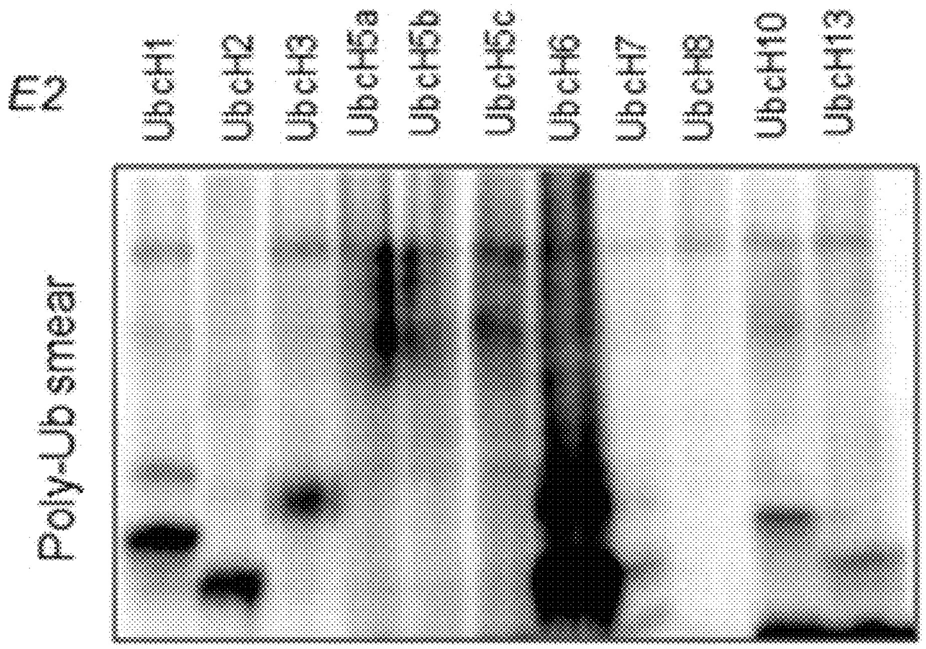
FIG. 4 illustrates identification of the E2 conjugating enzyme responsible for ATGL ubiquitination by the E3 Ubiquitin Ligase, COP1. The presence of poly Ubiquitin smear only in case of UbcH6 indicate that is the specific E2 enzyme in the ubiquitination reaction of ATGL by COP1.

FIG. 4 illustrates identification of the E2 conjugating enzyme responsible for ATGL ubiquitination by the E3 Ubiquitin Ligase, COP1. As seen in FIG. 4, only UbcH6 (UBE2E1) was able to mediate the ubiquitination of ATGL by COP1. Therefore, UbcH6 was used as the E2 enzyme to check the effect of ATGL ubiquitination by COP1 upon treatment with the small molecule inhibitors.

Having identified the E2 ubiquitin conjugating enzyme as UbcH6, ubiquitination assay was set up in vitro as described previously with 5 μM of the compound 9, 107, 171, 179 and 73 followed by quenching and analysis by western blotting.

Ubiquitination of a target protein is carried out in a three step process involving three different enzymes: E1 ubiquitin activating enzyme, E2 ubiquitin conjugating enzyme and E3 ubiquitin ligase. In humans, there is only one E1 ubiquitin activating enzyme and multiple E2 and E3 enzymes. COP1 is an E3 ubiquitin ligase and the E2 enzyme responsible for ATGL ubiquitination is not known. In order to assert the specificity of the compounds of the present disclosure to inhibit COP1 and decrease ubiquitination of ATGL, the in vitro ubiquitinylation reaction was reconstituted with purified ATGL protein, total cell lysate of COP1 overexpressing HEK293A cells as source of E3 ubiquitin ligase, UbcH6 as E2 enzyme, 5 μM of the compounds 9, 107, 171, 179 and 73 and other components required to carry out the ubiquitinylation reaction as per the manufacturer's instructions.

Figure 5:
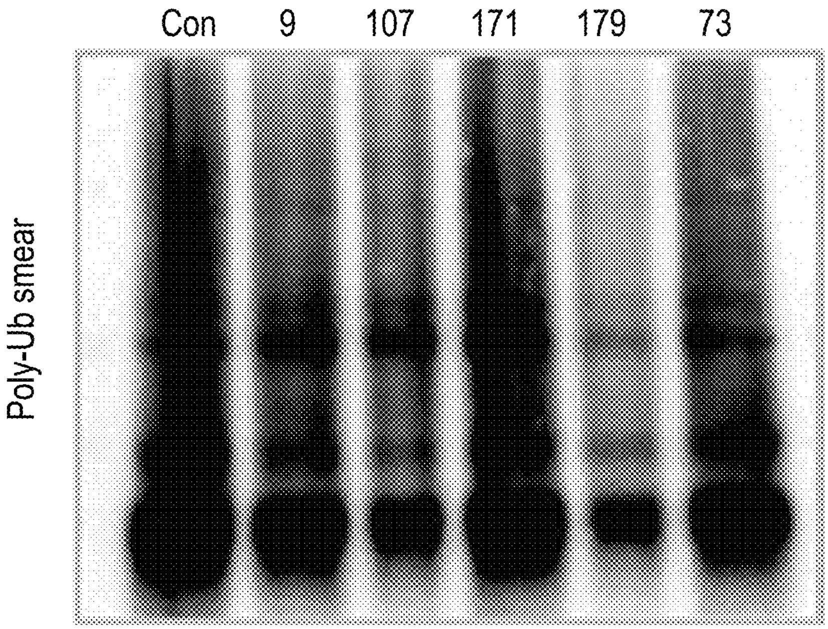
FIG. 5 illustrates effect of compounds 9, 107, 171, 179 and 73 on ATGL ubiquitination in vitro. The above compounds were effective in reducing the ubiquitination of ATGL by COP1 in an in vitro reaction reconstituted with purified ATGL protein, COP1 overexpressing cell lysate, recombinant UbcH6 identified in the experiment before and other essential components of the reaction.

FIG. 5 illustrates effect of compounds 9, 107, 171, 179 and 73 on ATGL ubiquitination in vitro. As seen in the figure, compounds 9, 107 and 179 showed significant efficacy in curbing ATGL ubiquitination by COP1. This experiment also points, to the specificity of the compounds in inhibiting COP1 since the source of E3 ubiquitin ligase is majorly COP1 and purified ATGL protein has been used as its substrate.

Example 287

Status of ATGL Ubiquitination and COP1 Autoubiquitination Upon Compound Treatment Assessed by Immunoprecipitation Assay COP1 is an E3 ubiquitin ligase and ATGL is one of its targets which gets ubiquitinated and ultimately degraded via proteasomal mediated pathway. Thus, the molecules inhibiting COP1 by targeting the VP motif of ATGL are actually expected to bring about a reduction in the ubiquitination levels of ATGL. The compounds of the present disclosure have shown a reduction in the lipid droplet count with a corresponding increase in ATGL protein levels while gene expression remained unaltered. However, it is of utmost importance to check the changes taking place at the ubiquitination level of ATGL upon treatment with the compounds.

To this end, an immunoprecipitation assay was performed wherein HepG2 cells overexpressing myc-ATGL were transfected with HA-Ubiquitin and treated with 5 μM of the compounds 9, 10, 107, 215, 219 and 238. MG-132, a proteasomal inhibitor, was added 4 hours before harvesting the cells. Immune complexes were pulled down with anti-myc antibody and immunoblot was done using anti-HA antibody. The resultant smears on the blot reflect the ubiquitination status of ATGL.

Figure 6A:
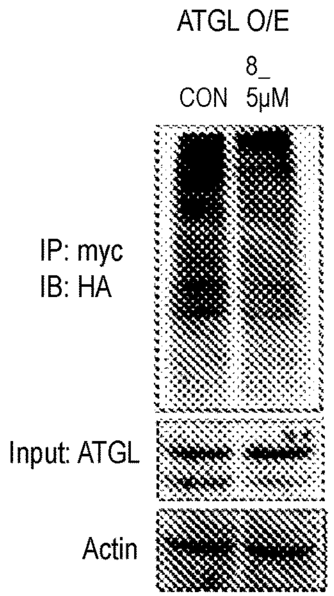
FIGS. 6A-6F illustrate results of immunoprecipitation assay to check ubiquitination status of ATGL and COP1 after treatment with compounds. Compound 9 and 107 was effective in reducing the ATGL ubiquitination by COP1 in HepG2 cells as well as COP1 autoubiquitination as evidenced by the decrease in the intensity of the poly Ubiquitin smear. Compound 107 was effective in reducing ATGL ubiquitination by COP1 whereas compounds 215 and 219 had no such effects.
Figure 6B:
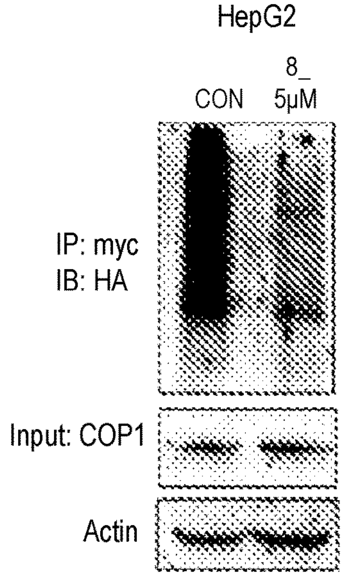
Figure 6C:
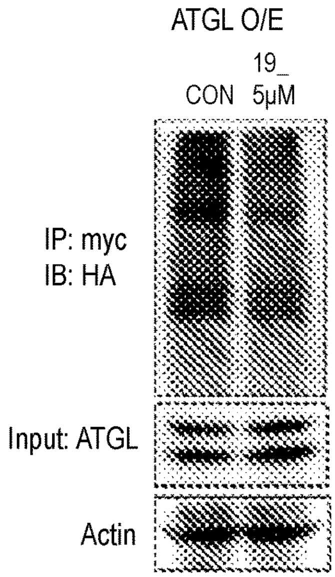
Figure 6D:
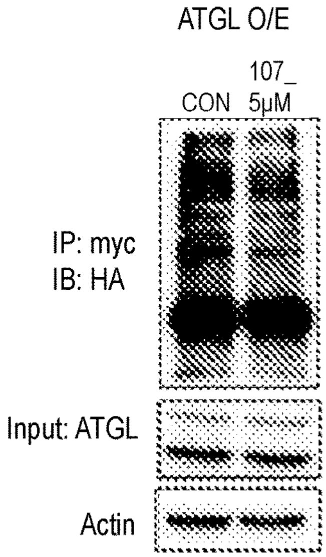
Figure 6E:
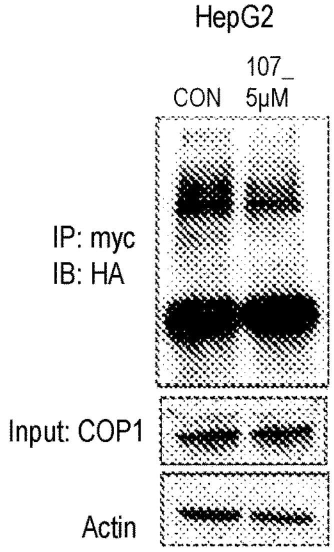
Figure 6F:
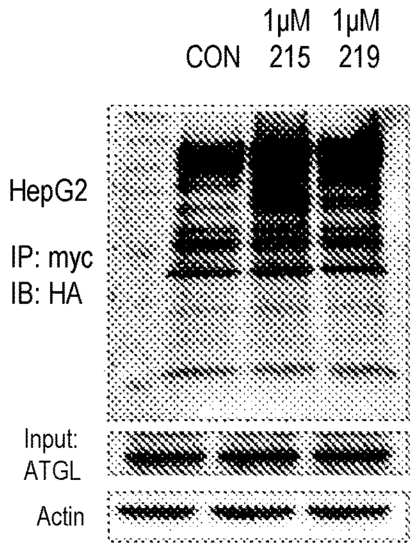

FIGS. 6A-6G illustrate results of immunoprecipitation assay to check ubiquitination status of ATGL and COP1 after treatment with compounds 9, 10, 107, 215, 219 and 238. For compound 9, a subtle reduction in the ubiquitination smear upon treatment was observed as compared with control. This reduction, however, could not be seen in cells treated with compound 10 which indicates that compound 9 might be more potent in inhibiting COP1 by blocking the ubiquitination of ATGL to some extent compared to compound 10. Compound 107, also seemed to exhibit the capability of subtly reducing ubiquitination of ATGL (FIGS. 6A, 6C and 6D). For compounds 215 and 219, no subtle reduction in the ubiquitination smear upon treatment was observed as compared with control (FIG. 6F).

COP1 is capable of auto ubiquitinating its own self and getting degraded via the proteasomal pathway. To probe into this, HepG2 cells were co-transfected with HA tagged Ubiquitin and myc-flag tagged COP1. The transfected cells were treated with 5 μM of compounds 9, 10, 107 and 238 for 24 hours. MG-132, a proteasomal inhibitor, was added 4 hours before harvesting the cells. Immune complexes were pulled down with anti-myc antibody and immunoblot was done using anti-HA antibody. Interestingly, the compounds being COP1 inhibitors could markedly reduce COP1's auto ubiquitination property as shown in FIGS. 6B and 6E compared to control. This shows that indeed the compounds are able to block the ubiquitination of COP1 as well as of its target, ATGL. Thus, the compounds of the present disclosure could be potent therapeutic targets by being able to block the proteasomal degradation of ATGL which would then be able to carry out its lipolytic action and reverse the symptoms of steatosis.

Example 288

Compounds 9 and 10 could Reverse the Decrease in ATGL Level Brought about by Overexpression of COP1 in HepG2 Cells COP1 is an E3 ubiquitin ligase with ATGL as one of its targets for ubiquitination and subsequent proteasomal degradation by 26S proteasome. Therefore, it is only legit for ATGL levels to decrease upon COP1 overexpression. To this end, HepG2 cells were transfected with 500 ng of myc-DDK-COP1 plasmid using Lipofectamine 2000 and treated with 5 μM of the compounds 9 and 10 for 24 hours. 48 hours post transfection, cells were harvested and western blot was carried out. Indeed, myc DDK-COP1 construct were transfected in HepG2 cells, ATGL level was dampened significantly. On treatment of the compounds of the present disclosure in COP1 overexpressing cells for 24 hours, ATGL level was sufficiently restored.

Figure 7:
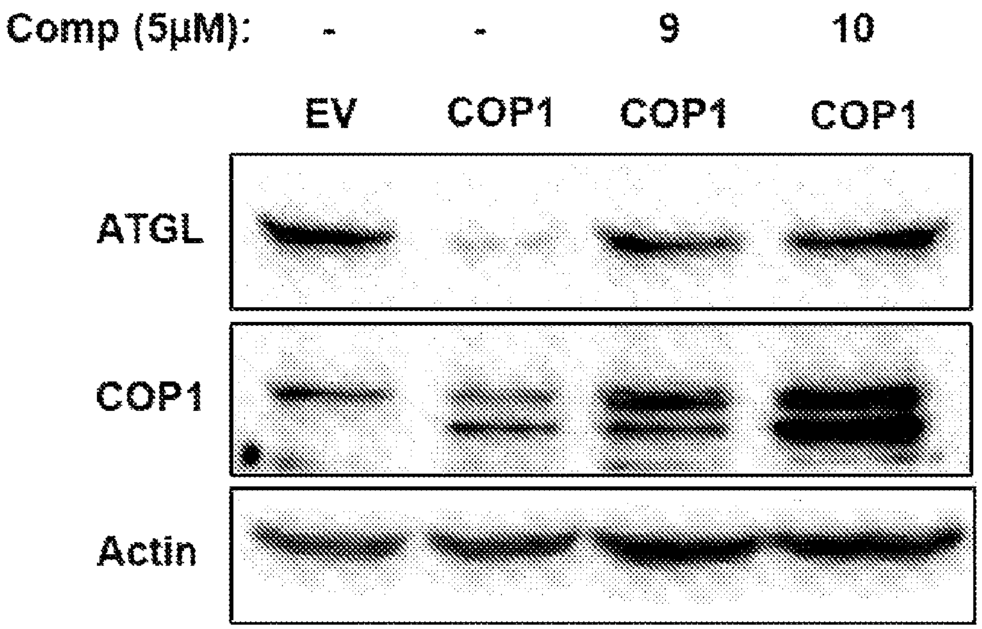
FIG. 7 illustrates reversal of ATGL degradation promoted by COP1 upon treatment with compounds. COP1 overexpression reduces ATGL level in HepG2 cells by causing increased ubiquitination and degradation of ATGL. Treatment with compounds 9 and 10 could restore the reduced ATGL level in cells overexpressing COP1.

FIG. 7 illustrates reversal of ATGL degradation promoted by COP1 upon treatment with compounds. Both compounds 9 and 10 could restore ATGL to its normal level upon COP1 overexpression. Thus, indeed the compounds could counteract the decrease of ATGL by COP1 and ultimately regulate the turnover of ATGL.

Example 289

Compounds Exert No Effect on the mRNA Levels of ATGL

Figure 8:
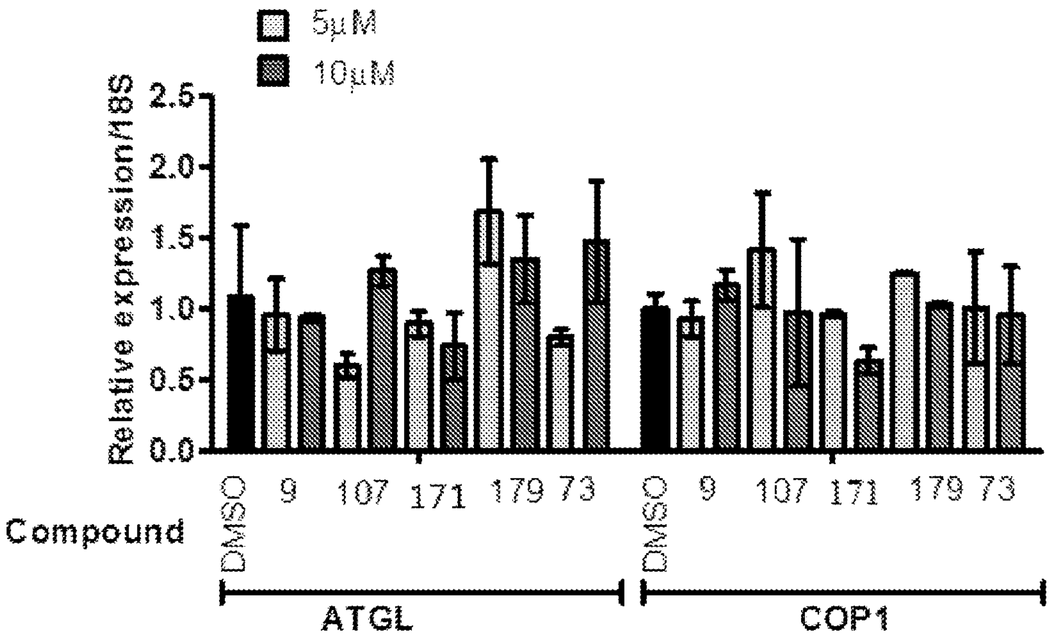
FIG. 8 illustrates that compounds exert no effect on the mRNA levels of ATGL. Beacuse ubiquitination of ATGL by COP1 is a post translational modification, the resultant decrease in ATGL protein due to ubiquitination mediated degradation must not have any impact on its corresponding mRNA status. Thus the compounds do not alter the mRNA level of ATGL in HepG2 cells.

Ubiquitination of ATGL by COP1 is a post translational event, therefore, it is expected that the mRNA level of ATGL will not change compared to control upon treatment with the compound of the present disclosure which inhibit COP1. To establish this, HepG2 cells were treated with 5 μM and 10 μM of the compounds 9, 107, 171, 179 and 73 for 24 hours. RNA was isolated using TRIzol reagent followed by chloroform treatment and precipitation with isopropanol. cDNA was obtained from the isolated RNA and qPCR was carried out using SyBr green reagent. COP1 and ATGL gene expression levels were checked. 18s was used as control. FIG. 8 illustrates that compounds exert no effect on the mRNA levels of ATGL. As is evident, there was no significant changes at the mRNA levels of both COP1 and ATGL upon treatment with the compound.

Example 290

In Vivo Study of Compound to Check the Expression Level of ATGL and COP1 in Liver 6-8 weeks old healthy female C57BL/6 mice (average weight: 25 grams) were taken for the study. These were then divided into three groups comprising of three mice per group (Control, compound 107 fed for 8 hours and compound 107 fed for 16 hours). Mice were fed with 30 mg/kg of compound 107 orally. The compound was dissolved in 25% DMSO and 75% PBS. The control group was fed only with the solvent in which the compound was dissolved. Post 8 hours and 16 hours of feeding, mice were sacrificed and a portion of the excised liver tissue was homogenized in lysis buffer containing protease inhibitor cocktail. The homogenate was centrifuged at 20,000 g for 30 minutes following which the supernatant containing the protein lysate was collected. The lysate was then diluted accordingly and protein estimation was carried out by Bradford Assay. This was followed by Western Blotting wherein the levels of ATGL and COP1 were checked. Actin was used as the loading control.

Figure 9:
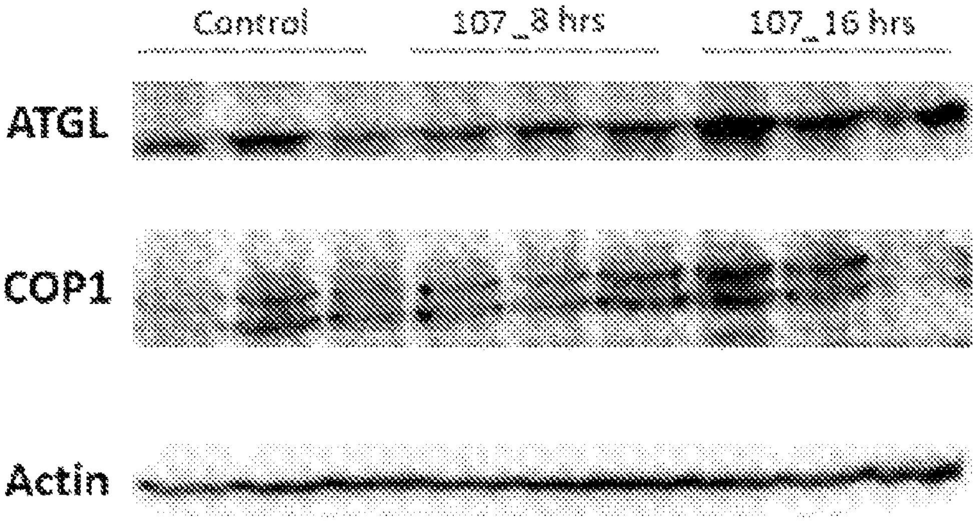
FIG. 9 illustrates results of in vivo study of compounds in mice measuring ATGL and COP1 levels. Compound 107 could modestly increase ATGL level, with no such effect on COP1, in mice after 8 hours and 16 hours feeding of mice via oral gavage.

FIG. 9 illustrates results of in vivo study of compounds in mice measuring ATGL and COP1 levels. The western blotting from liver lysates revealed that the compound 107 was effective in increasing ATGL and COP1 levels after 16 hours of feeding. 8 hours of feeding had no significant impact on either ATGL or COP1.

Example 291

In Vivo Ubiquitination

For checking the change in the ubiquitination status of ATGL on compound treatment, Myc-ATGL expressing HepG2 cells (ATGL overexpressing cell line) was transfected with 2 μg of a plasmid harboring the HA tagged ubiquitin gene using Lipofectamine 2000 reagent (Invitrogen) in OptiMEM media (HiMedia). Fresh DMEM complete media was added after 8-10 hours of transfection. After roughly 24 hours of transfection, 5 μM of the compounds 9, 10 and 107 was added and cells were harvested post 24 hours of treatment. 4 hours prior to cell harvesting, 10 μM of proteasomal inhibitor MG132 (Calbiochem, Merck Millipore) was added to the cells. Proteins were isolated from the cells and protein concentration was estimated as described previously. 30 μl of PureProteome Protein A/G Mix Magnetic Beads (Merck Millipore) was taken in a 1.5 ml microcentrifuge tube, placed in a Magna Rack (Merck Millipore) and allowed to adhere to the side of the tube. 200 μg of protein was used for immunoprecipitation reaction in a reaction volume of 1 ml. 2 μl of anti-Myc primary antibody (Cell Signaling Technology) was added and the tube was incubated overnight at 4° C. in a rotary shaker. The next day, the tube was placed back in the Magna Rack and the beads were allowed to attach to the tube. To remove non-specific and unattached reactants, 1×PBS and 0.1% Triton-X was used for washing. 2× loading dye and Lysis Buffer was added and heated at 95° C. for 10 minutes to allow the immune complex to dislodge from the magnetic beads. Western Blot was performed subsequently as described before with anti-HA primary antibody for immunoblotting (Cell Signaling Technology). The activity trends of the synthesized compounds are disclosed in Table-5.

FIGS. 10A, 10B, 10C, and 10D illustrate compilation of effect of compounds in increasing ATGL and COP1 levels in HepG2 cells in a dose dependent manner, ATGL ubiquitination assay and effect of ATGL and COP1 levels in primary mouse hepatocytes.

Figure 10A:
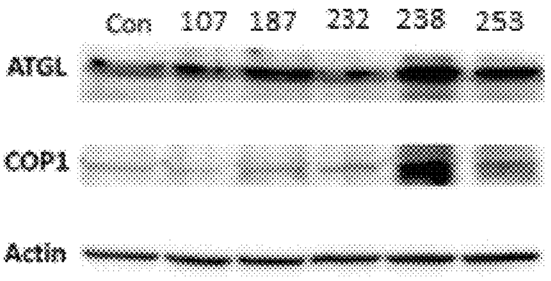
FIGS. 10A-10D illustrate compilation of effect of compounds in increasing ATGL and COP1 levels in HepG2, out of which compound 238 was most potent in increasing ATGL and COP1 levels in HepG2 cells alsoin dose dependent manner. Compound 238 could also decrease ATGL ubiquitination by COP1 in HepG2 cella and increase ATGL and COP1 levels dose dependently in primary mouse hepatocytes.
Figure 10B:
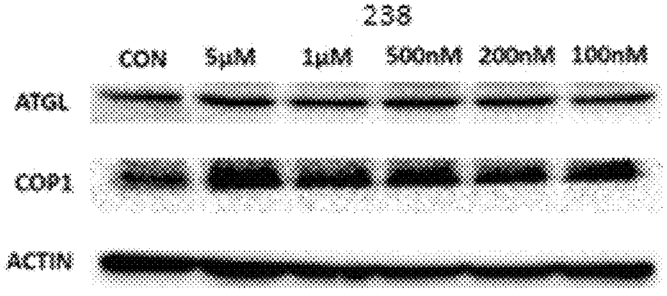
Figure 10C:
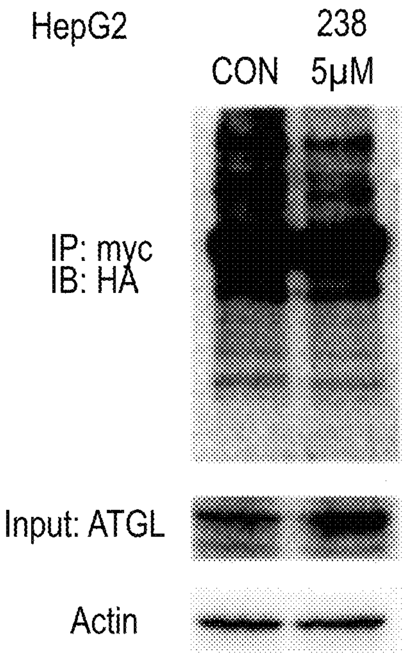
Figure 10D:
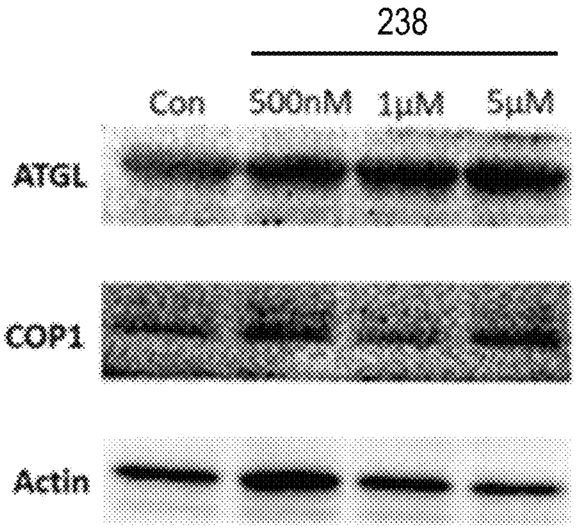

In FIGS. 10A and 10B, the compound 238 showed increase in ATGL and COP1 levels in HepG2 cells in dose dependent manner. In FIG. 10C, the ATGL ubiquitination level was found to be decreased upon treatment with compound 238 in in vivo ubiquitination assay carried out according to described protocol. FIG. 10D describes treatment of compound 238 in primary mouse hepatocytes, for 24 hours could enhance ATGL levels at 1 μM and 5 μM doses. COP1 levels increased only with 5 μM concentration.

For checking the autoubiquitination status of COP1, HepG2 cells were cotransfected with 2 μg each of Myc-DDK-COP1 and HA-Ub plasmids using Lipofectamine 2000 reagent (Invitrogen) in OptiMEM media (HiMedia). The rest of the procedure is similar to that done for Myc-ATGL.

TABLE 5

| Sl No. | Compound Number | Structure | Reduction in Lipid Droplets | Increase in ATGL level |
|---|---|---|---|---|
| 1 | 35 | 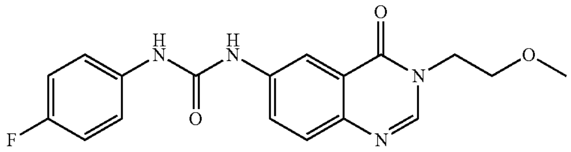 | + | + |
| 2 | 36 | 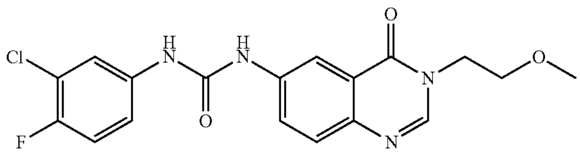 [SMILES: COCCn1cnc2ccc(NC(=O)Nc3ccc(F)c(Cl)c3)cc2c1=O] | + | +++ |
| 3 | 83 | 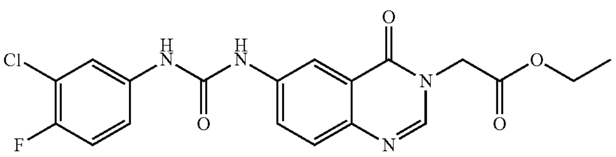 [SMILES: CCOC(=O)Cn1cnc2ccc(NC(=O)Nc3ccc(F)c(Cl)c3)cc2c1=O] | + | + |
| 4 | 9 | 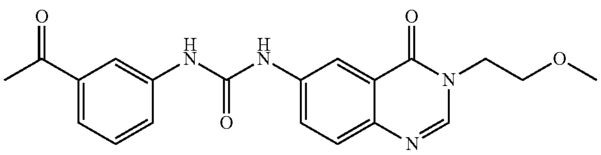 | ++++ | +++++ |

TABLE 5-continued
| Sl No. | Compound Number | Structure | Reduction in Lipid Droplets | Increase in ATGL level |
|---|---|---|---|---|
| 5 | 84 | 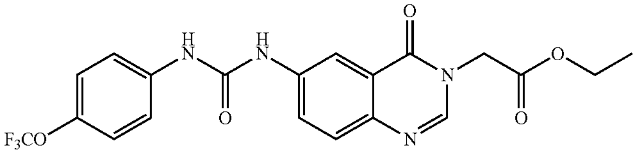 [SMILES: CCOC(=O)Cn1cnc2ccc(NC(=O)Nc3ccc(OC(F)(F)F)cc3)cc2c1=O] | +++ | ++ |
| 6 | 37 | 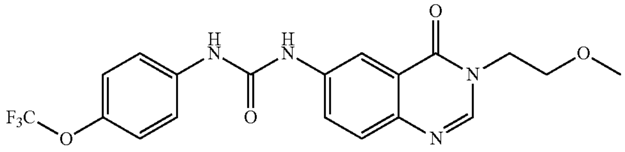 [SMILES: COCCn1cnc2ccc(NC(=O)Nc3ccc(OC(F)(F)F)cc3)cc2c1=O] | + | + |
| 7 | 8 | 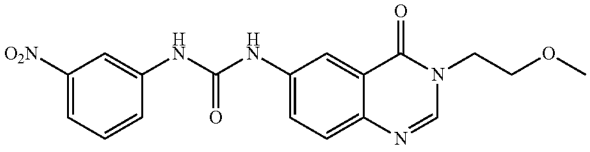 [SMILES: COCCn1cnc2ccc(NC(=O)Nc3cccc([N+](=O)[O-])c3)cc2c1=O] | ++ | + |
| 8 | 10 | 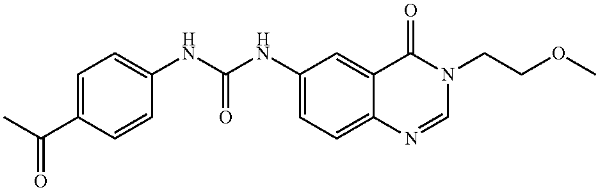 [SMILES: COCCn1cnc2ccc(NC(=O)Nc3ccc(C(C)=O)cc3)cc2c1=O] | ++++ | ++++ |
| 9 | 11 | 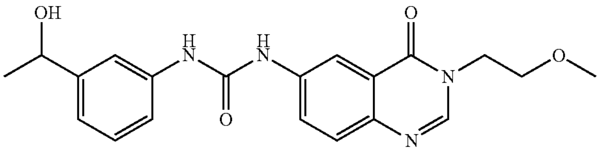 [SMILES: COCCn1cnc2ccc(NC(=O)Nc3cccc(C(C)O)c3)cc2c1=O] | + | + |
| 10 | 18 | 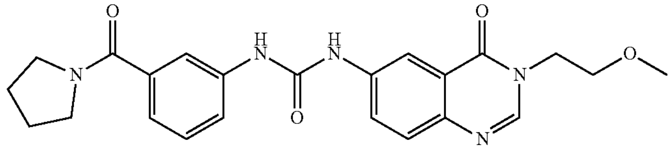 [SMILES: COCCn1cnc2ccc(NC(=O)Nc3cccc(C(=O)N4CCCC4)c3)cc2c1=O] | + | ++++ |
| 11 | 40 | 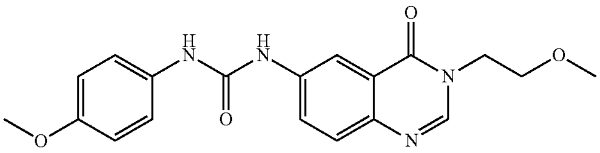 | ++ | ++++ |
| 12 | 20 | 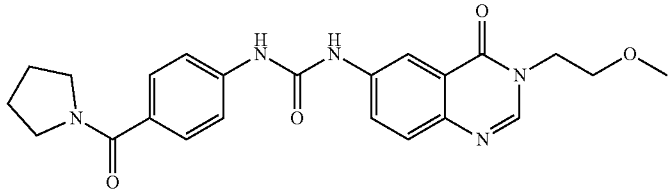 [SMILES: COCCn1cnc2ccc(NC(=O)Nc3ccc(C(=O)N4CCCC4)cc3)cc2c1=O] | ++ | ++ |

TABLE 5-continued
| Sl No. | Compound Number | Structure | Reduction in Lipid Droplets | Increase in ATGL level |
|---|---|---|---|---|
| 13 | 41 | 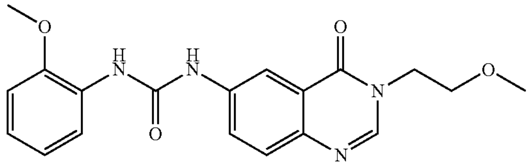 [SMILES: COCCn1cnc2ccc(NC(=O)Nc3ccccc3OC)cc2c1=O] | ++ | ++++ |
| 14 | 38 | 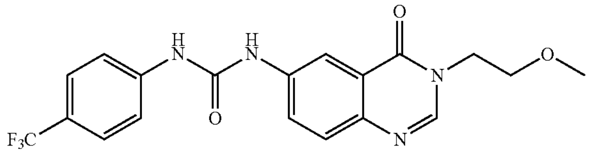 [SMILES: COCCn1cnc2ccc(NC(=O)Nc3ccc(C(F)(F)F)cc3)cc2c1=O] | NT | ++ |
| 15 | 39 | 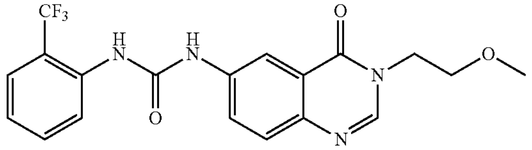 [SMILES: COCCn1cnc2ccc(NC(=O)Nc3ccccc3C(F)(F)F)cc2c1=O] | NT | ++ |
| 16 | 15 | 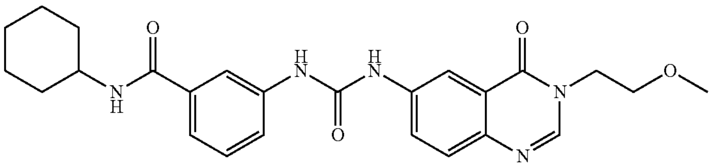 [SMILES: COCCn1cnc2ccc(NC(=O)Nc3cccc(C(=O)NC4CCCCC4)c3)cc2c1=O] | + | ++++ |
| 17 | 22 | 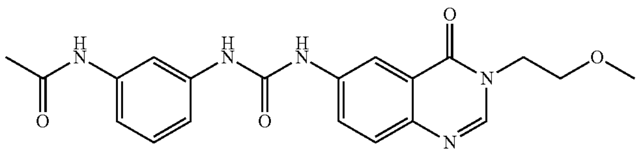 [SMILES: COCCn1cnc2ccc(NC(=O)Nc3cccc(NC(C)=O)c3)cc2c1=O] | + | + |
| 18 | 16 | 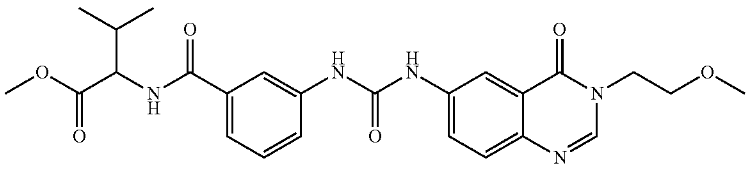 | +++ | ++++ |
| 19 | 12 | 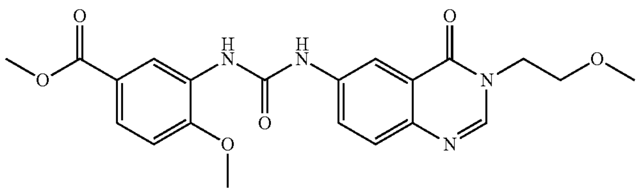 | ++ | +++ |
| 20 | 85 | 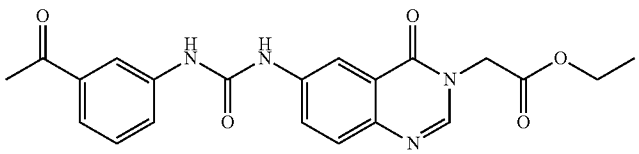 [SMILES: CCOC(=O)Cn1cnc2ccc(NC(=O)Nc3cccc(C(C)=O)c3)cc2c1=O] | + | + |
| 21 | 17 | 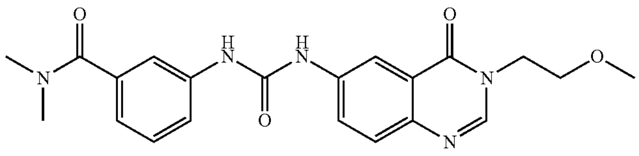 | +++ | +++ |

TABLE 5-continued
| Sl No. | Compound Number | Structure | Reduction in Lipid Droplets | Increase in ATGL level |
|---|---|---|---|---|
| 22 | 21 | 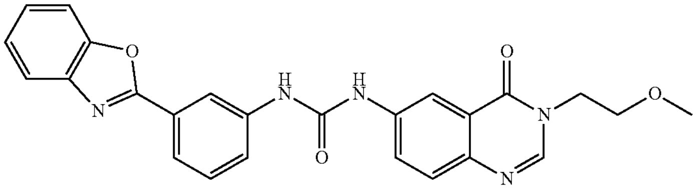 [SMILES: COCCn1cnc2ccc(NC(=O)Nc3cccc(-c4nc5ccccc5o4)c3)cc2c1=O] | + | + |
| 23 | 23 | 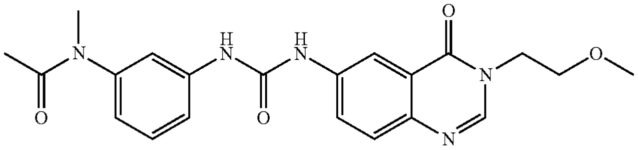 [SMILES: COCCn1cnc2ccc(NC(=O)Nc3cccc(N(C)C(C)=O)c3)cc2c1=O] | ++ | ++++ |
| 24 | 24 | 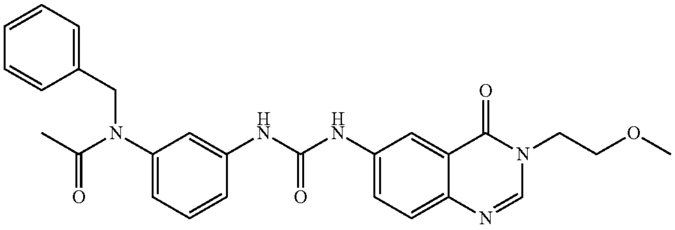 [SMILES: COCCn1cnc2ccc(NC(=O)Nc3cccc(N(Cc4ccccc4)C(C)=O)c3)cc2c1=O] | + | ++++ |
| 25 | 5 | 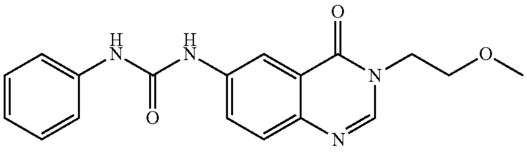 [SMILES: COCCn1cnc2ccc(NC(=O)Nc3ccccc3)cc2c1=O] | ++ | ++ |
| 26 | 13 | 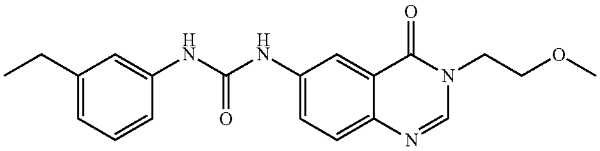 | + | + |
| 27 | 14 | 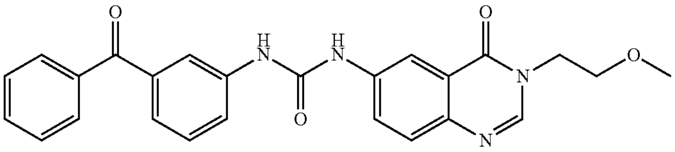 [SMILES: COCCn1cnc2ccc(NC(=O)Nc3cccc(C(=O)c4ccccc4)c3)cc2c1=O] | + | + |
| 28 | 42 | 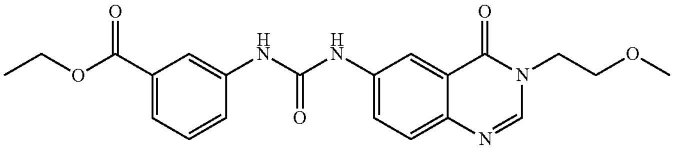 [SMILES: CCOC(=O)c1cccc(NC(=O)Nc2ccc3ncn(CCOC)c(=O)c3c2)c1] | + | + |
| 29 | 175 | 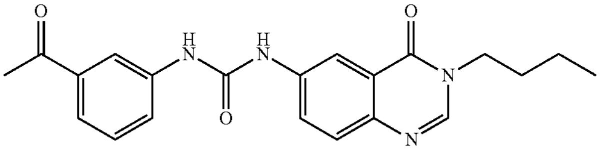 | + | + |

TABLE 5-continued
| Sl No. | Compound Number | Structure | Reduction in Lipid Droplets | Increase in ATGL level |
|---|---|---|---|---|
| 30 | 6 | 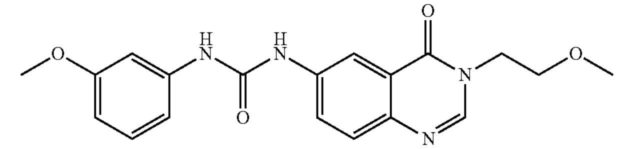 | ++++ | ++++ |
| 31 | 89 | 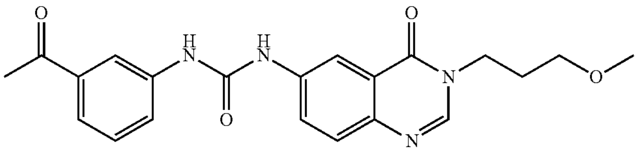 | +++ | + |
| 32 | 192 | 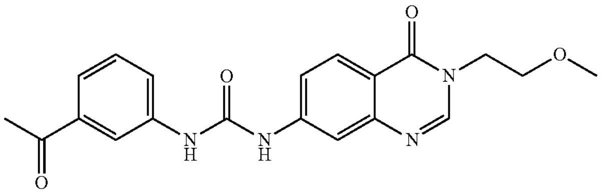 [SMILES: COCCn1cnc2cc(NC(=O)Nc3cccc(C(C)=O)c3)ccc2c1=O] | ++ | +++ |
| 33 | 193 | 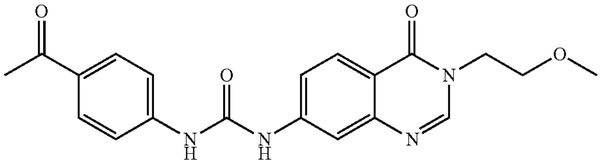 [SMILES: COCCn1cnc2cc(NC(=O)Nc3ccc(C(C)=O)cc3)ccc2c1=O] | + | + |
| 34 | 93 | 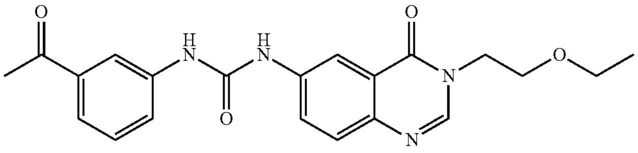 [SMILES: CCOCCn1cnc2ccc(NC(=O)Nc3cccc(C(C)=O)c3)cc2c1=O] | +++ | ++++ |
| 35 | 94 | 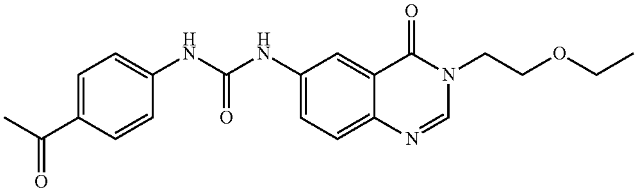 [SMILES: CCOCCn1cnc2ccc(NC(=O)Nc3ccc(C(C)=O)cc3)cc2c1=O] | ++ | + |
| 36 | 103 | 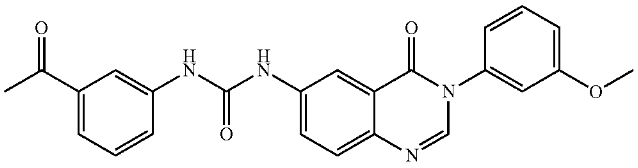 [SMILES: COc1cccc(-n2cnc3ccc(NC(=O)Nc4cccc(C(C)=O)c4)cc3c2=O)c1] | + | + |
| 37 | 107 | 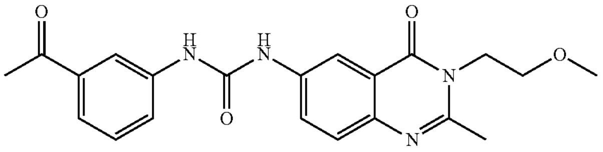 [SMILES: COCCn1c(C)nc2ccc(NC(=O)Nc3cccc(C(C)=O)c3)cc2c1=O] | ++++ | ++++ |

TABLE 5-continued
| Sl No. | Compound Number | Structure | Reduction in Lipid Droplets | Increase in ATGL level |
|---|---|---|---|---|
| 38 | 111 | 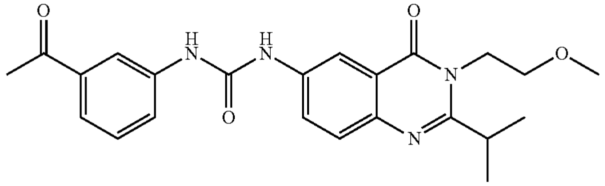 [SMILES: COCCn1c(C(C)C)nc2ccc(NC(=O)Nc3cccc(C(C)=O)c3)cc2c1=O] | ++ | +++ |
| 39 | 115 | 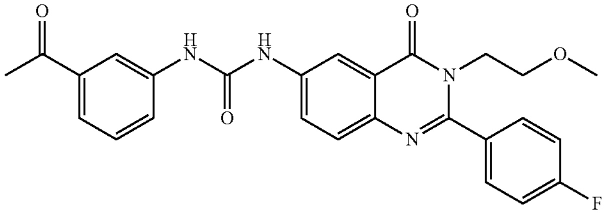 [SMILES: COCCn1c(-c2ccc(F)cc2)nc2ccc(NC(=O)Nc3cccc(C(C)=O)c3)cc2c1=O] | + | + |
| 40 | 119 | 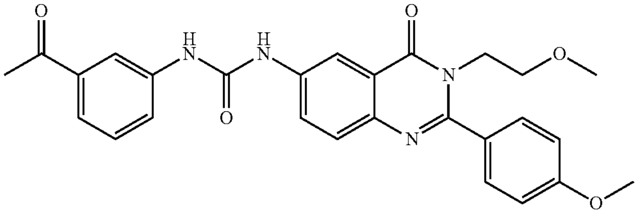 [SMILES: COCCn1c(-c2ccc(OC)cc2)nc2ccc(NC(=O)Nc3cccc(C(C)=O)c3)cc2c1=O] | + | + |
| 41 | 135 | 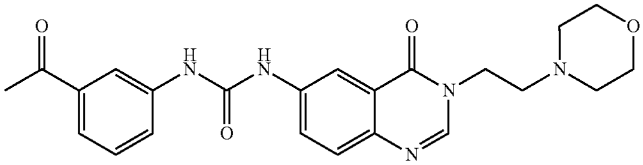 [SMILES: CC(=O)c1cccc(NC(=O)Nc2ccc3ncn(CCN4CCOCC4)c(=O)c3c2)c1] | ++ | +++ |
| 42 | 147 | 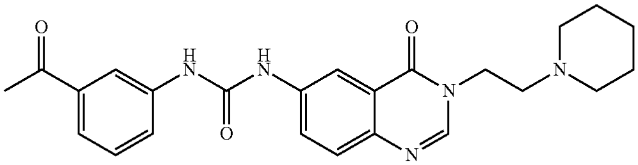 [SMILES: CC(=O)c1cccc(NC(=O)Nc2ccc3ncn(CCN4CCCCC4)c(=O)c3c2)c1] | ++ | +++ |
| 43 | 143 | 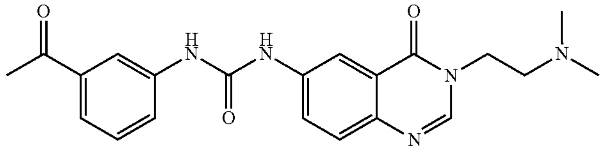 [SMILES: CC(=O)c1cccc(NC(=O)Nc2ccc3ncn(CCN(C)C)c(=O)c3c2)c1] | +++ | ++++ |
| 44 | 19 | 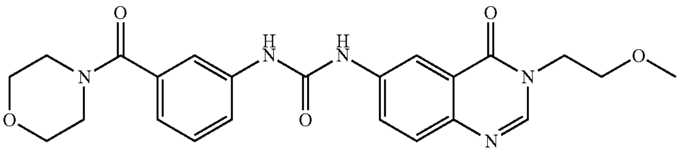 [SMILES: COCCn1cnc2ccc(NC(=O)Nc3cccc(C(=O)N4CCOCC4)c3)cc2c1=O] | ++ | + |
| 45 | 155 | 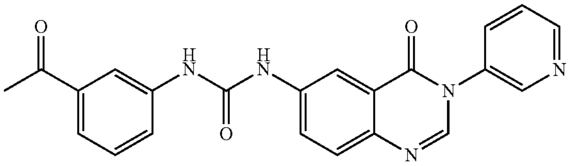 [SMILES: CC(=O)c1cccc(NC(=O)Nc2ccc3ncn(-c4cccnc4)c(=O)c3c2)c1] | +++ | ++ |

TABLE 5-continued
| Sl No. | Compound Number | Structure | Reduction in Lipid Droplets | Increase in ATGL level |
|---|---|---|---|---|
| 46 | 139 | 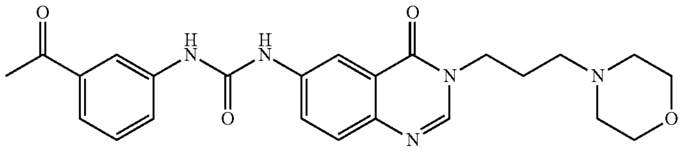 [SMILES: CC(=O)c1cccc(NC(=O)Nc2ccc3ncn(CCCN4CCOCC4)c(=O)c3c2)c1] | +++ | +++ |
| 47 | 163 | 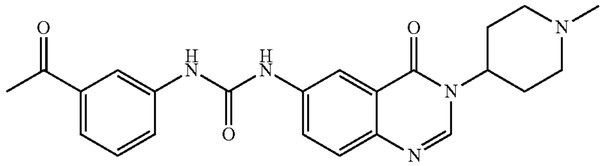 [SMILES: CC(=O)c1cccc(NC(=O)Nc2ccc3ncn(C4CCN(C)CC4)c(=O)c3c2)c1] | ++ | + |
| 48 | 123 | 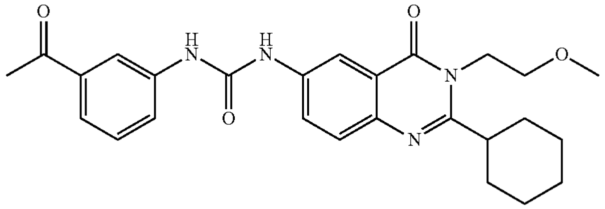 [SMILES: COCCn1c(C2CCCCC2)nc2ccc(NC(=O)Nc3cccc(C(C)=O)c3)cc2c1=O] | +++ | ++++ |
| 49 | 59 | 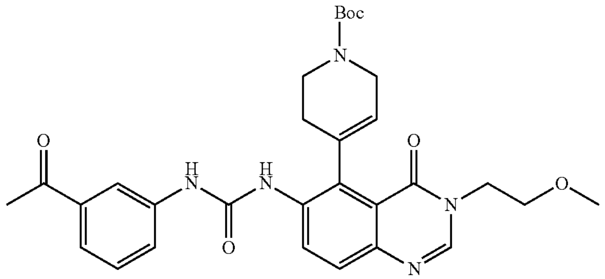 [SMILES: COCCn1cnc2ccc(NC(=O)Nc3cccc(C(C)=O)c3)c(C3=CCN(C(=O)OC(C)(C)C)CC3)c2c1=O] | NT | + |
| 50 | 60 | 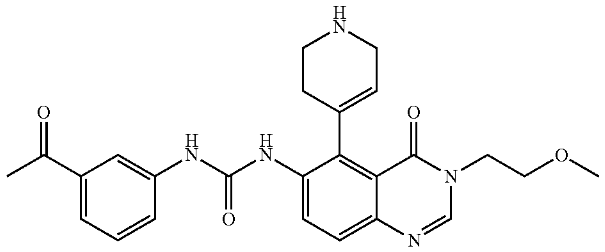 [SMILES: COCCn1cnc2ccc(NC(=O)Nc3cccc(C(C)=O)c3)c(C3=CCNCC3)c2c1=O] | NT | + |
| 51 | 25 | 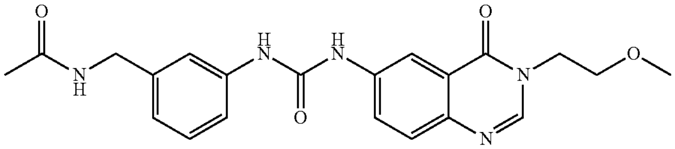 | NT | + |
| 52 | 61 | 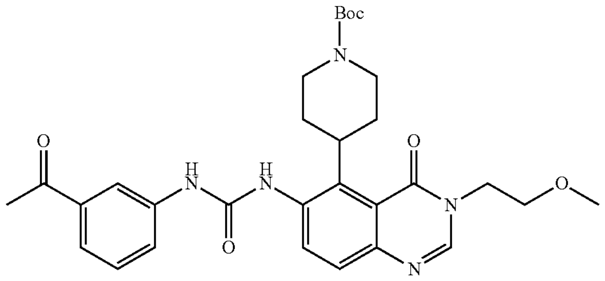 [SMILES: COCCn1cnc2ccc(NC(=O)Nc3cccc(C(C)=O)c3)c(C3CCN(C(=O)OC(C)(C)C)CC3)c2c1=O] | NT | + |

TABLE 5-continued
| Sl No. | Compound Number | Structure | Reduction in Lipid Droplets | Increase in ATGL level |
|---|---|---|---|---|
| 53 | 171 | 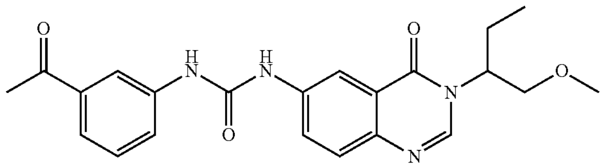 [SMILES: CCC(COC)n1cnc2ccc(NC(=O)Nc3cccc(C(C)=O)c3)cc2c1=O] | NT | +++ |
| 54 | 62 | 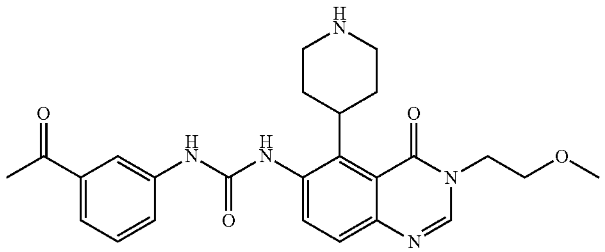 [SMILES: COCCn1cnc2ccc(NC(=O)Nc3cccc(C(C)=O)c3)c(C3CCNCC3)c2c1=O] | NT | +++ |
| 55 | 179 | 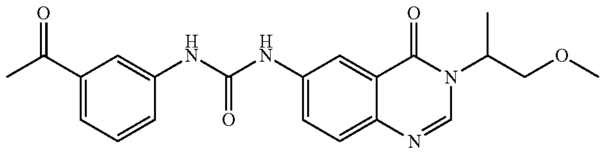 [SMILES: COCC(C)n1cnc2ccc(NC(=O)Nc3cccc(C(C)=O)c3)cc2c1=O] | NT | +++++ |
| 56 | 64 | 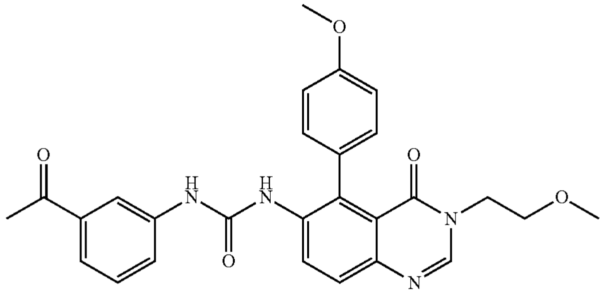 | NT | + |
| 57 | 47 | 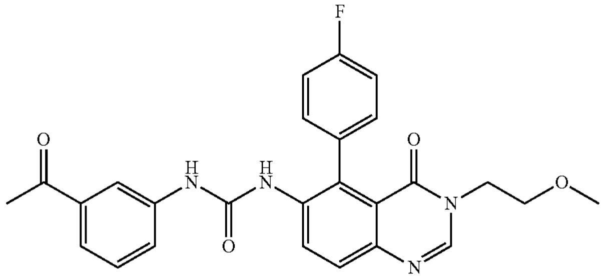 | NT | +++ |
| 58 | 285 | 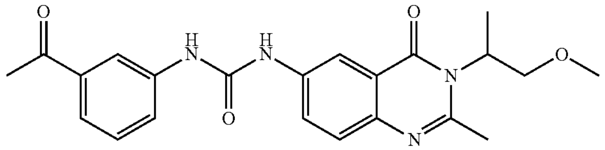 [SMILES: COCC(C)n1c(C)nc2ccc(NC(=O)Nc3cccc(C(C)=O)c3)cc2c1=O] | NT | + |
| 59 | 345 | 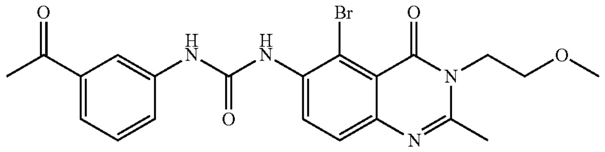 [SMILES: COCCn1c(C)nc2ccc(NC(=O)Nc3cccc(C(C)=O)c3)c(Br)c2c1=O] | NT | + |

TABLE 5-continued
| Sl No. | Compound Number | Structure | Reduction in Lipid Droplets | Increase in ATGL level |
|---|---|---|---|---|
| 60 | 183 | 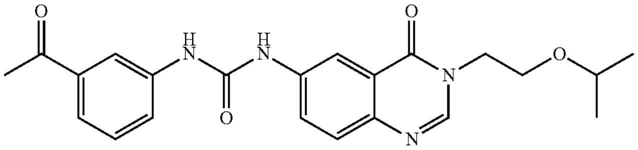 | NT | +++ |
| 61 | 253 | 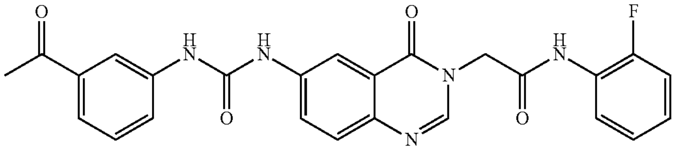 [SMILES: CC(=O)c1cccc(NC(=O)Nc2ccc3ncn(CC(=O)Nc4ccccc4F)c(=O)c3c2)c1] | ++ | + |
| 62 | 66 | 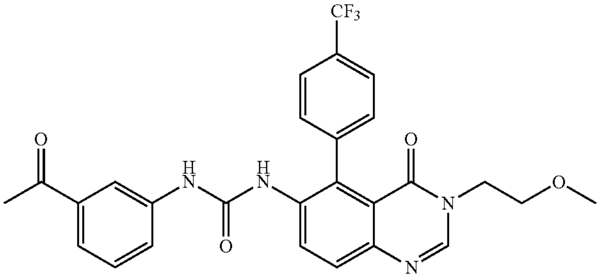 | NT | ++ |
| 63 | 281 | 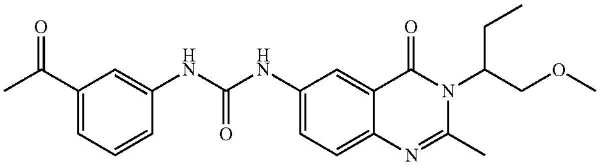 [SMILES: CCC(COC)n1c(C)nc2ccc(NC(=O)Nc3cccc(C(C)=O)c3)cc2c1=O] | NT | ++ |
| 64 | 232 | 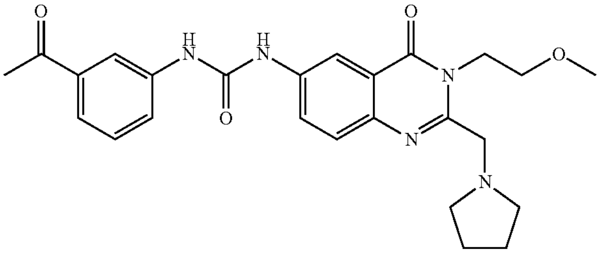 [SMILES: COCCn1c(CN2CCCC2)nc2ccc(NC(=O)Nc3cccc(C(C)=O)c3)cc2c1=O] | NT | +++ |
| 65 | 238 | 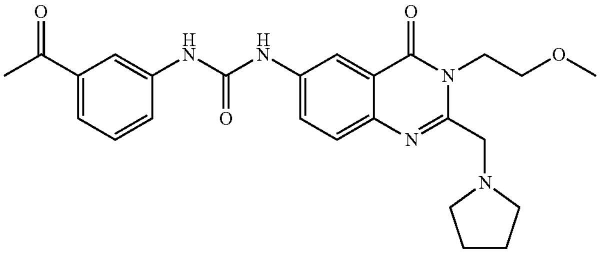 [SMILES: COCCn1c(CN2CCCC2)nc2ccc(NC(=O)Nc3cccc(C(C)=O)c3)cc2c1=O] | NT | +++++ |
| 66 | 187 | 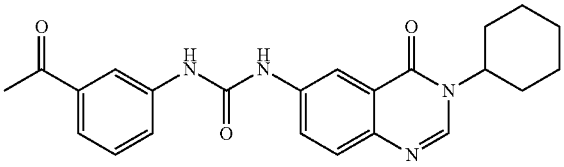 [SMILES: CC(=O)c1cccc(NC(=O)Nc2ccc3ncn(C4CCCCC4)c(=O)c3c2)c1] | NT | +++ |

TABLE 5-continued

| Sl No. | Compound Number | Structure | Reduction in Lipid Droplets | Increase in ATGL level |
|---|---|---|---|---|
| 67 | 259 | 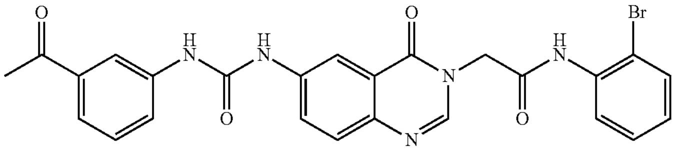 [SMILES: CC(=O)c1cccc(NC(=O)Nc2ccc3ncn(CC(=O)Nc4ccccc4Br)c(=O)c3c2)c1] | NT | +++ |
| 68 | 159 | 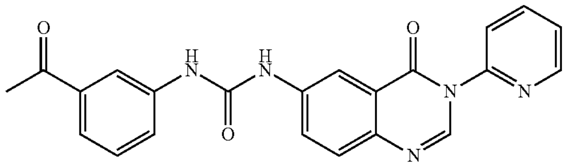 [SMILES: CC(=O)c1cccc(NC(=O)Nc2ccc3ncn(-c4ccccn4)c(=O)c3c2)c1] | NT | + |
| 69 | 131 | 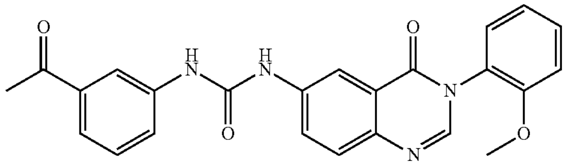 [SMILES: COc1ccccc1-n1cnc2ccc(NC(=O)Nc3cccc(C(C)=O)c3)cc2c1=O] | NT | + |
| 70 | 340 | 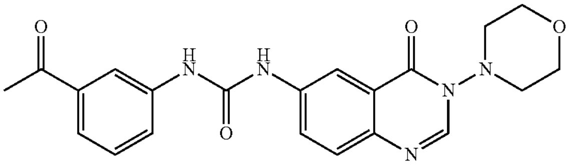 [SMILES: CC(=O)c1cccc(NC(=O)Nc2ccc3ncn(N4CCOCC4)c(=O)c3c2)c1] | NT | + |

The ability of the compounds in reduction in lipid droplets and the increase in ATGL level were scored with + = slight or in insignificant; ++ = Moderate; +++ and ++++ = active; +++++ = very active. NT = Not tested.

TABLE 6

| Sl No. | Compound No. | Structure | $EC_{50}$ (in-vitro) in nM |
|---|---|---|---|
| 1 | 127 | 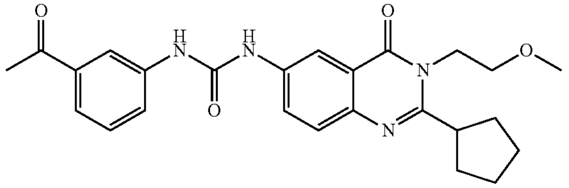 [SMILES: COCCn1c(C2CCCC2)nc2ccc(NC(=O)Nc3cccc(C(C)=O)c3)cc2c1=O] | 10.81 |
| 2 | 139 | 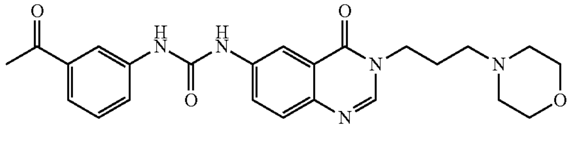 [SMILES: CC(=O)c1cccc(NC(=O)Nc2ccc3ncn(CCCN4CCOCC4)c(=O)c3c2)c1] | 1.19 |
| 3 | 211 | 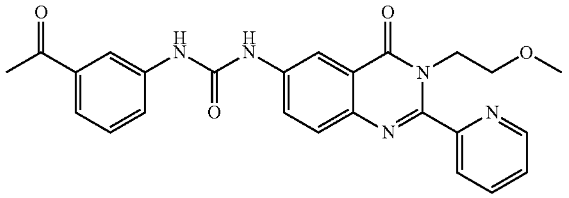 [SMILES: COCCn1c(-c2ccccn2)nc2ccc(NC(=O)Nc3cccc(C(C)=O)c3)cc2c1=O] | 199.06 |

TABLE 6-continued

| Sl No. | Compound No. | Structure | $EC_{50}$ (in-vitro) in nM |
|---|---|---|---|
| 4 | 215 | 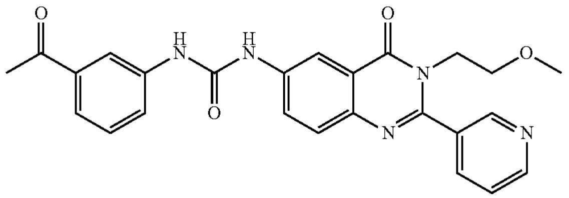 [SMILES: COCCn1c(-c2cccnc2)nc2ccc(NC(=O)Nc3cccc(C(C)=O)c3)cc2c1=O] | 30.19 |
| 5 | 219 | 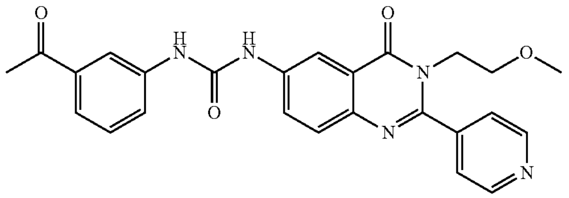 [SMILES: COCCn1c(-c2ccncc2)nc2ccc(NC(=O)Nc3cccc(C(C)=O)c3)cc2c1=O] | 29.51 |
| 6 | 223 | 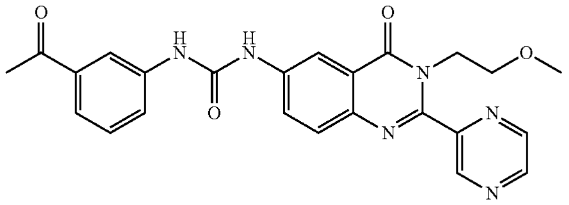 [SMILES: COCCn1c(-c2cnccn2)nc2ccc(NC(=O)Nc3cccc(C(C)=O)c3)cc2c1=O] | 70.30 |
| 7 | 232 | 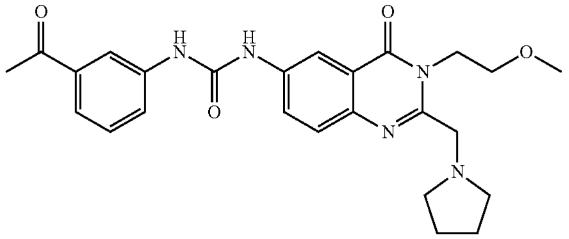 [SMILES: COCCn1c(CN2CCCC2)nc2ccc(NC(=O)Nc3cccc(C(C)=O)c3)cc2c1=O] | 433.50 |
| 8 | 238 | 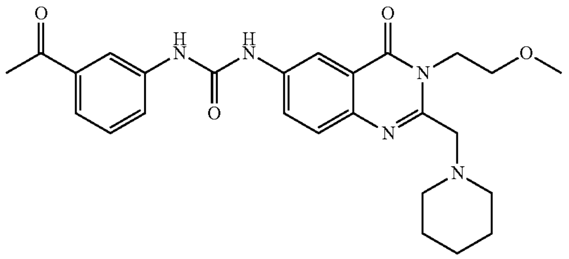 [SMILES: COCCn1c(CN2CCCCC2)nc2ccc(NC(=O)Nc3cccc(C(C)=O)c3)cc2c1=O] | 1.02 |
| 9 | 299 | 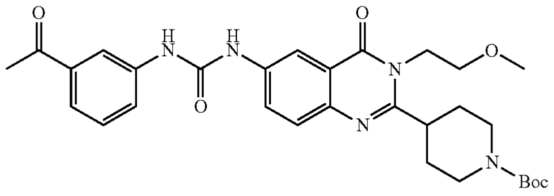 [SMILES: COCCn1c(C2CCN(C(=O)OC(C)(C)C)CC2)nc2ccc(NC(=O)Nc3cccc(C(C)=O)c3)cc2c1=O] | 289.73 |

Intensity of ATGL and thus its level compared to control will increase up to 1.6 fold with COP1 knockout using siCOP1. Accordingly, $EC_{50}$ was calculated for COP1 modulator. The fold increase of ATGL was measured with densitometry analysis in ImageJ software for different doses (10 nM, 20 nM, 50 nM, 100 nM, 200 nM, 500 nM, 1000 nM, 5000 nM) of following compounds: 127, 139, 211, 215, 219, 223, 232, 238 and 299. These value obtained were divided with the ATGL level that will go up to maximum 1.6 fold with siCOP1. Thus, the values obtained was expressed in percentage and was plotted against log[conc] of the respective compounds to obtain the $EC_{50}$ value in graphpad software.

Initial validation of the compounds has been done through (i) reduction of lipid droplets in or without presence of compounds, (ii) increase in ATGL level in or without presence of compounds through W-B (western blot) analysis. The compounds with desired properties from the above mentioned screening procedure were further assayed for their ability to ubiquitination of ATGL via immunoprecipitation assay (IP) in or without presence of compounds. Compound 6 was the initial hit as fulfilled the first two criteria (reduction of lipid droplet and increase in ATGL level). As compound 6 comprises terminal —OMe group in meta position in urea linked phenyl moiety, the inventors started investigating and derivatizing compounds keeping oxygen atom in that meta position assuming that hetroatom plays a role in ligand-protein interaction for showing potency. The investigation showed ketone function in compounds 9 and 10 is significant. Compound without the ketone function failed to increase ATGL level. Compound with amide group such as compounds 17, 18, 19, and 20 showed ability to increase ATGL level. Quinazolinone ring N-3 position was also substituted with substituted alkyl and aromatic moiety. Some compounds such as 89, 93, 135, 139, 143, 147, 163, 103, 155, and 159, showed some sort of increase in ATGL level and reduction in lipid droplets. Compound 175 was made, where no heteroatom is present in N-3 linker. Compound 175 did not increase ATGL level and reduced lipid droplets. Some aliphatic substituents at C-2 position of the quinazolinone ring such as isopropyl, cyclohexyl, cyclopentyl, piperidinyl, pyridinyl, pyrazinyl were also incorporated, which led to increase in the ATGL level.

Example 292

Lipophilicity Assay 1.56 g $NaH_2PO_4 \cdot 2H_2O$ was dissolved in 0.5 L water in a 1 L beaker. After adjusting pH to 7.4 using NaOH solution, the volume was made up to 1 L. Equal volumes of sodium phosphate buffer (10 mM, pH 7.4) and n-octanol were added to a separation funnel and mixed thoroughly by shaking and inverting the funnel several times. The two layers were allowed to separate for overnight and then dispensed in two separate glass bottles. 10 mM stock solution was prepared in 100% DMSO and stored at 4° C. 495 μL of organic phase (1-octanol) was added to each well of a 2 mL deep well plate, followed by 495 μL of buffer and 10 μL of test compound was added. The plate was incubated for 3 hr at room temperature on a plate shaker at 500 rpm. After incubation, the samples were allowed to equilibrate for 20 min and then centrifuged at 4000 rpm for 30 min for complete phase separation and analysed by LC-UV. The results obtained for the tested compounds is provided in table 7.

Log D=Log (area of octanol/area of buffer)

TABLE 7

| Sl No. | Compound No. | Structure | LogD @ pH 7.4 |
|---|---|---|---|
| 1 | 160 | 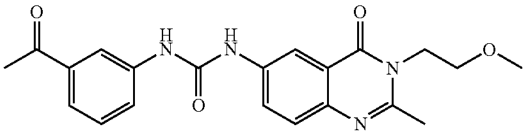 [SMILES: COCCn1c(C)nc2ccc(NC(=O)Nc3cccc(C(C)=O)c3)cc2c1=O] | 2.67 |
| 2 | 123 | 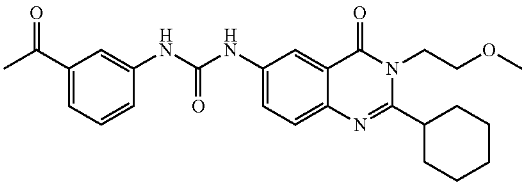 [SMILES: COCCn1c(C2CCCCC2)nc2ccc(NC(=O)Nc3cccc(C(C)=O)c3)cc2c1=O] | 0.84 |
| 3 | 73 | 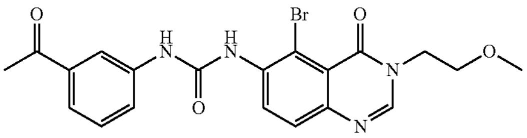 [SMILES: COCCn1cnc2ccc(NC(=O)Nc3cccc(C(C)=O)c3)c(Br)c2c1=O] | 1.95 |
| 4 | 179 | 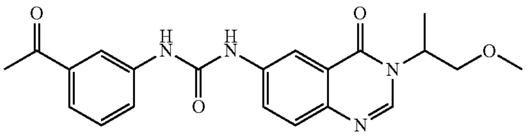 | 1.69 |
| 5 | 238 | 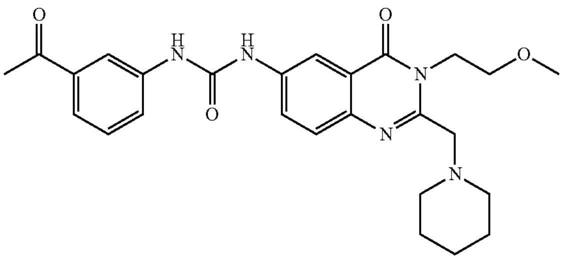 [SMILES: COCCn1c(CN2CCCCC2)nc2ccc(NC(=O)Nc3cccc(C(C)=O)c3)cc2c1=O] | 1.60 |

TABLE 7-continued
| Sl No. | Compound No. | Structure | LogD @ pH 7.4 |
|---|---|---|---|
| 6 | 241 | 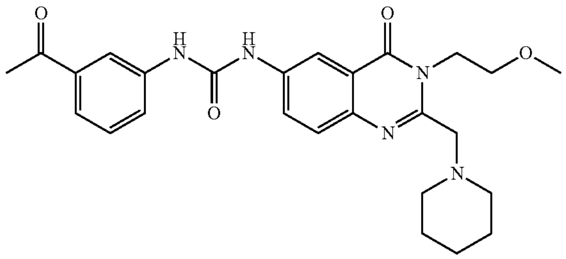 [SMILES: COCCn1c(CN2CCCCC2)nc2ccc(NC(=O)Nc3cccc(C(C)=O)c3)cc2c1=O] | 2.51 |
| 7 | 330a | 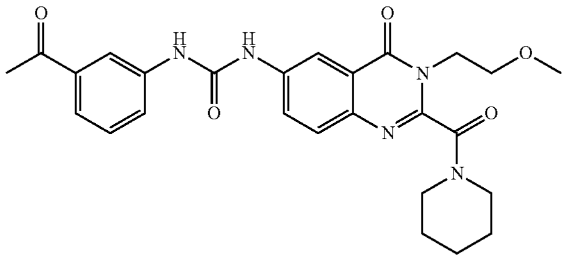 [SMILES: COCCn1c(C(=O)N2CCCCC2)nc2ccc(NC(=O)Nc3cccc(C(C)=O)c3)cc2c1=O] | 1.79 |
| 8 | 253 | 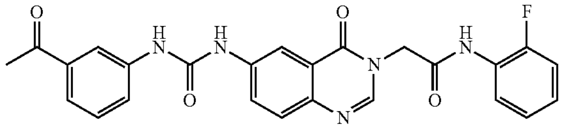 [SMILES: CC(=O)c1cccc(NC(=O)Nc2ccc3ncn(CC(=O)Nc4ccccc4F)c(=O)c3c2)c1] | 3.01 |
| 9 | 211 | 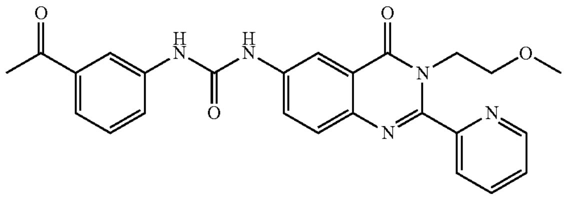 [SMILES: COCCn1c(-c2ccccn2)nc2ccc(NC(=O)Nc3cccc(C(C)=O)c3)cc2c1=O] | 2.48 |
| 10 | 139 | 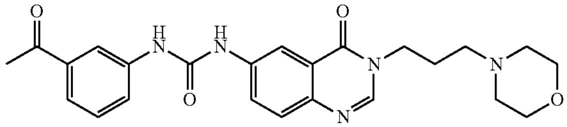 [SMILES: CC(=O)c1cccc(NC(=O)Nc2ccc3ncn(CCCN4CCOCC4)c(=O)c3c2)c1] | −0.50 |
| 11 | 215 | 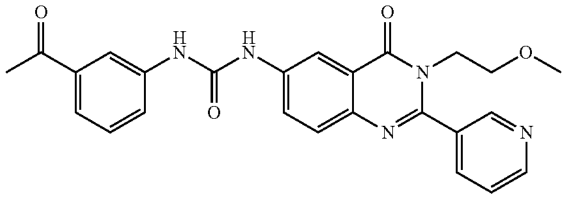 [SMILES: COCCn1c(-c2cccnc2)nc2ccc(NC(=O)Nc3cccc(C(C)=O)c3)cc2c1=O] | 0.42 |
| 12 | 219 | 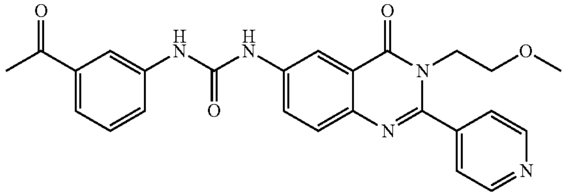 [SMILES: COCCn1c(-c2ccncc2)nc2ccc(NC(=O)Nc3cccc(C(C)=O)c3)cc2c1=O] | 0.19 |
| 13 | Quercetin (Control) | | 2.81 |
| 14 | Metroprolol (Control) | | −0.09 |
| 15 | Propranolol (Control) | | 1.39 |
Log D Criteria: <1: Hydrophilic; 1-4.2: Ideal Lipophilic; >4.3: High Lipophilic Lipophilicity assay revealed that compounds 123, 139, 215 and 219 are hydrophilic in nature whereas, rest of the compounds 73, 179, 238, 330a 160, 241, 253 and 211 have ideal lipophilicity with respect to the control compounds Quercetin, Metroprolol and Propranolol. The Log D value of the compound privides insight into possible oral bioavilibility of the compounds with compounds showing ideal lipophilicity may be suitable candidate for oral dosage.

Example 293

Plasma Stability Assay 1 mM Stock of test compound was prepared from 10 mM initial stock solution of compounds by diluting 10 μL of 10 mM stock with 90 μL of DMSO. Then 10 μL of 1 mM stock was diluted with 90 L of DMSO to give 100 μM concentration. The frozen plasma was thawed at room temperature and centrifuged at 1400 rpm at 4° C., for 15 minutes. Approximately 9000 of the clear supernatant fraction was transferred to a separate tube and was used for the assay. Final working stock of 1 μM was prepared by diluting 3 μL of 100 μM with 297 μL of plasma. Plasma containing the test compound was incubated for 120 min at 37° C. in shaker with 500 rpm. 50 μL of aliquot of sample at 0, 15, 30, 60 and 120 minutes were precipitated with 150 μL of acetonitrile containing internal standard and centrifuged at 4000 rpm at 4° C. for 20 minutes. 120 μL of supernatant was diluted with 120 μL of water and analyzed by LC-MS/MS. The results obtained for various compounds is provided in Table 8.

TABLE 8

| Sl No. | Compound No. | Structure | Mean % remaining at 2 hrs in human Plasma |
|---|---|---|---|
| 1 | 9 | 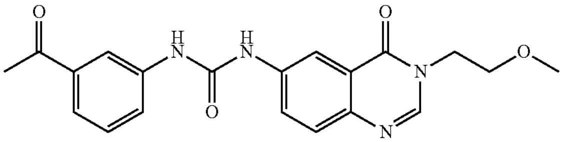 [SMILES: COCCn1cnc2ccc(NC(=O)Nc3cccc(C(C)=O)c3)cc2c1=O] | 16.9 |
| 2 | 123 | 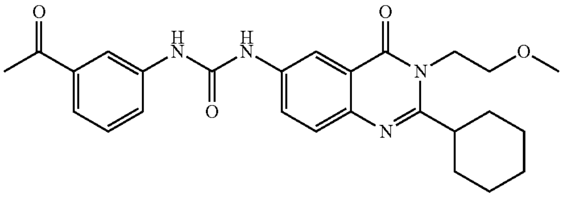 [SMILES: COCCn1c(C2CCCCC2)nc2ccc(NC(=O)Nc3cccc(C(C)=O)c3)cc2c1=O] | 48.5 |
| 3 | 73 | 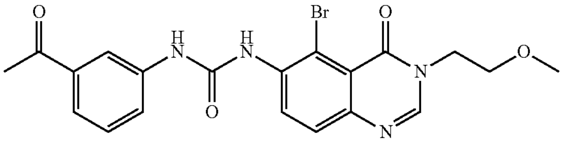 [SMILES: COCCn1cnc2ccc(NC(=O)Nc3cccc(C(C)=O)c3)c(Br)c2c1=O] | 10.3 |
| 4 | 179 | 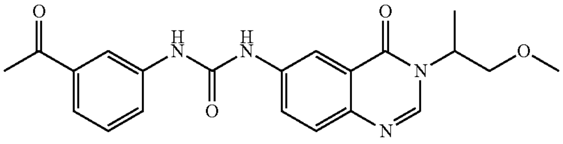 [SMILES: COCC(C)n1cnc2ccc(NC(=O)Nc3cccc(C(C)=O)c3)cc2c1=O] | 20.6 |
| 5 | 238 | 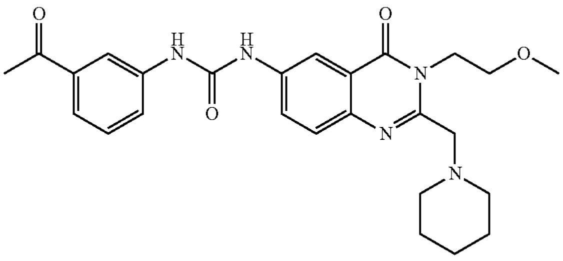 [SMILES: COCCn1c(CN2CCCCC2)nc2ccc(NC(=O)Nc3cccc(C(C)=O)c3)cc2c1=O] | 98.1 |

TABLE 8-continued
| Sl No. | Compound No. | Structure | Mean % remaining at 2 hrs in human Plasma |
|---|---|---|---|
| 6 | 241 | 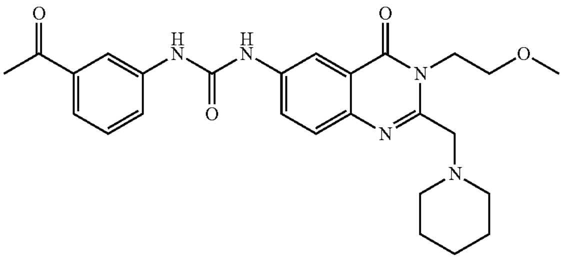 [SMILES: COCCn1c(CN2CCCCC2)nc2ccc(NC(=O)Nc3cccc(C(C)=O)c3)cc2c1=O] | 112.8 |
| 7 | 330a | 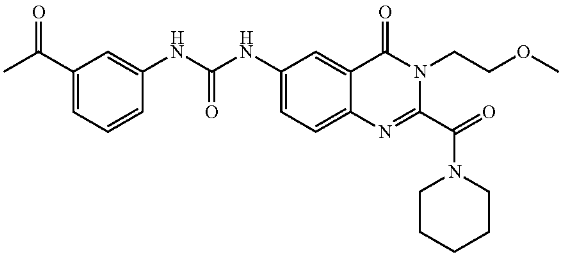 [SMILES: COCCn1c(C(=O)N2CCCCC2)nc2ccc(NC(=O)Nc3cccc(C(C)=O)c3)cc2c1=O] | 45.8 |
| 8 | 253 | 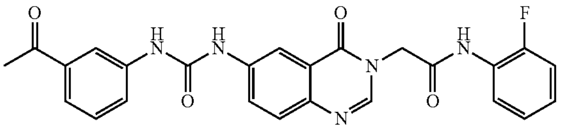 [SMILES: CC(=O)c1cccc(NC(=O)Nc2ccc3ncn(CC(=O)Nc4ccccc4F)c(=O)c3c2)c1] | 67.2 |
| 9 | 211 | 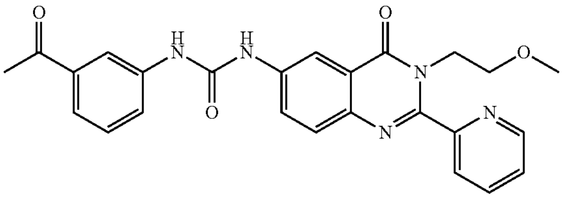 [SMILES: COCCn1c(-c2ccccn2)nc2ccc(NC(=O)Nc3cccc(C(C)=O)c3)cc2c1=O] | 110.3 |
| 10 | 139 | 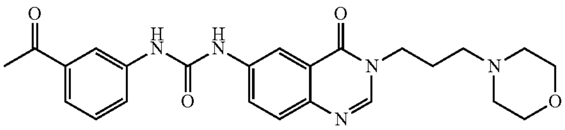 [SMILES: CC(=O)c1cccc(NC(=O)Nc2ccc3ncn(CCCN4CCOCC4)c(=O)c3c2)c1] | 55.50 |
| 11 | 215 | 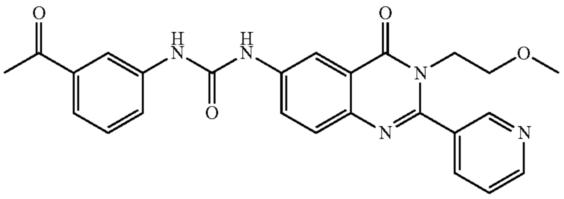 [SMILES: COCCn1c(-c2cccnc2)nc2ccc(NC(=O)Nc3cccc(C(C)=O)c3)cc2c1=O] | 80.70 |
| 12 | 219 | 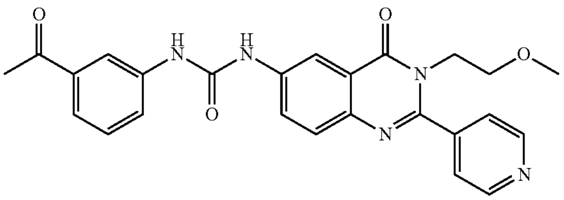 [SMILES: COCCn1c(-c2ccncc2)nc2ccc(NC(=O)Nc3cccc(C(C)=O)c3)cc2c1=O] | 73.9 |
| 13 | Propantheline (Control) | | 1.7 |
Plasma stability assay of synthesized compounds after 2 hours revealed that compounds 9, 73 and 179 have lower plasma stability whereas, compounds 123, 238, 241, 330a, 253, 211, 139, 215 and 219 have good plasma stability with respect to the control compound Propantheline. Plasma stability assay provides insight into the compound stability in plasma and the percentage concentration of the compounds remaining after certain time interval. The assay provides information regarding compound degradation in plasma.

Example 294

In-Vitro Evaluation of Metabolic Stability Using Human Liver Microsomes (Human Liver Microsomal Stability-HLM)

1 mM stock solution of test compound was prepared in DMSO and diluted with Acetonitrile:Water (1:1) to get a 100 μM working concentration. 100 mL of Milli Q water was added to $K_2HPO_4$ (1.398 g) and $KH_2PO_4$ (0.27 g) to get final pH 7.4 solution of potassium phosphate buffer. 3.333 mg/mL microsomal suspension was prepared by diluting 499.95 μL of 20 mg/mL microsomal stock to 2500.05 μL with buffer. 532.5 μL of 16 mM NADPH stock was added to 2467.5 μL of potassium phosphate buffer to get 2.84 mM working stock. 75 μL of 3.333 mg/mL working stock of liver microsomes and 85 μL of buffer was added to 2.5 μL of test compounds (100 μM). The above mixture was pre incubated for 15 minutes at 37° C. After pre incubation, 32.5 μL of the mixture was added to 17.5 μL of buffer, this was incubated for 60 minutes at 37° C. [60 min Without Cofactor (NADPH)]. 16.25 μL of the pre incubated mixture and 8.75 μL of cofactor was added to 150 μL of acetonitrile containing internal standard [0 min Sample]. 62 μL of cofactor was added to remaining pre incubation mixture [Incubation mixture]. 25 μL of incubation mixture at 0, 5, 15, 30, 60 min and 60 min without cofactor were precipitated with 150 μL of acetonitrile containing internal standard, vortexed and centrifuged at 4000 rpm at 4° C. for 20 minutes. 120 μL of supernatant was diluted with 120 μL of water and analyzed by LC-MS/MS [sample preparation]. The results obtained for the compounds is provided in Table 9.

TABLE 9

| Sl No. | Compound No. | Structure | % QH (Well stirred model) |
|---|---|---|---|
| 1 | 9 | 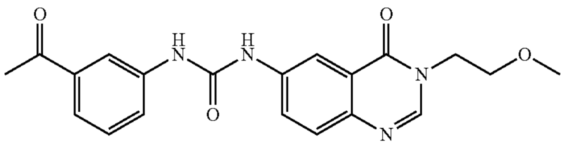 [SMILES: COCCn1cnc2ccc(NC(=O)Nc3cccc(C(C)=O)c3)cc2c1=O] | 21.26 |
| 2 | 238 | 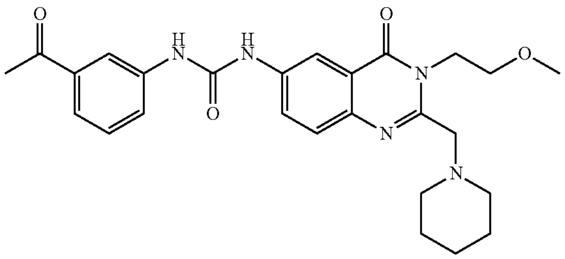 [SMILES: COCCn1c(CN2CCCCC2)nc2ccc(NC(=O)Nc3cccc(C(C)=O)c3)cc2c1=O] | 83.5 |
| 3 | 241 | 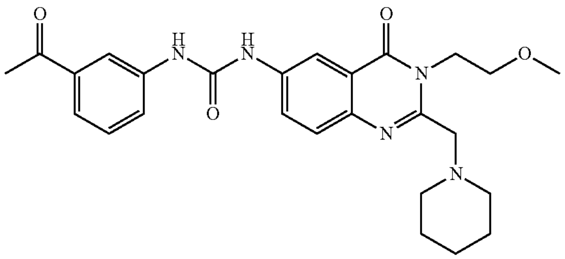 [SMILES: COCCn1c(CN2CCCCC2)nc2ccc(NC(=O)Nc3cccc(C(C)=O)c3)cc2c1=O] | 80.6 |
| 4 | 330a | 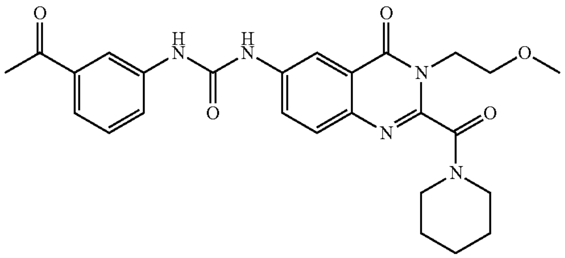 [SMILES: COCCn1c(C(=O)N2CCCCC2)nc2ccc(NC(=O)Nc3cccc(C(C)=O)c3)cc2c1=O] | 26.0 |

TABLE 9-continued

| Sl No. | Compound No. | Structure | % QH (Well stirred model) |
|---|---|---|---|
| 5 | 253 | 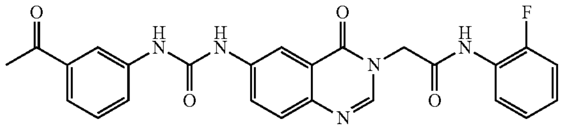 [SMILES: CC(=O)c1cccc(NC(=O)Nc2ccc3ncn(CC(=O)Nc4ccccc4F)c(=O)c3c2)c1] | 29.8 |
| 6 | 211 | 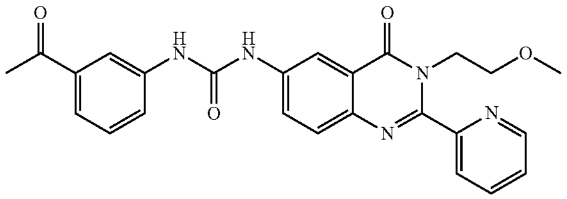 [SMILES: COCCn1c(-c2ccccn2)nc2ccc(NC(=O)Nc3cccc(C(C)=O)c3)cc2c1=O] | 38.8 |
| 7 | 139 | 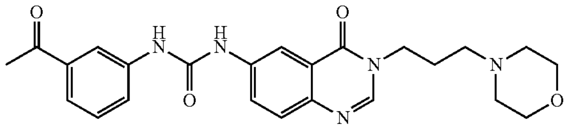 [SMILES: CC(=O)c1cccc(NC(=O)Nc2ccc3ncn(CCCN4CCOCC4)c(=O)c3c2)c1] | 35.3 |
| 8 | 215 | 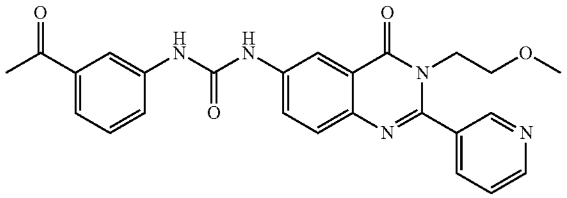 | 15.5 |
| 9 | 219 | 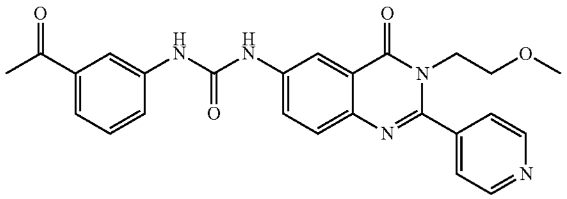 | 24.5 |
| 10 | Verapamil HCl (Control) | | 81.6 |

Classifications criteria: % QH; <30: Low Clearance 30-70: Medium Clearance >70: High Clearance In-Vitro evaluation of metabolic stability using Human Liver Microsomes (HLM) study revealed that compounds 9, 330a, 253, 215, and 219 have lower clearance. Compounds 211, and 139 have medium clearance and compounds 238, and 241 have higher clearance with respect to the control compound verapamil HCl. The liver microsomal stability assay primarily provides insight into the Phase I metabolism or biotransformation of the compounds.

Figure 11:
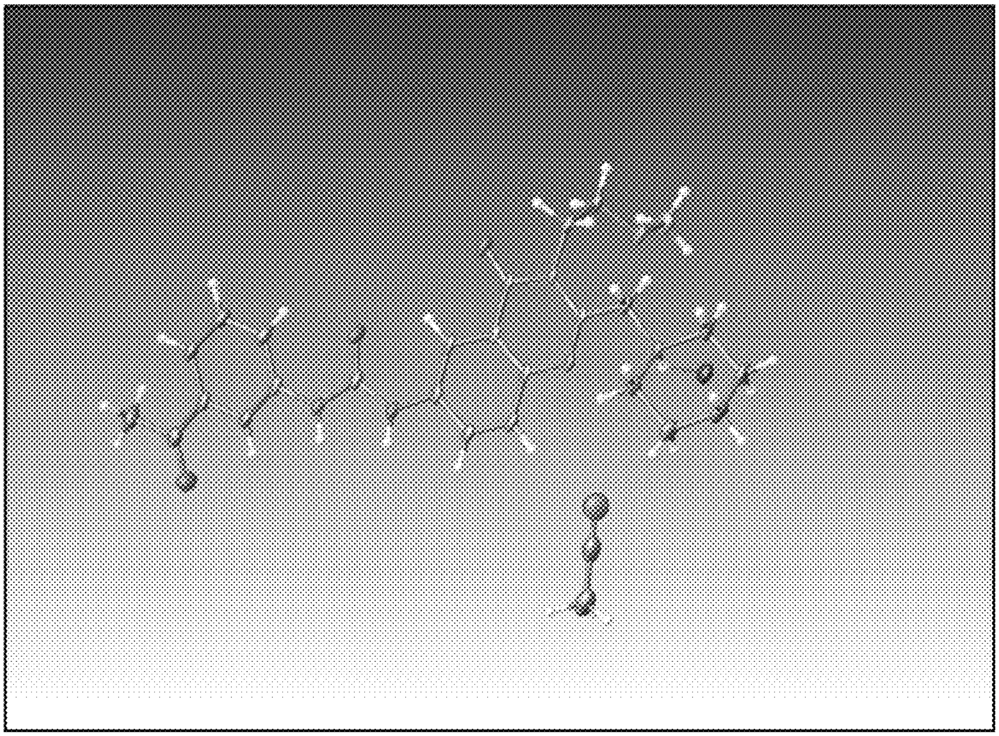
FIG. 11 illustrates crystal structure of 238a (HCl salt) CCDC Deposition no 1988445.

FIG. 11 describes compound 238a (HCl salt of compound 238) co-crystallized with acetonirile as solvent. CCDC deposition no 1988445.

Example 295

Basal Oxygen Consumption Rate (OCR) Determination by Seahorse

Figure 12:
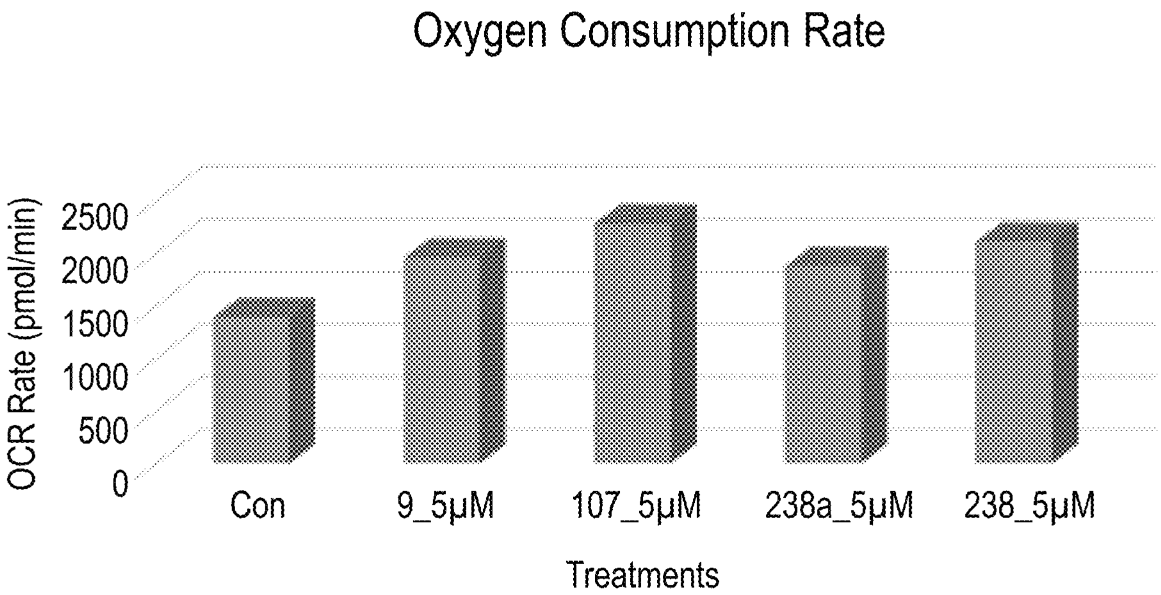
FIG. 12 illustrates basal oxygen consumption rate of compounds. Compounds 9, 107, 238a, 238 at 5 μM concentration showed higher oxygen consumption rate compared to control indicative of an increase in the basal respiration rate of the cell.

HepG2 cells were plated in Seahorse cell culture microplates (24 well). Cells were treated with 5 µM of compounds 9, 107, 238 and 238a for 24 hours. The calibrator plate was dipped in the calibrator solution and incubated overnight at 37° C. in a non-$CO_2$ incubator. The next day, cells were washed with Agilent Seahorse XF Base Medium, Minimal DMEM twice, making sure to leave at least 50 µl of media in the wells and incubated for 1 hour at 37° C. in a non-$CO_2$ incubator. Following this, oxygen consumption rate was measured in the Seahorse instrument. FIG. 12 illustrates basal oxygen consumption rate of compounds 9, 107, 238a, and 238. The results showed an increase in the basal OCR values in compound treatments with respect to control which signifies an increase in the basal respiration rate of the cells.

The compounds of the present disclosure having Structure I have several advantages including:

1. The compounds having structure Structure I are capable of modulating COP1 Ubiquitin Ligase enzyme through stabilization in hepatocytes.
2. The compounds having Structure I can reduce the level of triglycerides in hepatocytes.
3. The compounds having Structure I can be used in a clinical application for treating conditions involving Non-Alcoholic Fatty Liver Disease (NAFLD).

We claim:
1. A compound having Structure I or salts thereof,
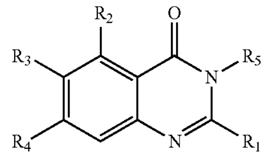
(I)
where:
$R_1$ is independently selected from the group consisting of —H,
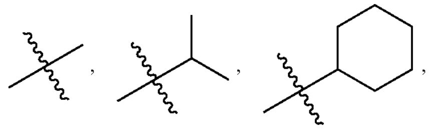
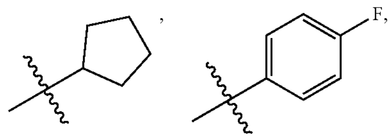
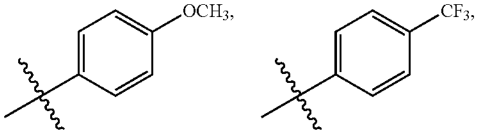
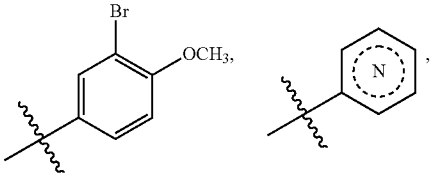
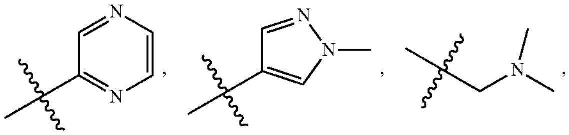
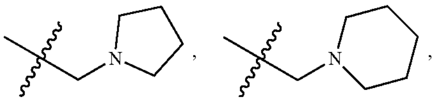
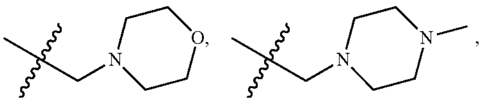
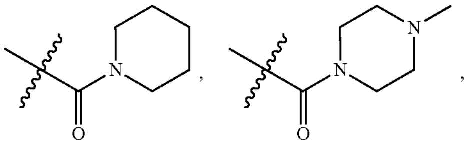
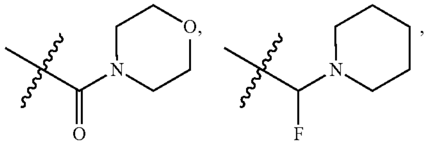
-continued
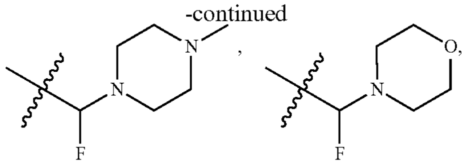
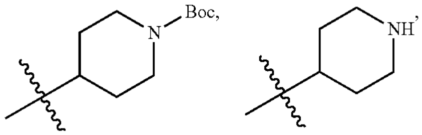
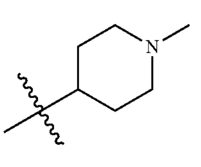
and
$R_2$ is independently selected from the group consisting of
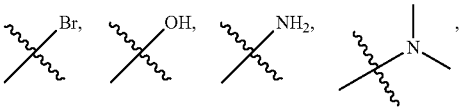
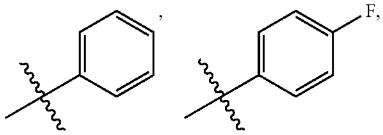
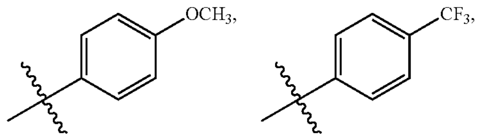
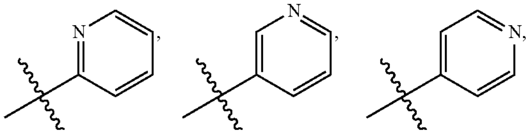
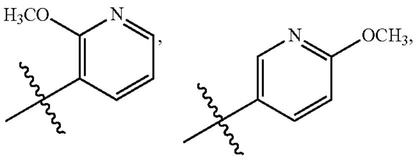
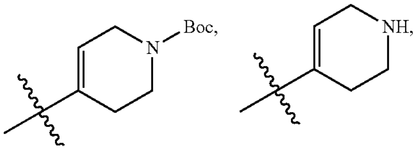
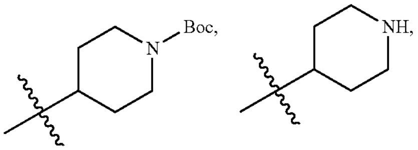
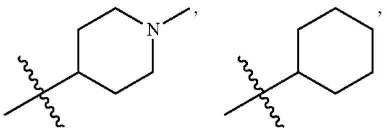

-continued
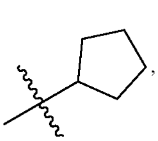, and 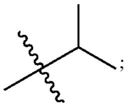;
R₃ is independently selected from the group consisting of,
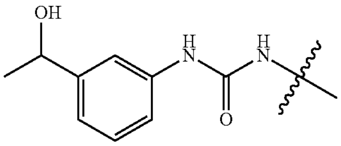,
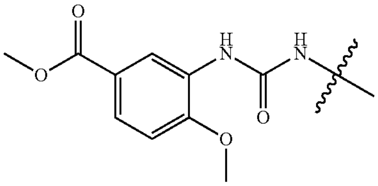,
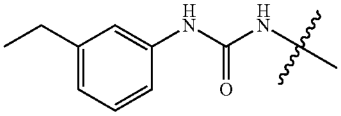,
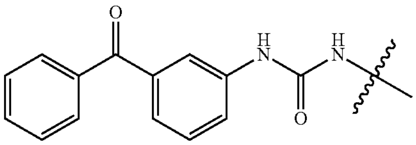,
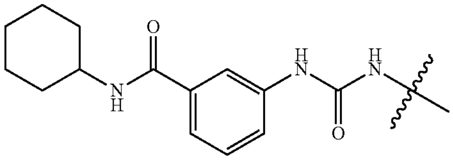,
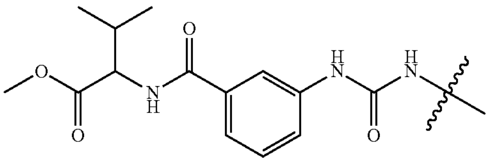,
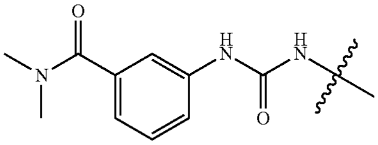,
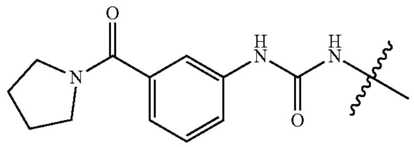,
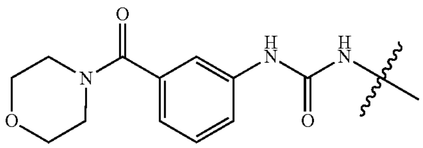,
-continued
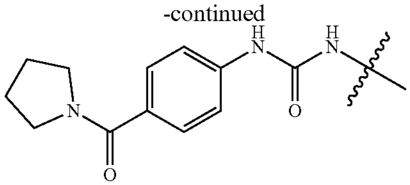,
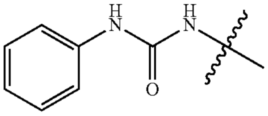,
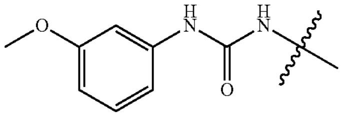,
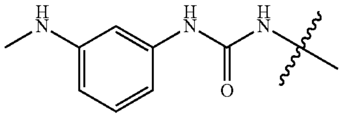,
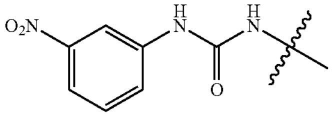,
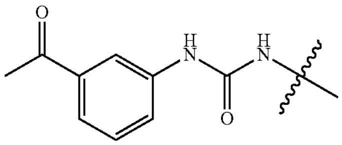,
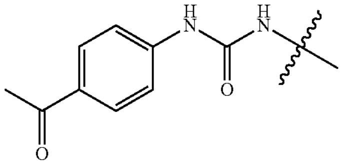,
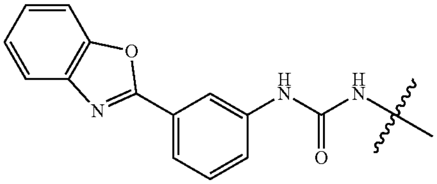,
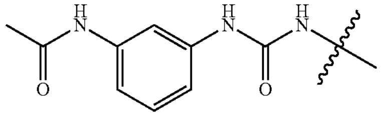,
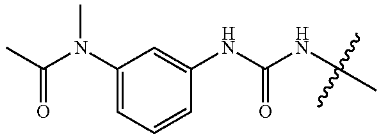,
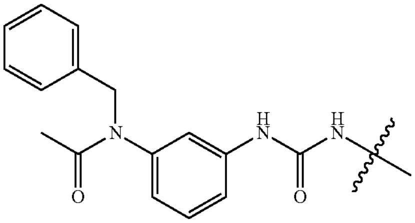,
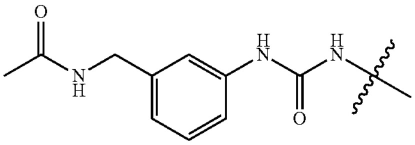, -continued
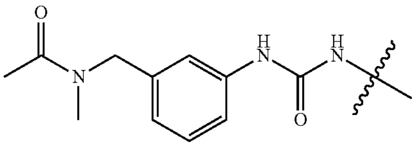,
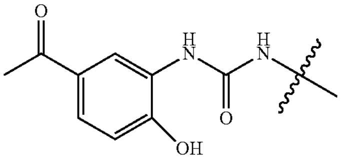,
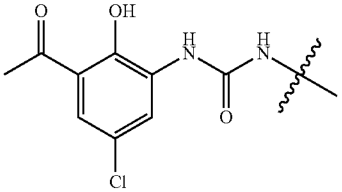,
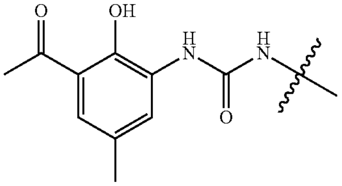,
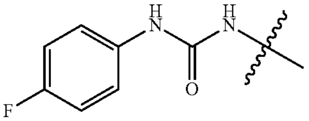,
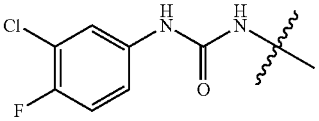,
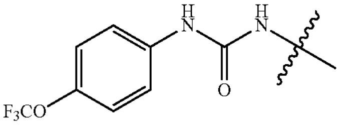,
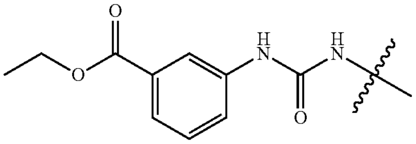,
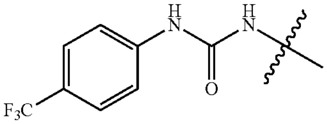,
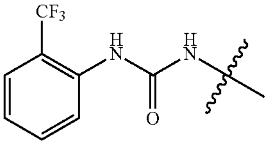,
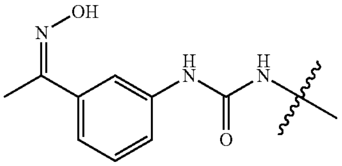,
-continued
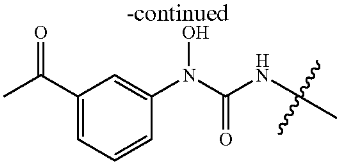,
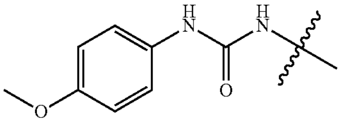,
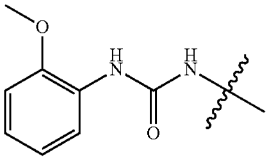, and
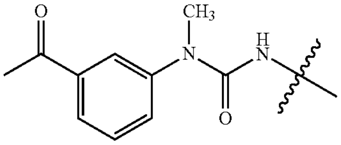;
$R_4$ is independently selected from the group consisting of —H,
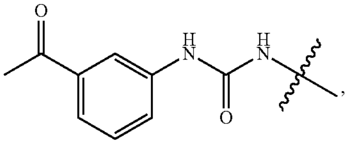,
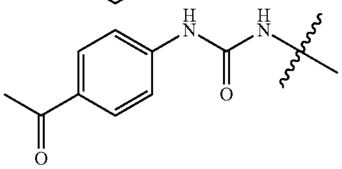,
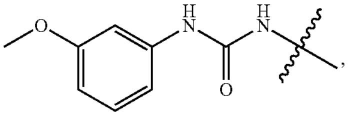,
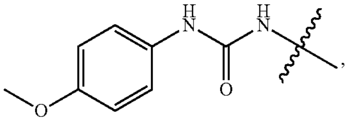,
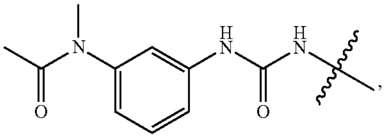,
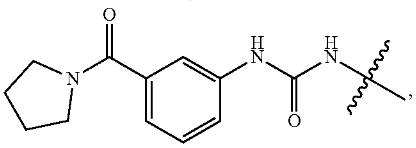, and
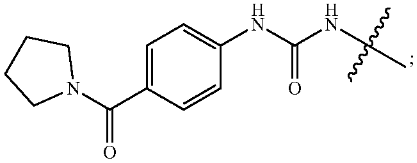;

and $R_5$ is independently selected from the group consisting of

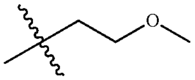, 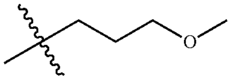, 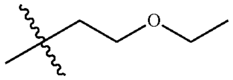, 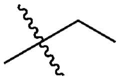, 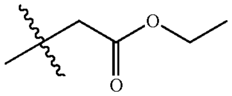, 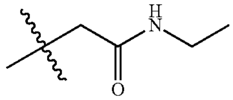, 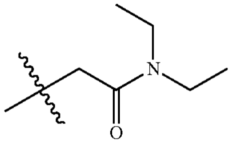, 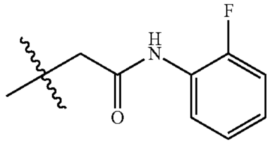, 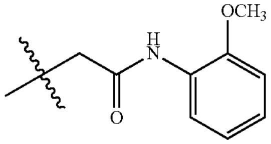, 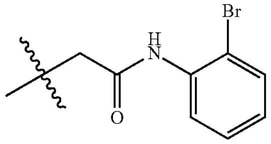, 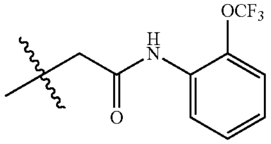, 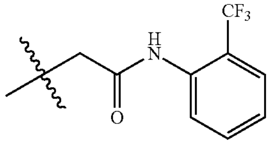, 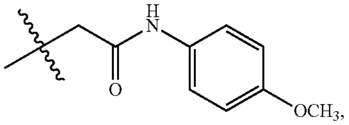 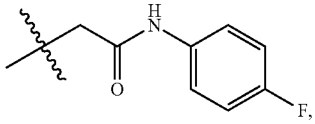 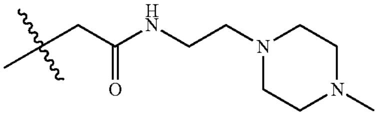, 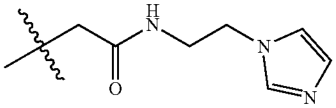, 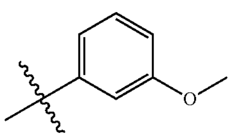, 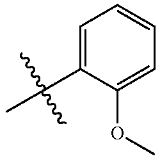, 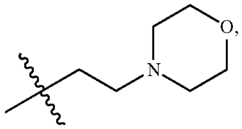 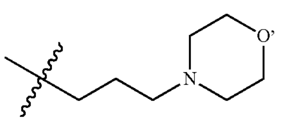 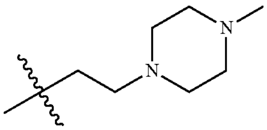, 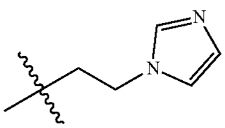, -continued

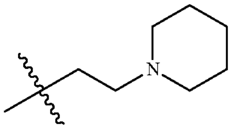, 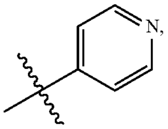 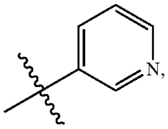 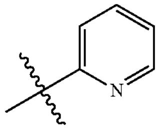, 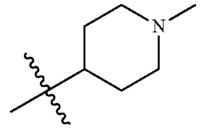, 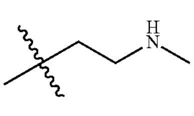, 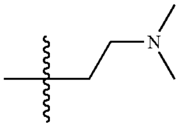, 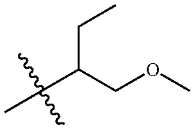, 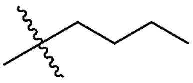, 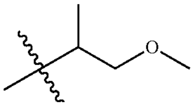, 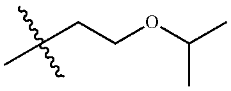, and 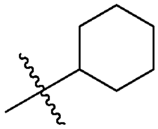.

2. The compound of claim 1, selected from the group consisting of:

1-(3-(2-methoxyethyl)-4-oxo-3,4-dihydroquinazolin-6-yl)-3-phenylurea (5);

1-(3-(2-methoxyethyl)-4-oxo-3,4-dihydroquinazolin-6-yl)-3-(3-methoxyphenyl)urea (6);

1-(3-(2-methoxyethyl)-4-oxo-3,4-dihydroquinazolin-6-yl)-3-(3-(methylamino)phenyl)urea (7);

1-(3-(2-methoxyethyl)-4-oxo-3,4-dihydroquinazolin-6-yl)-3-(3-nitrophenyl)urea (8);

1-(3-acetylphenyl)-3-(3-(2-methoxyethyl)-4-oxo-3,4-dihydroquinazolin-6-yl)urea (9);

1-(4-acetylphenyl)-3-(3-(2-methoxyethyl)-4-oxo-3,4-dihydroquinazolin-6-yl)urea (10);

1-(3-(1-hydroxyethyl)phenyl)-3-(3-(2-methoxyethyl)-4-oxo-3,4-dihydroquinazolin-6-yl)urea (11);

methyl 4-methoxy-3-(3-(3-(2-methoxyethyl)-4-oxo-3,4-dihydroquinazolin-6-yl)ureido)benzoate (12);

1-(3-ethylphenyl)-3-(3-(2-methoxyethyl)-4-oxo-3,4-dihydroquinazolin-6-yl)urea (13);

1-(3-benzoylphenyl)-3-(3-(2-methoxyethyl)-4-oxo-3,4-dihydroquinazolin-6-yl)urea (14);

N-cyclohexyl-3-(3-(3-(2-methoxyethyl)-4-oxo-3,4-dihydroquinazolin-6-yl)ureido)benzamide (15);

methyl 2-(3-(3-(3-(2-methoxyethyl)-4-oxo-3,4-dihydroquinazolin-6-yl)ureido)benzamido)-3-methylbutanoate (16);

3-(3-(3-(2-methoxyethyl)-4-oxo-3,4-dihydroquinazolin-6-yl)ureido)-N,N-dimethylbenzamide (17);

1-(3-(2-methoxyethyl)-4-oxo-3,4-dihydroquinazolin-6-yl)-3-(3-(pyrrolidine-1-carbonyl)phenyl)urea (18);

1-(3-(2-methoxyethyl)-4-oxo-3,4-dihydroquinazolin-6-yl)-3-(3-(morpholine-4-carbonyl)phenyl)urea (19);

1-(3-(2-methoxyethyl)-4-oxo-3,4-dihydroquinazolin-6-yl)-3-(4-(pyrrolidine-1-carbonyl)phenyl)urea (20);

1-(3-(benzo[d]oxazol-2-yl)phenyl)-3-(3-(2-methoxyethyl)-4-oxo-3,4-dihydroquinazolin-6-yl)urea (21);

N-(3-(3-(3-(2-methoxyethyl)-4-oxo-3,4-dihydroquinazolin-6-yl)ureido)phenyl)acetamide (22);

N-(3-(3-(3-(2-methoxyethyl)-4-oxo-3,4-dihydroquinazolin-6-yl)ureido)phenyl)-N-methylacetamide (23);

N-benzyl-N-(3-(3-(3-(2-methoxyethyl)-4-oxo-3,4-dihydroquinazolin-6-yl)ureido)phenyl)acetamide (24);

N-(3-(3-(3-(2-methoxyethyl)-4-oxo-3,4-dihydroquinazolin-6-yl)ureido)benzyl)acetamide (25);

N-(3-(3-(3-(2-methoxyethyl)-4-oxo-3,4-dihydroquinazolin-6-yl)ureido)benzyl)-N-methylacetamide (26);

1-(5-acetyl-2-hydroxyphenyl)-3-(3-(2-methoxyethyl)-4-oxo-3,4-dihydroquinazolin-6-yl)urea (32);

1-(3-acetyl-5-chloro-2-hydroxyphenyl)-3-(3-(2-methoxyethyl)-4-oxo-3,4-dihydroquinazolin-6-yl)urea (33);

1-(3-acetyl-2-hydroxy-5-methylphenyl)-3-(3-(2-methoxyethyl)-4-oxo-3,4-dihydroquinazolin-6-yl)urea (34);

1-(4-fluorophenyl)-3-(3-(2-methoxyethyl)-4-oxo-3,4-dihydroquinazolin-6-yl)urea (35);

1-(3-chloro-4-fluorophenyl)-3-(3-(2-methoxyethyl)-4-oxo-3,4-dihydroquinazolin-6-yl)urea (36);

1-(3-(2-methoxyethyl)-4-oxo-3,4-dihydroquinazolin-6-yl)-3-(4-(trifluoromethoxy)phenyl)urea (37);

1-(3-(2-methoxyethyl)-4-oxo-3,4-dihydroquinazolin-6-yl)-3-(4-(trifluoromethyl)phenyl) urea (38);

1-(3-(2-methoxyethyl)-4-oxo-3,4-dihydroquinazolin-6-yl)-3-(2-(trifluoromethyl)phenyl) urea (39);

1-(3-(2-methoxyethyl)-4-oxo-3,4-dihydroquinazolin-6-yl)-3-(4-methoxyphenyl)urea (40);

1-(3-(2-methoxyethyl)-4-oxo-3,4-dihydroquinazolin-6-yl)-3-(2-methoxyphenyl)urea (41);

ethyl 3-(3-(3-(2-methoxyethyl)-4-oxo-3,4-dihydroquinazolin-6-yl)ureido)benzoate (42);

3-(3-(3-(2-methoxyethyl)-4-oxo-3,4-dihydroquinazolin-6-yl)ureido)benzoic acid (42a);

1-(3-acetylphenyl)-3-(3-(2-methoxyethyl)-4-oxo-5-phenyl-3,4-dihydroquinazolin-6-yl)urea (45);

1-(3-acetylphenyl)-3-(5-(4-fluorophenyl)-3-(2-methoxyethyl)-4-oxo-3,4-dihydroquinazolin-6-yl)urea (47);

1-(3-acetylphenyl)-3-(3-(2-methoxyethyl)-4-oxo-5-(pyridin-2-yl)-3,4-dihydroquinazolin-6-yl)urea (49);

1-(3-acetylphenyl)-3-(3-(2-methoxyethyl)-4-oxo-5-(pyridin-3-yl)-3,4-dihydroquinazolin-6-yl)urea (51);

1-(3-acetylphenyl)-3-(3-(2-methoxyethyl)-4-oxo-5-(pyridin-4-yl)-3,4-dihydroquinazolin-6-yl)urea (53);

1-(3-acetylphenyl)-3-(3-(2-methoxyethyl)-5-(6-methoxypyridin-3-yl)-4-oxo-3,4-dihydroquinazolin-6-yl)urea (55);

1-(3-acetylphenyl)-3-(3-(2-methoxyethyl)-5-(2-methoxypyridin-3-yl)-4-oxo-3,4-dihydroquinazolin-6-yl)urea (57);

1 tert-butyl 4-(6-(3-(3-acetylphenyl)ureido)-3-(2-methoxyethyl)-4-oxo-3,4-dihydroquinazolin-5-yl)-5,6-dihydropyridine-1 (2H)-carboxylate (59);

1-(3-acetylphenyl)-3-(3-(2-methoxyethyl)-4-oxo-5-(1,2,3,6-tetrahydropyridin-4-yl)-3,4-dihydroquinazolin-6-yl)urea (60);

1 tert-butyl 4-(6-(3-(3-acetylphenyl)ureido)-3-(2-methoxyethyl)-4-oxo-3,4-dihydroquinazolin-5-yl) piperidine-1-carboxylate (61);

1-(3-acetylphenyl)-3-(3-(2-methoxyethyl)-4-oxo-5-(piperidin-4-yl)-3,4-dihydroquinazolin-6-yl)urea (62);

1-(3-acetylphenyl)-3-(3-(2-methoxyethyl)-5-(4-methoxyphenyl)-4-oxo-3,4-dihydroquinazolin-6-yl)urea (64);

1-(3-acetylphenyl)-3-(3-(2-methoxyethyl)-4-oxo-5-(4-(trifluoromethyl)phenyl)-3,4-dihydroquinazolin-6-yl) urea (66);

1-(3-acetylphenyl)-3-(5-cyclohexyl-3-(2-methoxyethyl)-4-oxo-3,4-dihydroquinazolin-6-yl)urea (68);

1-(3-acetylphenyl)-3-(5-cyclopentyl-3-(2-methoxyethyl)-4-oxo-3,4-dihydroquinazolin-6-yl)urea (70);

1-(3-acetylphenyl)-3-(5-isopropyl-3-(2-methoxyethyl)-4-oxo-3,4-dihydroquinazolin-6-yl)urea (72);

1-(3-acetylphenyl)-3-(5-bromo-3-(2-methoxyethyl)-4-oxo-3,4-dihydroquinazolin-6-yl)urea (73);

ethyl 2-(6-(3-(3-chloro-4-fluorophenyl)ureido)-4-oxoquinazolin-3 (4H)-yl)acetate (83);

ethyl 2-(4-oxo-6-(3-(4-(trifluoromethoxy)phenyl)ureido) quinazolin-3 (4H)-yl)acetate (84);

ethyl 2-(6-(3-(3-acetylphenyl)ureido)-4-oxoquinazolin-3 (4H)-yl)acetate (85);

2-(6-(3-(3-acetylphenyl)ureido)-4-oxoquinazolin-3 (4H)-yl) acetic acid (85a);

1-(3-acetylphenyl)-3-(3-(3-methoxypropyl)-4-oxo-3,4-dihydroquinazolin-6-yl)urea (89);

1-(3-acetylphenyl)-3-(3-(2-ethoxyethyl)-4-oxo-3,4-dihydroquinazolin-6-yl)urea (93);

1-(4-acetylphenyl)-3-(3-(2-ethoxyethyl)-4-oxo-3,4-dihydroquinazolin-6-yl)urea (94);

1-(3-acetylphenyl)-3-(3-ethyl-4-oxo-3,4-dihydroquinazolin-6-yl)urea (98);

1-(4-acetylphenyl)-3-(3-ethyl-4-oxo-3,4-dihydroquinazolin-6-yl)urea (99);

1-(3-acetylphenyl)-3-(3-(3-methoxyphenyl)-4-oxo-3,4-dihydroquinazolin-6-yl)urea (103);

1-(3-acetylphenyl)-3-(3-(2-methoxyethyl)-2-methyl-4-oxo-3,4-dihydroquinazolin-6-yl)urea (107);

1-(3-acetylphenyl)-3-(2-isopropyl-3-(2-methoxyethyl)-4-oxo-3,4-dihydroquinazolin-6-yl)urea (111);

1-(3-acetylphenyl)-3-(2-(4-fluorophenyl)-3-(2-methoxyethyl)-4-oxo-3,4-dihydroquinazolin-6-yl)urea (115);

1-(3-acetylphenyl)-3-(3-(2-methoxyethyl)-2-(4-methoxyphenyl)-4-oxo-3,4-dihydroquinazolin-6-yl)urea (119);

1-(3-acetylphenyl)-3-(2-cyclohexyl-3-(2-methoxyethyl)-4-oxo-3,4-dihydroquinazolin-6-yl)urea (123);

1-(3-acetylphenyl)-3-(2-cyclopentyl-3-(2-methoxyethyl)-4-oxo-3,4-dihydroquinazolin-6-yl)urea (127);

1-(3-acetylphenyl)-3-(3-(2-methoxyphenyl)-4-oxo-3,4-dihydroquinazolin-6-yl)urea (131);

1-(3-acetylphenyl)-3-(3-(2-morpholinoethyl)-4-oxo-3,4-dihydroquinazolin-6-yl)urea (135);

1-(3-acetylphenyl)-3-(3-(3-morpholinopropyl)-4-oxo-3,4-dihydroquinazolin-6-yl)urea (139);

1-(3-acetylphenyl)-3-(3-(2-(dimethylamino)ethyl)-4-oxo-3,4-dihydroquinazolin-6-yl)urea (143);

1-(3-acetylphenyl)-3-(4-oxo-3-(2-(piperidin-1-yl)ethyl)-3,4-dihydroquinazolin-6-yl)urea (147);

1-(3-acetylphenyl)-3-(4-oxo-3-(pyridin-4-yl)-3,4-dihydroquinazolin-6-yl)urea (151);

1-(3-acetylphenyl)-3-(4-oxo-3-(pyridin-3-yl)-3,4-dihydroquinazolin-6-yl)urea (155);

1-(3-acetylphenyl)-3-(4-oxo-3-(pyridin-2-yl)-3,4-dihydroquinazolin-6-yl)urea (159);

1-(3-acetylphenyl)-3-(3-(1-methylpiperidin-4-yl)-4-oxo-3,4-dihydroquinazolin-6-yl)urea (163);

1-(3-acetylphenyl)-3-(3-(2-(methylamino)ethyl)-4-oxo-3,4-dihydroquinazolin-6-yl)urea (167);

1-(3-acetylphenyl)-3-(3-(1-methoxybutan-2-yl)-4-oxo-3,4-dihydroquinazolin-6-yl)urea (171);

1-(3-acetylphenyl)-3-(3-butyl-4-oxo-3,4-dihydroquinazolin-6-yl)urea (175);

1-(3-acetylphenyl)-3-(3-(1-methoxypropan-2-yl)-4-oxo-3,4-dihydroquinazolin-6-yl)urea (179);

1-(3-acetylphenyl)-3-(3-(2-isopropoxyethyl)-4-oxo-3,4-dihydroquinazolin-6-yl)urea (183);

1-(3-acetylphenyl)-3-(3-cyclohexyl-4-oxo-3,4-dihydroquinazolin-6-yl)urea (187);

1-(3-acetylphenyl)-3-(3-(2-methoxyethyl)-4-oxo-3,4-dihydroquinazolin-7-yl)urea (192);

1-(4-acetylphenyl)-3-(3-(2-methoxyethyl)-4-oxo-3,4-dihydroquinazolin-7-yl)urea (193);

1-(3-(2-methoxyethyl)-4-oxo-3,4-dihydroquinazolin-7-yl)-3-(3-methoxyphenyl)urea (194);

1-(3-(2-methoxyethyl)-4-oxo-3,4-dihydroquinazolin-7-yl)-3-(4-methoxyphenyl)urea (195);

1-(3-(2-methoxyethyl)-4-oxo-3,4-dihydroquinazolin-7-yl)-3-(3-(pyrrolidine-1-carbonyl)phenyl)urea (196);

1-(3-(2-methoxyethyl)-4-oxo-3,4-dihydroquinazolin-7-yl)-3-(4-(pyrrolidine-1-carbonyl)phenyl)urea (197);

1-(3-(1-hydroxyethyl)phenyl)-3-(3-(2-methoxyethyl)-4-oxo-3,4-dihydroquinazolin-7-yl)urea (198);

N-(3-(3-(3-(2-methoxyethyl)-4-oxo-3,4-dihydroquinazolin-7-yl)ureido)phenyl)-N-methylacetamide (199);

1-(3-acetylphenyl)-3-(3-(2-methoxyethyl)-4-oxo-2-(4-(trifluoromethyl)phenyl)-3,4-dihydroquinazolin-6-yl)urea (203);

1-(3-acetylphenyl)-3-(2-(3-bromo-4-methoxyphenyl)-3-(2-methoxyethyl)-4-oxo-3,4-dihydroquinazolin-6-yl)urea (207);

1-(3-acetylphenyl)-3-(3-(2-methoxyethyl)-4-oxo-2-(pyridin-2-yl)-3,4-dihydroquinazolin-6-yl)urea (211);

1-(3-acetylphenyl)-3-(3-(2-methoxyethyl)-4-oxo-2-(pyridin-3-yl)-3,4-dihydroquinazolin-6-yl)urea (215);

1-(3-acetylphenyl)-3-(3-(2-methoxyethyl)-4-oxo-2-(pyridin-4-yl)-3,4-dihydroquinazolin-6-yl)urea (219);

1-(3-acetylphenyl)-3-(3-(2-methoxyethyl)-4-oxo-2-(pyrazin-2-yl)-3,4-dihydroquinazolin-6-yl)urea (223);

1-(3-acetylphenyl)-3-(3-(2-methoxyethyl)-2-(1-methyl-1H-pyrazol-4-yl)-4-oxo-3,4-dihydroquinazolin-6-yl)urea (227);

1-(3-acetylphenyl)-3-(3-(2-methoxyethyl)-4-oxo-2-(pyrrolidin-1-ylmethyl)-3,4-dihydroquinazolin-6-yl)urea (232);

1-(3-acetylphenyl)-3-(2-((dimethylamino)methyl)-3-(2-methoxyethyl)-4-oxo-3,4-dihydroquinazolin-6-yl)urea (235);

1-(3-acetylphenyl)-3-(3-(2-methoxyethyl)-4-oxo-2-(piperidin-1-ylmethyl)-3,4-dihydroquinazolin-6-yl)urea (238);

1-(3-acetylphenyl)-3-(3-(2-methoxyethyl)-2-(morpholinomethyl)-4-oxo-3,4-dihydroquinazolin-6-yl)urea (241);

1-(3-acetylphenyl)-3-(3-(2-methoxyethyl)-2-((4-methylpiperazin-1-yl)methyl)-4-oxo-3,4-dihydroquinazolin-6-yl)urea (244);

2-(6-(3-(3-acetylphenyl)ureido)-4-oxoquinazolin-3 (4H)-yl)-N-ethylacetamide (247);

2-(6-(3-(3-acetylphenyl)ureido)-4-oxoquinazolin-3 (4H)-yl)-N,N-diethylacetamide (250);

2-(6-(3-(3-acetylphenyl)ureido)-4-oxoquinazolin-3 (4H)-yl)-N-(2-fluorophenyl)acetamide (253);

2-(6-(3-(3-acetylphenyl)ureido)-4-oxoquinazolin-3 (4H)-yl)-N-(2-methoxyphenyl)acetamide (256);

2-(6-(3-(3-acetylphenyl)ureido)-4-oxoquinazolin-3 (4H)-yl)-N-(2-bromophenyl)acetamide (259);

2-(6-(3-(3-acetylphenyl)ureido)-4-oxoquinazolin-3 (4H)-yl)-N-(2-(trifluoromethoxy)phenyl)acetamide (262);

2-(6-(3-(3-acetylphenyl)ureido)-4-oxoquinazolin-3 (4H)-yl)-N-(2-(trifluoromethyl)phenyl)acetamide (265);

2-(6-(3-(3-acetylphenyl)ureido)-4-oxoquinazolin-3 (4H)-yl)-N-(4-methoxyphenyl)acetamide (268);

2-(6-(3-(3-acetylphenyl)ureido)-4-oxoquinazolin-3 (4H)-yl)-N-(4-fluorophenyl)acetamide (271);

2-(6-(3-(3-acetylphenyl)ureido)-4-oxoquinazolin-3 (4H)-yl)-N-(2-(4-methylpiperazin-1-yl)ethyl)acetamide (274);

N-(2-(1H-imidazol-1-yl)ethyl)-2-(6-(3-(3-acetylphenyl)ureido)-4-oxoquinazolin-3 (4H)-yl)acetamide (277);

1-(3-acetylphenyl)-3-(3-(1-methoxybutan-2-yl)-2-methyl-4-oxo-3,4-dihydroquinazolin-6-yl)urea (281);

1-(3-acetylphenyl)-3-(3-(1-methoxypropan-2-yl)-2-methyl-4-oxo-3,4-dihydroquinazolin-6-yl)urea (285);

1-(3-acetylphenyl)-3-(2-cyclohexyl-3-(1-methoxypropan-2-yl)-4-oxo-3,4-dihydroquinazolin-6-yl)urea (289);

1-(3-acetylphenyl)-3-(2-cyclohexyl-5-(4-fluorophenyl)-3-(2-methoxyethyl)-4-oxo-3,4-dihydroquinazolin-6-yl)urea (292);

1-(3-acetylphenyl)-3-(5-(4-fluorophenyl)-3-(1-methoxypropan-2-yl)-4-oxo-3,4-dihydroquinazolin-6-yl)urea (295);

tert-butyl 4-(6-(3-(3-acetylphenyl)ureido)-3-(2-methoxyethyl)-4-oxo-3,4-dihydroquinazolin-2-yl) piperidine-1-carboxylate (299);

1-(3-acetylphenyl)-3-(3-(2-methoxyethyl)-4-oxo-2-(piperidin-4-yl)-3,4-dihydroquinazolin-6-yl)urea (300);

1-(3-acetylphenyl)-3-(3-(2-methoxyethyl)-2-(1-methylpiperidin-4-yl)-4-oxo-3,4-dihydroquinazolin-6-yl)urea (304);

1-(3-acetylphenyl)-3-(2-(1-isopropylpiperidin-4-yl)-3-(2-methoxyethyl)-4-oxo-3,4-dihydroquinazolin-6-yl)urea (307);

1-(3-acetylphenyl)-1-hydroxy-3-(3-(2-methoxyethyl)-4-oxo-3,4-dihydroquinazolin-6-yl)urea (308);

1-(3-acetylphenyl)-3-(3-(2-methoxyethyl)-4-oxo-3,4-dihydroquinazolin-6-yl)-1-methylurea (309);

1-(3-acetylphenyl)-3-(5-(4-fluorophenyl)-3-(2-methoxyethyl)-4-oxo-3,4-dihydroquinazolin-6-yl)-1-hydroxyurea (310);

1-(3-acetylphenyl)-3-(5-(4-fluorophenyl)-3-(2-methoxyethyl)-4-oxo-3,4-dihydroquinazolin-6-yl)-1-methylurea (311);

1-(3-acetylphenyl)-1-hydroxy-3-(3-(2-methoxyethyl)-4-oxo-2-(piperidin-1-ylmethyl)-3,4-dihydroquinazolin-6-yl)urea (312);

1-(3-acetylphenyl)-3-(3-(2-methoxyethyl)-4-oxo-2-(piperidin-1-ylmethyl)-3,4-dihydroquinazolin-6-yl)-1-methylurea (313);

2-(6-(3-(3-acetylphenyl)-3-hydroxyureido)-4-oxoquinazolin-3 (4H)-yl)-N-(2-fluorophenyl)acetamide (314);

2-(6-(3-(3-acetylphenyl)-3-methylureido)-4-oxoquinazolin-3 (4H)-yl)-N-(2-fluorophenyl)acetamide (315);

1-(3-(2-methoxyethyl)-4-oxo-3,4-dihydroquinazolin-6-yl)-3-(3-(2,2,2-trifluoroacetyl)phenyl)urea (316);

1-(3-(2-methoxyethyl)-2-methyl-4-oxo-3,4-dihydroquinazolin-6-yl)-3-(3-(2,2,2-trifluoroacetyl)phenyl)urea (317);

1-(3-(2-methoxyethyl)-4-oxo-2-(piperidin-1-ylmethyl)-3,4-dihydroquinazolin-6-yl)-3-(3-(2,2,2-trifluoroacetyl)phenyl)urea (318);

1-(3-(2-methoxyethyl)-2-((4-methylpiperazin-1-yl)methyl)-4-oxo-3,4-dihydroquinazolin-6-yl)-3-(3-(2,2,2-trifluoroacetyl)phenyl)urea (319);

N-(2-fluorophenyl)-2-(4-oxo-6-(3-(3-(2,2,2-trifluoroacetyl)phenyl)ureido) quinazolin-3 (4H)-yl)acetamide (320);

1-(3-acetyl-4-fluorophenyl)-3-(3-(2-methoxyethyl)-4-oxo-3,4-dihydroquinazolin-6-yl)urea (321);

1-(3-acetyl-4-fluorophenyl)-3-(3-(2-methoxyethyl)-2-methyl-4-oxo-3,4-dihydroquinazolin-6-yl)urea (322);

1-(3-acetyl-4-fluorophenyl)-3-(3-(2-methoxyethyl)-4-oxo-2-(piperidin-1-ylmethyl)-3,4-dihydroquinazolin-6-yl)urea (323);

1-(3-acetyl-4-fluorophenyl)-3-(3-(2-methoxyethyl)-2-((4-methylpiperazin-1-yl)methyl)-4-oxo-3,4-dihydroquinazolin-6-yl)urea (324);

2-(6-(3-(3-acetyl-4-fluorophenyl)ureido)-4-oxoquinazolin-3 (4H)-yl)-N-(2-fluorophenyl)acetamide (325);

1-(3-acetylphenyl)-3-(2-(fluoro (piperidin-1-yl)methyl)-3-(2-methoxyethyl)-4-oxo-3,4-dihydroquinazolin-6-yl)urea (330);

1-(3-acetylphenyl)-3-(3-(2-methoxyethyl)-4-oxo-2-(piperidine-1-carbonyl)-3,4-dihydroquinazolin-6-yl)urea (330a);

1-(3-acetylphenyl)-3-(2-(fluoro (4-methylpiperazin-1-yl) methyl)-3-(2-methoxyethyl)-4-oxo-3,4-dihydroquinazolin-6-yl)urea (333);

1-(3-acetylphenyl)-3-(3-(2-methoxyethyl)-2-(4-methylpiperazine-1-carbonyl)-4-oxo-3,4-dihydroquinazolin-6-yl)urea (333 a);

1-(3-acetylphenyl)-3-(2-(fluoro (morpholino)methyl)-3-(2-methoxyethyl)-4-oxo-3,4-dihydroquinazolin-6-yl) urea (336);

1-(3-acetylphenyl)-3-(3-(2-methoxyethyl)-2-(morpholine-4-carbonyl)-4-oxo-3,4-dihydroquinazolin-6-yl) urea (336 a);

1-(3-acetylphenyl)-3-(3-morpholino-4-oxo-3,4-dihydroquinazolin-6-yl)urea (340);

(Z)-1-(3-(1-(hydroxyimino)ethyl)phenyl)-3-(3-(2-methoxyethyl)-4-oxo-3,4-dihydroquinazolin-6-yl)urea (341);

(Z)-1-(3-(1-(hydroxyimino)ethyl)phenyl)-3-(3-(2-methoxyethyl)-2-methyl-4-oxo-3,4-dihydroquinazolin-6-yl)urea (342);

(Z)-1-(3-(1-(hydroxyimino)ethyl)phenyl)-3-(3-(2-methoxyethyl)-4-oxo-2-(piperidin-1-ylmethyl)-3,4-dihydroquinazolin-6-yl)urea (343); and 1-(3-acetylphenyl)-3-(5-bromo-3-(2-methoxyethyl)-2-methyl-4-oxo-3,4-dihydroquinazolin-6-yl)urea (345).

3. A process for preparing the compound according to claim 1, the process comprising:

(i) reacting 2-amino-5-nitrobenzoic acid (1):

1

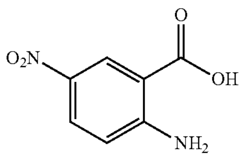

with an aliphatic or an aromatic amine selected from the group consisting of 2-methoxyethylamine, glycineethylester hydrochloride,3-methoxypropylamine, 2-ethoxyethylamine, ethylamine 2M in THF, 4-(2-aminoethyl) morpholine, 3-(4-morpholinyl) propylamine, N,N-dimethylethylenediamine, 1-(2-aminoethyl) piperidine, 4-amino-1-methylpiperidine, N-methylethylenediamine, 2-amino-1-methoxybutane, 1-butylamine, 1-methoxy-2-propylamine, 2-aminoethyl isopropyl ether, cyclohexylamine, 4-aminomorpholine, m-anisidine, o-anisidine, 4-aminopyridine, 3-aminopyridine, and 2-aminopyridine in presence of HATU/DMF followed by TEA as a base at room temperature for 1 to 3 hours to obtain an amide compound selected from the group consisting of 2, 80, 86, 90, 95, 132, 136, 140, 144, 160, 164, 168, 172, 176, 180, 184, 337, 100, 128, 148, 152, and 156;

2

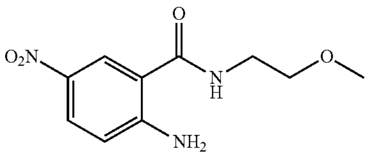

80

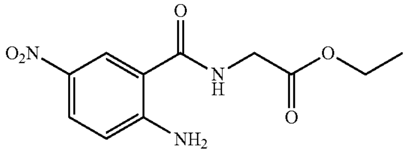

86

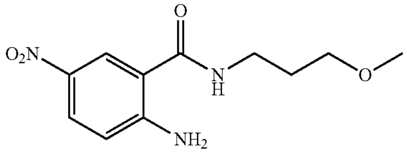

90

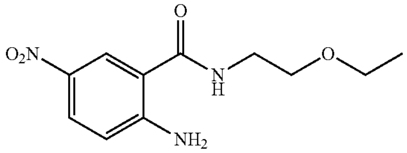

95

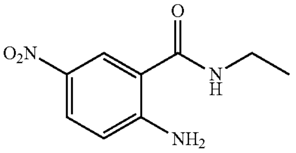

132

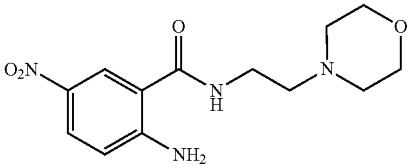

136

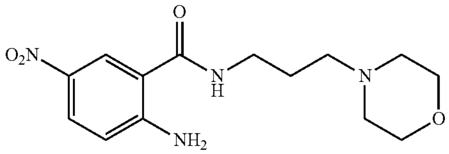

140

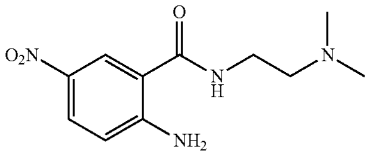

-continued

144

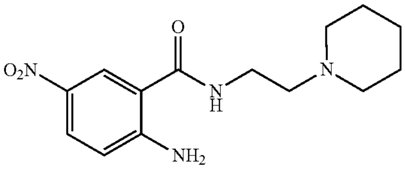

160

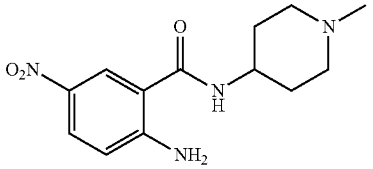

164

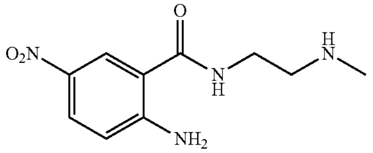

168

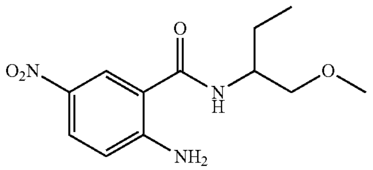

172

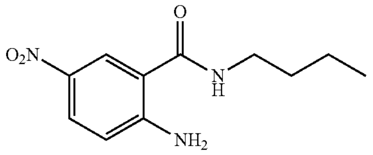

176

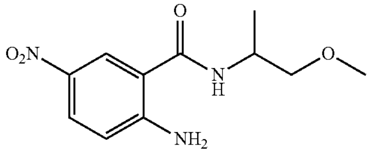

180

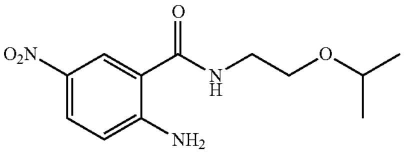

184

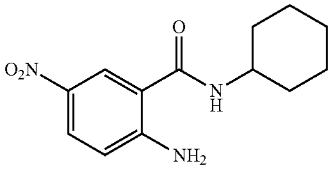

337

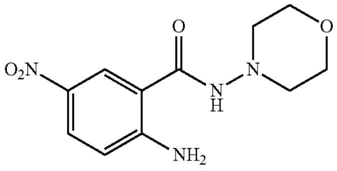

-continued

100

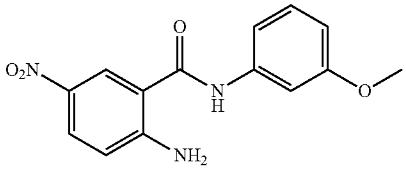

128

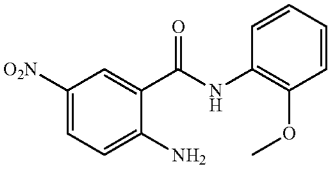

148

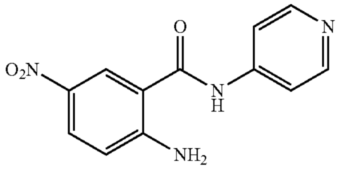

152

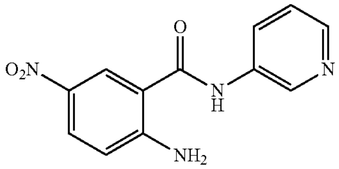

156

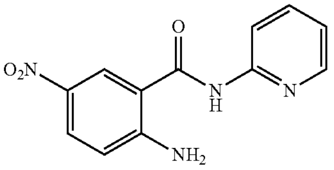

(ii) separately, reacting 2-amino-4-nitrobenzoic acid (compound 188) with 2-methoxyethylamine in presence of HATU/DMF followed by TEA as a base at room temperature for 1 hour to obtain a compound 189;

188

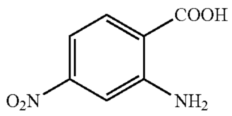

189

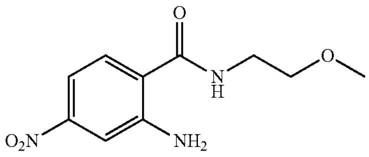

(iii) adding an acid chloride selected from the group consisting of acetyl chloride, isopropyl chloride, 4-fluorobenzoyl chloride, 4-methoxybenzoyl chloride, cyclohexanecarbonyl chloride, cyclopentanecarbonyl chloride, 4-(trifluoromethyl)benzoyl chloride, 3-Bromo-4-methoxybenzoyl chloride, Picolinoyl chloride, Nicotinoyl chloride, Isonicotinoyl chloride, Pyrazinecarbonyl chloride, 1-methyl-1H-pyrazole-4-carbonyl chloride, and 2-chloroacetyl chloride to compound 2 obtained in (i) in dichloromethane at a temperature from 0° C. to room temperature for 1 hour to 8 hours to obtain a compound selected from the group consisting of 104, 108, 112, 116, 120,124, 200, 204, 208, 212, 216, 220, 224, and 228;
104
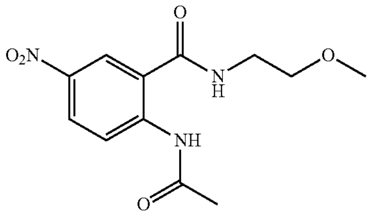
108
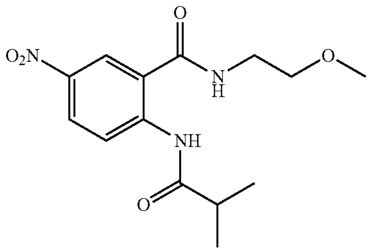
112
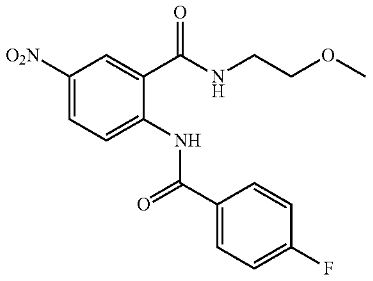
116
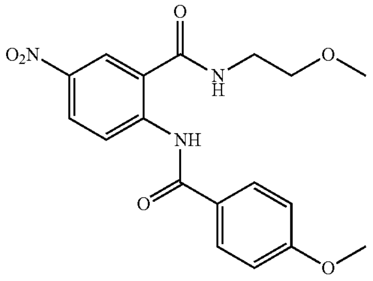
120
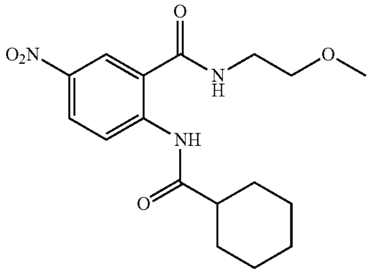
-continued
124
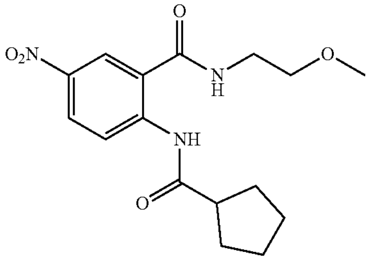
200
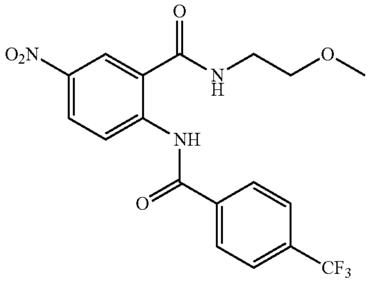
204
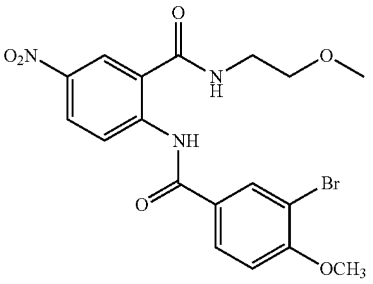
208
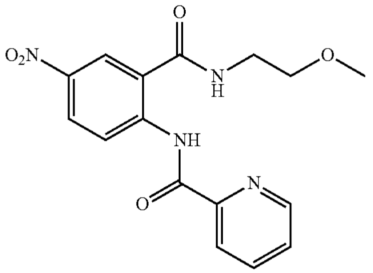
212
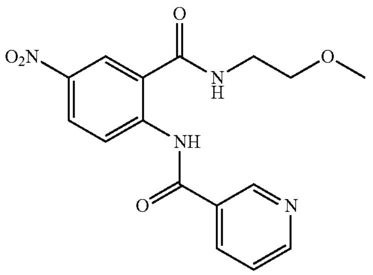

-continued

216

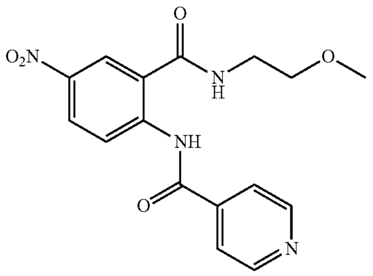

220

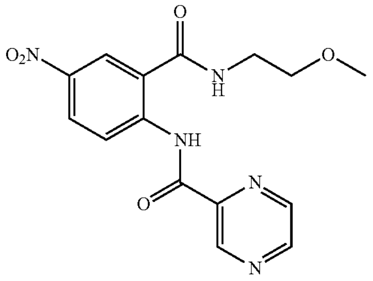

224

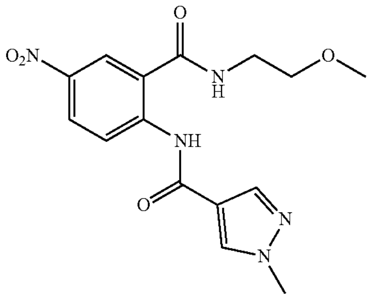

228

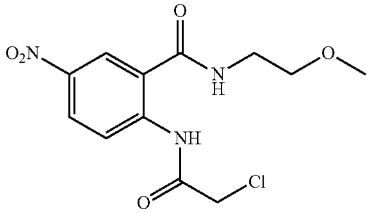

(iv) acetylating a compound selected from the group consisting of 168, and 176 obtained in (i) using acetyl chloride and triethylamine (TEA) as a base in dichloromethane at a temperature from 0° C. to room temperature for 8 hours to obtain a compound selected from the group consisting of 278 and 282;

168

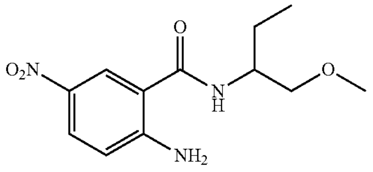

-continued

176

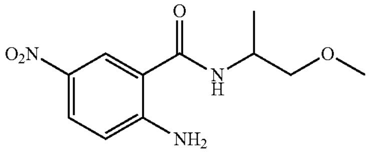

278

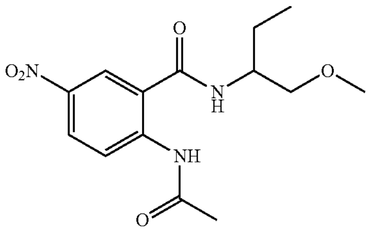

282

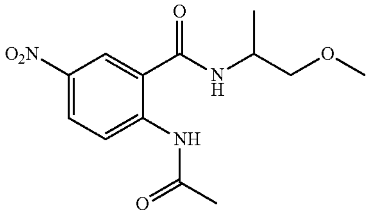

(v) alternately, adding cyclohexanecarbonyl chloride to compound 176 obtained in (i) to obtain a compound 286:

286

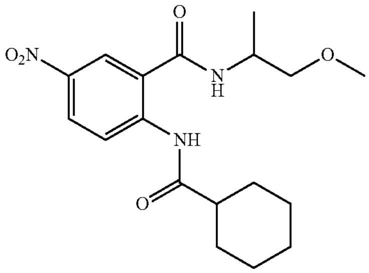

(vi) alternately, adding tert-butyl 4-(chlorocarbonyl) piperidine-1-carboxylate to compound 2 obtained in (i) to obtain a compound 296;

296

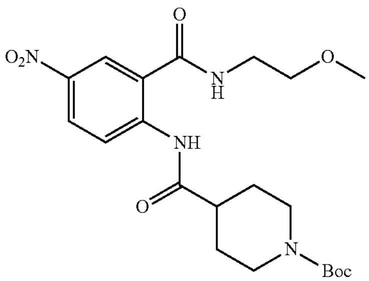

(vii) alternately, treating compound 2 obtained in (i) with 2-chloro-2-fluoroacetic acid or 2-chloro-2-difluoroacetic acid along with $POCl_3$ in pyridine solvent to obtain a compound selected from the group consisting of 326 and 326a;

326
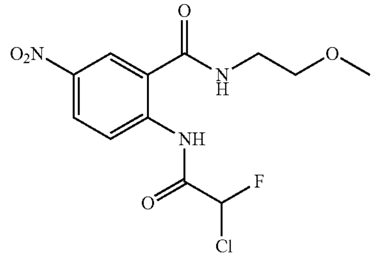
326a
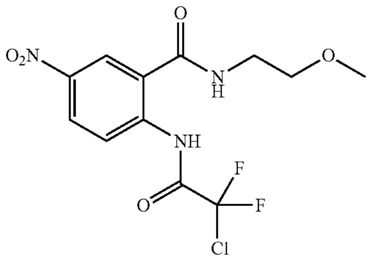
(viii) cyclizing the compound selected from the group consisting of 2, 80, 86, 90, 95, 100, 128, 132, 136, 140, 144, 148, 152, 156, 160, 164, 168, 172, 176, 180, 184, 189, and 337 obtained in (i) and (ii) using a cyclizing agent selected from trimethylorthoformate or triethylorthoformate at 100° C. for 12 to 16 hours to obtain a compound selected from the group consisting of 3, 81, 87, 91, 96, 101, 129, 133, 137, 141, 145, 149, 153, 157, 161, 165, 169, 173, 177, 181, 185, 190, and 338;
3
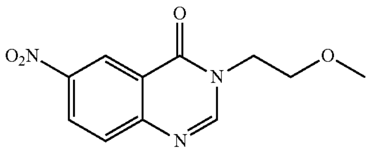
81
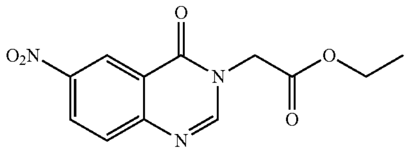
87
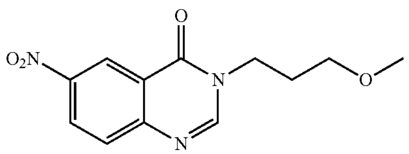
91
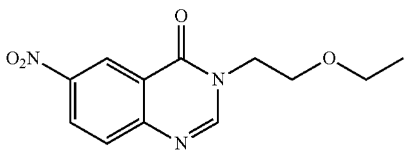
96
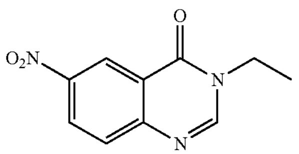
-continued
101
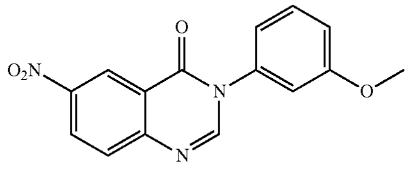
129
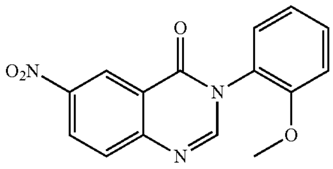
133
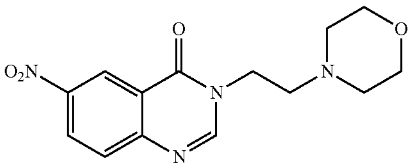
137
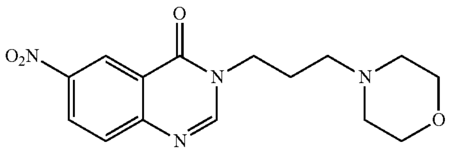
141
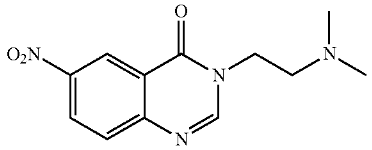
145
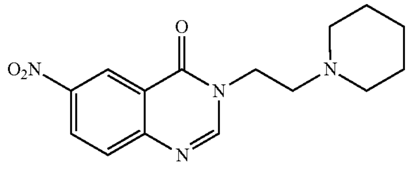
149
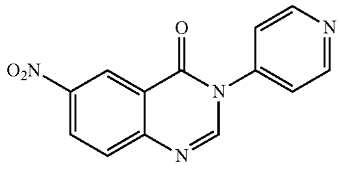
153
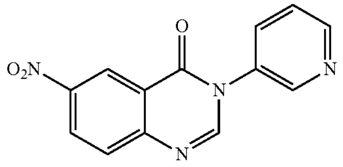
157
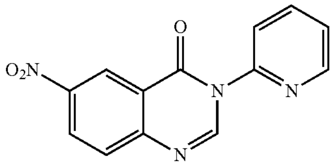

-continued
161
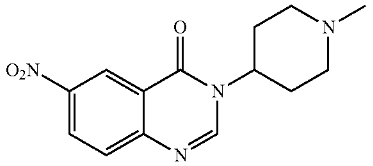
165
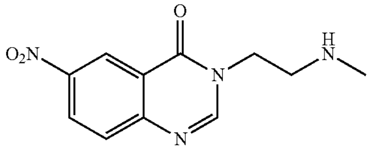
169
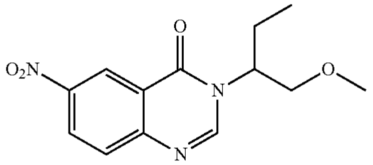
173
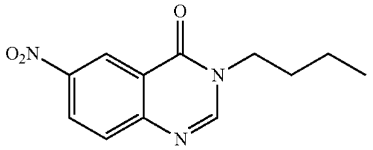
177
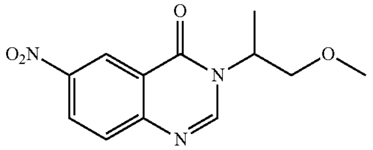
181
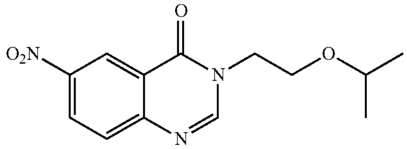
185
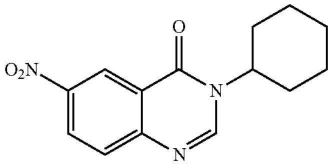
190
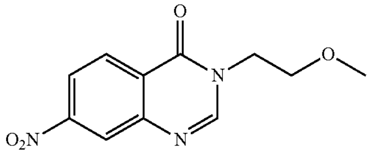
338
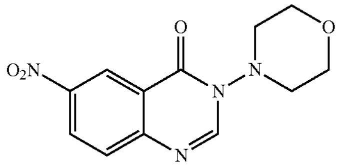
(ix) cyclizing the compound selected from the group consisting of 104, 108, 112, 116, 120, 124, 200, 204, 208, 212, 216, 220, 224, 228, 278, 282, 286, 296, 326, and 326a obtained in (iii), (iv), (v), (vi), or (vii) using
a cyclizing agent $ZnCl_2$ and hexamethyldisilazane (HMDS) in DMF at 100° C. for 12 to 16 hours to obtain a compound selected from the group consisting of 105, 109, 113, 117, 121, 125, 201, 205, 209, 213, 217, 221, 225, 229, 279, 283, 287, 297, 327 and 327a;
105
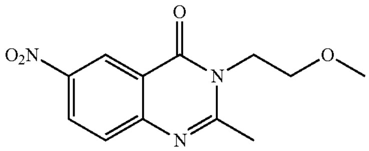
109
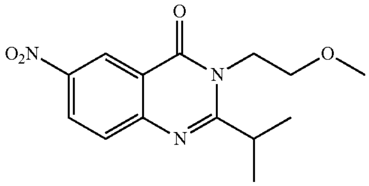
113
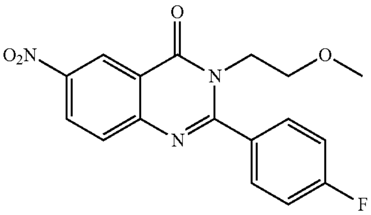
117
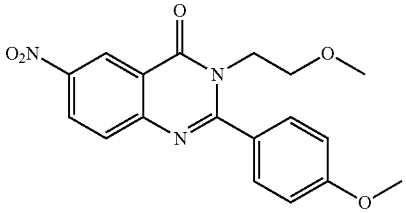
121
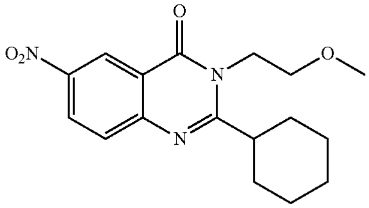
125
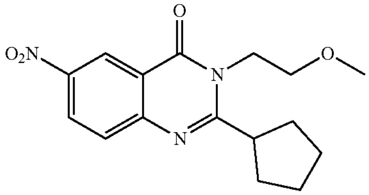
201
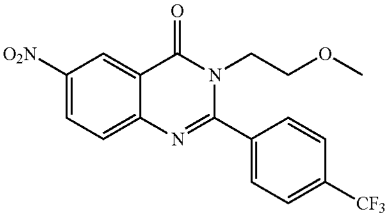

-continued

205

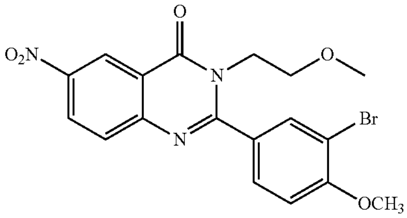

209

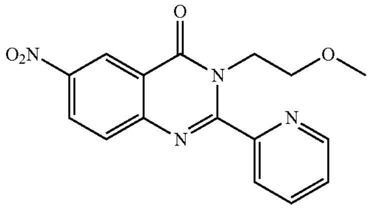

213

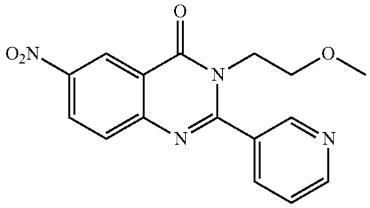

217

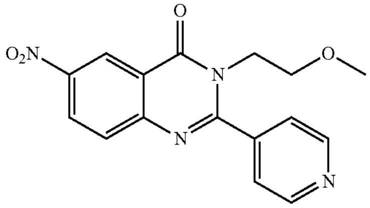

221

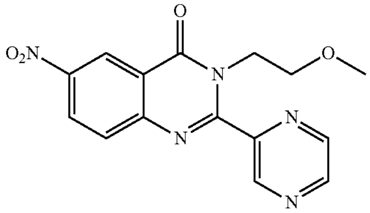

225

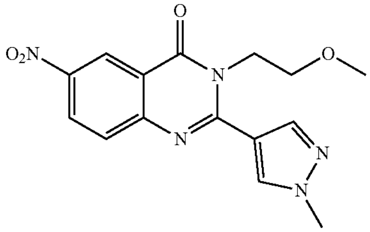

229

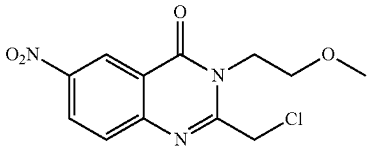

-continued

279

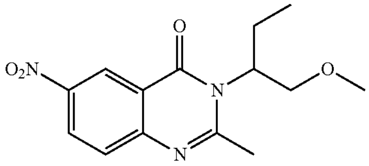

283

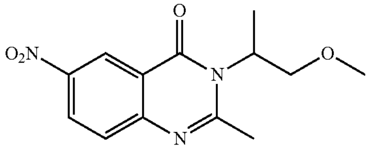

287

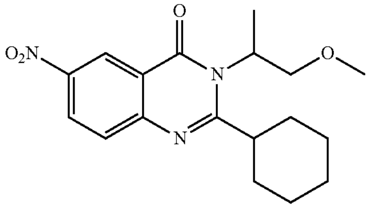

297

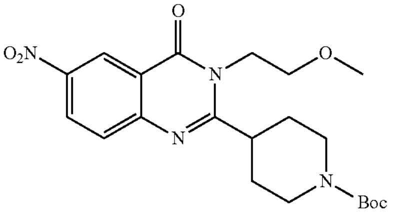

327

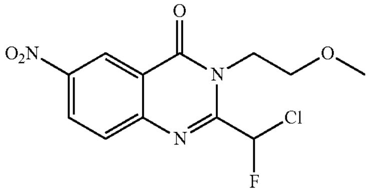

327a

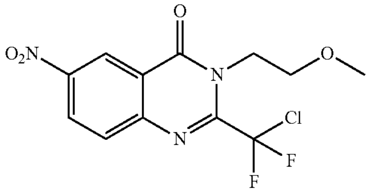

(x) reacting the compound 81 obtained in (viii) with an amine selected from the group consisting of ethyl amine, diethylamine, 2-fluroaniline, o-anisidine, 2-bromoaniline, 2-(trifluoromethoxy) aniline, 2-(trifluoromethyl) aniline, p-anisidine,4-fluoroaniline, 1-(2-aminoethyl)-4-methylpiperizine, and 1H-imidazole-1-ethanamine in the presence of anhydrous $AlCl_3$ in toluene at a temperature from room temperature to 110° C. to obtain a compound selected from the group consisting of 245, 248, 251, 254, 257, 260, 263, 266, 269, 272 and 275;

245
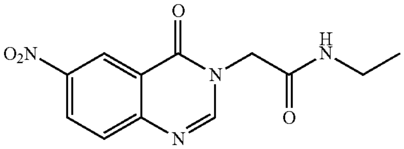
248
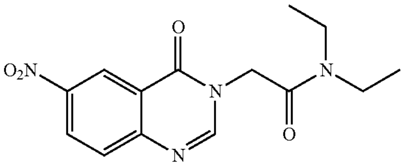
251
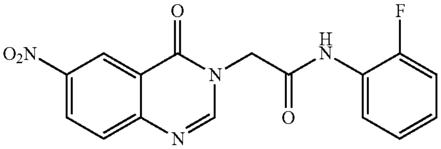
254
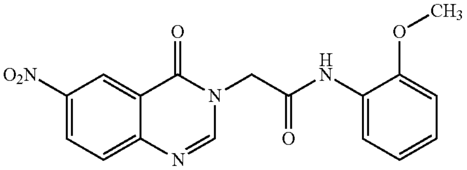
257
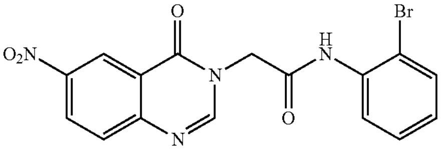
260
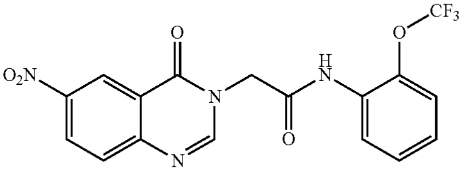
263
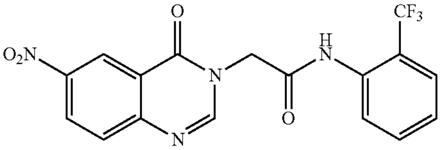
266
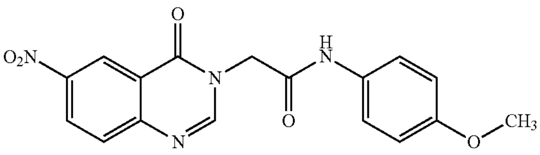
269
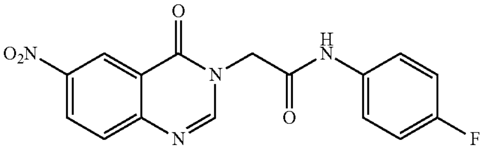
-continued
272
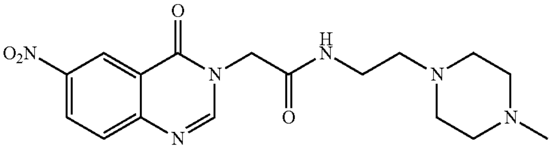
275
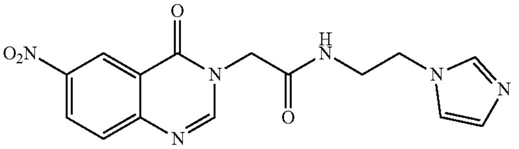
(xi) reacting the compound 229 obtained in (ix) with an amine selected from the group consisting of pyrrolidine, dimethylamine, piperidine, morpholine, and 1-methylpiperazine in toluene at 100° C. for 2 hours to obtain a compound selected from the group consisting of 230, 233, 236, 239, and 242;
230
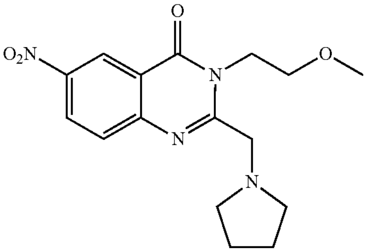
233
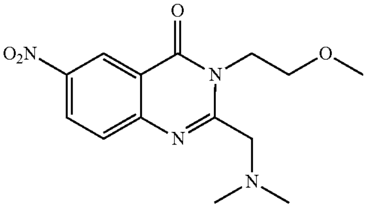
236
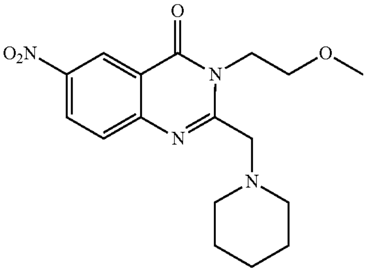
239
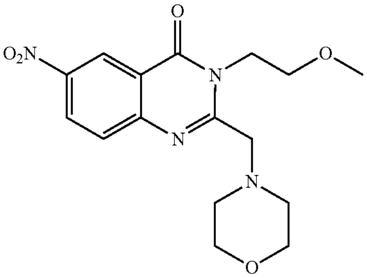

-continued

242

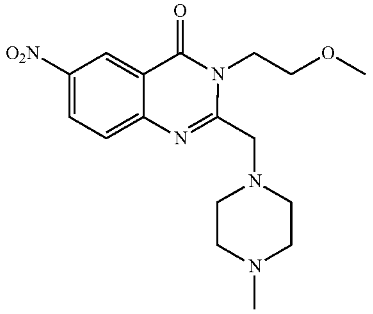

(xii) reacting the compound 327 obtained in (ix) with an amine selected from the group consisting of piperidine, 1-methylpiperazine, and morpholine in presence of toluene to obtain a compound selected from the group consisting of 328, 331, and 334;

328

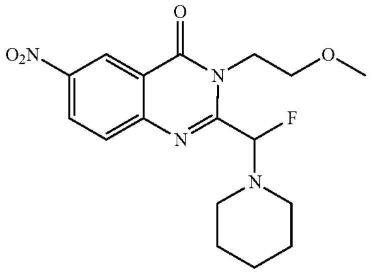

331

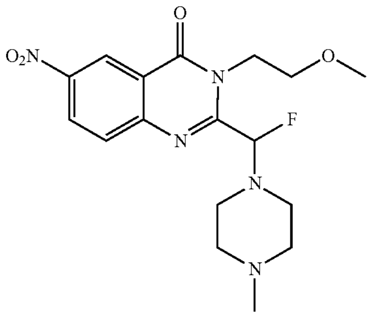

334

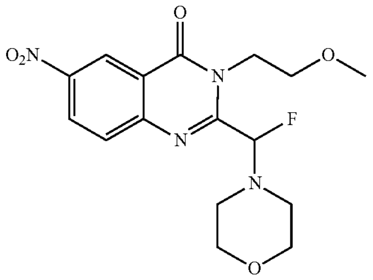

(xiii) reacting the compound 327a obtained in (ix) with an amine selected from the group consisting of piperidine, 1-methylpiperazine, and morpholine in the presence of a solvent selected from the group consisting of toluene, DMF, and THF in the absence or presence of a base selected from $K_2CO_3$, or N,N-diethylaniline to obtain a compound selected from the group consisting of 328a, 331a, and 334a;

328a

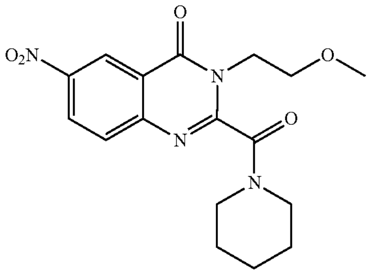

331a

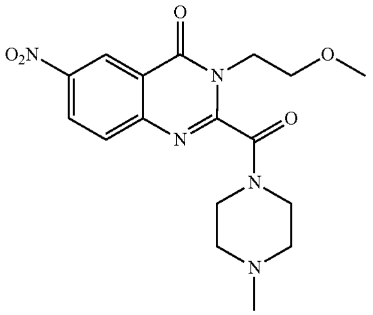

334a

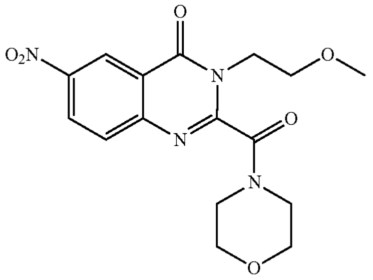

(xiv) separately reacting the compound 297 obtained in (ix) with trifluoroacetic acid (TFA) in DCM at a temperature from 0° C. to room temperature for 2 hours to obtain a compound 301;

301

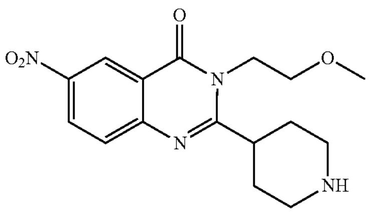

(xv) reacting the compound 301 obtained in (xiv) with sodium hydride (NaH) in DMF at a temperature from 0° C. to room temperature for 3 hours with methyl iodide and 2-chloropropane, respectively to obtain a compound selected from the group consisting of 302 and 305;

302
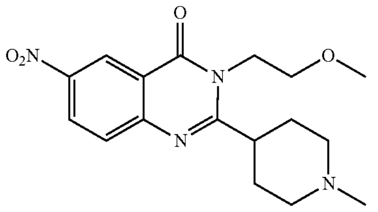
305
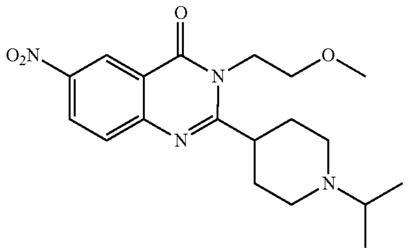
(xvi) reducing the compound selected from the group consisting of 3, 81, 87, 91, 96, 101, 105, 109, 113, 117, 121, 125, 129, 133, 137, 141, 145, 149, 153, 157, 161, 165, 169, 173, 177, 181, 185, 190, 201, 209, 213, 217, 221, 225, 230, 233, 236, 239, 242, 245, 248, 251, 254, 260, 263, 266, 269, 272, 275, 279, 283, 287, 297, 302, 305, 328, 328a, 331, 331a, 334, 334a and 338 obtained in (viii), (ix), (x), (xi), (xii), (xiii), or (xv) using Palladium-Charcoal (5% or 10% wet) at room temperature for 3 to 5 hours in the presence of $H_2$ to obtain an amine compound selected from the group consisting of 4, 82, 88, 92, 97, 102, 106, 110, 114, 118, 122, 126, 130, 134, 138, 142, 146, 150, 154, 158, 162, 166, 170, 174, 178, 182, 186, 191, 202, 210, 214, 218, 222, 226, 231, 234, 237, 240, 243, 246, 249, 252, 255, 261, 264, 267, 270, 273, 276, 280, 284, 288, 298, 303, 306, 329, 329a, 332, 332a, 335, 335a, and 339;
4
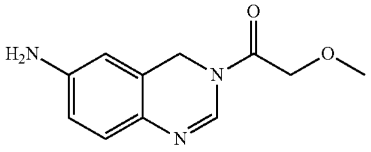
82
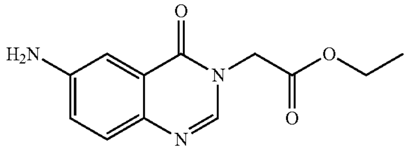
88
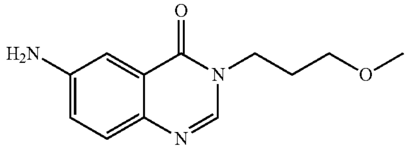
92
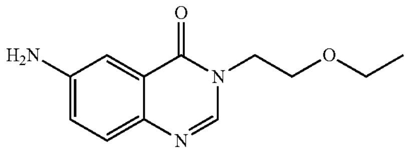
-continued
97
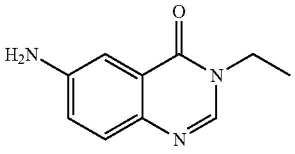
102
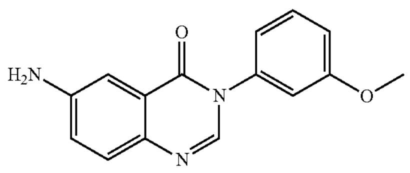
106
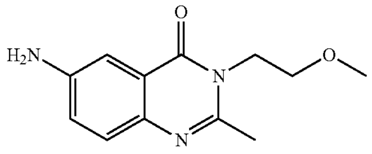
110
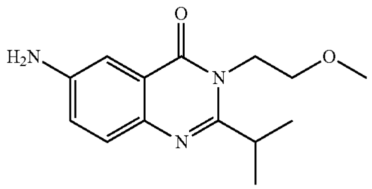
114
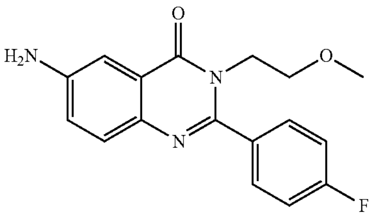
118
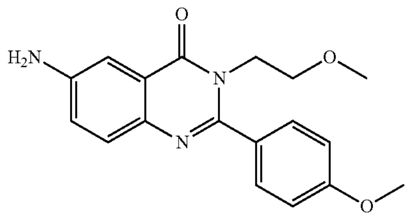
122
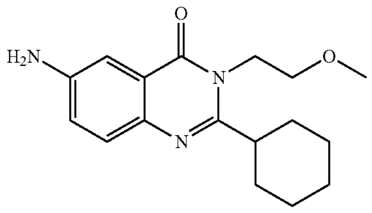
126
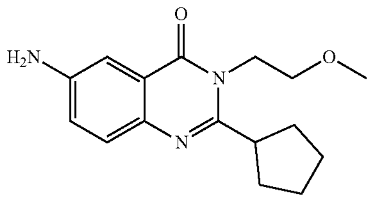

130
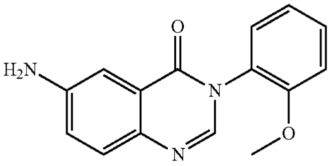
134
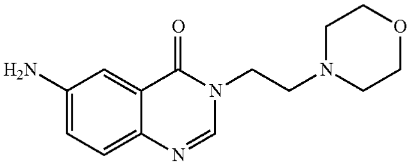
138
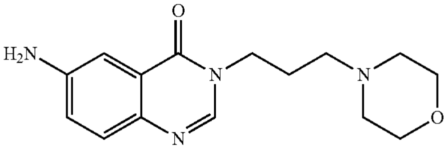
142
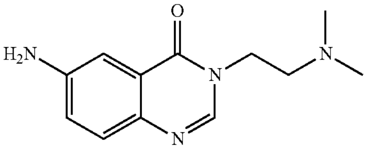
146
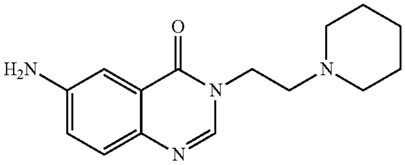
150
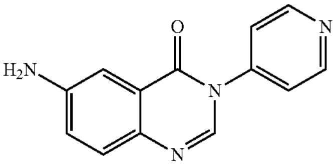
154
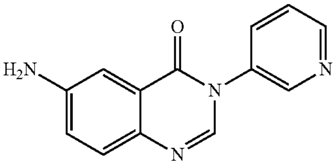
158
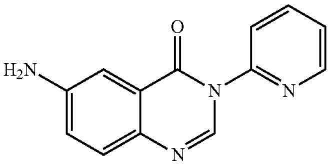
162
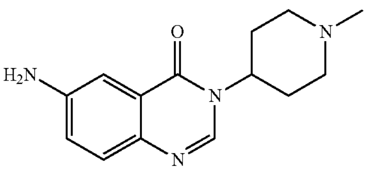
166
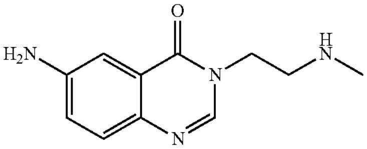
170
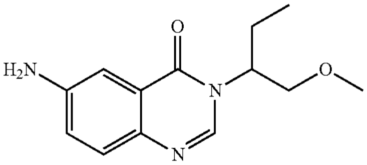
174
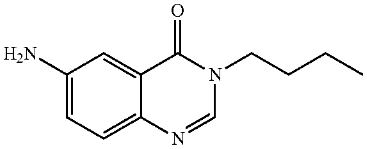
178
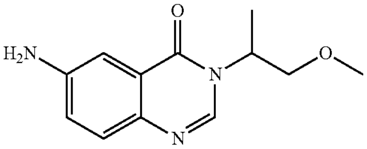
182
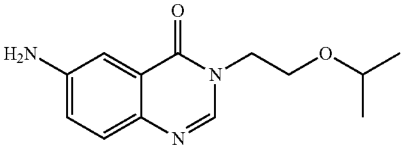
186
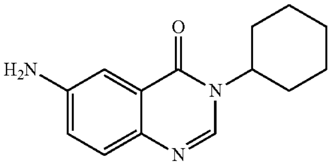
191
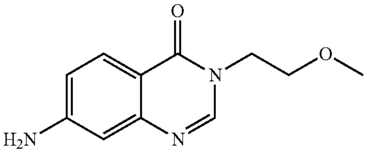
202
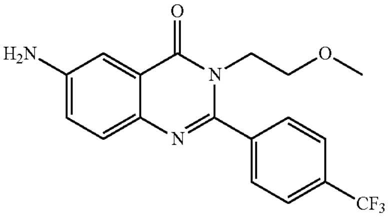
210
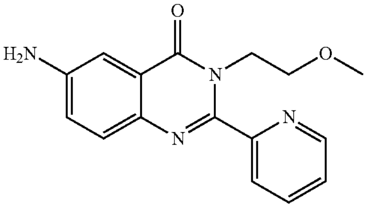

-continued
214
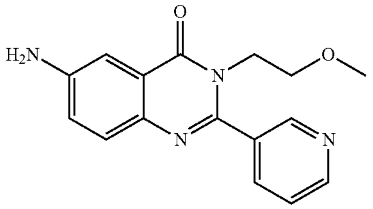
218
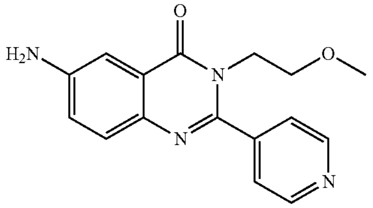
222
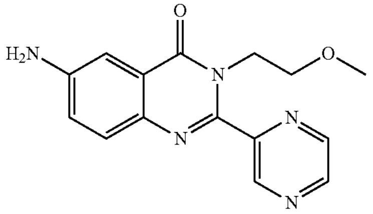
226
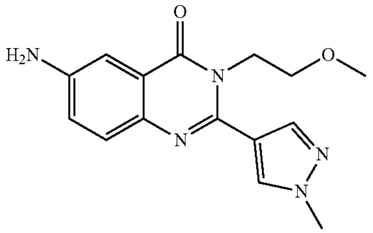
231
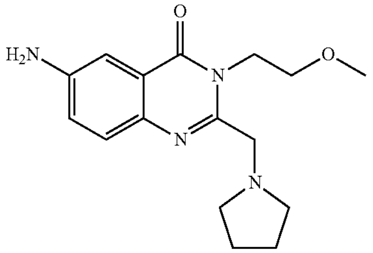
234
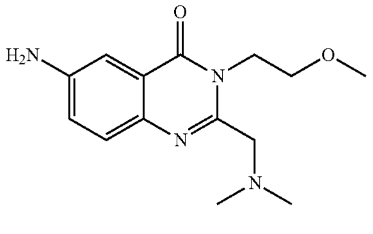
-continued
237
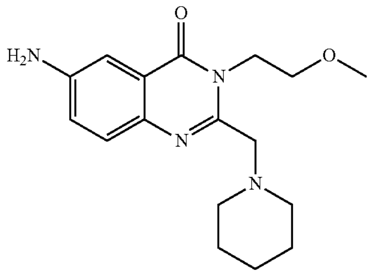
240
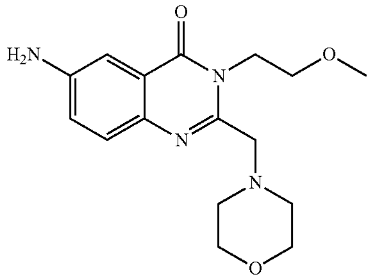
243
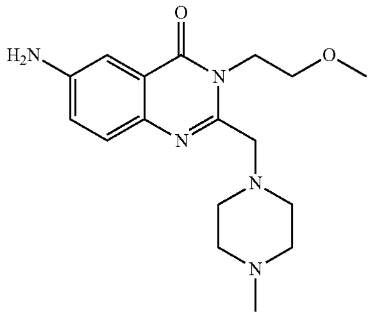
246
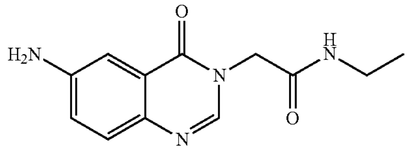
249
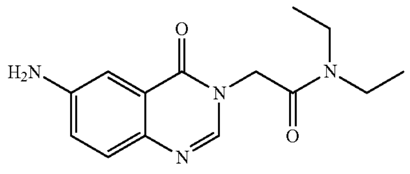
252
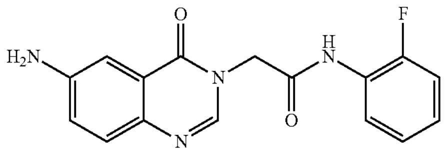
255
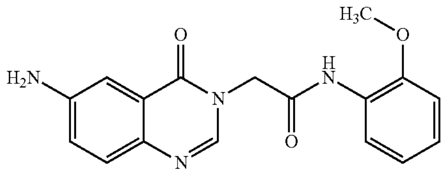

-continued
261
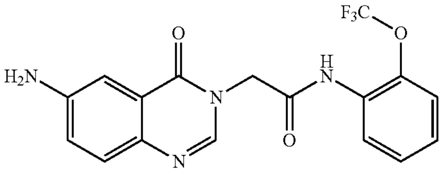
264
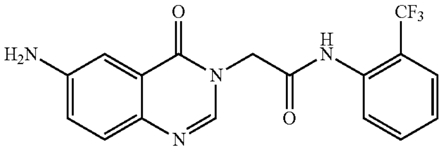
267
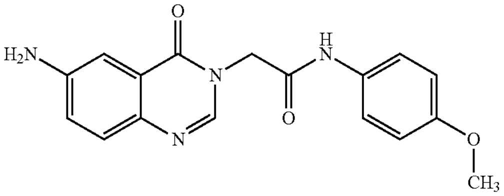
270
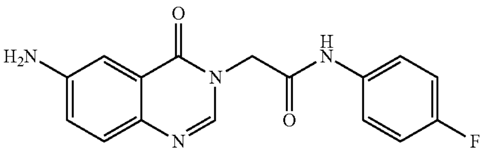
273
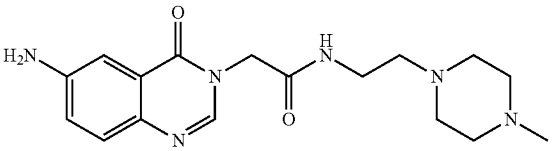
276
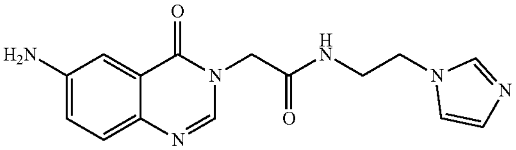
280
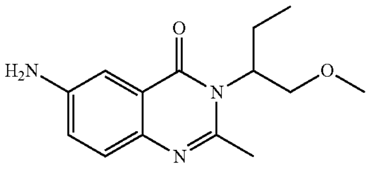
284
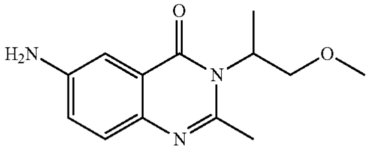
288
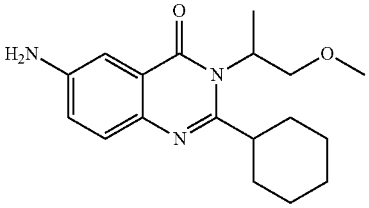
-continued
298
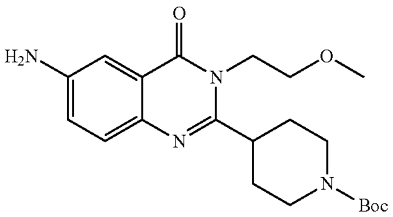
303
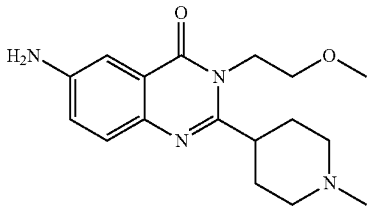
306
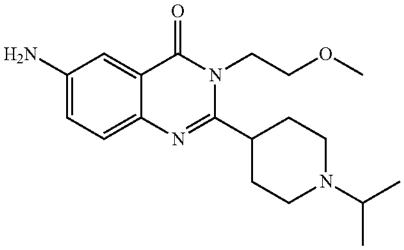
329
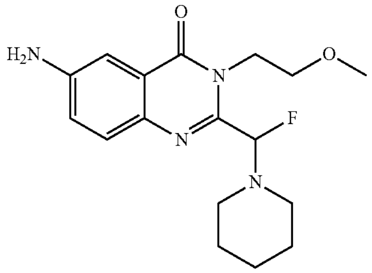
329a
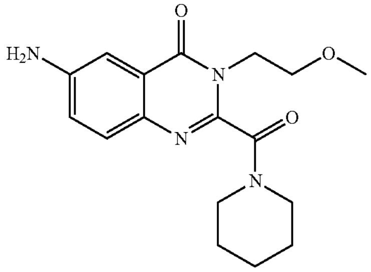
332
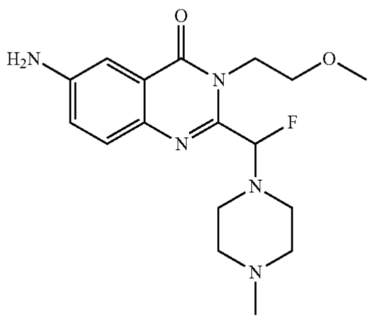

-continued

332a

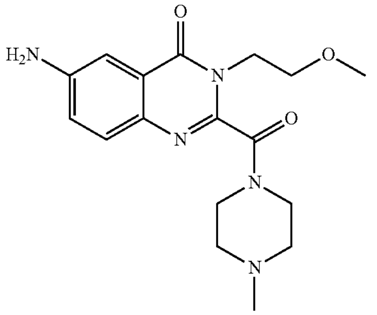

335

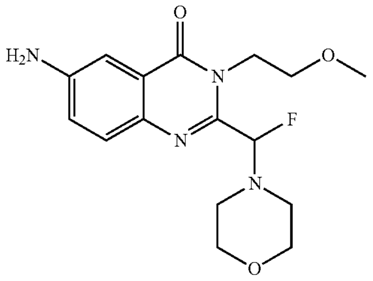

335a

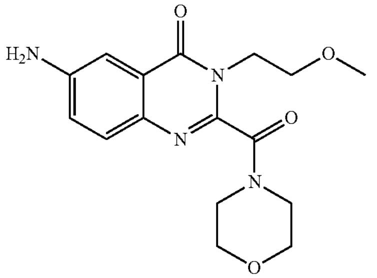

339

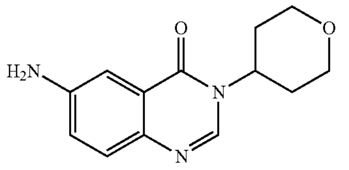

(xvii) reducing the compound selected from 205 or 257 obtained in (ix) and (x) using $SnCl_2 \cdot 2H_2O$ to obtain the compound selected from 206 or 258;

206

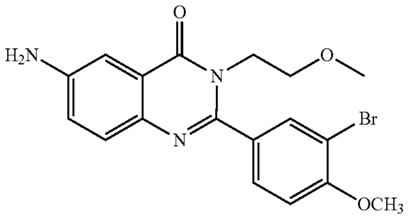

-continued

258

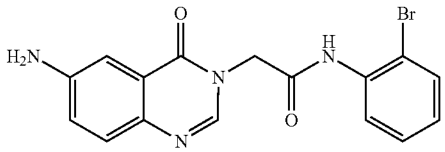

(xviii) brominating the compound selected from the group consisting of 4, 106, 122, and 178 obtained in (xvi) diluted in dichloromethane or chloroform solution by carrying out a reaction in acetic acid medium followed by dropwise addition of liquid bromine on the compound at room temperature for 3 to 4 hours to obtain a compound selected from the group consisting of 43, 344, 290, and 293;

43

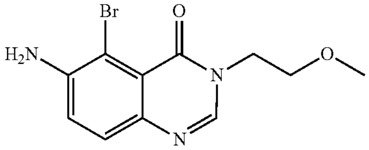

344

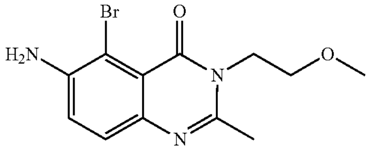

290

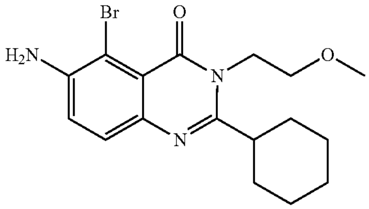

293

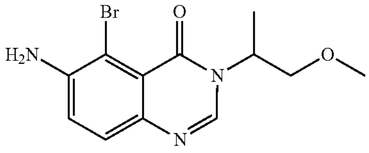

(xix) carrying out a Suzuki reaction on a compound selected from the group consisting of 43, 290, and 293 obtained in (xviii) by $Pd_2(dba)_3$ or $Pd(PPh_3)_4$ in the presence of $Cs_2CO_3$ or 2M $Na_2CO_3$ solution in dioxane and X-Phos as a ligand at 100° C. over a period of 10 to 12 hours along with a boronic acid selected from the group consisting of benzeneboronic acid, 4-fluorobenzeneboronic acid, pyridine-2-boronic acid, pyridine-3-boronic acid, pyridine-4-boronic acid, 6-methoxypyridine-3-boronic acid, 2-methoxypyridine-3-boronic acid, (1-(tert-butoxycarbonyl)-1,2,3,6-tetrahydropyridin-4-yl) boronic acid, 4-methoxybenzeneboronic acid, 4-trifluoromethylbenzeneboronic acid, cyclohexylboronic acid, cyclopentyl boronic acid, and isopropylboronic acid to obtain a compound selected from the group consisting of 44, 46, 48, 50, 52, 54, 56, 58, 63, 65, 67, 69, 71, 291, and 294 which is treated with 4-nitrophenylchloroformate in presence of TEA as a base followed by reaction with 3-aminoacetophenone in dry THF at room temperature for 5 to 8 hours to obtain the compound having Structure I selected from the group consisting of 45, 47, 49, 51, 53, 55, 57, 59, 64, 66, 68, 70, 72, 292, and 295;
44
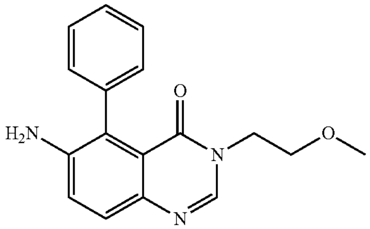
45
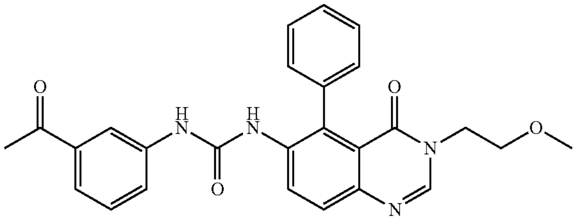
46
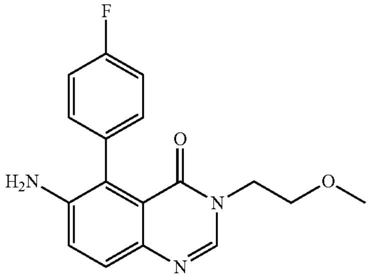
47
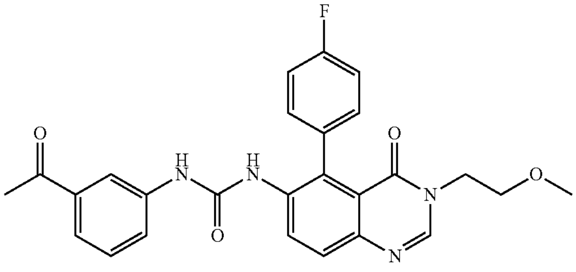
48
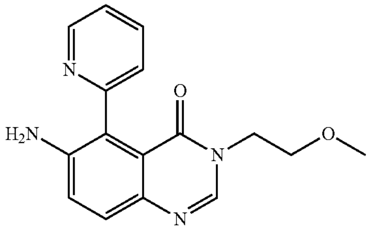
-continued
49
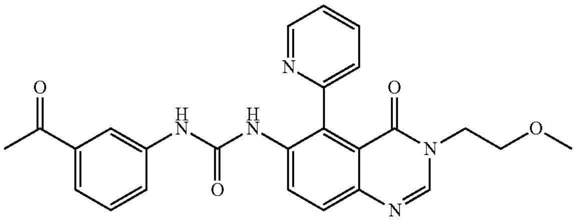
50
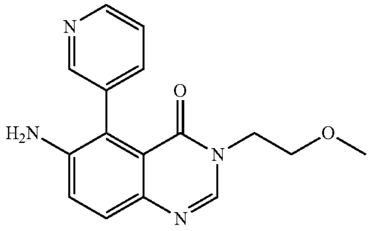
51
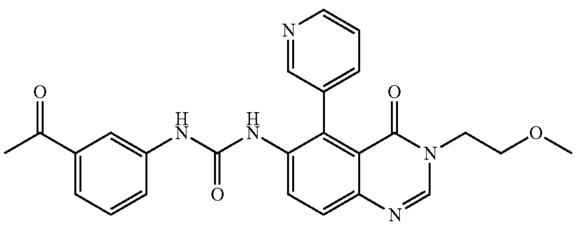
52
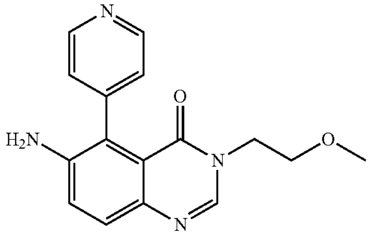
53
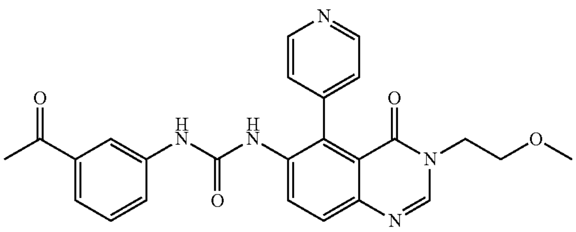
54
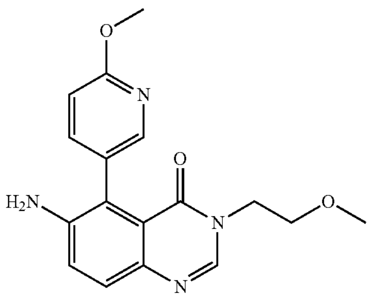

-continued
55
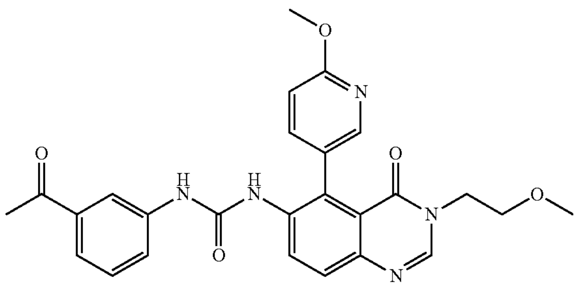
56
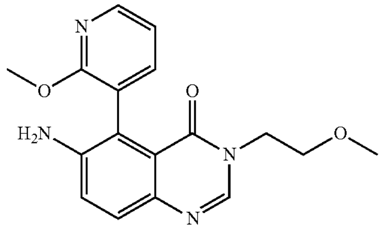
57
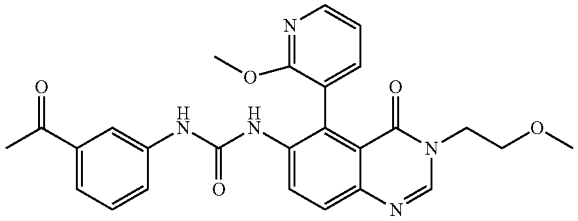
58
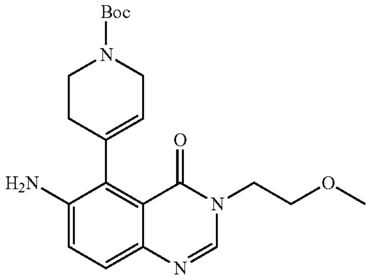
59
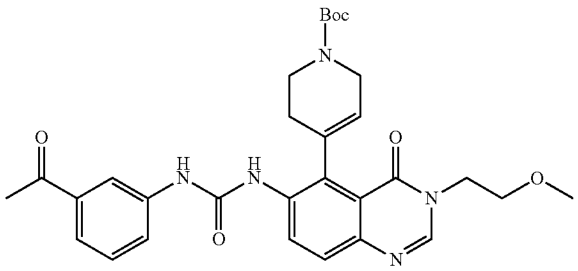
-continued
63
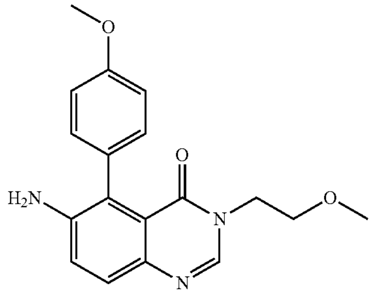
64
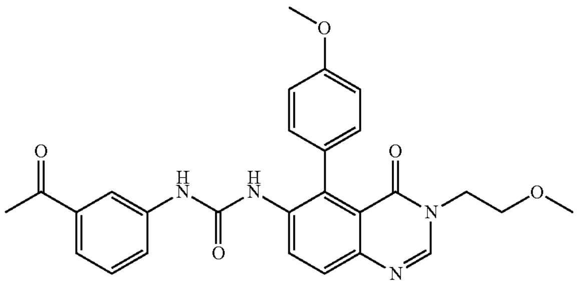
65
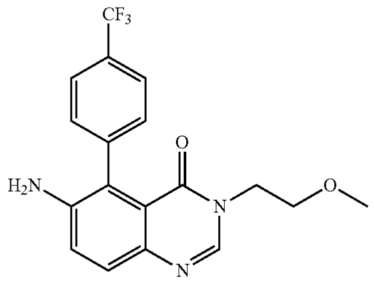
66
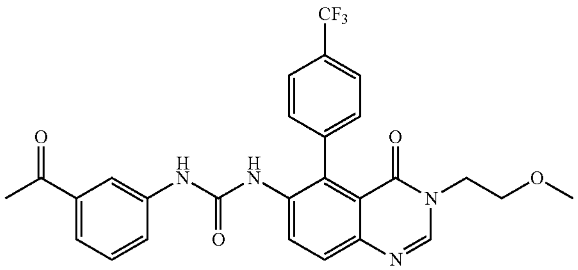
67
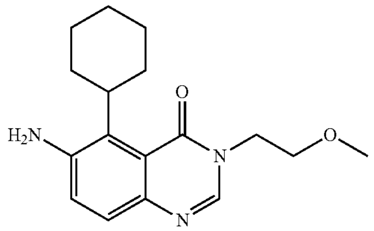

-continued

68

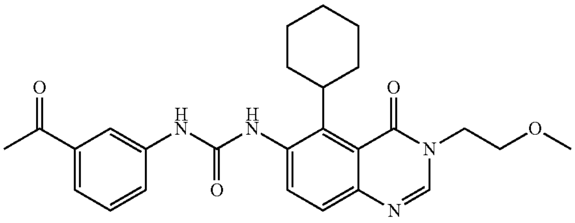

69

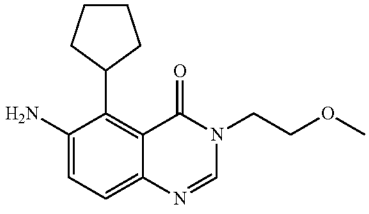

70

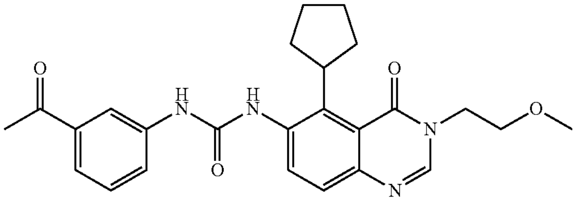

71

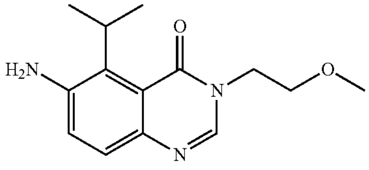

72

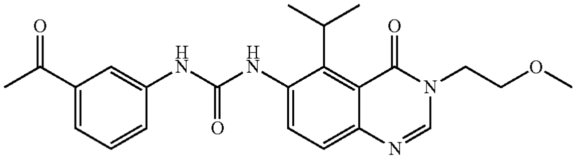

291

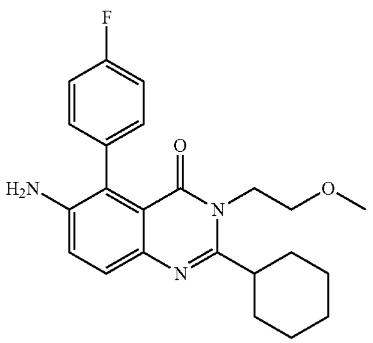

-continued

292

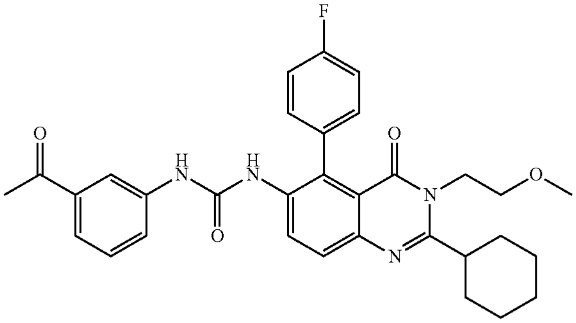

294

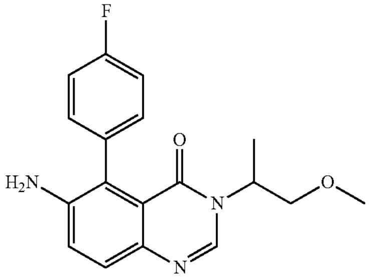

295

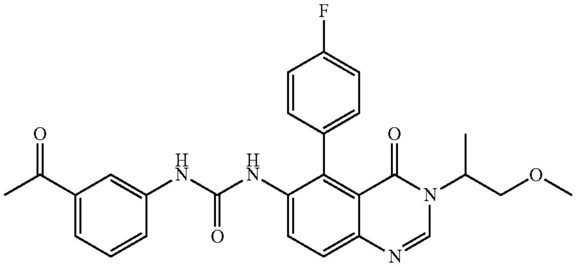

(xx) alternately, treating compound 4 obtained in (xvi) with 4-nitrophenylchloroformate in the presence of TEA as a base followed by reaction with an amine selected from the group consisting of aniline, m-anisidine, N1-methylbenzene-1,3-diamine, m-nitroaniline, 3-aminoacetophenone, 4-aminoacetophenone, 1-(3-aminophenyl) ethanol, methyl 3-amino-4-methoxybenzoate, 3-ethylaniline, 3'-aminobenzophenone, 3-amino-N-cyclohexylbenzamide, methyl 2-(3-aminobenzamido)-3-methylbutanoate, 3-amino-N,N-dimethylbenzamide, (3-aminophenyl) (pyrrolidin-1-yl) methanone, (3-aminophenyl) (pyrrolidin-1-yl) methanone, (4-aminophenyl) (pyrrolidin-1-yl) methanone, 3-(benzo[d]oxazol-2-yl) aniline, N-(3-aminophenyl) acetamide, N-(3-aminophenyl)-N-methylacetamide, N-(3-aminophenyl)-N-benzylacetamide, N-(3-aminobenzyl)acetamide, N-(3-aminobenzyl)-N-methylacetamide, dimethylamine, piperdine, 4-amino-1-methylpiperdine, 4-benzylpiperidine, 1-benzylpiperidin-4-amine, 1-(3-amino-4-hydroxyphenyl)ethanone, 1-(3-amino-5-chloro-2-hydroxyphenyl)ethanone, 1-(3-amino-2-hydroxy-5-methylphenyl)ethanone, and 1-(3-aminophenyl)-2,2,2-trifluoroethanol in dry THF at room temperature for 3 to 8 hours to obtain the compound having Structure I selected from the group consisting of 5, 6, 7, 8, 9, 10, 11, 12, 13, 14, 15, 16, 17, 18, 19, 20, 21, 22, 23, 24, 25, 26, 27, 28, 29, 30, 31, 32, 33, and 34;

5
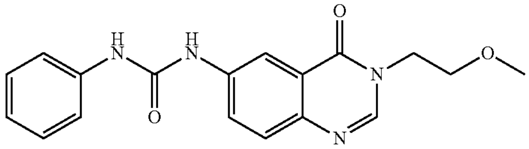
6
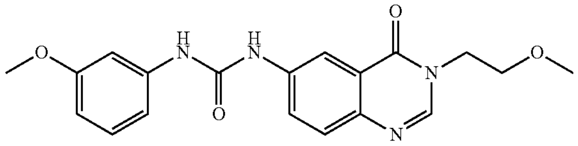
7
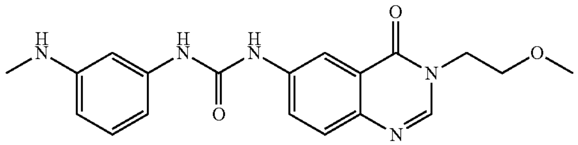
8
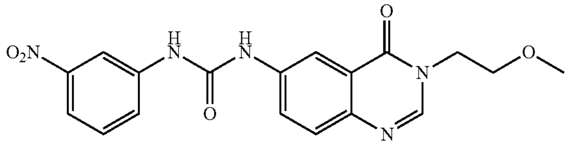
9
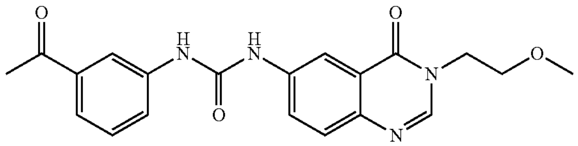
10
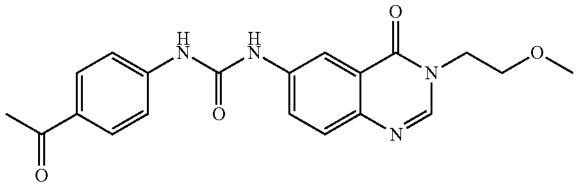
11
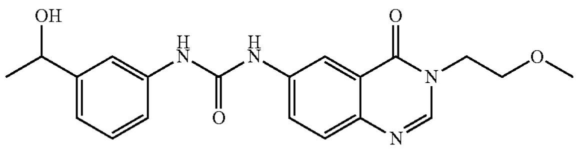
12
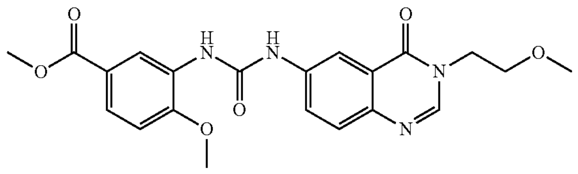
13
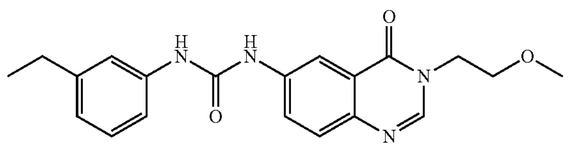
-continued
14
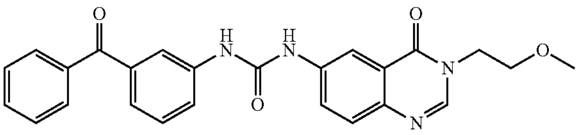
15
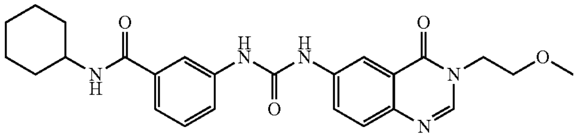
16
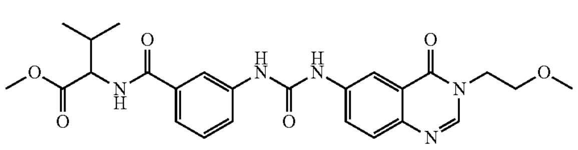
17
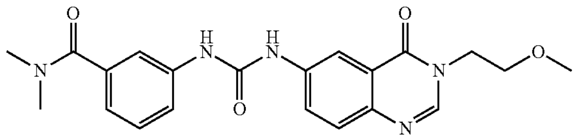
18
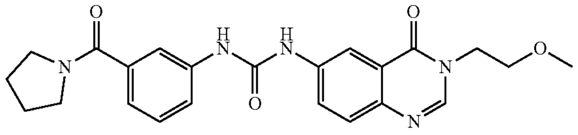
19
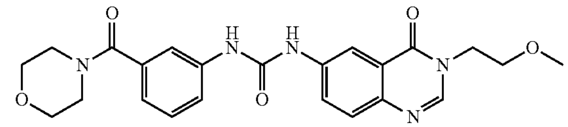
20
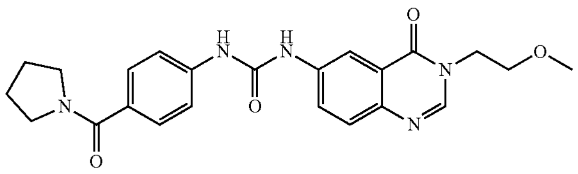
21
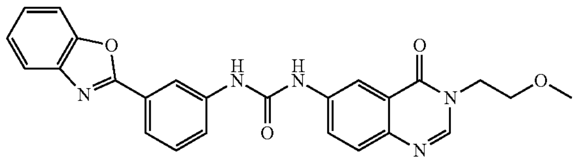
22
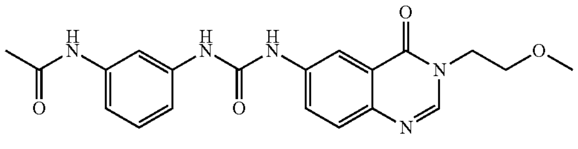

-continued

23

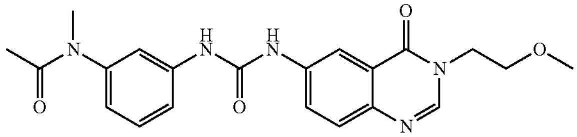

24

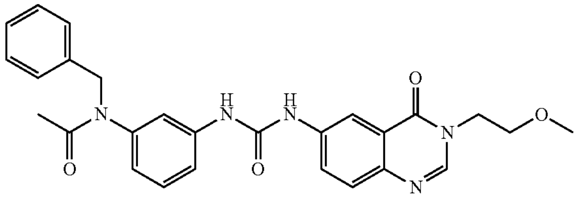

25

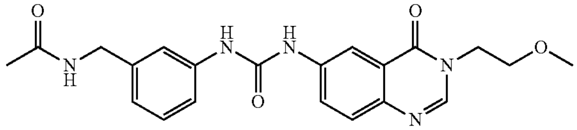

26

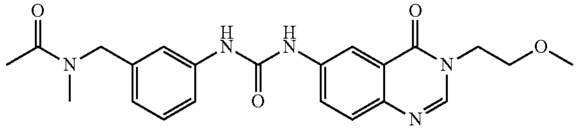

27

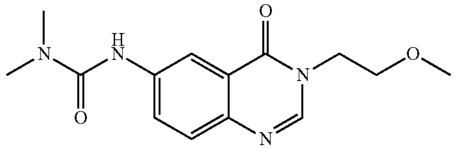

28

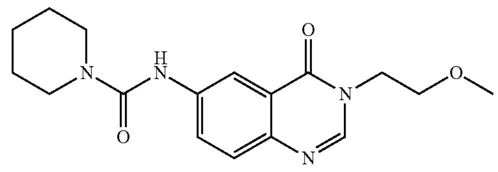

29

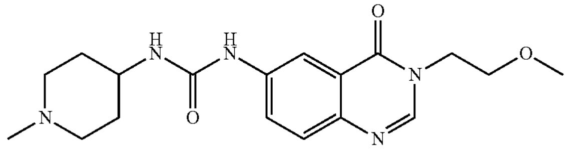

-continued

30

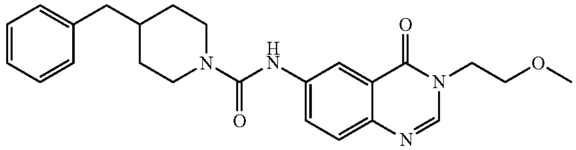

31

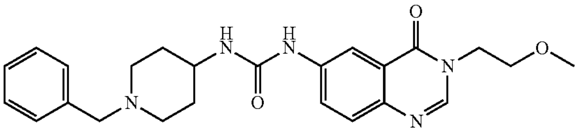

32

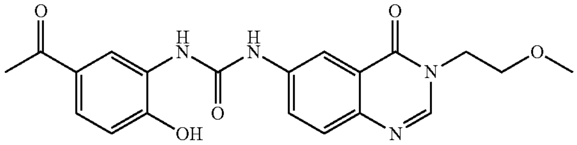

33

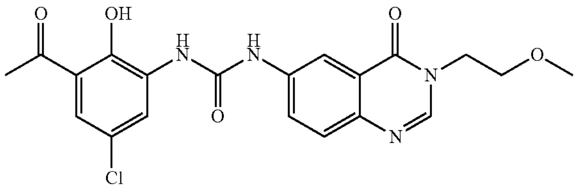

34

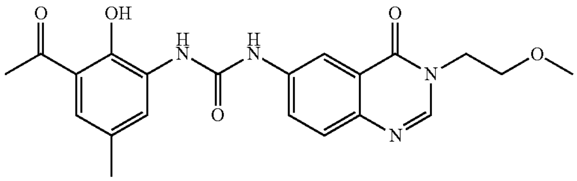

(xxi) alternately, treating the compound selected from the group consisting of 43, 88, 106, 110, 114, 118, 122, 126, 130, 138, 150, 154, 158, 162, 166, 170, 174, 178, 182, 186, 191, 202, 206, 210, 214, 218, 222, 226, 231, 234, 237, 240, 243, 246, 249, 252, 255, 258, 261, 264, 267, 270, 273, 276, 280, 284, 288, 298, 303, 306, 329, 329a, 332, 332a, 335, 335a, 339, and 344 obtained in (xvi), (xvii), or (xviii) with 4-nitrophenylchloroformate in presence of TEA as a base followed by reaction with 3-aminoacetophenonein dry THF at room temperature for 3 to 8 hours to obtain the compound having Structure I selected from the group consisting of 73, 89, 107, 111, 115, 119, 123, 127, 131, 139, 151, 155, 159, 163, 167, 171, 175, 179, 183, 187, 192, 193, 194, 195, 196, 197, 198, 199, 203, 207, 211, 215, 219, 223, 227, 232, 235, 238, 241, 244, 247, 253, 256, 259, 262, 268, 274, 277, 281, 285, 289, 304, 307, 330, 330a, 333, 333a, 336, 336a, 340, and 345;

73
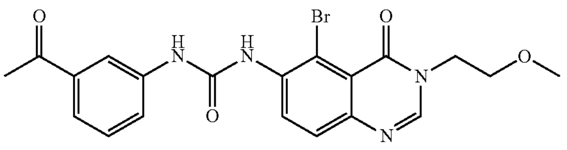
107
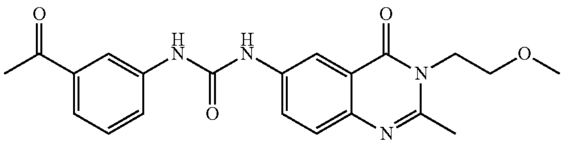
115
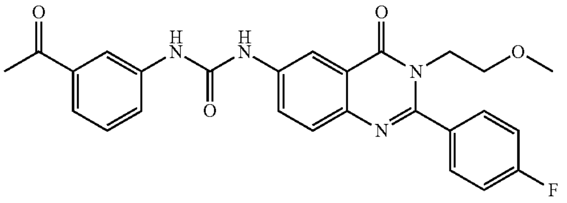
123
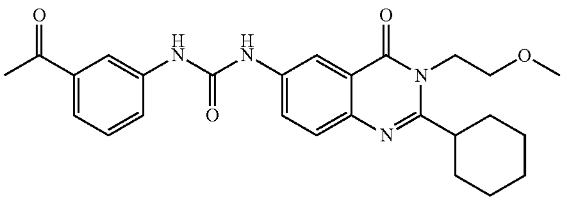
131
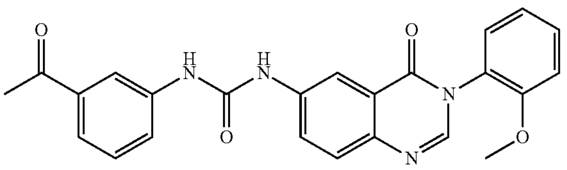
151
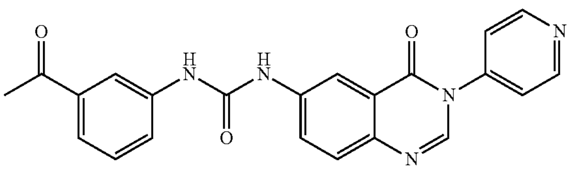
159
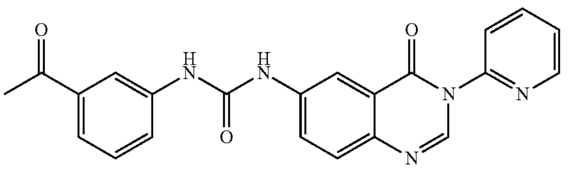
167
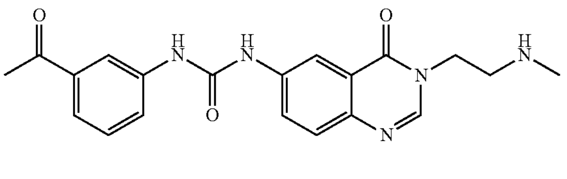
89
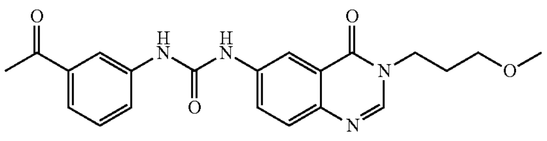
111
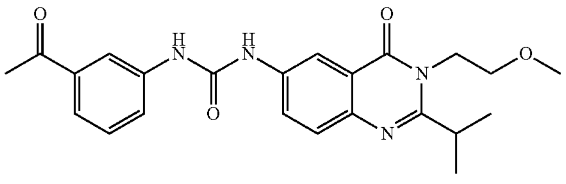
119
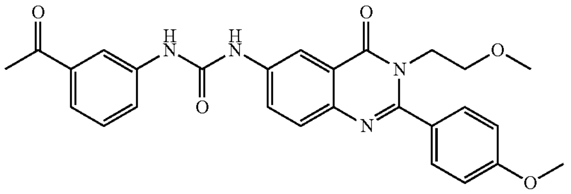
127
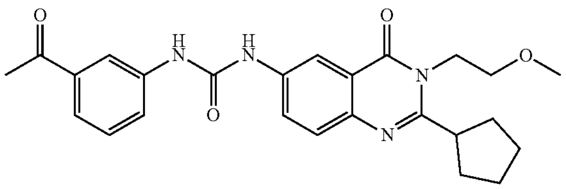
139
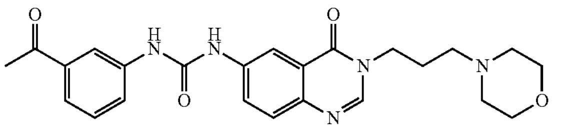
155
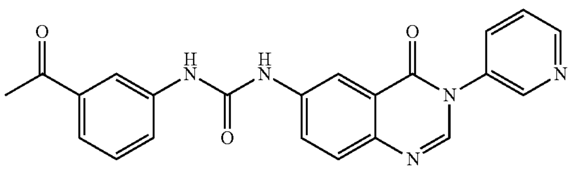
163
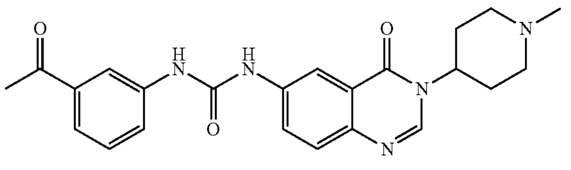
171
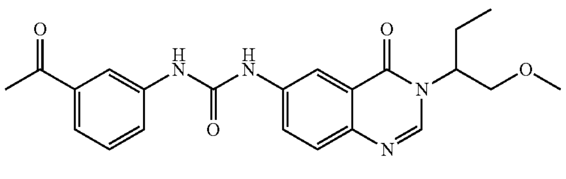

-continued
175
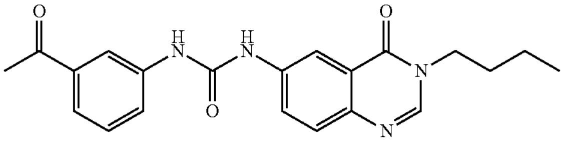
179
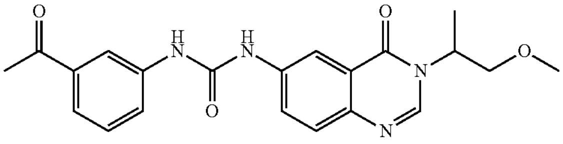
183
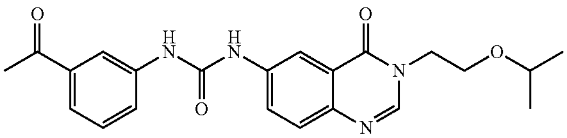
187
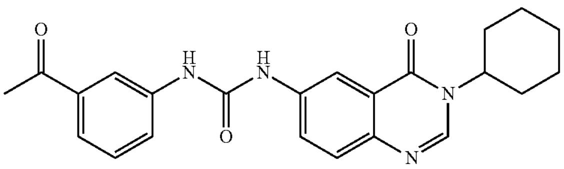
192
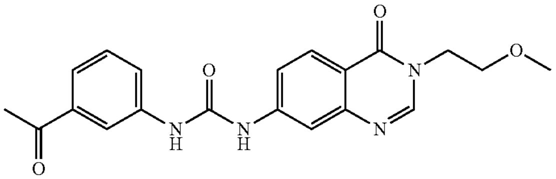
193
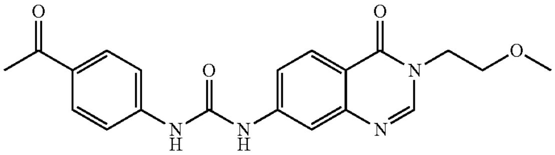
194
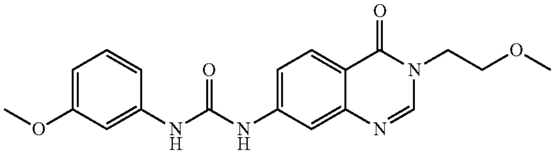
195
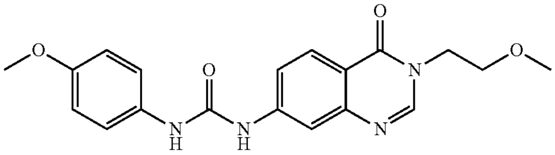
196
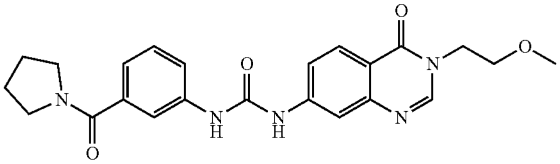
197
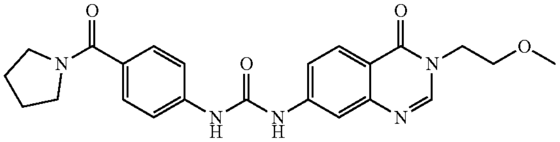
198
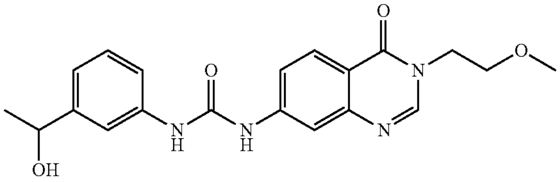
199
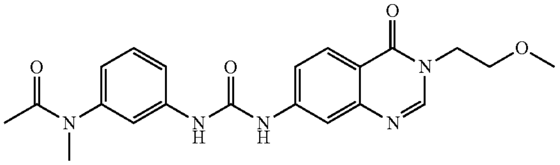
203
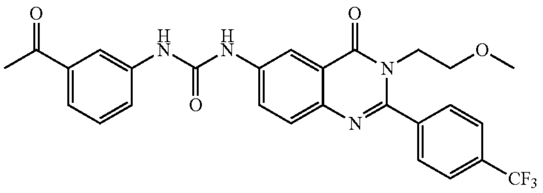
207
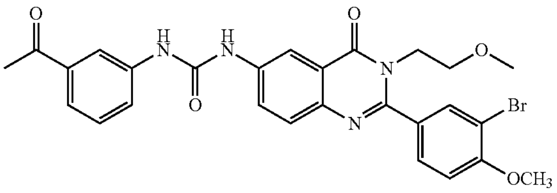
211
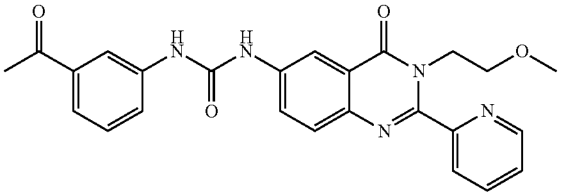
215
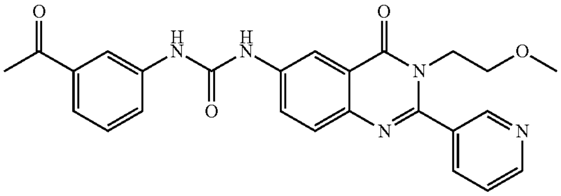 [SMILES: COCCn1c(-c2cccnc2)nc2ccc(NC(=O)Nc3cccc(C(C)=O)c3)cc2c1=O]

-continued
219
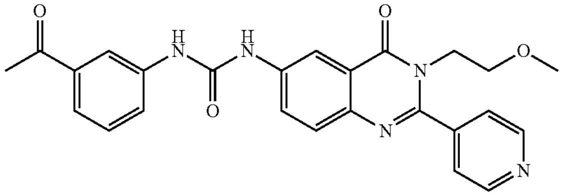 [SMILES: COCCn1c(-c2ccncc2)nc2ccc(NC(=O)Nc3cccc(C(C)=O)c3)cc2c1=O]
223
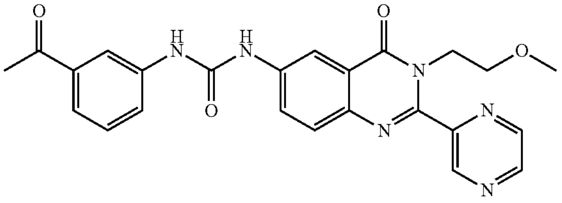
227
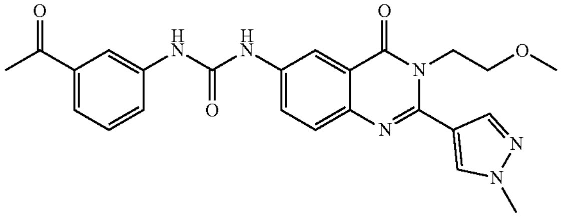
232
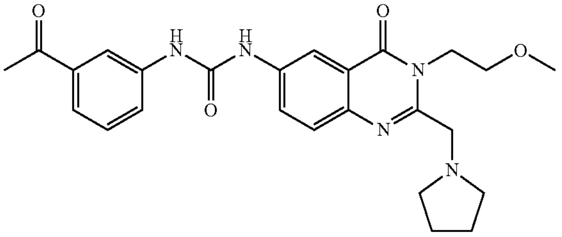
235
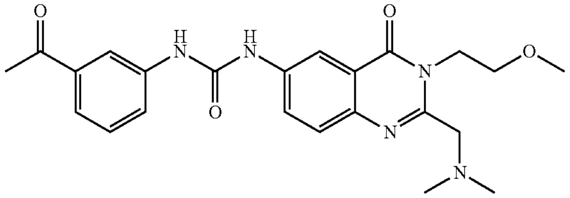
238
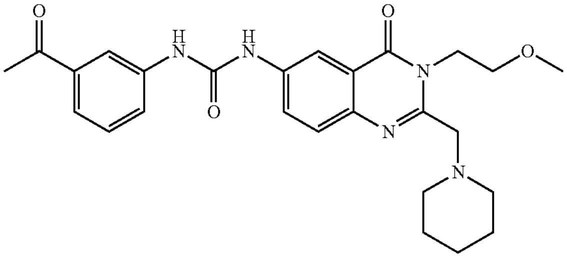
241
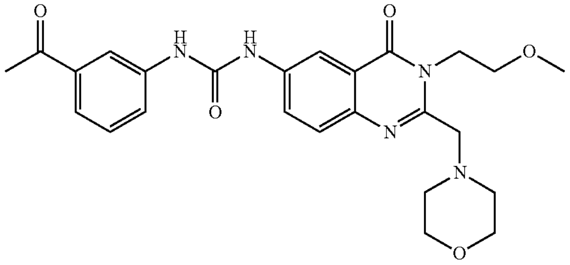
244
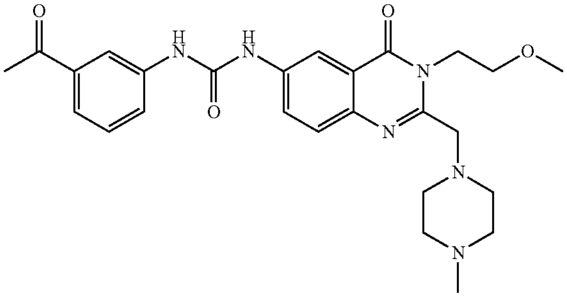
247
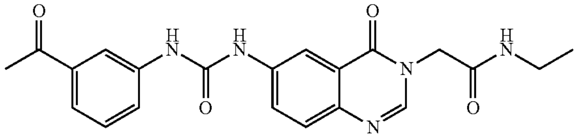
253
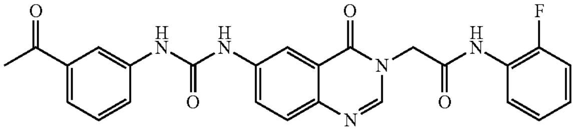
256
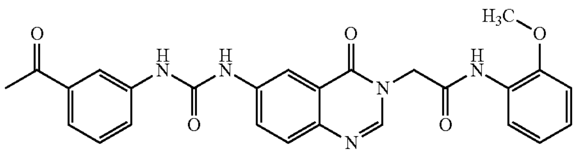
259
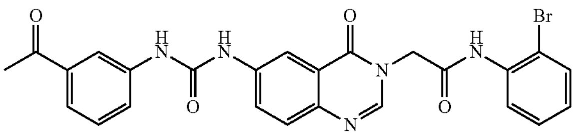
262
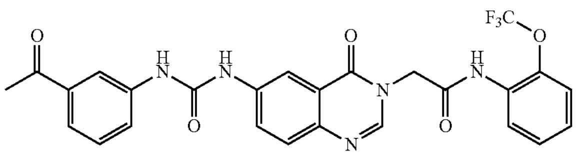
268
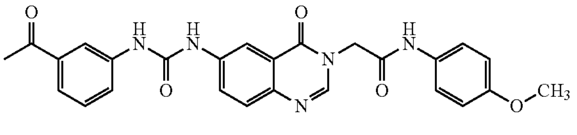

-continued
274
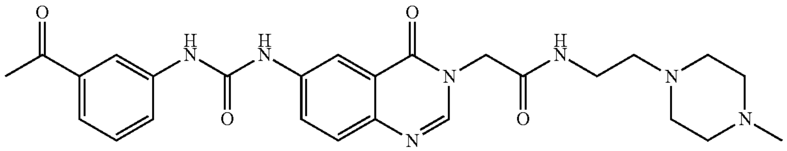
277
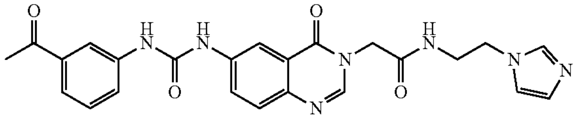
281
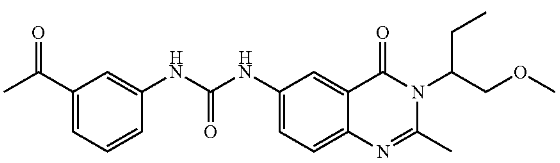
285
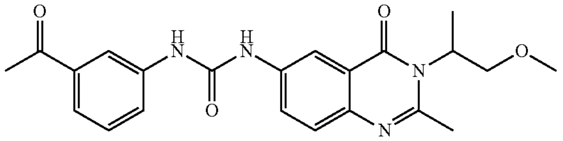
289
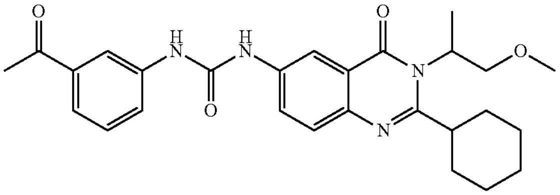
304
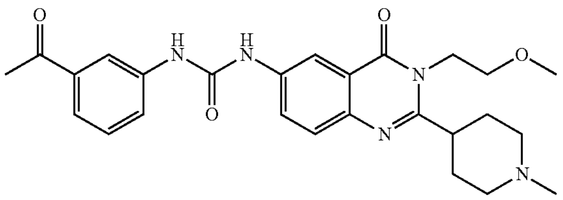
307
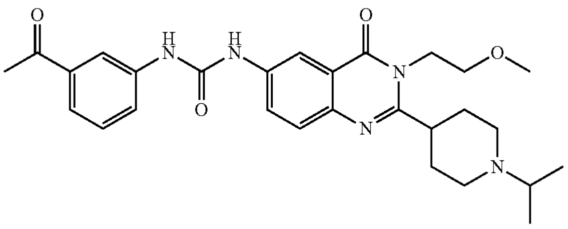
330
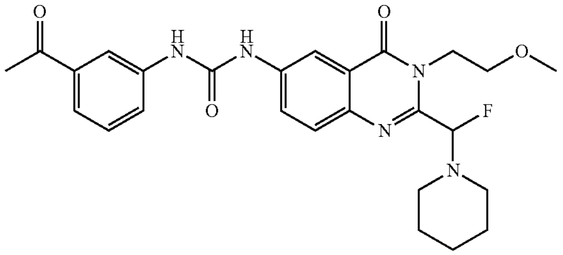
330a
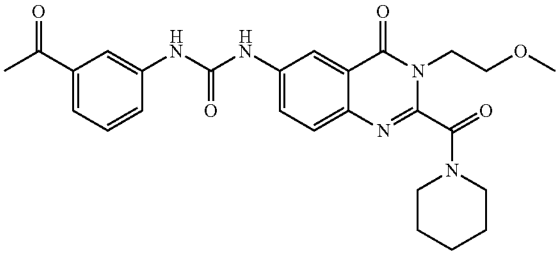
333
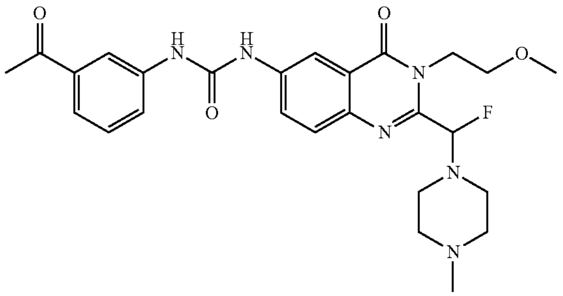
333a
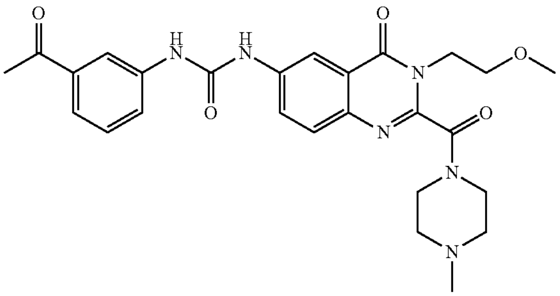

-continued

336

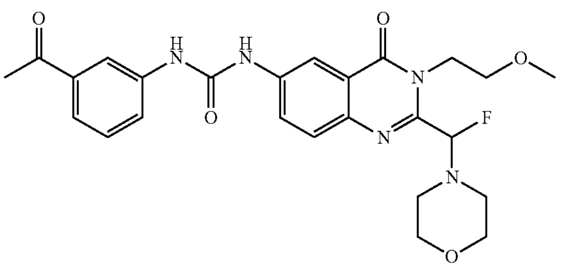

336a

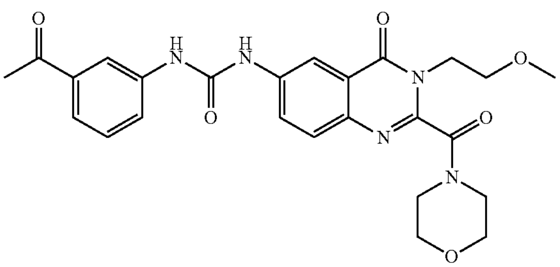

340

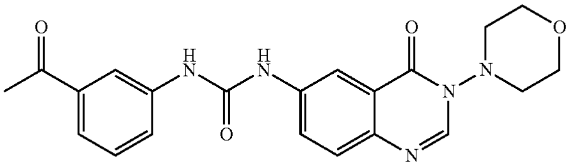

345

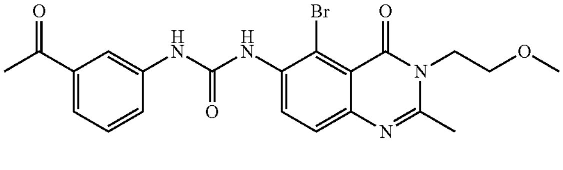

(xxii) alternately, treating the compound selected from the group consisting of 4, 82, 92, 97, 102, 134, 142, and 146 obtained in (xvi) with a substituted aromatic isocyanate selected from the group consisting of 4-fluorophenylisocyanate, 3-chloro-4-fluorophenylisocyanate, (4-trifluoromethoxy)phenylisocyanate, (4-trifluoromethyl)phenylisocyanate, (2-trifluoromethyl)phenylisocyanate, 4-methoxyphenylisocyanate, 2-methoxyphenylisocyanate, ethyl-3-isocyanatobenzoate, 3-acetylphenylisocyanate, and 4-acetylphenylisocyanate in the presence of TEA as a base in dry THF at room temperature for 3 to 8 hours to obtain the compound having Structure I selected from the group consisting of 35, 36, 37, 38, 39, 40, 41, 42, 83, 84, 85, 93, 94, 98, 99, 103, 135, 143, and 147;

35

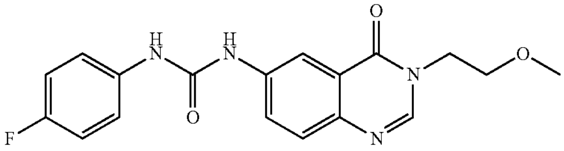

36

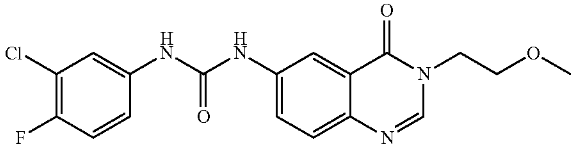

37

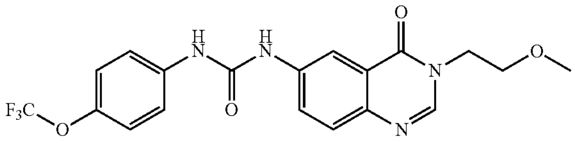

-continued

38

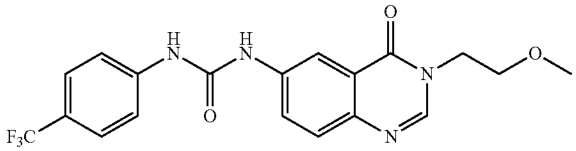

39

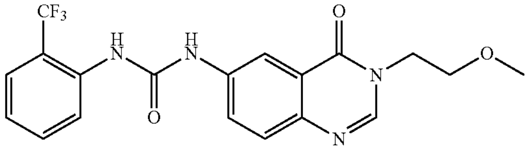

40

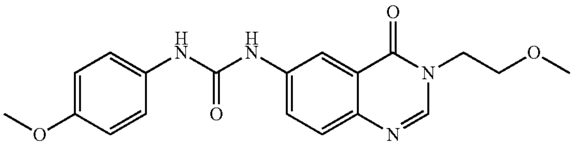

41

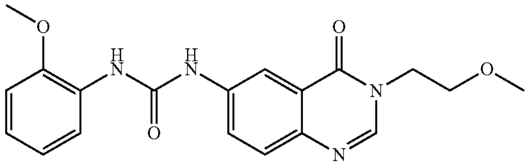

42

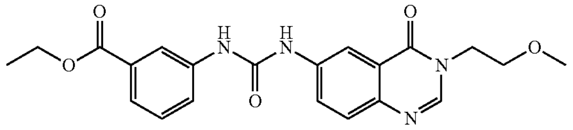

83

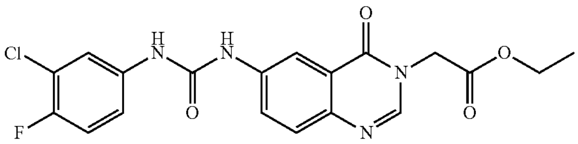

-continued

84

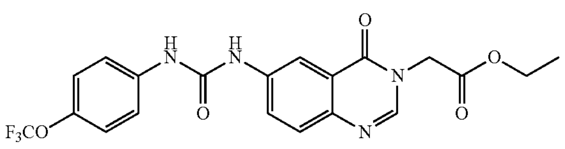

85

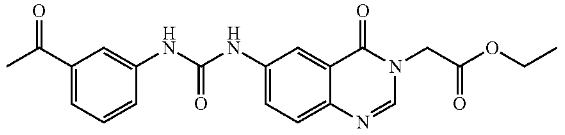

93

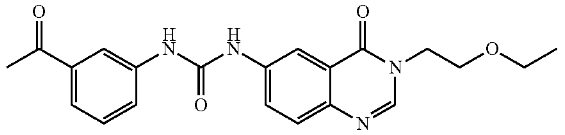

94

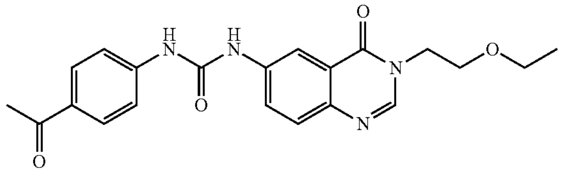

98

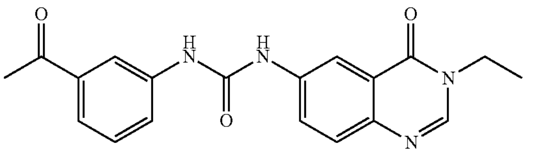

99

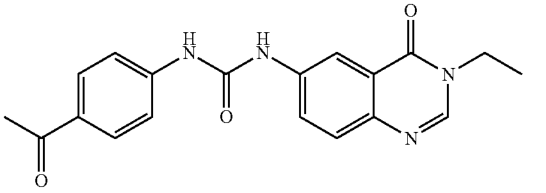

103

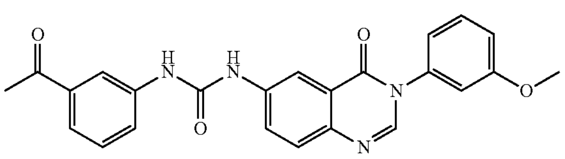

135

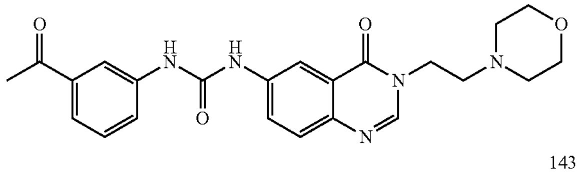

143

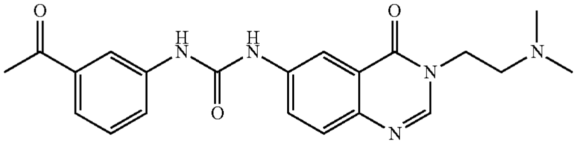

-continued

147

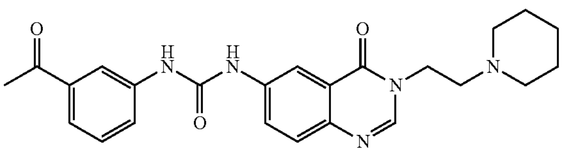

(xxiii) alternately, reacting compound 4 obtained in (xvi) with HATU/TEA in DMF at room temperature with 5 hours of stirring to obtain a compound 74;

74

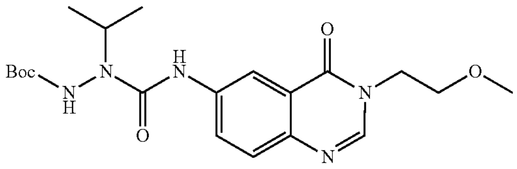

(xxiv) separately adding 3-nitrobenzoyl chloride (3-nitrobenzoic acid and Oxalyl Chloride) at 0° C. in DCM and TEA and stirring for 5 hours at room temperature to obtain a compound 77;

77

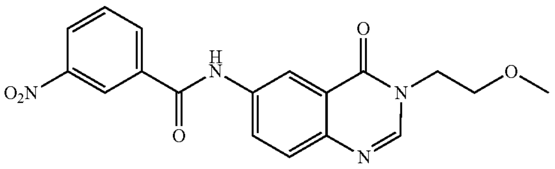

(xxv) separately Boc deprotecting the compound 59 obtained in (xix) and the compound 74 obtained in (xxiii) by TFA at room temperature for 2 hours to obtain a compound selected from 60 or 75;

60

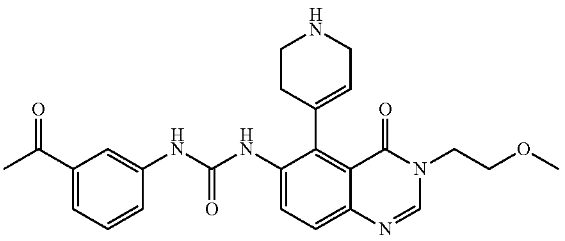

75

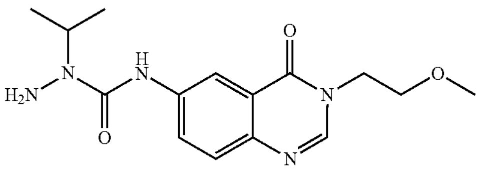

(xxvi) treating the compound 59 obtained in (xix) and compound 60 obtained in (xxv) with $H_2$/Pd—C(5% wet) to obtain the compound having Structure I selected from the group consisting of 61 and 62;

61

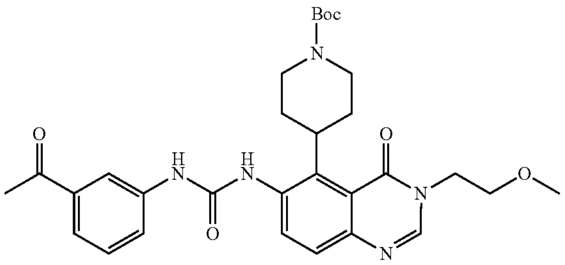

62

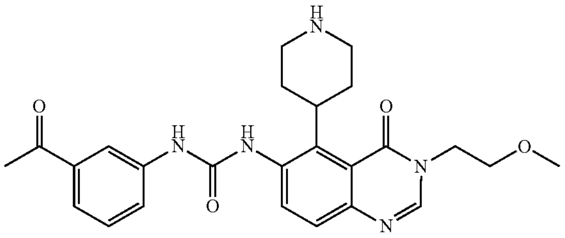

(xxvii) alternately, treating the compound selected from the group consisting of 191, 4, 46, 237, 249, 106, 243, and 252 obtained in (xvi) and (xix) with 4-nitrophenylchloroformate in presence of TEA as a base followed by reaction with an amine selected from the group consisting of 3-aminoacetophenone, 4-aminoacetophenone, m-anisidine, p-anisidine, (3-aminophenyl) (pyrrolidin-1-yl) methanone, (4-aminophenyl) (pyrrolidin-1-yl) methanone, 1-(3-aminophenyl)-2,2,2-trifluoroethanol, 1-(3-aminophenyl)-N-methylacetamide, 1-(3-(hydroxyamino)phenyl)ethanone, 1-(3-(methylamino)phenyl)ethanone, and 1-(3-aminophenyl)-2,2,2-trifluoroethanone in dry THF at room temperature for 3 to 8 hours to obtain the compound having Structure I selected from the group consisting of 194, 195, 196, 197, 198, 199, 308, 309, 310, 311, 312, 313, 314, 315, 316, 317, 318, 319, 320, 321, 322, 323, 324, and 325;

194

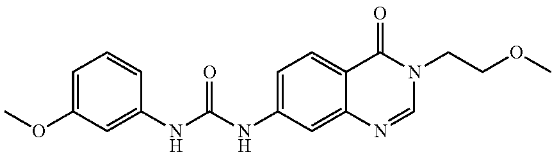

195

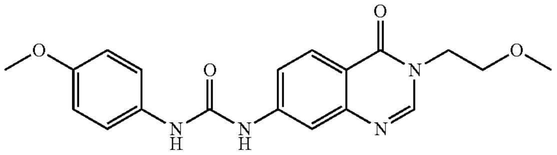

196

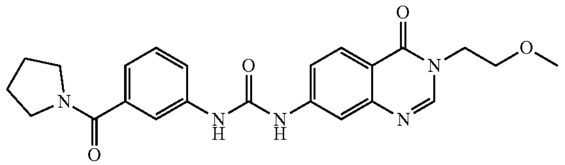

-continued

197

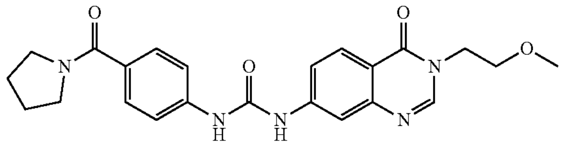

198

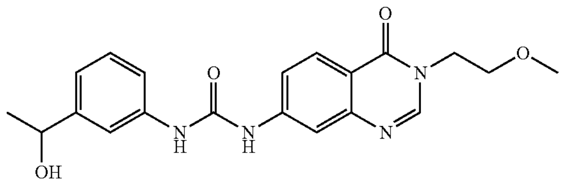

199

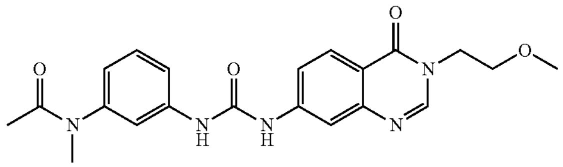

308

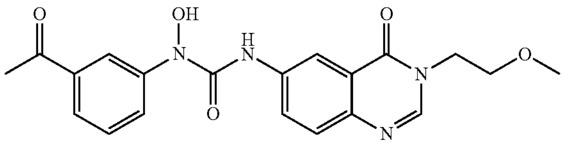

309

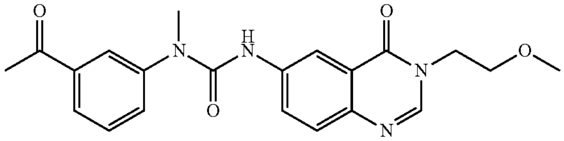

310

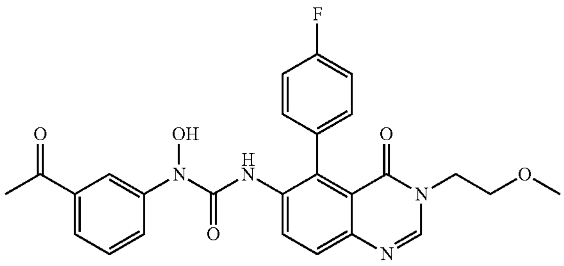

311

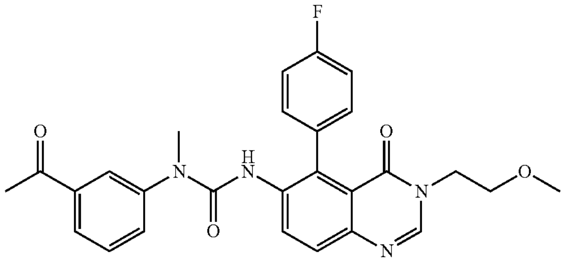

-continued
312
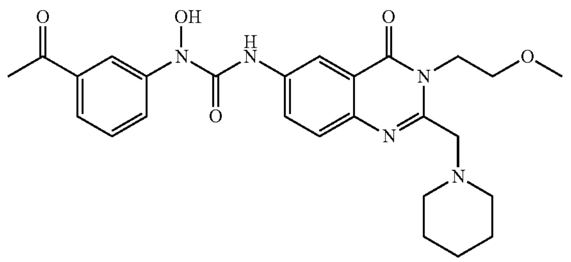
313
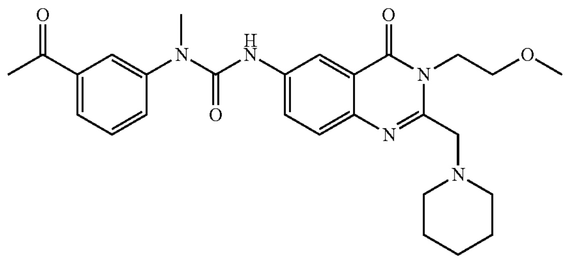
314
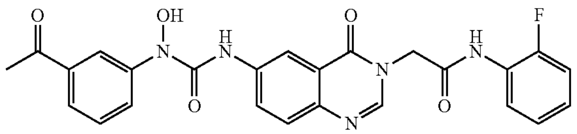
315
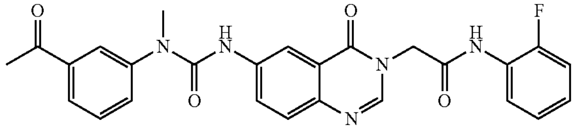
316
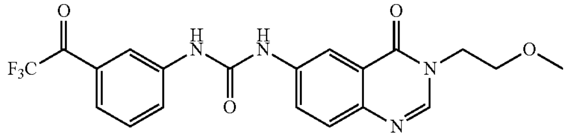
317
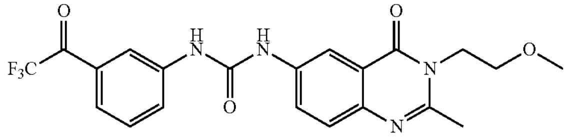
318
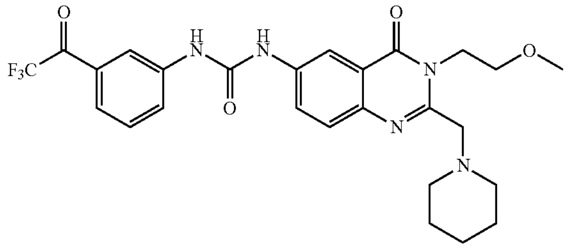
-continued
319
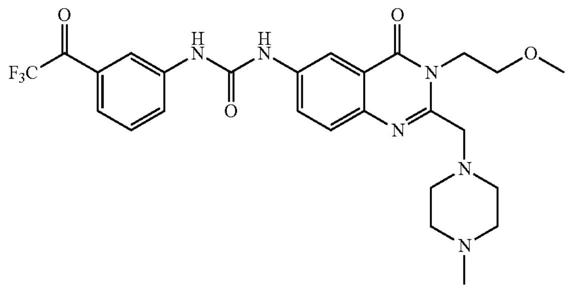
320
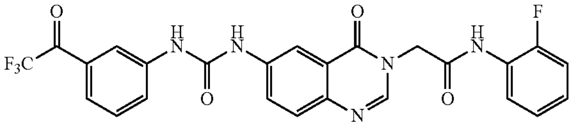
321
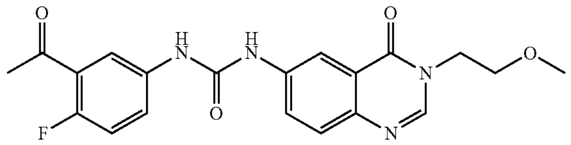
322
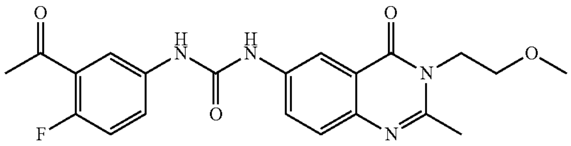
323
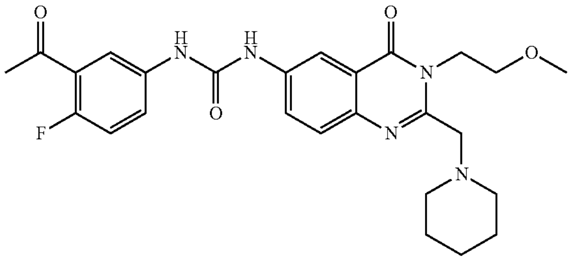
324
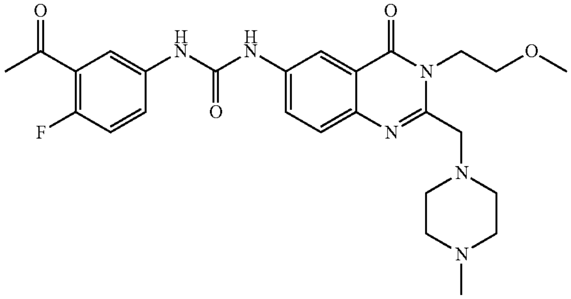
325
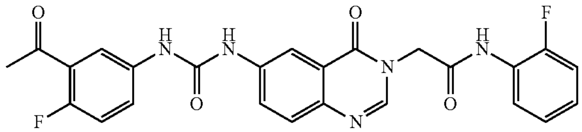

(xxviii) subjecting the compound selected from 42 and 85 obtained in (xxii) to ester hydrolysis by LiOH monohydrate in presence of THF:EtOH:Water (3:2:1) proportion at room temperature for 1 to 2 hours to obtain the compound having Structure I selected from the group consisting of 42a and 85a;

42a

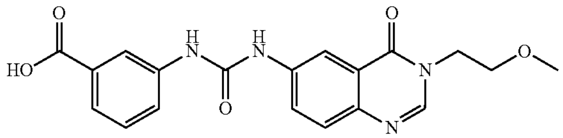

85a

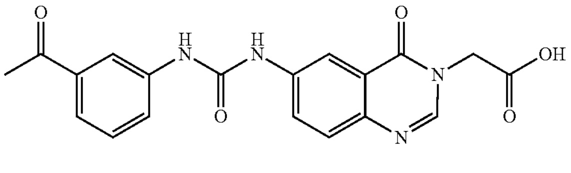

(xxix) reacting the compound 238 obtained in (xxi) with 1M HCl in dioxane to obtain the compound having Structure I 238a; and 238a

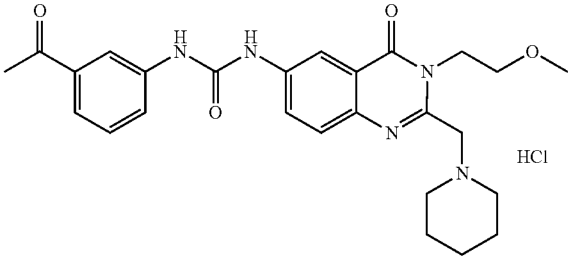

(xxx) reacting the compound selected from the group consisting of 9, 107, and 238 obtained in (xx) and (xxi) with hydroxylamine hydrochloride ($NH_2OH \cdot HCl$) in ethanol (EtOH) at 80° C. for 12 to 16 hours to obtain the compound having Structure I selected from the group consisting of 341, 342 and 343

341

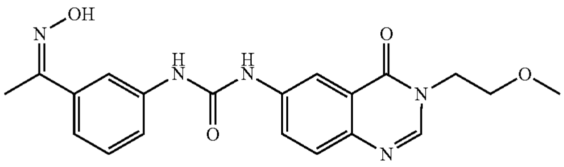

-continued

342

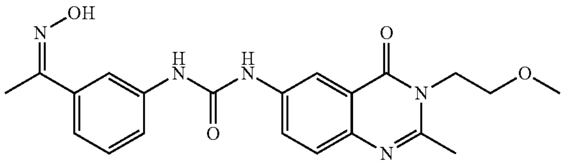

343

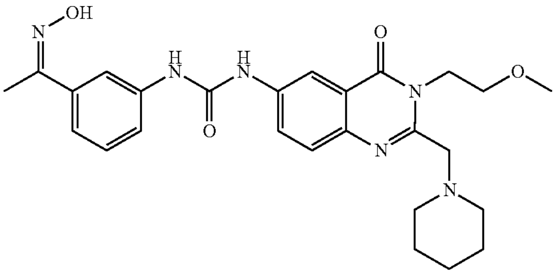

.

4. A method for treating a disease or disorder related to modulation of COP1 enzyme, the method comprising administering a compound according to claim 1 to a subject in need thereof, thereby stabilizing the COP1 enzyme or modulating ATGL in the subject.

5. A method for decreasing a level of triglycerides in hepatocytes of a subject, the method comprising administering a compound according to claim 1 to the subject.

6. A method for treating Non-Alcoholic Fatty Liver Disease (NAFLD) or Non-Alcoholic Steatohepatitis (NASH) in a subject having NAFLD or NASH, the method comprising administering a compound according to claim 1 to the subject.

7. A composition comprising a compound according to claim 1 in combination with at least one pharmaceutically acceptable excipient.

8. A method of modulating a COP1 enzyme, the method comprising stabilizing the COP1 enzyme with a compound according to claim 1.

9. A method of increasing a level of ATGL in a subject, the method comprising administering to the subject a compound according to claim 1.

* * * * *